United States Patent
Diener et al.

(10) Patent No.: US 12,264,188 B2
(45) Date of Patent: Apr. 1, 2025

(54) RELAXIN-2 FUSION PROTEINS

(71) Applicant: TECTONIC OPERATING COMPANY, INC., Watertown, MA (US)

(72) Inventors: John Diener, Watertown, MA (US); Ryan Knihtila, Watertown, MA (US); Franz Gruswitz, Watertown, MA (US)

(73) Assignee: TECTONIC OPERATING COMPANY, INC., Watertown, MA (US)

( * ) Notice: Subject to any disclaimer, the term of this patent is extended or adjusted under 35 U.S.C. 154(b) by 0 days.

(21) Appl. No.: 18/799,714

(22) Filed: Aug. 9, 2024

(65) Prior Publication Data

US 2024/0409601 A1    Dec. 12, 2024

Related U.S. Application Data

(63) Continuation of application No. PCT/US2024/030016, filed on May 17, 2024.

(60) Provisional application No. 63/617,398, filed on Jan. 3, 2024, provisional application No. 63/611,732, filed on Dec. 18, 2023, provisional application No. 63/586,868, filed on Sep. 29, 2023, provisional application No. 63/585,849, filed on Sep. 27, 2023, provisional application No. 63/503,101, filed on May 18, 2023.

(51) Int. Cl.
*C07K 14/64* (2006.01)
*A61P 43/00* (2006.01)
*A61K 38/00* (2006.01)

(52) U.S. Cl.
CPC ............. *C07K 14/64* (2013.01); *A61P 43/00* (2018.01); *A61K 38/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 8,389,475 B2 | 3/2013 | Park et al. |
| 8,445,635 B2 | 5/2013 | Medin et al. |
| 8,735,539 B2 | 5/2014 | Kraynov et al. |
| 9,056,922 B2 | 6/2015 | Bathgate et al. |
| 9,381,231 B2 | 7/2016 | Conrad |
| 9,382,305 B2 | 7/2016 | Wilmen et al. |
| 9,434,780 B2 | 9/2016 | Forssmann et al. |
| 9,561,261 B2 | 2/2017 | Garvin et al. |
| 9,907,833 B2 | 3/2018 | Conrad |
| 10,081,662 B2 | 9/2018 | Bathgate et al. |
| 10,226,512 B2 | 3/2019 | Dschietzig |
| 10,253,083 B2 | 4/2019 | Kraynov et al. |
| 10,266,578 B2 | 4/2019 | Dubowchik et al. |
| 10,286,078 B2 | 5/2019 | Shen et al. |
| 10,842,851 B2 | 11/2020 | Dschietzig |
| 10,961,295 B2 | 3/2021 | Duclos et al. |
| 10,988,523 B2 | 4/2021 | Brasseur et al. |
| 10,988,524 B2 | 4/2021 | Illiano et al. |
| 11,192,931 B2 | 12/2021 | Hao et al. |
| 11,344,607 B2 | 5/2022 | Garvin et al. |
| 11,439,685 B2 | 9/2022 | Grinstaff et al. |
| 11,723,957 B2 | 8/2023 | Nazarian et al. |
| 11,795,205 B2 | 10/2023 | Sermadiras et al. |
| 2011/0243942 A1 | 10/2011 | Wang |
| 2011/0245469 A1 | 10/2011 | Wang |
| 2014/0148390 A1 | 5/2014 | Haupts et al. |
| 2015/0299294 A1 | 10/2015 | Dooper et al. |
| 2016/0244482 A1 | 8/2016 | Elliott |
| 2016/0296632 A1 | 10/2016 | Chipman |
| 2016/0326562 A1 | 11/2016 | Kopetzki et al. |
| 2021/0275642 A1 | 9/2021 | Schwartzman et al. |
| 2021/0380655 A1 | 12/2021 | Grinstaff et al. |
| 2022/0275042 A1 | 9/2022 | Verdino et al. |
| 2022/0289809 A1 | 9/2022 | Schwartzman et al. |
| 2023/0174610 A1 | 6/2023 | Kruse et al. |
| 2023/0340058 A1 | 10/2023 | Diener et al. |

FOREIGN PATENT DOCUMENTS

| | | |
|---|---|---|
| EP | 0251615 B1 | 12/1992 |
| EP | 3522911 B1 | 12/2021 |
| WO | WO-2012031327 A1 | 3/2012 |
| WO | WO-2013004607 A1 | 1/2013 |
| WO | WO-2013177529 A1 | 11/2013 |
| WO | WO-2014040008 A1 | 3/2014 |
| WO | WO-2015038938 A1 | 3/2015 |
| WO | WO-2015073727 A1 | 5/2015 |
| WO | WO-2016144968 A1 | 9/2016 |
| WO | WO-2017201340 A2 | 11/2017 |
| WO | WO-2018023170 A1 | 2/2018 |
| WO | WO-2018138170 A1 | 8/2018 |
| WO | WO-2018148419 A1 | 8/2018 |
| WO | WO-2021094626 A1 | 5/2021 |

(Continued)

OTHER PUBLICATIONS

Al-Omary et al., "Pulmonary Hypertension Due to Left Heart Disease: Diagnosis, Pathophysiology, and Therapy", Hypertension, 2020, 75(6):1397-1408.

(Continued)

*Primary Examiner* — Christine J Saoud
(74) *Attorney, Agent, or Firm* — Dechert LLP; Andrew T. Wilkins; David M. Lee

(57) ABSTRACT

Relaxin-2 fusion protein analogs with enhanced in vivo half-life and methods for making the same are described. Also described are methods of treating relaxin-2-associated disorders or diseases using the relaxin-2 fusion protein analogs.

21 Claims, 22 Drawing Sheets
Specification includes a Sequence Listing.

(56) References Cited

FOREIGN PATENT DOCUMENTS

| | | |
|---|---|---|
| WO | WO-2021226439 A2 | 11/2021 |
| WO | WO-2021255127 A1 | 12/2021 |
| WO | WO-2022037469 A1 | 2/2022 |
| WO | WO-2022147897 A1 | 7/2022 |
| WO | WO-2023028008 A2 | 3/2023 |
| WO | WO-2023041845 A1 | 3/2023 |
| WO | WO-2023056044 A1 | 4/2023 |
| WO | WO-2023086913 A2 | 5/2023 |
| WO | WO-2023111112 A1 | 6/2023 |
| WO | WO-2023216981 A1 | 11/2023 |
| WO | WO-2024047130 A1 | 3/2024 |
| WO | 2024121362 A1 | 6/2024 |
| WO | 2024159903 A1 | 8/2024 |
| WO | 2024184206 A1 | 9/2024 |
| WO | 2024197033 A1 | 9/2024 |
| WO | 2024238955 A2 | 11/2024 |

OTHER PUBLICATIONS

Australian New Zealand Clinical Trials Registry, Trial Registration No. ACTRN12623001054606, titled "To evaluate the Safety, Tolerability, Pharmacokinetics, and Pharmacodynamics of TX000045 (single ascending dose) in Healthy Volunteers", registered on Sep. 29, 2023 (record retrieved on Jul. 11, 2024), pp. 1-7.

Bani et al., "Relaxin activates the L-arginine-nitric oxide pathway in vascular smooth muscle cells in culture", Hypertension, 1998, (6):1240-1247.

Barilli et al., "Structural and Hemodynamic Changes of the Right Ventricle in PH-HFpEF", Int J Mol Sci, 2022, 23(9):4554, pp. 1-12.

Bathgate et al., "The relaxin receptor as a therapeutic target—perspectives from evolution and drug targeting", Pharmacology & Therapeutics, 2018, 187:114-132.

Beck, "RELAX-AHF-2 Results on Serelaxin in Acute Heart Failure Published", Medscape, Aug. 21, 2019 (retrieved Mar. 3, 2023), pp. 1-2.

Belyavskiy et al., "Phosphodiesterase 5 inhibitor sildenafil in patients with heart failure with preserved ejection fraction and combined pre- and postcapillary pulmonary hypertension: a randomized open-label pilot study", BMC Cardiovasc Disord, 2020, 20(1):408, pp. 1-15.

Bogzil et al., "Relaxin-induced changes in renal sodium excretion in the anesthetized male rat", Am J Physiol Regul Integr Comp Physiol, 2005, 288:R322-R328.

Bumbaca et al., "Physiochemical and biochemical factors influencing the pharmacokinetics of antibody therapeutics", AAPS J, 2012, 14(3):554-558.

Chen et al., "The Pharmacokinetics of Recombinant Human Relaxin in Nonpregnant Women After Intravenous, Intravaginal, and Intracervical Administration", Pharmaceutical Research, 1993, 10(6):834-838.

Choi et al., "Interpretation of Non-Clinical Data for Prediction of Human Pharmacokinetic Parameters: In Vitro-In Vivo Extrapolation and Allometric Scaling", Pharmaceutics, 2019, 11(4):168, pp. 1-33.

Conrad and Shroff, "Effects of relaxin on arterial dilation, remodeling, and mechanical properties", Curr Hypertens Rep, 2011, 13(6):409-420.

Cortis, "Industry Perspectives: Reflections on how advances in computation and informatics can drive or significantly impact new classes of therapeutic products," Presentation at: CUP (Customers, Users, and Programmers) XXIII OpenEye Annual Meeting, Mar. 5-7, 2024, Santa Fe, New Mexico, USA, slides 1-46.

Dahlke et al., "Safety and tolerability of serelaxin, a recombinant human relaxin-2 in development for the treatment of acute heart failure, in healthy Japanese volunteers and a comparison of pharmacokinetics and pharmacodynamics in healthy Japanese and Caucasian populations", The Journal of Clinical Pharmacology, 2014, 55(4):415-422.

Delcroix et al., "Long-Term Outcome of Patients With Chronic Thromboembolic Pulmonary Hypertension: Results From an International Prospective Registry", Circulation, 2016, 133(9):859-871.

Dschietzig et al., "First Clinical Experience with Intravenous Recombinant Human Relaxin in Compensated Heart Failure", Annals of the New York Academy of Sciences, 2009, 1160:387-392.

Dschietzig et al., "Relaxin, a pregnancy hormone, is a functional endothelin-1 antagonist: attenuation of endothelin-1-mediated vasoconstriction by stimulation of endothelin type-B receptor expression via ERK-1/2 and nuclear factor-kappaB", Circ Res, 2003, 92(1):32-40.

Duarte et al., "Endothelial nitric oxide synthase genotype is associated with pulmonary hypertension severity in left heart failure patients", Pulm Circ, 2018, 8(2):2045894018773049, pp. 1-8.

Erlandson et al., "Engineering and characterization of a long half-life relaxin receptor RXFP1 agonist", bioRxiv, Apr. 19, 2022, pp. 1-23.

Erlandson et al., "The relaxin receptor RXFP1 signals through a mechanism of autoinhibition", bioRxiv, Jan. 2022, pp. 1-36.

Erlandson et al., "The relaxin receptor RXFP1 signals through a mechanism of autoinhibition", Nat Chem. Biol, 2023, 19(8):1013-1021.

EU Clinical Trials Register, EUCT No. 2023-508969-32-00, titled, "A single-dose, open-label study of TX000045 in patients with CpcPH or IpcPH and HFpEF", authorized on Apr. 4, 2024 (record retrieved on Jul. 11, 2024), pp. 1-10.

Failli et al., "Relaxin up-regulates inducible nitric oxide synthase expression and nitric oxide generation in rat coronary endothelial cells", FASEB J, 2002, 16(2):252-254.

Galiè et al., "2015 ESC/ERS Guidelines for the diagnosis and treatment of pulmonary hypertension: The Joint Task Force for the Diagnosis and Treatment of Pulmonary Hypertension of the European Society of Cardiology (ESC) and the European Respiratory Society (ERS): Endorsed by: Association for European Paediatric and Congenital Cardiology (AEPC), International Society for Heart and Lung Transplantation (ISHLT)", Eur Heart J, 2016, 37(1):67-119.

Genbank Accession No. 2MV1_B, "Chain B, Relaxin B Chain", National Center for Biotechnology Information, Retrieved from: https://www.ncbi.nlm.nih.gov/protein/753536198/, Dec. 1, 2020, 1 page.

Genbank Accession No. 4CDH_A, "Chain A, IG GAMMA-1 Chain C Region", National Center for Biotechnology Information, Retrieved from: https://www.ncbi.nlm.nih.gov/protein/4CDH_A, Dec. 1, 2020, pp. 1-3.

Genbank Accession No. AEO21920.1, "Immunoglobulin heavy chain constant region G1m17, 1,I422, partial [Homo sapiens]", National Center for Biotechnology Information, Retrieved from: https://www.ncbi.nlm.nih.gov/protein/AE021920.1, Jul. 25, 2016, pp. 1-3.

Genbank Accession No. CAA81742.1, "Relaxin precursor, partial [Gorilla gorilla]", National Center for Biotechnology Information, Retrieved from: https://www.ncbi.nlm.nih.gov/protein/753536198/, Jul. 26, 2016, 1 page.

Ghofrani et al., "Riociguat for the treatment of chronic thromboembolic pulmonary hypertension", N Engl J Med, 2013, 369(4):319-29.

Heeg et al., "The antifibrotic effects of relaxin in human renal fibroblasts are mediated in part by inhibition of the Smad2 pathway", Kidney Int, 2005, 68(1):96-109.

Hoeper et al., "Pulmonary hypertension in heart failure with preserved ejection fraction: a plea for proper phenotyping and further research", Eur Heart J, 2016 (Epub), 38(38):2869-2873.

Hossain et al., "The Minimal Active Structure of Human Relaxin-2", The Journal of Biological Chemistry, 2011, 286(43): 37555-37565.

Hsu and Tedford, "Will we be singing a different tune on combined post- and pre-capillary pulmonary hypertension?", Eur Respir J, 2018, 51:1702589, pp. 1-3.

Humbert et al., "2022 ESC/ERS Guidelines for the diagnosis and treatment of pulmonary hypertension", European Heart Journal, 2022, 43(38):3618-3731.

Humbert et al., "Sotatercept for the Treatment of Pulmonary Arterial Hypertension", N Engl J Med, 2021, 384(13):1204-1215.

(56) References Cited

OTHER PUBLICATIONS

Ibe et al., "Combined pre- and post-capillary pulmonary hypertension: The clinical implications for patients with heart failure", PLoS One, 2021, 16(3):e0247987, pp. 1-14.
Igawa et al., "Reduced elimination of IgG antibodies by engineering the variable region", Protein Eng Des Sel, 2010, 23(5):385-392.
Jang et al., "Pulmonary Hypertension in Heart Failure," Int J Heart Fail, 2021, 3(3):147-159.
Jelinic et al., "Peptide hormone relaxin: from bench to bedside", Am J Physiol Regul Integr Comp Physiol, 2018 (Epub), 314(6):R753-R760.
Kamath, "Translational pharmacokinetics and pharmacodynamics of monoclonal antibodies", Drug Discov Today Technol, 2016, 21-22:75-83.
Kapelios et al., "Epidemiology, Clinical Characteristics and Cause-specific Outcomes in Heart Failure with Preserved Ejection Fraction", Card Fail Rev, 2023, 9:e14, pp. 1-11.
Khanna et al., "Recombinant Human Relaxin in the Treatment of Systemic Sclerosis With Diffuse Cutaneous Involvement: A Randomized, Double-Blind, Placebo-Controlled Trial", Arthritis & Rheumatism, 2009, 60(4):1102-1111.
Kim et al., "Biased Relaxin-RXFP1 Agonist ML290 Attenuates the Development of Pulmonary Hypertension", Poster session presented at: Dartmouth Geisel School of Medicine, Feb. 1, 2022, Hanover, New Hampshire, USA.
Kraft et al., "Heparin chromatography as an in vitro predictor for antibody clearance rate through pinocytosis", MAbs, 2020, 12(1):1683432.
Lang et al., "Chronic Thromboembolic Disease and Chronic Thromboembolic Pulmonary Hypertension", Clin Chest Med, 2021, 42(1):81-90.
Lapinskas et al., "Serelaxin Improves Regional Myocardial Function in Experimental Heart Failure: An In Vivo Cardiac Magnetic Resonance Study", J Am Heart Assoc, 2020 (Epub), 9(3):e013702, pp. 1-12.
Leo et al., "Vascular actions of relaxin: nitric oxide and beyond", British Journal of Pharmacology, 2017, 174(10):1002-1014.
Li et al., "Framework selection can influence pharmacokinetics of a humanized therapeutic antibody through differences in molecule charge", MAbs, 2014, 6(5):1255-1264.
Liu, "Pharmacokinetics of monoclonal antibodies and Fc-fusion proteins", Protein Cell, 2018, 9(1):15-32.
Lteif et al., "Therapeutic Challenges and Emerging Treatment Targets for Pulmonary Hypertension in Left Heart Disease", J Am Heart Assoc, 2021, 10(11):e020633, pp. 1-19.
Madani et al., "Pulmonary endarterectomy: recent changes in a single institution's experience of more than 2,700 patients", Ann Thorac Surg, 2012, 94(1):97-103, discussion 103.
Maggioni et al., "Efficacy and safety of serelaxin when added to standard of care in patients with acute heart failure: results from a PROBE study, RELAX-AHF-EU", Eur J Heart Fail, 2019, 21(3):322-333.
Mandras et al., "Pulmonary Hypertension: A Brief Guide for Clinicians", Mayo Clin Proc, 2020, 95(9):1978-1988.
Maron et al., "Cardiopulmonary Hemodynamics in Pulmonary Hypertension and Heart Failure: JACC Review Topic of the Week", J Am Coll Car diol, 2020, 76(22):2671-2681.
Martin et al., "Relaxin Inhibits Ventricular Arrhythmia and Asystole in Rats With Pulmonary Arterial Hypertension", Frontiers in Cardiovascular Medicine, Jul. 2021, 8:668222, pp. 1-11.
Martin et al., "Relaxin reverses inflammatory and immune signals in aged hearts", PLoS One, 2018, 13(1):e0190935, pp. 1-17.
McNamara, "Discovery & Optimization of Novel GPCR Biologics", Presentation at: 3rd GPCRs Targeted Drug Discovery Summit, Mar. 7, 2024, Boston, Massachussetts, USA, slides 1-31.
McNamara, "Discovery of a long-acting RXFP1 agonist for cardiorenal disease", Presentation at: Discovery on Target, Sep. 28, 2023, Boston, Massachussetts, USA, slides 1-22.
Metra et al., "Effects of Serelaxin in Patients with Acute Heart Failure", N Engl J Med, 2019, 381(8):716-726.
Moles and Grafton, "Pulmonary Hypertension in Heart Failure with Preserved Ejection Fraction", Cardiol Clin, 2022, 40(4):533-540.
Moore et al., "Diverse Regulation of Cardiac Expression of Relaxin Receptor by alpha1- and beta1-Adrenoceptors", Cardiovasc Drugs Ther, 2014, 28(3):221-228.
Nogueira-Ferreira et al., "Exploring the monocrotaline animal model for the study of pulmonary arterial hypertension: A network approach", Pulmonary Pharmacology & Therapeutics, 2015, 35:8-16.
Palazzini et al., "Pulmonary hypertension due to left heart disease: analysis of survival according to the haemodynamic classification of the 2015 ESC/ERS guidelines and insights for future changes", Eur J Heart Fail, 2017 (Epub), 20(2):248-255.
Pinar et al., "Relaxin Can Mediate Its Anti-Fibrotic Effects by Targeting the Myofibroblast NLRP3 Inflammasome at the Level of Caspase-1", Front Pharmacol, 2020, 11:1201, pp. 1-14.
Ponikowski et al., "A randomized, double-blind, placebo-controlled, multicentre study to assess haemodynamic effects of serelaxin in patients with acute heart failure", European Heart Journal, 2014, 35(7):431-441.
Ranchoux et al., "Metabolic Syndrome Exacerbates Pulmonary Hypertension due to Left Heart Disease", Circ Res, 2019, 125(4):449-466.
Samuel et al., "Relaxin regulates collagen overproduction associated with experimental progressive renal fibrosis", Ann N Y Acad Sci, 2005, 1041:182-184.
Samuel et al., "The Relaxin Gene-Knockout Mouse: A Model of Progressive Fibrosis", Ann N Y Acad Sci, 2005, 1041(1):173-181.
Samuel et al., "Relaxin modulates cardiac fibroblast proliferation, differentiation, and collagen production and reverses cardiac fibrosis in vivo", Endocrinology, May 2004 (Epub), 145(9):4125-4133.
Samuel et al., "Serelaxin is a more efficacious antifibrotic than enalapril in an experimental model of heart disease", Hypertension, 2014, 64(2):315-322.
Sato et al., "Evaluating the Efficacy, Safety, and Tolerability of Serelaxin When Added to Standard Therapy in Asian Patients With Acute Heart Failure: Design and Rationale of RELAX-AHF-ASIA Trial", J Card Fail, 2017, 23(1):63-71.
Satoh et al., "Metabolic Syndrome Mediates ROS-miR-193b-NFYA-Dependent Downregulation of Soluble Guanylate Cyclase and Contributes to Exercise-Induced Pulmonary Hypertension in Heart Failure With Preserved Ejection Fraction", Circulation, 2021, 144(8):615-637.
Schiffner et al., "Effects of human relaxin-2 (serelaxin) on hypoxic pulmonary vasoconstriction during acute hypoxia in a sheep model", Hypoxia, 2018, 6:11-22.
Shuai et al., "Relaxin-2 improves diastolic function of pressure-overloaded rats via phospholamban by activating Akt", Int J Cardiol, 2016, 218:305-311.
Snowdon et al., "Serelaxin as a potential treatment for renal dysfunction in cirrhosis: Preclinical evaluation and results of a randomized phase 2 trial", PLoS Med, 2017, 14(2):e1002248, pp. 1-29.
Sun et al., "Human Relaxin-2 Fusion Protein Treatment Prevents and Reverses Isoproterenol-Induced Hypertrophy and Fibrosis in Mouse Heart", J Am Heart Assoc, 2019, 8(24):e013465, pp. 1-16.
Tectonic Therapeutic and AVROBIO, "Transforming the Discovery of Novel GPCR-Targeted Therapies", Jan. 2024, slides 1-33.
Tectonic Therapeutic and AVROBIO, "Transforming the Discovery of Novel GPCR-Targeted Therapies", Apr. 2024, slides 1-33.
Tectonic Therapeutic, "Corporate Overview", Dec. 2023, slides 1-40.
Tectonic Therapeutic, "Corporate Presentation", Apr. 2021, slides 1-10.
Tectonic Therapeutic, "Corporate Presentation", Feb. 2023, slides 1-31.
Tectonic Therapeutic, "Corporate Presentation", Jan. 2022, slides 1-21.
Tectonic Therapeutic, "Corporate Presentation", Jan. 2023, slides 1-16.
Tectonic Therapeutic, "Corporate Presentation", Sep. 2022, slides 1-23.

(56) References Cited

OTHER PUBLICATIONS

Tectonic Therapeutic, "GEODe(TM) Platform: Proprietary, validated platform that enables reproducible discovery of GPCR targeted biologics", Presentation at: PEGS Europe, Nov. 16, 2022, Barcelona, Spain, slides 1-18.

Tectonic Therapeutic, "Form S-4/A", Edgar, Securities and Exchange Commission, Mar. 26, 2024, pp. 1-872.

Tectonic Therapeutic, "Tectonic Therapeutic: Corporate Overview", Jan. 2024, slides 1-26.

Tectonic Therapeutic, "Transforming the Discovery of GPCR-Targeted Therapies", Jan. 2023, slides 1-20.

Tectonic Therapeutic, "Transforming the Discovery of GPCR-Targeted Therapies", Nov. 2022, slides 1-29.

Tectonic Therapeutic, "Transforming the Discovery of GPCR-Targeted Therapies", Presentation at: 2nd GPCRs Targeted Drug Discovery Summit, Feb. 23, 2023, Boston, Massachussetts, USA, slides 1-23.

Teerlink et al., "Effects of serelaxin in patients admitted for acute heart failure: A meta-analysis", European Journal of Heart Failure, 2020, 22(2):315-329.

Teerlink et al., "Serelaxin, recombinant human relaxin-2, for treatment of acute heart failure (RELAX-AHF): A randomised, placebo-controlled trial", Lancet, 2013, 381(9860):29-39.

Thenappan et al., "Clinical Characteristics of Pulmonary Hypertension in Patients With Heart Failure and Preserved Ejection Fraction", Circ Heart Fail, 2011 (Epub), 4(3):257-265.

Thenappan, "Pulmonary Hypertension Due to Left Heart Disease-Combine or Not Combined? DPG In or Out? A Practical Approach to the Patient With Suspected Left Heart Disease", Advances in Pulmonary Hypertension, 2019, 18(3):87-91.

Tozzi et al., "Recombinant human relaxin reduces hypoxic pulmonary hypertension in the rat", Pulmonary Pharmacology & Therapeutics, 2005, 18(5):346-353.

Ufnal et al., "Safety, pharmacokinetics, and pharmacodynamics of AZD3427, a functionally selective long-acting relaxin mimetic agonist of the RXFP1 receptor", Poster session presented at: European Society of Cardiology—Heart Failure, 2023, Prague, Czechia.

UniProt Accession No. Q16317, "Hypothetical protein", National Center for Biotechnology Information, Oct. 31, 2006, 1 page.

Vachiery et al., "Pulmonary hypertension due to left heart disease", Eur Respir J, 2019, 53(1):1801897, pp. 1-12.

Vasilenko et al., "Growth-Promoting Effects of Relaxin and Related Compositional Changes in the Uterus, Cervix, and Vagina of the Rat", Endocrinology, 1987, 120(4):1370-1376.

Vasilenko et al., "Uterine Growth-Promoting Effects of Relaxin: A Morphometric and Histological Analysis", Biology of Reproduction, 1986, 35(4):987-995.

Verdino et al., "Development of a long-acting relaxin analogue, LY3540378, for treatment of chronic heart failure", Br J Pharmacol, 2023, 180(15):1965-1980.

Wang et al., "Long-acting relaxin (LY3540378) demonstrated an improved renal hemodynamic responses in preclinical and clinical studies", Poster session presented at: European Society of Cardiology—Heart Failure, 2023, Prague, Czechia.

Wilhelmi et al., "Serelaxin alleviates cardiac fibrosis through inhibiting endothelial-to-mesenchymal transition via RXFP1", Theranostics, 2020, 10(9):3905-3924.

Wu et al., "The role of inflammation in a rat model of chronic thromboembolic pulmonary hypertension induced by carrageenan", Ann Transl Med, 2020, 8(7):492, pp. 1-14.

Yang et al., "Abstract 16068: Biased Relaxin-RXFP1 Agonist ML290 Attenuates the Development of Pulmonary Hypertension", Circulation, 2019, 140(Suppl_1):A16068, 1 page.

Yang et al., "ML290, an Allosteric Relaxin-RXFP1 Agonist, Attenuates Experimental Pulmonary Hypertension", Am J Respir Crit Care Med, 2018, 197:A4626, 1 page.

Yung et al., "ML290, an Allosteric Agonist of RXFP1, Attenuates Experimental Pulmonary Hypertension", Circulation, 2018, 138(suppl1): Abstract 16555, pp. 1-3.

Ahmad et al., "Heart Failure with Preserved Ejection Fraction: Many Emperors with Many Clothes," JACC: Heart Failure. 2020;8(3):185-187.

Bartsch et al., "Phosphodiesterase 4 Inhibition Synergizes with Relaxin Signaling to Promote Decidualization of Human Endometrial Stromal Cells," The Journal of Clinical Endocrinology & Metabolism. 2004;89(1):324-334.

Committee for Medicinal Products for Human Use (CHMP), "Reasanz: European Public Assessment Report," European Medicines Agency, EMA/303748/2014, 2014;1-112.

Connolly et al., "Novel Relaxin Receptor RXFP1 Agonist AZD3427 in the Treatment of Heart Failure: A Phase 1a/b, First-in-Human, Randomized, Single-Blind, Placebo-Controlled Study," J Am Heart Assoc. 2024;13:e034067:1-12. DOI: 10.1161/JAHA.123.034067.

Dachs et al., "Riociguat in Pulmonary Hypertension and Heart Failure with Preserved Ejection Fraction: the haemoDYNAMIC trial," European Heart Journal. 2022;43:3402-3413.

Del Buono et al., "Primary and Secondary Diastolic Dysfunction in Heart Failure with Preserved Ejection Fraction," The American Journal of Cardiology. 2018;00:1-10.

Dschietzig and Salama, "Relaxin-2 for heart failure with preserved ejection fraction: a comment on the termination of a phase-II trial investigating the relaxin-2 analogue, LY3540378," Global Cardiology. 2024;4:1-3.

Garcia-Morales et al., "The CAMP effectors PKA and Epac activate endothelial NO synthase through PI3K/Akt pathway in human endothelial cells," Biochemical Pharmacology. 2017;145:94-101.

Guazzi et al., "Pulmonary Hypertension in Heart Failure With Preserved Ejection Fraction: A Target of Phosphodiesterase-5 Inhibition in a 1-Year Study," Circulation. 2011;124:164-174.

Hisaw, "Experimental relaxation of the pubic ligament of the guinea pig," Proceedings of the Society for Experimental Biology and Medicine. 1926;23(8):661-663.

Huang et al., "Activation of Relaxin Family Receptor 1 from Different Mammalian Species by Relaxin Peptide and Small-Molecule agonist ML290," Frontiers in Endocrinology. 2015;6(128)1-12.

Matos, "International Search Report and Written Opinion for PCT Patent Application No. PCT/US2024/030016," Nov. 25, 2024;1-13.

Mease et al., "Biomarkers for nonclinical infusion reactions in marketed biotherapeutics and considerations for study design," Current Opinion in Toxicology. 2017;4:1-15.

Ogawa and Ono, "Modulation of cyclic AMP and autoregulation of renal blood flow, analysed by the use of forskolin and 1-methyl-3-isobutylxanthine," J. Pharm. Pharmacol. 1988;40:207-209.

Pfeffer et al., "Heart Failure with Preserved Ejection Fraction: In Perspective," Circ. Res. 2019;124:1598-1617.

Rodriquez, "International Search Report and Written Opinion for PCT Patent Application No. PCT/US2021/031260," Jan. 13, 2022;1-12.

Rojko et al., "Formation, Clearance, Deposition, Pathogenicity, and Identification of Biopharmaceutical-related Immune Complexes: Review and Case Studies," Toxicol Pathol. 2014;42(4):725-764.

Shah and Pfeffer, "The many faces of heart failure with preserved ejection fraction," Nat. Rev. Cardiol. Advance online publication 2012;1-2.

Tham et al., "Volenrelaxin (LY3540378) increases renal plasma flow: a randomized Phase 1 trial," Nephrol Dial Transplant. 2024;0:1-14.

Thomas, "International Search Report and Written Opinion for PCT Patent Application No. PCT/US2022/079681," May 23, 2023;1-13.

Wang, "Long-acting relaxin (LY3540378) demonstrates improved renal hemodynamics response in preclinical and clinical studies," Abstracts of the Heart Failure 2023 and the World Congress on Acute Heart Failure, Prague, Czechia. Eur J Heart Fail. 2023;25(S2):168.

RELAXIN-2 FUSION PROTEINS

RELATED APPLICATIONS

This application is a U.S. bypass continuation of PCT/US2024/030016, filed May 17, 2024, which claims priority to U.S. Provisional Patent Application Ser. Nos. 63/503,101, filed May 18, 2023, 63/585,849, filed Sep. 27, 2023, 63/586,868, filed Sep. 29, 2023, 63/611,732, filed Dec. 18, 2023, and 63/617,398, filed Jan. 3, 2024, the entire disclosures of which are hereby incorporated by reference herein.

REFERENCE TO SEQUENCE LISTING

This application contains a sequence listing which has been submitted electronically in XML format and is hereby incorporated by reference in its entirety (said XML copy, created Aug. 9, 2024, is named "209591_seqlist.xml" and is 728,176 bytes in size).

BACKGROUND

Relaxin-2 exhibits strong antifibrotic activity. In injured tissues, fibroblast activation and proliferation cause increased collagen production and interstitial fibrosis. Fibrosis in the heart is increased by biomechanical overload, and influences ventricular dysfunction, remodeling, and arrhythmogenesis. However, due to the limited in vivo half-life of relaxin, compound administration has to be performed as a continuous infusion for at least 48 hours. Further, the synthesis of relaxin-2 is difficult. Due to the low solubility of the B-chain and the requirement for the laborious, specific introduction of cysteine bridges between the A and B-chains, yields of active peptide obtained by these methods are extremely low.

There is a need for an engineered relaxin-2 analog with greater half-life and greater ease in production.

SUMMARY

This disclosure provides fusion proteins that are engineered relaxin-2 analogs with improved pharmacokinetic properties. This disclosure also provides methods of using these fusion proteins to enhance relaxin-2 related activity in a subject and to treat or prevent relaxin-2 related diseases. The structure of the fusion proteins described herein is based, at least in part, upon the surprising discovery that reducing the isoelectric point (pI) of relaxin-2 fusion protein analogs increases their circulating half-life and improves their pharmacokinetic and pharmacodynamic properties.

Accordingly, in one aspect, the present disclosure provides a fusion protein comprising, from N-terminus to C-terminus, a first peptide; a linker peptide; and a second peptide, wherein: (a) the first peptide comprises an amino acid sequence that has 0, 1, 2, 3, 4, or 5 amino acid modifications relative to the amino acid sequence of SEQ ID NO: 502 and the second peptide comprises an amino acid sequence that that has 0, 1, 2, 3, 4, or 5 amino acid modifications relative to the amino acid sequence of SEQ ID NO: 503 or 504; or the first peptide comprises an amino acid sequence that has 0, 1, 2, 3, 4, or 5 amino acid modifications relative to the amino acid sequence of SEQ ID NO: 503 or 504 and the second peptide comprises an amino acid sequence that that has 0, 1, 2, 3, 4, or 5 amino acid modifications relative to the amino acid sequence of SEQ ID NO: 502; and optionally, (b) the fusion protein has a pI from 6.0 to 8.2.

In some embodiments, the fusion protein has a pI from about 6.0 to about 9.4. In some embodiments, the fusion protein has a pI from about 6.0 to about 8.2. In some embodiments, the fusion protein has a pI that is less than about 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, or 6.1. In some embodiments, the fusion protein has a pI that is less than 9.0. In some embodiments, the fusion protein has a pI that is less than about 8.2. In some embodiments, the fusion protein has a pI of about 6.8. In some embodiments, the fusion protein has a pI of about 7.0. In some embodiments, the fusion protein has a pI of about 7.1. In some embodiments, the fusion protein has a pI of about 7.4. In some embodiments, the fusion protein has a pI of about 7.5. In some embodiments, the fusion protein has a pI of about 7.9. In some embodiments, the fusion protein has a pI of about 8.0. In some embodiments, the fusion protein has a pI of about 8.4. In some embodiments, the fusion protein has a pI of about 8.5. In some embodiments, the fusion protein has a pI of about 8.8. In some embodiments, the fusion protein has a pI of about 8.9.

In some embodiments, the first peptide comprises the amino acid sequence $X_{11}$LCGRELVRAQIAIC (SEQ ID NO: 505), wherein $X_{11}$ is K, Q, D, E, L, I or Y. In some embodiments, the first peptide consists of 15, 16, 17, 18, 19, 20, 21, 22, 23, 24, 25, 26, 27, 28, or 29 amino acids.

In some embodiments, the first peptide comprises the amino acid sequence $X_{12}CCX_{13}VGCTX_{14}X_{15}SLAX_{16}FC$ (SEQ ID NO: 506), wherein: $X_{12}$ is K, Q, D, E, L, I, or Y; $X_{13}$ is any amino acid except M, W, or C; $X_{14}$ is K, Q, D, E, L, I, or Y; $X_{15}$ is Q, D, E, L, I, Y or R; and $X_{16}$ is R or Q. In some embodiments, the first peptide comprises the amino acid sequence $X_{12}CCX_{13}VGCTX_{14}X_{15}SLAX_{16}FC$ (SEQ ID NO: 506), wherein: $X_{12}$ is K, Q, D, E, L, I, or Y; $X_{13}$ is H, K, Q, Y, L, N, I, S, T, or F; $X_{14}$ is K, Q, D, E, L, I, or Y; $X_{15}$ is Q, D, E, L, I, Y or R; and $X_{16}$ is R or Q. In some embodiments, $X_{13}$ is Q. In some embodiments, the first peptide consists of 16, 17, 18, 19, 20, 21, 22, 23, 24, or 25 amino acids.

In some embodiments, the second peptide comprises the amino acid sequence $X_{11}$LCGRELVRAQIAIC (SEQ ID NO: 505), wherein $X_{11}$ is K, Q, D, E, L, I or Y. In some embodiments, the second peptide consists of 15, 16, 17, 18, 19, 20, 21, 22, 23, 24, 25, 26, 27, 28, or 29 amino acids.

In some embodiments, the second peptide comprises the amino acid sequence $X_{12}CCX_{13}VGCTX_{14}X_{15}SLAX_{16}FC$ (SEQ ID NO: 506), wherein: $X_{12}$ is K, Q, D, E, L, I, or Y; $X_{13}$ is any amino acid except M, W, or C; $X_{14}$ is K, Q, D, E, L, I, or Y; $X_{15}$ is Q, D, E, L, I, Y or R; and $X_{16}$ is R or Q. In some embodiments, the second peptide comprises the amino acid sequence $X_{12}CCX_{13}VGCTX_{14}X_{15}SLAX_{16}FC$ (SEQ ID NO: 506), wherein: $X_{12}$ is K, Q, D, E, L, I, or Y; $X_{13}$ is H, K, Q, Y, L, N, I, S, T, or F; $X_{14}$ is K, Q, D, E, L, I, or Y; $X_{15}$ is Q, D, E, L, I, Y or R; and $X_{16}$ is R or Q. In some embodiments, $X_{13}$ is Q. In some embodiments, the second peptide consists of 16, 17, 18, 19, 20, 21, 22, 23, 24, or 25 amino acids.

In some embodiments, the linker peptide comprises an amino acid sequence with 12-15 amino acids. In some embodiments, the linker peptide comprises the amino acid sequence ASDAAGAX$_8$AX$_9$AGA (SEQ ID NO: 17), wherein: $X_8$ is D, E, N, or Q; and $X_9$ is D, E, N, or Q; or the linker peptide comprises the amino acid sequence GGEGSGGEGX$_{10}$GGG (SEQ ID NO: 25), wherein: $X_{10}$ is E or S. In some embodiments, $X_8$ is D, E, N, or Q, and $X_9$ is D, E, or Q; or $X_8$ is D, E, or Q, and $X_9$ is D, E, N, or Q. In some embodiments, the linker peptide comprises an amino acid sequence selected from the group consisting of SEQ ID NOs: 18, 19, 20, 21, 22, 23, 24, 26, and 27.

In another aspect, the present disclosure provides a fusion protein comprising, from N-terminus to C-terminus, a first peptide; a linker peptide; and a second peptide, wherein: (a) the first peptide comprises an amino acid sequence that has 0, 1, 2, 3, 4, or 5 amino acid modifications relative to the amino acid sequence of SEQ ID NO: 1, wherein the amino acid at at least one of positions 4 or 25 of the first peptide is not M; and the second peptide comprises an amino acid sequence that has 0, 1, 2, 3, 4, or 5 amino acid modifications relative to the amino acid sequence of SEQ ID NO: 8, wherein the amino acid at position 22 of the second peptide is not R; or the first peptide comprises an amino acid sequence that has 0, 1, 2, 3, 4, or 5 amino acid modifications relative to the amino acid sequence of SEQ ID NO: 8, wherein the amino acid at position 22 of the second peptide is not R; and the second peptide comprises an amino acid sequence that has 0, 1, 2, 3, 4, or 5 amino acid modifications relative to the amino acid sequence of SEQ ID NO: 1, wherein the amino acid at at least one of positions 4 or 25 of the first peptide is not M; and optionally, (b) the fusion protein has a pI from 6.0 to 8.2.

In some embodiments, the fusion protein has a pI from about 6.0 to about 9.4. In some embodiments, the fusion protein has a pI from about 6.0 to about 8.2. In some embodiments, the fusion protein has a pI that is less than about 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, or 6.1. In some embodiments, the fusion protein has a pI that is less than 9.0. In some embodiments, the fusion protein has a pI that is less than about 8.2. In some embodiments, the fusion protein has a pI of about 6.8. In some embodiments, the fusion protein has a pI of about 7.0. In some embodiments, the fusion protein has a pI of about 7.1. In some embodiments, the fusion protein has a pI of about 7.4. In some embodiments, the fusion protein has a pI of about 7.5. In some embodiments, the fusion protein has a pI of about 7.9. In some embodiments, the fusion protein has a pI of about 8.0. In some embodiments, the fusion protein has a pI of about 8.4. In some embodiments, the fusion protein has a pI of about 8.5. In some embodiments, the fusion protein has a pI of about 8.8. In some embodiments, the fusion protein has a pI of about 8.9.

In some embodiments, the linker peptide comprises an amino acid sequence with 12-15 amino acids. In some embodiments, the linker peptide comprises the amino acid sequence ASDAAGAXSAX$_9$AGA (SEQ ID NO: 17), wherein: X$_8$ is D, E, N, or Q; and X$_9$ is D, E, N, or Q; or the linker peptide comprises the amino acid sequence GGEGSGGEGX$_{10}$GGG (SEQ ID NO: 25), wherein: X$_{10}$ is E or S. In some embodiments, X$_8$ is D, E, N, or Q, and X$_9$ is D, E, or Q; or X$_8$ is D, E, or Q, and X$_9$ is D, E, N, or Q.

In another aspect, the present disclosure provides a fusion protein comprising, from N-terminus to C-terminus: a first peptide; a linker peptide; and a second peptide, wherein: the linker peptide comprises the amino acid sequence ASDAAGAXSAX$_9$AGA (SEQ ID NO: 17), wherein: X$_8$ is D, E, N, or Q; and X$_9$ is D, E, N, or Q; or the linker peptide comprises the amino acid sequence GGEGSGGEGX$_{10}$GGG (SEQ ID NO: 25), wherein: X$_{10}$ is E or S. In some embodiments, the linker peptide comprises an amino acid sequence selected from the group consisting of SEQ ID NOs: 18, 19, 20, 21, 22, 23, 24, 26, and 27.

In some embodiments, the first peptide comprises the amino acid sequence DSX$_1$QEEVIX$_2$LCGRELVRAQIAICGX$_3$ST (SEQ ID NO: 7), wherein: X$_1$ is not M, H, or C; X$_2$ is K, Q, D, E, L, I or Y; and X$_3$ is K or Q. In some embodiments, the first peptide comprises the amino acid sequence DSX$_1$QEEVIX$_2$LCGRELVRAQIAICGX$_3$ST (SEQ ID NO: 7), wherein: X$_1$ is W, Y, F, L, I, V or A; X$_2$ is K, Q, D, E, L, I or Y; and X$_3$ is K or Q. In some embodiments, X$_1$ is Y. In some embodiments, the first peptide comprises an amino acid sequence selected from the group consisting of SEQ ID NOs: 1, 2, 3, 4, 5, and 6. In some embodiments, the first peptide consists of 27, 28, or 29 amino acids.

In some embodiments, the first peptide comprises the amino acid sequence QLYSALANX$_4$CCX$_5$VGCTX$_6$X$_7$SLAQFC (SEQ ID NO: 16), wherein: X$_4$ is K, Q, D, E, L, I, or Y; X$_5$ is any amino acid except M, W, or C; X$_6$ is K, Q, D, E, L, I, or Y; and X$_7$ is Q, D, E, L, I, Y or R. In some embodiments, the first peptide comprises the amino acid sequence QLYSALANX$_4$CCX$_5$VGCTX$_6$X$_7$SLAQFC (SEQ ID NO: 16), wherein: X$_4$ is K, Q, D, E, L, I, or Y; X$_5$ is H, K, Q, Y, L, N, I, S, T, or F; X$_6$ is K, Q, D, E, L, I, or Y; and X$_7$ is Q, D, E, L, I, Y or R. In some embodiments, X$_5$ is Q. In some embodiments, the first peptide comprises an amino acid sequence selected from the group consisting of SEQ ID NOs: 8, 9, 10, 11, 12, 13, 14, 15, and 507. In some embodiments, the first peptide consists of 24 or 25 amino acids.

In some embodiments, the second peptide comprises the amino acid sequence DSXIQEEVIX$_2$LCGRELVRAQIAICGX$_3$ST (SEQ ID NO: 7), wherein: X$_1$ is not M, H, or C; X$_2$ is K, Q, D, E, L, I or Y; and X$_3$ is K or Q. In some embodiments, the second peptide comprises the amino acid sequence DSX$_1$QEEVIX$_2$LCGRELVRAQIAICGX$_3$ST (SEQ ID NO: 7), wherein: X$_1$ is W, Y, F, L, I, V or A; X$_2$ is K, Q, D, E, L, I, or Y; and X$_3$ is K or Q. In some embodiments, X$_1$ is Y. In some embodiments, the second peptide comprises an amino acid sequence selected from the group consisting of SEQ ID NOs: 1, 2, 3, 4, 5, and 6. In some embodiments, the second peptide consists of 27, 28, or 29 amino acids.

In some embodiments, the second peptide comprises the amino acid sequence QLYSALANX$_4$CCX$_5$VGCTX$_6$X$_7$SLAQFC (SEQ ID NO: 16), wherein: X$_4$ is K, Q, D, E, L, I, or Y; X$_5$ is any amino acid except M, W, or C; X$_6$ is K, Q, D, E, L, I, or Y; and X$_7$ is Q, D, E, L, I, Y or R. In some embodiments, the second peptide comprises the amino acid sequence QLYSALANX$_4$CCX$_5$VGCTX$_6$X$_7$SLAQFC (SEQ ID NO: 16), wherein: X$_4$ is K, Q, D, E, L, I, or Y; X$_5$ is H, K, Q, Y, L, N, I, S, T, or F; X$_6$ is K, Q, D, E, L, I, or Y; and X$_7$ is Q, D, E, L, I, Y or R. In some embodiments, X$_5$ is Q. In some embodiments, the second peptide comprises an amino acid sequence selected from the group consisting of SEQ ID NOs: 8, 9, 10, 11, 12, 13, 14, 15, and 507. In some embodiments, the second peptide consists of 24 or 25 amino acids.

In some embodiments, the first peptide comprises the amino acid sequence of SEQ ID NO: 1 and the second peptide comprises the amino acid sequence of SEQ ID NO: 8; the first peptide comprises the amino acid sequence of SEQ ID NO: 1 and the second peptide comprises the amino acid sequence of SEQ ID NO: 9; the first peptide comprises the amino acid sequence of SEQ ID NO: 1 and the second peptide comprises the amino acid sequence of SEQ ID NO: 10; the first peptide comprises the amino acid sequence of SEQ ID NO: 1 and the second peptide comprises the amino acid sequence of SEQ ID NO: 11; the first peptide comprises the amino acid sequence of SEQ ID NO: 1 and the second peptide comprises the amino acid sequence of SEQ ID NO: 12; the first peptide comprises the amino acid sequence of SEQ ID NO: 1 and the second peptide comprises the amino acid sequence of SEQ ID NO: 13; the first peptide comprises the amino acid sequence of SEQ ID NO: 1 and the second peptide comprises the amino acid sequence of SEQ ID NO: 14; the first peptide comprises the amino acid sequence of SEQ ID NO: 1 and the second peptide comprises the amino acid sequence of SEQ ID NO: 15; the first peptide comprises the amino acid sequence of SEQ ID NO: 1 and the second peptide comprises the amino acid sequence of SEQ ID NO: 507; the first peptide comprises the amino acid sequence of SEQ ID NO: 2 and the second peptide comprises the amino acid sequence of SEQ ID NO: 8; the first peptide comprises the amino acid sequence of SEQ ID NO: 2 and the second peptide comprises the amino acid sequence of SEQ ID NO: 9; the first peptide comprises the amino acid sequence of SEQ ID NO: 2 and the second peptide comprises the amino acid sequence of SEQ ID NO: 10; the first peptide comprises the amino acid sequence of SEQ ID NO: 2 and the second peptide comprises the amino acid sequence of SEQ ID NO: 11; the first peptide comprises the amino acid sequence of SEQ ID NO: 2 and the second peptide comprises the amino acid sequence of SEQ ID NO: 12; the first peptide comprises the amino acid sequence of SEQ ID NO: 2 and the second peptide comprises the amino acid sequence of SEQ ID NO: 13; the first peptide comprises the amino acid sequence of SEQ ID NO: 2 and the second peptide comprises the amino acid sequence of SEQ ID NO: 14; the first peptide comprises the amino acid sequence of SEQ ID NO: 2 and the second peptide comprises the amino acid sequence of SEQ ID NO: 15; the first peptide comprises the amino acid sequence of SEQ ID NO: 2 and the second peptide comprises the amino acid sequence of SEQ ID NO: 507; the first peptide comprises the amino acid sequence of SEQ ID NO: 3 and the second peptide comprises the amino acid sequence of SEQ ID NO: 8; the first peptide comprises the amino acid sequence of SEQ ID NO: 3 and the second peptide comprises the amino acid sequence of SEQ ID NO: 9; the first peptide comprises the amino acid sequence of SEQ ID NO: 3 and the second peptide comprises the amino acid sequence of SEQ ID NO: 10; the first peptide comprises the amino acid sequence of SEQ ID NO: 3 and the second peptide comprises the amino acid sequence of SEQ ID NO: 11; the first peptide comprises the amino acid sequence of SEQ ID NO: 3 and the second peptide comprises the amino acid sequence of SEQ ID NO: 12; the first peptide comprises the amino acid sequence of SEQ ID NO: 3 and the second peptide comprises the amino acid sequence of SEQ ID NO: 13; the first peptide comprises the amino acid sequence of SEQ ID NO: 3 and the second peptide comprises the amino acid sequence of SEQ ID NO: 14; the first peptide comprises the amino acid sequence of SEQ ID NO: 3 and the second peptide comprises the amino acid sequence of SEQ ID NO: 15; the first peptide comprises the amino acid sequence of SEQ ID NO: 3 and the second peptide comprises the amino acid sequence of SEQ ID NO: 507; the first peptide comprises the amino acid sequence of SEQ ID NO: 4 and the second peptide comprises the amino acid sequence of SEQ ID NO: 8; the first peptide comprises the amino acid sequence of SEQ ID NO: 4 and the second peptide comprises the amino acid sequence of SEQ ID NO: 9; the first peptide comprises the amino acid sequence of SEQ ID NO: 4 and the second peptide comprises the amino acid sequence of SEQ ID NO: 10; the first peptide comprises the amino acid sequence of SEQ ID NO: 4 and the second peptide comprises the amino acid sequence of SEQ ID NO: 11; the first peptide comprises the amino acid sequence of SEQ ID NO: 4 and the second peptide comprises the amino acid sequence of SEQ ID NO: 12; the first peptide comprises the amino acid sequence of SEQ ID NO: 4 and the second peptide comprises the amino acid sequence of SEQ ID NO: 13; the first peptide comprises the amino acid sequence of SEQ ID NO: 4 and the second peptide comprises the amino acid sequence of SEQ ID NO: 14; the first peptide comprises the amino acid sequence of SEQ ID NO: 4 and the second peptide comprises the amino acid sequence of SEQ ID NO: 15; the first peptide comprises the amino acid sequence of SEQ ID NO: 4 and the second peptide comprises the amino acid sequence of SEQ ID NO: 507; the first peptide comprises the amino acid sequence of SEQ ID NO: 5 and the second peptide comprises the amino acid sequence of SEQ ID NO: 8; the first peptide comprises the amino acid sequence of SEQ ID NO: 5 and the second peptide comprises the amino acid sequence of SEQ ID NO: 9; the first peptide comprises the amino acid sequence of SEQ ID NO: 5 and the second peptide comprises the amino acid sequence of SEQ ID NO: 10; the first peptide comprises the amino acid sequence of SEQ ID NO: 5 and the second peptide comprises the amino acid sequence of SEQ ID NO: 11; the first peptide comprises the amino acid sequence of SEQ ID NO: 5 and the second peptide comprises the amino acid sequence of SEQ ID NO: 12; the first peptide comprises the amino acid sequence of SEQ ID NO: 5 and the second peptide comprises the amino acid sequence of SEQ ID NO: 13; the first peptide comprises the amino acid sequence of SEQ ID NO: 5 and the second peptide comprises the amino acid sequence of SEQ ID NO: 14; the first peptide comprises the amino acid sequence of SEQ ID NO: 5 and the second peptide comprises the amino acid sequence of SEQ ID NO: 15; the first peptide comprises the amino acid sequence of SEQ ID NO: 5 and the second peptide comprises the amino acid sequence of SEQ ID NO: 507; the first peptide comprises the amino acid sequence of SEQ ID NO: 6 and the second peptide comprises the amino acid sequence of SEQ ID NO: 8; the first peptide comprises the amino acid sequence of SEQ ID NO: 6 and the second peptide comprises the amino acid sequence of SEQ ID NO: 9; the first peptide comprises the amino acid sequence of SEQ ID NO: 6 and the second peptide comprises the amino acid sequence of SEQ ID NO: 10; the first peptide comprises the amino acid sequence of SEQ ID NO: 6 and the second peptide comprises the amino acid sequence of SEQ ID NO: 11; the first peptide comprises the amino acid sequence of SEQ ID NO: 6 and the second peptide comprises the amino acid sequence of SEQ ID NO: 12; the first peptide comprises the amino acid sequence of SEQ ID NO: 6 and the second peptide comprises the amino acid sequence of SEQ ID NO: 13; the first peptide comprises the amino acid sequence of SEQ ID NO: 6 and the second peptide comprises the amino acid sequence of SEQ ID NO: 14; the first peptide comprises the amino acid sequence of SEQ ID NO: 6 and the second peptide comprises the amino acid sequence of SEQ ID NO: 15; or the first peptide comprises the amino acid sequence of SEQ ID NO: 6 and the second peptide comprises the amino acid sequence of SEQ ID NO: 507.

In some embodiments, the first peptide comprises the amino acid sequence of SEQ ID NO: 8 and the second peptide comprises the amino acid sequence of SEQ ID NO: 1; the first peptide comprises the amino acid sequence of SEQ ID NO: 8 and the second peptide comprises the amino acid sequence of SEQ ID NO: 2; the first peptide comprises the amino acid sequence of SEQ ID NO: 8 and the second peptide comprises the amino acid sequence of SEQ ID NO: 3; the first peptide comprises the amino acid sequence of SEQ ID NO: 8 and the second peptide comprises the amino acid sequence of SEQ ID NO: 4; the first peptide comprises the amino acid sequence of SEQ ID NO: 8 and the second peptide comprises the amino acid sequence of SEQ ID NO: 5; the first peptide comprises the amino acid sequence of SEQ ID NO: 8 and the second peptide comprises the amino acid sequence of SEQ ID NO: 6; the first peptide comprises the amino acid sequence of SEQ ID NO: 9 and the second peptide comprises the amino acid sequence of SEQ ID NO: 1; the first peptide comprises the amino acid sequence of SEQ ID NO: 9 and the second peptide comprises the amino acid sequence of SEQ ID NO: 2; the first peptide comprises the amino acid sequence of SEQ ID NO: 9 and the second peptide comprises the amino acid sequence of SEQ ID NO: 3; the first peptide comprises the amino acid sequence of SEQ ID NO: 9 and the second peptide comprises the amino acid sequence of SEQ ID NO: 4; the first peptide comprises the amino acid sequence of SEQ ID NO: 9 and the second peptide comprises the amino acid sequence of SEQ ID NO: 5; the first peptide comprises the amino acid sequence of SEQ ID NO: 9 and the second peptide comprises the amino acid sequence of SEQ ID NO: 6; the first peptide comprises the amino acid sequence of SEQ ID NO: 10 and the second peptide comprises the amino acid sequence of SEQ ID NO: 1; the first peptide comprises the amino acid sequence of SEQ ID NO: 10 and the second peptide comprises the amino acid sequence of SEQ ID NO: 2; the first peptide comprises the amino acid sequence of SEQ ID NO: 10 and the second peptide comprises the amino acid sequence of SEQ ID NO: 3; the first peptide comprises the amino acid sequence of SEQ ID NO: 10 and the second peptide comprises the amino acid sequence of SEQ ID NO: 4; the first peptide comprises the amino acid sequence of SEQ ID NO: 10 and the second peptide comprises the amino acid sequence of SEQ ID NO: 5; the first peptide comprises the amino acid sequence of SEQ ID NO: 10 and the second peptide comprises the amino acid sequence of SEQ ID NO: 6; the first peptide comprises the amino acid sequence of SEQ ID NO: 11 and the second peptide comprises the amino acid sequence of SEQ ID NO: 1; the first peptide comprises the amino acid sequence of SEQ ID NO: 11 and the second peptide comprises the amino acid sequence of SEQ ID NO: 2; the first peptide comprises the amino acid sequence of SEQ ID NO: 11 and the second peptide comprises the amino acid sequence of SEQ ID NO: 3; the first peptide comprises the amino acid sequence of SEQ ID NO: 11 and the second peptide comprises the amino acid sequence of SEQ ID NO: 4; the first peptide comprises the amino acid sequence of SEQ ID NO: 11 and the second peptide comprises the amino acid sequence of SEQ ID NO: 5; the first peptide comprises the amino acid sequence of SEQ ID NO: 11 and the second peptide comprises the amino acid sequence of SEQ ID NO: 6; the first peptide comprises the amino acid sequence of SEQ ID NO: 12 and the second peptide comprises the amino acid sequence of SEQ ID NO: 1; the first peptide comprises the amino acid sequence of SEQ ID NO: 12 and the second peptide comprises the amino acid sequence of SEQ ID NO: 2; the first peptide comprises the amino acid sequence of SEQ ID NO: 12 and the second peptide comprises the amino acid sequence of SEQ ID NO: 3; the first peptide comprises the amino acid sequence of SEQ ID NO: 12 and the second peptide comprises the amino acid sequence of SEQ ID NO: 4; the first peptide comprises the amino acid sequence of SEQ ID NO: 12 and the second peptide comprises the amino acid sequence of SEQ ID NO: 5; the first peptide comprises the amino acid sequence of SEQ ID NO: 12 and the second peptide comprises the amino acid sequence of SEQ ID NO: 6; the first peptide comprises the amino acid sequence of SEQ ID NO: 13 and the second peptide comprises the amino acid sequence of SEQ ID NO: 1; the first peptide comprises the amino acid sequence of SEQ ID NO: 13 and the second peptide comprises the amino acid sequence of SEQ ID NO: 2; the first peptide comprises the amino acid sequence of SEQ ID NO: 13 and the second peptide comprises the amino acid sequence of SEQ ID NO: 3; the first peptide comprises the amino acid sequence of SEQ ID NO: 13 and the second peptide comprises the amino acid sequence of SEQ ID NO: 4; the first peptide comprises the amino acid sequence of SEQ ID NO: 13 and the second peptide comprises the amino acid sequence of SEQ ID NO: 5; the first peptide comprises the amino acid sequence of SEQ ID NO: 13 and the second peptide comprises the amino acid sequence of SEQ ID NO: 6; the first peptide comprises the amino acid sequence of SEQ ID NO: 14 and the second peptide comprises the amino acid sequence of SEQ ID NO: 1; the first peptide comprises the amino acid sequence of SEQ ID NO: 14 and the second peptide comprises the amino acid sequence of SEQ ID NO: 2; the first peptide comprises the amino acid sequence of SEQ ID NO: 14 and the second peptide comprises the amino acid sequence of SEQ ID NO: 3; the first peptide comprises the amino acid sequence of SEQ ID NO: 14 and the second peptide comprises the amino acid sequence of SEQ ID NO: 4; the first peptide comprises the amino acid sequence of SEQ ID NO: 14 and the second peptide comprises the amino acid sequence of SEQ ID NO: 5; the first peptide comprises the amino acid sequence of SEQ ID NO: 14 and the second peptide comprises the amino acid sequence of SEQ ID NO: 6; the first peptide comprises the amino acid sequence of SEQ ID NO: 15 and the second peptide comprises the amino acid sequence of SEQ ID NO: 1; the first peptide comprises the amino acid sequence of SEQ ID NO: 15 and the second peptide comprises the amino acid sequence of SEQ ID NO: 2; the first peptide comprises the amino acid sequence of SEQ ID NO: 15 and the second peptide comprises the amino acid sequence of SEQ ID NO: 3; the first peptide comprises the amino acid sequence of SEQ ID NO: 15 and the second peptide comprises the amino acid sequence of SEQ ID NO: 4; the first peptide comprises the amino acid sequence of SEQ ID NO: 15 and the second peptide comprises the amino acid sequence of SEQ ID NO: 5; the first peptide comprises the amino acid sequence of SEQ ID NO: 15 and the second peptide comprises the amino acid sequence of SEQ ID NO: 6; the first peptide comprises the amino acid sequence of SEQ ID NO: 507 and the second peptide comprises the amino acid sequence of SEQ ID NO: 1; the first peptide comprises the amino acid sequence of SEQ ID NO: 507 and the second peptide comprises the amino acid sequence of SEQ ID NO: 2; the first peptide comprises the amino acid sequence of SEQ ID NO: 507 and the second peptide comprises the amino acid sequence of SEQ ID NO: 3; the first peptide comprises the amino acid sequence of SEQ ID NO: 507 and the second peptide comprises the amino acid sequence of SEQ ID NO: 4; the first peptide comprises the amino acid sequence of SEQ ID NO: 507 and the second peptide comprises the amino acid sequence of SEQ ID NO: 5; or the first peptide comprises the amino acid sequence of SEQ ID NO: 507 and the second peptide comprises the amino acid sequence of SEQ ID NO: 6.

In some embodiments, the fusion protein comprises an amino acid sequence selected from the group consisting of SEQ ID NOs: 28-75 and 508-515.

In some embodiments, the fusion protein further comprises an IgG Fc. In some embodiments, the IgG Fc comprises the amino acid alanine at each of EU positions 234 and 235. In some embodiments, the IgG Fc comprises the amino acid alanine at EU position 329.

In some embodiments, the IgG Fc comprises the amino acid alanine at each of EU positions 234, 235, and 329. In some embodiments, the IgG Fc comprises the amino acids alanine, alanine, alanine, leucine, and serine at EU positions 234, 235, 329, 428, and 434, respectively.

In some embodiments, the IgG Fc comprises the amino acids lysine, phenylalanine, and tyrosine at EU positions 433, 434, and 436, respectively. In some embodiments, the IgG Fc comprises the amino acids tyrosine, threonine, and glutamate at EU positions 252, 254, and 256, respectively. In some embodiments, the IgG Fc comprises the amino acids leucine and serine at EU positions 428 and 434, respectively.

In some embodiments, the IgG Fc comprises an amino acid sequence at least 85% identical to the amino acid sequence of a human IgG1 Fc. In some embodiments, the IgG Fc comprises the amino acid sequence of a human IgG1 Fc.

In some embodiments, the IgG Fc comprises an amino acid sequence at least 95% identical to an amino acid sequence selected from the group consisting of SEQ ID NOs: 76-83.

In some embodiments, the IgG Fc comprises an amino acid sequence selected from the group consisting of SEQ ID NOs: 76-83.

In some embodiments, the IgG Fc is linked to the N-terminus of the first peptide. In some embodiments, the IgG Fc is linked to the C-terminus of the second peptide.

In some embodiments, the fusion protein comprises an amino acid sequence selected from the group consisting of SEQ ID NOs: 84-138 and 516-523. In some embodiments, the fusion protein comprises an amino acid sequence selected from the group consisting of SEQ ID NOs: 139-193, 524-531, and 549.

In another aspect, the present disclosure provides a polypeptide comprising an amino acid sequence selected from the group consisting of SEQ ID NOs: 1-6, 8-15, 18-24, 26-75, 84-193, 507-531, and 549-558.

In another aspect, the present disclosure provides a polynucleotide comprising a nucleotide sequence encoding any one of the fusion proteins described herein, or any one of the polypeptides described herein.

In some embodiments, the polynucleotide is a DNA molecule. In some embodiments, the polynucleotide comprises a nucleotide sequence selected from the group consisting of SEQ ID NOs: 194-248, 410-464, and 532-547.

In some embodiments, the polynucleotide is an RNA molecule.

In another aspect, the present disclosure provides an expression vector comprising the any one of the polynucleotides described herein.

In some embodiments, the expression vector is a plasmid. In some embodiments, the expression vector is a viral vector.

In another aspect, the present disclosure provides a host cell comprising any one of the polynucleotides described herein, or any one of the expression vectors described herein.

In some embodiments, the host cell is a prokaryotic cell. In some embodiments, the prokaryotic cell is an E. coli cell or a Bacillus cell. In some embodiments, the host cell is a eukaryotic cell. In some embodiments, the eukaryotic cell is selected from the group consisting of a yeast cell, an insect cell, and a mammalian cell. In some embodiments, the mammalian cell is selected from the group consisting of a CHO cell, a HeLa cell, and a 293 cell.

In another aspect, the present disclosure provides a population of cells comprising two or more of any of the host cells described herein.

In another aspect, the present disclosure provides a method of producing any one of the fusion proteins described herein, or any one of the polypeptides described herein, comprising culturing any one of the host cells described herein, under conditions such that the fusion protein is produced.

In another aspect, the present disclosure provides a pharmaceutical composition comprising an effective amount of any one of the fusion proteins described herein, any one of the polypeptides described herein, any one of the polynucleotides described herein, or any one of the expression vectors described herein.

In some embodiments, the fusion protein has a circulating half-life of at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, or at least 23 days. In some embodiments, the fusion protein has a circulating half-life of at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, or at least 23 days when administered (e.g., to a human).

In some embodiments, the fusion protein has bioavailability of at least 40%, at least 45%, at least 50%, at least 55%, at least 60%, at least 65%, or at least 70% when administered (e.g., to a human). In some embodiments, administration of the pharmaceutical composition is via intravenous administration or subcutaneous administration.

In another aspect, the present disclosure provides a method of enhancing a relaxin-2-related activity in a primary cell, comprising contacting the primary cell with any one of the fusion proteins described herein, thereby enhancing relaxin-2-related activity in the cell.

In some embodiments, the fusion protein activates relaxin-2 receptor (RXFP1) on a cell surface.

In some embodiments, the method elevates cAMP levels in the primary cell, inducing vasodilation, inducing the expression of angiogenic factors, inducing the expression of MMPs, and inducing collagen degradation.

In some embodiments, the primary cell is selected from the group consisting of endothelial cells, vascular smooth muscle cells, other vascular cells, cardiomyocytes, other cardiac cells, and fibroblasts.

In some embodiments, the primary cell is within a subject. In some embodiments, the subject has a relaxin-2-associated disorder. In some embodiments, the relaxin-2-associated disorder is selected from the group consisting of kidney diseases, fibrotic diseases, and cardiovascular diseases. In some embodiments, the disorder is selected from the group consisting of pulmonary hypertension, pulmonary arterial hypertension (PAH), pulmonary hypertension due to left heart disease (PH-LHD), combined precapillary and postcapillary pulmonary hypertension (CpcPH), isolated postcapillary pulmonary hypertension (IpcPH), heart failure, heart failure with preserved ejection fraction (HFpEF), heart failure with mid-range ejection fraction (HFmrEF), heart failure with reduced ejection fraction (HFrEF), valvular heart disease, joint disease, frozen shoulder (also known as adhesive capsulitis), kidney disease, chronic kidney disease, and hypertensive kidney disease.

In some embodiments, the disorder is combined precapillary and postcapillary pulmonary hypertension (CpcPH) with heart failure with preserved ejection fraction (HFpEF). In some embodiments, the disorder is isolated postcapillary pulmonary hypertension (IpcPH) with heart failure with preserved ejection fraction (HFpEF). In some embodiments, the disorder is combined precapillary and postcapillary pulmonary hypertension (CpcPH) with heart failure with mid-range ejection fraction (HFmrEF). In some embodiments, the disorder is isolated postcapillary pulmonary hypertension (IpcPH) with heart failure with mid-range ejection fraction (HFmrEF).

In another aspect, the present disclosure provides a method of treating a relaxin-associated disorder in a subject in need thereof, comprising administering to the subject an effective amount of any one of the fusion proteins described herein, any one of the polynucleotides described herein, any one of the expression vectors described herein, or any one of the pharmaceutical compositions described herein, thereby treating the relaxin-associated disorder.

In some embodiments, the relaxin-2-associated disorder is selected from the group consisting of kidney diseases, fibrotic diseases, and cardiovascular diseases. In some embodiments, the disorder is selected from the group consisting of pulmonary hypertension, pulmonary arterial hypertension (PAH), pulmonary hypertension due to left heart disease (PH-LHD), combined precapillary and postcapillary pulmonary hypertension (CpcPH), isolated postcapillary pulmonary hypertension (IpcPH), heart failure, heart failure with preserved ejection fraction (HFpEF), heart failure with mid-range ejection fraction (HFmrEF), heart failure with reduced ejection fraction (HFrEF), kidney disease, chronic kidney disease, and hypertensive kidney disease. In some embodiments, the method decreases arterial pressure, increases renal artery blood flow, increases cardiac filling at diastole, resolves established fibrosis, and/or suppresses new fibrosis development in the subject.

In some embodiments, the method increases renal plasma flow in the subject. In some embodiments, the increase in the renal plasma flow in the subject persists after 1 week, 2 weeks, 3 weeks, 4 weeks, 5 weeks, or 1 month after a single administration of the fusion protein. In some embodiments, the increase in the renal plasma flow in the subject is maintained by at least about 30%, at least about 40%, at least about 50%, at least about 60%, at least about 70%, at least about 75%, at least about 80%, at least about 85%, at least about 90%, or at least about 95% 1 week, 2 weeks, 3 weeks, 4 weeks, 5 weeks, or 1 month after a single administration of the fusion protein.

In some embodiments, the disorder is combined precapillary and postcapillary pulmonary hypertension (CpcPH) with heart failure with preserved ejection fraction (HFpEF). In some embodiments, the disorder is isolated postcapillary pulmonary hypertension (IpcPH) with heart failure with preserved ejection fraction (HFpEF). In some embodiments, the disorder is combined precapillary and postcapillary pulmonary hypertension (CpcPH) with heart failure with mid-range ejection fraction (HFmrEF). In some embodiments, the disorder is isolated postcapillary pulmonary hypertension (IpcPH) with heart failure with mid-range ejection fraction (HFmrEF).

In some embodiments, the subject is administered the fusion protein by intravenous administration. In some embodiments, the subject is administered from about 0.1 mg/kg to about 20 mg/kg of the fusion protein. In some embodiments, the subject is administered about 0.3 mg/kg of the fusion protein. In some embodiments, the subject is administered about 1 mg/kg of the fusion protein. In some embodiments, the subject is administered about 3 mg/kg of the fusion protein. In some embodiments, the subject is administered about 10 mg/kg of the fusion protein.

In some embodiments, the subject is administered the fusion protein by intravenous infusion. In some embodiments, the subject is administered the fusion protein by intravenous infusion over 30 minutes. In some embodiments, the subject is administered the fusion protein by intravenous infusion over 60 minutes. In some embodiments, the subject is administered the fusion protein by intravenous infusion over 30 to 60 minutes.

In some embodiments, the subject is administered the fusion protein by subcutaneous administration. In some embodiments, the subject is administered about 100 mg to about 1500 mg of the fusion protein. In some embodiments, the subject is administered about 150 mg of the fusion protein. In some embodiments, the subject is administered at least 150 mg of the fusion protein. In some embodiments, the subject is administered about 300 mg of the fusion protein. In some embodiments, the subject is administered about 600 mg of the fusion protein.

In some embodiments, the subject is administered the fusion protein once every 1 week, 2 weeks, 3 weeks, 4 weeks, 5 weeks, or 1 month.

BRIEF DESCRIPTION OF THE DRAWINGS

FIG. 5A shows the increase in RABF in rats treated with SEQ ID NO: 87 or SEQ ID NO: 497 over time. FIG. 5B shows that rats treated with SEQ ID NO: 87 demonstrate significant increase in RABF compared to SEQ ID NO: 497 by area under the curve analysis.

FIG. 17A shows the concentration of SEQ ID NO: 87 over time in dosed patients (solid lines), as well as the PK profile of SEQ ID NO: 87 as predicted using non-human primate modeling (dashed line). FIG. 17B shows the change in renal plasma flow over baseline on days 2, 8, and 17, in healthy patients dosed with SEQ ID NO: 87 or placebo (PBO).

DETAILED DESCRIPTION

Figures 1A, 1B:
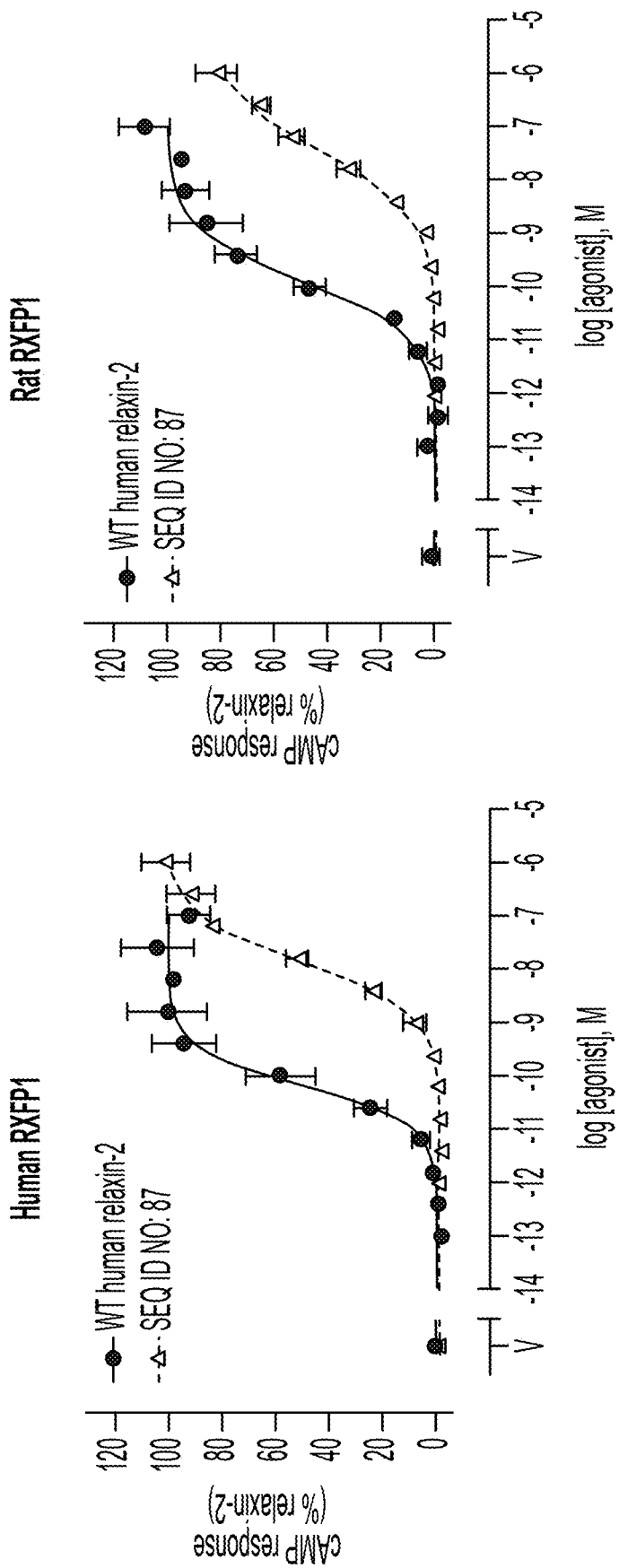
FIGS. 1A-IC are graphs depicting cAMP response induced by SEQ ID NO: 87 and wild-type (WT) human relaxin-2 in HEK293 cells transiently expressing human (FIG. 1A), rat (FIG. 1B), and monkey (FIG. 1C) RXFP1, respectively.

The therapeutic potential of relaxin-2 was highlighted in the RELAX-AHF trials (see, e.g., Teerlink et al., (2013) Lancet 381(9860):29-39). However, the therapeutic protein used, human relaxin-2 (Serelaxin), had not been modified in any way to extend half-life in vivo, and the protein had to be administered by continuous IV infusion over a 48-hour period. Half-life extended versions of relaxin-2 have been generated via fusion of the peptide hormone to human IgG1 Fc or to an albumin binding nanobody, but such fusion proteins have shown extremely rapid clearance from plasma. The present disclosure is based in part on the discovery by the inventors that reducing the positive charge and heparin binding of relaxin-2 results in greatly improved pharmacokinetic and pharmacodynamic profiles.

The disclosure provides fusion proteins comprising a human relaxin-2 B chain, or a derivative thereof, and a human relaxin-2 A chain, or a derivative thereof, joined by a peptide linker, wherein the fusion proteins have high in vivo circulating half-life when administered to mammals. In some embodiments, the in vivo circulating half-life of the fusion proteins provided in this disclosure is greater than 2 hours. In some embodiments, the fusion proteins provided in this disclosure have low pI. In some embodiments, the pI of the fusion proteins provided in this disclosure is less than 8.5. In some embodiments, the low pI of the fusion proteins provided in this disclosure is caused by acidic amino acid residues present in the peptide linker. In some embodiments, the peptide linker of the fusion protein comprises 2 or more acidic amino acids. In some embodiments, the peptide linker is 10-15 total amino acids in length.

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an," and "the" include plural referents unless the context clearly dictates otherwise. In this application, the use of "or" means "and/or" unless stated otherwise. Furthermore, use of the term "including" as well as other forms, such as "include," "includes," and "included," is not limiting. The section headings used herein are for organizational purposes only and are not to be construed as limiting the subject matter described.

The term "polynucleotide" as used herein refers to a polymer of DNA or RNA. The polynucleotide sequence can be single-stranded or double-stranded; contain natural, non-natural, or altered nucleotides; and contain a natural, non-natural, or altered internucleotide linkage, such as a phosphoroamidate linkage or a phosphorothioate linkage, instead of the phosphodiester found between the nucleotides of an unmodified polynucleotide sequence. Polynucleotide sequences include, but are not limited to, all polynucleotide sequences which are obtained by any means available in the art, including, without limitation, recombinant means, e.g., the cloning of polynucleotide sequences from a recombinant library or a cell genome, using ordinary cloning technology and polymerase chain reaction, and the like, and by synthetic means.

The terms "protein" and "polypeptide" are used interchangeably herein and refer to a polymer of amino acids connected by one or more peptide bonds. As used herein, "amino acid sequence" refers to the information describing the relative order and identity of amino acid residues which make up a polypeptide.

As used herein, the term "an amino acid sequence that has 0, 1, 2, 3, 4, or 5 amino acid modifications" with reference to an amino acid sequence, refers to an amino acid sequence that comprises up to 5 amino acid substitutions, alterations, inversions, additions, or deletions compared to a reference amino acid sequence.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F, (1990) *PNAS* 87: 2264-2268, modified as in Karlin S & Altschul S F, (1993) *PNAS* 90: 5873-5877, each of which is herein incorporated by reference in its entirety. Such an algorithm is incorporated into the NBLAST and XBLAST programs of Altschul S F et al., (1990) *J Mol Biol* 215: 403, which is herein incorporated by reference in its entirety. BLAST nucleotide searches can be performed with the NBLAST nucleotide program parameters set, e.g., at score=100, wordlength=12 to obtain nucleotide sequences homologous to a nucleic acid molecule described herein. BLAST protein searches can be performed with the XBLAST program parameters set, e.g., at score=50, wordlength=3 to obtain amino acid sequences homologous to a protein molecule described herein. To obtain gapped alignments for comparison purposes, Gapped BLAST can be utilized as described in Altschul S F et al., (1997) *Nuc Acids Res* 25: 3389-3402, which is herein incorporated by reference in its entirety. Alternatively, PSI BLAST can be used to perform an iterated search which detects distant relationships between molecules. Id. When utilizing BLAST, Gapped BLAST, and PSI BLAST programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, (1988) *CABIOS* 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "linked to" refers to covalent or noncovalent binding between two molecules or moieties. The skilled worker will appreciate that when a first molecule or moiety is linked to a second molecule or moiety, the linkage need not be direct, but instead, can be via an intervening molecule or moiety.

As used herein, the terms "human relaxin-2 B chain" or "relaxin B chain" or "relaxin B" or "rel B" refer to a peptide comprising or consisting of the amino acid sequence as set forth in DSWMEEVIKLCGRELVRAQIAICGMSTWS (SEQ ID NO: 249) or derivatives thereof. In some embodiments, a derivative of a relaxin B chain comprises the amino acid sequence of SEQ ID NO: 154 with 1, 2, 3, 4, or 5 amino acid changes.

As used herein, the terms "human relaxin-2 A chain" or "relaxin A chain" or "relaxin A" or "rel A" refer to a peptide comprising or consisting of the amino acid sequence as set forth in QLYSALANKCCHVGCTKRSLARFC (SEQ ID NO: 257) or derivatives thereof. In some embodiments, a derivative of a relaxin A chain comprises the amino acid sequence of SEQ ID NO: 155 with 1, 2, 3, 4, or 5 amino acid changes.

As used herein, the term "linker peptide" refers to a peptide that links the relaxin A chain and the relaxin B chain in the fusion proteins described herein.

As used herein, the term "acidic amino acid" refers to an amino acid that has a carboxylic acid in its side chain. In some embodiments, the acidic amino acid is aspartate, glutamate, 2-aminoadipic acid, 2-aminobutyric acid or 2-aminopimelic acid. In some embodiments, acid amino acids include aspartate and glutamate.

As used herein, the term "non-acidic amino acid" refers to amino acids that are not acidic amino acids. In some embodiments, non-acidic amino acids include glycine, proline, and serine. In some embodiments, non-specific amino acids also include arginine, histidine, lysine, threonine, asparagine, glutamine, cysteine, alanine, valine, isoleucine, leucine, methionine, phenylalanine, tyrosine, and tryptophan.

As used herein, the term "IgG Fc" refers to the immunoglobulin G (IgG) fragment crystallizable (Fc) region. In some embodiments, the IgG Fc is the human IgG1, IgG2, IgG3, or IgG4 Fc region. In some embodiments, the IgG Fc is the IgG1 Fc region.

As used herein, the term "EU numbering system" refers to the EU numbering convention for the constant regions of an antibody, as described in Edelman, G. M. et al., Proc. Natl. Acad. USA, 63, 78-85 (1969) and Kabat et al., Sequences of Proteins of Immunological Interest, U.S. Dept. Health and Human Services, 5th edition, 1991, each of which is herein incorporated by reference in its entirety.

As used herein, the term "relaxin-2 receptor," "human relaxin-2 receptor," "human relaxin receptor 1," "RXFP1," or "LGR7" is the native receptor of relaxin-2 in humans. In some embodiments, RXFP1 comprises the amino acid sequence shown in NCBI Reference Sequence: NP_067647.2, NP_001240656.1, NP_001240657.1, NP_001240658.1, NP_001240659.1, NP_001240661.1, NP_001240662.1, or NP_001350705.1 incorporated herein by reference in its entirety.

As used herein, the terms "treat," "treating," and "treatment" refer to therapeutic or preventative measures described herein. In some embodiments, the methods of "treatment" employ administration of a fusion protein to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

As used herein, the term "pI" means the isoelectric point, i.e., the pH of a solution at which the next charge on a fusion protein is zero. In some embodiments, the pI is the calculated or theoretical pI. In some embodiments, the pI is measured experimentally by an instrument.

Fusion Proteins

The disclosure provides fusion proteins comprising a human relaxin-2 B chain, or a derivative thereof, and a human relaxin-2 A chain, or a derivative thereof, linked by a peptide linker, wherein the fusion proteins have high in vivo circulating half-life when administered to mammals. In some embodiments, the fusion protein comprises, from N-terminus to C-terminus, a human relaxin-2 B chain, or a derivative thereof, a peptide linker and a human relaxin-2 A chain, or a derivative thereof. In some embodiments, the fusion protein comprises, from N-terminus to C-terminus, a human relaxin-2 A chain, or a derivative thereof, a peptide linker and a human relaxin-2 B chain, or a derivative thereof. In some embodiments, the fusion protein further comprises an IgG Fc. The IgG Fc is linked to the N-terminus or C-terminus of the human relaxin B chain-linker protein-human relaxin A chain fusion protein or the human relaxin A chain-linker protein-human relaxin B chain fusion protein. In some embodiments, the fusion proteins form homodimers via interaction between IgG Fc moieties. In some embodiments, the IgG Fc described above is replaced with PEG.

Human Relaxin-2 B Chain Derivatives

The disclosure provides human relaxin-2 B chain derivatives, wherein the derivatives have 1, 2, 3, 4, or 5 amino acid changes when compared to the amino acid sequence of SEQ ID NO: 249. In some embodiments, the amino acid that corresponds with position 13 of SEQ ID NO: 249 must be arginine. In some embodiments, the amino acid that corresponds with position 17 of SEQ ID NO: 249 must be arginine. In some embodiments, the amino acid that corresponds with position 20 of SEQ ID NO: 249 must be isoleucine. In some embodiments, the amino acid that corresponds with position 13 of SEQ ID NO: 249 must be arginine; the amino acid that corresponds with position 17 of SEQ ID NO: 249 must be arginine; and the amino acid that corresponds with position 20 of SEQ ID NO: 249 must be isoleucine.

In some embodiments, the human relaxin-2 B chain derivatives comprise or consist of the following formula: DSWX$_{19}$EEVIKLCGRELVRAQIAICGX$_{20}$ST (SEQ ID NO: 250), wherein X$_{19}$ and X$_{20}$ are absent or any amino acid. In some embodiments, X$_{19}$ is methionine (M), glutamine (Q), glutamic acid (E), asparagine (N), aspartic acid (D), serine (S), or threonine (T). In some embodiments, X$_{19}$ is methionine (M), lysine (K) or glutamine (Q). In some embodiments, X$_{20}$ is methionine (M), lysine (K), glutamine (Q), or asparagine (N). In some embodiments, X$_{20}$ is methionine (M) or lysine (K). In some embodiments, X$_{20}$ is lysine (K). In some embodiments, X$_{19}$ is methionine (M), lysine (K) or glutamine (Q), and X$_{20}$ is methionine (M) or lysine (K).

The disclosure provides human relaxin-2 B chain derivatives, wherein the derivatives comprise an amino acid sequence that has 0, 1, 2, 3, 4, or 5 amino acid modifications relative to the amino acid sequence of SEQ ID NO: 1, wherein the amino acid at position 4 is not methionine (M), or the amino acid at position 25 of is not methionine (M). In some embodiments, the derivatives comprise an amino acid sequence that has 0, 1, 2, 3, 4, or 5 amino acid modifications relative to the amino acid sequence of SEQ ID NO: 1, wherein the amino acid at position 4 is not methionine (M), and the amino acid at position 25 of is not methionine (M). In some embodiments, the derivatives comprise an amino acid sequence that has 0, 1, 2, 3, 4, or 5 amino acid modifications relative to the amino acid sequence of SEQ ID NO: 1, wherein the amino acid at at least one of positions 4 or 25 of the first peptide is not methionine (M).

In some embodiments, the human relaxin-2 B chain derivatives comprise or consist of the following formula: DSX$_1$QEEVIX$_2$LCGRELVRAQIAICGX$_3$ST (SEQ ID NO: 7), wherein X$_1$ is tryptophan (W), tyrosine (Y), phenylalanine (F), leucine (L), isoleucine (I), valine (V), or alanine (A); X$_2$ is lysine (K), glutamine (Q), aspartic acid (D), glutamic acid (E), leucine (L), isoleucine (I), or tyrosine (Y); and X$_3$ is lysine (K) or glutamine (Q). In some embodiments, the human relaxin-2 B chain derivatives comprise or consist of the following formula: DSX$_1$QEEVIX$_2$LCGRELVRAQIAICGX$_3$ST (SEQ ID NO: 7), wherein X$_1$ is tryptophan (W), tyrosine (Y), phenylalanine (F), leucine (L), isoleucine (I), valine (V), or alanine (A); X$_2$ is lysine (K), glutamine (Q), aspartic acid (D), glutamic acid (E), leucine (L), isoleucine (I), or tyrosine (Y); and X$_3$ is methionine (M), lysine (K), glutamine (Q), or asparagine (N). In some embodiments, the human relaxin-2 B chain derivatives comprise or consist of the following formula: DSX$_1$QEEVIX$_2$LCGRELVRAQIAICGX$_3$ST (SEQ ID NO: 7), wherein X$_1$ is any amino acid except for methionine (M), histidine (H), and cysteine (C); X$_2$ is lysine (K), glutamine (Q), aspartic acid (D), glutamic acid (E), leucine (L), isoleucine (I), or tyrosine (Y); and X$_3$ is lysine (K) or glutamine (Q). In some embodiments, the human relaxin-2 B chain derivatives comprise or consist of the following formula: DSX$_1$QEEVIX$_2$LCGRELVRAQIAICGX$_3$ST (SEQ ID NO: 7), wherein X$_1$ is any amino acid except for methionine (M), histidine (H), and cysteine (C); X$_2$ is lysine (K), glutamine (Q), aspartic acid (D), glutamic acid (E), leucine (L), isoleucine (I), or tyrosine (Y); and X$_3$ is methionine (M), lysine (K), glutamine (Q), or asparagine (N).

In some embodiments, the human relaxin-2 B chain derivatives comprise an amino acid sequence that has 0, 1, 2, 3, 4, or 5 amino acid modifications relative to the amino acid sequence of SEQ ID NO: 502. In some embodiments, the human relaxin-2 B chain derivatives comprise or consist of the following formula: X$_{11}$LCGRELVRAQIAIC (SEQ ID NO: 505), wherein X$_{11}$ is lysine (K), glutamine (Q), aspartic acid (D), glutamic acid (E), leucine (L), isoleucine (I), or tyrosine (Y).

In some embodiments, the human relaxin-2 B chain derivatives used in the fusion proteins described herein do not include the amino acid sequences of SEQ ID NOs: 251-254 as set forth below:

```
                                        (SEQ ID NO: 251)
DSWKEEVIKLCGRELVRAQIAICGKSTAS;

(SEQ ID NO: 252)
DSWKEEVIKLCGRELVRAQIAICGKSTWS;

(SEQ ID NO: 253)
DSWMEEVIKLCGRELVRAQIAICGKSTAS;
and (SEQ ID NO: 254)
DSWMEEVIKLCGRELVRAQIAICGKSTWS.
```

In some embodiments, the human relaxin-2 B chain derivatives are from 22, 23, 24, 25, 26, 27, 28, 29, 30, 31, or 32 amino acids in length. In some embodiments, the human relaxin-2 B chain derivatives are 25, 26, 27, 28, or 29 amino acids in length. In some embodiments, the human relaxin-2 B chain derivatives are 27 amino acids in length. In some embodiments, the human relaxin-2 B chain derivatives are 15-29 amino acids in length. In some embodiments, the human relaxin-2 B chain derivatives are 15, 16, 17, 18, 19, 20, 21, 22, 23, 24, 25, 26, 27, 28, or 29 amino acids in length.

In some embodiments, the human relaxin-2 B chain derivatives comprise or consist of the amino acid sequences shown in Table 1, below.

TABLE 1

Human Relaxin-2 B Chain Derivative Sequences

| SEQ ID NO: | Amino Acid Sequence |
|---|---|
| 1 | DSWQEEVIKLCGRELVRAQIAICGKST |
| 2 | DSWQEEVIKLCGRELVRAQIAICGQST |
| 3 | DSYQEEVIKLCGRELVRAQIAICGKST |
| 4 | DSFQEEVIKLCGRELVRAQIAICGKST |
| 5 | DSLQEEVIKLCGRELVRAQIAICGKST |
| 6 | DSIQEEVIKLCGRELVRAQIAICGKST |
| 249 | DSWMEEVIKLCGRELVRAQIAICGMSTWS |
| 255 | DSWKEEVIKLCGRELVRAQIAICGKST |
| 256 | DSWMEEVIKLCGRELVRAQIAICGKST |
| 502 | KLCGRELVRAQIAIC |

In some embodiments, the human relaxin-2 B chain derivatives comprise or consist of SEQ ID NO: 1. In some embodiments, the human relaxin-2 B chain derivatives comprise or consist of SEQ ID NO: 2. In some embodiments, the human relaxin-2 B chain derivatives comprise or consist of SEQ ID NO: 3. In some embodiments, the human relaxin-2 B chain derivatives comprise or consist of SEQ ID NO: 4. In some embodiments, the human relaxin-2 B chain derivatives comprise or consist of SEQ ID NO: 5. In some embodiments, the human relaxin-2 B chain derivatives comprise or consist of SEQ ID NO: 6. In some embodiments, the human relaxin-2 B chain derivatives comprise or consist of SEQ ID NO: 249. In some embodiments, the human relaxin-2 B chain derivatives comprise or consist of SEQ ID NO: 255. In some embodiments, the human relaxin-2 B chain derivatives comprise or consist of SEQ ID NO: 256. In some embodiments, the human relaxin-2 B chain derivatives comprise or consist of SEQ ID NO: 502.

In some embodiments, the human relaxin-2 B chain derivatives comprise or consist of SEQ ID NO: 1, wherein the amino acid at position 9 is lysine, (K), glutamine (Q), aspartic acid (D), glutamic acid (E), leucine (L), isoleucine (I), or tyrosine (Y). In some embodiments, the human relaxin-2 B chain derivatives comprise or consist of SEQ ID NO: 2, wherein the amino acid at position 9 is lysine, (K), glutamine (Q), aspartic acid (D), glutamic acid (E), leucine (L), isoleucine (I), or tyrosine (Y). In some embodiments, the human relaxin-2 B chain derivatives comprise or consist of SEQ ID NO: 3, wherein the amino acid at position 9 is lysine, (K), glutamine (Q), aspartic acid (D), glutamic acid (E), leucine (L), isoleucine (I), or tyrosine (Y). In some embodiments, the human relaxin-2 B chain derivatives comprise or consist of SEQ ID NO: 4, wherein the amino acid at position 9 is lysine, (K), glutamine (Q), aspartic acid (D), glutamic acid (E), leucine (L), isoleucine (I), or tyrosine (Y). In some embodiments, the human relaxin-2 B chain derivatives comprise or consist of SEQ ID NO: 5, wherein the amino acid at position 9 is lysine, (K), glutamine (Q), aspartic acid (D), glutamic acid (E), leucine (L), isoleucine (I), or tyrosine (Y). In some embodiments, the human relaxin-2 B chain derivatives comprise or consist of SEQ ID NO: 6, wherein the amino acid at position 9 is lysine, (K), glutamine (Q), aspartic acid (D), glutamic acid (E), leucine (L), isoleucine (I), or tyrosine (Y). In some embodiments, the human relaxin-2 B chain derivatives comprise or consist of SEQ ID NO: 249, wherein the amino acid at position 9 is lysine, (K), glutamine (Q), aspartic acid (D), glutamic acid (E), leucine (L), isoleucine (I), or tyrosine (Y). In some embodiments, the human relaxin-2 B chain derivatives comprise or consist of SEQ ID NO: 255, wherein the amino acid at position 9 is lysine, (K), glutamine (Q), aspartic acid (D), glutamic acid (E), leucine (L), isoleucine (I), or tyrosine (Y). In some embodiments, the human relaxin-2 B chain derivatives comprise or consist of SEQ ID NO: 256, wherein the amino acid at position 9 is lysine, (K), glutamine (Q), aspartic acid (D), glutamic acid (E), leucine (L), isoleucine (I), or tyrosine (Y). In some embodiments, the human relaxin-2 B chain derivatives comprise or consist of SEQ ID NO: 502, wherein the amino acid at position 1 is lysine, (K), glutamine (Q), aspartic acid (D), glutamic acid (E), leucine (L), isoleucine (I), or tyrosine (Y).

In some embodiments, the human relaxin-2 B chain derivatives further comprise two residues at the C-terminal end. For example, SEQ ID NOs: 1-7, 250, 255, and 256 can further comprise two residues at the C-terminal end, e.g., the tryptophan (W) and serine (S) at the C-terminal end of SEQ ID NO: 249. In some embodiments, the human relaxin-2 B chain derivatives further comprise an X amino acid and serine (S) at the C-terminal end, wherein the X amino acid can be any amino acid except cysteine (C). Accordingly, in some embodiments, the C-terminal end of the human relaxin-2 B chain derivatives are XS, wherein X is any amino acid except cysteine (C).

In some embodiments, the human relaxin-2 B chain derivatives further comprise one or more substitutions that improve the stability of the relaxin-2 B chain derivatives, e.g., stability of the relaxin-2 B chain derivatives after light or heat exposure, as measured by methods known in the art, e.g., SEC to assess aggregate formation, and CE-SDS to assess purity. In some embodiments, the amino acid in the human relaxin-2 B chain derivatives corresponding to amino acid position 3 in SEQ ID NO: 3 is a tyrosine (Y).

Human Relaxin-2 A Chain Derivatives

The disclosure provides human relaxin-2 A chain derivatives, wherein the derivatives have 1, 2, 3, 4, or 5 amino acid changes when compared to the amino acid sequence of SEQ ID NO: 257. In some embodiments, the amino acid that corresponds with position 3 of SEQ ID NO: 257 must be tyrosine. In some embodiments, the amino acid that corresponds with position 23 of SEQ ID NO: 257 must be phenylalanine. In some embodiments, the amino acid that corresponds with position 3 of SEQ ID NO: 257 must be tyrosine; and the amino acid that corresponds with position 23 of SEQ ID NO: 257 must be phenylalanine.

In some embodiments, the human relaxin-2 A chain derivatives comprise or consist of the following formula: $X_{21}QX_{22}YSALANKCCHVGCTKRSLAX_{23}FC$ (SEQ ID NO: 258), wherein $X_{21}$, $X_{22}$, and $X_{23}$ are absent or any amino acid. In some embodiments, $X_{21}$ is arginine (R), lysine (K), glutamine (Q), asparagine (N), histidine (H), serine (S), threonine (T), proline (P), glycine (G), or absent. In some embodiments, $X_{21}$ is arginine (R), glycine (G), or absent. In some embodiments, $X_{21}$ is arginine (R) or absent. In some embodiments, $X_{22}$ is leucine (L), aspartic acid (D), glutamic acid (E), asparagine (N), glutamine (Q), serine (S), or threonine (T). In some embodiments, $X_{22}$ is leucine (L) or aspartic acid (D). In some embodiments, $X_{23}$ is arginine (R), glutamine (Q), glutamic acid (E), aspartic acid (D), asparagine (N), serine (S), or threonine (T). In some embodiments, $X_{23}$ is arginine (R), glutamine (Q), or glutamic acid (E). In some embodiments, $X_{21}$ is arginine (R) or absent, $X_{22}$ is leucine (L) or aspartic acid (D), and $X_{23}$ is arginine (R), glutamine (Q), or glutamic acid (E).

The disclosure provides human relaxin-2 A chain derivatives, wherein the derivatives comprise an amino acid sequence that has 0, 1, 2, 3, 4, or 5 amino acid modifications relative to the amino acid sequence of SEQ ID NO: 8 wherein the amino acid at position 22 of the second peptide is not arginine (R).

In some embodiments, the human relaxin-2 A chain derivatives comprise or consist of the following formula: $QLYSALANX_4CCX_5VGCTX_6X_7SLAQFC$ (SEQ ID NO: 16), wherein $X_4$ is lysine (K), glutamine (Q), aspartic acid (D), glutamic acid (E), leucine (L), isoleucine (I), or tyrosine (Y); $X_5$ is histidine (H), lysine (K), glutamine (Q), tyrosine (Y), leucine (L), asparagine (N), isoleucine (I), serine (S), threonine (T), or phenylalanine (F); $X_6$ is lysine (K), glutamine (Q), aspartic acid (D), glutamic acid (E), leucine (L), isoleucine (I), or tyrosine (Y); and $X_7$ is glutamine (Q), aspartic acid (D), glutamic acid (E), leucine (L), isoleucine (I), tyrosine (Y), or arginine (R). In some embodiments, the human relaxin-2 A chain derivatives comprise or consist of the following formula: $QLYSALANX_4CCX_5VGCTX_6X_7SLAQFC$ (SEQ ID NO: 16), wherein $X_4$ is lysine (K), glutamine (Q), aspartic acid (D), glutamic acid (E), leucine (L), isoleucine (I), or tyrosine (Y); $X_5$ is any amino acid except methionine (M), tryptophan (W), and cysteine (C); $X_6$ is lysine (K), glutamine (Q), aspartic acid (D), glutamic acid (E), leucine (L), isoleucine (I), or tyrosine (Y); and $X_7$ is glutamine (Q), aspartic acid (D), glutamic acid (E), leucine (L), isoleucine (I), tyrosine (Y), or arginine (R).

In some embodiments, the human relaxin-2 A chain derivatives comprise an amino acid sequence that has 0, 1, 2, 3, 4, or 5 amino acid modifications relative to the amino acid sequence of SEQ ID NO: 503 or 504. In some embodiments, the human relaxin-2 A chain derivatives comprise or consist of the following formula: $X_{12}CCX_{13}VGCTX_{14}X_{15}SLAX_{16}FC$ (SEQ ID NO: 506), wherein $X_{12}$ is lysine (K), glutamine (Q), aspartic acid (D), glutamic acid (E), leucine (L), isoleucine (I), or tyrosine (Y); $X_{13}$ is histidine (H), lysine (K), glutamine (Q), tyrosine (Y), leucine (L), asparagine (N), isoleucine (I), serine (S), threonine (T), or phenylalanine (F); $X_{14}$ is lysine (K), glutamine (Q), aspartic acid (D), glutamic acid (E), leucine (L), isoleucine (I), or tyrosine (Y); $X_{15}$ is glutamine (Q), aspartic acid (D), glutamic acid (E), leucine (L), isoleucine (I), tyrosine (Y), or arginine (R); and $X_{16}$ is arginine (R) or glutamine (Q). In some embodiments, the human relaxin-2 A chain derivatives comprise or consist of the following formula: $X_{12}CCX_{13}VGCTX_{14}X_{15}SLAX_{16}FC$ (SEQ ID NO: 506), wherein $X_{12}$ is lysine (K), glutamine (Q), aspartic acid (D), glutamic acid (E), leucine (L), isoleucine (I), or tyrosine (Y); $X_{13}$ is histidine (H), lysine (K), glutamine (Q), tyrosine (Y), leucine (L), asparagine (N), isoleucine (I), serine (S), threonine (T), or phenylalanine (F); $X_{14}$ is lysine (K), glutamine (Q), aspartic acid (D), glutamic acid (E), leucine (L), isoleucine (I), or tyrosine (Y); $X_{15}$ is glutamine (Q), aspartic acid (D), glutamic acid (E), leucine (L), isoleucine (I), tyrosine (Y), or arginine (R); and $X_{16}$ is arginine (R), glutamine (Q), glutamic acid (E), aspartic acid (D), asparagine (N), serine (S), or threonine (T). In some embodiments, the human relaxin-2 A chain derivatives comprise or consist of the following formula: $X_{12}CCX_{13}VGCTX_{14}X_{15}SLAX_{16}FC$ (SEQ ID NO: 506), wherein $X_{12}$ is lysine (K), glutamine (Q), aspartic acid (D), glutamic acid (E), leucine (L), isoleucine (I), or tyrosine (Y); $X_{13}$ is any amino acid except methionine (M), tryptophan (W), and cysteine (C); $X_{14}$ is lysine (K), glutamine (Q), aspartic acid (D), glutamic acid (E), leucine (L), isoleucine (I), or tyrosine (Y); $X_{15}$ is glutamine (Q), aspartic acid (D), glutamic acid (E), leucine (L), isoleucine (I), tyrosine (Y), or arginine (R); and $X_{16}$ is arginine (R) or glutamine (Q). In some embodiments, the human relaxin-2 A chain derivatives comprise or consist of the following formula: $X_{12}CCX_{13}VGCTX_{14}X_{15}SLAX_{16}FC$ (SEQ ID NO: 506), wherein $X_{12}$ is lysine (K), glutamine (Q), aspartic acid (D), glutamic acid (E), leucine (L), isoleucine (I), or tyrosine (Y); $X_{13}$ is any amino acid except methionine (M), tryptophan (W), and cysteine (C); $X_{14}$ is lysine (K), glutamine (Q), aspartic acid (D), glutamic acid (E), leucine (L), isoleucine (I), or tyrosine (Y); $X_{15}$ is glutamine (Q), aspartic acid (D), glutamic acid (E), leucine (L), isoleucine (I), tyrosine (Y), or arginine (R); and $X_{16}$ is arginine (R), glutamine (Q), glutamic acid (E), aspartic acid (D), asparagine (N), serine (S), or threonine (T).

In some embodiments, the human relaxin-2 A chain derivatives are from 19, 20, 21, 22, 23, 24, 25, 26, 27, 28, 29, or 30 amino acids in length. In some embodiments, the human relaxin-2 A chain derivatives are 22, 23, 24, 25, or 26 amino acids in length. In some embodiments, the human relaxin-2 A chain derivatives are 24 amino acids in length. In some embodiments, the human relaxin-2 A chain derivatives are 25 amino acids in length. In some embodiments, the human relaxin-2 A chain derivatives are 16-25 amino acids in length. In some embodiments, the human relaxin-2 A chain derivatives are 16, 17, 18, 19, 20, 21, 22, 23, 24, or 25 amino acids in length.

In some embodiments, the human relaxin-2 A chain derivatives comprise or consist of the amino acid sequences shown in Table 2, below.

TABLE 2

Human Relaxin-2 A Chain Derivative Sequences

| SEQ ID NO: | Amino Acid Sequence |
|---|---|
| 8 | QLYSALANKCCHVGCTKRSLAQFC |
| 9 | QLYSALANKCCHVGCTKQSLAQFC |
| 10 | QLYSALANKCCYVGCTKRSLAQFC |
| 11 | QLYSALANKCCLVGCTKRSLAQFC |
| 12 | QLYSALANKCCQVGCTKRSLAQFC |
| 13 | QLYSALANKCCKVGCTKRSLAQFC |
| 14 | QLYSALANKCCYVGCTKQSLAQFC |
| 15 | QLYSALANKCCKVGCTKQSLAQFC |
| 257 | QLYSALANKCCHVGCTKRSLARFC |
| 259 | RQLYSALANKCCHVGCTKRSLARFC |
| 260 | RQLYSALANKCCHVGCTKRSLAQFC |
| 261 | RQLYSALANKCCHVGCTKRSLAEFC |
| 503 | KCCHVGCTKRSLARFC |
| 504 | KCCHVGCTKRSLAQFC |
| 507 | QLYSALANKCCQVGCTKQSLAQFC |
| 550 | QLYSALANKCCHVGCTKRSLAEFC |
| 551 | RQLYSALANKCCHVGCTKQSLAQFC |
| 552 | RQLYSALANKCCYVGCTKRSLAQFC |
| 553 | RQLYSALANKCCLVGCTKRSLAQFC |
| 554 | RQLYSALANKCCQVGCTKRSLAQFC |
| 555 | RQLYSALANKCCKVGCTKRSLAQFC |
| 556 | RQLYSALANKCCYVGCTKQSLAQFC |
| 557 | RQLYSALANKCCKVGCTKQSLAQFC |
| 558 | RQLYSALANKCCQVGCTKQSLAQFC |

In some embodiments, the human relaxin-2 A chain derivatives comprise or consist of SEQ ID NO: 8. In some embodiments, the human relaxin-2 A chain derivatives comprise or consist of SEQ ID NO: 9. In some embodiments, the human relaxin-2 A chain derivatives comprise or consist of SEQ ID NO: 10. In some embodiments, the human relaxin-2 A chain derivatives comprise or consist of SEQ ID NO: 11. In some embodiments, the human relaxin-2 A chain derivatives comprise or consist of SEQ ID NO: 12. In some embodiments, the human relaxin-2 A chain derivatives comprise or consist of SEQ ID NO: 13. In some embodiments, the human relaxin-2 A chain derivatives comprise or consist of SEQ ID NO: 14. In some embodiments, the human relaxin-2 A chain derivatives comprise or consist of SEQ ID NO: 15. In some embodiments, the human relaxin-2 A chain derivatives comprise or consist of SEQ ID NO: 257. In some embodiments, the human relaxin-2 A chain derivatives comprise or consist of SEQ ID NO: 259. In some embodiments, the human relaxin-2 A chain derivatives comprise or consist of SEQ ID NO: 260. In some embodiments, the human relaxin-2 A chain derivatives comprise or consist of SEQ ID NO: 261. In some embodiments, the human relaxin-2 A chain derivatives comprise or consist of SEQ ID NO: 503. In some embodiments, the human relaxin-2 A chain derivatives comprise or consist of SEQ ID NO: 504. In some embodiments, the human relaxin-2 A chain derivatives comprise or consist of SEQ ID NO: 507. In some embodiments, the human relaxin-2 A chain derivatives comprise or consist of SEQ ID NO: 550. In some embodiments, the human relaxin-2 A chain derivatives comprise or consist of SEQ ID NO: 551. In some embodiments, the human relaxin-2 A chain derivatives comprise or consist of SEQ ID NO: 552. In some embodiments, the human relaxin-2 A chain derivatives comprise or consist of SEQ ID NO: 553. In some embodiments, the human relaxin-2 A chain derivatives comprise or consist of SEQ ID NO: 554. In some embodiments, the human relaxin-2 A chain derivatives comprise or consist of SEQ ID NO: 555. In some embodiments, the human relaxin-2 A chain derivatives comprise or consist of SEQ ID NO: 556. In some embodiments, the human relaxin-2 A chain derivatives comprise or consist of SEQ ID NO: 557. In some embodiments, the human relaxin-2 A chain derivatives comprise or consist of SEQ ID NO: 558.

In some embodiments, the human relaxin-2 A chain derivatives comprise or consist of SEQ ID NO: 8, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 9, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 10, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 11, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 12, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 13, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 14, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 15, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 257, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 259, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 260, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 261, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 503, wherein the amino acid at position 1 is lysine (K), glutamine (Q), aspartic acid (D), glutamic acid (E), leucine (L), isoleucine (I), or tyrosine (Y); the amino acid at position 9 is lysine (K), glutamine (Q), aspartic acid (D), glutamic acid (E), leucine (L), isoleucine (I), or tyrosine (Y); and the amino acid at position 10 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 504, wherein the amino acid at position 1 is lysine (K), glutamine (Q), aspartic acid (D), glutamic acid (E), leucine (L), isoleucine (I), or tyrosine (Y); the amino acid at position 9 is lysine (K), glutamine (Q), aspartic acid (D), glutamic acid (E), leucine (L), isoleucine (I), or tyrosine (Y); and the amino acid at position 10 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 507, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 550, wherein the amino acid at position 9 is lysine (K), glutamine (Q), aspartic acid (D), glutamic acid (E), leucine (L), isoleucine (I), or tyrosine (Y); the amino acid at position 17 is lysine (K), glutamine (Q), aspartic acid (D), glutamic acid (E), leucine (L), isoleucine (I), or tyrosine (Y); and the amino acid at position 18 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 550, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 551, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 553, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 554, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 555, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 556, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 557, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R). In some embodiments, the human relaxin-2 A chain derivatives comprise or consist of SEQ ID NO: 558, wherein the amino acid at position 10 is lysine (K), glutamine (Q), aspartic acid (D), glutamic acid (E), leucine (L), isoleucine (I), or tyrosine (Y); the amino acid at position 18 is lysine (K), glutamine (Q), aspartic acid (D), glutamic acid (E), leucine (L), isoleucine (I), or tyrosine (Y); and the amino acid at position 19 is glutamine (Q), aspartic acid (D), glutamic acid (E), leucine (L), isoleucine (I), tyrosine (Y), or arginine (R).

In some embodiments, the human relaxin-2 A chain derivatives further comprise one or more substitutions that improve the stability of the relaxin-2 A chain derivatives, e.g., stability of the relaxin-2 A chain derivatives after light or heat exposure, as measured by methods known in the art, e.g., SEC to assess aggregate formation, and CE-SDS to assess purity. In some embodiments, the amino acid in the human relaxin-2 A chain derivatives corresponding to amino acid position 12 in SEQ ID NO: 12 is a glutamine (Q).

Linker Peptides

The disclosure provides linker peptides, wherein the peptides have at least two acidic amino acids. In some embodiments, the acidic amino acid is glutamate. In some embodiments, the acidic amino acid is aspartate. In some embodiments, the acidic amino acid is a non-standard amino acid. In some embodiments, the acidic amino acid is 2-aminoadipic acid, 2-aminobutyric acid or 2-aminopimelic acid. In some embodiments, the linker peptide has 2, 3, 4, 5, 6, 7, 8, 9, or 10 acidic amino acids.

In some embodiments, the linker peptide is 8, 9, 10, 11, 12, 13, 14, or 15 amino acids in length. In some embodiments, the linker peptide is 12, 13, 14, or 15 amino acids in length. In some embodiments, the linker peptide has 2, 3, 4, or 5 acidic amino acids. In some embodiments, the linker peptide is 12, 13, 14, or 15 amino acids in length and has 2, 3, 4, or 5 acidic amino acids. In some embodiments, the remaining amino acids are non-acidic amino acids. In some embodiments, the non-acidic amino acids can be any standard amino acid that is not aspartate or glutamate. In some embodiments, non-acidic amino acids can be any amino acid that does not have a carboxylic acid in its side chain. In some embodiments, the non-acidic amino acid is glycine, proline, serine, arginine, histidine, lysine, threonine, asparagine, glutamine, cysteine, alanine, valine, isoleucine, leucine, methionine, phenylalanine, tyrosine, or tryptophan. In some embodiments, the non-acidic amino acid is glycine, proline, or cysteine. In some embodiments, the non-acidic amino acid is glycine.

In some embodiments, the linker peptide comprises acidic amino acids, wherein all the acidic amino acids are the same amino acids. In some embodiments, the acidic amino acids in the linker peptide are both/all glutamates. In some embodiments, the acidic amino acids in the linker peptide are both/all aspartates. In some embodiments, the linker peptide comprises amino acids that are a mixture of acidic amino acids. In some embodiments, the linker peptide comprises both glutamate and aspartate as acidic amino acids.

In some embodiments, the linker peptide comprises an amino acid sequence selected from the group consisting of $X_{17}X_{17}X_{17}X_{18}X_{17}X_{17}X_{17}X_{18}X_{17}X_{17}X_{17}X_{18}X_{17}$;

$X_{17}X_{17}X_{17}X_{18}X_{17}X_{17}X_{17}X_{18}X_{17}X_{17}X_{17}X_{18}X_{17}X_{17}X_{17}$;

$X_{17}X_{17}X_{18}X_{17}X_{17}X_{17}X_{18}X_{18}X_{17}X_{17}X_{17}X_{18}X_{17}X_{17}$;

$X_{17}X_{17}X_{17}X_{18}X_{18}X_{17}X_{17}X_{17}X_{18}X_{18}X_{17}X_{17}X_{17}$;
and $X_{17}X_{17}X_{18}X_{17}X_{18}X_{17}X_{17}X_{18}X_{17}X_{18}X_{17}X_{17}X_{17}$, wherein $X_{17}$ is a non-acidic amino acid and $X_{18}$ is an acidic amino acid.

In some embodiments, the linker peptide comprises non-acidic amino acids, wherein all the non-acidic amino acids are the same amino acids. In some embodiments, the non-acidic amino acids in the linker peptide are all glycine. In some embodiments, the linker peptide comprises amino acids that are a mixture of non-acidic amino acids. In some embodiments, the linker peptide comprises 2, 3, 4, 5, 6, 7, 8, 9, or 10 different types of non-acidic amino acids.

In some embodiments, the linker peptide comprises the amino acid sequence ASDAAGAX$_8$AX$_9$AGA (SEQ ID NO: 17), wherein $X_8$ is aspartic acid (D), glutamic acid (E), asparagine (N), or glutamine (Q); and $X_9$ is aspartic acid (D), glutamic acid (E), asparagine (N), or glutamine (Q). In some embodiments, $X_8$ is aspartic acid (D), glutamic acid (E), asparagine (N), or glutamine (Q), and $X_9$ is aspartic acid (D), glutamic acid (E), or glutamine (Q). In some embodiments, $X_8$ is aspartic acid (D), glutamic acid (E), or glutamine (Q), and $X_9$ is aspartic acid (D), glutamic acid (E), asparagine (N), or glutamine (Q).

In some embodiments, the linker peptide comprises GGEGSGGEGX$_{10}$GGG (SEQ ID NO: 25), wherein $X_{10}$ is glutamic acid (E) or serine (S).

In some embodiments, the linker peptide comprises or consists of the amino acid sequences shown in Table 3, below.

TABLE 3

Linker Peptide Sequences

| SEQ ID NO: | Amino Acid Sequence |
|---|---|
| 18 | ASDAAGADADAGA |
| 19 | ASDAAGADANAGA |
| 20 | ASDAAGADAQAGA |
| 21 | ASDAAGAEAEAGA |
| 22 | ASDAAGANADAGA |
| 23 | ASDAAGAQADAGA |
| 24 | ASDAAGAQAQAGA |
| 26 | GGEGSGGEGEGGG |
| 27 | GGEGSGGEGSGGG |
| 267 | GGGE |
| 268 | GEGE |
| 269 | GGEG |
| 270 | GEGG |
| 271 | GGEE |
| 272 | GGGEGGGEGGGEG |
| 273 | GGGEGGGEGGGEGGG |
| 274 | GEGGGEEGGGEGG |
| 275 | GGGEEGGGEEGGG |
| 276 | GGEGEGGEGEGGS |

In some embodiments, the linker peptide comprises 2, 3, 4, or 5 repeats of SEQ ID NO: 267, 268, 269, 270, or 271. For example, 3 repeats of SEQ ID NO: 267 would be the amino acid sequence of GGGEGGGEGGGE (SEQ ID NO: 277).

In some embodiments, the linker peptide comprises or consists of SEQ ID NO: 18. In some embodiments, the linker peptide comprises or consists of SEQ ID NO: 19. In some embodiments, the linker peptide comprises or consists of SEQ ID NO: 20. In some embodiments, the linker peptide comprises or consists of SEQ ID NO: 21. In some embodiments, the linker peptide comprises or consists of SEQ ID NO: 22. In some embodiments, the linker peptide comprises or consists of SEQ ID NO: 23. In some embodiments, the linker peptide comprises or consists of SEQ ID NO: 24. In some embodiments, the linker peptide comprises or consists of SEQ ID NO: 26. In some embodiments, the linker peptide comprises or consists of SEQ ID NO: 27. In some embodiments, the linker peptide comprises or consists of SEQ ID NO: 267. In some embodiments, the linker peptide comprises or consists of SEQ ID NO: 268. In some embodiments, the linker peptide comprises or consists of SEQ ID NO: 269. In some embodiments, the linker peptide comprises or consists of SEQ ID NO: 270. In some embodiments, the linker peptide comprises or consists of SEQ ID NO: 271. In some embodiments, the linker peptide comprises or consists of SEQ ID NO: 272. In some embodiments, the linker peptide comprises or consists of SEQ ID NO: 273. In some embodiments, the linker peptide comprises or consists of SEQ ID NO: 274. In some embodiments, the linker peptide comprises or consists of SEQ ID NO: 275. In some embodiments, the linker peptide comprises or consists of SEQ ID NO: 276. In some embodiments, the linker peptide comprises or consists of SEQ ID NO: 277.

Relaxin/Linker Peptide Combinations for the Fusion Protein

In some embodiments, the fusion protein comprises an N-terminal or first peptide, a linker peptide, and a C-terminal or second peptide. In some embodiments, the N-terminal peptide comprises a human relaxin-2 A chain or a derivative thereof (RelA) and the C-terminal peptide comprises a human relaxin-2 B chain or a derivative thereof (RelB). In some embodiments, the N-terminal peptide comprises a human relaxin-2 B chain or a derivative thereof and the C-terminal peptide comprises a human relaxin-2 A chain or a derivative thereof. Any combination of any of the embodiments of the human relaxin-2 A chain or a derivative thereof, with a human relaxin-2 A chain or a derivative thereof linked by any of the linker peptides disclosed herein can be used to construct embodiments of the fusion proteins described herein. In some embodiments, at least one of the N-terminal peptide and the C-terminal peptide is a derivative of a human relaxin-2 A chain or a human relaxin-2 B chain. In some embodiments, the N-terminal peptide comprises a human relaxin-2 A chain derivative and the C-terminal peptide comprises a human relaxin-2 B chain derivative. In some embodiments, the N-terminal peptide comprises a human relaxin-2 B chain derivative and the C-terminal peptide comprises a human relaxin-2 A chain derivative.

In some embodiments, the human relaxin-2 B chain derivative consists of 15 amino acids and the human relaxin-2 A chain derivative consists of 16-25 amino acids. In some embodiments, the human relaxin-2 B chain derivative consists of 16 amino acids and the human relaxin-2 A chain derivative consists of 16-25 amino acids. In some embodiments, the human relaxin-2 B chain derivative consists of 17 amino acids and the human relaxin-2 A chain derivative consists of 16-25 amino acids. In some embodiments, the human relaxin-2 B chain derivative consists of 18 amino acids and the human relaxin-2 A chain derivative consists of 16-25 amino acids. In some embodiments, the human relaxin-2 B chain derivative consists of 19 amino acids and the human relaxin-2 A chain derivative consists of 16-25 amino acids. In some embodiments, the human relaxin-2 B chain derivative consists of 20 amino acids and the human relaxin-2 A chain derivative consists of 16-25 amino acids. In some embodiments, the human relaxin-2 B chain derivative consists of 21 amino acids and the human relaxin-2 A chain derivative consists of 16-25 amino acids. In some embodiments, the human relaxin-2 B chain derivative consists of 22 amino acids and the human relaxin-2 A chain derivative consists of 16-25 amino acids. In some embodiments, the human relaxin-2 B chain derivative consists of 23 amino acids and the human relaxin-2 A chain derivative consists of 16-25 amino acids. In some embodiments, the human relaxin-2 B chain derivative consists of 24 amino acids and the human relaxin-2 A chain derivative consists of 16-25 amino acids. In some embodiments, the human relaxin-2 B chain derivative consists of 25 amino acids and the human relaxin-2 A chain derivative consists of 16-25 amino acids. In some embodiments, the human relaxin-2 B chain derivative consists of 26 amino acids and the human relaxin-2 A chain derivative consists of 16-25 amino acids. In some embodiments, the human relaxin-2 B chain derivative consists of 27 amino acids and the human relaxin-2 A chain derivative consists of 16-25 amino acids. In some embodiments, the human relaxin-2 B chain derivative consists of 28 amino acids and the human relaxin-2 A chain derivative consists of 16-25 amino acids. In some embodiments, the human relaxin-2 B chain derivative consists of 29 amino acids and the human relaxin-2 A chain derivative consists of 16-25 amino acids.

In some embodiments, the human relaxin-2 B chain derivative consists of 15-29 amino acids and the human relaxin-2 A chain derivative consists of 16 amino acids. In some embodiments, the human relaxin-2 B chain derivative consists of 15-29 amino acids and the human relaxin-2 A chain derivative consists of 17 amino acids. In some embodiments, the human relaxin-2 B chain derivative consists of 15-29 amino acids and the human relaxin-2 A chain derivative consists of 18 amino acids. In some embodiments, the human relaxin-2 B chain derivative consists of 15-29 amino acids and the human relaxin-2 A chain derivative consists of 19 amino acids. In some embodiments, the human relaxin-2 B chain derivative consists of 15-29 amino acids and the human relaxin-2 A chain derivative consists of 20 amino acids. In some embodiments, the human relaxin-2 B chain derivative consists of 15-29 amino acids and the human relaxin-2 A chain derivative consists of 21 amino acids. In some embodiments, the human relaxin-2 B chain derivative consists of 15-29 amino acids and the human relaxin-2 A chain derivative consists of 22 amino acids. In some embodiments, the human relaxin-2 B chain derivative consists of 15-29 amino acids and the human relaxin-2 A chain derivative consists of 23 amino acids. In some embodiments, the human relaxin-2 B chain derivative consists of 15-29 amino acids and the human relaxin-2 A chain derivative consists of 24 amino acids. In some embodiments, the human relaxin-2 B chain derivative consists of 15-29 amino acids and the human relaxin-2 A chain derivative consists of 25 amino acids.

Specific embodiments of the fusion proteins provided in this disclosure are shown below in Table 4.

TABLE 4

| Fusion Proteins | | | | | |
|---|---|---|---|---|---|
| N-terminal Peptide SEQ ID NO: | Linker peptide | C-terminal Peptide | N-terminal Peptide SEQ ID NO: | Linker peptide | C-terminal Peptide |
| RelB-linker (SEQ ID NO: 18)-RelA | | | RelB-linker (SEQ ID NO: 19)-RelA | | |
| 1 | 18 | 8 | 1 | 19 | 8 |
| 2 | 18 | 8 | 2 | 19 | 8 |
| 3 | 18 | 8 | 3 | 19 | 8 |
| 4 | 18 | 8 | 4 | 19 | 8 |
| 5 | 18 | 8 | 5 | 19 | 8 |
| 6 | 18 | 8 | 6 | 19 | 8 |
| 249 | 18 | 8 | 249 | 19 | 8 |
| 255 | 18 | 8 | 255 | 19 | 8 |
| 256 | 18 | 8 | 256 | 19 | 8 |
| 502 | 18 | 8 | 502 | 19 | 8 |
| 1 | 18 | 9 | 1 | 19 | 9 |
| 2 | 18 | 9 | 2 | 19 | 9 |
| 3 | 18 | 9 | 3 | 19 | 9 |
| 4 | 18 | 9 | 4 | 19 | 9 |
| 5 | 18 | 9 | 5 | 19 | 9 |
| 6 | 18 | 9 | 6 | 19 | 9 |
| 249 | 18 | 9 | 249 | 19 | 9 |
| 255 | 18 | 9 | 255 | 19 | 9 |
| 256 | 18 | 9 | 256 | 19 | 9 |
| 502 | 18 | 9 | 502 | 19 | 9 |
| 1 | 18 | 10 | 1 | 19 | 10 |
| 2 | 18 | 10 | 2 | 19 | 10 |
| 3 | 18 | 10 | 3 | 19 | 10 |
| 4 | 18 | 10 | 4 | 19 | 10 |
| 5 | 18 | 10 | 5 | 19 | 10 |
| 6 | 18 | 10 | 6 | 19 | 10 |
| 249 | 18 | 10 | 249 | 19 | 10 |
| 255 | 18 | 10 | 255 | 19 | 10 |
| 256 | 18 | 10 | 256 | 19 | 10 |
| 502 | 18 | 10 | 502 | 19 | 10 |
| 1 | 18 | 11 | 1 | 19 | 11 |
| 2 | 18 | 11 | 2 | 19 | 11 |
| 3 | 18 | 11 | 3 | 19 | 11 |
| 4 | 18 | 11 | 4 | 19 | 11 |
| 5 | 18 | 11 | 5 | 19 | 11 |
| 6 | 18 | 11 | 6 | 19 | 11 |
| 249 | 18 | 11 | 249 | 19 | 11 |
| 255 | 18 | 11 | 255 | 19 | 11 |
| 256 | 18 | 11 | 256 | 19 | 11 |
| 502 | 18 | 11 | 502 | 19 | 11 |
| 1 | 18 | 12 | 1 | 19 | 12 |
| 2 | 18 | 12 | 2 | 19 | 12 |
| 3 | 18 | 12 | 3 | 19 | 12 |
| 4 | 18 | 12 | 4 | 19 | 12 |
| 5 | 18 | 12 | 5 | 19 | 12 |
| 6 | 18 | 12 | 6 | 19 | 12 |
| 249 | 18 | 12 | 249 | 19 | 12 |
| 255 | 18 | 12 | 255 | 19 | 12 |
| 256 | 18 | 12 | 256 | 19 | 12 |
| 502 | 18 | 12 | 502 | 19 | 12 |
| 1 | 18 | 13 | 1 | 19 | 13 |
| 2 | 18 | 13 | 2 | 19 | 13 |
| 3 | 18 | 13 | 3 | 19 | 13 |
| 4 | 18 | 13 | 4 | 19 | 13 |
| 5 | 18 | 13 | 5 | 19 | 13 |
| 6 | 18 | 13 | 6 | 19 | 13 |
| 249 | 18 | 13 | 249 | 19 | 13 |
| 255 | 18 | 13 | 255 | 19 | 13 |
| 256 | 18 | 13 | 256 | 19 | 13 |
| 502 | 18 | 13 | 502 | 19 | 13 |
| 1 | 18 | 14 | 1 | 19 | 14 |
| 2 | 18 | 14 | 2 | 19 | 14 |
| 3 | 18 | 14 | 3 | 19 | 14 |
| 4 | 18 | 14 | 4 | 19 | 14 |
| 5 | 18 | 14 | 5 | 19 | 14 |
| 6 | 18 | 14 | 6 | 19 | 14 |
| 249 | 18 | 14 | 249 | 19 | 14 |
| 255 | 18 | 14 | 255 | 19 | 14 |
| 256 | 18 | 14 | 256 | 19 | 14 |
| 502 | 18 | 14 | 502 | 19 | 14 |
| 1 | 18 | 15 | 1 | 19 | 15 |
| 2 | 18 | 15 | 2 | 19 | 15 |
| 3 | 18 | 15 | 3 | 19 | 15 |
| 4 | 18 | 15 | 4 | 19 | 15 |
| 5 | 18 | 15 | 5 | 19 | 15 |
| 6 | 18 | 15 | 6 | 19 | 15 |
| 249 | 18 | 15 | 249 | 19 | 15 |
| 255 | 18 | 15 | 255 | 19 | 15 |
| 256 | 18 | 15 | 256 | 19 | 15 |
| 502 | 18 | 15 | 502 | 19 | 15 |
| 1 | 18 | 257 | 1 | 19 | 257 |
| 2 | 18 | 257 | 2 | 19 | 257 |
| 3 | 18 | 257 | 3 | 19 | 257 |
| 4 | 18 | 257 | 4 | 19 | 257 |
| 5 | 18 | 257 | 5 | 19 | 257 |
| 6 | 18 | 257 | 6 | 19 | 257 |
| 249 | 18 | 257 | 249 | 19 | 257 |
| 255 | 18 | 257 | 255 | 19 | 257 |
| 256 | 18 | 257 | 256 | 19 | 257 |
| 502 | 18 | 257 | 502 | 19 | 257 |
| 1 | 18 | 259 | 1 | 19 | 259 |
| 2 | 18 | 259 | 2 | 19 | 259 |
| 3 | 18 | 259 | 3 | 19 | 259 |
| 4 | 18 | 259 | 4 | 19 | 259 |
| 5 | 18 | 259 | 5 | 19 | 259 |
| 6 | 18 | 259 | 6 | 19 | 259 |
| 249 | 18 | 259 | 249 | 19 | 259 |
| 255 | 18 | 259 | 255 | 19 | 259 |
| 256 | 18 | 259 | 256 | 19 | 259 |

TABLE 4-continued

Fusion Proteins

| N-terminal Peptide | Linker peptide SEQ ID NO: | C-terminal Peptide | N-terminal Peptide | Linker peptide SEQ ID NO: | C-terminal Peptide |
|---|---|---|---|---|---|
| 502 | 18 | 259 | 502 | 19 | 259 |
| 1 | 18 | 260 | 1 | 19 | 260 |
| 2 | 18 | 260 | 2 | 19 | 260 |
| 3 | 18 | 260 | 3 | 19 | 260 |
| 4 | 18 | 260 | 4 | 19 | 260 |
| 5 | 18 | 260 | 5 | 19 | 260 |
| 6 | 18 | 260 | 6 | 19 | 260 |
| 249 | 18 | 260 | 249 | 19 | 260 |
| 255 | 18 | 260 | 255 | 19 | 260 |
| 256 | 18 | 260 | 256 | 19 | 260 |
| 502 | 18 | 260 | 502 | 19 | 260 |
| 1 | 18 | 261 | 1 | 19 | 26 |
| 2 | 18 | 261 | 2 | 19 | 261 |
| 3 | 18 | 261 | 3 | 19 | 261 |
| 4 | 18 | 26 | 4 | 19 | 261 |
| 5 | 18 | 261 | 5 | 19 | 261 |
| 6 | 18 | 26 | 6 | 19 | 261 |
| 249 | 18 | 26 | 249 | 19 | 261 |
| 255 | 18 | 261 | 255 | 19 | 261 |
| 256 | 18 | 261 | 256 | 19 | 261 |
| 502 | 18 | 26 | 502 | 19 | 261 |
| 1 | 18 | 503 | 1 | 19 | 503 |
| 2 | 18 | 503 | 2 | 19 | 503 |
| 3 | 18 | 503 | 3 | 19 | 503 |
| 4 | 18 | 503 | 4 | 19 | 503 |
| 5 | 18 | 503 | 5 | 19 | 503 |
| 6 | 18 | 503 | 6 | 19 | 503 |
| 249 | 18 | 503 | 249 | 19 | 503 |
| 255 | 18 | 503 | 255 | 19 | 503 |
| 256 | 18 | 503 | 256 | 19 | 503 |
| 502 | 18 | 503 | 502 | 19 | 503 |
| 1 | 18 | 504 | 1 | 19 | 504 |
| 2 | 18 | 504 | 2 | 19 | 504 |
| 3 | 18 | 504 | 3 | 19 | 504 |
| 4 | 18 | 504 | 4 | 19 | 504 |
| 5 | 18 | 504 | 5 | 19 | 504 |
| 6 | 18 | 504 | 6 | 19 | 504 |
| 249 | 18 | 504 | 249 | 19 | 504 |
| 255 | 18 | 504 | 255 | 19 | 504 |
| 256 | 18 | 504 | 256 | 19 | 504 |
| 502 | 18 | 504 | 502 | 19 | 504 |
| 1 | 18 | 507 | 1 | 19 | 507 |
| 2 | 18 | 507 | 2 | 19 | 507 |
| 3 | 18 | 507 | 3 | 19 | 507 |
| 4 | 18 | 507 | 4 | 19 | 507 |
| 5 | 18 | 507 | 5 | 19 | 507 |
| 6 | 18 | 507 | 6 | 19 | 507 |
| 249 | 18 | 507 | 249 | 19 | 507 |
| 255 | 18 | 507 | 255 | 19 | 507 |
| 256 | 18 | 507 | 256 | 19 | 507 |
| 502 | 18 | 507 | 502 | 19 | 507 |
| 1 | 18 | 550 | 1 | 19 | 550 |
| 2 | 18 | 550 | 2 | 19 | 550 |
| 3 | 18 | 550 | 3 | 19 | 550 |
| 4 | 18 | 550 | 4 | 19 | 550 |
| 5 | 18 | 550 | 5 | 19 | 550 |
| 6 | 18 | 550 | 6 | 19 | 550 |
| 249 | 18 | 550 | 249 | 19 | 550 |
| 255 | 18 | 550 | 255 | 19 | 550 |
| 256 | 18 | 550 | 256 | 19 | 550 |
| 502 | 18 | 550 | 502 | 19 | 550 |
| 1 | 18 | 551 | 1 | 19 | 551 |
| 2 | 18 | 551 | 2 | 19 | 551 |
| 3 | 18 | 551 | 3 | 19 | 551 |
| 4 | 18 | 551 | 4 | 19 | 551 |
| 5 | 18 | 551 | 5 | 19 | 551 |
| 6 | 18 | 551 | 6 | 19 | 551 |
| 249 | 18 | 551 | 249 | 19 | 551 |
| 255 | 18 | 551 | 255 | 19 | 551 |
| 256 | 18 | 551 | 256 | 19 | 551 |
| 502 | 18 | 551 | 502 | 19 | 551 |
| 1 | 18 | 552 | 1 | 19 | 552 |
| 2 | 18 | 552 | 2 | 19 | 552 |
| 3 | 18 | 552 | 3 | 19 | 552 |
| 4 | 18 | 552 | 4 | 19 | 552 |
| 5 | 18 | 552 | 5 | 19 | 552 |
| 6 | 18 | 552 | 6 | 19 | 552 |
| 249 | 18 | 552 | 249 | 19 | 552 |
| 255 | 18 | 552 | 255 | 19 | 552 |
| 256 | 18 | 552 | 256 | 19 | 552 |
| 502 | 18 | 552 | 502 | 19 | 552 |
| 1 | 18 | 553 | 1 | 19 | 553 |
| 2 | 18 | 553 | 2 | 19 | 553 |
| 3 | 18 | 553 | 3 | 19 | 553 |
| 4 | 18 | 553 | 4 | 19 | 553 |
| 5 | 18 | 553 | 5 | 19 | 553 |
| 6 | 18 | 553 | 6 | 19 | 553 |
| 249 | 18 | 553 | 249 | 19 | 553 |
| 255 | 18 | 553 | 255 | 19 | 553 |
| 256 | 18 | 553 | 256 | 19 | 553 |
| 502 | 18 | 553 | 502 | 19 | 553 |
| 1 | 18 | 554 | 1 | 19 | 554 |
| 2 | 18 | 554 | 2 | 19 | 554 |
| 3 | 18 | 554 | 3 | 19 | 554 |
| 4 | 18 | 554 | 4 | 19 | 554 |
| 5 | 18 | 554 | 5 | 19 | 554 |
| 6 | 18 | 554 | 6 | 19 | 554 |
| 249 | 18 | 554 | 249 | 19 | 554 |
| 255 | 18 | 554 | 255 | 19 | 554 |
| 256 | 18 | 554 | 256 | 19 | 554 |
| 502 | 18 | 554 | 502 | 19 | 554 |
| 1 | 18 | 555 | 1 | 19 | 555 |
| 2 | 18 | 555 | 2 | 19 | 555 |
| 3 | 18 | 555 | 3 | 19 | 555 |
| 4 | 18 | 555 | 4 | 19 | 555 |
| 5 | 18 | 555 | 5 | 19 | 555 |
| 6 | 18 | 555 | 6 | 19 | 555 |
| 249 | 18 | 555 | 249 | 19 | 555 |
| 255 | 18 | 555 | 255 | 19 | 555 |
| 256 | 18 | 555 | 256 | 19 | 555 |
| 502 | 18 | 555 | 502 | 19 | 555 |
| 1 | 18 | 556 | 1 | 19 | 556 |
| 2 | 18 | 556 | 2 | 19 | 556 |
| 3 | 18 | 556 | 3 | 19 | 556 |
| 4 | 18 | 556 | 4 | 19 | 556 |
| 5 | 18 | 556 | 5 | 19 | 556 |
| 6 | 18 | 556 | 6 | 19 | 556 |
| 249 | 18 | 556 | 249 | 19 | 556 |
| 255 | 18 | 556 | 255 | 19 | 556 |
| 256 | 18 | 556 | 256 | 19 | 556 |
| 502 | 18 | 556 | 502 | 19 | 556 |
| 1 | 18 | 557 | 1 | 19 | 557 |
| 2 | 18 | 557 | 2 | 19 | 557 |
| 3 | 18 | 557 | 3 | 19 | 557 |
| 4 | 18 | 557 | 4 | 19 | 557 |
| 5 | 18 | 557 | 5 | 19 | 557 |
| 6 | 18 | 557 | 6 | 19 | 557 |
| 249 | 18 | 557 | 249 | 19 | 557 |
| 255 | 18 | 557 | 255 | 19 | 557 |
| 256 | 18 | 557 | 256 | 19 | 557 |
| 502 | 18 | 557 | 502 | 19 | 557 |
| 1 | 18 | 558 | 1 | 19 | 558 |
| 2 | 18 | 558 | 2 | 19 | 558 |
| 3 | 18 | 558 | 3 | 19 | 558 |
| 4 | 18 | 558 | 4 | 19 | 558 |
| 5 | 18 | 558 | 5 | 19 | 558 |
| 6 | 18 | 558 | 6 | 19 | 558 |
| 249 | 18 | 558 | 249 | 19 | 558 |
| 255 | 18 | 558 | 255 | 19 | 558 |
| 256 | 18 | 558 | 256 | 19 | 558 |
| 502 | 18 | 558 | 502 | 19 | 558 |
| RelB-linker (SEQ ID NO: 20)-RelA | | | RelB-linker (SEQ ID NO: 21)-RelA | | |
| 1 | 20 | 8 | 1 | 21 | 8 |
| 2 | 20 | 8 | 2 | 21 | 8 |
| 3 | 20 | 8 | 3 | 21 | 8 |
| 4 | 20 | 8 | 4 | 21 | 8 |

TABLE 4-continued

Fusion Proteins

| N-terminal Peptide SEQ ID NO: | Linker peptide | C-terminal Peptide | N-terminal Peptide SEQ ID NO: | Linker peptide | C-terminal Peptide | N-terminal Peptide SEQ ID NO: | Linker peptide | C-terminal Peptide | N-terminal Peptide SEQ ID NO: | Linker peptide | C-terminal Peptide |
|---|---|---|---|---|---|---|---|---|---|---|---|
| 5 | 20 | 8 | 5 | 21 | 8 | 256 | 20 | 15 | 256 | 21 | 15 |
| 6 | 20 | 8 | 6 | 21 | 8 | 502 | 20 | 15 | 502 | 21 | 15 |
| 249 | 20 | 8 | 249 | 21 | 8 | 1 | 20 | 257 | 1 | 21 | 257 |
| 255 | 20 | 8 | 255 | 21 | 8 | 2 | 20 | 257 | 2 | 21 | 257 |
| 256 | 20 | 8 | 256 | 21 | 8 | 3 | 20 | 257 | 3 | 21 | 257 |
| 502 | 20 | 8 | 502 | 21 | 8 | 4 | 20 | 257 | 4 | 21 | 257 |
| 1 | 20 | 9 | 1 | 21 | 9 | 5 | 20 | 257 | 5 | 21 | 257 |
| 2 | 20 | 9 | 2 | 21 | 9 | 6 | 20 | 257 | 6 | 21 | 257 |
| 3 | 20 | 9 | 3 | 21 | 9 | 249 | 20 | 257 | 249 | 21 | 257 |
| 4 | 20 | 9 | 4 | 21 | 9 | 255 | 20 | 257 | 255 | 21 | 257 |
| 5 | 20 | 9 | 5 | 21 | 9 | 256 | 20 | 257 | 256 | 21 | 257 |
| 6 | 20 | 9 | 6 | 21 | 9 | 502 | 20 | 257 | 502 | 21 | 257 |
| 249 | 20 | 9 | 249 | 21 | 9 | 1 | 20 | 259 | 1 | 21 | 259 |
| 255 | 20 | 9 | 255 | 21 | 9 | 2 | 20 | 259 | 2 | 21 | 259 |
| 256 | 20 | 9 | 256 | 21 | 9 | 3 | 20 | 259 | 3 | 21 | 259 |
| 502 | 20 | 9 | 502 | 21 | 9 | 4 | 20 | 259 | 4 | 21 | 259 |
| 1 | 20 | 10 | 1 | 21 | 10 | 5 | 20 | 259 | 5 | 21 | 259 |
| 2 | 20 | 10 | 2 | 21 | 10 | 6 | 20 | 259 | 6 | 21 | 259 |
| 3 | 20 | 10 | 3 | 21 | 10 | 249 | 20 | 259 | 249 | 21 | 259 |
| 4 | 20 | 10 | 4 | 21 | 10 | 255 | 20 | 259 | 255 | 21 | 259 |
| 5 | 20 | 10 | 5 | 21 | 10 | 256 | 20 | 259 | 256 | 21 | 259 |
| 6 | 20 | 10 | 6 | 21 | 10 | 502 | 20 | 259 | 502 | 21 | 259 |
| 249 | 20 | 10 | 249 | 21 | 10 | 1 | 20 | 260 | 1 | 21 | 260 |
| 255 | 20 | 10 | 255 | 21 | 10 | 2 | 20 | 260 | 2 | 21 | 260 |
| 256 | 20 | 10 | 256 | 21 | 10 | 3 | 20 | 260 | 3 | 21 | 260 |
| 502 | 20 | 10 | 502 | 21 | 10 | 4 | 20 | 260 | 4 | 21 | 260 |
| 1 | 20 | 11 | 1 | 21 | 11 | 5 | 20 | 260 | 5 | 21 | 260 |
| 2 | 20 | 11 | 2 | 21 | 11 | 6 | 20 | 260 | 6 | 21 | 260 |
| 3 | 20 | 11 | 3 | 21 | 11 | 249 | 20 | 260 | 249 | 21 | 260 |
| 4 | 20 | 11 | 4 | 21 | 11 | 255 | 20 | 260 | 255 | 21 | 260 |
| 5 | 20 | 11 | 5 | 21 | 11 | 256 | 20 | 260 | 256 | 21 | 260 |
| 6 | 20 | 11 | 6 | 21 | 11 | 502 | 20 | 260 | 502 | 21 | 260 |
| 249 | 20 | 11 | 249 | 21 | 11 | 1 | 20 | 261 | 1 | 21 | 261 |
| 255 | 20 | 11 | 255 | 21 | 11 | 2 | 20 | 261 | 2 | 21 | 261 |
| 256 | 20 | 11 | 256 | 21 | 11 | 3 | 20 | 261 | 3 | 21 | 261 |
| 502 | 20 | 11 | 502 | 21 | 11 | 4 | 20 | 261 | 4 | 21 | 261 |
| 1 | 20 | 12 | 1 | 21 | 12 | 5 | 20 | 261 | 5 | 21 | 261 |
| 2 | 20 | 12 | 2 | 21 | 12 | 6 | 20 | 261 | 6 | 21 | 261 |
| 3 | 20 | 12 | 3 | 21 | 12 | 249 | 20 | 261 | 249 | 21 | 261 |
| 4 | 20 | 12 | 4 | 21 | 12 | 255 | 20 | 261 | 255 | 21 | 261 |
| 5 | 20 | 12 | 5 | 21 | 12 | 256 | 20 | 261 | 256 | 21 | 261 |
| 6 | 20 | 12 | 6 | 21 | 12 | 502 | 20 | 261 | 502 | 21 | 261 |
| 249 | 20 | 12 | 249 | 21 | 12 | 1 | 20 | 503 | 1 | 21 | 503 |
| 255 | 20 | 12 | 255 | 21 | 12 | 2 | 20 | 503 | 2 | 21 | 503 |
| 256 | 20 | 12 | 256 | 21 | 12 | 3 | 20 | 503 | 3 | 21 | 503 |
| 502 | 20 | 12 | 502 | 21 | 12 | 4 | 20 | 503 | 4 | 21 | 503 |
| 1 | 20 | 13 | 1 | 21 | 13 | 5 | 20 | 503 | 5 | 21 | 503 |
| 2 | 20 | 13 | 2 | 21 | 13 | 6 | 20 | 503 | 6 | 21 | 503 |
| 3 | 20 | 13 | 3 | 21 | 13 | 249 | 20 | 503 | 249 | 21 | 503 |
| 4 | 20 | 13 | 4 | 21 | 13 | 255 | 20 | 503 | 255 | 21 | 503 |
| 5 | 20 | 13 | 5 | 21 | 13 | 256 | 20 | 503 | 256 | 21 | 503 |
| 6 | 20 | 13 | 6 | 21 | 13 | 502 | 20 | 503 | 502 | 21 | 503 |
| 249 | 20 | 13 | 249 | 21 | 13 | 1 | 20 | 504 | 1 | 21 | 504 |
| 255 | 20 | 13 | 255 | 21 | 13 | 2 | 20 | 504 | 2 | 21 | 504 |
| 256 | 20 | 13 | 256 | 21 | 13 | 3 | 20 | 504 | 3 | 21 | 504 |
| 502 | 20 | 13 | 502 | 21 | 13 | 4 | 20 | 504 | 4 | 21 | 504 |
| 1 | 20 | 14 | 1 | 21 | 14 | 5 | 20 | 504 | 5 | 21 | 504 |
| 2 | 20 | 14 | 2 | 21 | 14 | 6 | 20 | 504 | 6 | 21 | 504 |
| 3 | 20 | 14 | 3 | 21 | 14 | 249 | 20 | 504 | 249 | 21 | 504 |
| 4 | 20 | 14 | 4 | 21 | 14 | 255 | 20 | 504 | 255 | 21 | 504 |
| 5 | 20 | 14 | 5 | 21 | 14 | 256 | 20 | 504 | 256 | 21 | 504 |
| 6 | 20 | 14 | 6 | 21 | 14 | 502 | 20 | 504 | 502 | 21 | 504 |
| 249 | 20 | 14 | 249 | 21 | 14 | 1 | 20 | 507 | 1 | 21 | 507 |
| 255 | 20 | 14 | 255 | 21 | 14 | 2 | 20 | 507 | 2 | 21 | 507 |
| 256 | 20 | 14 | 256 | 21 | 14 | 3 | 20 | 507 | 3 | 21 | 507 |
| 502 | 20 | 14 | 502 | 21 | 14 | 4 | 20 | 507 | 4 | 21 | 507 |
| 1 | 20 | 15 | 1 | 21 | 15 | 5 | 20 | 507 | 5 | 21 | 507 |
| 2 | 20 | 15 | 2 | 21 | 15 | 6 | 20 | 507 | 6 | 21 | 507 |
| 3 | 20 | 15 | 3 | 21 | 15 | 249 | 20 | 507 | 249 | 21 | 507 |
| 4 | 20 | 15 | 4 | 21 | 15 | 255 | 20 | 507 | 255 | 21 | 507 |
| 5 | 20 | 15 | 5 | 21 | 15 | 256 | 20 | 507 | 256 | 21 | 507 |
| 6 | 20 | 15 | 6 | 21 | 15 | 502 | 20 | 507 | 502 | 21 | 507 |
| 249 | 20 | 15 | 249 | 21 | 15 | 1 | 20 | 550 | 1 | 21 | 550 |
| 255 | 20 | 15 | 255 | 21 | 15 | 2 | 20 | 550 | 2 | 21 | 550 |

TABLE 4-continued

Fusion Proteins

| N-terminal Peptide | Linker peptide | C-terminal Peptide | N-terminal Peptide | Linker peptide | C-terminal Peptide | N-terminal Peptide | Linker peptide | C-terminal Peptide | N-terminal Peptide | Linker peptide | C-terminal Peptide |
|---|---|---|---|---|---|---|---|---|---|---|---|
| SEQ ID NO: | | | SEQ ID NO: | | | SEQ ID NO: | | | SEQ ID NO: | | |
| 3 | 20 | 550 | 3 | 21 | 550 | 249 | 20 | 557 | 249 | 21 | 557 |
| 4 | 20 | 550 | 4 | 21 | 550 | 255 | 20 | 557 | 255 | 21 | 557 |
| 5 | 20 | 550 | 5 | 21 | 550 | 256 | 20 | 557 | 256 | 21 | 557 |
| 6 | 20 | 550 | 6 | 21 | 550 | 502 | 20 | 557 | 502 | 21 | 557 |
| 249 | 20 | 550 | 249 | 21 | 550 | 1 | 20 | 558 | 1 | 21 | 558 |
| 255 | 20 | 550 | 255 | 21 | 550 | 2 | 20 | 558 | 2 | 21 | 558 |
| 256 | 20 | 550 | 256 | 21 | 550 | 3 | 20 | 558 | 3 | 21 | 558 |
| 502 | 20 | 550 | 502 | 21 | 550 | 4 | 20 | 558 | 4 | 21 | 558 |
| 1 | 20 | 551 | 1 | 21 | 551 | 5 | 20 | 558 | 5 | 21 | 558 |
| 2 | 20 | 551 | 2 | 21 | 551 | 6 | 20 | 558 | 6 | 21 | 558 |
| 3 | 20 | 551 | 3 | 21 | 551 | 249 | 20 | 558 | 249 | 21 | 558 |
| 4 | 20 | 551 | 4 | 21 | 551 | 255 | 20 | 558 | 255 | 21 | 558 |
| 5 | 20 | 551 | 5 | 21 | 551 | 256 | 20 | 558 | 256 | 21 | 558 |
| 6 | 20 | 551 | 6 | 21 | 551 | 502 | 20 | 558 | 502 | 21 | 558 |
| 249 | 20 | 551 | 249 | 21 | 551 | RelB-linker (SEQ ID NO: 22)-RelA | | | RelB-linker (SEQ ID NO: 23)-RelA | | |
| 255 | 20 | 551 | 255 | 21 | 551 | | | | | | |
| 256 | 20 | 551 | 256 | 21 | 551 | | | | | | |
| 502 | 20 | 551 | 502 | 21 | 551 | 1 | 22 | 8 | 1 | 23 | 8 |
| 1 | 20 | 552 | 1 | 21 | 552 | 2 | 22 | 8 | 2 | 23 | 8 |
| 2 | 20 | 552 | 2 | 21 | 552 | 3 | 22 | 8 | 3 | 23 | 8 |
| 3 | 20 | 552 | 3 | 21 | 552 | 4 | 22 | 8 | 4 | 23 | 8 |
| 4 | 20 | 552 | 4 | 21 | 552 | 5 | 22 | 8 | 5 | 23 | 8 |
| 5 | 20 | 552 | 5 | 21 | 552 | 6 | 22 | 8 | 6 | 23 | 8 |
| 6 | 20 | 552 | 6 | 21 | 552 | 249 | 22 | 8 | 249 | 23 | 8 |
| 249 | 20 | 552 | 249 | 21 | 552 | 255 | 22 | 8 | 255 | 23 | 8 |
| 255 | 20 | 552 | 255 | 21 | 552 | 256 | 22 | 8 | 256 | 23 | 8 |
| 256 | 20 | 552 | 256 | 21 | 552 | 502 | 22 | 8 | 502 | 23 | 8 |
| 502 | 20 | 552 | 502 | 21 | 552 | 1 | 22 | 9 | 1 | 23 | 9 |
| 1 | 20 | 553 | 1 | 21 | 553 | 2 | 22 | 9 | 2 | 23 | 9 |
| 2 | 20 | 553 | 2 | 21 | 553 | 3 | 22 | 9 | 3 | 23 | 9 |
| 3 | 20 | 553 | 3 | 21 | 553 | 4 | 22 | 9 | 4 | 23 | 9 |
| 4 | 20 | 553 | 4 | 21 | 553 | 5 | 22 | 9 | 5 | 23 | 9 |
| 5 | 20 | 553 | 5 | 21 | 553 | 6 | 22 | 9 | 6 | 23 | 9 |
| 6 | 20 | 553 | 6 | 21 | 553 | 249 | 22 | 9 | 249 | 23 | 9 |
| 249 | 20 | 553 | 249 | 21 | 553 | 255 | 22 | 9 | 255 | 23 | 9 |
| 255 | 20 | 553 | 255 | 21 | 553 | 256 | 22 | 9 | 256 | 23 | 9 |
| 256 | 20 | 553 | 256 | 21 | 553 | 502 | 22 | 9 | 502 | 23 | 9 |
| 502 | 20 | 553 | 502 | 21 | 553 | 1 | 22 | 10 | 1 | 23 | 10 |
| 1 | 20 | 554 | 1 | 21 | 554 | 2 | 22 | 10 | 2 | 23 | 10 |
| 2 | 20 | 554 | 2 | 21 | 554 | 3 | 22 | 10 | 3 | 23 | 10 |
| 3 | 20 | 554 | 3 | 21 | 554 | 4 | 22 | 10 | 4 | 23 | 10 |
| 4 | 20 | 554 | 4 | 21 | 554 | 5 | 22 | 10 | 5 | 23 | 10 |
| 5 | 20 | 554 | 5 | 21 | 554 | 6 | 22 | 10 | 6 | 23 | 10 |
| 6 | 20 | 554 | 6 | 21 | 554 | 249 | 22 | 10 | 249 | 23 | 10 |
| 249 | 20 | 554 | 249 | 21 | 554 | 255 | 22 | 10 | 255 | 23 | 10 |
| 255 | 20 | 554 | 255 | 21 | 554 | 256 | 22 | 10 | 256 | 23 | 10 |
| 256 | 20 | 554 | 256 | 21 | 554 | 502 | 22 | 10 | 502 | 23 | 10 |
| 502 | 20 | 554 | 502 | 21 | 554 | 1 | 22 | 11 | 1 | 23 | 11 |
| 1 | 20 | 555 | 1 | 21 | 555 | 2 | 22 | 11 | 2 | 23 | 11 |
| 2 | 20 | 555 | 2 | 21 | 555 | 3 | 22 | 11 | 3 | 23 | 11 |
| 3 | 20 | 555 | 3 | 21 | 555 | 4 | 22 | 11 | 4 | 23 | 11 |
| 4 | 20 | 555 | 4 | 21 | 555 | 5 | 22 | 11 | 5 | 23 | 11 |
| 5 | 20 | 555 | 5 | 21 | 555 | 6 | 22 | 11 | 6 | 23 | 11 |
| 6 | 20 | 555 | 6 | 21 | 555 | 249 | 22 | 11 | 249 | 23 | 11 |
| 249 | 20 | 555 | 249 | 21 | 555 | 255 | 22 | 11 | 255 | 23 | 11 |
| 255 | 20 | 555 | 255 | 21 | 555 | 256 | 22 | 11 | 256 | 23 | 11 |
| 256 | 20 | 555 | 256 | 21 | 555 | 502 | 22 | 11 | 502 | 23 | 11 |
| 502 | 20 | 555 | 502 | 21 | 555 | 1 | 22 | 12 | 1 | 23 | 12 |
| 1 | 20 | 556 | 1 | 21 | 556 | 2 | 22 | 12 | 2 | 23 | 12 |
| 2 | 20 | 556 | 2 | 21 | 556 | 3 | 22 | 12 | 3 | 23 | 12 |
| 3 | 20 | 556 | 3 | 21 | 556 | 4 | 22 | 12 | 4 | 23 | 12 |
| 4 | 20 | 556 | 4 | 21 | 556 | 5 | 22 | 12 | 5 | 23 | 12 |
| 5 | 20 | 556 | 5 | 21 | 556 | 6 | 22 | 12 | 6 | 23 | 12 |
| 6 | 20 | 556 | 6 | 21 | 556 | 249 | 22 | 12 | 249 | 23 | 12 |
| 249 | 20 | 556 | 249 | 21 | 556 | 255 | 22 | 12 | 255 | 23 | 12 |
| 255 | 20 | 556 | 255 | 21 | 556 | 256 | 22 | 12 | 256 | 23 | 12 |
| 256 | 20 | 556 | 256 | 21 | 556 | 502 | 22 | 12 | 502 | 23 | 12 |
| 502 | 20 | 556 | 502 | 21 | 556 | 1 | 22 | 13 | 1 | 23 | 13 |
| 1 | 20 | 557 | 1 | 21 | 557 | 2 | 22 | 13 | 2 | 23 | 13 |
| 2 | 20 | 557 | 2 | 21 | 557 | 3 | 22 | 13 | 3 | 23 | 13 |
| 3 | 20 | 557 | 3 | 21 | 557 | 4 | 22 | 13 | 4 | 23 | 13 |
| 4 | 20 | 557 | 4 | 21 | 557 | 5 | 22 | 13 | 5 | 23 | 13 |
| 5 | 20 | 557 | 5 | 21 | 557 | 6 | 22 | 13 | 6 | 23 | 13 |
| 6 | 20 | 557 | 6 | 21 | 557 | 249 | 22 | 13 | 249 | 23 | 13 |

TABLE 4-continued

Fusion Proteins

| N-terminal Peptide SEQ ID NO: | Linker peptide | C-terminal Peptide | N-terminal Peptide SEQ ID NO: | Linker peptide | C-terminal Peptide |
|---|---|---|---|---|---|
| 255 | 22 | 13 | 255 | 23 | 13 |
| 256 | 22 | 13 | 256 | 23 | 13 |
| 502 | 22 | 13 | 502 | 23 | 13 |
| 1 | 22 | 14 | 1 | 23 | 14 |
| 2 | 22 | 14 | 2 | 23 | 14 |
| 3 | 22 | 14 | 3 | 23 | 14 |
| 4 | 22 | 14 | 4 | 23 | 14 |
| 5 | 22 | 14 | 5 | 23 | 14 |
| 6 | 22 | 14 | 6 | 23 | 14 |
| 249 | 22 | 14 | 249 | 23 | 14 |
| 255 | 22 | 14 | 255 | 23 | 14 |
| 256 | 22 | 14 | 256 | 23 | 14 |
| 502 | 22 | 14 | 502 | 23 | 14 |
| 1 | 22 | 15 | 1 | 23 | 15 |
| 2 | 22 | 15 | 2 | 23 | 15 |
| 3 | 22 | 15 | 3 | 23 | 15 |
| 4 | 22 | 15 | 4 | 23 | 15 |
| 5 | 22 | 15 | 5 | 23 | 15 |
| 6 | 22 | 15 | 6 | 23 | 15 |
| 249 | 22 | 15 | 249 | 23 | 15 |
| 255 | 22 | 15 | 255 | 23 | 15 |
| 256 | 22 | 15 | 256 | 23 | 15 |
| 502 | 22 | 15 | 502 | 23 | 15 |
| 1 | 22 | 257 | 1 | 23 | 257 |
| 2 | 22 | 257 | 2 | 23 | 257 |
| 3 | 22 | 257 | 3 | 23 | 257 |
| 4 | 22 | 257 | 4 | 23 | 257 |
| 5 | 22 | 257 | 5 | 23 | 257 |
| 6 | 22 | 257 | 6 | 23 | 257 |
| 249 | 22 | 257 | 249 | 23 | 257 |
| 255 | 22 | 257 | 255 | 23 | 257 |
| 256 | 22 | 257 | 256 | 23 | 257 |
| 502 | 22 | 257 | 502 | 23 | 257 |
| 1 | 22 | 259 | 1 | 23 | 259 |
| 2 | 22 | 259 | 2 | 23 | 259 |
| 3 | 22 | 259 | 3 | 23 | 259 |
| 4 | 22 | 259 | 4 | 23 | 259 |
| 5 | 22 | 259 | 5 | 23 | 259 |
| 6 | 22 | 259 | 6 | 23 | 259 |
| 249 | 22 | 259 | 249 | 23 | 259 |
| 255 | 22 | 259 | 255 | 23 | 259 |
| 256 | 22 | 259 | 256 | 23 | 259 |
| 502 | 22 | 259 | 502 | 23 | 259 |
| 1 | 22 | 260 | 1 | 23 | 260 |
| 2 | 22 | 260 | 2 | 23 | 260 |
| 3 | 22 | 260 | 3 | 23 | 260 |
| 4 | 22 | 260 | 4 | 23 | 260 |
| 5 | 22 | 260 | 5 | 23 | 260 |
| 6 | 22 | 260 | 6 | 23 | 260 |
| 249 | 22 | 260 | 249 | 23 | 260 |
| 255 | 22 | 260 | 255 | 23 | 260 |
| 256 | 22 | 260 | 256 | 23 | 260 |
| 502 | 22 | 260 | 502 | 23 | 260 |
| 1 | 22 | 261 | 1 | 23 | 261 |
| 2 | 22 | 261 | 2 | 23 | 261 |
| 3 | 22 | 261 | 3 | 23 | 261 |
| 4 | 22 | 26 | 4 | 23 | 261 |
| 5 | 22 | 261 | 5 | 23 | 261 |
| 6 | 22 | 261 | 6 | 23 | 261 |
| 249 | 22 | 261 | 249 | 23 | 261 |
| 255 | 22 | 261 | 255 | 23 | 261 |
| 256 | 22 | 261 | 256 | 23 | 261 |
| 502 | 22 | 261 | 502 | 23 | 261 |
| 1 | 22 | 503 | 1 | 23 | 503 |
| 2 | 22 | 503 | 2 | 23 | 503 |
| 3 | 22 | 503 | 3 | 23 | 503 |
| 4 | 22 | 503 | 4 | 23 | 503 |
| 5 | 22 | 503 | 5 | 23 | 503 |
| 6 | 22 | 503 | 6 | 23 | 503 |
| 249 | 22 | 503 | 249 | 23 | 503 |
| 255 | 22 | 503 | 255 | 23 | 503 |
| 256 | 22 | 503 | 256 | 23 | 503 |
| 502 | 22 | 503 | 502 | 23 | 503 |
| 1 | 22 | 504 | 1 | 23 | 504 |
| 2 | 22 | 504 | 2 | 23 | 504 |
| 3 | 22 | 504 | 3 | 23 | 504 |
| 4 | 22 | 504 | 4 | 23 | 504 |
| 5 | 22 | 504 | 5 | 23 | 504 |
| 6 | 22 | 504 | 6 | 23 | 504 |
| 249 | 22 | 504 | 249 | 23 | 504 |
| 255 | 22 | 504 | 255 | 23 | 504 |
| 256 | 22 | 504 | 256 | 23 | 504 |
| 502 | 22 | 504 | 502 | 23 | 504 |
| 1 | 22 | 507 | 1 | 23 | 507 |
| 2 | 22 | 507 | 2 | 23 | 507 |
| 3 | 22 | 507 | 3 | 23 | 507 |
| 4 | 22 | 507 | 4 | 23 | 507 |
| 5 | 22 | 507 | 5 | 23 | 507 |
| 6 | 22 | 507 | 6 | 23 | 507 |
| 249 | 22 | 507 | 249 | 23 | 507 |
| 255 | 22 | 507 | 255 | 23 | 507 |
| 256 | 22 | 507 | 256 | 23 | 507 |
| 502 | 22 | 507 | 502 | 23 | 507 |
| 1 | 22 | 550 | 1 | 23 | 550 |
| 2 | 22 | 550 | 2 | 23 | 550 |
| 3 | 22 | 550 | 3 | 23 | 550 |
| 4 | 22 | 550 | 4 | 23 | 550 |
| 5 | 22 | 550 | 5 | 23 | 550 |
| 6 | 22 | 550 | 6 | 23 | 550 |
| 249 | 22 | 550 | 249 | 23 | 550 |
| 255 | 22 | 550 | 255 | 23 | 550 |
| 256 | 22 | 550 | 256 | 23 | 550 |
| 502 | 22 | 550 | 502 | 23 | 550 |
| 1 | 22 | 551 | 1 | 23 | 551 |
| 2 | 22 | 551 | 2 | 23 | 551 |
| 3 | 22 | 551 | 3 | 23 | 551 |
| 4 | 22 | 551 | 4 | 23 | 551 |
| 5 | 22 | 551 | 5 | 23 | 551 |
| 6 | 22 | 551 | 6 | 23 | 551 |
| 249 | 22 | 551 | 249 | 23 | 551 |
| 255 | 22 | 551 | 255 | 23 | 551 |
| 256 | 22 | 551 | 256 | 23 | 551 |
| 502 | 22 | 551 | 502 | 23 | 551 |
| 1 | 22 | 552 | 1 | 23 | 552 |
| 2 | 22 | 552 | 2 | 23 | 552 |
| 3 | 22 | 552 | 3 | 23 | 552 |
| 4 | 22 | 552 | 4 | 23 | 552 |
| 5 | 22 | 552 | 5 | 23 | 552 |
| 6 | 22 | 552 | 6 | 23 | 552 |
| 249 | 22 | 552 | 249 | 23 | 552 |
| 255 | 22 | 552 | 255 | 23 | 552 |
| 256 | 22 | 552 | 256 | 23 | 552 |
| 502 | 22 | 552 | 502 | 23 | 552 |
| 1 | 22 | 553 | 1 | 23 | 553 |
| 2 | 22 | 553 | 2 | 23 | 553 |
| 3 | 22 | 553 | 3 | 23 | 553 |
| 4 | 22 | 553 | 4 | 23 | 553 |
| 5 | 22 | 553 | 5 | 23 | 553 |
| 6 | 22 | 553 | 6 | 23 | 553 |
| 249 | 22 | 553 | 249 | 23 | 553 |
| 255 | 22 | 553 | 255 | 23 | 553 |
| 256 | 22 | 553 | 256 | 23 | 553 |
| 502 | 22 | 553 | 502 | 23 | 553 |
| 1 | 22 | 554 | 1 | 23 | 554 |
| 2 | 22 | 554 | 2 | 23 | 554 |
| 3 | 22 | 554 | 3 | 23 | 554 |
| 4 | 22 | 554 | 4 | 23 | 554 |
| 5 | 22 | 554 | 5 | 23 | 554 |
| 6 | 22 | 554 | 6 | 23 | 554 |
| 249 | 22 | 554 | 249 | 23 | 554 |
| 255 | 22 | 554 | 255 | 23 | 554 |
| 256 | 22 | 554 | 256 | 23 | 554 |
| 502 | 22 | 554 | 502 | 23 | 554 |
| 1 | 22 | 555 | 1 | 23 | 555 |
| 2 | 22 | 555 | 2 | 23 | 555 |
| 3 | 22 | 555 | 3 | 23 | 555 |
| 4 | 22 | 555 | 4 | 23 | 555 |
| 5 | 22 | 555 | 5 | 23 | 555 |

TABLE 4-continued

Fusion Proteins

| N-terminal Peptide | Linker peptide | C-terminal Peptide | N-terminal Peptide | Linker peptide | C-terminal Peptide | N-terminal Peptide | Linker peptide | C-terminal Peptide | N-terminal Peptide | Linker peptide | C-terminal Peptide |
|---|---|---|---|---|---|---|---|---|---|---|---|
| | SEQ ID NO: | | | SEQ ID NO: | | | SEQ ID NO: | | | SEQ ID NO: | |
| 6 | 22 | 555 | 6 | 23 | 555 | 249 | 24 | 11 | 249 | 26 | 11 |
| 249 | 22 | 555 | 249 | 23 | 555 | 255 | 24 | 11 | 255 | 26 | 11 |
| 255 | 22 | 555 | 255 | 23 | 555 | 256 | 24 | 11 | 256 | 26 | 11 |
| 256 | 22 | 555 | 256 | 23 | 555 | 502 | 24 | 11 | 502 | 26 | 11 |
| 502 | 22 | 555 | 502 | 23 | 555 | 1 | 24 | 12 | 1 | 26 | 12 |
| 1 | 22 | 556 | 1 | 23 | 556 | 2 | 24 | 12 | 2 | 26 | 12 |
| 2 | 22 | 556 | 2 | 23 | 556 | 3 | 24 | 12 | 3 | 26 | 12 |
| 3 | 22 | 556 | 3 | 23 | 556 | 4 | 24 | 12 | 4 | 26 | 12 |
| 4 | 22 | 556 | 4 | 23 | 556 | 5 | 24 | 12 | 5 | 26 | 12 |
| 5 | 22 | 556 | 5 | 23 | 556 | 6 | 24 | 12 | 6 | 26 | 12 |
| 6 | 22 | 556 | 6 | 23 | 556 | 249 | 24 | 12 | 249 | 26 | 12 |
| 249 | 22 | 556 | 249 | 23 | 556 | 255 | 24 | 12 | 255 | 26 | 12 |
| 255 | 22 | 556 | 255 | 23 | 556 | 256 | 24 | 12 | 256 | 26 | 12 |
| 256 | 22 | 556 | 256 | 23 | 556 | 502 | 24 | 12 | 502 | 26 | 12 |
| 502 | 22 | 556 | 502 | 23 | 556 | 1 | 24 | 13 | 1 | 26 | 13 |
| 1 | 22 | 557 | 1 | 23 | 557 | 2 | 24 | 13 | 2 | 26 | 13 |
| 2 | 22 | 557 | 2 | 23 | 557 | 3 | 24 | 13 | 3 | 26 | 13 |
| 3 | 22 | 557 | 3 | 23 | 557 | 4 | 24 | 13 | 4 | 26 | 13 |
| 4 | 22 | 557 | 4 | 23 | 557 | 5 | 24 | 13 | 5 | 26 | 13 |
| 5 | 22 | 557 | 5 | 23 | 557 | 6 | 24 | 13 | 6 | 26 | 13 |
| 6 | 22 | 557 | 6 | 23 | 557 | 249 | 24 | 13 | 249 | 26 | 13 |
| 249 | 22 | 557 | 249 | 23 | 557 | 255 | 24 | 13 | 255 | 26 | 13 |
| 255 | 22 | 557 | 255 | 23 | 557 | 256 | 24 | 13 | 256 | 26 | 13 |
| 256 | 22 | 557 | 256 | 23 | 557 | 502 | 24 | 13 | 502 | 26 | 13 |
| 502 | 22 | 557 | 502 | 23 | 557 | 1 | 24 | 14 | 1 | 26 | 14 |
| 1 | 22 | 558 | 1 | 23 | 558 | 2 | 24 | 14 | 2 | 26 | 14 |
| 2 | 22 | 558 | 2 | 23 | 558 | 3 | 24 | 14 | 3 | 26 | 14 |
| 3 | 22 | 558 | 3 | 23 | 558 | 4 | 24 | 14 | 4 | 26 | 14 |
| 4 | 22 | 558 | 4 | 23 | 558 | 5 | 24 | 14 | 5 | 26 | 14 |
| 5 | 22 | 558 | 5 | 23 | 558 | 6 | 24 | 14 | 6 | 26 | 14 |
| 6 | 22 | 558 | 6 | 23 | 558 | 249 | 24 | 14 | 249 | 26 | 14 |
| 249 | 22 | 558 | 249 | 23 | 558 | 255 | 24 | 14 | 255 | 26 | 14 |
| 255 | 22 | 558 | 255 | 23 | 558 | 256 | 24 | 14 | 256 | 26 | 14 |
| 256 | 22 | 558 | 256 | 23 | 558 | 502 | 24 | 14 | 502 | 26 | 14 |
| 502 | 22 | 558 | 502 | 23 | 558 | 1 | 24 | 15 | 1 | 26 | 15 |
| RelB-linker (SEQ ID NO: 24)-RelA | | | RelB-linker (SEQ ID NO: 26)-RelA | | | 2 | 24 | 15 | 2 | 26 | 15 |
| | | | | | | 3 | 24 | 15 | 3 | 26 | 15 |
| | | | | | | 4 | 24 | 15 | 4 | 26 | 15 |
| 1 | 24 | 8 | 1 | 26 | 8 | 5 | 24 | 15 | 5 | 26 | 15 |
| 2 | 24 | 8 | 2 | 26 | 8 | 6 | 24 | 15 | 6 | 26 | 15 |
| 3 | 24 | 8 | 3 | 26 | 8 | 249 | 24 | 15 | 249 | 26 | 15 |
| 4 | 24 | 8 | 4 | 26 | 8 | 255 | 24 | 15 | 255 | 26 | 15 |
| 5 | 24 | 8 | 5 | 26 | 8 | 256 | 24 | 15 | 256 | 26 | 15 |
| 6 | 24 | 8 | 6 | 26 | 8 | 502 | 24 | 15 | 502 | 26 | 15 |
| 249 | 24 | 8 | 249 | 26 | 8 | 1 | 24 | 257 | 1 | 26 | 257 |
| 255 | 24 | 8 | 255 | 26 | 8 | 2 | 24 | 257 | 2 | 26 | 257 |
| 256 | 24 | 8 | 256 | 26 | 8 | 3 | 24 | 257 | 3 | 26 | 257 |
| 502 | 24 | 8 | 502 | 26 | 8 | 4 | 24 | 257 | 4 | 26 | 257 |
| 1 | 24 | 9 | 1 | 26 | 9 | 5 | 24 | 257 | 5 | 26 | 257 |
| 2 | 24 | 9 | 2 | 26 | 9 | 6 | 24 | 257 | 6 | 26 | 257 |
| 3 | 24 | 9 | 3 | 26 | 9 | 249 | 24 | 257 | 249 | 26 | 257 |
| 4 | 24 | 9 | 4 | 26 | 9 | 255 | 24 | 257 | 255 | 26 | 257 |
| 5 | 24 | 9 | 5 | 26 | 9 | 256 | 24 | 257 | 256 | 26 | 257 |
| 6 | 24 | 9 | 6 | 26 | 9 | 502 | 24 | 257 | 502 | 26 | 257 |
| 249 | 24 | 9 | 249 | 26 | 9 | 1 | 24 | 259 | 1 | 26 | 259 |
| 255 | 24 | 9 | 255 | 26 | 9 | 2 | 24 | 259 | 2 | 26 | 259 |
| 256 | 24 | 9 | 256 | 26 | 9 | 3 | 24 | 259 | 3 | 26 | 259 |
| 502 | 24 | 9 | 502 | 26 | 9 | 4 | 24 | 259 | 4 | 26 | 259 |
| 1 | 24 | 10 | 1 | 26 | 10 | 5 | 24 | 259 | 5 | 26 | 259 |
| 2 | 24 | 10 | 2 | 26 | 10 | 6 | 24 | 259 | 6 | 26 | 259 |
| 3 | 24 | 10 | 3 | 26 | 10 | 249 | 24 | 259 | 249 | 26 | 259 |
| 4 | 24 | 10 | 4 | 26 | 10 | 255 | 24 | 259 | 255 | 26 | 259 |
| 5 | 24 | 10 | 5 | 26 | 10 | 256 | 24 | 259 | 256 | 26 | 259 |
| 6 | 24 | 10 | 6 | 26 | 10 | 502 | 24 | 259 | 502 | 26 | 259 |
| 249 | 24 | 10 | 249 | 26 | 10 | 1 | 24 | 260 | 1 | 26 | 260 |
| 255 | 24 | 10 | 255 | 26 | 10 | 2 | 24 | 260 | 2 | 26 | 260 |
| 256 | 24 | 10 | 256 | 26 | 10 | 3 | 24 | 260 | 3 | 26 | 260 |
| 502 | 24 | 10 | 502 | 26 | 10 | 4 | 24 | 260 | 4 | 26 | 260 |
| 1 | 24 | 11 | 1 | 26 | 11 | 5 | 24 | 260 | 5 | 26 | 260 |
| 2 | 24 | 11 | 2 | 26 | 11 | 6 | 24 | 260 | 6 | 26 | 260 |
| 3 | 24 | 11 | 3 | 26 | 11 | 249 | 24 | 260 | 249 | 26 | 260 |
| 4 | 24 | 11 | 4 | 26 | 11 | 255 | 24 | 260 | 255 | 26 | 260 |
| 5 | 24 | 11 | 5 | 26 | 11 | 256 | 24 | 260 | 256 | 26 | 260 |
| 6 | 24 | 11 | 6 | 26 | 11 | 502 | 24 | 260 | 502 | 26 | 260 |

TABLE 4-continued

Fusion Proteins

| N-terminal Peptide | Linker peptide | C-terminal Peptide | N-terminal Peptide | Linker peptide | C-terminal Peptide |
|---|---|---|---|---|---|
| SEQ ID NO: | | | SEQ ID NO: | | |
| 1 | 24 | 261 | 1 | 26 | 261 |
| 2 | 24 | 261 | 2 | 26 | 261 |
| 3 | 24 | 261 | 3 | 26 | 261 |
| 4 | 24 | 261 | 4 | 26 | 261 |
| 5 | 24 | 26 | 5 | 26 | 261 |
| 6 | 24 | 261 | 6 | 26 | 261 |
| 249 | 24 | 261 | 249 | 26 | 261 |
| 255 | 24 | 261 | 255 | 26 | 261 |
| 256 | 24 | 261 | 256 | 26 | 261 |
| 502 | 24 | 261 | 502 | 26 | 261 |
| 1 | 24 | 503 | 1 | 26 | 503 |
| 2 | 24 | 503 | 2 | 26 | 503 |
| 3 | 24 | 503 | 3 | 26 | 503 |
| 4 | 24 | 503 | 4 | 26 | 503 |
| 5 | 24 | 503 | 5 | 26 | 503 |
| 6 | 24 | 503 | 6 | 26 | 503 |
| 249 | 24 | 503 | 249 | 26 | 503 |
| 255 | 24 | 503 | 255 | 26 | 503 |
| 256 | 24 | 503 | 256 | 26 | 503 |
| 502 | 24 | 503 | 502 | 26 | 503 |
| 1 | 24 | 504 | 1 | 26 | 504 |
| 2 | 24 | 504 | 2 | 26 | 504 |
| 3 | 24 | 504 | 3 | 26 | 504 |
| 4 | 24 | 504 | 4 | 26 | 504 |
| 5 | 24 | 504 | 5 | 26 | 504 |
| 6 | 24 | 504 | 6 | 26 | 504 |
| 249 | 24 | 504 | 249 | 26 | 504 |
| 255 | 24 | 504 | 255 | 26 | 504 |
| 256 | 24 | 504 | 256 | 26 | 504 |
| 502 | 24 | 504 | 502 | 26 | 504 |
| 1 | 24 | 507 | 1 | 26 | 507 |
| 2 | 24 | 507 | 2 | 26 | 507 |
| 3 | 24 | 507 | 3 | 26 | 507 |
| 4 | 24 | 507 | 4 | 26 | 507 |
| 5 | 24 | 507 | 5 | 26 | 507 |
| 6 | 24 | 507 | 6 | 26 | 507 |
| 249 | 24 | 507 | 249 | 26 | 507 |
| 255 | 24 | 507 | 255 | 26 | 507 |
| 256 | 24 | 507 | 256 | 26 | 507 |
| 502 | 24 | 507 | 502 | 26 | 507 |
| 1 | 24 | 550 | 1 | 26 | 550 |
| 2 | 24 | 550 | 2 | 26 | 550 |
| 3 | 24 | 550 | 3 | 26 | 550 |
| 4 | 24 | 550 | 4 | 26 | 550 |
| 5 | 24 | 550 | 5 | 26 | 550 |
| 6 | 24 | 550 | 6 | 26 | 550 |
| 249 | 24 | 550 | 249 | 26 | 550 |
| 255 | 24 | 550 | 255 | 26 | 550 |
| 256 | 24 | 550 | 256 | 26 | 550 |
| 502 | 24 | 550 | 502 | 26 | 550 |
| 1 | 24 | 551 | 1 | 26 | 551 |
| 2 | 24 | 551 | 2 | 26 | 551 |
| 3 | 24 | 551 | 3 | 26 | 551 |
| 4 | 24 | 551 | 4 | 26 | 551 |
| 5 | 24 | 551 | 5 | 26 | 551 |
| 6 | 24 | 551 | 6 | 26 | 551 |
| 249 | 24 | 551 | 249 | 26 | 551 |
| 255 | 24 | 551 | 255 | 26 | 55 |
| 256 | 24 | 551 | 256 | 26 | 551 |
| 502 | 24 | 551 | 502 | 26 | 551 |
| 1 | 24 | 552 | 1 | 26 | 552 |
| 2 | 24 | 552 | 2 | 26 | 552 |
| 3 | 24 | 552 | 3 | 26 | 552 |
| 4 | 24 | 552 | 4 | 26 | 552 |
| 5 | 24 | 552 | 5 | 26 | 552 |
| 6 | 24 | 552 | 6 | 26 | 552 |
| 249 | 24 | 552 | 249 | 26 | 552 |
| 255 | 24 | 552 | 255 | 26 | 552 |
| 256 | 24 | 552 | 256 | 26 | 552 |
| 502 | 24 | 552 | 502 | 26 | 552 |
| 1 | 24 | 553 | 1 | 26 | 553 |
| 2 | 24 | 553 | 2 | 26 | 553 |
| 3 | 24 | 553 | 3 | 26 | 553 |
| 4 | 24 | 553 | 4 | 26 | 553 |
| 5 | 24 | 553 | 5 | 26 | 553 |
| 6 | 24 | 553 | 6 | 26 | 553 |
| 249 | 24 | 553 | 249 | 26 | 553 |
| 255 | 24 | 553 | 255 | 26 | 553 |
| 256 | 24 | 553 | 256 | 26 | 553 |
| 502 | 24 | 553 | 502 | 26 | 553 |
| 1 | 24 | 554 | 1 | 26 | 554 |
| 2 | 24 | 554 | 2 | 26 | 554 |
| 3 | 24 | 554 | 3 | 26 | 554 |
| 4 | 24 | 554 | 4 | 26 | 554 |
| 5 | 24 | 554 | 5 | 26 | 554 |
| 6 | 24 | 554 | 6 | 26 | 554 |
| 249 | 24 | 554 | 249 | 26 | 554 |
| 255 | 24 | 554 | 255 | 26 | 554 |
| 256 | 24 | 554 | 256 | 26 | 554 |
| 502 | 24 | 554 | 502 | 26 | 554 |
| 1 | 24 | 555 | 1 | 26 | 555 |
| 2 | 24 | 555 | 2 | 26 | 555 |
| 3 | 24 | 555 | 3 | 26 | 555 |
| 4 | 24 | 555 | 4 | 26 | 555 |
| 5 | 24 | 555 | 5 | 26 | 555 |
| 6 | 24 | 555 | 6 | 26 | 555 |
| 249 | 24 | 555 | 249 | 26 | 555 |
| 255 | 24 | 555 | 255 | 26 | 555 |
| 256 | 24 | 555 | 256 | 26 | 555 |
| 502 | 24 | 555 | 502 | 26 | 555 |
| 1 | 24 | 556 | 1 | 26 | 556 |
| 2 | 24 | 556 | 2 | 26 | 556 |
| 3 | 24 | 556 | 3 | 26 | 556 |
| 4 | 24 | 556 | 4 | 26 | 556 |
| 5 | 24 | 556 | 5 | 26 | 556 |
| 6 | 24 | 556 | 6 | 26 | 556 |
| 249 | 24 | 556 | 249 | 26 | 556 |
| 255 | 24 | 556 | 255 | 26 | 556 |
| 256 | 24 | 556 | 256 | 26 | 556 |
| 502 | 24 | 556 | 502 | 26 | 556 |
| 1 | 24 | 557 | 1 | 26 | 557 |
| 2 | 24 | 557 | 2 | 26 | 557 |
| 3 | 24 | 557 | 3 | 26 | 557 |
| 4 | 24 | 557 | 4 | 26 | 557 |
| 5 | 24 | 557 | 5 | 26 | 557 |
| 6 | 24 | 557 | 6 | 26 | 557 |
| 249 | 24 | 557 | 249 | 26 | 557 |
| 255 | 24 | 557 | 255 | 26 | 557 |
| 256 | 24 | 557 | 256 | 26 | 557 |
| 502 | 24 | 557 | 502 | 26 | 557 |
| 1 | 24 | 558 | 1 | 26 | 558 |
| 2 | 24 | 558 | 2 | 26 | 558 |
| 3 | 24 | 558 | 3 | 26 | 558 |
| 4 | 24 | 558 | 4 | 26 | 558 |
| 5 | 24 | 558 | 5 | 26 | 558 |
| 6 | 24 | 558 | 6 | 26 | 558 |
| 249 | 24 | 558 | 249 | 26 | 558 |
| 255 | 24 | 558 | 255 | 26 | 558 |
| 256 | 24 | 558 | 256 | 26 | 558 |
| 502 | 24 | 558 | 502 | 26 | 558 |
| RelB-linker (SEQ ID NO: 27)-RelA | | | RelB-linker (SEQ ID NO: 272)-RelA | | |
| 1 | 27 | 8 | 1 | 272 | 8 |
| 2 | 27 | 8 | 2 | 272 | 8 |
| 3 | 27 | 8 | 3 | 272 | 8 |
| 4 | 27 | 8 | 4 | 272 | 8 |
| 5 | 27 | 8 | 5 | 272 | 8 |
| 6 | 27 | 8 | 6 | 272 | 8 |
| 249 | 27 | 8 | 249 | 272 | 8 |
| 255 | 27 | 8 | 255 | 272 | 8 |
| 256 | 27 | 8 | 256 | 272 | 8 |
| 502 | 27 | 8 | 502 | 272 | 8 |
| 1 | 27 | 9 | 1 | 272 | 9 |
| 2 | 27 | 9 | 2 | 272 | 9 |
| 3 | 27 | 9 | 3 | 272 | 9 |
| 4 | 27 | 9 | 4 | 272 | 9 |
| 5 | 27 | 9 | 5 | 272 | 9 |

TABLE 4-continued

Fusion Proteins

| N-terminal Peptide SEQ ID NO: | Linker peptide | C-terminal Peptide | N-terminal Peptide SEQ ID NO: | Linker peptide | C-terminal Peptide | N-terminal Peptide SEQ ID NO: | Linker peptide | C-terminal Peptide | N-terminal Peptide SEQ ID NO: | Linker peptide | C-terminal Peptide |
|---|---|---|---|---|---|---|---|---|---|---|---|
| 6 | 27 | 9 | 6 | 272 | 9 | 502 | 27 | 257 | 502 | 272 | 257 |
| 249 | 27 | 9 | 249 | 272 | 9 | 1 | 27 | 259 | 1 | 272 | 259 |
| 255 | 27 | 9 | 255 | 272 | 9 | 2 | 27 | 259 | 2 | 272 | 259 |
| 256 | 27 | 9 | 256 | 272 | 9 | 3 | 27 | 259 | 3 | 272 | 259 |
| 502 | 27 | 9 | 502 | 272 | 9 | 4 | 27 | 259 | 4 | 272 | 259 |
| 1 | 27 | 10 | 1 | 272 | 10 | 5 | 27 | 259 | 5 | 272 | 259 |
| 2 | 27 | 10 | 2 | 272 | 10 | 6 | 27 | 259 | 6 | 272 | 259 |
| 3 | 27 | 10 | 3 | 272 | 10 | 249 | 27 | 259 | 249 | 272 | 259 |
| 4 | 27 | 10 | 4 | 272 | 10 | 255 | 27 | 259 | 255 | 272 | 259 |
| 5 | 27 | 10 | 5 | 272 | 10 | 256 | 27 | 259 | 256 | 272 | 259 |
| 6 | 27 | 10 | 6 | 272 | 10 | 502 | 27 | 259 | 502 | 272 | 259 |
| 249 | 27 | 10 | 249 | 272 | 10 | 1 | 27 | 260 | 1 | 272 | 260 |
| 255 | 27 | 10 | 255 | 272 | 10 | 2 | 27 | 260 | 2 | 272 | 260 |
| 256 | 27 | 10 | 256 | 272 | 10 | 3 | 27 | 260 | 3 | 272 | 260 |
| 502 | 27 | 10 | 502 | 272 | 10 | 4 | 27 | 260 | 4 | 272 | 260 |
| 1 | 27 | 11 | 1 | 272 | 11 | 5 | 27 | 260 | 5 | 272 | 260 |
| 2 | 27 | 11 | 2 | 272 | 11 | 6 | 27 | 260 | 6 | 272 | 260 |
| 3 | 27 | 11 | 3 | 272 | 11 | 249 | 27 | 260 | 249 | 272 | 260 |
| 4 | 27 | 11 | 4 | 272 | 11 | 255 | 27 | 260 | 255 | 272 | 260 |
| 5 | 27 | 11 | 5 | 272 | 11 | 256 | 27 | 260 | 256 | 272 | 260 |
| 6 | 27 | 11 | 6 | 272 | 11 | 502 | 27 | 260 | 502 | 272 | 260 |
| 249 | 27 | 11 | 249 | 272 | 11 | 1 | 27 | 261 | 1 | 272 | 261 |
| 255 | 27 | 11 | 255 | 272 | 11 | 2 | 27 | 261 | 2 | 272 | 261 |
| 256 | 27 | 11 | 256 | 272 | 11 | 3 | 27 | 261 | 3 | 272 | 261 |
| 502 | 27 | 11 | 502 | 272 | 11 | 4 | 27 | 261 | 4 | 272 | 261 |
| 1 | 27 | 12 | 1 | 272 | 12 | 5 | 27 | 261 | 5 | 272 | 261 |
| 2 | 27 | 12 | 2 | 272 | 12 | 6 | 27 | 261 | 6 | 272 | 261 |
| 3 | 27 | 12 | 3 | 272 | 12 | 249 | 27 | 261 | 249 | 272 | 261 |
| 4 | 27 | 12 | 4 | 272 | 12 | 255 | 27 | 261 | 255 | 272 | 261 |
| 5 | 27 | 12 | 5 | 272 | 12 | 256 | 27 | 261 | 256 | 272 | 261 |
| 6 | 27 | 12 | 6 | 272 | 12 | 502 | 27 | 261 | 502 | 272 | 261 |
| 249 | 27 | 12 | 249 | 272 | 12 | 1 | 27 | 503 | 1 | 272 | 503 |
| 255 | 27 | 12 | 255 | 272 | 12 | 2 | 27 | 503 | 2 | 272 | 503 |
| 256 | 27 | 12 | 256 | 272 | 12 | 3 | 27 | 503 | 3 | 272 | 503 |
| 502 | 27 | 12 | 502 | 272 | 12 | 4 | 27 | 503 | 4 | 272 | 503 |
| 1 | 27 | 13 | 1 | 272 | 13 | 5 | 27 | 503 | 5 | 272 | 503 |
| 2 | 27 | 13 | 2 | 272 | 13 | 6 | 27 | 503 | 6 | 272 | 503 |
| 3 | 27 | 13 | 3 | 272 | 13 | 249 | 27 | 503 | 249 | 272 | 503 |
| 4 | 27 | 13 | 4 | 272 | 13 | 255 | 27 | 503 | 255 | 272 | 503 |
| 5 | 27 | 13 | 5 | 272 | 13 | 256 | 27 | 503 | 256 | 272 | 503 |
| 6 | 27 | 13 | 6 | 272 | 13 | 502 | 27 | 503 | 502 | 272 | 503 |
| 249 | 27 | 13 | 249 | 272 | 13 | 1 | 27 | 504 | 1 | 272 | 504 |
| 255 | 27 | 13 | 255 | 272 | 13 | 2 | 27 | 504 | 2 | 272 | 504 |
| 256 | 27 | 13 | 256 | 272 | 13 | 3 | 27 | 504 | 3 | 272 | 504 |
| 502 | 27 | 13 | 502 | 272 | 13 | 4 | 27 | 504 | 4 | 272 | 504 |
| 1 | 27 | 14 | 1 | 272 | 14 | 5 | 27 | 504 | 5 | 272 | 504 |
| 2 | 27 | 14 | 2 | 272 | 14 | 6 | 27 | 504 | 6 | 272 | 504 |
| 3 | 27 | 14 | 3 | 272 | 14 | 249 | 27 | 504 | 249 | 272 | 504 |
| 4 | 27 | 14 | 4 | 272 | 14 | 255 | 27 | 504 | 255 | 272 | 504 |
| 5 | 27 | 14 | 5 | 272 | 14 | 256 | 27 | 504 | 256 | 272 | 504 |
| 6 | 27 | 14 | 6 | 272 | 14 | 502 | 27 | 504 | 502 | 272 | 504 |
| 249 | 27 | 14 | 249 | 272 | 14 | 1 | 27 | 507 | 1 | 272 | 507 |
| 255 | 27 | 14 | 255 | 272 | 14 | 2 | 27 | 507 | 2 | 272 | 507 |
| 256 | 27 | 14 | 256 | 272 | 14 | 3 | 27 | 507 | 3 | 272 | 507 |
| 502 | 27 | 14 | 502 | 272 | 14 | 4 | 27 | 507 | 4 | 272 | 507 |
| 1 | 27 | 15 | 1 | 272 | 15 | 5 | 27 | 507 | 5 | 272 | 507 |
| 2 | 27 | 15 | 2 | 272 | 15 | 6 | 27 | 507 | 6 | 272 | 507 |
| 3 | 27 | 15 | 3 | 272 | 15 | 249 | 27 | 507 | 249 | 272 | 507 |
| 4 | 27 | 15 | 4 | 272 | 15 | 255 | 27 | 507 | 255 | 272 | 507 |
| 5 | 27 | 15 | 5 | 272 | 15 | 256 | 27 | 507 | 256 | 272 | 507 |
| 6 | 27 | 15 | 6 | 272 | 15 | 502 | 27 | 507 | 502 | 272 | 507 |
| 249 | 27 | 15 | 249 | 272 | 15 | 1 | 27 | 550 | 1 | 272 | 550 |
| 255 | 27 | 15 | 255 | 272 | 15 | 2 | 27 | 550 | 2 | 272 | 550 |
| 256 | 27 | 15 | 256 | 272 | 15 | 3 | 27 | 550 | 3 | 272 | 550 |
| 502 | 27 | 15 | 502 | 272 | 15 | 4 | 27 | 550 | 4 | 272 | 550 |
| 1 | 27 | 257 | 1 | 272 | 257 | 5 | 27 | 550 | 5 | 272 | 550 |
| 2 | 27 | 257 | 2 | 272 | 257 | 6 | 27 | 550 | 6 | 272 | 550 |
| 3 | 27 | 257 | 3 | 272 | 257 | 249 | 27 | 550 | 249 | 272 | 550 |
| 4 | 27 | 257 | 4 | 272 | 257 | 255 | 27 | 550 | 255 | 272 | 550 |
| 5 | 27 | 257 | 5 | 272 | 257 | 256 | 27 | 550 | 256 | 272 | 550 |
| 6 | 27 | 257 | 6 | 272 | 257 | 502 | 27 | 550 | 502 | 272 | 550 |
| 249 | 27 | 257 | 249 | 272 | 257 | 1 | 27 | 551 | 1 | 272 | 551 |
| 255 | 27 | 257 | 255 | 272 | 257 | 2 | 27 | 551 | 2 | 272 | 551 |
| 256 | 27 | 257 | 256 | 272 | 257 | 3 | 27 | 551 | 3 | 272 | 551 |

TABLE 4-continued

Fusion Proteins

| N-terminal Peptide SEQ ID NO: | Linker peptide | C-terminal Peptide | N-terminal Peptide SEQ ID NO: | Linker peptide | C-terminal Peptide |
|---|---|---|---|---|---|
| 4 | 27 | 551 | 4 | 272 | 551 |
| 5 | 27 | 551 | 5 | 272 | 551 |
| 6 | 27 | 551 | 6 | 272 | 551 |
| 249 | 27 | 551 | 249 | 272 | 551 |
| 255 | 27 | 551 | 255 | 272 | 551 |
| 256 | 27 | 551 | 256 | 272 | 551 |
| 502 | 27 | 551 | 502 | 272 | 551 |
| 1 | 27 | 552 | 1 | 272 | 552 |
| 2 | 27 | 552 | 2 | 272 | 552 |
| 3 | 27 | 552 | 3 | 272 | 552 |
| 4 | 27 | 552 | 4 | 272 | 552 |
| 5 | 27 | 552 | 5 | 272 | 552 |
| 6 | 27 | 552 | 6 | 272 | 552 |
| 249 | 27 | 552 | 249 | 272 | 552 |
| 255 | 27 | 552 | 255 | 272 | 552 |
| 256 | 27 | 552 | 256 | 272 | 552 |
| 502 | 27 | 552 | 502 | 272 | 552 |
| 1 | 27 | 553 | 1 | 272 | 553 |
| 2 | 27 | 553 | 2 | 272 | 553 |
| 3 | 27 | 553 | 3 | 272 | 553 |
| 4 | 27 | 553 | 4 | 272 | 553 |
| 5 | 27 | 553 | 5 | 272 | 553 |
| 6 | 27 | 553 | 6 | 272 | 553 |
| 249 | 27 | 553 | 249 | 272 | 553 |
| 255 | 27 | 553 | 255 | 272 | 553 |
| 256 | 27 | 553 | 256 | 272 | 553 |
| 502 | 27 | 553 | 502 | 272 | 553 |
| 1 | 27 | 554 | 1 | 272 | 554 |
| 2 | 27 | 554 | 2 | 272 | 554 |
| 3 | 27 | 554 | 3 | 272 | 554 |
| 4 | 27 | 554 | 4 | 272 | 554 |
| 5 | 27 | 554 | 5 | 272 | 554 |
| 6 | 27 | 554 | 6 | 272 | 554 |
| 249 | 27 | 554 | 249 | 272 | 554 |
| 255 | 27 | 554 | 255 | 272 | 554 |
| 256 | 27 | 554 | 256 | 272 | 554 |
| 502 | 27 | 554 | 502 | 272 | 554 |
| 1 | 27 | 555 | 1 | 272 | 555 |
| 2 | 27 | 555 | 2 | 272 | 555 |
| 3 | 27 | 555 | 3 | 272 | 555 |
| 4 | 27 | 555 | 4 | 272 | 555 |
| 5 | 27 | 555 | 5 | 272 | 555 |
| 6 | 27 | 555 | 6 | 272 | 555 |
| 249 | 27 | 555 | 249 | 272 | 555 |
| 255 | 27 | 555 | 255 | 272 | 555 |
| 256 | 27 | 555 | 256 | 272 | 555 |
| 502 | 27 | 555 | 502 | 272 | 555 |
| 1 | 27 | 556 | 1 | 272 | 556 |
| 2 | 27 | 556 | 2 | 272 | 556 |
| 3 | 27 | 556 | 3 | 272 | 556 |
| 4 | 27 | 556 | 4 | 272 | 556 |
| 5 | 27 | 556 | 5 | 272 | 556 |
| 6 | 27 | 556 | 6 | 272 | 556 |
| 249 | 27 | 556 | 249 | 272 | 556 |
| 255 | 27 | 556 | 255 | 272 | 556 |
| 256 | 27 | 556 | 256 | 272 | 556 |
| 502 | 27 | 556 | 502 | 272 | 556 |
| 1 | 27 | 557 | 1 | 272 | 557 |
| 2 | 27 | 557 | 2 | 272 | 557 |
| 3 | 27 | 557 | 3 | 272 | 557 |
| 4 | 27 | 557 | 4 | 272 | 557 |
| 5 | 27 | 557 | 5 | 272 | 557 |
| 6 | 27 | 557 | 6 | 272 | 557 |
| 249 | 27 | 557 | 249 | 272 | 557 |
| 255 | 27 | 557 | 255 | 272 | 557 |
| 256 | 27 | 557 | 256 | 272 | 557 |
| 502 | 27 | 557 | 502 | 272 | 557 |
| 1 | 27 | 558 | 1 | 272 | 558 |
| 2 | 27 | 558 | 2 | 272 | 558 |
| 3 | 27 | 558 | 3 | 272 | 558 |
| 4 | 27 | 558 | 4 | 272 | 558 |
| 5 | 27 | 558 | 5 | 272 | 558 |
| 6 | 27 | 558 | 6 | 272 | 558 |
| 249 | 27 | 558 | 249 | 272 | 558 |
| 255 | 27 | 558 | 255 | 272 | 558 |
| 256 | 27 | 558 | 256 | 272 | 558 |
| 502 | 27 | 558 | 502 | 272 | 558 |
| RelB-linker (SEQ ID NO: 273)-RelA | | | RelB-linker (SEQ ID NO: 274)-RelA | | |
| 1 | 273 | 8 | 1 | 274 | 8 |
| 2 | 273 | 8 | 2 | 274 | 8 |
| 3 | 273 | 8 | 3 | 274 | 8 |
| 4 | 273 | 8 | 4 | 274 | 8 |
| 5 | 273 | 8 | 5 | 274 | 8 |
| 6 | 273 | 8 | 6 | 274 | 8 |
| 249 | 273 | 8 | 249 | 274 | 8 |
| 255 | 273 | 8 | 255 | 274 | 8 |
| 256 | 273 | 8 | 256 | 274 | 8 |
| 502 | 273 | 8 | 502 | 274 | 8 |
| 1 | 273 | 9 | 1 | 274 | 9 |
| 2 | 273 | 9 | 2 | 274 | 9 |
| 3 | 273 | 9 | 3 | 274 | 9 |
| 4 | 273 | 9 | 4 | 274 | 9 |
| 5 | 273 | 9 | 5 | 274 | 9 |
| 6 | 273 | 9 | 6 | 274 | 9 |
| 249 | 273 | 9 | 249 | 274 | 9 |
| 255 | 273 | 9 | 255 | 274 | 9 |
| 256 | 273 | 9 | 256 | 274 | 9 |
| 502 | 273 | 9 | 502 | 274 | 9 |
| 1 | 273 | 10 | 1 | 274 | 10 |
| 2 | 273 | 10 | 2 | 274 | 10 |
| 3 | 273 | 10 | 3 | 274 | 10 |
| 4 | 273 | 10 | 4 | 274 | 10 |
| 5 | 273 | 10 | 5 | 274 | 10 |
| 6 | 273 | 10 | 6 | 274 | 10 |
| 249 | 273 | 10 | 249 | 274 | 10 |
| 255 | 273 | 10 | 255 | 274 | 10 |
| 256 | 273 | 10 | 256 | 274 | 10 |
| 502 | 273 | 10 | 502 | 274 | 10 |
| 1 | 273 | 11 | 1 | 274 | 11 |
| 2 | 273 | 11 | 2 | 274 | 11 |
| 3 | 273 | 11 | 3 | 274 | 11 |
| 4 | 273 | 11 | 4 | 274 | 11 |
| 5 | 273 | 11 | 5 | 274 | 11 |
| 6 | 273 | 11 | 6 | 274 | 11 |
| 249 | 273 | 11 | 249 | 274 | 11 |
| 255 | 273 | 11 | 255 | 274 | 11 |
| 256 | 273 | 11 | 256 | 274 | 11 |
| 502 | 273 | 11 | 502 | 274 | 11 |
| 1 | 273 | 12 | 1 | 274 | 12 |
| 2 | 273 | 12 | 2 | 274 | 12 |
| 3 | 273 | 12 | 3 | 274 | 12 |
| 4 | 273 | 12 | 4 | 274 | 12 |
| 5 | 273 | 12 | 5 | 274 | 12 |
| 6 | 273 | 12 | 6 | 274 | 12 |
| 249 | 273 | 12 | 249 | 274 | 12 |
| 255 | 273 | 12 | 255 | 274 | 12 |
| 256 | 273 | 12 | 256 | 274 | 12 |
| 502 | 273 | 12 | 502 | 274 | 12 |
| 1 | 273 | 13 | 1 | 274 | 13 |
| 2 | 273 | 13 | 2 | 274 | 13 |
| 3 | 273 | 13 | 3 | 274 | 13 |
| 4 | 273 | 13 | 4 | 274 | 13 |
| 5 | 273 | 13 | 5 | 274 | 13 |
| 6 | 273 | 13 | 6 | 274 | 13 |
| 249 | 273 | 13 | 249 | 274 | 13 |
| 255 | 273 | 13 | 255 | 274 | 13 |
| 256 | 273 | 13 | 256 | 274 | 13 |
| 502 | 273 | 13 | 502 | 274 | 13 |
| 1 | 273 | 14 | 1 | 274 | 14 |
| 2 | 273 | 14 | 2 | 274 | 14 |
| 3 | 273 | 14 | 3 | 274 | 14 |
| 4 | 273 | 14 | 4 | 274 | 14 |
| 5 | 273 | 14 | 5 | 274 | 14 |
| 6 | 273 | 14 | 6 | 274 | 14 |
| 249 | 273 | 14 | 249 | 274 | 14 |
| 255 | 273 | 14 | 255 | 274 | 14 |

TABLE 4-continued

Fusion Proteins

| N-terminal Peptide SEQ ID NO: | Linker peptide | C-terminal Peptide | N-terminal Peptide SEQ ID NO: | Linker peptide | C-terminal Peptide | N-terminal Peptide SEQ ID NO: | Linker peptide | C-terminal Peptide | N-terminal Peptide SEQ ID NO: | Linker peptide | C-terminal Peptide |
|---|---|---|---|---|---|---|---|---|---|---|---|
| 256 | 273 | 14 | 256 | 274 | 14 | 3 | 273 | 507 | 3 | 274 | 507 |
| 502 | 273 | 14 | 502 | 274 | 14 | 4 | 273 | 507 | 4 | 274 | 507 |
| 1 | 273 | 15 | 1 | 274 | 15 | 5 | 273 | 507 | 5 | 274 | 507 |
| 2 | 273 | 15 | 2 | 274 | 15 | 6 | 273 | 507 | 6 | 274 | 507 |
| 3 | 273 | 15 | 3 | 274 | 15 | 249 | 273 | 507 | 249 | 274 | 507 |
| 4 | 273 | 15 | 4 | 274 | 15 | 255 | 273 | 507 | 255 | 274 | 507 |
| 5 | 273 | 15 | 5 | 274 | 15 | 256 | 273 | 507 | 256 | 274 | 507 |
| 6 | 273 | 15 | 6 | 274 | 15 | 502 | 273 | 507 | 502 | 274 | 507 |
| 249 | 273 | 15 | 249 | 274 | 15 | 1 | 273 | 550 | 1 | 274 | 550 |
| 255 | 273 | 15 | 255 | 274 | 15 | 2 | 273 | 550 | 2 | 274 | 550 |
| 256 | 273 | 15 | 256 | 274 | 15 | 3 | 273 | 550 | 3 | 274 | 550 |
| 502 | 273 | 15 | 502 | 274 | 15 | 4 | 273 | 550 | 4 | 274 | 550 |
| 1 | 273 | 257 | 1 | 274 | 257 | 5 | 273 | 550 | 5 | 274 | 550 |
| 2 | 273 | 257 | 2 | 274 | 257 | 6 | 273 | 550 | 6 | 274 | 550 |
| 3 | 273 | 257 | 3 | 274 | 257 | 249 | 273 | 550 | 249 | 274 | 550 |
| 4 | 273 | 257 | 4 | 274 | 257 | 255 | 273 | 550 | 255 | 274 | 550 |
| 5 | 273 | 257 | 5 | 274 | 257 | 256 | 273 | 550 | 256 | 274 | 550 |
| 6 | 273 | 257 | 6 | 274 | 257 | 502 | 273 | 550 | 502 | 274 | 550 |
| 249 | 273 | 257 | 249 | 274 | 257 | 1 | 273 | 551 | 1 | 274 | 551 |
| 255 | 273 | 257 | 255 | 274 | 257 | 2 | 273 | 551 | 2 | 274 | 551 |
| 256 | 273 | 257 | 256 | 274 | 257 | 3 | 273 | 551 | 3 | 274 | 551 |
| 502 | 273 | 257 | 502 | 274 | 257 | 4 | 273 | 551 | 4 | 274 | 551 |
| 1 | 273 | 259 | 1 | 274 | 259 | 5 | 273 | 551 | 5 | 274 | 551 |
| 2 | 273 | 259 | 2 | 274 | 259 | 6 | 273 | 551 | 6 | 274 | 551 |
| 3 | 273 | 259 | 3 | 274 | 259 | 249 | 273 | 551 | 249 | 274 | 551 |
| 4 | 273 | 259 | 4 | 274 | 259 | 255 | 273 | 551 | 255 | 274 | 551 |
| 5 | 273 | 259 | 5 | 274 | 259 | 256 | 273 | 551 | 256 | 274 | 551 |
| 6 | 273 | 259 | 6 | 274 | 259 | 502 | 273 | 551 | 502 | 274 | 551 |
| 249 | 273 | 259 | 249 | 274 | 259 | 1 | 273 | 552 | 1 | 274 | 552 |
| 255 | 273 | 259 | 255 | 274 | 259 | 2 | 273 | 552 | 2 | 274 | 552 |
| 256 | 273 | 259 | 256 | 274 | 259 | 3 | 273 | 552 | 3 | 274 | 552 |
| 502 | 273 | 259 | 502 | 274 | 259 | 4 | 273 | 552 | 4 | 274 | 552 |
| 1 | 273 | 260 | 1 | 274 | 260 | 5 | 273 | 552 | 5 | 274 | 552 |
| 2 | 273 | 260 | 2 | 274 | 260 | 6 | 273 | 552 | 6 | 274 | 552 |
| 3 | 273 | 260 | 3 | 274 | 260 | 249 | 273 | 552 | 249 | 274 | 552 |
| 4 | 273 | 260 | 4 | 274 | 260 | 255 | 273 | 552 | 255 | 274 | 552 |
| 5 | 273 | 260 | 5 | 274 | 260 | 256 | 273 | 552 | 256 | 274 | 552 |
| 6 | 273 | 260 | 6 | 274 | 260 | 502 | 273 | 552 | 502 | 274 | 552 |
| 249 | 273 | 260 | 249 | 274 | 260 | 1 | 273 | 553 | 1 | 274 | 553 |
| 255 | 273 | 260 | 255 | 274 | 260 | 2 | 273 | 553 | 2 | 274 | 553 |
| 256 | 273 | 260 | 256 | 274 | 260 | 3 | 273 | 553 | 3 | 274 | 553 |
| 502 | 273 | 260 | 502 | 274 | 260 | 4 | 273 | 553 | 4 | 274 | 553 |
| 1 | 273 | 261 | 1 | 274 | 261 | 5 | 273 | 553 | 5 | 274 | 553 |
| 2 | 273 | 261 | 2 | 274 | 261 | 6 | 273 | 553 | 6 | 274 | 553 |
| 3 | 273 | 261 | 3 | 274 | 261 | 249 | 273 | 553 | 249 | 274 | 553 |
| 4 | 273 | 261 | 4 | 274 | 261 | 255 | 273 | 553 | 255 | 274 | 553 |
| 5 | 273 | 261 | 5 | 274 | 261 | 256 | 273 | 553 | 256 | 274 | 553 |
| 6 | 273 | 261 | 6 | 274 | 261 | 502 | 273 | 553 | 502 | 274 | 553 |
| 249 | 273 | 261 | 249 | 274 | 261 | 1 | 273 | 554 | 1 | 274 | 554 |
| 255 | 273 | 261 | 255 | 274 | 261 | 2 | 273 | 554 | 2 | 274 | 554 |
| 256 | 273 | 261 | 256 | 274 | 261 | 3 | 273 | 554 | 3 | 274 | 554 |
| 502 | 273 | 261 | 502 | 274 | 261 | 4 | 273 | 554 | 4 | 274 | 554 |
| 1 | 273 | 503 | 1 | 274 | 503 | 5 | 273 | 554 | 5 | 274 | 554 |
| 2 | 273 | 503 | 2 | 274 | 503 | 6 | 273 | 554 | 6 | 274 | 554 |
| 3 | 273 | 503 | 3 | 274 | 503 | 249 | 273 | 554 | 249 | 274 | 554 |
| 4 | 273 | 503 | 4 | 274 | 503 | 255 | 273 | 554 | 255 | 274 | 554 |
| 5 | 273 | 503 | 5 | 274 | 503 | 256 | 273 | 554 | 256 | 274 | 554 |
| 6 | 273 | 503 | 6 | 274 | 503 | 502 | 273 | 554 | 502 | 274 | 554 |
| 249 | 273 | 503 | 249 | 274 | 503 | 1 | 273 | 555 | 1 | 274 | 555 |
| 255 | 273 | 503 | 255 | 274 | 503 | 2 | 273 | 555 | 2 | 274 | 555 |
| 256 | 273 | 503 | 256 | 274 | 503 | 3 | 273 | 555 | 3 | 274 | 555 |
| 502 | 273 | 503 | 502 | 274 | 503 | 4 | 273 | 555 | 4 | 274 | 555 |
| 1 | 273 | 504 | 1 | 274 | 504 | 5 | 273 | 555 | 5 | 274 | 555 |
| 2 | 273 | 504 | 2 | 274 | 504 | 6 | 273 | 555 | 6 | 274 | 555 |
| 3 | 273 | 504 | 3 | 274 | 504 | 249 | 273 | 555 | 249 | 274 | 555 |
| 4 | 273 | 504 | 4 | 274 | 504 | 255 | 273 | 555 | 255 | 274 | 555 |
| 5 | 273 | 504 | 5 | 274 | 504 | 256 | 273 | 555 | 256 | 274 | 555 |
| 6 | 273 | 504 | 6 | 274 | 504 | 502 | 273 | 555 | 502 | 274 | 555 |
| 249 | 273 | 504 | 249 | 274 | 504 | 1 | 273 | 556 | 1 | 274 | 556 |
| 255 | 273 | 504 | 255 | 274 | 504 | 2 | 273 | 556 | 2 | 274 | 556 |
| 256 | 273 | 504 | 256 | 274 | 504 | 3 | 273 | 556 | 3 | 274 | 556 |
| 502 | 273 | 504 | 502 | 274 | 504 | 4 | 273 | 556 | 4 | 274 | 556 |
| 1 | 273 | 507 | 1 | 274 | 507 | 5 | 273 | 556 | 5 | 274 | 556 |
| 2 | 273 | 507 | 2 | 274 | 507 | 6 | 273 | 556 | 6 | 274 | 556 |

TABLE 4-continued

Fusion Proteins

| N-terminal Peptide | Linker peptide | C-terminal Peptide | N-terminal Peptide | Linker peptide | C-terminal Peptide | N-terminal Peptide | Linker peptide | C-terminal Peptide | N-terminal Peptide | Linker peptide | C-terminal Peptide |
|---|---|---|---|---|---|---|---|---|---|---|---|
| \multicolumn{6}{c}{SEQ ID NO:} | \multicolumn{6}{c}{SEQ ID NO:} |
| 249 | 273 | 556 | 249 | 274 | 556 | 255 | 275 | 12 | 255 | 276 | 12 |
| 255 | 273 | 556 | 255 | 274 | 556 | 256 | 275 | 12 | 256 | 276 | 12 |
| 256 | 273 | 556 | 256 | 274 | 556 | 502 | 275 | 12 | 502 | 276 | 12 |
| 502 | 273 | 556 | 502 | 274 | 556 | 1 | 275 | 13 | 1 | 276 | 13 |
| 1 | 273 | 557 | 1 | 274 | 557 | 2 | 275 | 13 | 2 | 276 | 13 |
| 2 | 273 | 557 | 2 | 274 | 557 | 3 | 275 | 13 | 3 | 276 | 13 |
| 3 | 273 | 557 | 3 | 274 | 557 | 4 | 275 | 13 | 4 | 276 | 13 |
| 4 | 273 | 557 | 4 | 274 | 557 | 5 | 275 | 13 | 5 | 276 | 13 |
| 5 | 273 | 557 | 5 | 274 | 557 | 6 | 275 | 13 | 6 | 276 | 13 |
| 6 | 273 | 557 | 6 | 274 | 557 | 249 | 275 | 13 | 249 | 276 | 13 |
| 249 | 273 | 557 | 249 | 274 | 557 | 255 | 275 | 13 | 255 | 276 | 13 |
| 255 | 273 | 557 | 255 | 274 | 557 | 256 | 275 | 13 | 256 | 276 | 13 |
| 256 | 273 | 557 | 256 | 274 | 557 | 502 | 275 | 13 | 502 | 276 | 13 |
| 502 | 273 | 557 | 502 | 274 | 557 | 1 | 275 | 14 | 1 | 276 | 14 |
| 1 | 273 | 558 | 1 | 274 | 558 | 2 | 275 | 14 | 2 | 276 | 14 |
| 2 | 273 | 558 | 2 | 274 | 558 | 3 | 275 | 14 | 3 | 276 | 14 |
| 3 | 273 | 558 | 3 | 274 | 558 | 4 | 275 | 14 | 4 | 276 | 14 |
| 4 | 273 | 558 | 4 | 274 | 558 | 5 | 275 | 14 | 5 | 276 | 14 |
| 5 | 273 | 558 | 5 | 274 | 558 | 6 | 275 | 14 | 6 | 276 | 14 |
| 6 | 273 | 558 | 6 | 274 | 558 | 249 | 275 | 14 | 249 | 276 | 14 |
| 249 | 273 | 558 | 249 | 274 | 558 | 255 | 275 | 14 | 255 | 276 | 14 |
| 255 | 273 | 558 | 255 | 274 | 558 | 256 | 275 | 14 | 256 | 276 | 14 |
| 256 | 273 | 558 | 256 | 274 | 558 | 502 | 275 | 14 | 502 | 276 | 14 |
| 502 | 273 | 558 | 502 | 274 | 558 | 1 | 275 | 15 | 1 | 276 | 15 |
| \multicolumn{3}{c}{RelB-linker (SEQ ID NO: 275)-RelA} | \multicolumn{3}{c}{RelB-linker (SEQ ID NO: 276)-RelA} | 2 | 275 | 15 | 2 | 276 | 15 |
| | | | | | | 3 | 275 | 15 | 3 | 276 | 15 |
| | | | | | | 4 | 275 | 15 | 4 | 276 | 15 |
| 1 | 275 | 8 | 1 | 276 | 8 | 5 | 275 | 15 | 5 | 276 | 15 |
| 2 | 275 | 8 | 2 | 276 | 8 | 6 | 275 | 15 | 6 | 276 | 15 |
| 3 | 275 | 8 | 3 | 276 | 8 | 249 | 275 | 15 | 249 | 276 | 15 |
| 4 | 275 | 8 | 4 | 276 | 8 | 255 | 275 | 15 | 255 | 276 | 15 |
| 5 | 275 | 8 | 5 | 276 | 8 | 256 | 275 | 15 | 256 | 276 | 15 |
| 6 | 275 | 8 | 6 | 276 | 8 | 502 | 275 | 15 | 502 | 276 | 15 |
| 249 | 275 | 8 | 249 | 276 | 8 | 1 | 275 | 257 | 1 | 276 | 257 |
| 255 | 275 | 8 | 255 | 276 | 8 | 2 | 275 | 257 | 2 | 276 | 257 |
| 256 | 275 | 8 | 256 | 276 | 8 | 3 | 275 | 257 | 3 | 276 | 257 |
| 502 | 275 | 8 | 502 | 276 | 8 | 4 | 275 | 257 | 4 | 276 | 257 |
| 1 | 275 | 9 | 1 | 276 | 9 | 5 | 275 | 257 | 5 | 276 | 257 |
| 2 | 275 | 9 | 2 | 276 | 9 | 6 | 275 | 257 | 6 | 276 | 257 |
| 3 | 275 | 9 | 3 | 276 | 9 | 249 | 275 | 257 | 249 | 276 | 257 |
| 4 | 275 | 9 | 4 | 276 | 9 | 255 | 275 | 257 | 255 | 276 | 257 |
| 5 | 275 | 9 | 5 | 276 | 9 | 256 | 275 | 257 | 256 | 276 | 257 |
| 6 | 275 | 9 | 6 | 276 | 9 | 502 | 275 | 257 | 502 | 276 | 257 |
| 249 | 275 | 9 | 249 | 276 | 9 | 1 | 275 | 259 | 1 | 276 | 259 |
| 255 | 275 | 9 | 255 | 276 | 9 | 2 | 275 | 259 | 2 | 276 | 259 |
| 256 | 275 | 9 | 256 | 276 | 9 | 3 | 275 | 259 | 3 | 276 | 259 |
| 502 | 275 | 9 | 502 | 276 | 9 | 4 | 275 | 259 | 4 | 276 | 259 |
| 1 | 275 | 10 | 1 | 276 | 10 | 5 | 275 | 259 | 5 | 276 | 259 |
| 2 | 275 | 10 | 2 | 276 | 10 | 6 | 275 | 259 | 6 | 276 | 259 |
| 3 | 275 | 10 | 3 | 276 | 10 | 249 | 275 | 259 | 249 | 276 | 259 |
| 4 | 275 | 10 | 4 | 276 | 10 | 255 | 275 | 259 | 255 | 276 | 259 |
| 5 | 275 | 10 | 5 | 276 | 10 | 256 | 275 | 259 | 256 | 276 | 259 |
| 6 | 275 | 10 | 6 | 276 | 10 | 502 | 275 | 259 | 502 | 276 | 259 |
| 249 | 275 | 10 | 249 | 276 | 10 | 1 | 275 | 260 | 1 | 276 | 260 |
| 255 | 275 | 10 | 255 | 276 | 10 | 2 | 275 | 260 | 2 | 276 | 260 |
| 256 | 275 | 10 | 256 | 276 | 10 | 3 | 275 | 260 | 3 | 276 | 260 |
| 502 | 275 | 10 | 502 | 276 | 10 | 4 | 275 | 260 | 4 | 276 | 260 |
| 1 | 275 | 11 | 1 | 276 | 11 | 5 | 275 | 260 | 5 | 276 | 260 |
| 2 | 275 | 11 | 2 | 276 | 11 | 6 | 275 | 260 | 6 | 276 | 260 |
| 3 | 275 | 11 | 3 | 276 | 11 | 249 | 275 | 260 | 249 | 276 | 260 |
| 4 | 275 | 11 | 4 | 276 | 11 | 255 | 275 | 260 | 255 | 276 | 260 |
| 5 | 275 | 11 | 5 | 276 | 11 | 256 | 275 | 260 | 256 | 276 | 260 |
| 6 | 275 | 11 | 6 | 276 | 11 | 502 | 275 | 260 | 502 | 276 | 260 |
| 249 | 275 | 11 | 249 | 276 | 11 | 1 | 275 | 26 | 1 | 276 | 261 |
| 255 | 275 | 11 | 255 | 276 | 11 | 2 | 275 | 261 | 2 | 276 | 261 |
| 256 | 275 | 11 | 256 | 276 | 11 | 3 | 275 | 26 | 3 | 276 | 261 |
| 502 | 275 | 11 | 502 | 276 | 11 | 4 | 275 | 261 | 4 | 276 | 261 |
| 1 | 275 | 12 | 1 | 276 | 12 | 5 | 275 | 261 | 5 | 276 | 261 |
| 2 | 275 | 12 | 2 | 276 | 12 | 6 | 275 | 261 | 6 | 276 | 261 |
| 3 | 275 | 12 | 3 | 276 | 12 | 249 | 275 | 26 | 249 | 276 | 261 |
| 4 | 275 | 12 | 4 | 276 | 12 | 255 | 275 | 26 | 255 | 276 | 261 |
| 5 | 275 | 12 | 5 | 276 | 12 | 256 | 275 | 26 | 256 | 276 | 261 |
| 6 | 275 | 12 | 6 | 276 | 12 | 502 | 275 | 261 | 502 | 276 | 261 |
| 249 | 275 | 12 | 249 | 276 | 12 | 1 | 275 | 503 | 1 | 276 | 503 |

TABLE 4-continued

Fusion Proteins

| N-terminal Peptide | Linker peptide SEQ ID NO: | C-terminal Peptide | N-terminal Peptide | Linker peptide SEQ ID NO: | C-terminal Peptide |
|---|---|---|---|---|---|
| 2 | 275 | 503 | 2 | 276 | 503 |
| 3 | 275 | 503 | 3 | 276 | 503 |
| 4 | 275 | 503 | 4 | 276 | 503 |
| 5 | 275 | 503 | 5 | 276 | 503 |
| 6 | 275 | 503 | 6 | 276 | 503 |
| 249 | 275 | 503 | 249 | 276 | 503 |
| 255 | 275 | 503 | 255 | 276 | 503 |
| 256 | 275 | 503 | 256 | 276 | 503 |
| 502 | 275 | 503 | 502 | 276 | 503 |
| 1 | 275 | 504 | 1 | 276 | 504 |
| 2 | 275 | 504 | 2 | 276 | 504 |
| 3 | 275 | 504 | 3 | 276 | 504 |
| 4 | 275 | 504 | 4 | 276 | 504 |
| 5 | 275 | 504 | 5 | 276 | 504 |
| 6 | 275 | 504 | 6 | 276 | 504 |
| 249 | 275 | 504 | 249 | 276 | 504 |
| 255 | 275 | 504 | 255 | 276 | 504 |
| 256 | 275 | 504 | 256 | 276 | 504 |
| 502 | 275 | 504 | 502 | 276 | 504 |
| 1 | 275 | 507 | 1 | 276 | 507 |
| 2 | 275 | 507 | 2 | 276 | 507 |
| 3 | 275 | 507 | 3 | 276 | 507 |
| 4 | 275 | 507 | 4 | 276 | 507 |
| 5 | 275 | 507 | 5 | 276 | 507 |
| 6 | 275 | 507 | 6 | 276 | 507 |
| 249 | 275 | 507 | 249 | 276 | 507 |
| 255 | 275 | 507 | 255 | 276 | 507 |
| 256 | 275 | 507 | 256 | 276 | 507 |
| 502 | 275 | 507 | 502 | 276 | 507 |
| 1 | 275 | 550 | 1 | 276 | 550 |
| 2 | 275 | 550 | 2 | 276 | 550 |
| 3 | 275 | 550 | 3 | 276 | 550 |
| 4 | 275 | 550 | 4 | 276 | 550 |
| 5 | 275 | 550 | 5 | 276 | 550 |
| 6 | 275 | 550 | 6 | 276 | 550 |
| 249 | 275 | 550 | 249 | 276 | 550 |
| 255 | 275 | 550 | 255 | 276 | 550 |
| 256 | 275 | 550 | 256 | 276 | 550 |
| 502 | 275 | 550 | 502 | 276 | 550 |
| 1 | 275 | 551 | 1 | 276 | 551 |
| 2 | 275 | 551 | 2 | 276 | 551 |
| 3 | 275 | 551 | 3 | 276 | 551 |
| 4 | 275 | 551 | 4 | 276 | 551 |
| 5 | 275 | 551 | 5 | 276 | 551 |
| 6 | 275 | 551 | 6 | 276 | 551 |
| 249 | 275 | 551 | 249 | 276 | 551 |
| 255 | 275 | 551 | 255 | 276 | 551 |
| 256 | 275 | 551 | 256 | 276 | 551 |
| 502 | 275 | 551 | 502 | 276 | 551 |
| 1 | 275 | 552 | 1 | 276 | 552 |
| 2 | 275 | 552 | 2 | 276 | 552 |
| 3 | 275 | 552 | 3 | 276 | 552 |
| 4 | 275 | 552 | 4 | 276 | 552 |
| 5 | 275 | 552 | 5 | 276 | 552 |
| 6 | 275 | 552 | 6 | 276 | 552 |
| 249 | 275 | 552 | 249 | 276 | 552 |
| 255 | 275 | 552 | 255 | 276 | 552 |
| 256 | 275 | 552 | 256 | 276 | 552 |
| 502 | 275 | 552 | 502 | 276 | 552 |
| 1 | 275 | 553 | 1 | 276 | 553 |
| 2 | 275 | 553 | 2 | 276 | 553 |
| 3 | 275 | 553 | 3 | 276 | 553 |
| 4 | 275 | 553 | 4 | 276 | 553 |
| 5 | 275 | 553 | 5 | 276 | 553 |
| 6 | 275 | 553 | 6 | 276 | 553 |
| 249 | 275 | 553 | 249 | 276 | 553 |
| 255 | 275 | 553 | 255 | 276 | 553 |
| 256 | 275 | 553 | 256 | 276 | 553 |
| 502 | 275 | 553 | 502 | 276 | 553 |
| 1 | 275 | 554 | 1 | 276 | 554 |
| 2 | 275 | 554 | 2 | 276 | 554 |
| 3 | 275 | 554 | 3 | 276 | 554 |
| 4 | 275 | 554 | 4 | 276 | 554 |
| 5 | 275 | 554 | 5 | 276 | 554 |
| 6 | 275 | 554 | 6 | 276 | 554 |
| 249 | 275 | 554 | 249 | 276 | 554 |
| 255 | 275 | 554 | 255 | 276 | 554 |
| 256 | 275 | 554 | 256 | 276 | 554 |
| 502 | 275 | 554 | 502 | 276 | 554 |
| 1 | 275 | 555 | 1 | 276 | 555 |
| 2 | 275 | 555 | 2 | 276 | 555 |
| 3 | 275 | 555 | 3 | 276 | 555 |
| 4 | 275 | 555 | 4 | 276 | 555 |
| 5 | 275 | 555 | 5 | 276 | 555 |
| 6 | 275 | 555 | 6 | 276 | 555 |
| 249 | 275 | 555 | 249 | 276 | 555 |
| 255 | 275 | 555 | 255 | 276 | 555 |
| 256 | 275 | 555 | 256 | 276 | 555 |
| 502 | 275 | 555 | 502 | 276 | 555 |
| 1 | 275 | 556 | 1 | 276 | 556 |
| 2 | 275 | 556 | 2 | 276 | 556 |
| 3 | 275 | 556 | 3 | 276 | 556 |
| 4 | 275 | 556 | 4 | 276 | 556 |
| 5 | 275 | 556 | 5 | 276 | 556 |
| 6 | 275 | 556 | 6 | 276 | 556 |
| 249 | 275 | 556 | 249 | 276 | 556 |
| 255 | 275 | 556 | 255 | 276 | 556 |
| 256 | 275 | 556 | 256 | 276 | 556 |
| 502 | 275 | 556 | 502 | 276 | 556 |
| 1 | 275 | 557 | 1 | 276 | 557 |
| 2 | 275 | 557 | 2 | 276 | 557 |
| 3 | 275 | 557 | 3 | 276 | 557 |
| 4 | 275 | 557 | 4 | 276 | 557 |
| 5 | 275 | 557 | 5 | 276 | 557 |
| 6 | 275 | 557 | 6 | 276 | 557 |
| 249 | 275 | 557 | 249 | 276 | 557 |
| 255 | 275 | 557 | 255 | 276 | 557 |
| 256 | 275 | 557 | 256 | 276 | 557 |
| 502 | 275 | 557 | 502 | 276 | 557 |
| 1 | 275 | 558 | 1 | 276 | 558 |
| 2 | 275 | 558 | 2 | 276 | 558 |
| 3 | 275 | 558 | 3 | 276 | 558 |
| 4 | 275 | 558 | 4 | 276 | 558 |
| 5 | 275 | 558 | 5 | 276 | 558 |
| 6 | 275 | 558 | 6 | 276 | 558 |
| 249 | 275 | 558 | 249 | 276 | 558 |
| 255 | 275 | 558 | 255 | 276 | 558 |
| 256 | 275 | 558 | 256 | 276 | 558 |
| 502 | 275 | 558 | 502 | 276 | 558 |

In some embodiments, there are additional amino acids between the N-terminal peptide and the linker peptide. In some embodiments, there are additional amino acids between the C-terminal peptide and the linker peptide. In some embodiments, there are no additional amino acids between the N-terminal peptide and the linker peptide. In some embodiments, there are no additional amino acids between the C-terminal peptide and the linker peptide.

In some embodiments, the portion of the fusion protein comprising the N-terminal peptide, the linker peptide, and the C-terminal peptide comprises or consists of the amino acid sequences shown in Table 5, below.

TABLE 5

| Peptide Combinations for the Fusion Protein | |
|---|---|
| SEQ ID NO: | Amino Acid Sequence |
| 28 | DSWQEEVIKLCGRELVRAQIAICGKSTASDAAGADANAGARQLYSALANK CCHVGCTKRSLAQFC |
| 29 | DSWQEEVIKLCGRELVRAQIAICGKSTASDAAGANADAGARQLYSALANK CCHVGCTKRSLAQFC |
| 30 | DSWQEEVIKLCGRELVRAQIAICGKSTASDAAGADADAGARQLYSALANK CCHVGCTKRSLAQFC |
| 31 | DSWQEEVIKLCGRELVRAQIAICGKSTASDAAGAEAEAGARQLYSALANK CCHVGCTKRSLAQFC |
| 32 | DSWQEEVIKLCGRELVRAQIAICGKSTASDAAGAQADAGARQLYSALANK CCHVGCTKRSLAQFC |
| 33 | DSWQEEVIKLCGRELVRAQIAICGKSTASDAAGADAQAGARQLYSALANK CCHVGCTKRSLAQFC |
| 34 | DSWQEEVIKLCGRELVRAQIAICGKSTASDAAGAQAQAGARQLYSALANK CCHVGCTKRSLAQFC |
| 35 | DSWQEEVIKLCGRELVRAQIAICGQSTASDAAGADANAGARQLYSALANK CCHVGCTKRSLAQFC |
| 36 | DSWQEEVIKLCGRELVRAQIAICGQSTASDAAGANADAGARQLYSALANK CCHVGCTKRSLAQFC |
| 37 | DSWQEEVIKLCGRELVRAQIAICGQSTASDAAGADADAGARQLYSALANK CCHVGCTKRSLAQFC |
| 38 | DSWQEEVIKLCGRELVRAQIAICGQSTASDAAGAEAEAGARQLYSALANK CCHVGCTKRSLAQFC |
| 39 | DSWQEEVIKLCGRELVRAQIAICGQSTASDAAGAQADAGARQLYSALANK CCHVGCTKRSLAQFC |
| 40 | DSWQEEVIKLCGRELVRAQIAICGQSTASDAAGADAQAGARQLYSALANK CCHVGCTKRSLAQFC |
| 41 | DSWQEEVIKLCGRELVRAQIAICGQSTASDAAGAQAQAGARQLYSALANK CCHVGCTKRSLAQFC |
| 42 | DSWQEEVIKLCGRELVRAQIAICGKSTASDAAGADANAGARQLYSALANK CCHVGCTKQSLAQFC |
| 43 | DSWQEEVIKLCGRELVRAQIAICGKSTASDAAGANADAGARQLYSALANK CCHVGCTKQSLAQFC |
| 44 | DSWQEEVIKLCGRELVRAQIAICGKSTASDAAGADADAGARQLYSALANK CCHVGCTKQSLAQFC |
| 45 | DSWQEEVIKLCGRELVRAQIAICGKSTASDAAGAEAEAGARQLYSALANK CCHVGCTKQSLAQFC |
| 46 | DSWQEEVIKLCGRELVRAQIAICGKSTASDAAGAQADAGARQLYSALANK CCHVGCTKQSLAQFC |
| 47 | DSWQEEVIKLCGRELVRAQIAICGKSTASDAAGADAQAGARQLYSALANK CCHVGCTKQSLAQFC |
| 48 | DSWQEEVIKLCGRELVRAQIAICGKSTASDAAGAQAQAGARQLYSALANK CCHVGCTKQSLAQFC |
| 49 | DSWQEEVIKLCGRELVRAQIAICGQSTASDAAGADANAGARQLYSALANK CCHVGCTKQSLAQFC |
| 50 | DSWQEEVIKLCGRELVRAQIAICGQSTASDAAGANADAGARQLYSALANK CCHVGCTKQSLAQFC |
| 51 | DSWQEEVIKLCGRELVRAQIAICGQSTASDAAGADADAGARQLYSALANK CCHVGCTKQSLAQFC |
| 52 | DSWQEEVIKLCGRELVRAQIAICGQSTASDAAGAEAEAGARQLYSALANK CCHVGCTKQSLAQFC |

TABLE 5-continued

Peptide Combinations for the Fusion Protein

| SEQ ID NO: | Amino Acid Sequence |
|---|---|
| 53 | DSWQEEVIKLCGRELVRAQIAICGQSTASDAAGAQADAGARQLYSALANK<br>CCHVGCTKQSLAQFC |
| 54 | DSWQEEVIKLCGRELVRAQIAICGQSTASDAAGADAQAGARQLYSALANK<br>CCHVGCTKQSLAQFC |
| 55 | DSWQEEVIKLCGRELVRAQIAICGQSTASDAAGAQAQAGARQLYSALANK<br>CCHVGCTKQSLAQFC |
| 56 | DSYQEEVIKLCGRELVRAQIAICGKSTASDAAGAEAEAGARQLYSALANK<br>CCHVGCTKRSLAQFC |
| 57 | DSFQEEVIKLCGRELVRAQIAICGKSTASDAAGAEAEAGARQLYSALANK<br>CCHVGCTKRSLAQFC |
| 58 | DSLQEEVIKLCGRELVRAQIAICGKSTASDAAGAEAEAGARQLYSALANK<br>CCHVGCTKRSLAQFC |
| 59 | DSIQEEVIKLCGRELVRAQIAICGKSTASDAAGAEAEAGARQLYSALANK<br>CCHVGCTKRSLAQFC |
| 60 | DSWQEEVIKLCGRELVRAQIAICGKSTASDAAGAEAEAGARQLYSALANK<br>CCYVGCTKRSLAQFC |
| 61 | DSWQEEVIKLCGRELVRAQIAICGKSTASDAAGAEAEAGARQLYSALANK<br>CCLVGCTKRSLAQFC |
| 62 | DSWQEEVIKLCGRELVRAQIAICGKSTASDAAGAEAEAGARQLYSALANK<br>CCQVGCTKRSLAQFC |
| 63 | DSWQEEVIKLCGRELVRAQIAICGKSTASDAAGAEAEAGARQLYSALANK<br>CCKVGCTKRSLAQFC |
| 64 | DSYQEEVIKLCGRELVRAQIAICGKSTASDAAGAEAEAGARQLYSALANK<br>CCYVGCTKRSLAQFC |
| 65 | DSYQEEVIKLCGRELVRAQIAICGKSTASDAAGAEAEAGARQLYSALANK<br>CCKVGCTKRSLAQFC |
| 66 | DSYQEEVIKLCGRELVRAQIAICGKSTGGEGSGGEGEGGGRQLYSALANK<br>CCYVGCTKRSLAQFC |
| 67 | DSYQEEVIKLCGRELVRAQIAICGKSTGGEGSGGEGEGGGRQLYSALANK<br>CCKVGCTKRSLAQFC |
| 68 | DSYQEEVIKLCGRELVRAQIAICGKSTGGEGSGGEGSGGGRQLYSALANK<br>CCYVGCTKRSLAQFC |
| 69 | DSYQEEVIKLCGRELVRAQIAICGKSTGGEGSGGEGSGGGRQLYSALANK<br>CCKVGCTKRSLAQFC |
| 70 | DSYQEEVIKLCGRELVRAQIAICGKSTASDAAGAEAEAGARQLYSALANK<br>CCYVGCTKQSLAQFC |
| 71 | DSYQEEVIKLCGRELVRAQIAICGKSTASDAAGAEAEAGARQLYSALANK<br>CCKVGCTKQSLAQFC |
| 72 | DSYQEEVIKLCGRELVRAQIAICGKSTGGEGSGGEGEGGGRQLYSALANK<br>CCYVGCTKQSLAQFC |
| 73 | DSYQEEVIKLCGRELVRAQIAICGKSTGGEGSGGEGEGGGRQLYSALANK<br>CCKVGCTKQSLAQFC |
| 74 | DSYQEEVIKLCGRELVRAQIAICGKSTGGEGSGGEGSGGGRQLYSALANK<br>CCYVGCTKQSLAQFC |
| 75 | DSYQEEVIKLCGRELVRAQIAICGKSTGGEGSGGEGSGGGRQLYSALANK<br>CCKVGCTKQSLAQFC |
| 278 | DSWKEEVIKLCGRELVRAQIAICGKSTGGGEGGGEGGGEGRQLYSALANK<br>CCHVGCTKRSLARFC |
| 279 | DSWKEEVIKLCGRELVRAQIAICGKSTGGGEGGGEGGGEGGGQLYSALAN<br>KCCHVGCTKRSLARFC |

TABLE 5-continued

Peptide Combinations for the Fusion Protein

| SEQ ID NO: | Amino Acid Sequence |
|---|---|
| 280 | DSWMEEVIKLCGRELVRAQIAICGKSTGGGEGGGEGGGEGRQLYSALANK CCHVGCTKRSLARFC |
| 281 | DSWQEEVIKLCGRELVRAQIAICGKSTGGGEGGGEGGGEGRQLYSALANK CCHVGCTKRSLARFC |
| 282 | DSWMEEVIKLCGRELVRAQIAICGKSTGGGEGGGEGGGEGGGQLYSALAN KCCHVGCTKRSLARFC |
| 283 | DSWQEEVIKLCGRELVRAQIAICGKSTGGGEGGGEGGGEGGGQLYSALAN KCCHVGCTKRSLARFC |
| 284 | DSWMEEVIKLCGRELVRAQIAICGKSTGGGEGGGEEGGGEGGQLYSALANK CCHVGCTKRSLARFC |
| 285 | DSWQEEVIKLCGRELVRAQIAICGKSTGGGEGGGEEGGGEGGQLYSALANK CCHVGCTKRSLARFC |
| 286 | DSWMEEVIKLCGRELVRAQIAICGKSTGGGEGGGEEGGGEGGQLYSALANK CCHVGCTKRSLARFC |
| 287 | DSWQEEVIKLCGRELVRAQIAICGKSTGGGEGGGEEGGGEGGQLYSALANK CCHVGCTKRSLARFC |
| 288 | DSWQEEVIKLCGRELVRAQIAICGKSTGGGEGGGEGGGEGRQLYSALANK CCHVGCTKRSLAQFC |
| 289 | DSWQEEVIKLCGRELVRAQIAICGKSTGGGEGGGEGGGEGRQLYSALANK CCHVGCTKRSLARFC |
| 290 | DSWQEEVIKLCGRELVRAQIAICGKSTGGGEGGGEGGGEGRQLYSALANK CCHVGCTKRSLAQFC |
| 291 | DSWQEEVIKLCGRELVRAQIAICGKSTGGGEEGGGEEGGGRQLYSALANK CCHVGCTKRSLARFC |
| 292 | DSWQEEVIKLCGRELVRAQIAICGKSTGGGEEGGGEEGGGRQLYSALANK CCHVGCTKRSLAQFC |
| 293 | DSWQEEVIKLCGRELVRAQIAICGKSTGGGEEGGGEEGGGRQLYSALANK CCHVGCTKRSLARFC |
| 294 | DSWQEEVIKLCGRELVRAQIAICGKSTGGGEEGGGEEGGGRQLYSALANK CCHVGCTKRSLAQFC |
| 295 | DSWQEEVIKLCGRELVRAQIAICGKSTGGGEGEGGEGEGGSRQLYSALANK CCHVGCTKRSLAQFC |
| 296 | DSWQEEVIKLCGRELVRAQIAICGKSTGGGEGEGGEGEGGSRQLYSALANK CCHVGCTKRSLARFC |
| 297 | DSWQEEVIKLCGRELVRAQIAICGKSTGGGEGEGGEGEGGSRQLYSALANK CCHVGCTKRSLAQFC |
| 508 | DSYQEEVIKLCGRELVRAQIAICGKSTGGEGSGGEGEGGGRQLYSALANK CCHVGCTKRSLAQFC |
| 509 | DSYQEEVIKLCGRELVRAQIAICGKSTGGEGSGGEGEGGGRQLYSALANK CCQVGCTKRSLAQFC |
| 510 | DSYQEEVIKLCGRELVRAQIAICGKSTGGEGSGGEGEGGGRQLYSALANK CCHVGCTKQSLAQFC |
| 511 | DSYQEEVIKLCGRELVRAQIAICGKSTGGEGSGGEGEGGGRQLYSALANK CCQVGCTKQSLAQFC |
| 512 | DSYQEEVIKLCGRELVRAQIAICGKSTGGEGSGGEGSGGGRQLYSALANK CCHVGCTKRSLAQFC |
| 513 | DSYQEEVIKLCGRELVRAQIAICGKSTGGEGSGGEGSGGGRQLYSALANK CCQVGCTKRSLAQFC |

TABLE 5-continued

Peptide Combinations for the Fusion Protein

| SEQ ID NO: | Amino Acid Sequence |
|---|---|
| 514 | DSYQEEVIKLCGRELVRAQIAICGKSTGGEGSGGEGSGGGRQLYSALANK CCHVGCTKQSLAQFC |
| 515 | DSYQEEVIKLCGRELVRAQIAICGKSTGGEGSGGEGSGGGRQLYSALANK CCQVGCTKQSLAQFC |

IgG Fc

In some embodiments, the fusion proteins provided herein further comprise an IgG Fe (or Fc region). As used herein, the term "IgG Fc" or "Fc region" refers to the portion of an immunoglobulin formed by the Fe domains of its two heavy chains. The Fc region can be a wild-type Fc region (native Fc region) or a variant Fc region. A native Fc region is homodimeric. In some embodiments, the fusion proteins provided herein form dimers (e.g., homodimers via interaction between Fc regions. In some embodiments, two fusion proteins are linked into a dimer (e.g., a homodimer) via 2 hinge region interchain disulfide bonds between the Fc regions of each fusion protein (e.g., at the N-terminus). In some embodiments, the Fc region comprises one intrachain disulfide bond in the CH2 domain and one intrachain disulfide bond in the CH3 domain.

The Fc region of the fusion proteins provided herein can be derived from any native immunoglobulin. In some embodiments, the Fc region is formed from an IgA, IgD, IgE, or IgG heavy chain constant region. In some embodiments, the Fc region is formed from an IgG heavy chain constant region. In some embodiments, the IgG heavy chain is an IgG1, IgG2, IgG3 or IgG4 heavy chain constant region. In some embodiments, the Fc region is formed from an IgG1 heavy chain constant region. In some embodiments, the IgG1 heavy chain constant region comprises a G1m1(a), G1m2(x), G1m3(f), or G1m17(z) allotype. See, e.g., Jefferis and Lefranc (2009) mAbs 1(4): 332-338, and de Taeye et al. (2020) Front Immunol. 11:740, incorporated herein by reference in their entirety. The IgG Fc can be linked to the N-terminal end of the N-terminal peptide or the C-terminal end of the C-terminal peptide. The IgG Fc can be linked directly to the N-terminal peptide or the C-terminal peptide or they can be linked to the N-terminal peptide or the C-terminal peptide through an IgG Fc linker. In some embodiments, the IgG Fc linker comprises or consists of 1, 2, 3, 4, 5, 6, 7, 8, 9, or 10 amino acids. In some embodiments, the IgG Fc linker comprises or consists of 1, 2, 3, 4, or 5 amino acids. In some embodiments, the IgG Fc linker comprises or consists of 3 or 4 amino acids. In some embodiments, the IgG Fc linker comprises or consists of the amino acid sequence of GGS. In some embodiments, the IgG Fc linker comprises or consists of the amino acid sequence of EGGS (SEQ ID NO: 299).

In some embodiments, the IgG Fc comprises a C-terminal lysine (K). It is known in the art that the C-terminal lysine (K) in many monoclonal antibodies is flexible, and is often clipped off during expression and purification with no known impairment in activity. In some embodiments, the C-terminal lysine (K) is replaced with a C-terminal glutamic acid (E). As such, in some embodiments, the IgG Fc comprises a C-terminal glutamic acid (E).

In some embodiments, the IgG Fc comprises the amino acid sequence of one of SEQ ID NOs: 76-83 with GGS as the IgG Fc linker at the C-terminal end of the IgG Fc. In some embodiments, the IgG Fc comprises the amino acid sequence of one of SEQ ID NOs: 76-83 with SEQ ID NO: 299 as the IgG Fc linker at the C-terminal end of the IgG Fc.

In some embodiments, one, two, or more mutations (e.g., amino acid substitutions) are introduced into the Fc region of an antibody described herein (e.g., CH2 domain (residues 231-340 of human IgG1) and/or CH3 domain (residues 341-447 of human IgG1)) and/or the hinge region, numbered according to the EU numbering system, to alter one or more functional properties of the antibody, such as serum half-life, complement fixation, Fc receptor binding, and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425, herein incorporated by reference in its entirety. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375, and 6,165,745, all of which are herein incorporated by reference in their entireties, for examples of mutations that will alter (e.g., decrease or increase) the half-life of an antibody in vivo. In certain embodiments, one, two, or more amino acid mutations (e.g., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two, or more amino acid mutations (e.g., substitutions, insertions, or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human IgG1) and/or the third constant (CH3) domain (residues 341-447 of human IgG1), numbered according to the EU numbering system. In a specific embodiment, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See, U.S. Pat. No. 7,658,921, which is herein incorporated by reference in its entirety. This type of mutant IgG, referred to as "YTE mutant" has been shown to display fourfold increased half-life as compared to wild-type versions of the same antibody (see, Dall'Acqua W F et al., (2006) *J Biol Chem* 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into the Fc region of an antibody described herein (e.g., CH2 domain (residues 231-340 of human IgG1) and/or CH3 domain (residues 341-447 of human IgG1)) and/or the hinge region, numbered according to the EU numbering system, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) *PNAS* 109: 6181-6186, U.S. Pat. No. 6,737,056, and International Publication Nos. WO 02/060919; WO 98/23289; and WO 97/34631, all of which are herein incorporated by reference in their entireties.

In certain embodiments, the antibody comprises a heavy chain constant region that is a variant of a wild-type heavy chain constant region, wherein the variant heavy chain constant region binds to FcγRIIB with higher affinity than the wild-type heavy chain constant region binds to FcγRIIB. In certain embodiments, the variant heavy chain constant region is a variant human heavy chain constant region, e.g., a variant human IgG1, a variant human IgG2, or a variant human IgG4 heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant domain Fc region to alter the effector function(s) of the antibody. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on the Fc region, which may reduce Fc receptor binding (see, e.g., Shields R L et al., (2001) *J Biol Chem* 276: 6591-604, which is herein incorporated by reference in its entirety). In various embodiments, one or more of the following mutations in the constant region of an antibody described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution (PA); an A332L substitution; an I332E substitution; or a P396L substitution, numbered according to the EU numbering system.

In certain embodiments, a mutation selected from the group consisting of D265A, P329A, and a combination thereof, numbered according to the EU numbering system, may be made in the constant region of an antibody described herein. In certain embodiments, a mutation selected from the group consisting of L235A, L237A, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein. In certain embodiments, a mutation selected from the group consisting of S239D, I332E, optionally A330L, and a combination thereof, numbered according to the EU numbering system, may be made in the constant region of an antibody described herein. In certain embodiments, a mutation selected from the group consisting of L235V, F243L, R292P, Y300L, P396L, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein.

In a specific embodiment, an antibody described herein comprises the constant domain of an IgG1 with an N297Q or N297A amino acid substitution, numbered according to the EU numbering system. In one embodiment, an antibody described herein comprises the constant domain of an IgG1 with a mutation selected from the group consisting of D265A, P329A, and a combination thereof, numbered according to the EU numbering system. In another embodiment, an antibody described herein comprises the constant domain of an IgG1 with a mutation selected from the group consisting of L234A, L235A (LALA), and a combination thereof, numbered according to the EU numbering system. In another embodiment, an antibody described herein comprises the constant domain of an IgG1 with a mutation selected from the group consisting of L234F, L235F, N297A, and a combination thereof, numbered according to the EU numbering system. In certain embodiments, amino acid residues in the constant region of an antibody described herein in the positions corresponding to positions L234, L235, and D265 in a human IgG1 heavy chain, numbered according to the EU numbering system, are not L, L, and D, respectively. This approach is described in detail in International Publication No. WO 14/108483, which is herein incorporated by reference in its entirety. In a particular embodiment, the amino acids corresponding to positions L234, L235, and D265 in a human IgG1 heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In certain embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In some embodiments, the IgG Fc is an IgG1 Fc, or a derivative thereof. In some embodiments, the IgG Fc or IgG1 Fc comprises an amino acid sequence at least 85, 90, 95, 96, 97, 98, or 99% identical to the amino acid sequence of IgG1 Fc. In some embodiments, the IgG Fc or IgG1 Fc comprises an amino acid sequence at least 85, 90, 95, 96, 97, 98, 99, or 100% identical to an amino acid sequence provided below in Table 6.

TABLE 6

IgG Fc Amino Acid Sequences

| SEQ ID NO: | Description | Sequence |
|---|---|---|
| 76 | IgG1 Fc | DKTHTCPPCPAPELLGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 77 | IgG1 Fc LALA | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 78 | IgG1 Fc LALA PA | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALAAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 79 | IgG1 Fc LALA PA LS | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALAAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVLHEALHSHYTQKSLSLSPGK |
| 80 | IgG1 Fc without C-terminal lysine | DKTHTCPPCPAPELLGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPG |
| 81 | IgG1 Fc LALA without C-terminal lysine | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPG |

TABLE 6-continued

IgG Fc Amino Acid Sequences

| SEQ ID NO: | Description | Sequence |
|---|---|---|
| 82 | IgG1 Fc LALA PA without C-terminal lysine | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALAAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPG |
| 83 | IgG1 Fc LALA PA LS without C-terminal lysine | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALAAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVLHEALHSHYTQKSLSLSPG |

In some embodiments, any IgG Fc, or derivative thereof, can be linked to the N-terminus or C-terminus of any of the embodiments described in Table 4 or 5 above with or without an IgG Fc linker. In some embodiments, human IgG1 Fc, or a derivative thereof, can be linked to the N-terminus or C-terminus of any of the embodiments described in Table 4 or 5 above with or without an IgG Fc linker. In some embodiments, the amino acid sequence of the human IgG1 Fc comprises or consists of the amino acid sequence of SEQ ID NO: 76 or 80. In some embodiments, the derivative if human IgG1 Fc comprises an amino acid sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or 99% identical to the amino acid sequence of SEQ ID NO: 76 or 80.

In some embodiments, a human IgG1 Fc comprising a LALA mutation, or a derivative thereof, can be linked to the N-terminus or C-terminus of any of the embodiments described in Table 4 or 5 above with or without an IgG Fc linker. In some embodiments, the amino acid sequence of the human IgG1 Fc comprising a LALA mutation comprises or consists of the amino acid sequence of SEQ ID NO: 77 or 81. In some embodiments, the derivative if human IgG1 Fc comprising a LALA mutation comprises an amino acid sequence at least 85, 90, 95, 96, 97, 98, or 99% identical to the amino acid sequence of SEQ ID NO: 77 or 81.

In some embodiments, a human IgG1 Fc comprising a LALA PA mutation, or a derivative thereof, can be linked to the N-terminus or C-terminus of any of the embodiments described in Table 4 or 5 above with or without an IgG Fc linker. In some embodiments, the amino acid sequence of the human IgG1 Fc comprising a LALA PA mutation comprises or consists of the amino acid sequence of SEQ ID NO: 78 or 82. In some embodiments, the derivative if human IgG1 Fc comprising a LALA PA mutation comprises an amino acid sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or 99% identical to the amino acid sequence of SEQ ID NO: 78 or 82.

In some embodiments, a human IgG1 Fc comprising a LALA PA LS mutation, or a derivative thereof, can be linked to the N-terminus or C-terminus of any of the embodiments described in Table 4 or 5 above with or without an IgG Fc linker. In some embodiments, the amino acid sequence of the human IgG1 Fc comprising a LALA PA LS mutation comprises or consists of the amino acid sequence of SEQ ID NO: 79 or 83. In some embodiments, the derivative if human IgG1 Fc comprising a LALA PA LS mutation comprises an amino acid sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or 99% identical to the amino acid sequence of SEQ ID NO: 79 or 83.

In some embodiments, the fusion protein comprises an amino acid sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or 99% identical to the amino acid sequences shown in Table 7. In some embodiments, the fusion protein comprises or consists of the amino acid sequences shown in Table 7.

TABLE 7

Fusion Protein Amino Acid Sequences

| SEQ ID NO: | Sequence |
|---|---|
| 84 | DKTHTCPPCPAPEAAGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALAA PIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVLHEALHSHYTQKS LSLSPGKGGSDSWQEEVIKLCGRELVRAQIAICGKSTASDAAGADANAGARQLYS ALANKCCHVGCTKRSLAQFC |

TABLE 7-continued

Fusion Protein Amino Acid Sequences

| SEQ ID NO: | Sequence |
|---|---|
| 85 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGANADAGARQLYS<br>ALANKCCHVGCTKRSLAQFC |
| 86 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGADADAGARQLYS<br>ALANKCCHVGCTKRSLAQFC |
| 87 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGAEAEAGARQLYS<br>ALANKCCHVGCTKRSLAQFC |
| 88 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGAQADAGARQLYS<br>ALANKCCHVGCTKRSLAQFC |
| 89 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGADAQAGARQLYS<br>ALANKCCHVGCTKRSLAQFC |
| 90 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGAQAQAGARQLYS<br>ALANKCCHVGCTKRSLAQFC |
| 91 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGADANAGARQLYS<br>ALANKCCHVGCTKRSLAQFC |
| 92 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGANADAGARQLYS<br>ALANKCCHVGCTKRSLAQFC |
| 93 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGADADAGARQLYS<br>ALANKCCHVGCTKRSLAQFC |
| 94 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGAEAEAGARQLYS<br>ALANKCCHVGCTKRSLAQFC |
| 95 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG |

TABLE 7-continued

Fusion Protein Amino Acid Sequences

| SEQ ID NO: | Sequence |
|---|---|
| | QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGAQADAGARQLYS<br>ALANKCCHVGCTKRSLAQFC |
| 96 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGADAQAGARQLYS<br>ALANKCCHVGCTKRSLAQFC |
| 97 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGAQAQAGARQLYS<br>ALANKCCHVGCTKRSLAQFC |
| 98 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGADANAGARQLYS<br>ALANKCCHVGCTKRSLAQFC |
| 99 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGANADAGARQLYS<br>ALANKCCHVGCTKRSLAQFC |
| 100 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGADADAGARQLYS<br>ALANKCCHVGCTKRSLAQFC |
| 101 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGAEAEAGARQLYS<br>ALANKCCHVGCTKRSLAQFC |
| 102 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGAQADAGARQLYS<br>ALANKCCHVGCTKRSLAQFC |
| 103 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGADAQAGARQLYS<br>ALANKCCHVGCTKRSLAQFC |
| 104 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGAQAQAGARQLYS<br>ALANKCCHVGCTKRSLAQFC |
| 105 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGADANAGARQLYS<br>ALANKCCHVGCTKQSLAQFC |

TABLE 7-continued

Fusion Protein Amino Acid Sequences

| SEQ ID NO: | Sequence |
|---|---|
| 106 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGANADAGARQLYS<br>ALANKCCHVGCTKQSLAQFC |
| 107 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGADADAGARQLYS<br>ALANKCCHVGCTKQSLAQFC |
| 108 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGAEAEAGARQLYS<br>ALANKCCHVGCTKQSLAQFC |
| 109 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGAQADAGARQLYS<br>ALANKCCHVGCTKQSLAQFC |
| 110 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGADAQAGARQLYS<br>ALANKCCHVGCTKQSLAQFC |
| 111 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGKSTASDAAGAQAQAGARQLYS<br>ALANKCCHVGCTKQSLAQFC |
| 112 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGADANAGARQLYS<br>ALANKCCHVGCTKQSLAQFC |
| 113 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGANADAGARQLYS<br>ALANKCCHVGCTKQSLAQFC |
| 114 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGADADAGARQLYS<br>ALANKCCHVGCTKQSLAQFC |
| 115 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGAEAEAGARQLYS<br>ALANKCCHVGCTKQSLAQFC |
| 116 | DKTHTCPPCPAPEAAGGPSVFLFPPKPKDTLMISRTPEVTCVVVDVSHEDPEVKE<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG |

TABLE 7-continued

Fusion Protein Amino Acid Sequences

| SEQ ID NO: | Sequence |
|---|---|
| | QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGAQADAGARQLYS<br>ALANKCCHVGCTKQSLAQFC |
| 117 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGADAQAGARQLYS<br>ALANKCCHVGCTKQSLAQFC |
| 118 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGEGGSDSWQEEVIKLCGRELVRAQIAICGQSTASDAAGAQAQAGARQLYS<br>ALANKCCHVGCTKQSLAQFC |
| 119 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTASDAAGAEAEAGARQLYS<br>ALANKCCHVGCTKRSLAQFC |
| 120 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSFQEEVIKLCGRELVRAQIAICGKSTASDAAGAEAEAGARQLYS<br>ALANKCCHVGCTKRSLAQFC |
| 121 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSLQEEVIKLCGRELVRAQIAICGKSTASDAAGAEAEAGARQLYS<br>ALANKCCHVGCTKRSLAQFC |
| 122 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSIQEEVIKLCGRELVRAQIAICGKSTASDAAGAEAEAGARQLYS<br>ALANKCCHVGCTKRSLAQFC |
| 123 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGAEAEAGARQLYS<br>ALANKCCYVGCTKRSLAQFC |
| 124 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGAEAEAGARQLYS<br>ALANKCCLVGCTKRSLAQFC |
| 125 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGAEAEAGARQLYS<br>ALANKCCQVGCTKRSLAQFC |
| 126 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTASDAAGAEAEAGARQLYS<br>ALANKCCKVGCTKRSLAQFC |

TABLE 7-continued

Fusion Protein Amino Acid Sequences

| SEQ ID NO: | Sequence |
|---|---|
| 127 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGEGGSDSYQEEVIKLCGRELVRAQIAICGKSTASDAAGAEAEAGARQLYS
ALANKCCYVGCTKRSLAQFC |
| 128 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGEGGSDSYQEEVIKLCGRELVRAQIAICGKSTASDAAGAEAEAGARQLYS
ALANKCCKVGCTKRSLAQFC |
| 129 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGEGGSDSYQEEVIKLCGRELVRAQIAICGKSTGGEGSGGEGEGGGRQLYS
ALANKCCYVGCTKRSLAQFC |
| 130 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGEGGSDSYQEEVIKLCGRELVRAQIAICGKSTGGEGSGGEGEGGGRQLYS
ALANKCCKVGCTKRSLAQFC |
| 131 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGEGGSDSYQEEVIKLCGRELVRAQIAICGKSTGGEGSGGEGSGGGRQLYS
ALANKCCYVGCTKRSLAQFC |
| 132 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGEGGSDSYQEEVIKLCGRELVRAQIAICGKSTGGEGSGGEGSGGGRQLYS
ALANKCCKVGCTKRSLAQFC |
| 133 | DKTHTCPPCPAPEAAGGPSVFLFPPKPKDTLMISRTPEVTCVVVDVSHEDPEVKF
NWYVDGVEVHNAKTKPREEQYNSTYRVVSVLIVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGKGGSDSYQEEVIKLCGRELVRAQIAICGKSTASDAAGAEAEAGARQLYS
ALANKCCKVGCTKQSLAQFC |
| 134 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGKGGSDSYQEEVIKLCGRELVRAQIAICGKSTASDAAGAEAEAGARQLYS
ALANKCCKVGCTKQSLAQFC |
| 135 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGKGGSDSYQEEVIKLCGRELVRAQIAICGKSTGGEGSGGEGEGGGRQLYS
ALANKCCYVGCTKQSLAQFC |
| 136 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS
LSLSPGKGGSDSYQEEVIKLCGRELVRAQIAICGKSTGGEGSGGEGEGGGRQLYS
ALANKCCKVGCTKQSLAQFC |
| 137 | DKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALAA
PIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVLHEALHSHYTQKS |

TABLE 7-continued

Fusion Protein Amino Acid Sequences

| SEQ ID NO: | Sequence |
|---|---|
| | LSLSPGKGGSDSYQEEVIKLCGRELVRAQIAICGKSTGGEGSGGEGSGGGRQLYS<br>ALANKCCYVGCTKQSLAQFC |
| 138 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTGGEGSGGEGSGGGRQLYS<br>ALANKCCKVGCTKQSLAQFC |
| 300 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWKEEVIKLCGRELVRAQIAICGKSTGGGEGGGEGGGEGRQLYS<br>ALANKCCHVGCTKRSLARFC |
| 301 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWKEEVIKLCGRELVRAQIAICGKSTGGGEGGGEGGGEGGGQLY<br>SALANKCCHVGCTKRSLARFC |
| 302 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWMEEVIKLCGRELVRAQIAICGKSTGGGEGGGEGGGEGRQLYS<br>ALANKCCHVGCTKRSLARFC |
| 303 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWQEEVIKLCGRELVRAQIAICGKSTGGGEGGGEGGGEGRQLYS<br>ALANKCCHVGCTKRSLARFC |
| 304 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTGGGEGGGEGGGEGRQLYS<br>ALANKCCHVGCTKRSLARFC |
| 305 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWMEEVIKLCGRELVRAQIAICGKSTGGGEGGGEGGGEGGGQLY<br>SALANKCCHVGCTKRSLARFC |
| 306 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWQEEVIKLCGRELVRAQIAICGKSTGGGEGGGEGGGEGGGQLY<br>SALANKCCHVGCTKRSLARFC |
| 307 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTGGGEGGGEGGGEGGGQLY<br>SALANKCCHVGCTKRSLARFC |
| 308 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWMEEVIKLCGRELVRAQIAICGKSTGGEGGGEEGGGEGGGQLYS<br>ALANKCCHVGCTKRSLARFC |

TABLE 7-continued

Fusion Protein Amino Acid Sequences

| SEQ ID NO: | Sequence |
|---|---|
| 309 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWQEEVIKLCGRELVRAQIAICGKSTGGEGGGEEGGGEGGQLYS<br>ALANKCCHVGCTKRSLARFC |
| 310 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGGGSDSWMEEVIKLCGRELVRAQIAICGKSTGGEGGGEEGGGEGGQLYSA<br>LANKCCHVGCTKRSLARFC |
| 311 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGGGSDSWQEEVIKLCGRELVRAQIAICGKSTGGEGGGEEGGGEGGQLYSA<br>LANKCCHVGCTKRSLARFC |
| 312 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWQEEVIKLCGRELVRAQIAICGKSTGGGEGGGEGGGEGRQLYS<br>ALANKCCHVGCTKRSLAQFC |
| 313 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTGGGEGGGEGGGEGRQLYS<br>ALANKCCHVGCTKRSLAQFC |
| 314 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGGGSDSWQEEVIKLCGRELVRAQIAICGKSTGGGEGGGEGGGEGRQLYSA<br>LANKCCHVGCTKRSLARFC |
| 315 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGGGSDSWQEEVIKLCGRELVRAQIAICGKSTGGGEGGGEGGGEGRQLYSA<br>LANKCCHVGCTKRSLARFC |
| 316 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGGGSDSWQEEVIKLCGRELVRAQIAICGKSTGGGEGGGEGGGEGRQLYSA<br>LANKCCHVGCTKRSLAQFC |
| 317 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGGGSDSWQEEVIKLCGRELVRAQIAICGKSTGGGEGGGEGGGEGRQLYSA<br>LANKCCHVGCTKRSLAQFC |
| 318 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWQEEVIKLCGRELVRAQIAICGKSTGGGEEGGGEEGGGRQLYS<br>ALANKCCHVGCTKRSLARFC |
| 319 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG |

TABLE 7-continued

Fusion Protein Amino Acid Sequences

| SEQ ID NO: | Sequence |
|---|---|
| | QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTGGGEEGGGEEGGGRQLYS<br>ALANKCCHVGCTKRSLARFC |
| 320 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWQEEVIKLCGRELVRAQIAICGKSTGGGEEGGGEEGGGRQLYS<br>ALANKCCHVGCTKRSLAQFC |
| 321 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTGGGEEGGGEEGGGRQLYS<br>ALANKCCHVGCTKRSLAQFC |
| 322 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGGGSDSWQEEVIKLCGRELVRAQIAICGKSTGGGEEGGGEEGGGRQLYSA<br>LANKCCHVGCTKRSLARFC |
| 323 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGGGSDSWQEEVIKLCGRELVRAQIAICGKSTGGGEEGGGEEGGGRQLYSA<br>LANKCCHVGCTKRSLARFC |
| 324 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGGGSDSWQEEVIKLCGRELVRAQIAICGKSTGGGEEGGGEEGGGRQLYSA<br>LANKCCHVGCTKRSLAQFC |
| 325 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGGGSDSWQEEVIKLCGRELVRAQIAICGKSTGGGEEGGGEEGGGRQLYSA<br>LANKCCHVGCTKRSLAQFC |
| 326 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTGGEGEGGEGEGGSRQLYS<br>ALANKCCHVGCTKRSLAQFC |
| 327 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGGGSDSWQEEVIKLCGRELVRAQIAICGKSTGGEGEGGEGEGGSRQLYSA<br>LANKCCHVGCTKRSLARFC |
| 328 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGGGSDSWQEEVIKLCGRELVRAQIAICGKSTGGEGEGGEGEGGSRQLYSA<br>LANKCCHVGCTKRSLAQFC |
| 359 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWKEEVIKLCGRELVRAQIAICGKSTASDAAGANANAGARQLYS<br>ALANKCCHVGCTKRSLAQFC |

TABLE 7-continued

Fusion Protein Amino Acid Sequences

| SEQ ID NO: | Sequence |
|---|---|
| 360 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGKGGSDSWKEEVIKLCGRELVRAQIAICGKSTASDAAGANANAGARQLYS<br>ALANKCCHVGCTKRSLAEFC |
| 361 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWKEEVIKLCGRELVRAQIAICGKSTGGGEGGGEGGGEGRQLYS<br>ALANKCCHVGCTKRSLARFC |
| 362 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWKEEVIKLCGRELVRAQIAICGKSTGGGEGGGEGGGEGGGQLY<br>SALANKCCHVGCTKRSLARFC |
| 363 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWMEEVIKLCGRELVRAQIAICGKSTGGGEGGGEGGGEGRQLYS<br>ALANKCCHVGCTKRSLARFC |
| 364 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWMEEVIKLCGRELVRAQIAICGKSTGGGEGGGEGGGEGGGQLY<br>SALANKCCHVGCTKRSLARFC |
| 365 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWMEEVIKLCGRELVRAQIAICGKSTGGGEGGGEEGGGEGGGQLYS<br>ALANKCCHVGCTKRSLARFC |
| 366 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWQEEVIKLCGRELVRAQIAICGKSTGGGEGGGEEGGGEGGGQLYS<br>ALANKCCHVGCTKRSLARFC |
| 367 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGGGSDSWMEEVIKLCGRELVRAQIAICGKSTGGEGGGEEGGGEGGGQLYSA<br>LANKCCHVGCTKRSLARFC |
| 368 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGGGSDSWQEEVIKLCGRELVRAQIAICGKSTGGEGGGEEGGGEGGGQLYSA<br>LANKCCHVGCTKRSLARFC |
| 369 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSWKEEVIKLCGRELVRAQIAICGKSTASDAAGANANAGARQLYS<br>ALANKCCHVGCTKRSLAQFC |
| 370 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS |

TABLE 7-continued

Fusion Protein Amino Acid Sequences

| SEQ ID NO: | Sequence |
|---|---|
| | LSLSPGKGGSDSWKEEVIKLCGRELVRAQIAICGKSTASDAAGANANAGARQLYS<br>ALANKCCHVGCTKRSLAEFC |
| 516 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTGGEGSGGEGEGGGRQLYS<br>ALANKCCHVGCTKRSLAQFC |
| 517 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTGGEGSGGEGEGGGRQLYS<br>ALANKCCQVGCTKRSLAQFC |
| 518 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTGGEGSGGEGEGGGRQLYS<br>ALANKCCHVGCTKQSLAQFC |
| 519 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTGGEGSGGEGEGGGRQLYS<br>ALANKCCQVGCTKQSLAQFC |
| 520 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTGGEGSGGEGSGGGRQLYS<br>ALANKCCHVGCTKRSLAQFC |
| 521 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTGGEGSGGEGSGGGRQLYS<br>ALANKCCQVGCTKRSLAQFC |
| 522 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTGGEGSGGEGSGGGRQLYS<br>ALANKCCHVGCTKQSLAQFC |
| 523 | DKTHTCPPCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALAA<br>PIEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVLHEALHSHYTQKS<br>LSLSPGKGGSDSYQEEVIKLCGRELVRAQIAICGKSTGGEGSGGEGSGGGRQLYS<br>ALANKCCQVGCTKQSLAQFC |

In some embodiments, the IgG Fc comprises a mouse IgG kappa signal sequence comprising the amino acid sequence of METDTLLLWVLLLWVPGSTG (SEQ ID NO: 329). In some embodiments, the IgG Fc comprises a mouse IgG heavy chain signal sequence. In some embodiments, the IgG Fc comprises a signal sequence comprising the amino acid sequence of MGWSCIILFLVATATGVHS (SEQ ID NO: 548). In some embodiments a different signal sequence is used. In some embodiments, no signal sequence is present on the fusion protein as produced.

In some embodiments, the fusion protein comprises an amino acid sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or 99% identical to the amino acid sequences shown in Table 8. In some embodiments, the fusion protein comprises or consists of the amino acid sequences shown in Table 8.

TABLE 8

Fusion Protein Amino Acid Sequences

| SEQ ID NO: | Sequence |
|---|---|
| 139 | METDTLLLWVLLLWVPGSTGDKTHTCPPCPAPEAAGGPSVFLFPPKPKDTLMISR TPEVTCVVVDVSHEDPEVKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGKGGSDSWQEEVIKLCGRELVRAQIAICGK STASDAAGADANAGARQLYSALANKCCHVGCTKRSLAQFC |
| 140 | METDTLLLWVLLLWVPGSTGDKTHTCPPCPAPEAAGGPSVFLFPPKPKDTLMISR TPEVTCVVVDVSHEDPVEKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGKGGSDSWQEEVIKLCGRELVRAQIAICGK STASDAAGANADAGARQLYSALANKCCHVGCTKRSLAQFC |
| 141 | METDTLLLWVLLLWVPGSTGDKTHTCPPCPAPEAAGGPSVFLFPPKPKDTLMISR TPEVTCVVVDVSHEDPEVKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGKGGSDSWQEEVIKLCGRELVRAQIAICGK STASDAAGADADAGARQLYSALANKCCHVGCTKRSLAQFC |
| 142 | METDTLLLWVLLLWVPGSTGDKTHTCPPCPAPEAAGGPSVFLFPPKPKDTLMISR TPEVTCVVVDVSHEDPEVKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGKGGSDSWQEEVIKLCGRELVRAQIAICGK STASDAAGAEAEAGARQLYSALANKCCHVGCTKRSLAQFC |
| 143 | METDTLLLWVLLLWVPGSTGDKTHTCPPCPAPEAAGGPSVFLFPPKPKDTLMISR TPEVTCVVVDVSHEDPEVKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGKGGSDSWQEEVIKLCGRELVRAQIAICGK STASDAAGAQADAGARQLYSALANKCCHVGCTKRSLAQFC |
| 144 | METDTLLLWVLLLWVPGSTGDKTHTCPPCPAPEAAGGPSVFLFPPKPKDTLMISR TPEVTCVVVDVSHEDPEVKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGKGGSDSWQEEVIKLCGRELVRAQIAICGK STASDAAGADAQAGARQLYSALANKCCHVGCTKRSLAQFC |
| 145 | METDTLLLWVLLLWVPGSTGDKTHTCPPCPAPEAAGGPSVFLFPPKPKDTLMISR TPEVTCVVVDVSHEDPEVKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGKGGSDSWQEEVIKLCGRELVRAQIAICGK STASDAAGAQAQAGARQLYSALANKCCHVGCTKRSLAQFC |
| 146 | METDTLLLWVLLLWVPGSTGDKTHTCPPCPAPEAAGGPSVFLFPPKPKDTLMISR TPEVTCVVVDVSHEDPEVKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGEGGSDSWQEEVIKLCGRELVRAQIAICGK STASDAAGADANAGARQLYSALANKCCHVGCTKRSLAQFC |
| 147 | METDTLLLWVLLLWVPGSTGDKTHTCPPCPAPEAAGGPSVFLFPPKPKDTLMISR TPEVTCVVVDVSHEDPVEKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGEGGSDSWQEEVIKLCGRELVRAQIAICGK STASDAAGANADAGARQLYSALANKCCHVGCTKRSLAQFC |
| 148 | METDTLLLWVLLLWVPGSTGDKTHTCPPCPAPEAAGGPSVFLFPPKPKDTLMISR TPEVTCVVVDVSHEDPEVKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG NVFSCSVLHEALHSHYTQKSLSLSPGEGGSDSWQEEVIKLCGRELVRAQIAICGK STASDAAGADADAGARQLYSALANKCCHVGCTKRSLAQFC |
| 149 | METDTLLLWVLLLWVPGSTGDKTHTCPPCPAPEAAGGPSVFLFPPKPKDTLMISR TPEVTCVVVDVSHEDPEVKFNWYVDGVEVHNAKTKPREEQYNSTYRVVSVLTVLH QDWLNGKEYKCKVSNKALAAPIEKTISKAKGQPREPQVYTLPPSRDELTKNQVSL TCLVKGFYPSDIAVEWESNGQPENNYKTTPPVLDSDGSFFLYSKLTVDKSRWQQG |

TABLE 8-continued

Fusion Protein Amino Acid Sequences

| SEQ ID NO: | Sequence |
|---|---|
| | NVFSCSVLHEALHSHYTQKSLSLSPGEGGSDSWQEEVIKLCGRELVRAQIAICGK<br>STASDAAGAEAEAGARQLYSALANKCCHVGCTKRSLAQFC |
| 150 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGAQADAGARQLYSALANKCCHVGCTKRSLAQFC |
| 151 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGADAQAGARQLYSALANKCCHVGCTKRSLAQFC |
| 152 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGAQAQAGARQLYSALANKCCHVGCTKRSLAQFC |
| 153 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGADANAGARQLYSALANKCCHVGCTKRSLAQFC |
| 154 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGANADAGARQLYSALANKCCHVGCTKRSLAQFC |
| 155 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGADADAGARQLYSALANKCCHVGCTKRSLAQFC |
| 156 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGAEAEAGARQLYSALANKCCHVGCTKRSLAQFC |
| 157 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGAQADAGARQLYSALANKCCHVGCTKRSLAQFC |
| 158 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGADAQAGARQLYSALANKCCHVGCTKRSLAQFC |
| 159 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGAQAQAGARQLYSALANKCCHVGCTKRSLAQFC |

TABLE 8-continued

Fusion Protein Amino Acid Sequences

| SEQ ID NO: | Sequence |
|---|---|
| 160 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGADANAGARQLYSALANKCCHVGCTKQSLAQFC |
| 161 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGANADAGARQLYSALANKCCHVGCTKQSLAQFC |
| 162 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGADADAGARQLYSALANKCCHVGCTKQSLAQFC |
| 163 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGAEAEAGARQLYSALANKCCHVGCTKQSLAQFC |
| 164 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGAQADAGARQLYSALANKCCHVGCTKQSLAQFC |
| 165 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGADAQAGARQLYSALANKCCHVGCTKQSLAQFC |
| 166 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGK<br>STASDAAGAQAQAGARQLYSALANKCCHVGCTKQSLAQFC |
| 167 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGADANAGARQLYSALANKCCHVGCTKQSLAQFC |
| 168 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGANADAGARQLYSALANKCCHVGCTKQSLAQFC |
| 169 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGADADAGARQLYSALANKCCHVGCTKQSLAQFC |
| 170 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL |

TABLE 8-continued

Fusion Protein Amino Acid Sequences

| SEQ ID NO: | Sequence |
|---|---|
| | TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGAEAEAGARQLYSALANKCCHVGCTKQSLAQFC |
| 171 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGAQADAGARQLYSALANKCCHVGCTKQSLAQFC |
| 172 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGADAQAGARQLYSALANKCCHVGCTKQSLAQFC |
| 173 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSWQEEVIKLCGRELVRAQIAICGQ<br>STASDAAGAQAQAGARQLYSALANKCCHVGCTKQSLAQFC |
| 174 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STASDAAGAEAEAGARQLYSALANKCCHVGCTKRSLAQFC |
| 175 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSFQEEVIKLCGRELVRAQIAICGK<br>STASDAAGAEAEAGARQLYSALANKCCHVGCTKRSLAQFC |
| 176 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSLQEEVIKLCGRELVRAQIAICGK<br>STASDAAGAEAEAGARQLYSALANKCCHVGCTKRSLAQFC |
| 177 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSIQEEVIKLCGRELVRAQIAICGK<br>STASDAAGAEAEAGARQLYSALANKCCHVGCTKRSLAQFC |
| 178 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STASDAAGAEAEAGARQLYSALANKCCYVGCTKRSLAQFC |
| 179 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STASDAAGAEAEAGARQLYSALANKCCLVGCTKRSLAQFC |
| 180 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STASDAAGAEAEAGARQLYSALANKCCQVGCTKRSLAQFC |

TABLE 8-continued

Fusion Protein Amino Acid Sequences

| SEQ ID NO: | Sequence |
|---|---|
| 181 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STASDAAGAEAEAGARQLYSALANKCCKVGCTKRSLAQFC |
| 182 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSYQEEVIKLCGRELVRAQIAICGK<br>STASDAAGAEAEAGARQLYSALANKCCKVGCTKRSLAQFC |
| 183 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSYQEEVIKLCGRELVRAQIAICGK<br>STASDAAGAEAEAGARQLYSALANKCCKVGCTKRSLAQFC |
| 184 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSYQEEVIKLCGRELVRAQIAICGK<br>STGGEGSGGEGEGGGRQLYSALANKCCKVGCTKRSLAQFC |
| 185 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSYQEEVIKLCGRELVRAQIAICGK<br>STGGEGSGGEGEGGGRQLYSALANKCCKVGCTKRSLAQFC |
| 186 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSYQEEVIKLCGRELVRAQIAICGK<br>STGGEGSGGEGSGGGRQLYSALANKCCKVGCTKRSLAQFC |
| 187 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGEGGSDSYQEEVIKLCGRELVRAQIAICGK<br>STGGEGSGGEGSGGGRQLYSALANKCCKVGCTKRSLAQFC |
| 188 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STASDAAGAEAEAGARQLYSALANKCCYVGCTKQSLAQFC |
| 189 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STASDAAGAEAEAGARQLYSALANKCCKVGCTKQSLAQFC |
| 190 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGEGGGRQLYSALANKCCYVGCTKQSLAQFC |
| 191 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG |

TABLE 8-continued

Fusion Protein Amino Acid Sequences

| SEQ ID NO: | Sequence |
|---|---|
| | NVFSCSVLHEALHSHYTQKSLSLSPGKGGSDSYQEEVIKLCGRELVRAQIAICGK<br>STGGEGSGGEGEGGGRQLYSALANKCCKVGCTKQSLAQFC |
| 192 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGSGGGRQLYSALANKCCYVGCTKQSLAQFC |
| 193 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGSGGGRQLYSALANKCCKVGCTKQSLAQFC |
| 330 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWKEEVIKLCGRELVRAQIAICGK<br>STGGGEGGGEGGGEGRQLYSALANKCCHVGCTKRSLARFC |
| 331 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWKEEVIKLCGRELVRAQIAICGK<br>STGGGEGGGEGGGEGGGQLYSALANKCCHVGCTKRSLARFC |
| 332 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWMEEVIKLCGRELVRAQIAICGK<br>STGGGEGGGEGGGEGRQLYSALANKCCHVGCTKRSLARFC |
| 333 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWQEEVIKLCGRELVRAQIAICGK<br>STGGGEGGGEGGGEGRQLYSALANKCCHVGCTKRSLARFC |
| 334 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STGGGEGGGEGGGEGRQLYSALANKCCHVGCTKRSLARFC |
| 335 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWMEEVIKLCGRELVRAQIAICGK<br>STGGGEGGGEGGGEGGGQLYSALANKCCHVGCTKRSLARFC |
| 336 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWQEEVIKLCGRELVRAQIAICGK<br>STGGGEGGGEGGGEGGGQLYSALANKCCHVGCTKRSLARFC |
| 337 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STGGGEGGGEGGGEGGGQLYSALANKCCHVGCTKRSLARFC |

TABLE 8-continued

Fusion Protein Amino Acid Sequences

| SEQ ID NO: | Sequence |
|---|---|
| 338 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWMEEVIKLCGRELVRAQIAICGK<br>STGGEGGGEEGGGEGGQLYSALANKCCHVGCTKRSLARFC |
| 339 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWQEEVIKLCGRELVRAQIAICGK<br>STGGEGGGEEGGGEGGQLYSALANKCCHVGCTKRSLARFC |
| 340 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGGGSDSWMEEVIKLCGRELVRAQIAICGKS<br>TGGEGGGEEGGGEGGQLYSALANKCCHVGCTKRSLARFC |
| 341 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGGGSDSWQEEVIKLCGRELVRAQIAICGKS<br>TGGEGGGEEGGGEGGQLYSALANKCCHVGCTKRSLARFC |
| 342 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWQEEVIKLCGRELVRAQIAICGK<br>STGGEGGGEGGGEGRQLYSALANKCCHVGCTKRSLAQFC |
| 343 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STGGEGGGEGGGEGRQLYSALANKCCHVGCTKRSLAQFC |
| 344 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGGGSDSWQEEVIKLCGRELVRAQIAICGKS<br>TGGGEGGGEGGGEGRQLYSALANKCCHVGCTKRSLARFC |
| 345 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGGGSDSWQEEVIKLCGRELVRAQIAICGKS<br>TGGGEGGGEGGGEGRQLYSALANKCCHVGCTKRSLARFC |
| 346 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGGGSDSWQEEVIKLCGRELVRAQIAICGKS<br>TGGGEGGGEGGGEGRQLYSALANKCCHVGCTKRSLAQFC |
| 347 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGGGSDSWQEEVIKLCGRELVRAQIAICGKS<br>TGGGEGGGEGGGEGRQLYSALANKCCHVGCTKRSLAQFC |
| 348 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL |

TABLE 8-continued

Fusion Protein Amino Acid Sequences

| SEQ ID NO: | Sequence |
|---|---|
| | TCLVKGFYPSDIAVEWESNGQPENNYKTTPPVLDSDGSFFLYSKLTVDKSRWQQG<br>NVFSCSVMHEALHNHYTQKSLSLSPGKGGSDSWQEEVIKLCGRELVRAQIAICGK<br>STGGGEEGGGEEGGGRQLYSALANKCCHVGCTKRSLARFC |
| 349 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STGGGEEGGGEEGGGRQLYSALANKCCHVGCTKRSLARFC |
| 350 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGKGGSDSWQEEVIKLCGRELVRAQIAICGK<br>STGGGEEGGGEEGGGRQLYSALANKCCHVGCTKRSLAQFC |
| 351 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STGGGEEGGGEEGGGRQLYSALANKCCHVGCTKRSLAQFC |
| 352 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGGGSDSWQEEVIKLCGRELVRAQIAICGKS<br>TGGGEEGGGEEGGGRQLYSALANKCCHVGCTKRSLARFC |
| 353 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGGGSDSWQEEVIKLCGRELVRAQIAICGKS<br>TGGGEEGGGEEGGGRQLYSALANKCCHVGCTKRSLARFC |
| 354 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVMHEALHNHYTQKSLSLSPGGGSDSWQEEVIKLCGRELVRAQIAICGKS<br>TGGGEEGGGEEGGGRQLYSALANKCCHVGCTKRSLAQFC |
| 355 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGGGSDSWQEEVIKLCGRELVRAQIAICGKS<br>TGGGEEGGGEEGGGRQLYSALANKCCHVGCTKRSLAQFC |
| 356 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STGGEGEGGEGEGGSRQLYSALANKCCHVGCTKRSLAQFC |
| 357 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGGGSDSWQEEVIKLCGRELVRAQIAICGKS<br>TGGEGEGGEGEGGSRQLYSALANKCCHVGCTKRSLARFC |
| 358 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGGGSDSWQEEVIKLCGRELVRAQIAICGKS<br>TGGEGEGGEGEGGSRQLYSALANKCCHVGCTKRSLAQFC |

TABLE 8-continued

Fusion Protein Amino Acid Sequences

| SEQ ID NO: | Sequence |
|---|---|
| 371 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWKEEVIKLCGRELVRAQIAICGK<br>STGGGEGGGEGGGEGRQLYSALANKCCHVGCTKRSLARFC |
| 372 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWKEEVIKLCGRELVRAQIAICGK<br>STGGGEGGGEGGGEGGGQLYSALANKCCHVGCTKRSLARFC |
| 373 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWMEEVIKLCGRELVRAQIAICGK<br>STGGGEGGGEGGGEGRQLYSALANKCCHVGCTKRSLARFC |
| 374 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWMEEVIKLCGRELVRAQIAICGK<br>STGGGEGGGEGGGEGGGQLYSALANKCCHVGCTKRSLARFC |
| 375 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWMEEVIKLCGRELVRAQIAICGK<br>STGGGEGGGEEGGGEGGGQLYSALANKCCHVGCTKRSLARFC |
| 376 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWQEEVIKLCGRELVRAQIAICGK<br>STGGEGGGEEGGGEGGGQLYSALANKCCHVGCTKRSLARFC |
| 377 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGGGSDSWMEEVIKLCGRELVRAQIAICGKS<br>TGGEGGGEEGGGEGGQLYSALANKCCHVGCTKRSLARFC |
| 378 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGGGSDSWQEEVIKLCGRELVRAQIAICGKS<br>TGGEGGGEEGGGEGGQLYSALANKCCHVGCTKRSLARFC |
| 379 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWKEEVIKLCGRELVRAQIAICGK<br>STASDAAGANANAGARQLYSALANKCCHVGCTKRSLAQFC |
| 380 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSWKEEVIKLCGRELVRAQIAICGK<br>STASDAAGANANAGARQLYSALANKCCHVGCTKRSLAEFC |
| 498 | METDTLLLWVLLLWVPGSTGDKTHTCPPCPAPELLGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQQG |

TABLE 8-continued

Fusion Protein Amino Acid Sequences

| SEQ ID NO: | Sequence |
|---|---|
|  | NVFSCSVMHEALHNHYTQKSLSLSPGKGGGGSGGGGSGGGGSQLYSALANKCCHV<br>GCTKRSLARFCGGGGSGGGGSGGGGSSWMEEVIKLCGRELVRAQIAICGMSTWS |
| 524 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGEGGGRQLYSALANKCCHVGCTKRSLAQFC |
| 525 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGEGGGRQLYSALANKCCQVGCTKRSLAQFC |
| 526 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGEGGGRQLYSALANKCCHVGCTKQSLAQFC |
| 527 | METDTLLLWVLLLWVPGSTGDKTHTCPPCPAPEAAGGPSVFLFPPKPKDTLMISR<br>TPEVTCVVVDVSHEDPVEKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGEGGGRQLYSALANKCCQVGCTKQSLAQFC |
| 528 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGSGGGRQLYSALANKCCHVGCTKRSLAQFC |
| 529 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGSGGGRQLYSALANKCCQVGCTKRSLAQFC |
| 530 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGSGGGRQLYSALANKCCHVGCTKQSLAQFC |
| 531 | METDTLLLWVLLLWVPGSTGDKTHTCPPCPAPEAAGGPSVFLFPPKPKDTLMISR<br>TPEVTCVVVDVSHEDPEVKFNWYVDGVEVHNAKTKPREEQYNSTYRVVSVLTVLH<br>QDWLNGKEYKCKVSNKALAAPIEKTISKAKGQPREPQVYTLPPSRDELTKNQVSL<br>TCLVKGFYPSDIAVEWESNGQPENNYKTTPPVLDSDGSFFLYSKLTVDKSRWQQG<br>NVFSCSVLHEALHSHYTQKSLSLSPGKGGSDSYQEEVIKLCGRELVRAQIAICGK<br>STGGEGSGGEGSGGGRQLYSALANKCCQVGCTKQSLAQFC |
| 549 | MGWSCIILFLVATATGVHSDKTHTCPPCPAPEAAGGPSVFLFPPKPKDTLMISRT<br>PEVTCVVVDVSHEDPVEKFNWYVDGVEVHNAKTKPREEQYNSTYRVVSVLTVLHQ<br>DWLNGKEYKCKVSNKALAAPIEKTISKAKGQPREPQVYTLPPSRDELTKNQVSLT<br>CLVKGFYPSDIAVEWESNGQPENNYKTTPPVLDSDGSFFLYSKLTVDKSRWQQGN<br>VFSCSVLHEALHSHYTQKSLSLSPGKGGSDSWQEEVIKLCGRELVRAQIAICGKS<br>TASDAAGAEAEAGARQLYSALANKCCHVGCTKRSLAQFC |

Other Half-Life Extending Moieties

As used herein, the term "half-life extending moiety" includes non-proteinaceous, half-life extending moieties, such as PEG or HES, and proteinaceous half-life extending moieties such as Fc domain. In some embodiments, non-proteinaceous half-life extending moieties are linked to the fusion proteins described herein. In some embodiments, the non-proteinaceous half-life extending moieties are linked to the fusion proteins instead of IgG Fc. In some embodiments, the non-proteinaceous half-life extending moieties are linked to the fusion proteins in addition to IgG Fc.

Examples of suitable polymer molecules that act as non-proteinaceous half-life extending moieties include polymer molecules selected from the group consisting of polyalkylene oxide (PAO), including polyalkylene glycol (PAG), such as polyethylene glycol (PEG) and polypropylene glycol (PPG), branched PEGs, hydroxyalkyl starch (HAS), such as hydroxyethyl starch (HES), polysialic acid (PSA), polyvinyl alcohol (PVA), poly-carboxylate, poly-(vinylpyrrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG has the advantage of having only few reactive groups capable of cross-linking compared to, e.g., polysaccharides such as dextran. In particular, monofunctional PEG, e.g., methoxypolyethylene glycol (mPEG), is of interest since its coupling chemistry is relatively simple (only one reactive group is available for conjugating with attachment groups on the polypeptide). Consequently, as the risk of cross-linking is eliminated, the resulting conjugated fusion proteins described herein are more homogeneous, and the reaction of the polymer molecules with the variant polypeptide is easier to control.

To effect covalent attachment of the polymer molecule(s) to the fusion proteins described herein, the hydroxyl end groups of the polymer molecule must be provided in activated form, i.e., with reactive functional groups (examples of which include primary amino groups, hydrazide (HZ), thiol, succinate (SUC), succinimidyl succinate (SS), succinimidyl succinamide (SSA), succinimidyl propionate (SPA), succinimidyl butyrate (SBA), succinimidyl carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g., from Shearwater Polymers, Inc., Huntsville, Ala., USA, or from PolyMASC Pharmaceuticals plc, UK.

Alternatively, the polymer molecules can be activated by conventional methods known in the art, e.g., as disclosed in WO 90/13540. Specific examples of activated linear or branched polymer molecules for use herein are described in the Shearwater Polymers, Inc. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g., SPA-PEG, SSPA-PEG, SBA-PEG, SS-PEG, SSA-PEG, SC-PEG, SG-PEG, and SCM-PEG), and NOR-PEG, BTC-PEG, EPOXPEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. Nos. 5,932,462 and 5,643,575, both of which are incorporated herein by reference. Furthermore, the following publications disclose useful polymer molecules and/or PEGylation chemistries: U.S. Pat. Nos. 5,824,778, 5,476,653, WO 97/32607, EP 229,108, EP 402, 378, U.S. Pat. Nos. 4,902,502, 5,281,698, 5,122,614, 5,219, 564, WO 92/16555, WO 94/04193, WO 94/14758, WO 94/17039, WO 94/18247, WO 94/28024, WO 95/00162, WO 95/11924, WO 95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. Nos. 5,473,034, 5,516,673, EP 605 963, U.S. Pat. No. 5,382,657, EP 510 356, EP 400 472, EP 183 503, and EP 154 316.

Specific examples of activated PEG polymers particularly preferred for coupling to cysteine residues, include the following linear PEGs: vinylsulfone-PEG (VS-PEG), preferably vinylsulfone-mPEG (VS-mPEG); maleimide-PEG (MAL-PEG), preferably maleimide-mPEG (MAL-mPEG) and orthopyridyl-disulfide-PEG (OPSS-PEG), preferably orthopyridyl-disulfide-mPEG (OPSS-mPEG). Typically, such PEG or mPEG polymers will have a size of about 5 kDa, about 10 kDa, about 12 kDa or about 20 kDa.

The conjugation of the fusion proteins described herein and the activated polymer molecules is conducted by use of any conventional method, e.g., as described in the following references (which also describe suitable methods for activation of polymer molecules): Harris and Zalipsky, eds., Poly(ethylene glycol) *Chemistry and Biological Applications*, AZC Washington; R. F. Taylor, (1991), "Protein immobilisation. Fundamental and applications," Marcel Dekker, N.Y.; S. S. Wong, (1992), "Chemistry of Protein Conjugation and Crosslinking," CRC Press, Boca Raton; G. T. Hermanson et al., (1993), "Immobilized Affinity Ligand Techniques", Academic Press, N.Y.

The skilled person will be aware that the activation method and/or conjugation chemistry to be used depends on the attachment group(s) of the fusion protein (examples of which are given further above), as well as the functional groups of the polymer (e.g., being amine, hydroxyl, carboxyl, aldehyde, sulfhydryl, succinimidyl, maleimide, vinylsulfone or haloacetate). The PEGylation may be directed towards conjugation to all available attachment groups on the fusion protein (i.e., such attachment groups that are exposed at the surface of the polypeptide) or may be directed towards one or more specific attachment groups, e.g., the N-terminal amino group as described in U.S. Pat. No. 5,985,265 or to cysteine residues. Furthermore, the conjugation may be achieved in one step or in a stepwise manner (e.g., as described in WO 99/55377).

For PEGylation to cysteine residues (see above) the fusion protein is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to 16 hours.

It will be understood that the PEGylation is designed so as to produce the optimal molecule with respect to the number of PEG molecules attached, the size and form of such molecules (e.g., whether they are linear or branched), and the attachment site(s) in the fusion protein. The molecular weight of the polymer to be used may e.g., be chosen on the basis of the desired effect to be achieved.

In connection with conjugation to only a single attachment group on the fusion protein (e.g., the N-terminal amino group), it may be advantageous that the polymer molecule, which may be linear or branched, has a high molecular weight, preferably about 10-25 kDa, such as about 15-25 kDa, e.g., about 20 kDa.

Normally, the polymer conjugation is performed under conditions aimed at reacting as many of the available polymer attachment groups with polymer molecules. This is achieved by means of a suitable molar excess of the polymer relative to the polypeptide. Typically, the molar ratios of activated polymer molecules to polypeptide are up to about 1000-1, such as up to about 200-1, or up to about 100-1. In some cases, the ratio may be somewhat lower, however, such as up to about 50-1, 10-1, 5-1, 2-1 or 1-1 in order to obtain optimal reaction.

It is also contemplated to couple the polymer molecules to the fusion protein through a linker. Suitable linkers are well known to the skilled person. A preferred example is cyanuric chloride (Abuchowski et al., (1977), J. Biol. Chem., 252, 3578-3581; U.S. Pat. No. 4,179,337; Shafer et al., (1986), J. Polym. Sci. Polym. Chem. Ed., 24, 375-378).

Subsequent to the conjugation, residual activated polymer molecules are blocked according to methods known in the art, e.g., by addition of primary amine to the reaction mixture, and the resulting inactivated polymer molecules are removed by a suitable method.

It will be understood that depending on the circumstances, e.g., the amino acid sequence of the fusion protein, the nature of the activated PEG compound being used and the specific PEGylation conditions, including the molar ratio of PEG to polypeptide, varying degrees of PEGylation may be obtained, with a higher degree of PEGylation generally being obtained with a higher ratio of PEG to fusion protein. The PEGylated fusion proteins resulting from any given PEGylation process will, however, normally comprise a stochastic distribution of conjugated fusion protein having slightly different degrees of PEGylation.

For improvement of the biological half-life of the fusion proteins described herein, chemical modification such as PEGylation, or HESylation are applicable.

HAS and HES non-proteinaceous polymers, as well as methods of producing HAS or HES conjugates are disclosed for example in WO 02/080979, WO 03/070772, WO 057092391 and WO 057092390.

Polysialytion is another technology, which uses the natural polymer polysialic acid (PSA) to prolong the half-life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the fusion protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Biological Activity of the Relaxin-2 Fusion Proteins

In some embodiments, the relaxin-2 fusion proteins described herein have high levels of biological activity as compared to native relaxin-2. In some embodiments, any of the relaxin-2 fusion proteins described herein have from about 1% to about 200% of a biological activity as compared to native relaxin-2. In some embodiments, the relaxin-2 fusion protein has at least about 5%, about 10%, about 15%, about 20%, about 25%, about 30%, about 35%, about 40%, about 50%, about 60%, about 70%, about 80%, about 90%, about 100%, about 125% about 150%, about 175%, or about 200% of a biological activity as compared to native relaxin-2.

In some embodiments, any of the relaxin-2 fusion proteins described herein have from about 1% to about 200% of maximal biological activity as compared to native relaxin-2. In some embodiments, maximal biological activity is the maximum response ($E_{max}$) of relaxin-2 or relaxin-2 fusion protein. In some embodiments, the relaxin-2 fusion protein has at least about 5%, about 10%, about 15%, about 20%, about 25%, about 30%, about 35%, about 40%, about 50%, about 60%, about 70%, about 80%, about 90%, about 100%, about 125% about 150%, about 175%, or about 200% of a maximal biological activity as compared to native relaxin-2.

In some embodiments, any of the relaxin-2 fusion proteins described herein have about at least about 0.001-fold to about at least 1,000-fold enhanced potency as compared to native relaxin-2. In some embodiments, potency is the concentration of relaxin-2 or relaxin-2 fusion protein to elicit a half-maximal response ($EC_{50}$). In some embodiments, the relaxin-2 fusion protein has at least about 0.001-fold, about 0.01-fold, about 0.1-fold, about 1-fold, about 10-fold, about 100-fold, or about 1,000-fold of the potency as compared to native relaxin-2.

The biological activity can be any biological activity of native relaxin-2. For example, the biological activity can be the capacity to bind the receptor of native relaxin-2, RXFP1. The binding of relaxin-2 to RXFP1 can be measured by any well-known methods in the art, such as radioligand binding. In some embodiments, the fusion proteins described herein bind to RXFP1 when it is expressed on a cell surface.

In some embodiments, the biological activity can be the capacity to activate RXFP1 on a cell surface. The activation of RXFP1 by the relaxin-2 fusion proteins described herein can be determined by the increase of cAMP using any methods well known in the art, such as measuring the activity of a cAMP-driven reporter gene, e.g., β-galactosidase. The activation of RXFP1 by the relaxin-2 fusion proteins described herein in a cell may also be determined by using a biosensor such as the GloSensor biosensor. The activation of RXFP1 by the relaxin-2 fusion proteins described herein in a cell may also be determined by measuring the expression of certain genes, such as angiogenic factors, e.g., VEGF, or the expression of MMPs using well-known methods in the art. In some embodiments, the biological activity is a physiological, biochemical activity or any other effect-inducing activity of the relaxin-2. Exemplary biological activities include, but are not limited to, vasodilation, collagen degradation, angiogenesis, decreasing arterial blood pressure, increasing renal artery blood flow, increasing renal plasma flow, increasing cardiac filling at diastole, resolving established fibrosis, and suppressing new fibrosis development.

In some embodiments, the fusion proteins described herein have improved pharmacokinetics profiles. Without wishing to be bound by any theory, the structure of the fusion proteins described herein is based upon, at least in part, the surprising discovery that reducing the pI of relaxin-2 fusion protein analogs increases their circulating half-life. In some embodiments, the fusion proteins described herein have high bioavailability. In some embodiments, the fusion proteins described herein have high and/or stable serum levels. In some embodiments, the circulating half-life, bioavailability, high serum level, and/or stable serum level is in a mammal. In some embodiments, the mammal is a rodent or a primate. In some embodiments, the rodent is a rat or a mouse. In some embodiments, the primate is a human or a monkey. In some embodiments, the monkey is a cynomolgus monkey. In some embodiments, the mammal is a human.

In some embodiments, the fusion proteins described herein may have a circulating half-life of greater than about 5 hours, 10 hours, 20 hours, 50 hours, 75 hours, 100 hours, 125 hours, 150 hours, or more. In some embodiments, the fusion proteins described herein may have a circulating half-life of 5-10 hours, 10-20 hours, 20-50 hours, 50-75 hours, 75-100 hours, 100-125 hours, or 125-150 hours. In some embodiments, the fusion proteins described herein may have a circulating half-life of about 10 days, about 11 days, about 12 days, about 13 days, about 14 days, about 15 days, about 16 days, about 17 days, about 18 days, about 19 days, about 20 days, about 21 days, about 22 days, or about 23 days. In some embodiments, the fusion proteins described herein may have a circulating half-life of 10 days, 11 days, 12 days, 13 days, 14 days, 15 days, 16 days, 17 days, 18 days, 19 days, 20 days, 21 days, 22 days, or 23 days. In some embodiments, the fusion proteins described herein may have a circulating half-life of at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, or at least 23 days. In some embodiments, the fusion proteins described herein may have a circulating half-life of greater than about 5 hours, 10 hours, 20 hours, 50 hours, 75 hours, 100 hours, 125 hours, 150 hours, or more, when administered to a human. In some embodiments, the fusion proteins described herein may have a circulating half-life of 5-10 hours, 10-20 hours, 20-50 hours, 50-75 hours, 75-100 hours, 100-125 hours, or 125-150 hours, when administered to a human. In some embodiments, the fusion proteins described herein may have a circulating half-life of about 10 days, about 11 days, about 12 days, about 13 days, about 14 days, about 15 days, about 16 days, about 17 days, about 18 days, about 19 days, about 20 days, about 21 days, about 22 days, or about 23 days, when administered to a human. In some embodiments, the fusion proteins described herein may have a circulating half-life of 10 days, 11 days, 12 days, 13 days, 14 days, 15 days, 16 days, 17 days, 18 days, 19 days, 20 days, 21 days, 22 days, or 23 days, when administered to a human. In some embodiments, the fusion proteins described herein may have a circulating half-life of at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, or at least 23 days, when administered to a human. Values and ranges intermediate to the recited values are also intended to be part of this disclosure. In some embodiments, the fusion proteins described herein have a longer circulating half-life than a native two chain relaxin-2. For example, the circulating half-life of a native two chain relaxin-2 may be less than about 5 hours. (See, e.g., Chen et al., The Pharmacokinetics of Recombinant Human Relaxin in Non-Pregnant Women after Intravenous, Intravaginal, and Intracervical Administration, Pharm. Res. 10: 834038 (1993), incorporated herein by reference).

This increased half-life can be, at least in part, attributed to the reduced pI of the fusion proteins described herein. In some embodiments, the fusion protein has a pI that is less than about 9.4. As used herein, the term "about" when referring to pI encompasses variations of ±1% of a given value or range, as is appropriate to perform the methods disclosed herein. In some embodiments, the fusion protein has a pI that is less than 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, or 6.1, or is less than about 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, or 6.1. In some embodiments, the fusion protein has a pI that is less than 9.0. In some embodiments, the fusion protein has a pI that is less than about 8.2. In some embodiments, the fusion protein has a pI from about 6.0 to about 9.4. In some embodiments, the fusion protein has a pI from about 6.5 to about 8.5, about 6.6 to about 8.4, about 6.7 to about 8.3, about 6.8 to about 8.2, about 6.8 to about 8.1, about 6.8 to about 8.0, about 6.8 to about 7.9, about 6.0 to about 8.2, about 6.0 to about 8.1, about 6.0 to about 8.0, about 6.0 to about 7.9, about 6.0 to about 7.8, about 6.0 to about 7.7, about 6.0 to about 7.6, about 6.0 to about 7.5, about 6.0 to about 7.4, about 6.0 to about 7.3, about 6.0 to about 7.2, about 6.0 to about 7.1, about 6.0 to about 7.0, about 6.0 to about 6.9, about 6.0 to about 6.8, about 6.0 to about 6.7, about 6.0 to about 6.6, about 6.0 to about 6.5, about 6.0 to about 6.4, about 6.0 to about 6.3, about 6.0 to about 6.2, or about 6.0 to about 6.1. In some embodiments, the fusion protein has a pI from about 6.0 to about 8.2. In some embodiments, the fusion protein has a pI of 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, or 8.2, or is about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, or 8.2, or is between any two such values. In some embodiments, the fusion protein has a pI of about 6.8. In some embodiments, the fusion protein has a pI of about 7.0. In some embodiments, the fusion protein has a pI of about 7.1. In some embodiments, the fusion protein has a pI of about 7.4. In some embodiments, the fusion protein has a pI of about 7.5. In some embodiments, the fusion protein has a pI of about 7.9. In some embodiments, the fusion protein has a pI of about 8.0. In some embodiments, the fusion protein has a pI of about 8.4. In some embodiments, the fusion protein has a pI of about 8.5. In some embodiments, the fusion protein has a pI of about 8.8. In some embodiments, the fusion protein has a pI of about 8.9. In some embodiments, any of the pIs referred to above is the calculated or theoretical pI. In some embodiments, any of the pIs referred to above is the experimentally measured pI.

As used herein, the term "about" when referring to dosages encompasses variations of ±10% of a given value or range, as is appropriate to perform the methods disclosed herein.

"Circulating half-life," as used herein, refers to the time it takes for the blood plasma concentration of a drug to halve its steady-state when circulating in the full blood of an organism. Circulating half-life of a particular agent may vary depending on a multitude of factors including, but not limited to, dosage, formulation, and/or administration route of the agent. One of ordinary skill in the art is able to determine the circulating half-life of an agent using well known methods in the art, such as the method described Chen supra.

In some embodiments, the fusion proteins described herein have high bioavailability. In some embodiments, the fusion proteins have high bioavailability when administered, e.g., intravenously or subcutaneously. In some embodiments, the fusion proteins have high bioavailability when administered subcutaneously. In some embodiments, the fusion proteins have high subcutaneous bioavailability. In some embodiments, the fusion proteins have bioavailability of at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. In some embodiments, the fusion proteins have bioavailability of about 40%, about 45%, about 50%, about 55%, about 60%, about 65%, about 70%, about 75%, about 80%, about 85%, about 90%, about 95%, about 98%, about 99%, or about 100%. In some embodiments, the fusion proteins have bioavailability of 40%, 45%, 50%, 55%, 60%, 65%, 70%, 75%, 80%, 85%, 90%, 95%, 98%, 99%, or 100%. In some embodiments, the fusion proteins have bioavailability of about 40% to about 80%, about 40% to about 75%, about 40% to about 70%, about 40% to about 60%, about 50% to about 80%, about 50% to about 70%, about 50% to about 60%, about 60% to about 80%, or about 70% to about 80. In some embodiments, the fusion proteins have bioavailability of about 50% to about 60% (e.g., 50% to 60%). In some embodiments, the fusion proteins have bioavailability, when administered subcutaneously, of at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. In some embodiments, the fusion proteins have bioavailability, when administered subcutaneously, of about 40%, about 45%, about 50%, about 55%, about 60%, about 65%, about 70%, about 75%, about 80%, about 85%, about 90%, about 95%, about 98%, about 99%, or about 100%. In some embodiments, the fusion proteins have bioavailability, when administered subcutaneously, of 40%, 45%, 50%, 55%, 60%, 65%, 70%, 75%, 80%, 85%, 90%, 95%, 98%, 99%, or 100%. In some embodiments, the fusion proteins have bioavailability, when administered subcutaneously, of about 40% to about 80%, about 40% to about 75%, about 40% to about 70%, about 40% to about 60%, about 50% to about 80%, about 50% to about 70%, about 50% to about 60%, about 60% to about 80%, or about 70% to about 80. In some embodiments, the fusion proteins have bioavailability, when administered subcutaneously, of about 50% to about 60% (e.g., 50% to 60%).

"Bioavailability," as used herein, refers to the fraction of administered drug that arrives in systemic circulation. Bioavailability of a particular agent may vary depending on a multitude of factors including, but not limited to, dosage, formulation, administration route, and/or properties of the agent. One of ordinary skill in the art is able to determine the bioavailability of an agent using well known methods in the art.

In some embodiments, the fusion proteins have high and/or stable serum levels when administered to a subject, e.g., intravenously, subcutaneously, and/or according to any of the methods described herein. In some embodiments the fusion proteins are present in subject serum at a level of at least about 0.5 µg/mL, at least about 1 µg/mL, at least about 2 µg/mL, at least about 3 µg/mL, at least about 4 µg/mL, at least about 5 µg/mL, at least about 6 µg/mL, at least about 7 µg/mL, at least about 8 µg/mL, or at least about 9 µg/mL 0.5 days, 1 day, 2 days, 3 days, 4 days, 5 days, 6 days, 7 days, 8 days, 9 days, 10 days, or more after administration. In some embodiments the fusion proteins are present in subject serum at a level of at least about 0.5 µg/mL (e.g., at least about 1 µg/mL, at least about 2 µg/mL, at least about 3 µg/mL, at least about 4 µg/mL, at least about 5 µg/mL, at least about 6 µg/mL, at least about 7 µg/mL, at least about 8 µg/mL, or at least about 9 µg/mL) for at least 0.5 days, at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, or more after administration. In some embodiments the fusion proteins are present in subject serum at a level of at least about 0.5 µg/mL (e.g., at least about 1 µg/mL, at least about 2 µg/mL, at least about 3 µg/mL, at least about 4 µg/mL, at least about 5 µg/mL, at least about 6 µg/mL, at least about 7 µg/mL, at least about 8 µg/mL, or at least about 9 µg/mL) for at least 0.5 days, at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, or more after intravenous administration. In some embodiments the fusion proteins are present in subject serum at a level of at least about 0.5 µg/mL (e.g., at least about 1 µg/mL, at least about 2 µg/mL, at least about 3 µg/mL, at least about 4 µg/mL, at least about 5 µg/mL, at least about 6 µg/mL, at least about 7 µg/mL, at least about 8 µg/mL, or at least about 9 µg/mL) for at least 0.5 days, at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, or more after subcutaneous administration.

Vectors and Host Cells

The disclosure also provides nucleic acid molecules that encode any of the fusion proteins or peptides described herein. In some embodiments, the nucleic acid molecules described herein are DNA molecules. In some embodiments, the nucleic acid molecules described herein are RNA molecules.

The nucleic acid molecules described herein can be transcribed from a promoter in an expression vector. In some embodiments, the vector is a non-viral vector. Exemplary non-viral vectors include, but are not limited to, plasmid DNA, transposons, episomal plasmids, minicircles, ministrings, and oligonucleotides (e.g., mRNA, naked DNA). In some embodiments, the vector is a DNA plasmid vector.

In some embodiments, the vector is a viral vector. Viral vectors can be replication competent or replication incompetent. Viral vectors can be integrating or non-integrating. A number of viral based systems have been developed for gene transfer into mammalian cells, and a suitable viral vector can be selected by a person of ordinary skill in the art. Exemplary viral vectors include, but are not limited to, adenovirus vectors (e.g., adenovirus 5), adeno-associated virus (AAV) vectors (e.g., AAV2, 3, 5, 6, 8, 9), retrovirus vectors (MMSV, MSCV), lentivirus vectors (e.g., HIV-1, HIV-2), gammaretrovirus vectors, herpes virus vectors (e.g., HSV1, HSV2), alphavirus vectors (e.g., SFV, SIN, VEE, M1), flavivirus (e.g., Kunjin, West Nile, Dengue virus), rhabdovirus vectors (e.g., rabies virus, VSV), measles virus vector (e.g., MV-Edm), Newcastle disease virus vectors, poxvirus vectors (e.g., VV), measles virus, and picornavirus vectors (e.g., Coxsackievirus).

In some embodiments, the vector or expression cassette comprises one or more additional elements. Additional elements include, but are not limited to, promoters, enhancers, polyadenylation (polyA) sequences, and selection genes.

In some embodiments, the vector comprises a polynucleotide sequence that encodes an amino acid sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or 99% identical to an amino acid sequence recited in any of Tables 1-8. In some embodiments, the vector comprises a polynucleotide sequence that encodes an amino acid sequence that comprises or consists of an amino acid sequence recited in any of Tables 1-8. In some embodiments, the vector comprises a polynucleotide sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or 99% identical to a sequence recited in Table 9, below. In some embodiments, the vector comprises a polynucleotide sequence that comprises or consists of a sequence recited in Table 9, below.

TABLE 9

Nucleotide Sequences Encoding Fusion Proteins and Peptide Components

| SEQ ID NO: | Sequence |
|---|---|
| 410 | GACAAGACCCATACATGTCCGCCTTGTCCTGCGCCTGAGGCAGCAGGCG GACCATCAGTCTTCTTGTTTCCCCCCAAGCCGAAGGACACCCTTATGATC TCACGCACCCCCGAAGTAACTTGTGTAGTCGTTGATGTCTCACACGAAG ACCCGGAAGTAAAGTTTAATTGGTATGTCGATGGTGTTGAGGTCCACAA CGCTAAAACGAAACCGCGGGAAGAACAATACAACTCCACATATCGAGT AGTCTCCGTCCTGACTGTTCTTCACCAGGACTGGCTGAATGGTAAAGAAT ACAAATGTAAAGTGAGTAACAAGGCCCTTGCAGCACCCATCGAGAAGAC GATATCCAAAGCCAAGGGGCAACCGCGCGAGCCACAAGTTTACACGCTC CCACCCTCAAGAGACGAACTCACCAAAAATCAAGTGTCCCTGACATGTC TGGTGAAAGGATTCTATCCCAGCGACATAGCTGTAGAATGGGAGAGTAA TGGCCAACCCGAAAACAATTACAAAACTACCCCCCCGGTTTTGGATAGT GATGGTTCATTCTTCCTCTATAGTAAACTTACCGTGGATAAGTCTCGGTG GCAGCAGGGGAACGTGTTTAGCTGTTCAGTCCTCCATGAGGCACTCCAT AGTCACTATACGCAAAAGTCATTGTCCCTTTCTCCGGGCAAGGGCGGGT CAGACTCCTGGCAGGAAGAGGTAATTAAGCTTTGTGGGCGAGAACTCGT TAGGGCACAGATAGCAATCTGCGGGAAAAGTACAGCTTCCGATGCTGCC GGGGCTGACGCCAATGCGGGAGCACGCCAGCTCTACTCAGCCCTCGCCA ACAAGTGTTGTCATGTAGGTTGCACCAAAAGAAGTCTGGCACAGTTTTG C |
| 411 | GACAAGACGCATACTTGTCCTCCCTGCCCAGCTCCCGAAGCGGCTGGGG GGCCCTCTGTCTTTCTGTTTCCGCCTAAGCCCAAGGACACGCTCATGATA AGTCGCACTCCGGAAGTCACCTGTGTTGTCGTCGATGTTAGCCATGAAG ATCCAGAGGTGAAATTTAACTGGTACGTCGACGGAGTGGAGGTTCACAA TGCTAAAACCAAACCGCGAGAAGAGCAATACAATTCCACGTATAGGGTC GTCTCCGTCCTGACAGTACTCCATCAGGATTGGCTGAATGGAAAAGAAT ACAAGTGCAAGGTTTCCAATAAAGCCTTGGCCGCACCTATTGAGAAAAC GATATCAAAAGCTAAGGGACAACCTCGGGAGCCGCAAGTATATACACTC CCCCCTTCTAGGGACGAACTGACAAAAAACCAAGTTAGTCTGACTTGTC TTGTGAAAGGTTTTTACCCGAGTGATATAGCCGTAGAATGGGAGAGCAA TGGCCAGCCCGAAAACAATTACAAAACAACTCCCCCAGTATTGGACAGT GACGGGTCATTTTTTTTGTATTCTAAATTGACCGTAGACAAGTCACGCTG GCAACAAGGGAATGTATTTAGCTGTTCCGTCCTTCATGAGGCGCTCCATA GCCATTACACTCAGAAGTCTTTGTCACTGTCACCGGGCAAGGGTGGTTCT GATTCATGGCAAGAGGAAGTGATTAAGCTGTGCGGTCGGGAGTTGGTAA GAGCTCAAATTGCGATTTGTGGCAAGAGCACTGCGTCCGATGCCGCAGG TGCTAATGCCGACGCCGGTGCGAGACAGCTTTATTCTGCGCTGGCCAAC AAGTGCTGCCACGTCGGATGCACCAAACGGAGCCTTGCTCAGTTTTGC |
| 412 | GACAAAACTCATACTTGTCCACCATGCCCAGCCCCCGAGGCGGCTGGCG GCCCCAGCGTATTCCTTTTCCCCCCAAAACCTAAGGACACGCTTATGATA TCTAGAACCCCGGAGGTCACATGTGTCGTCGTAGACGTAAGTCACGAAG ATCCTGAAGTCAAGTTTAACTGGTACGTCGATGGAGTCGAGGTCCATAA TGCTAAAACGAAGCCTCGCGAAGAACAGTATAATTCTACCTATCGCGTA GTCTCTGTCCTCACCGTCTTGCATCAAGACTGGTTGAACGGCAAGGAGTA CAAGTGTAAGGTTTCAAACAAAGCCCTTGCCGCGCCGATAGAGAAAACA ATTAGCAAAGCGAAGGGCAGCCGAGAGAGCCGCAAGTGTATACCCTTC CTCCTAGTAGAGACGAGTTGACCAAAAACCAGGTGTCACTTACATGCCT CGTGAAAGGCTTCTACCCGAGTGATATTGCAGTCGAGTGGGAATCCAAC GGCCAGCCCGAGAATAACTACAAAACGACGCCGCCCGTACTGGACAGTG ATGGAAGTTTTTTTTTGTACTCAAAACTCACGGTTGACAAAAGTCGGTGG CAGCAAGGGAACGTTTTTAGCTGCTCTGTCCTCCATGAAGCACTCCATTC TCATTATACCCAGAAGTCTCTGTCTCTCTCCCCTGGTAAGGGAGGTTCTG ACAGTTGGCAGGAAGAGGTAATAAAACTCTGCGGTCGAGAGCTTGTTCG AGCACAAATTGCTATATGTGGAAAATCTACCGCTTCAGACGCCGCCGGA GCTGATGCGGATGCCGGGGCTCGCCAGCTCTATAGCGCCTTGGCCAACA AATGTTGTCACGTTGGCTGCACGAAGCGCTCCCTGGCTCAGTTTTGC |
| 413 | GATAAAACCCACACTTGCCCACCTTGCCCTGCGCCGGAAGCCGCCGGAG GACCTAGTGTTTTCCTCTTTCCCCCTAAGCCCAAAGACACGTTGATGATC TCTCGGACACCGGAAGTAACTTGTGTCGTTGTGGATGTGTCACATGAGG ATCCCGAGGTGAAATTTAATTGGTACGTTGACGGCGTGGAGGTGCATAA CGCAAAGACTAAACCACGCGAGGAGCAGTATAATTCTACATACCGGGTT GTCTCAGTTCTCACAGTTCTTCATCAGGATTGTTGAATGGAAAGGAGTA CAAATGCAAAGTGTCCAACAAAGCGCTTGCTGCGCCGATTGAAAAGACG ATTTCAAAGGCAAAAGGGCAGCCCCGCGAACCCCAAGTATATACTTTGC CTCCCTCACGCGATGAACTGACTAAGAACCAGGTGAGCCTGACTTGTTT |

TABLE 9-continued

Nucleotide Sequences Encoding Fusion Proteins and Peptide Components

| SEQ ID NO: | Sequence |
|---|---|
| | GGTTAAGGGTTTTTATCCAAGTGACATTGCTGTTGAATGGGAGTCCAATG
GCCAGCCTGAGAATAACTACAAAACGACACCTCCTGTACTTGACAGCGA
CGGCTCCTTTTTTCTTTATTCAAAACTCACAGTGGACAAATCCAGGTGGC
AGCAGGGTAACGTCTTTTCTTGCAGCGTGCTCCACGAAGCTTTGCATTCA
CATTATACGCAAAAATCCTTGTCATTGTCCCCAGGTAAGGGCGGAAGCG
ACTCATGGCAAGAAGAAGTCATTAAACTTTGTGGACGGGAGCTGGTTAG
GGCACAGATTGCTATTTGTGGTAAGTCTACGGCTAGTGACGCAGCGGGC
GCCGAAGCGGAAGCTGGTGCAAGGCAGCTTTACTCTGCTCTGGCTAACA
AGTGTTGTCACGTTGGGTGTACCAAGCGGTCCCTTGCGCAATTCTGC |
| 414 | GATAAAACTCATACTTGCCCCCCCTGCCCCGCGCCTGAAGCTGCAGGGG
GGCCATCAGTCTTCTTGTTTCCACCAAAACCTAAGGATACTCTCATGATT
AGCCGGACCCCTGAGGTGACATGTGTTGTGGTCGATGTATCTCATGAAG
ATCCCGAAGTAAAATTTAACTGGTACGTAGACGGGGTTGAAGTTCATAA
CGCGAAAACGAAACCTCGGGAGGAGCAATATAATAGCACGTATAGAGT
TGTTTCAGTCCTTACAGTTCTCCACCAAGACTGGCTGAATGGCAAGGAGT
ATAAGTGTAAAGTATCCAATAAAGCCTTGGCTGCGCCAATCGAGAAGAC
GATCAGCAAAGCCAAAGGTCAGCCTCGCGAACCGCAGGTCTATACATTG
CCCCCCTTCACGCGACGAACTCACGAAAAATCAAGTCTCTTTGACTTGCCT
TGTGAAAGGCTTCTACCCCTCCGATATTGCCGTCGAATGGGAAAGCAAT
GGACAGCCGGAAAATAATTACAAAACGACACCCCCCGTGTTGGATTCCG
ATGGGTCCTTCTTCCTCTATTCCAAGCTGACGGTCGATAAGTCTCGATGG
CAGCAGGGAAATGTCTTCTCTTGCTCCGTCCTTCATGAGGCATTGCACAG
CCATTATACTCAAAAGAGTCTCTCTCTGTCTCCAGGCAAAGGGGGTTCCG
ACTCTTGGCAAGAAGAGGTCATAAAACTGTGCGGCCGGGAGCTCGTCAG
AGCGCAGATCGCTATATGTGGAAAATCCACCGCGAGTGACGCAGCAGGT
GCACAAGCCGACGCAGGAGCTAGCAACTGTACTCAGCCCTTGCCAATA
AGTGTTGTCACGTAGGTTGTACTAAACGCTCCCTGGCACAATTTTGT |
| 415 | GATAAGACACACACGTGCCCACCCTGCCCTGCCCCAGAGGCAGCCGGAG
GTCCTAGTGTGTTTCTGTTCCCCCCAAAGCCCAAGGACACCCTTATGATA
TCTAGGACACCAGAAGTTACGTGCGTCGTTGTGGACGTTAGCCACGAAG
ACCCAGAAGTGAAGTTTAATTGGTACGTTGATGGAGTCGAAGTGCACAA
TGCAAAAACAAAACCACGAGAAGAGCAGTATAACAGTACTTATAGAGT
AGTCAGCGTCCTTACTGTATTGCATCAGGATTGGCTGAATGGGAAGGAA
TATAAATGTAAGGTTAGCAATAAAGCCCTTGCGGCTCCTATCGAGAAAA
CTATTAGCAAAGCAAAGGGCCAACCCCGAGAGCCCCAAGTTTATACACT
GCCACCCAGTCGAGATGAGCTGACTAAAAATCAAGTATCCCTGACCTGC
TTGGTTAAGGGGTTTTATCCTAGTGACATCGCGGTTGAGTGGGAATCCAA
CGGCCAACCGGAGAATAATTACAAAACCACGCCACCTGTATTGGATTCC
GATGGTAGCTTCTTTCTCTATAGTAAACTTACAGTCGATAAGTCAAGATG
GCAGCAGGGAAACGTATTTTCATGCTCAGTTCTGCATGAGGCCTTGCACT
CCCATTACACTCAAAAATCACTGAGCCTCAGTCCTGGTAAGGGTGGCTCT
GACTCATGGCAGGAGGAAGTAATCAAGCTGTGTGGGAGGGAATTGGTA
AGGGCTCAGATTGCAATTTGTGGAAAGAGCACAGCGTCTGACGCTGCAG
GTGCCGACGCACAGGCGGGCGCGAGGCAGCTCTACAGTGCTCTTGCGAA
CAAGTGTTGTCATGTAGGTTGCACGAAACGAAGTTTGGCGCAATTCTGT |
| 416 | GATAAAACACACACCTGCCCCCCTTGCCCAGCACCTGAAGCAGCGGGTG
GTCCCAGCGTTTTTCTTTTCCCCCCTAAGCCAAAGGACACGCTCATGATA
AGTCGCACCCCGGAGGTCACCTGCGTCGTTGTTGACGTATCACATGAAG
ATCCTGAGGTGAAGTTTAATTGGTACGTAGATGGTGTTGAGGTCCACAA
CGCAAAGACGAAACCGAGGGAAGAACAGTACAACAGTACTTATCGCGT
AGTCTCCGTTCTGACTGTCCTGCATCAAGATTGGTTGAACGGGAAGGAG
TACAAGTGCAAAGTTAGTAACAAGGCTCTCGCGGCCCCAATTGAGAAGA
CGATATCCAAAGCGAAAGGACAGCCGAGAGAGCCCCAAGTCTACACTCT
GCCCCCTTCCAGGGATGAGCTCACCAAAAATCAGGTCAGTCTCACGTGC
CTGGTTAAGGGGATTCTACCCAAGTGATATAGCAGTTGAATGGGAGAGTA
ACGGCCAGCCCGAGAACAACTATAAAACTACACCGCCCGTTCTTGATTC
CGATGGGTCTTTCTTCCTTTATAGTAAGCTCACCGTTGATAAGTCCCGAT
GGCAGCAAGGTAATGTCTTCTCATGTTCAGTTCTTCATGAAGCCCTGCAT
TCCCATTATACACAAAAGAGCTTGTCCTTGTCACCGGGCAAAGGCGGTA
GCGATTCTTGGCAAGAAGAAGTTATAAAGTTGTGCGGTAGGGAACTGGT
ACGCGCTCAAATAGCTATATGCGGTAAGTCTACTGCTTCAGATGCGGCT
GGCGCACAGGCACAGGCCGGTGCTAGACAACTCTATAGTGCGCTGGCCA
ACAAGTGCTGCCATGTGGGGTGTACAAAACGGAGTCTTGCCCAGTTTTG
T |
| 417 | GACAAAACTCATACATGCCCCCCATGCCCAGCACCCGAAGCGGCCGGAG
GTCCGTCGTCTCTTTCTGTTTCCGCCGAAACCTAAAGATACGTTGATGATT
AGCAGAACCCCTGAGGTAACATGTGTGGTAGTCGATGTCTCCCATGAGG
ACCCCGAGGTAAAGTTCAATTGGTATGTTGACGGCGTCGAAGTCCATAA
CGCAAAAACGAAGCCCCGAGAGGAGCAATATAACTCTACCTATCGCGTT
GTTTCTGTTTTGACTGTGTTGCACCAGGATTGGCTCAACGGCAAGGAATA |

TABLE 9-continued

Nucleotide Sequences Encoding Fusion Proteins and Peptide Components

| SEQ ID NO: | Sequence |
|---|---|
| | CAAATGTAAAGTGTCCAACAAGGCCCTTGCTGCACCTATCGAAAAAACG<br>ATTAGTAAGGCAAAGGGACAACCGCGCGAACCACAGGTATATACTTTGC<br>CGCCTAGCAGAGATGAACTCACCAAGAATCAAGTTTCCCTTACCTGTTTG<br>GTTAAAGGATTTTACCCGTCTGACATAGCTGTTGAATGGGAGAGCAATG<br>GTCAGCCGGAAAATAATTATAAAACCACCCCGCCAGTATTGGATTCAGA<br>TGGGTCCTTTTTCTTGTATTCTAAACTTACCGTGGATAAGTCTAGGTGGC<br>AACAGGGAAACGTCTTTTCATGTAGTGTACTTCATGAAGCCCTCCATAGT<br>CACTACACGCAGAAATCCTTGTCTCTTAGTCCGGGTGAAGGTGGGTCTG<br>ATTCCTGGCAGGAAGAGGTGATAAAGCTCTGTGGTCGGGAACTTGTTAG<br>GGCGCAGATCGCTATTTGCGGCAAATCTACAGCATCAGATGCCGCCGGA<br>GCTGATGCGAACGCAGGAGCGAGGCAGCTGTACTCCGCACTTGCTAACA<br>AGTGTTGCCATGTCGGCTGCACCAAGAGGAGTCTTGCTCAATTCTGC |
| 418 | GATAAGACCCATACATGCCCGCCATGTCCCGCACCCGAGGCAGCGGGTG<br>GACCCTCTGTCTTTCTGTTCCCTCCAAAGCCAAAAGATACCCTGATGATT<br>AGCCGAACCCCGGAGGTGACTTGTGTCGTAGTAGATGTCAGTCACGAGG<br>ATCCCGAAGTAAAGTTTAATTGGTATGTGGACGGTGTGGAGGTACATAA<br>CGCTAAGACGAAACCCCGAGAGGAACAATACAACTCTACGTACAGGGTC<br>GTCTCAGTGCTCACGGTCCTGCACCAGGACTGGCTTAATGGGAAGGAAT<br>ATAAATGCAAAGTCTCTAATAAGGCGCTTGCTGCACCTATTGAAAAAAC<br>GATTTCTAAGGCGAAGGGACAACCCCGGGAGCCACAAGTCTACACCCTT<br>CCTCCAAGCAGAGATGAGCTTACGAAAAATCAAGTGTCTCTTACGTGCC<br>TCGTAAAGGGCTTTTACCCATCCGACATTGCGGTGGAGTGGGAATCAAA<br>CGGGCAGCCGGAAAATAACTACAAAACAACGCCGCCTGTATTGGATTCC<br>GACGGCTCTTTCTTCCTTTACAGCAAACTGACAGTCGATAAATCCAGATG<br>GCAACAAGGGAACGTTTTTTCATGTTCCGTTCTGCATGAAGCCCTTCACA<br>GTCATTACACCCAAAAGTCACTTTCACTTTCACCGGGCGAGGGGGGTC<br>AGACTCCTGGCAAGAGGAAGTTATAAAGTTGTGCGGCAGGGAACTGGTT<br>AGAGCGCAGATAGCGATTTGCGAAAATCTACTGCGAGTGATGCTGCGG<br>GAGCGAATGCGGACGCCGGGCCCGACAGCTCTATTCCGCACTCGCCAA<br>TAAGTGCTGCCATGTTGGTTGTACGAAGAGAAGTCTTGCACAATTTTGC |
| 419 | GATAAGACACATACATGCCCCCCTGCCCGGCTCCCGAAGCTGCCGGGG<br>GACCGTCAGTGTTTTTGTTTCCGCCCAAGCCGAAGGATACTTTGATGATT<br>AGTCGGACACCAGAAGTGACATGTGTTGTCGTTGACGTGAGTCACGAGG<br>ATCCCGAGGTCAAGTTCAACTGGTACGTTGATGGGGTTGAAGTTCACAA<br>CGCTAAAACGAAACCCCGCGAAGAGCAGTATAACTCCACTTACCGGGTC<br>GTCAGTGTCCTGACGGTCTTGCACCAGGACTGGCTGAATGGAAGGAAT<br>ACAAGTGTAAAGTTTCCAATAAAGCACTGGCCGCCCCGATCGAAAAAAC<br>AATTTCCAAAGCTAAGGGACAGCCCAGGGAACCGCAAGTTTATACTCTT<br>CCACCCTCCCGGGATGAACTGACCAAAAACCAAGTGTCTTTGACGTGCC<br>TCGTAAAGGGCTTCTACCCGTCAGACATAGCTGTCGAATGGGAGTCTAA<br>TGGACAGCCGGAAAACAATTATAAGACTACACCGCCGGTGCTTGATAGT<br>GATGGAAGTTTCTTTTTGTACTCCAAACTTACGGTCGATAAAAGCCGGTG<br>GCAGCAGGGAAACGTATTCAGTTGTAGCGTTCTGCATGAAGCTCTTCATT<br>CTCACTACACCCAGAAGTCTCTGTCTCTGAGCCCCGGAGAGGGTGGATC<br>TGATTCTTGGCAGGAAGAAGTGATAAAGTTGTGCGGCCGGGAATTGGTA<br>CGCGCCCAGATAGCCATTTGCGGGAAGTCTACGGCGAGTGACGCAGCAG<br>GTGCTGACGCGGACGCTGGTGCTAGACAGCTGTATTCTGCCCTGGCTAAT<br>AAGTGTTGCCACGTTGGCTGCACCAAGAGATCCCTGGCCCAATTCTGT |
| 420 | GACAAGACACATACTTGTCCCCCCTGCCCAGCTCCAGAAGCTGCCGGAG<br>GGCCGTCAGTCTTCCTTTTCCCTCCAAAACCTAAGGATACGCTTATGATT<br>TCTCGAACGCCAGAGGTTACGTGTGTAGTCGTGGACGTTTCCCACGAGG<br>ATCCTGAGGTCAAGTTTAACTGGTATGTAGACGGGGTTGAGGTCCATAA<br>TGCCAAGACAAAGCCGCGCGAGGAACAATACAACAGTACATATAGGGT<br>GGTGAGCGTCCTCACAGTCTTGCATCAAGATTGGCTCAACGGCAAAGAG<br>TACAAATGTAAGGTTAGCAACAAAGCCCTCGCTGCTCCCATCGAAAAGA<br>CGATTTCTAAGGCGAAGGGCCAACCACGAGAACCGCAAGTATATACTCT<br>TCCCCCCTTCACGGGACGAGCTGACCAAAAACCAGGTATCCTTGACTTGC<br>CTGGTCAAAGGATTTTACCCCTCTGATATTGCGGTCGAGTGGGAGAGTA<br>ATGGGCAACCAGAAAATAATTATAAAACGACCCCCCCGGTACTCGACAG<br>TGATGGGTCTTTTTTCCTGTATTCTAAGCTTACGGTTGATAAGTCTAGAT<br>GGCAGCAAGGGAATGTCTTCTCATGTAGTGTTCTGCATGAAGCACTTCAT<br>TCTCACTATACTCAGAAATCTCTTTCCCTTAGTCGGGAGAAGGTGGGAG<br>CGATAGTTGGCAAGAGGAGGTGATAAAACTGTGTGGTCGGGAGCTGGTG<br>AGAGCCCAAATAGCTATCTGCGGCAAATCAACAGCAAGTGATGCGGCAG<br>GAGCGGAAGCGGAGGCGGGAGCGCGGCAATTGTATAGTGCCCTTGCTAA<br>TAAATGCTGTCACGTTGGGTGTACTAAACGATCTCTTGCTCAATTCTGC |
| 421 | GATAAAACCCATACATGCCTCCGTGTCCCGCTCCAGAAGCCGCTGGCG<br>GGCCATCTGTGTTTTTGTTCCCCCCCAAGCCTAAGGATACGTTGATGATC<br>AGCAGGACCCCGGAGGTTACATGCGTAGTAGTTGACGTTTCTCATGAAG<br>ACCCAGAAGTAAAATTTAACTGGTATGTCGATGGCGTCGAAGTACATAA |

TABLE 9-continued

Nucleotide Sequences Encoding Fusion Proteins and Peptide Components

| SEQ ID NO: | Sequence |
|---|---|
| | TGCTAAAACTAAGCCCAGGGAAGAGCAATACAATTCAACGTACCGAGTT<br>GTGAGTGTCCTTACGGTCCTGCACCAAGACTGGTTGAACGGCAAAGAGT<br>ACAAATGCAAAGTGTCTAACAAGGCATTGGCCGCGCCTATAGAAAAGAC<br>CATTAGCAAAGCAAAAGGGCAGCCTCGGGAACCCCAGGTCTACACGCTG<br>CCACCTTCCCGAGATGAATTGACGAAAAACCAGGTCTCTTTGACCTGCTT<br>GGTTAAAGGCTTCTACCCAAGCGACATTGCAGTGGAGTGGGAGTCTAAC<br>GGGCAACCCGAAAACAACTATAAGACGACTCCCCCTGTTCTTGATTCTG<br>ATGGGAGTTTTTTTCTGTACAGTAAGTTGACAGTGGATAAATCAAGATG<br>GCAGCAAGGTAATGTCTTCTCTTGTTCAGTGCTTCACGAAGCATTGCATT<br>CTCACTACACACAAAAGTCTTTGTCCTTGTCTCCAGGTGAAGGCGGTAGC<br>GATTCATGGCAAGAAGAAGTCATTAAGCTGTGTGGAAGGGAACTGGTTA<br>GGGCCCAAATTGCGATATGTGGAAAGTCTACGGCGAGTGATGCGGCCGG<br>TGCTCAAGCGGATGCGGGTGCTAGACAGTTGTACTCAGCCCTTGCGAAC<br>AAATGTTGTCACGTTGGCTGTACGAAACGCAGCCTTGCTCAATTCTGC |
| 422 | GATAAAACTCACACATGCCCCCCATGCCCAGCACCGGAAGCTGCCGGAG<br>GACCGTCTGTATTCCTCTTTCCGCCCAAACCGAAAGACACGTTGATGATT<br>TCTCGGACTCCCGAGGTAACTTGTGTCGTGGTCGACGTCTCACACGAGG<br>ACCCGGAGGTCAAATTTAACTGGTATGTCGATGGGGTGGAGGTCCATAA<br>TGCTAAGACGAAGCCCAGAGAAGAACAGTATAACTCTACTTATAGAGTT<br>GTAAGCGTGCTCACTGTATTGCACCAGGACTGGCTCAACGGGAAGAAT<br>ATAAGTGTAAGGTCTCAAACAAAGCTCTCGCAGCCCCGATAGAGAAAAC<br>AATATCTAAGGCCAAGGGCCAACCGCGCGAGCCGCAGGTTTATACACTT<br>CCACCCTCCCGCGATGAGCTGACCAAGAACCAGGTCTCTCTCACCTGTCT<br>CGTAAAGGGCTTTTATCCCTCCGACATTGCAGTGGAGTGGGAATCAAAC<br>GGCCAGCCGGAAAATAATTACAAGACCACTCCTCCCGTCCTCGACTCCG<br>ATGGGTCATTTTTCCTGTACAGTAAGCTCACCGTTGATAAGTCAAGGTGG<br>CAGCAGGGCAACGTGTTTAGCTGTAGTGTTCTGCATGAGGCGCTCCACA<br>GTCACTACACCCAGAAAAGTCTGAGCCTTTCCCCAGGTGAGGGTGGTAG<br>CGATAGCTGGCAGGAGGAAGTAATTAAACTCTGCGGTAGAGAATTGGTA<br>AGGGCCCAAATTGCCATCTGCGGAAAGAGCACCGCATCAGATGCTGCGG<br>GCGCGGATGCGCAGGCTGGTGCTAGGCAACTCTACTCTGCCCTGGCGAA<br>TAAATGTTGCCACGTCGGTTGCACGAAACGAAGTTTGGCTCAATTTTGC |
| 423 | GACAAAACACATACATGCCCCCCTTGCCCGGCTCCCGAGGCCGCCGGTG<br>GTCCTAGCGTCTTTCTTTTCCCTCCCAAACCCAAAGACACACTTATGATT<br>AGCAGAACTCCCGAGGTAACATGTGTGGTCGTAGACGTAAGTCACGAAG<br>ATCCCGAAGTTAAATTCAACTGGTACGTTGATGGTGTGGAAGTTCATAAT<br>GCAAAAACCAAACCGCGAGAGGAACAGTATAACTCTACCTACCGCGTGG<br>TCTCAGTGCTGACTGTCCTGCATCAGGACTGGCTCAACGGGAAGGAATA<br>TAAGTGCAAAGTGAGTAATAAGGCCCTTGCAGCTCCCATAGAAAAGACG<br>ATATCAAAGGCTAAAGGACAGCCGAGGGAGCCACAGGTGTACACTTTGC<br>CTCCGAGTAGAGATGAACTCACTAAAAACCAAGTAAGTTTGACATGCCT<br>GGTCAAAGGTTTTTACCCCAGTGATATAGCGGTTGAGTGGGAGTCCAAT<br>GGGCAACCGGAGAACAACTATAAGACTACTCCACCTGTCCTGGATAGCG<br>ATGGAAGTTTTTTTCTTTACTCAAAGCTGACGGTGGATAAGAGTCGATGG<br>CAGCAGGGCAATGTGTTTAGCTGTTCTGTGCTTCACGAAGCACTTCACTC<br>TCATTATACCCAGAAGTCATTGAGCCTTTCCCTGGTGAAGGAGGGTCA<br>GATTCCTGGCAGGAGGAGGTTATAAAGCTGTGTGGCCGGGAACTCGTGC<br>GAGCTCAAATTGCGATCTGTGGAAAATCCACCGCTAGTGATGCGGCGGG<br>AGCACAAGCTCAAGCGGGCGCTCGACAACTTTATAGCGCTTTGGCTAAT<br>AAGTGCTGCCATGTGGGTTGTACAAAGCGCAGCCTCGCTCAATTTTGC |
| 424 | GATAAGACGCACACTTGCCCTCCTTGCCCGGCACCCGAAGCCGCTGGTG<br>GGCCTAGTGTATTCCTGTTCCCCCCGAAGCCGAAGGATACTCTTATGATT<br>TCACGCACGCCCGAGGTTACATGCGTAGTAGTGGACGTATCTCACGAAG<br>ATCCCGAAGTCAAGTTCAATTGGTATGTCGACGGAGTAGAAGTTCACAA<br>CGCAAAGACAAAACCGCGGGAAGAGCAATACAACTCCACGTACCGCGT<br>CGTTTCTGTTCTTACGGTCTTGCACCAGGACTGGCTCAATGGCAAGGAGT<br>ATAAGTGCAAGGTATCCAACAAGGCCCTTGCCGCACCTATTGAAAAGAC<br>TATCAGCAAGGCCAAGGGACAGCCAAGGGAGCCTCAAGTCTACACGCTC<br>CCGCCTAGTAGAGACGAGTTGACAAAGAATCAAGTGAGTTTGACTTGTC<br>TGGTTAAAGGTTTTTACCCGTCAGATATTCAGTAGAATGGGAATCTAAC<br>GGACAACCCGAAAACAACTATAAAACGACGCCTCCTGTGTTGGATTCAG<br>ATGGGTCATTTTTTCTCTACTCAAAGCTCACGGTAGATAAATCAAGATGG<br>CAACAAGGCAATGTATTTTCCTGCTCCGTGCTCCACGAGGCTCTGCACAG<br>CCATTATACGCAAAAGAGTCTGTCTTTGAGCCCAGGTGAGGGTGGCTCC<br>GATTCCTGGCAGGAGGAAGTAATTAAGTTGTGCGGCAGGGAACTTGTTC<br>GCGCACACAAATAGCCATTTGTGGTCAGAGCACAGCATCAGATGCCGGG<br>AGCCGACGCCAACGCAGGTGCCCGCCAACTTTATTCTGCCCTCGCAAAC<br>AAATGCTGCCACGTCGGCTGCACGAAGAGGAGCCTCGCCCAATTTTGC |
| 425 | GATAAGACCCATACGTGCCCGCCATGTCCAGCCCCCGAGGCAGCCGGAG<br>GTCCTTCCGTTTTCCTTTTCCCCCCTAAGCCCAAGGACACTCTGATGATCT |

TABLE 9-continued

Nucleotide Sequences Encoding Fusion Proteins and Peptide Components

| SEQ ID NO: | Sequence |
|---|---|
|  | CCCGGACGCCTGAAGTCACTTGCGTAGTCGTAGACGTTTCACATGAGGA<br>TCCAGAAGTTAAATTTAACTGGTACGTCGATGGCGTCGAGGTCCATAAC<br>GCGAAAACCAAGCCCAGGGAGGAACAATATAACTCCACCTATAGGGTC<br>GTGAGTGTGCTCACCGTTTTGCACCAAGACTGGCTCAACGGGAAAGAGT<br>ACAAATGTAAAGTTTCAAATAAGGCTTTGGCCGCCCCAATAGAGAAGAC<br>TATATCCAAGGCTAAGGGACAGCCTCGAGAACCGCAGGTATATACGCTT<br>CCTCCGTCTAGGGATGAACTCACAAAAAACCAGGTTTCTTTGACCTGCTT<br>GGTAAAGGGATTTTATCCCTCCGACATTGCGGTCGAATGGGAGAGCAAC<br>GGACAGCCGGAAAACAATTACAAAACGACACCCCCGGTTTTGGACTCTG<br>ATGGAAGCTTCTTCCTCTATAGTAAGTTGACCGTAGACAAGTCTCGCTGG<br>CAGCAGGGAAACGTCTTCAGTTGCTCAGTTCTCCATGAGGCGTTGCATA<br>GTCACTATACACAGAAGAGTCTTAGTTTGTCTCCAGGAGAAGGAGGTTC<br>TGATTCTTGGCAAGAGGAGGTAATCAAATTGTGTGGCCGAGAACTTGTT<br>AGAGCTCAGATAGCCATCTGCGGACAGTCTACGGCGTCCGATGCGGCCG<br>GAGCTAATGCTGACGCAGGTGCGCGACAGCTGTACTCCGCACTGGCGAA<br>TAAGTGCTGCCACGTGGGATGCACTAAGCGGTCTCTCGCGCAATTCTGT |
| 426 | GATAAAACCCACACCTGTCCACCATGCCCGGCGCCGGAAGCCGCCGGGG<br>GACCCAGCGTATTTCTTTTCCCCCCCAAGCCCAAAGACACGCTGATGATT<br>TCACGAACGCCGGAGGTGACTTGCGTGGTAGTGGACGTCTCCCATGAGG<br>ATCCCGAAGTTAAATTTAATTGGTATGTAGATGGTGTTGAGGTCCATAAT<br>GCTAAAACAAAGCCGCGGGAAGAGCAATATAACTCCACCTATAGAGTG<br>GTCTCTGTACTCACTGTCCTGCACCAGGATTGGCTGAATGGGAAAGAGT<br>ACAAGTGTAAAGTTAGCAACAAAGCGCTCGCCGCGCCTATCGAAAAAAC<br>GATTTCCAAAGCAAAGGGCCAACCACGAGAACCCCAGGTTTACACCCTG<br>CCACCCAGTCGAGATGAACTCACTAAGAATCAGGTGTCCCTTACATGCC<br>TCGTCAAGGGATTCTATCCGAGCGATATAGCGGTGGAATGGGAGAGTAA<br>CGGTCAACCCGAAATAACTATAAAACCACTCCGCCGGTACTCGATTCT<br>GACGGTTCCTTCTTTCTTTATTCCAAACTGACTGTAGACAAATCACGGTG<br>GCAGCAGGGCAACGTGTTTAGCTGCTCTGTACTCCATGAGGCCTTGCATT<br>CTCATTATACTCAAAAGAGTCTGAGTCTGAGTCCAGGTGAAGGGGGTTC<br>CGATTCATGGCAAGAGGAAGTCATTAAACTCTGCGGAAGGGAACTTGTA<br>AGAGCACAAATCGCGATTTGTGGGCAATCTACCGCATCCGACGCGGCTG<br>GAGCAGATGCAGATGCCGGAGCGAGGCAGCTGTATTCAGCATTGGCTAA<br>CAAATGTTGCCATGTTGGATGTACGAAGAGATCACTTGCACAGTTCTGT |
| 427 | GATAAGACTCATACCTGCCCGCCCTGTCCCGCACCCGAGGCTGCCGGAG<br>GGCCATCAGTGTTCCTTTTCCCACCAAAGCCGAAGGATACACTTATGATC<br>AGCAGGACACCCGAAGTGACCTGTGTAGTCGTAGACGTGTCCCACGAAG<br>ACCCCGAAGTAAAATTTAATTGGTATGTCGATGGCGTAGAGGTCCACAA<br>CGCGAAAACGAAACCCCGCGAAGAACAATATAATTCCACATACCGAGTT<br>GTCAGCGTCCTCACTGTTCTCCATCAGGACTGGCTGAATGGGAAGGAAT<br>ATAAGTGCAAGGTCTCAAACAAGGCGCTGGCGGCCCCCATAGAGAAAA<br>CGATTTCTAAGGCCAAAGGACAGCCACGGGAACCGCAGGTCTATACGCT<br>CCCCACCTAGTAGGGATGAGTTGACCAAGAATCAGGTATCCCTCACATGT<br>CTCGTCAAGGGATTCTATCCCAGCGACATAGCCGTGGAGTGGGAATCTA<br>ACGGTCAACCTGAGAATAACTATAAAACAACCCCCCGGTCCTCGACTC<br>CGATGGTAGCTTCTTTTCTGTATTCCAAACTGACGGTAGATAAAAGCCGAT<br>GGCAACAGGGTAACGTCTTTAGTTGTTCTGTATTGCACGAGGCGCTCCAT<br>AGTCACTACACACAGAAGTCTTTGAGCCTCTCACCTGGGGAGGGGGGTA<br>GCGATTCTTGGCAGGAGGAAGTGATCAAACTGTGCGGCAGGGAACTGGT<br>CAGAGCACAGATAGCAATATGCGGTCAGAGTACGGCCTCTGACGCCGCC<br>GGTGCGGAGGCTGAGGCAGGGGCGAGACAGCTCTACAGCGCTCTTGCAA<br>ATAAGTGTTGTCACGTGGGGTGCACAAAGAGATCCTTGGCGCAATTTTG<br>T |
| 428 | GATAAGACCCACACATGTCCGCCATGTCCAGCCCCAGAGGCAGCAGGGG<br>GCCCGTCCGTATTCTTGTTTCCCCCGAAACCCAAAGATACCCTTATGATT<br>AGTCGAACTCCAGAAGTCACGTGTGTGGTGGTGGACGTATCCCACGAGG<br>ACCCCGAAGTGAAATTCAATTGGTATGTGGACGGGGTGGAAGTCCATAA<br>CGCTAAGACGAAGCCCAGAGAGGAGCAGTACAATTCTACCTATCGGGTT<br>GTATCTGTGCTTACTGTTCTCCATCAAGATTGGCTGAACGGGAAGGAATA<br>CAAATGTAAAGTTAGTAACAAAGCATTGGCAGCTCCTATCGAAAAGACG<br>ATAAGCAAGGCTAAAGGTCAACCCCGAGAGCCTCAGGTCTACACTTTGC<br>CGCCCTCCAGGGATGAGCTTACCAAGAACCAAGTGAGCTTGACGTGTCT<br>CGTGAAGGGATTCTACCCATCAGATATAGCGGTAGAATGGGAGTCTAAT<br>GGGCAGCCCGAGAACAACTATAAGACCACCCCTCCCGTTCTTGACTCCG<br>ACGGTTCCTTTTCTTGTACTCCAAACTCACGGTCGACAAGTCTAGGTGG<br>CAGCAAGGCAATGTTTTCAGTTGTTCCGTGCTGCACGAAGCTCTTCATTC<br>TCACTATACGCAAAAAGCCTGAGTCTTTCACCTGGAGAGGGGGGTTCC<br>GATTCTTGGCAGGAAGAAGTCATTAAGCTGTGCGGCAGAGAACTTGTGC<br>GCGCACAAATTGCTATTTGTGGACAGTCAACTGCATCTGACGCCGCTGG<br>AGCCCAAGCGGACGCAGGGGCAAGGCAGCTTTATTCAGCGCTTGCGAAT<br>AAGTGTTGCCATGTGGGTTGCACGAAACGAAGCCTGGCGCAATTTTGT |

TABLE 9-continued

Nucleotide Sequences Encoding Fusion Proteins and Peptide Components

| SEQ ID NO: | Sequence |
|---|---|
| 429 | GATAAGACACATACATGTCCTCCCTGTCCCGCTCCGGAGGCAGCCGGTG<br>GGCCTTCAGTTTTCTTGTTTCCGCCGAAGCCTAAGGACACGTTGATGATA<br>TCCCGAACACCAGAGGTCACATGCGTCGTCGTGGACGTCTCACACGAGG<br>ACCCTGAAGTGAAATTCAACTGGTATGTAGACGGGGTCGAAGTTCACAA<br>TGCGAAAACTAAACCTCGCGAGGAGCAATATAACTCAACATACCGCGTA<br>GTGTCCGTCTTGACTGTCCTTCATCAGGATTGGCTGAATGGTAAAGAATA<br>TAAATGTAAAGTTTCTAATAAAGCGCTTGCGGCACCCATTGAGAAGACA<br>ATTTCCAAAGCCAAAGGCCAACCCCGAGAGCCTCAGGTATATACGCTGC<br>CTCCGTCTCGAGATGAGTTGACAAAAAATCAAGTCAGCTTGACTTGTCTT<br>GTAAAGGGGTTCTATCCGTCAGACATAGCAGTGGAGTGGGAATCCAACG<br>GGCAACCAGAAAATAATTACAAAACCACTCCGCCCGTGCTTGACTCAGA<br>TGGGAGCTTCTTCCTTTATAGCAAACTTACGGTAGATAAATCCAGATGGC<br>AGCAAGGCAACGTATTCAGCTGTAGTGTGCTGCATGAAGCGCTTCACTC<br>CCATTATACTCAAAAATCTCTTTCTCTGTCACCGGGCGAGGGCGGAAGTG<br>ATAGTTGGCAGGAAGAGGTCATCAAGCTCTGTGGGAGAGAGCTTGTACG<br>CGCTCAGATTGCTATATGCGGCCAGTCAACTGCAAGCGATGCAGCGGGT<br>GCCGATGCCCAAGCGGGGGCACGGCAACTCTACTCAGCCCTCGCGAATA<br>AATGTTGTCATGTAGGGTGTACTAAGAGAAGCCTCGCGCAATTTTGT |
| 430 | GATAAAACGCATACTTGCCCGCCGTGCCCAGCACCTGAGGCAGCCGGCG<br>GCCCTAGTGTCTTCTTGTTCCCGCCCAAGCCCAAGGATACACTCATGATC<br>TCCCGAACGCCAGAGGTCACATGCGTAGTTGTTGACGTTTCCCCATGAGG<br>ACCCTGAAGTGAAATTTAACTGGTACGTCGACGGCGTTGAGGTTCACAA<br>CGCTAAGACTAAGCCAAGAGAGGAACAGTACAATTCAACTTATAGAGTG<br>GTGTCTGTATTGACAGTTCTCCATCAGGATTGGCTGAACGGAAAAGAAT<br>ATAAGTGCAAGGTCTCAAATAAGGCGCTCGCTGCACCCATAGAAAAAAC<br>CATATCAAAAGCGAAGGGGCAACCAAGAGAACCCCAGGTGTACACGCT<br>CCCCCCGTCCAGAGATGAACTCACGAAGAATCAAGTGTCACTCACATGT<br>CTTGTAAAGGGGTTCTACCCCTCTGATATTGCCGTAGAATGGGAAAGCA<br>ACGGACAGCCCGAGAATAACTACAAGACGACACCGCCAGTTCTTGATTC<br>TGACGGAAGCTTTTTCCTCTATTCAAAATTGACCGTTGACAAGTCCCGAT<br>GGCAACAGGGCAACGTTTTCTCATGCTCCGTCCTTCACGAAGCCTTGCAT<br>TCCCACTATACGCAGAAGAGTCTCTCTTTGAGCCCCGGAGAGGGAGGCA<br>GTGATTCATGGCAAGAGGAAGTGATCAAACTTTGCGGCAGAGAATTGGT<br>TAGAGCCCAGATTGCCATTTGTGGACAAAGTACGGCCTCAGATGCTGCG<br>GGGGCACAAGCTCAGGCGGGCGCACGCCAGTTGTACAGTGCTCTGGCGA<br>ATAAGTGCTGCCACGTTGGTTGCACCAAGCGATCCTTGGCGCAATTTTGC |
| 431 | GACAAGACTCATACTTGTCCGCCCTGCCCCGCTCCTGAGGCTGCCGGAG<br>GCCCTTCAGTATTCTTGTTTCCGCCGAAACCGAAGGATACCTTGATGATT<br>AGTAGGACACCGGAAGTCACCTGCGTAGTGGTGGACGTAAGCCACGAA<br>GATCCCGAAGTAAAGTTTAATTGGTATGTTGATGGCGTAGAGGTGCATA<br>ATGCGAAAACCAAACCTAGGGAGGAACAGTACAATAGTACTTACCGCGT<br>AGTGTCAGTGCTTACCGTGCTGCATCAGGACTGGCTTAATGGGAAGGAA<br>TACAAATGTAAAGTATCCAATAAAGCGCTGGCGGCTCCCATCGAGAAAA<br>CGATCTCAAAAGCCAAAGGACAACCACGGGAACCGCAGGTCTATACTCT<br>GCCACCTTCAAGAGACGAACTTACCAAGAACCAAGTCTCATTGACGTGC<br>TTGGTAAAAGGTTTTTATCCGTCTGACATCGCTGTTGAATGGGAGTCTAA<br>CGGCCAGCCGGAGAACAATTACAAAACAACTCCACCAGTCTTGGATTCA<br>GATGGGTCTTTTTTTTGTATTCAAAGCTTACCGTTGACAAAAGCCGCTG<br>GCAACAAGGAAACGTTTTCAGCTGCAGTGTGCTGCACGAAGCGCTCCAC<br>AGTCATTATACCCAGAAATCTTTTGAGCCTGTCTCCAGGGGAAGGTGGGA<br>GTGACTCTTGGCAAGAAGAGGTTATCAAACTTTGCGGGCGGGAGCTGGT<br>AAGGGCCCAAATTGCAATATGCGGCAAAAGTACTGCATCTGATGCCGCT<br>GGGGCCGATGCTAACGCGGGCGCAAGACAACTTTATAGCGCGTTGGCGA<br>ACAAATGCTGTCATGTGGGATGCACCAAACAAAGTTTGGCGCAATTTTG<br>T |
| 432 | GATAAAACTCACACGTGTCCGCCATGCCCCGCACCTGAAGCGGCGGGTG<br>GTCCGAGCGTGTTTTTGTTTCCGCCTAAGCCCAAGGATACCCTGATGATT<br>AGTCGGACACCCGAAGTAACATGTGTCGTCGTGGATGTAAGTCACGAGG<br>ATCCCGAAGTGAAATTCAACTGGTATGTGGATGGAGTTGAAGTCCATAA<br>TGCGAAAACAAAACCGAGAGAGGAACAGTACAACTCAACATACCGGGT<br>GGTAAGTGTACTGACGGTACTCCACCAGGACTGGCTGAATGGTAAGGAG<br>TACAAATGCAAAGTTTCAAATAAGGCGCTCGCTGCCCCATCGAGAAAA<br>CCATTAGTAAGGCTAAAGGTCAACCTAGGGAGCCACAAGTATATACATT<br>GCCGCCTTCTAGAGATGAGCTGACCAAAAACCAGGTCAGCCTGACCTGT<br>TTGGTGAAAGCTTCTATCCAAGCGACATTGCTGTCGAGTGGGAGTCAA<br>ATGGGCAGCCGGAAAATAACTATAAAACGACTCCTCCTGTTCTCGACTC<br>CGATGGTTCATTCTTCCTCTACTCAAAGCTTACCGTGATAAATCCAGGT<br>GGCAACAAGGTAACGTGTTCTCATGTTCCGTTCTGCACGAAGCACTGCAT<br>TCCCATTATACACAAAAATCCCTGAGCCTCTCACCTGGGGAGGGCGGAA<br>GCGATAGTTGGCAAGAGGAAGTAATAAAGCTGTGTGGCAGGGAACTCGT |

TABLE 9-continued

Nucleotide Sequences Encoding Fusion Proteins and Peptide Components

| SEQ ID NO: | Sequence |
|---|---|
| | AAGGGCTCAGATTGCGATATGTGGAAAAAGCACTGCTTCTGACGCCGCA GGGGCCAACGCAGATGCTGGCGCCCGACAACTCTATTCTGCGCTTGCGA ACAAGTGTTGTCATGTAGGATGTACCAAGCAAAGCCTTGCTCAGTTCTGT |
| 433 | GACAAAACCCACACTTGTCCGCCCTGTCCCGCTCCGGAGGCTGCAGGCG GCCCAAGTGTGTTTCTTTTCCCCCCAAAGCCGAAAGACACCTTGATGATA TCCCGCACACCCGAAGTGACTTGCGTTGTCGTCGACGTGTCTCATGAGGA CCCAGAAGTCAAGTTTAATTGGTACGTTGATGGCGTGGAAGTTCACAAT GCGAAAACTAAGCCCAGAGAGGAGCAATATAACTCAACCTACCGGGTG GTAAGTGTTCTGACAGTTCTCCACCAGGACTGGTTGAACGGAAAAGAAT ACAAATGCAAAGTGAGTAACAAAGCCCTGGCTGCCCCTATCGAAAAGAC CATATCCAAAGCGAAGGGCCAGCCACGGGAACCGCAAGTATATACACTT CCACCATCTAGAGATGAGCTTACAAAGAACCAGGTGTCCCTTACCTGCC TTGTCAAAGGCTTCTATCCCTCTGACATCGCAGTGGAGTGGGAGTCCAAC GGACAACCAGAGAACAACTATAAGCAACGCCGCCAGTACTGGATTCA GATGGTTCATTCTTCTTGTATTCTAAACTGACTGTTGATAAATCCCGATG GCAGCAGGGCAACGTTTTTAGTTGTAGTGTTCTGCACGAAGCCCTTCATT CCCATTATACACAAAAATCTCTTTCCCTCAGCCCAGGCGAGGGAGGAAG TGACAGTTGGCAAGAGGAGGTGATAAAGCTCTGTGGGAGGGAGCTGGT ACGCGCACAGATTGCAATCTGCGGAAAGAGCACAGCAAGCGATGCTGCT GGGGCCGATGCCGATGCTGGCGCTCGACAATTGTATTCAGCTCTTGCTAA CAAATGCTGTCACGTAGGATGCACTAAACAGAGCCTTGCTCAATTTTGT |
| 434 | GATAAGACCCACACATGTCCACCATGCCCAGCCCCAGAAGCGGCAGGTG GTCCTTCTGTGTTTCTCTTTCCTCCCAAACCGAAAGATACTCTGATGATA AGCCGGACCCCAGAAGTTACGTGCGTTGTAGTAGACGTGTCTCACGAGG ACCCAGAAGTGAAGTTTAACTGGTATGTCGACGGTGTAGAAGTTCATAA TGCGAAAACAAAGCCCAGGGAAGAACAATATAATTCAACGTACCGGGT CGTTTCCGTGCTGACAGTTCTGCACCAAGATTGGCTCAACGGGAAAGAG TACAAATGCAAAGTATCAAATAAGGCCTTGGCTGCGCCGATTGAAAAGA CGATTTCCAAAGCAAAGGGCCAGCCAAGGGAACCCCAGGTCTATACCCT CCCTCCTAGCAGAGATGAACTTACAAAAAACCAAGTCTCCCTCACCTGC CTGGTCAAAGGATTCTATCCCTCAGATATAGCAGTAGAATGGGAAAGTA ACGGGCAGCCCGAAAACAATTATAAGACCACTCCTCCAGTACTCGATTC AGACGGTAGCTTCTTTCTGTATTCCAAGCTGACCGTAGATAAAAGTAGGT GGCAGCAAGGTAATGTCTTCTCATGTAGTGTACTTCATGAGGCGTTGCAT TCCCATTACACGCAAAAGTCTTTGAGTCTCAGTCCGGGTGAAGGAGGTA GCGATTCTTGGCAGGAAGAAGTAATTAAGCTGTGCGGCCGGGAGCTCGT CAGGGCTCAGATAGCTATATGCGGCAAGAGCACGGCCAGTGATGCTGCT GGTGCAGAGGCTGAAGCAGGTGCCAGGCAGTTGTACAGCGCACTCGCTA ATAAGTGTTGCCACGTGGGGTGTACAAAGCAATCTTTGGCACAATTCTGT |
| 435 | GATAAGACCCATACTTGTCCTCCGTGCCCGGCACCAGAGGCTGCGGGTG GCCCATCGTTTCTGTTTCCGCCAAAGCCTAAGGATACTCTGATGATT TCACGCACACCCGAAGTGACCTGCGTGGTGGTCGACGTATCTCACGAAG ACCCAGAGGTAAAATTCAATTGGTACGTGGACGGCGTCGAGGTTCATAA CGCGAAAACTAAGCCGAGAGAAGAGCAGTACAACTCTACGTATCGCGTG GTGTCCGTACTGACAGTATTGCATCAGGACTGGTTGAATGGCAAGGAGT ATAAGTGCAAGGTATCTAATAAGGCATTGGCTGCCCCAATAGAGAAAAC GATCAGCAAAGCAAAGGGGCAGCCGCGCGAGCCGCAGGTATATACACT TCCACCATCACGGGATGAGTTGACGAAAAATCAAGTCTCTCTCACATGT CTGGTAAAAGGTTTCTATCCTTCTGATATCGCCGTGGAATGGGAAAGCA ACGGCCAACCCGAAAACAACTATAAGACGACGCCGCCGGTACTCGACA GCGACGGAAGCTTTTTCTTGTATTCCAAGTTGACAGTGGACAAGTCTCGA TGGCAGCAAGGAAACGTGTTCTCATGTTCTGTTCTTCACGAAGCCCTTCA TAGCCATTATACTCAGAAATCTCTCTCACTCTCCCCAGGTGAAGGGGGA AGTGACTCTTGGCAAGAAGAAGTCATTAAGCTTTGCGGTCGAGAATTGG TTCGGGCTCAAATAGCTATTTGTGGCAAGTCCACGGCAAGTGATGCAGC GGGGGCTCAGGCAGACGCGGGCGCAAGGCAGCTTTATTCCGCACTTGCA AATAAGTGCTGTCACGTCGGATGTACTAAACAATCACTTGCACAATTCTG C |
| 436 | GACAAGACACATACATGTCCCCCATGCCCTGCACCCGAAGCTGCTGGGG GGCCCAGCGTGTTCCTGTTTCCGCCGAAGCCCAAGGACACATTGATGATT AGTAGAACCCCAGAGGTAACTTGTGTTGTGGTCGATGTGTCACATGAAG ACCCCGAGGTAAAGTTTAACTGGTATGTGGATGGGGTAGAGGTACATAA TGCAAAAACCAAGCCGCGGGAGGAGCAGTATAATTCAACCTATCGAGTC GTGTCAGTCTTGACCGTGCTCCACCAGGACTGGCTTAACGGTAAGGAGT ATAAATGCAAAGTCAGTAATAAGGCATTGGCCGCCCCATTGAGAAGAC CATCAGTAAAGCTAAGGGGCAACCTAGAGAGCCACAGGTTTACACCCTC CCTCCCTCCCGGGATGAACTCACCAAAAACCAGGTGTCCCTTACCTGTTT GGTAAAGGGCTTTTATCCTTCTGATATTGCTGTTGAATGGGAGTCTAACG GCAACCTGAAAATAACTACAAAACAACTCCCCCCGTTCTGGACTCTGA TGGGTCATTCTTCCTTTATTCAAAATTGACAGTTGATAAGAGTAGATGGC |

TABLE 9-continued

Nucleotide Sequences Encoding Fusion Proteins and Peptide Components

| SEQ ID NO: | Sequence |
|---|---|
| | AACAAGGCAACGTATTTTCATGTTCTGTGCTCCACGAGGCTCTCCATTCC<br>CACTACACACAGAAAAGTCTCTCACTGTCCCCAGGAGAGGGCGGGAGCG<br>ACTCTTGGCAGGAAGAAGTAATCAAGTTGTGTGGCAGGGAACTCGTACG<br>CGCTCAGATTGCAATATGCGGGAAATCCACGGCAAGTGACGCTGCCGGG<br>GCCGACGCGCAAGCAGGGGCACGGCAGCTTTACTCCGCCCTCGCAAATA<br>AATGTTGTCATGTGGGATGCACTAAACAGTCCCTTGCCCAGTTTTGC |
| 437 | GATAAAACCCATACCTGTCCACCATGCCCCGCGCCAGAGGCAGCGGGTG<br>GTCCAAGCGTTTTCCTTTTTCCACCGAAACCAAAAGATACACTTATGATA<br>TCAAGGACCCCCGAGGTAACGTGCGTCGTAGTTGACGTTTCTCACGAAG<br>ATCCCGAGGTGAAATTCAATTGGTACGTAGATGGTGTAGAGGTACACAA<br>TGCGAAGACAAAACCGCGGGAAGAGCAGTATAATAGCACATACAGAGT<br>CGTGAGCGTCCTCACCGTACTTCACCAAGATTGGCTGAATGGAAAGGAG<br>TACAAATGTAAGGTAAGTAATAAAGCACTTGCGGCCCCATCGAGAAAA<br>CTATCAGTAAAGCAAAAGGGCAACCACGAGAACCCCAGGTCTACACTTT<br>GCCACCATCACGGGATGAACTGACAAAAAATCAGGTGTCACTCACTTGC<br>CTTGTTAAAGGGTTCTATCCTAGTGACATAGCGGTAGAATGGGAGTCTA<br>ACGGGCAGCCTGAGAACAATTATAAAACTACGCCCCTGTTCTTGATTCC<br>GATGGATCATTTTTTCTCTACTCCAAACTCACCGTAGACAAATCCCGCTG<br>GCAGCAGGGCAACGTGTTTAGTTGCAGCGTTCTTCACGAAGCACTTCACT<br>CACATTACACACAAAAGTCCCTGAGCTTGAGTCCTGGGGAGGGTGGATC<br>TGATTCTTGGCAGGAAGAAGTTATAAAACTTTGTGGCAGAGAGTTGGTC<br>CGCGCACAAATCGCCATATGTGGTAAAAGCACAGCGTCTGACGCGGCGG<br>GAGCGCAAGCCCAGGCGGGGGCTCGGCAACTCTACTCAGCCCTGGCTAA<br>CAAGTGCTGTCACGTGGGATGCACTAAACAAAGTCTGGCGCAGTTCTGC |
| 438 | GACAAAACCCATACGTGTCCCCGTGTCCGGCTCCAGAGGCTGCGGGAG<br>GACCGTCTGTGTTCTTGTTCCCGCCGAAGCCTAAAGATACGCTGATGATT<br>AGTCGGACCCCCGAGGTGACCTGCGTGGTAGTAGACGTATCTCATGAAG<br>ATCCGGAAGTAAAGTTTAACTGGTACGTAGACGGCGTCGAGGTACATAA<br>TGCCAAGACGAAACCCAGAGAAGAGCAATATAATAGCACTTATCGAGTT<br>GTAAGCGTATTGACGGTCCTTCACCAGGACTGGTTGAACGGCAAAGAGT<br>ACAAATGTAAGGTATCCAATAAAGCATTGGCTGCGCCAATTGAAAAGAC<br>AATTTCCAAAGCGAAGGGGCAACCTCGAGAGCCGCAAGTCTACACGCTG<br>CCACCGAGTAGGGATGAATTGACTAAGAATCAGGTGAGTCTCACGTGTC<br>TCGTGAAGGGGTTTTACCCCAGTGATATTGCGGTAGAATGGGAGTCCAA<br>CGGTCAGCCAGAAAATAATTATAAAACAACGCCCCCTGTATTGGATTCT<br>GACGGGAGCTTTTTCCTGTACTCAAAACTCACCGTAGATAAGAGTCGCT<br>GGCAACAGGGCAACGTATTCTCATGTAGCGTTCTGCACGAGGCGCTGCA<br>CTCTCACTACACACAGAAGAGTTTGAGTTTGTCCCCTGGCGAAGGAGGT<br>TCTGATTCCTGGCAGGAGGAGGTGATTAAGCTGTGTGGCCGCGAATTGG<br>TGAGGGCTCAAATTGCTATTTGCGGACAGAGCACAGCGTCCGATGCCGC<br>CGGCGCAGATGCTAATGCCGGTGCAAGGCAACTGTACTCCGCTCTCGCC<br>AATAAGTGTTGTCATGTCGGCTGCACCAAGCAATCCCTGGCCCAGTTTTG<br>C |
| 439 | GACAAGACTCACACTTGTCCCCCATGTCCAGCACCGGAAGCTGCCGGCG<br>GTCCCTCAGTTTTCCTTTTCCCCCCAAACCCAAGGACACCCTTATGATTTT<br>CAAGGACACCAGAGGTAACGTGCGTAGTGGTGGACGTCAGTCATGAAG<br>ACCCAGAGGTAAAGTTTAACTGGTACGTGGATGGGGTAGAGGTTCATAA<br>TGCTAAAACAAAACCACGCGAGGAACAGTACAATAGTACGTATAGAGT<br>GGTCTCCGTTCTTACGGTGCTGCATCAGGACTGGCTGAACGGAAAAGAG<br>TACAAGTGTAAGGTTAGCAATAAGGCGCTGGCGGCCCCAATCGAAAAGA<br>CGATTTCTAAGGCCAAAGGCCAGCCAAGGGAGCCACAAGTATATACCCT<br>TCCCCCTTCCCGAGATGAGCTGACTAAGAATCAAGTCAGTCTCACCTGCC<br>TTGTCAAAGGGTTCTACCCATCCGATATTGCTGTTGAATGGGAGTCTAAT<br>GGCCAGCCGGAGAACAATTACAAGACAACTCCGCCTGTATTGGATTCCG<br>ACGGGTCTTTTTTCCTCTATTCAAAACTCACAGTAGACAAAGTCGATGG<br>CAGCAAGGTAACGTGTTTTCTTGCTCTGTGTTGCATGAAGCACTTCATTC<br>TCATTATACTCAAAAATCATTGAGCCTCAGTCCAGGCGAAGGGGTAGT<br>GACTCATGGCAGGAGGAGGTAATCAAGCTTTGCGGACGAGAGTTGGTCA<br>GGGCCCAGATAGCTATTTGTGGTCAGTCCACGGCGAGTGACGCAGCAGG<br>GGCGAATGCCGATGCAGGAGCAAGCACAACTGTATTCTGCTCTGGCCAAC<br>AAGTGTTGTCATGTAGGGTGTACTAAACAAAGTCTCGCCCAGTTCTGC |
| 440 | GATAAAACCCACACCTGTCCCCCATGTCCGGCTCCCGAAGCAGCGGGGG<br>GCCCTTCAGTTTTTCTCTTTCCCCCCAAACCGAAAGACACGCTGATGATT<br>AGCAGAACTCCAGAGGTTACCTGTGTAGTTGTGGACGTTTCACACGAGG<br>ATCCCGAGGTTAAATTCAACTGGTATGTGGACGGCGTCGAAGTGCATAA<br>TGCAAAAACAAAGCCCCGGGAAGAACAATATAATAGTACCTATAGGGTC<br>GTTTCCGTACTGACCGTACTTCATCAAGATTGGCTCAATGGGAAGGAAT<br>ACAAATGTAAAGTGAGTAATAAAGCCCTGGCGGCACCGATCGAAAAAA<br>CCATTTCAAAGGCTAAGGGACAACCGCGCGAACCTCAGGTCTATACCTT<br>GCCCCCTTCACGCGACGAGCTTACGAAGAATCAGGTAAGCCTTACTTGT |

TABLE 9-continued

Nucleotide Sequences Encoding Fusion Proteins and Peptide Components

| SEQ ID NO: | Sequence |
|---|---|
| | CTTGTCAAGGGTTTTTACCCCAGCGACATAGCTGTCGAGTGGGAATCCA ATGGCCAACCGGAGAATAATTACAAAACTACCCCTCCTGTTCTTGATAG CGACGGAAGCTTCTTCTTGTATTCCAAACTCACAGTAGATAAAAGTAGG TGGCAGCAGGGCAATGTATTTTCTTGCAGCGTCCTGCATGAAGCACTGC ATAGCCATTATACTCAAAAGTCCCTGTCTTTGTCTCCTGGAGAGGCGGA AGCCGATTCTTGGCAAGAGGAAGTTATTAAGCTGTGCGGGCGCGAACTTG TGAGGGCTCAAATAGCGATATGTGGTCAGAGCACCGCTAGCGATGCGGC TGGTGCAGACGCCGATGCCGGTGCTAGGCAACTTTACAGTGCACTTGCG AATAAGTGCTGTCACGTCGGATGTACTAAACAAAGCCTCGCCCAGTTCT GC |
| 441 | GATAAAACACATACTTGCCCTCCTTGTCCGGCTCCCGAAGCCGCAGGTG GACCTTCCGTCTTTCTTTTCCCACCCAAACCTAAAGACACTTTGATGATT AGCCGGACCCCCGAGGTAACCTGTGTCGTAGTTGACGTTTCCCATGAAG ACCCCGAAGTTAAGTTCAACTGGTATGTCGACGGCGTCGAGGTGCACAA CGCGAAGACTAAGCCAAGAGAGGAGCAATACAATTCAACTTACAGGGT CGTGTCCGTCTTGACAGTGCTTCATCAAGACTGGCTTAATGGAAAGGAA TACAAATGTAAAGTCTCCAACAAGGCTCTCGCAGCGCCCATTGAGAAAA CGATATCCAAAGCGAAGGGTCAACCAAGAGAACCCCAGGTTTACACCCT CCCCCCTAGTCGGGACGAGCTTACGAAGAACCAGGTCAGTTTGACATGC CTGGTGAAAGGCTTCTATCCGTCAGACATCGCCGTAGAGTGGGAAAGCA ACGGGCAACCCGAGAACAACTATAAGACGACTCCCCCGGTGTTGGATAG CGATGGCTCTTTCTTCCTGTACTCTAAGCTGACCGTAGATAAATCCAGGT GGCAACAGGGGAACGTGTTTTCATGCTCAGTGCTCCATGAAGCCCTCCA TTCACACTATACACAAAAGTCTTTGTCACTGTCCCCCGGTGAAGGCGGCA GTGATAGCTGGCAAGAAGAAGTCATAAAGCTCTGTGGTCGCGAGCTTGT TAGGGCCCAAATTGCGATCTGTGGTCAGTCAACGGCTTCTGACGCCGCC GGAGCGGAAGCCGAGGCGGGTGCTCGGCAATTGTATTCAGCACTGGCGA ACAAATGTTGCCATGTTGGTTGTACTAAACAAAGCCTGGCCCAGTTTTGC |
| 442 | GACAAGACTCACACTTGTCCACCCTGTCCAGCACCTGAAGCCGCTGGTG GACCATCTGTCTTTCTGTTCCCCCCTAAACCAAAGGATACACTTATGATC AGCAGAACACCTGAAGTCACATGCGTTGTGGTAGACGTTTCCCACGAGG ATCCTGAAGTGAAGTTTAACTGGTACGTGGATGGCGTTGAGGTTCATAA TGCCAAGACGAAACCTCGGGAGGAGCAGTATAATTCTACTTATAGGGTG GTAAGCGTACTGACAGTCCTCCATCAAGACTGGTTGAACGGAAGGAAT ACAAGTGTAAAGTTTCCAACAAAGCTCTGGCGGCGCCTATAGAAAAGAC AATATCAAAAGCGAAAGGGCAACCCAGAGAGCCTCAAGTATATACATTG CCCCCTAGCAGAGACGAATTGACGAAAAATCAGGTCTCTCTCACGTGCC TCGTGAAGGGCTTCTATCCTAGTGATATAGCTGTGGAATGGGAATCCAA TGGACAGCCAGAAAACAACTACAAGACCACGCCCCCCGTCTTGGATTCC GACGGGTCATTCTTCCTGTACAGCAAGCTGACTGTCGACAAGAGTCGAT GGCAACAGGGCAACGTCTTTAGCTGCAGCGTCCTGCACGAAGCTCTGCA TAGTCATTACACCCAAAAGTCCCTTTCTCTCTCCCCTGGTAAGGCGGTT CCGATTCATGGCAAGAAGAAGTAATTAAGCTCTGTGGACGAGAGCTTGT CCGAGCACAAATTGCGATCTGCGGGCAGAGTACCGCATCTGACGCTGCT GGCGCGCAGGCAGATGCGGGTGCACGGCAGCTTTATTCAGCTCTCGCCA ACAAGTGTTGTCATGTGGGGTGTACAAAGCAGAGCCTTGCCCAGTTTTGT |
| 443 | GATAAGACCCATACGTGTCCCCCTTGCCCTGCACCCGAGGCGGCTGGGG GCCCTTCCGTATTCTTGTTTCCTCCTAAGCCCAAAGATACCTTGATGATA AGTCGAACGCCAGAAGTGACTTGCGTTGTTGTGGATGTCTCCCACGAGG ATCCAGAAGTCAAATTTAACTGGTATGTCGATGGGGTCGAAGTGCATAA TGCTAAAACGAAACCCAGAGAGGAACAATACAATTCAACATACCGCGTA GTCAGTGTTCTTACTGTGCTCCATCAGGATTGGCTCAATGGGAAAGAATA CAAGTGTAAAGTCTCAAATAAAGCATTGGCGGCCCCTATAGAGAAGACC ATAAGCAAGGCTAAAGGTCAGCCTAGGGAGCCTCAAGTATATACCTTGC CTCCTAGCAGAGATGAGTTGACCAAGAACCAGGTCAGCCTCACATGCCT GGTGAAAGGGTTTTACCCATCTGATATTGCCGTCGAGTGGGAAGTAAT GGGCAGCCAGAGAACAACTACAAGACGACACCACCGGTACTGGATAGT GACGGAAGTTTTTTCTTTACAGTAAGCTCACAGTCGACAAAAGCCGGT GGCAACAAGGAAATGTATTTTCATGTAGCGTACTTCATGAAGCCCTCCA CTCTCATTACACGCAGAAGTCACTTTCACTTAGTCCGGTGAGGGTGGA AGCGATAGCTGGCAAGAGGAGGTTATCAAGCTCTGTGGACGAGAACTCG TGAGAGCGCAAATTGCAATCTGCGGGCAGAGCACGGCGAGTGATGCGG CCGGGGCGGACGCGCAAGCAGGAGCACGACAACTTTATAGTGCTTTGGC TAATAAATGTTGCCACGTTGGATGTACTAAACAGAGCTTGGCACAGTTTT GC |
| 444 | GATAAAACGCACACTTGTCCGCCATGTCCGGCACCTGAGGCAGCGGGAG GACCGTCCGTGTTTCTGTTTCCCCCTAAACCAAAGGACACGCTGATGATC AGCCGAACACCTGAAGTAACATGCGTGGTCGTTGACGTGTCTCACGAGG ATCCAGAAGTAAAGTTCAATTGGTATGTTGACGGAGTTGAAGTACATAA TGCTAAGACTAAACCCCGCGAAGAACAATATAATTCTACGTACAGAGTT |

TABLE 9-continued

Nucleotide Sequences Encoding Fusion Proteins and Peptide Components

| SEQ ID NO: | Sequence |
|---|---|
| | GTATCCGTGCTCACGGTACTTCACCAAGATTGGCTTAACGGGAAAGAAT<br>ATAAGTGTAAGGTCTCAAATAAGGCCCTGGCTGCTCCGATCGAAAAAC<br>GATATCAAAGGCAAAGGGTCAACCTCGGGAGCCTCAAGTATATACCCTC<br>CCCCCATCTAGGGATGAGCTGACAAAGAACCAAGTTTCACTGACCTGTC<br>TCGTAAAGGGTTTCTATCCTTCTGACATCGCAGTTGAATGGGAGTCCAAC<br>GGCCAACCAGAGAACAACTATAAGACGACACCCCCGTGTTGGACAGTG<br>ACGGAAGTTTTTCCTGTACTCCAAGCTGACGGTTGATAAAGTAGATG<br>GCAACAAGGAAATGTTTTCAGTTGTTCTGTGTTGCACGAGGCCCTCCACT<br>CACACTATACCCAAAAAAGTTTGTCTCTGAGTCCCGGTGAAGGCGGGAG<br>CGATTCATGGCAGGAGGAAGTAATCAAACTTTGTGGGCAGAACTGGTC<br>AGGGCGCAAATAGCGATATGTGGGCAAAGCACAGCTTCAGATGCAGCC<br>GGTGCTCAAGCTCAGGCTGGAGCTCGACAGCTTTATAGCGCCTTGGCTA<br>ATAAATGTTGTCACGTTGGCTGTACGAAGCAGAGCCTGGCACAGTTCTG<br>C |
| 445 | GATAAACCCACACTTGCCCACCTTGCCCTGCGCCGGAAGCCGCCGGAG<br>GACCTAGTGTTTTCCTCTTTCCCCCTAAGCCCAAAGACACGTTGATGATC<br>TCTCGGACACCGGAAGTAACTTGTGTCGTTGTGGATGTGTCACATGAGG<br>ATCCCGAGGTGAAATTTAATTGGTACGTTGACGGCGTGGAGGTGCATAA<br>CGCAAAGACTAAACCACGCGAGGAGCAGTATAATTCTACATACCGGGTT<br>GTCTCAGTTCTCACAGTTCTTCATCAGGATTGGTTGAATGGAAAGGAGTA<br>CAAATGCAAAGTGTCCAACAAAGCGCTTGCTGCGCCGATTGAAAAGACG<br>ATTTCAAAGGCAAAAGGGCAGCCCCGCGAACCCCAAGTATATACTTTGC<br>CTCCCTCACGCGATGAACTGACTAAGAACCAGGTGAGCCTGACTTGTTT<br>GGTTAAGGGTTTTTATCCAAGTGACATTGCTGTTGAATGGGAGTCCAATG<br>GCCAGCCTGAGAATAACTACAAAACGACACCTCCTGTACTTGACAGCGA<br>CGGCTCCTTTTTTCTTTATTCAAAACTCACAGTGGACAAATCCAGGTGGC<br>AGCAGGGTAACGTCTTTTCTTGCAGCGTGCTCCACGAAGCTTTGCATTCA<br>CATTATACGCAAAAATCCTTGTCATTGTCCCCAGGTAAGGGCGGAAGCG<br>ACTCATACCAAGAAGAAGTCATTAAACTTTGTGGACGGGAGCTGGTTAG<br>GGCACAGATTGCTATTTGTGGTAAGTCTACGGCTAGTGACGCAGCGGGC<br>GCCGAAGCGGAAGCTGGTGCAAGGCAGCTTTACTCTGCTCTGGCTAACA<br>AGTGTTGTCACGTTGGGTGTACCAAGCGGTCCCTTGCGCAATTCTGC |
| 446 | GATAAACCCACACTTGCCCACCTTGCCCTGCGCCGGAAGCCGCCGGAG<br>GACCTAGTGTTTTCCTCTTTCCCCCTAAGCCCAAAGACACGTTGATGATC<br>TCTCGGACACCGGAAGTAACTTGTGTCGTTGTGGATGTGTCACATGAGG<br>ATCCCGAGGTGAAATTTAATTGGTACGTTGACGGCGTGGAGGTGCATAA<br>CGCAAAGACTAAACCACGCGAGGAGCAGTATAATTCTACATACCGGGTT<br>GTCTCAGTTCTCACAGTTCTTCATCAGGATTGGTTGAATGGAAAGGAGTA<br>CAAATGCAAAGTGTCCAACAAAGCGCTTGCTGCGCCGATTGAAAAGACG<br>ATTTCAAAGGCAAAAGGGCAGCCCCGCGAACCCCAAGTATATACTTTGC<br>CTCCCTCACGCGATGAACTGACTAAGAACCAGGTGAGCCTGACTTGTTT<br>GGTTAAGGGTTTTTATCCAAGTGACATTGCTGTTGAATGGGAGTCCAATG<br>GCCAGCCTGAGAATAACTACAAAACGACACCTCCTGTACTTGACAGCGA<br>CGGCTCCTTTTTTCTTTATTCAAAACTCACAGTGGACAAATCCAGGTGGC<br>AGCAGGGTAACGTCTTTTCTTGCAGCGTGCTCCACGAAGCTTTGCATTCA<br>CATTATACGCAAAAATCCTTGTCATTGTCCCCAGGTAAGGGCGGAAGCG<br>ACTCATTTCAAGAAGAAGTCATTAAACTTTGTGGACGGGAGCTGGTTAG<br>GGCACAGATTGCTATTTGTGGTAAGTCTACGGCTAGTGACGCAGCGGGC<br>GCCGAAGCGGAAGCTGGTGCAAGGCAGCTTTACTCTGCTCTGGCTAACA<br>AGTGTTGTCACGTTGGGTGTACCAAGCGGTCCCTTGCGCAATTCTGC |
| 447 | GATAAACCCACACTTGCCCACCTTGCCCTGCGCCGGAAGCCGCCGGAG<br>GACCTAGTGTTTTCCTCTTTCCCCCTAAGCCCAAAGACACGTTGATGATC<br>TCTCGGACACCGGAAGTAACTTGTGTCGTTGTGGATGTGTCACATGAGG<br>ATCCCGAGGTGAAATTTAATTGGTACGTTGACGGCGTGGAGGTGCATAA<br>CGCAAAGACTAAACCACGCGAGGAGCAGTATAATTCTACATACCGGGTT<br>GTCTCAGTTCTCACAGTTCTTCATCAGGATTGGTTGAATGGAAAGGAGTA<br>CAAATGCAAAGTGTCCAACAAAGCGCTTGCTGCGCCGATTGAAAAGACG<br>ATTTCAAAGGCAAAAGGGCAGCCCCGCGAACCCCAAGTATATACTTTGC<br>CTCCCTCACGCGATGAACTGACTAAGAACCAGGTGAGCCTGACTTGTTT<br>GGTTAAGGGTTTTTATCCAAGTGACATTGCTGTTGAATGGGAGTCCAATG<br>GCCAGCCTGAGAATAACTACAAAACGACACCTCCTGTACTTGACAGCGA<br>CGGCTCCTTTTTCTTTATTCAAAACTCACAGTGGACAAATCCAGGTGGC<br>AGCAGGGTAACGTCTTTTCTTGCAGCGTGCTCCACGAAGCTTTGCATTCA<br>CATTATACGCAAAAATCCTTGTCATTGTCCCCAGGTAAGGGCGGAAGCG<br>ACTCACTTCAAGAAGAAGTCATTAAACTTTGTGGACGGGAGCTGGTTAG<br>GGCACAGATTGCTATTTGTGGTAAGTCTACGGCTAGTGACGCAGCGGGC<br>GCCGAAGCGGAAGCTGGTGCAAGGCAGCTTTACTCTGCTCTGGCTAACA<br>AGTGTTGTCACGTTGGGTGTACCAAGCGGTCCCTTGCGCAATTCTGC |
| 448 | GATAAACCCACACTTGCCCACCTTGCCCTGCGCCGGAAGCCGCCGGAG<br>GACCTAGTGTTTTCCTCTTTCCCCCTAAGCCCAAAGACACGTTGATGATC |

TABLE 9-continued

Nucleotide Sequences Encoding Fusion Proteins and Peptide Components

| SEQ ID NO: | Sequence |
|---|---|
| | TCTCGGACACCGGAAGTAACTTGTGTCGTTGTGGATGTGTCACATGAGG<br>ATCCCGAGGTGAAATTTAATTGGTACGTTGACGGCGTGGAGGTGCATAA<br>CGCAAAGACTAAACCACGCGAGGAGCAGTATAATTCTACATACCGGGTT<br>GTCTCAGTTCTCACAGTTCTTCATCAGGATTGGTTGAATGGAAAGGAGTA<br>CAAATGCAAAGTGTCCAACAAAGCGCTTGCTGCGCCGATTGAAAAGACG<br>ATTTCAAAGGCAAAAGGGCAGCCCCGCGAACCCCAAGTATATACTTTGC<br>CTCCCTCACGCGATGAACTGACTAAGAACCAGGTGAGCCTGACTTGTTT<br>GGTTAAGGGTTTTTATCCAAGTGACATTGCTGTTGAATGGGAGTCCAATG<br>GCCAGCCTGAGAATAACTACAAAACGACACCTCCTGTACTTGACAGCGA<br>CGGCTCCTTTTTTCTTTATTCAAAACTCACAGTGGACAAATCCAGGTGGC<br>AGCAGGGTAACGTCTTTTCTTGCAGCGTGCTCCACGAAGCTTTGCATTCA<br>CATTATACGCAAAAATCCTTGTCATTGTCCCCAGGTAAGGGCGGAAGCG<br>ACTCAATTCAAGAAGAAGTCATTAAACTTTGTGGACGGGAGCTGGTTAG<br>GGCACAGATTGCTATTTGTGGTAAGTCTACGGCTAGTGACGCAGCGGGC<br>GCCGAAGCGGAAGCTGGTGCAAGGCAGCTTTACTCTGCTCTGGCTAACA<br>AGTGTTGTCACGTTGGGTGTACCAAGCGGTCCCTTGCGCAATTCTGC |
| 449 | GATAAAACCCACACTTGCCCACCTTGCCCTGCGCCGGAAGCCGCCGGAG<br>GACCTAGTGTTTTCCTCTTTCCCCCTAAGCCCAAAGACACGTTGATGATC<br>TCTCGGACACCGGAAGTAACTTGTGTCGTTGTGGATGTGTCACATGAGG<br>ATCCCGAGGTGAAATTTAATTGGTACGTTGACGGCGTGGAGGTGCATAA<br>CGCAAAGACTAAACCACGCGAGGAGCAGTATAATTCTACATACCGGGTT<br>GTCTCAGTTCTCACAGTTCTTCATCAGGATTGGTTGAATGGAAAGGAGTA<br>CAAATGCAAAGTGTCCAACAAAGCGCTTGCTGCGCCGATTGAAAAGACG<br>ATTTCAAAGGCAAAAGGGCAGCCCCGCGAACCCCAAGTATATACTTTGC<br>CTCCCTCACGCGATGAACTGACTAAGAACCAGGTGAGCCTGACTTGTTT<br>GGTTAAGGGTTTTTATCCAAGTGACATTGCTGTTGAATGGGAGTCCAATG<br>GCCAGCCTGAGAATAACTACAAAACGACACCTCCTGTACTTGACAGCGA<br>CGGCTCCTTTTTTCTTTATTCAAAACTCACAGTGGACAAATCCAGGTGGC<br>AGCAGGGTAACGTCTTTTCTTGCAGCGTGCTCCACGAAGCTTTGCATTCA<br>CATTATACGCAAAAATCCTTGTCATTGTCCCCAGGTAAGGGCGGAAGCG<br>ACTCATGGCAAGAAGAAGTCATTAAACTTTGTGGACGGGAGCTGGTTAG<br>GGCACAGATTGCTATTTGTGGTAAGTCTACGGCTAGTGACGCAGCGGGC<br>GCCGAAGCGGAAGCTGGTGCAAGGCAGCTTTACTCTGCTCTGGCTAACA<br>AGTGTTGTTACGTTGGGTGTACCAAGCGGTCCCTTGCGCAATTCTGC |
| 450 | GATAAAACCCACACTTGCCCACCTTGCCCTGCGCCGGAAGCCGCCGGAG<br>GACCTAGTGTTTTCCTCTTTCCCCCTAAGCCCAAAGACACGTTGATGATC<br>TCTCGGACACCGGAAGTAACTTGTGTCGTTGTGGATGTGTCACATGAGG<br>ATCCCGAGGTGAAATTTAATTGGTACGTTGACGGCGTGGAGGTGCATAA<br>CGCAAAGACTAAACCACGCGAGGAGCAGTATAATTCTACATACCGGGTT<br>GTCTCAGTTCTCACAGTTCTTCATCAGGATTGGTTGAATGGAAAGGAGTA<br>CAAATGCAAAGTGTCCAACAAAGCGCTTGCTGCGCCGATTGAAAAGACG<br>ATTTCAAAGGCAAAAGGGCAGCCCCGCGAACCCCAAGTATATACTTTGC<br>CTCCCTCACGCGATGAACTGACTAAGAACCAGGTGAGCCTGACTTGTTT<br>GGTTAAGGGTTTTTATCCAAGTGACATTGCTGTTGAATGGGAGTCCAATG<br>GCCAGCCTGAGAATAACTACAAAACGACACCTCCTGTACTTGACAGCGA<br>CGGCTCCTTTTTTCTTTATTCAAAACTCACAGTGGACAAATCCAGGTGGC<br>AGCAGGGTAACGTCTTTTCTTGCAGCGTGCTCCACGAAGCTTTGCATTCA<br>CATTATACGCAAAAATCCTTGTCATTGTCCCCAGGTAAGGGCGGAAGCG<br>ACTCATGGCAAGAAGAAGTCATTAAACTTTGTGGACGGGAGCTGGTTAG<br>GGCACAGATTGCTATTTGTGGTAAGTCTACGGCTAGTGACGCAGCGGGC<br>GCCGAAGCGGAAGCTGGTGCAAGGCAGCTTTACTCTGCTCTGGCTAACA<br>AGTGTTGTCTTGTTGGGTGTACCAAGCGGTCCCTTGCGCAATTCTGC |
| 451 | GATAAAACCCACACTTGCCCACCTTGCCCTGCGCCGGAAGCCGCCGGAG<br>GACCTAGTGTTTTCCTCTTTCCCCCTAAGCCCAAAGACACGTTGATGATC<br>TCTCGGACACCGGAAGTAACTTGTGTCGTTGTGGATGTGTCACATGAGG<br>ATCCCGAGGTGAAATTTAATTGGTACGTTGACGGCGTGGAGGTGCATAA<br>CGCAAAGACTAAACCACGCGAGGAGCAGTATAATTCTACATACCGGGTT<br>GTCTCAGTTCTCACAGTTCTTCATCAGGATTGGTTGAATGGAAAGGAGTA<br>CAAATGCAAAGTGTCCAACAAAGCGCTTGCTGCGCCGATTGAAAAGACG<br>ATTTCAAAGGCAAAAGGGCAGCCCCGCGAACCCCAAGTATATACTTTGC<br>CTCCCTCACGCGATGAACTGACTAAGAACCAGGTGAGCCTGACTTGTTT<br>GGTTAAGGGTTTTTATCCAAGTGACATTGCTGTTGAATGGGAGTCCAATG<br>GCCAGCCTGAGAATAACTACAAAACGACACCTCCTGTACTTGACAGCGA<br>CGGCTCCTTTTTTCTTTATTCAAAACTCACAGTGGACAAATCCAGGTGGC<br>AGCAGGGTAACGTCTTTTCTTGCAGCGTGCTCCACGAAGCTTTGCATTCA<br>CATTATACGCAAAAATCCTTGTCATTGTCCCCAGGTAAGGGCGGAAGCG<br>ACTCATGGCAAGAAGAAGTCATTAAACTTTGTGGACGGGAGCTGGTTAG<br>GGCACAGATTGCTATTTGTGGTAAGTCTACGGCTAGTGACGCAGCGGGC<br>GCCGAAGCGGAAGCTGGTGCAAGGCAGCTTTACTCTGCTCTGGCTAACA<br>AGTGTTGTCAAGTTGGGTGTACCAAGCGGTCCCTTGCGCAATTCTGC |

TABLE 9-continued

Nucleotide Sequences Encoding Fusion Proteins and Peptide Components

| SEQ ID NO: | Sequence |
|---|---|
| 452 | GATAAAACCCACACTTGCCCACCTTGCCCTGCGCCGGAAGCCGCCGGAG<br>GACCTAGTGTTTTCCTCTTTCCCCCTAAGCCCAAAGACACGTTGATGATC<br>TCTCGGACACCGGAAGTAACTTGTGTCGTTGTGGATGTGTCACATGAGG<br>ATCCCGAGGTGAAATTTAATTGGTACGTTGACGGCGTGGAGGTGCATAA<br>CGCAAAGACTAAACCACGCGAGGAGCAGTATAATTCTACATACCGGGTT<br>GTCTCAGTTCTCACAGTTCTTCATCAGGATTGGTTGAATGGAAAGGAGTA<br>CAAATGCAAAGTGTCCAACAAAGCGCTTGCTGCGCCGATTGAAAAGACG<br>ATTTCAAAGGCAAAAGGGCAGCCCCGCGAACCCCAAGTATATACTTTGC<br>CTCCCTCACGCGATGAACTGACTAAGAACCAGGTGAGCCTGACTTGTTT<br>GGTTAAGGGTTTTTATCCAAGTGACATTGCTGTTGAATGGGAGTCCAATG<br>GCCAGCCTGAGAATAACTACAAAACGACACCTCCTGTACTTGACAGCGA<br>CGGCTCCTTTTTTCTTTATTCAAAACTCACAGTGGACAAATCCAGGTGGC<br>AGCAGGGTAACGTCTTTTCTTGCAGCGTGCTCCACGAAGCTTTGCATTCA<br>CATTATACGCAAAAATCCTTGTCATTGTCCCCAGGTAAGGGCGGAAGCG<br>ACTCATGGCAAGAAGAAGTCATTAAACTTTGTGGACGGGAGCTGGTTAG<br>GGCACAGATTGCTATTTGTGGTAAGTCTACGGCTAGTGACGCAGCGGGC<br>GCCGAAGCGGAAGCTGGTGCAAGGCAGCTTTACTCTGCTCTGGCTAACA<br>AGTGTTGTAAAGTTGGGTGTACCAAGCGGTCCCTTGCGCAATTCTGC |
| 453 | GATAAAACCCACACTTGCCCACCTTGCCCTGCGCCGGAAGCCGCCGGAG<br>GACCTAGTGTTTTCCTCTTTCCCCCTAAGCCCAAAGACACGTTGATGATC<br>TCTCGGACACCGGAAGTAACTTGTGTCGTTGTGGATGTGTCACATGAGG<br>ATCCCGAGGTGAAATTTAATTGGTACGTTGACGGCGTGGAGGTGCATAA<br>CGCAAAGACTAAACCACGCGAGGAGCAGTATAATTCTACATACCGGGTT<br>GTCTCAGTTCTCACAGTTCTTCATCAGGATTGGTTGAATGGAAAGGAGTA<br>CAAATGCAAAGTGTCCAACAAAGCGCTTGCTGCGCCGATTGAAAAGACG<br>ATTTCAAAGGCAAAAGGGCAGCCCCGCGAACCCCAAGTATATACTTTGC<br>CTCCCTCACGCGATGAACTGACTAAGAACCAGGTGAGCCTGACTTGTTT<br>GGTTAAGGGTTTTTATCCAAGTGACATTGCTGTTGAATGGGAGTCCAATG<br>GCCAGCCTGAGAATAACTACAAAACGACACCTCCTGTACTTGACAGCGA<br>CGGCTCCTTTTTTCTTTATTCAAAACTCACAGTGGACAAATCCAGGTGGC<br>AGCAGGGTAACGTCTTTTCTTGCAGCGTGCTCCACGAAGCTTTGCATTCA<br>CATTATACGCAAAAATCCTTGTCATTGTCCCCAGGTGAAGGCGGAAGCG<br>ACTCATACCAAGAAGAAGTCATTAAACTTTGTGGACGGGAGCTGGTTAG<br>GGCACAGATTGCTATTTGTGGTAAGTCTACGGCTAGTGACGCAGCGGGC<br>GCCGAAGCGGAAGCTGGTGCAAGGCAGCTTTACTCTGCTCTGGCTAACA<br>AGTGTTGTTACGTTGGGTGTACCAAGCGGTCCCTTGCGCAATTCTGC |
| 454 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTGAAGGCGGAAGCGACTCATACCAAGAAGAAGTCATTAAACTTTGTGGACG<br>GGAGCTGGTTAGGGCACAGATTGCTATTTGTGGTAAGTCTACGGCTAGTGACGCAG<br>CGGGCGCCGAAGCGGAAGCTGGTGCAAGGCAGCTTTACTCTGCTCTGGCTAACAAG<br>TGTTGTAAAGTTGGGTGTACCAAGCGGTCCCTTGCGCAATTCTGC |
| 455 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTGAAGGCGGAAGCGACTCATACCAAGAAGAAGTCATTAAACTTTGTGGACG<br>GGAGCTGGTTAGGGCACAGATTGCTATTTGTGGTAAGTCTACGGGAGGAAGGCT<br>CTGGAGGCGAAGGAGAAGGGGGCGGAAGACAGCTTTACTCTGCTCTGGCTAACAAG<br>TGTTGTTACGTTGGGTGTACCAAGCGGTCCCTTGCGCAATTCTGC |
| 456 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG |

US 12,264,188 B2

TABLE 9-continued

Nucleotide Sequences Encoding Fusion Proteins and Peptide Components

| SEQ ID NO: | Sequence |
|---|---|
| | AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTGAAGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGAGAAGGGGCGGAAGACAGCTTTACTCTGCTCTGGCTAACAAG<br>TGTTGTAAAGTTGGGTGTACCAAGCGGTCCCTTGCGCAATTCTGC |
| 457 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTGAAGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGATCTGGGGCGGAAGACAGCTTTACTCTGCTCTGGCTAACAAG<br>TGTTGTTACGTTGGGTGTACCAAGCGGTCCCTTGCGCAATTCTGC |
| 458 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTGAAGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGATCTGGGGCGGAAGACAGCTTTACTCTGCTCTGGCTAACAAG<br>TGTTGTAAAGTTGGGTGTACCAAGCGGTCCCTTGCGCAATTCTGC |
| 459 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTAAGGGCGGAAGCGACTCATACCAAGAAGAAGTCATTAAACTTTGTGGACG<br>GGAGCTGGTTAGGGCACAGATTGCTATTTGTGGTAAGTCTACGGCTAGTGACGCAG<br>CGGGCGCCGAAGCGGAAGCTGGTGCAAGGCAGCTTTACTCTGCTCTGGCTAACAAG<br>TGTTGTTACGTTGGGTGTACCAAGCAATCCCTTGCGCAATTCTGC |
| 460 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA |

TABLE 9-continued

Nucleotide Sequences Encoding Fusion Proteins and Peptide Components

| SEQ ID NO: | Sequence |
|---|---|
| | AGGGTTTTTATCCAAGTGACATTGCTGTTGAATGGGAGTCCAATGGCCAGCCTGAG
AATAACTACAAAACGACACCTCCTGTACTTGACAGCGACGGCTCCTTTTTTCTTTA
TTCAAAACTCACAGTGGACAAATCCAGGTGGCAGCAGGGTAACGTCTTTTCTTGCA
GCGTGCTCCACGAAGCTTTGCATTCACATTATACGCAAAAATCCTTGTCATTGTCC
CCAGGTAAGGGCGGAAGCGACTCATACCAAGAAGAAGTCATTAAACTTTGTGGACG
GGAGCTGGTTAGGGCACAGATTGCTATTTGTGGTAAGTCTACGGCTAGTGACGCAG
CGGGCGCCGAAGCGGAAGCTGGTGCAAGGCAGCTTTACTCTGCTCTGGCTAACAAG
TGTTGTAAAGTTGGGTGTACCAAGCAATCCCTTGCGCAATTCTGC |
| 461 | GATAAACCCACACTTGCCCACCTTGCCCTGCGCCGGAAGCCGCCGGAGGACCTAG
TGTTTTCCTCTTTCCCCCTAAGCCCAAAGACACGTTGATGATCTCTCGGACACCGG
AAGTAACTTGTGTCGTTGTGGATGTGTCACATGAGGATCCCGAGGTGAAATTTAAT
TGGTACGTTGACGGCGTGGAGGTGCATAACGCAAAGACTAAACCACGCGAGGAGCA
GTATAATTCTACATACCGGGTTGTCTCAGTTCTCACAGTTCTTCATCAGGATTGGT
TGAATGGAAAGGAGTACAAATGCAAAGTGTCCAACAAAGCGCTTGCTGCGCCGATT
GAAAAGACGATTTCAAAGGCAAAAGGGCAGCCCCGCGAACCCCAAGTATATACTTT
GCCTCCCTCACGCGATGAACTGACTAAGAACCAGGTGAGCCTGACTTGTTTGGTTA
AGGGTTTTTATCCAAGTGACATTGCTGTTGAATGGGAGTCCAATGGCCAGCCTGAG
AATAACTACAAAACGACACCTCCTGTACTTGACAGCGACGGCTCCTTTTTTCTTTA
TTCAAAACTCACAGTGGACAAATCCAGGTGGCAGCAGGGTAACGTCTTTTCTTGCA
GCGTGCTCCACGAAGCTTTGCATTCACATTATACGCAAAAATCCTTGTCATTGTCC
CCAGGTAAGGGCGGAAGCGACTCATACCAAGAAGAAGTCATTAAACTTTGTGGACG
GGAGCTGGTTAGGGCACAGATTGCTATTTGTGGTAAGTCTACGGGAGGAGAAGGCT
CTGGAGGCGAAGGAGAAGGGGGCGGAAGACAGCTTTACTCTGCTCTGGCTAACAAG
TGTTGTACGTTGGGTGTACCAAGCAATCCCTTGCGCAATTCTGC |
| 462 | GATAAACCCACACTTGCCCACCTTGCCCTGCGCCGGAAGCCGCCGGAGGACCTAG
TGTTTTCCTCTTTCCCCCTAAGCCCAAAGACACGTTGATGATCTCTCGGACACCGG
AAGTAACTTGTGTCGTTGTGGATGTGTCACATGAGGATCCCGAGGTGAAATTTAAT
TGGTACGTTGACGGCGTGGAGGTGCATAACGCAAAGACTAAACCACGCGAGGAGCA
GTATAATTCTACATACCGGGTTGTCTCAGTTCTCACAGTTCTTCATCAGGATTGGT
TGAATGGAAAGGAGTACAAATGCAAAGTGTCCAACAAAGCGCTTGCTGCGCCGATT
GAAAAGACGATTTCAAAGGCAAAAGGGCAGCCCCGCGAACCCCAAGTATATACTTT
GCCTCCCTCACGCGATGAACTGACTAAGAACCAGGTGAGCCTGACTTGTTTGGTTA
AGGGTTTTTATCCAAGTGACATTGCTGTTGAATGGGAGTCCAATGGCCAGCCTGAG
AATAACTACAAAACGACACCTCCTGTACTTGACAGCGACGGCTCCTTTTTTCTTTA
TTCAAAACTCACAGTGGACAAATCCAGGTGGCAGCAGGGTAACGTCTTTTCTTGCA
GCGTGCTCCACGAAGCTTTGCATTCACATTATACGCAAAAATCCTTGTCATTGTCC
CCAGGTAAGGGCGGAAGCGACTCATACCAAGAAGAAGTCATTAAACTTTGTGGACG
GGAGCTGGTTAGGGCACAGATTGCTATTTGTGGTAAGTCTACGGGAGGAGAAGGCT
CTGGAGGCGAAGGAGAAGGGGGCGGAAGACAGCTTTACTCTGCTCTGGCTAACAAG
TGTTGTAAAGTTGGGTGTACCAAGCAATCCCTTGCGCAATTCTGC |
| 463 | GATAAACCCACACTTGCCCACCTTGCCCTGCGCCGGAAGCCGCCGGAGGACCTAG
TGTTTTCCTCTTTCCCCCTAAGCCCAAAGACACGTTGATGATCTCTCGGACACCGG
AAGTAACTTGTGTCGTTGTGGATGTGTCACATGAGGATCCCGAGGTGAAATTTAAT
TGGTACGTTGACGGCGTGGAGGTGCATAACGCAAAGACTAAACCACGCGAGGAGCA
GTATAATTCTACATACCGGGTTGTCTCAGTTCTCACAGTTCTTCATCAGGATTGGT
TGAATGGAAAGGAGTACAAATGCAAAGTGTCCAACAAAGCGCTTGCTGCGCCGATT
GAAAAGACGATTTCAAAGGCAAAAGGGCAGCCCCGCGAACCCCAAGTATATACTTT
GCCTCCCTCACGCGATGAACTGACTAAGAACCAGGTGAGCCTGACTTGTTTGGTTA
AGGGTTTTTATCCAAGTGACATTGCTGTTGAATGGGAGTCCAATGGCCAGCCTGAG
AATAACTACAAAACGACACCTCCTGTACTTGACAGCGACGGCTCCTTTTTTCTTTA
TTCAAAACTCACAGTGGACAAATCCAGGTGGCAGCAGGGTAACGTCTTTTCTTGCA
GCGTGCTCCACGAAGCTTTGCATTCACATTATACGCAAAAATCCTTGTCATTGTCC
CCAGGTAAGGGCGGAAGCGACTCATACCAAGAAGAAGTCATTAAACTTTGTGGACG
GGAGCTGGTTAGGGCACAGATTGCTATTTGTGGTAAGTCTACGGGAGGAGAAGGCT
CTGGAGGCGAAGGATCTGGGGGCGGAAGACAGCTTTACTCTGCTCTGGCTAACAAG
TGTTGTACGTTGGGTGTACCAAGCAATCCCTTGCGCAATTCTGC |
| 464 | GATAAACCCACACTTGCCCACCTTGCCCTGCGCCGGAAGCCGCCGGAGGACCTAG
TGTTTTCCTCTTTCCCCCTAAGCCCAAAGACACGTTGATGATCTCTCGGACACCGG
AAGTAACTTGTGTCGTTGTGGATGTGTCACATGAGGATCCCGAGGTGAAATTTAAT
TGGTACGTTGACGGCGTGGAGGTGCATAACGCAAAGACTAAACCACGCGAGGAGCA
GTATAATTCTACATACCGGGTTGTCTCAGTTCTCACAGTTCTTCATCAGGATTGGT
TGAATGGAAAGGAGTACAAATGCAAAGTGTCCAACAAAGCGCTTGCTGCGCCGATT
GAAAAGACGATTTCAAAGGCAAAAGGGCAGCCCCGCGAACCCCAAGTATATACTTT
GCCTCCCTCACGCGATGAACTGACTAAGAACCAGGTGAGCCTGACTTGTTTGGTTA
AGGGTTTTTATCCAAGTGACATTGCTGTTGAATGGGAGTCCAATGGCCAGCCTGAG
AATAACTACAAAACGACACCTCCTGTACTTGACAGCGACGGCTCCTTTTTTCTTTA
TTCAAAACTCACAGTGGACAAATCCAGGTGGCAGCAGGGTAACGTCTTTTCTTGCA
GCGTGCTCCACGAAGCTTTGCATTCACATTATACGCAAAAATCCTTGTCATTGTCC
CCAGGTAAGGGCGGAAGCGACTCATACCAAGAAGAAGTCATTAAACTTTGTGGACG
GGAGCTGGTTAGGGCACAGATTGCTATTTGTGGTAAGTCTACGGGAGGAGAAGGCT |

TABLE 9-continued

Nucleotide Sequences Encoding Fusion Proteins and Peptide Components

| SEQ ID NO: | Sequence |
|---|---|
|  | CTGGAGGCGAAGGATCTGGGGGCGGAAGACAGCTTTACTCTGCTCTGGCTAACAAG<br>TGTTGTAAAGTTGGGTGTACCAAGCAATCCCTTGCGCAATTCTGC |
| 465 | GATAAAACACACACGTGTCCCCCCTGCCCGGCTCCAGAGGCGGCTGGTGGTCCCAG<br>CGTATTCTTGTTTCCTCCCAAACCTAAGGATACGCTCATGATATCCCGCACCCCAG<br>AAGTTACGTGTGTAGTCGTCGACGTCAGTCACGAAGATCCAGAGGTCAAATTTAAC<br>TGGTATGTCGACGGAGTAGAGGTCCACAATGCGAAAACCAAGCCCAGAGAAGAGCA<br>GTACAACTCCACGTATCGCGTCGTCTCCGTCCTCACCGTACTCCATCAAGATTGGC<br>TGAATGGGAAAGAGTATAAATGCAAAGTATCTAACAAGGCTCTGCCAGCTCCGATA<br>GAAAAGACTATATCAAAGGCCAAGGGGCAGCCAAGGGAGCCTCAAGTCTATACTTT<br>GCCCCCATCTCGGGATGAGCTTACGAAAAACCAGGTCAGCCTTACCTGTCTTGTTA<br>AAGGTTTTTATCCGAGTGACATCGCAGTGGAATGGGAATCTAATGGTCAACCTGAA<br>AACAATTACAAAACCACACCGCCAGTATTGGACAGCGATGGTAGTTTTTTTCTTTA<br>CTCAAAACTGACTGTAGATAAAAGCAGATGGCAGCAGGGCAATGTCTTTTCATGTA<br>GCGTTATGCATGAGGCTCTTCACAACCACTATACCCAAAAGTCATTGTCTCTTAGT<br>CCCGGAAAGGGCGGAAGTGATTCTTGGAAGGAGGAGGTAATCAAGTTGTGCGGGCG<br>AGAGTTGGTACGGGCACAGATCGCGATATGCGGAAATCCACAGGTGGGGGCGAAG<br>GAGGAGGTGAGGGTGGAGGTGAAGGACGACAGTTGTATTCCGCCTTGGCAAACAAG<br>TGTTGCCATGTGGGTTGCACAAAACGCAGTCTTGCCCGCTTCTGT |
| 466 | GATAAGACACATACATGCCCTCCCTGTCCGGCTCCAGAGGCAGCCGGGGGTCCATC<br>AGTCTTCCTTTTTCCGCCTAAACCTAAGGATACACTGATGATCTCTCGAACACCGG<br>AGGTCACTTGTGTTGTCGTTGACGTATCACATGAGGATCCCGAAGTAAAGTTCAAC<br>TGGTATGTCGATGGTGTGGAGGTTCATAATGCTAAAACTAAACCACGGGAGGAGCA<br>ATATAATTCCACATATAGGGTCGTGAGCGTGTTGACGGTGCTTCATCAAGACTGGC<br>TTAATGGGAAGGAATATAAATGCAAAGTGTCAAATAAAGCACTTCCTGCGCCAATC<br>GAGAAAACAATTAGTAAGGCAAAGGGGCAGCCGCGAGAACCTCAGGTGTACACCTT<br>GCCGCCTTCTAGAGACGAGCTCACAAAGAACCAAGTTTCCCTGACTTGCCTCGTTA<br>AGGGGTTTTATCCGTCCGATATAGCCGTGGAGTGGGAGTCAAACGGCCAACCGGAA<br>AATAATTACAAAACGACACCCCCAGTATTGGATAGTGACGGCTCTTTTTTCCTTTA<br>TTCTAAGCTGACTGTGGACAAAAGCCGCTGGCAGCAGGGCAATGTCTTTTCATGCA<br>GCGTAATGCATGAAGCCCTGCACAACCACTACACGCAAAAATCCCTTTCCTTGTCA<br>CCCGGCAAGGGCGGCTCTGACTCCTGGAAAGAGGAAGTTATAAAACTCTGTGGCCG<br>AGAACTTGTTCGAGCTCAAATCGCGATTTGTGGTAAGTCAACGGGTGGGGGCGAAG<br>GTGGAGGCGAGGGTGGGGGAGAAGGAGGAGGCCAGTTGTACTCAGCTCTTGCAAAT<br>AAGTGTTGCCACGTTGGTTGTACGAAGCGGAGCCTTGCTCGCTTCTGC |
| 467 | GACAAAACACATACTTGTCCGCCTTGCCCGGCACCCGAAGCGGCCGGCGGACCCAG<br>TGTCTTTCTCTTCCCACCCAAACCGAAAGACACTCTGATGATTTCCAGGACGCCTG<br>AAGTGACCTGCGTTGTAGTTGATGTATCACACGAGGATCCCGAGGTCAAGTTCAAT<br>TGGTATGTAGATGGGGTGGAGGTCCATAATGCAAAGACGAAGCCACGGGAGGAACA<br>GTACAACTCTACGTACAGAGTTGTCAGTGTTTTGACCGTCCTTCATCAGGATTGGC<br>TGAACGGTAAAGAATATAAATGCAAGGTTAGCAATAAAGCTTTGCCCGCCCCTATA<br>GAGAAAACGATCAGTAAGGCGAAGGGGCAGCCTAGGGAACCCCAGGTATATACCTT<br>GCCGCCAAGTCGAGATGAGCTGACGAAGAACCAAGTGAGTCTGACATGCCTCGTGA<br>AGGGCTTCTATCCGAGCGATATCGCTGTCGAATGGGAGAGCAATGGGCAGCCTGAG<br>AATAACTATAAAACAACGCCACCCGTCCTCGACTCCGATGGCTCATTCTTCCTGTA<br>CAGTAAACTTACAGTAGATAAGAGTAGATGGCAGCAGGGTAACGTCTTTAGTTGCT<br>CCGTGATGCACGAGGCATTGCACAATCATTACACTCAAAAATCTCTGTCCCTGAGT<br>CCGGGCAAAGGCGGTTCAGATAGCTGGATGGAGGAGGTCATAAAGCTTTGTGGACG<br>AGAACTCGTTCGCGCCCAGATAGCTATTTGTGGGAAATCAACCGGGGGTGGAGAAG<br>GTGGCGGAGAAGGGGAGGCGAAGGGCGCCAACTGTATTCTGCATTGGCTAATAAG<br>TGCTGTCACGTAGGATGTACAAAAAGGTCTCTGGCGAGATTCTGC |
| 468 | GACAAGACGCACACTTGTCCACCTTGCCCTGCGCCGGAAGCTGCTGGAGGCCCCAG<br>TGTCTTTTTGTTCCCGCCCAAACCGAAGGACACTTTGATGATAAGTCGCACGCCCG<br>AGGTTACCTGTGTGGTTGTCGATGTCTCACACGAAGATCCGGAGGTGAAGTTTAAT<br>TGGTATGTAGATGGCGTGGAGGTTCATAACGCCAAAACGAAACCCAGAGAAGAACA<br>ATATAACAGTACATATCGAGTAGTATCCGTTCTCACTGTCCTGCATCAAGACTGGT<br>TGAACGGGAAGGAATATAAGTGCAAGGTGAGCAATAAAGCACTCCCGGCCCCAATC<br>GAAAAGACCATCAGCAAAGCGAAGGGGCAACCTCGAGAACCCCAGGTATATACGCT<br>CCCCCCTAGTCGGGATGAACTTACTAAAAATCAGGTTAGCCTCACTTGCCTTGTTA<br>AAGGGTTCTATCCCAGTGATATTGCCGTCGAATGGGAATCAAACGGGCAGCCGGAA<br>AATAACTACAAGACAACCCCTCCTGTGCTCGATAGCGATGGCTCTTTTTTCCTCTA<br>CAGCAAACTTACCGTTGATAAGAGCCGGTGGCAACAAGGTAATGTTTTCTCCTGCT<br>CCGTTATGCATGAAGCACTCCATAACCATTATACCCAAAAAGCCTGTCACTTAGT<br>CCGGGTAAAGGAGGTAGTGATTCTTGGCAGGAGGAGGTAATCAAACTTTGTGGGAG<br>GGAGCTGGTACGAGCTCAGATTGCTATATGTGGAAAAAGCACGGGCGGAGGAGAAG<br>GAGGTGGCGAAGGCGGGGGTGAAGGTCGGCAACTCTACTCCGCTCTCGCTAATAAG<br>TGCTGCCACGTCGGGTGTACGAAGCGCTCCCTGGCGCGATTCTGC |
| 469 | GATAAAACGCACACGTGTCCGCCCTGCCCAGCGCCTGAAGCCGCAGGCGGGCCGTC<br>CGTCTTCCTCTTTCCTCCAAAACCCAAAGACACACTTATGATCAGTAGGACCCCAG<br>AGGTAACCTGCGTCGTGGTCGACGTTTCCCATGAAGACCCAGAGGTCAAGTTCAAC |

TABLE 9-continued

Nucleotide Sequences Encoding Fusion Proteins and Peptide Components

| SEQ ID NO: | Sequence |
|---|---|
| | TGGTACGTCGACGGTGTCGAAGTACATAATGCTAAAACGAAGCCTCGGGAAGAGCA
GTACAACTCTACCTACCGCGTCGTTTCCGTACTCACCGTACTTCACCAGGACTGGC
TTAACGGTAAAGAGTATAAATGCAAAGTATCTAATAAGGCTCTCGCCGCGCCGATT
GAGAAGACAATTTCAAAGGCCAAGGGGCAGCCGCGGGAGCCCCAAGTGTATACCTT
GCCCCCGTCCCGAGATGAGCTGACTAAAAACCAAGTAAGCTTGACTTGCTTGGTCA
AAGGCTTCTACCCTTCCGATATAGCTGTCGAATGGGAGTCAAATGGCCAACCAGAG
AACAATTATAAAACTACACCCCCGGTCTTGGATTCTGATGGCTCATTTTTTCTCTA
TTCTAAACTGACCGTGGATAAGTCTCGCTGGCAGCAAGGTAACGTGTTCAGTTGCT
CTGTTCTTCACGAAGCACTGCACAGTCATTACACTCAGAAGAGTCTTAGCCTGAGC
CCTGGTAAAGGGGGTTCTGATTCCTGGCAGGAGGAAGTAATAAAACTCTGTGGCCG
GGAGTTGGTACGGGCGCAGATTGCGATATGCGGTAAGAGCACCGGCGGAGGCGAAG
GCGGTGGGGAAGGAGGAGGAGAAGGGAGACAACTCTATTCCGCATTGGCAAATAAG
TGCTGCCACGTCGGGTGTACCAAACGATCCCTTGCACGGTTCTGT |
| 470 | GATAAGACCCATACGTGCCCCCCTTGCCCTGCGCCTGAGGCAGCGGGTGGCCCATC
AGTCTTTTTGTTCCCGCCCAAGCCAAAGGACACCCTCATGATTAGTAGAACACCGG
AGGTTACGTGCGTCGTAGTGGATGTCAGCCACGAGGATCCCGAGGTTAAGTTTAAC
TGGTACGTTGATGGGGTTGAGGTCCATAATGCGAAGACTAAGCCGAGAGAGGAACA
GTACAATTCCACGTATAGAGTTGTCTCTGTACTGACTGTGCTGCATCAAGATTGGC
TTAACGGTAAGGAGTACAAGTGCAAAGTCTCTAATAAGGCTCTTCCTGCACCCATT
GAGAAAACTATAAGCAAAGCAAAAGGTCAACCTCGCGAACCTCAGGTGTACACACT
GCCACCCTCTAGGGACGAGCTTACCAAAAATCAAGTATCTCTTACCTGCCTTGTGA
AAGGGTTTTATCCCTCAGATATTGCGGTTGAGTGGGAGTCTAACGGACAACCTGAG
AACAACTATAAGACTACTCCCCCGGTGCTTGATTCAGACGGGAGTTTTTTTTGTA
TAGCAAACTTACCGTCGACAAAAGCCGGTGGCAACAGGGCAATGTATTCAGTTGTT
CTGTAATGCATGAAGCTTTGCATAATCATTACACCCAAAAGAGTCTTTCCCTGTCT
CCTGGAAAAGGGGGTCAGACTCCTGGATGGAGGAGGTGATCAAACTGTGTGGGAG
AGAGCTCGTCCGGGCTCAGATAGCTATATGCGGCAAGTCTACGGGTGGGGAGAGG
GCGGAGGAGAGGCGGTGGAGAAGGAGGCGGCCAACTCTACAGCGCTCTGGCCAAT
AAATGTTGTCATGTCGGGTGTACTAAGCGCTCACTGGCACGCTTTTGC |
| 471 | GACAAGACGCATACATGCCCGCCATGCCCGGCCCCCGAAGCTGCTGGGGGACCATC
CGTATTCCTCTTCCCTCCCAAACCAAAAGACACGTTGATGATAAGTAGAACACCAG
AGGTAACGTGCGTGGTTGTCGATGTTTCCCACGAAGATCCGGAGGTAAAATTCAAT
TGGTATGTAGATGGGGTGGAAGTGCACAATGCCAAAACAAAGCCGCGAGAAGAACA
ATACAATAGTACTTACCGGGTTGTGAGCGTGCTCACGGTGTTGCACCAAGACTGGC
TCAACGGCAAGGAATACAAGTGCAAAGTATCTAATAAAGCTCTGCCTGCGCCGATA
GAGAAGACCCATCAGTAAGGCCAAAGGGCAGCCCCGAGAGCCGCAAGTTTACACTCT
TCCTCCGAGCAGAGATGAATTGACCAAGAACCAAGTAAGTTTGACGTGCCTGGTGA
AGGGCTTCTACCCCTCAGACATTGCGGTGGAGTGGGAAAGTAATGGTCAACCGGAA
AACAACTACAAGACCACGCCGCCCGTCCTCGACTCCGATGGGTCTTTCTTTCTTTA
TTCAAAGTTGACAGTAGATAAGTCAAGGTGGCAGCAAGGTAACGTGTTTAGTTGTA
GTGTAATGCACGAGGCCCTGCATAATCATTATACCCAAAAGAGTTTGAGCCTCTCA
CCAGGAAAAGGCGGATCAGACAGCTGGCAGGAGGAGGTAATTAAATTGTGTGGACG
GGAGTTGGTCAGGGCGCAAATAGCCATCTGCGGTAAGAGCACGGGTGGAGGAGAGG
GTGGAGGGGAAGGTGGGGAGAAGGCGGCGGGCAGCTCTATTCTGCACTCGCCAAC
AAGTGTTGTCACGTCGGATGCACAAAGAGATCTCTTGCTCGATTCTGC |
| 472 | GACAAAACACACACCTGTCCGCCTTGCCCGGCTCCTGAAGCCGCGGGTGGCCCTAG
TGTGTTTTTGTTTCCGCCGAAACCTAAGGATACCCTCATGATAAGCCGGACGCCCG
AGGTTACCTGTCGTGGTCGATGTTAGTCATGAGGATCCAGAAGTCAAGTTTAAT
TGGTACGTCGACGGCGTTGAAGTCCACAATGCAAAACTAAACCGCGAGAAGAACA
GTACAACTCCACCTACAGAGTTGTCTCAGTTTTGACAGTTCTCCATCAGGATTGGC
TCAATGGAAAGGAATATAAGTGCAAGGTCAGCAATAAAGCGCTTGCCGCCCCTATA
GAGAAGACCATTAGCAAGGCGAAAGGACAGCCCCGCGAGCCCCAGGTCTATACGCT
GCCTCCTAGCAGAGATGAGCTCACGAAAAATCAGGTCAGCTTGACATGCTTGGTGA
AGGGCTTCTACCCCAGTGACATCGCAGTTGAATGGGAGAGCAACGGCCAACCTGAG
AACAACTACAAAACAACGCCCCCGGTTCTTGACAGCGATGGGTCCTTCTTTCTTTA
CTCTAAGCTTACAGTTGATAAAAGCAGGTGGCAGCAGGGAATGTGTTCTCATGTT
CCGTACTGCATGAGGCTCTGCATTCTCACTACACCCAAAAAGCCTTAGCCTGAGC
CCCGGTAAGGAGGTAGTGACTCATGGCAAGAGGGAAGTGATTAAGCTCTGCGGCCG
GGAGTTGGTGAGAGCCCAAATCGCCATTTGCGGTAAAAGTACCGGAGGGGCGAGG
GAGGAGGCGAAGGTGGAGGTGAAGGAGGTGGACAGTTGTACTCAGCTCTTGCAAAT
AAATGTTGTCATGTTGGTTGCACGAAAAGATCTCTTGCGAGGTTCTGT |
| 473 | GATAAGACGCATACTTGTCCACCGTGCCCCGCACCGGAAGCGGCTGGTGGTCCATC
AGTTTTTCTGTTCCCACCGAAACCTAAGGACACGTTGATGATATCACGGACACCAG
AGGTTACGTGCGTAGTGGTGGATGTGAGCCACGAGGATCCAGAAGTTAAATTTAAT
TGGTACGTAGATGGGAGTGGAGGTTCATAATGCGAAGACAAAGCCTCGCGAGGAACA
GTATAATTCCACCTATCGCGTCGTATCTGTGCTTACGGTACTTCACCAAGACTGGT
TGAACGGTAAGGAATATAAATGCAAGGTTTCCAATAAAGCACTTCCTGCGCCAATT
GAGAAGACAATATCCAAAGCTAAGGTCAACCCAGGGAACCGCAAGTCTACACTCT
CCCCCCGTCTCGCGATGAATTGACGAAGAACCAGGTTAGTCTCACCTGCCTGGTCA
AGGGGTTTTACCCCCTCTGACATAGCTGTAGAATGGGAGTCTAATGGACAGCCAGAG |

TABLE 9-continued

Nucleotide Sequences Encoding Fusion Proteins and Peptide Components

| SEQ ID NO: | Sequence |
|---|---|
|  | AACAATTACAAAACGACCCCCCCGGTCCTCGATTCTGATGGGAGTTTTTTCTTTA<br>TTCAAAATTGACTGTCGATAAGTCAAGATGGCAACAGGGTAACGTATTTTCTTGCA<br>GTGTTATGCATGAAGCATTGCACAACCACTATACACAAAAATCATTGAGTTTGAGT<br>CCCGGTAAAGGGGGAAGCGACTCATGGATGGAAGAAGTAATCAAGCTGTGCGGGCG<br>AGAGCTTGTGCGAGCTCAGATAGCAATCTGTGGTAAGTCTACAGGTGGAGAGGGTG<br>GCGGTGAAGAAGGCGGGGGAGAGGGAGGCCAGCTTTATTCTGCCCTGGCTAACAAG<br>TGCTGTCACGTTGGATGCACGAAGCGCTCCCTGGCCCGATTCTGC |
| 474 | GATAAGACGCATACTTGTCCCCCATGTCCCGCTCCGGAAGCCGCTGGCGGCCCCTC<br>CGTTTTTCTGTTCCCGCCGAAACCGAAAGACACCCTGATGATATCACGCACTCCCG<br>AGGTCACTTGCGTGGTAGTCGATGTTAGTCATGAAGATCCTGAGGTCAAATTCAAT<br>TGGTATGTAGATGGCGTTGAGGTACACAACGCGAAGACAAAACCCCGAGAAGAACA<br>GTATAACTCAACCTACCGCGTAGTTTCAGTTCTTACCGTACTGCACCAAGACTGGT<br>TGAACGGTAAAGAGTACAAATGTAAAGTCAGCAATAAAGCTTTGCCAGCACCTATC<br>GAAAAAACCATCAGTAAGGCCAAGGGTCAACCCAGGGAGCCGCAAGTGTACACTCT<br>TCCCCCTAGCAGGGATGAATTGACCAAGAATCAGGTCTCTTTGACGTGCCTCGTTA<br>AGGGTTTCTATCCCAGCGATATAGCCGTAGAATGGGAGTCTAACGGTCAGCCAGAA<br>AATAACTATAAGACAACCCCGCCTGTTTTGGATTCCGACGGCTCTTTTTTTCTCTA<br>CTCTAAGTTGACCGTTGATAAGAGCAGATGGCAGCAGGGAAACGTATTTTCTTGTT<br>CCGTGATGCACGAAGCCCTGCACAATCACTATACGCAAAAGTCTCTGAGCTTGAGT<br>CCGGGTAAAGGCGGTTCTGACTCCTGGCAGGAGGAAGTCATAAAACTCTGCGGAAG<br>AGAGCTCGTAAGGGCGCAAATCGCTATTTGTGGTAAGAGCACCGGTGGGGAAGGAG<br>GCGGTGAAGAGGGTGGCGGCGAGGGTGGGCAATTGTATTCCGCGCTTGCCAATAAA<br>TGTTGTCACGTAGGCTGCACAAAGCGAAGTCTCGCTAGGTTCTGC |
| 475 | GACAAGACCCACACATGTCCCCGTGTCCGGCACCAGAAGCAGCGGGGGGACCGTC<br>AGTATTCTTGTTTCCACCGAAGCCCAAAGACACATTGATGATTTCACGAACTCCTG<br>AAGTTACCTGTGTGGTTGTAGATGTATCACACGAAGACCCAGAAGTCAAATTCAAT<br>TGGTATGTCGACGGGGTTGAAGTTCACAATGCGAAGACGAAGCCCCGGGAGGAACA<br>GTACAACAGCACGTACAGGGTTGTGAGCGTTCTTACTGTATTGCACCAGGATTGGC<br>TCAACGGCAAGGAGTATAAATGTAAAGTTTCTAATAAGGCTCTTCCTGCCCCAATT<br>GAAAAAGACGATATCTAAAGCGAAGGGCCAACCACGGGAACCTCAGGTGTACACACT<br>TCCGCCTAGCAGGGATGAGTTGACCAAGAATCAAGTCTCTTTGACGTGCCTGGTCA<br>AGGGGTTTTACCCATCAGATATCGCCGTCGAATGGGAGTCAAACGGACAACCCGAA<br>AATAACTATAAAACTACTCCACCAGTTCTGGATAGCGACGGCTCATTTTTTCTGTA<br>TTCAAAGCTCACTGTAGACAAGTCTAGGTGGCAGCAGGGTAATGTCTTCTCCTGCT<br>CAGTAATGCATGAGGCTCTTCACAACCACTATACTCAAAAGAGCCTTTCCCTGTCA<br>CCTGGCGGTGGAAGCGACTCATGGATGGAGGAGGTAATAAAGCTCTGCGGAAGAGA<br>ACTGGTACGCGCACAAATCGCAATTTGTGGTAAGAGTACTGGCGGGGAAGGAGGTG<br>GGGAAGAAGGGGGCGGTGAGGGCGGACAGCTCTATTCTGCACTTGCAAACAAATGT<br>TGCCACGTGGGATGTACTAAGCGAAGCCTTGCAAGATTCTGC |
| 476 | GATAAAACCCACACATGCCCTCCATGCCCTGCTCCAGAGGCCGCCGGTGGGCCATC<br>AGTTTTCTTGTTTCCGCCTAAACCAAAGGACACGCTTATGATCTCCAGGACCCCCG<br>AAGTTACGTGTGTGGTGGTTGATGTTAGTCACGAGGACCCGGAAGTCAAGTTCAAC<br>TGGTACGTTGATGGTGTAGAGGTGCACAATGCAAAGACGAAGCCACGCGAAGAACA<br>ATACAACAGCACATATCGAGTTGTGAGCGTACTCACGGTACTGCATCAGGACTGGC<br>TGAACGGTAAAGAATACAAATGTAAAGTCTCCAATAAGGCACTTCCTGCGCCGATA<br>GAAAAAACGATCAGTAAGGCCAAGGGCCAACCCCGAGAACCACAGGTATATACGCT<br>CCCACCGTCACGAGACGAGTTGACAAAAAATCAGGTCTCCCTGACTTGCCTCGTGA<br>AAGGTTTTTATCCCTCAGATATTGCTGTTGAGTGGGAAAGCAATGGGCAGCCAGAG<br>AATAATTATAAGACGACTCCTCCGGTTTTGGATTCCGACGGTAGTTTTTTCTTGTA<br>TAGTAAGCTTACTGTAGACAAGTCAAGATGGCAACAAGGTAATGTGTTCTCTTGCT<br>CAGTTATGCATGAAGCTCTTCATAACCATTACACGCAAAAGAGTCTCAGTCTGAGC<br>CCCGGTGGCGGTAGCGACAGTTGGCAGGAAGAGGTGATTAAGTTGTGCGGTCGCGA<br>GCTCGTTCGGGCCCAAATTGCAATCTGCGGAAAATCTACGGGCGGAGAGGGCGGGG<br>GTGAGGAGGGTGGGGGTGAAGGTGGGCAGCTCTATAGCGCCCTTGCGAATAAATGT<br>TGTCACGTCGGATGCACAAAGAGGTCCCTCGCCAGGTTCTGC |
| 477 | GATAAGACCCACACTTGCCCCCCTTGCCCTGCCCCCGAAGCGGCCGGAGGTCCTTC<br>AGTATTTTTGTTTCCACCGAAACCCAAAGATACTTTGATGATATCAAGAACTCCTG<br>AAGTCACCTGCGTGGTAGTTGACGTATCTCATGAGGATCCCGAGGTGAAGTTCAAT<br>TGGTACGTCGATGGCGTCGAGGTTCATAACGCTAAGACTAAGCCGAGGGAAGAGCA<br>ATATAATTCCACTTATAGGGTGGTGTCCGTCTTGACTGTTTTGCACCAGGATTGGT<br>TGAACGGGAAGAGTACAAATGTAAGGTGAGTAATAAAGCTTTGGCTGCTCCCATC<br>GAAAAGACAATAAGCAAGGCCAAGGGGCAACCTCGGGAGCCGCAGGTGTACACCCT<br>TCCTCCCAGTAGAGACGAACTGACAAAAAACCAGGTGTCCCTGACCTGCCTTGTGA<br>AGGGGTTTTACCCGAGCGACATAGCGGTTGAATGGGAGAGCAACGGGCAACCCGAG<br>AACAACTACAAAACTACACCGCCTGTCCTGGACTCCGATGGAAGCTTCTTCCTCTA<br>CTCCAAACTGACCGTGGACAAAAGCAGATGGCAACAAGGAAACGTATTCTCATGCT<br>CAGTAATGCACGAAGCATTGCACAATCACTACACCCAAAAGTCCCTCTCACTCTCC<br>CCTGGTAAGGGCGGATCAGACTCATGGCAAGAGGAGGTAATTAAGTTGTGCGGGAG<br>GGAGCTCGTCCGCGCGCAAATAGCCATTTGTGGCAAGTCCACTGGAGGAGGCGAGG |

TABLE 9-continued

Nucleotide Sequences Encoding Fusion Proteins and Peptide Components

| SEQ ID NO: | Sequence |
|---|---|
| | GTGGAGGAGAGGGTGGTGGGGAGGGCAGGCAACTCTACAGTGCGCTCGCCAATAAA<br>TGCTGCCATGTTGGGTGCACGAAGCGCAGTCTCGCACAATTCTGC |
| 478 | GATAAGACCCACACGTGTCCTCCATGTCCGGCACCGGAGGCTGCTGGCGGGCCTTC<br>TGTATTCCTCTTCCCACCCAAGCCAAAAGACACATTGATGATATCAAGGACGCCGG<br>AAGTCACCTGTGTTGTTGTGGACGTTTCCCATGAAGACCCAGAGGTAAAATTCAAT<br>TGGTATGTGGACGGCGTAGAGGTTCACAACGCCAAAACCAAACCCCGAGAGGAACA<br>GTATAATAGCACATATCGAGTAGTATCTGTTCTCACAGTGCTCCATCAAGACTGGC<br>TTAATGGTAAAGAGTATAAATGCAAAGTTTCCAATAAAGCCCTCGCTGCACCGATC<br>GAGAAGACAATCAGTAAAGCGAAGGGCCAGCCTCGGGAACCGCAGGTGTATACTCT<br>TCCACCCTCAAGAGACGAGCTCACTAAAAACCAAGTTTCATTGACATGCCTCGTCA<br>AAGGTTTCTACCCATCAGACATCGCGGTCGAATGGGAAAGTAATGGGCAGCCGGAA<br>AACAACTATAAAACGACGCCGCCCGTCTTGGATTCTGATGGTTCATTTTTTCTTTA<br>CTCTAAATTGACCGTCGATAAAAGTAGGTGGCAACAAGGAAATGTTTTTTCCTGCT<br>CCGTCCTGCATGAAGCGTTGCACAGTCACTATACCCAGAAGAGTCTTTCTTTGTCA<br>CCCGGAAAAGGCGGTTCAGATTCATGGCAGGAAGAAGTAATTAAACTCTGTGGCCG<br>CGAGCTTGTTAGGGCGCAGATAGCCATATGTGGTAAAAGCACCGGAGGAGGTGAAG<br>GCGGAGGCGAAGGAGGTGGGGAAGGAAGACAATTGTATTCTGCACTTGCAAATAAA<br>TGCTGTCATGTGGGGTGCACGAAACGCAGTCTTGCACAATTTTGT |
| 479 | GACAAAACCCATACCTGCCCCCCTTGCCCTGCACCAGAAGCGGCGGGAGGACCTAG<br>CGTTTTTCTTTTTCCTCCGAAACCGAAAGATACCCTCATGATATCAAGAACACCTG<br>AGGTTACTTGCGTTGTCGTGGACGTGAGTCACGAAGACCCCGAGGTGAAGTTCAAC<br>TGGTATGTAGATGGAGTGGAGGTCCATAATGCAAAAACGAAACCGAGAGAAGAACA<br>ATACAACTCTACATATCGAGTCGTGTCAGTACTCACGGTTTTGCATCAAGATTGGC<br>TGAACGGTAAGGAGTACAAGTGTAAGGTTAGCAACAAGGCTCTCGCGGCGCCGATA<br>GAAAAGACTATAAGTAAAGCAAAAGGCCAGCCCAGAGAACCTCAAGTTTACACTCT<br>GCCTCCCAGCAGAGATGAACTGACTAAAAATCAGGTTTCATTGACCTGTCTCGTCA<br>AGGGTTTTTATCCAAGCGACATAGCAGTTGAATGGGAAAGCAACGGTCAACCAGAA<br>AATAATTACAAAACCACTCCACCAGTCTTGGACTCTGACGGATCCTTCTTTCTCTA<br>TTCAAAATTGACGGTGGATAAATCTAGGTGGCAGCAAGGCAACGTCTTCTCTTGTA<br>GCGTTATGCATGAGGCGCTGCAACCACTACACACAAAAGTCTCTTAGTTTGAGC<br>CCGGGCGGCGGAAGCGACTCTTGGCAAGAGGAAGTGATAAAACTCTGTGGTCGAGA<br>ATTGGTACGCGCGCAGATCGCTATCTGCGGCAAGTCCACAGGGGGAGGGGAAGGTG<br>GCGGGGAAGGTGGTGGCGAGGGCAGGCAGTTGTATAGTGCACTTGCCAACAAGTGC<br>TGCCATGTGGGGTGCACCAAGCGCAGTTTGGCACGGTTCTGC |
| 480 | GATAAAACTCACACTTGTCCCCCGTGTCCGGCACCAGAAGCCGCAGGAGGGCCATC<br>TGTCTTTCTTTTTCCCCCAAAACCCAAGGATACACTGATGATCTCCCGCACTCCCG<br>AAGTTACTTGTGTCGTAGTAGACGTTTCTCACGAGGACCCAGAGGTGAAATTCAAT<br>TGGTATGTTGACGGAGTAGAGGTGCATAATGCCAAGACAAAGCCCCGAGAGGAACA<br>ATACAATTCAACCTACAGAGTAGTGTCCGTTCTTACGGTTCTCCATCAGGATTGGC<br>TCAACGGTAAGGAATATAAGTGCAAGGTAAGCAACAAAGCGCTGGCCGCACCCATT<br>GAGAAAACCATTTCAAAAGCTAAAGGCCAACCCCGCGAACCACAAGTTTATACTCT<br>CCCCCCAAGTCGCGATGAACTTACAAAAAATCAAGTCTCATTGACGTGCTTGGTCA<br>AAGGCTTCTACCCGAGCGATATCGCTGTTGAATGGGAGTCTAATGGACAACCGGAA<br>AATAACTATAAAACTACACCCCCAGTCCTCGATTCAGACGGCAGCTTCTTCCTGTA<br>TTCAAAACTGACGGTTGACAAATCACGCTGGCAACAGGGTAACGTTTTTTCCTGTA<br>GCGTTCTTCATGAAGCCTTGCACAGTCACTACACCCAGAAGTCCCTTAGCTTGTCA<br>CCTGGCGGGGGTTCAGACTCTTGGCAGGAGGAGGTAATCAAACTGTGCGGAAGAGA<br>ACTGGTGAGGGCTCAGATTGCAATTTGTGGGAAGAGCACGGGTGGCGGTGAAGGAG<br>GTGGCGAGGGCGGAGGAGAGGGGAGGCAACTCTACAGTGCGTTGGCTAATAAATGC<br>TGTCACGTCGGCTGTACTAAGAGAAGCCTCGCCAGATTTTGC |
| 481 | GACAAGACGCATACTTGCCCTCCGTGCCCTGCACCAGAAGCCGCTGGTGGCCCATC<br>TGTGTTTTTGTTCCCCCCTAAGCCAAAAGACACATTGATGATTTCACGAACTCCAG<br>AAGTGACTTGCGTAGTTGTTGACGTATCACACGAAGACCCCGAGGTTAAATTTAAT<br>TGGTATGTGGACGGGGTCGAGGTGCATAACGCCAAAACCAAACCCCGGGAGGAACA<br>ATATAACTCTACGTATCGGGTCGTATCTGTGTTGACCGTCCTTCACCAAGATTGGT<br>TGAACGGCAAGGAATATAAGTGTAAAGTGTCTAATAAAGCATTGGCTGCCCCGATA<br>GAAAAGACGATCTCTAAAGCCAAGGGCCAACCCAGAGAGCCTCAAGTATATACTCT<br>CCCACCGAGTCGAGATGAGCTCACTAAGAACCAGGTGTCACTCACGTGTCTGGTTA<br>AAGGATTTTACCCTAGTGATATAGCCGTCGAGTGGGAATCAAATGGGCAGCCGGAG<br>AATAACTATAAGACCACGCCTCCAGTTCTCGATTCCGATGGTAGCTTTTTCCTTTA<br>CTCTAAACTTACGGTCGACAAGTCCAGGTGGCAACAGGGCAATGTATTTTCTTGCT<br>CCGTCATGCACGAGGCTTTGCACAACCATTACACGCAAAAGTCACTGTCCCTGTCT<br>CCTGGAGGCGGTTCTGACAGTTGGCAGGAGGAGGTAATCAAATTGTGTGGGCGGGA<br>GTTGGTTAGGGCGCAAATTGCTATTTGCGGCAAAAGTACTGGGGGCGGTGAAGGCG<br>GAGGCGAGGGAGGGAGGAGAAGGTCGACAACTGTATTCTGCCTTGGCGAACAAATGC<br>TGTCACGTCGGCTGTACGAAACGGTCTTTGGCCCAGTTTTGT |
| 482 | GATAAGACACACACTTGTCCGCCATGCCCTGCGCCGGAAGCGGCGGGAGGACCGTC<br>CGTTTTCCTGTTCCCTCCCAAACCCAAAGACACGTTGATGATTAGTCGCACGCCAG<br>AAGTTACGTGCGTTGTCGTAGATGTATCCCACGAAGACCCCGAGGTGAAGTTCAAT |

TABLE 9-continued

Nucleotide Sequences Encoding Fusion Proteins and Peptide Components

| SEQ ID NO: | Sequence |
|---|---|
| | TGGTATGTAGATGGGGTGGAGGTCCATAACGCTAAGACCAAACCACGCGAGGAACA
ATATAATTCTACGTACCGCGTAGTGAGCGTTCTCACAGTTCTTCACCAGGATTGGC
TTAACGGCAAGGAGTATAAGTGTAAGGTGTCTAATAAGGCCTTGGCTGCCCCGATC
GAAAAAACGATAAGTAAAGCAAAGGGTCAACCTAGAGAACCCCAAGTGTACACTCT
CCCGCCATCACGGGATGAATTGACTAAGAACCAAGTGTCACTCACGTGTCTTGTAA
AGGGCTTCTACCCATCCGATATAGCCGTTGAGTGGGAATCCAATGGTCAGCCAGAG
AACAACTATAAGACAACTCCGCCCGTACTTGATAGTGACGGTTCCTTTTTCCTTTA
CAGTAAATTGACGGTAGATAAGTCTCGCTGGCAGCAAGGAAACGTCTTTTCTTGTT
CAGTGCTTCATGAGGCGCTTCACTCACACTATACTCAGAAGAGTTTGAGTTTGTCT
CCAGGTGGAGGCAGCGACTCATGGCAAGAGGAAGTAATCAAACTGTGTGGTCGCGA
ATTGGTACGAGCACAGATCGCGATCTGCGGGAAATCAACAGGTGGCGGCGAAGGCG
GCGGGGAAGGCGGCGGCGAAGGTAGGCAACTTTACTCAGCCCTTGCGAACAAATGT
TGCCACGTAGGCTGTACTAAGAGAAGTCTCGCCCAGTTTTGC |
| 483 | GACAAGACTCATACCTGCCCCCCTTGTCCAGCACCAGAAGCAGCTGGCGGGCCAAG
CGTGTTCCTGTTTCCACCTAAGCCCAAAGATACGTTGATGATCAGCCGCACCCCGG
AAGTAACCTGTGTAGTAGTAGATGTGTCCCACGAAGACCCCGAAGTAAAGTTTAAT
TGGTACGTCGATGGTGTCGAAGTACATAACGCTAAAACGAAGCCCCGAGAAGAGCA
GTACAACAGTACTTACAGAGTAGTTTCTGTTCTTACAGTGCTGCATCAGGATTGGC
TGAACGGGAAGGAGTATAAATGTAAAGTCTCAAACAAGGCACTTGCGGCACCAATA
GAGAAGACAATATCTAAGGCCAAAGGGCAGCCTAGAGAGCCACAAGTATATACGCT
GCCCCCCAGCAGGGACGAGCTGACAAAGAACCAAGTGTCACTGACCTGCCTTGTTA
AGGGCTTCTATCCGAGTGATATTGCTGTTGAATGGGAAAGTAACGGACAGCCGGAG
AACAACTATAAAACTACTCCACCCGTGTTGGATAGTGACGGTAGCTTTTTTCTGTA
CTCCAAGTTGACGGTAGACAAAAGTCGGTGGCAGCAGGGGAACGTATTTCTTGTT
CTGTCATGCACGAAGCTCTTCACAATCACTATACGCAGAAGTCCCTCTCTCTCT
CCTGGGAAGGGTGGTTCCGACAGCTGGCAGGAGGAGGTCATTAAACTGTGTGGTAG
AGAGCTGGTACGGGCTCAAATTGCAATTTGTGGTAAGAGTACTGGCGGTGGCGAGG
AAGGGGGTGGGGAGGAGGGCGGAGGTAGGCAGCTCTACTCTGCTCTCGCCAACAAG
TGTTGTCACGTCGGGTGTACTAAAAGATCACTTGCCCGCTTTTGT |
| 484 | GACAAAACACATACATGCCCGCCGTGTCCGGCGCCTGAAGCAGCAGGAGGCCCCAG
TGTATTCCTTTTCCCTCCAAAGCCAAAAGATACGTTGATGATATCTAGGACACCTG
AGGTTACCTGCGTCGTAGTGGACGTATCCCACGAAGACCCAGAAGTCAAGTTTAAC
TGGTATGTGGACGGAGTGGAGGTACACAATGCAAAGACAAAGCCGCGAGAGGAACA
ATATAATTCCACCTATAGAGTCGTGTCAGTCCTTACGGTCTTGCCACCAGGACTGGC
TCAATGGTAAGGAGTATAAGTGCAAAGTATCAAACAAAGCTCTCGCAGCGCCCATC
GAAAAGACCATCAGCAAAGCTAAGGGCCAGCCAAGAGAGCCTCAAGTGTACACGTT
GCCGCCTTCAAGGGACGAGCTCACTAAAAATCAGGTATCACTTACGTGTCTTGTCA
AAGGGTTTTATCCTTCCGACATCGCGGTTGAATGGGAGAGCAATGGACAGCCGGAG
AATAATTATAAAACGACGCCGCCGGTCCTTGACAGCGATGGTTCATTTTTCCTTTA
CTCAAAGCTGACGGTTGATAAGTCTAGGTGGCAGCAGGGGAACGTCTTTTCCTGTA
GTGTACTTCATGAGGCGCTCCATTCTCATTACACTCAGAAGTCACTGAGCCTTTCA
CCCGGCAAAGTGGATCAGACTCCTGGCAAGAAGAGGTAATCAAACTCTGTGGGAG
GGAACTCGTTCGAGCCCAGATTGCAATCTGTGGGAAAAGCACAGGCGGAGGGGAAG
AAGGGGGTGGCGAAGAAGGTGGGGCAGGCAGCTCTATTCAGCTCTTGCCAACAAA
TGCTGTCATGTAGGCTGCACAAAGCGATCACTGGCGAGATTCTGT |
| 485 | GATAAAACTCATACTTGCCCACCCTGCCCGGCTCCCGAGGCAGCAGGTGGACCCTC
AGTATTTTGTTCCCTCCGAAACCTAAAGATACACTTATGATTAGCCGGACCCCTG
AGGTAACGTGTGGTGGTTGACGTAAGTCATGAAGATCCAGAAGTAAAGTTTAAC
TGGTACGTAGACGGTGTGGAGGTACATAATGCGAAGACAAAACCACGAGAGGAACA
GTATAACTCTACCTACCGCGTAGTAAGCGTACTTACTGTGCTCCACCAAGACTGGC
TTAACGGGAAAGAGTATAAGTGTAAAGTCAGTAATAAAGCACTGGCCGCCCCGATC
GAAAAAACAATCAGCAAGGCCAAAGGACAACCAAGGGAGCCTCAGGTCTATACTCT
TCCCCCGAGTAGGGATGAGCTTACCAAGAACCAGGTGTCTCTGACATGCCTTGTCA
AGGGATTTTACCCGAGTGACATAGCCGTAGAATGGGAGTCAAACGGCCAACCTGAA
AACAACTATAAGACCACGCCTCCCGTACTCGACTCAGATGGAAGCTTTTTCCTCTA
TAGCAAGCTGACCGTCGACAAAAGTAGGTGGCAACAGGGAAACGTCTTTAGTTGTT
CCGTCATGCACGAAGCTTTGCATAACCATTACACCCAGAAGAGTCTTTCCCTTTCC
CCTGGCAAGGGGGCTCCGACTCCTGGCAAGAGGAAGTAATCAAACTGTGTGGGCG
CGAGCTTGTCCGCGCGCAAATAGCCATTTGCGGAAAAAGTACTGGAGGAGGAGAGG
AAGGCGGCGGCGAGGAAGGTGGGGCAGGCAGCTGTACAGTGCCTTGGCTAACAAG
TGCTGCCATGTCGGCTGTACGAAAAGGTCTCTTGCTCAATTCTGT |
| 486 | GATAAGACACATACCTGTCCACCCTGCCCAGCACCTGAAGCTGCAGGCGGCCCCAG
CGTATTCCTGTTTCCTCCGAAGCCGAAAGACACACTTATGATTTCCCGGACGCCTG
AGGTAACTTGCGTCGTAGTAGATGTGTCTCACGAAGACCCCGAGGTGAAATTCAAC
TGGTACGTTGATGGTGTGGAAGTTCATAATGCGAAAACTAAACCACGAGAGGAGCA
ATATAACTCAACTTATAGAGTTGTGAGCGTCTTGACGGTACTGCACCAGGACTGGC
TGAATGGCAAAGAGTACAAATGCAAAGTCTCAAATAAGGCGTTGCGGCTCCCATA
GAGAAAACTATCAGCAAAGCCAAGGGTCAACCTCGGGAGCCACAAGTGTATACTCT
TCCGCCTAGTCGCGACGAGCTCACAAAGAATCAGGTGAGTCTTACTTGTTTGGTTA
AGGGTTTCTACCCCAGTGACATTGCGGTCGAGTGGGAAAGTAACGGACAGCCTGAA |

TABLE 9-continued

Nucleotide Sequences Encoding Fusion Proteins and Peptide Components

| SEQ ID NO: | Sequence |
|---|---|
| | AACAACTATAAAACAACGCCTCCAGTACTCGATTCAGATGGTTCATTCTTTCTTTA<br>TTCCAAACTCACAGTCGACAAGAGTAGATGGCAACAAGGGAACGTGTTTAGCTGTA<br>GCGTACTCCATGAGGCACTCCACTCTCACTATACCCAAAAGTCTCTCAGCTTGTCA<br>CCCGGAAAAGGCGGTTCTGACAGTTGGCAAGAGGAAGTGATTAAATTGTGTGGGCG<br>GGAACTTGTGAGGGCTCAAATCGCGATTTGCGGCAAGTCCACTGGTGGCGGCGAGG<br>AAGGAGGAGGTGAAGAAGGAGGAGGTAGGCAACTGTATTCAGCGTTGGCGAATAAA<br>TGCTGCCATGTTGGATGTACTAAACGGAGCCTTGCTCAGTTCTGC |
| 487 | GATAAAACGCATACTTGCCCTCCTTGCCCGGCACCTGAAGCTGCCGGAGGTCCTTC<br>CGTGTTCCTGTTCCCACCTAAGCCAAAAGACACACTTATGATTTCTCGCACACCAG<br>AAGTAACGTGCGTCGTAGTTGACGTCTCCCATGAAGACCCGGAGGTAAAATTTAAT<br>TGGTACGTCGACGGGGTAGAAGTTCATAACGCAAAGACTAAACCACGAGAAGAGCA<br>ATACAACTCTACATACAGAGTAGTAAGCGTTCTCACCGTTCTTCATCAAGATTGGC<br>TCAACGGAAAGGAGTATAAGTGTAAGGTGTCCAATAAAGCGTTGGCCGCACCAATC<br>GAAAAGACCATAAGCAAAGCCAAAGGCCAACCCCGCGAACCGCAGGTGTACACACT<br>TCCCCCGTCCAGGGATGAATTGACAAAAAACCAAGTTTCCCTCACGTGTCTCGTCA<br>AGGGATTCTACCCGAGTGATATCGCAGTTGAATGGGAAAGCAATGGTCAGCCCGAG<br>AATAACTACAAGACTACTCCCCCTGTGTTGGACTCAGACGGCTCATTCTTCCTCTA<br>CAGTAAGTTGACTGTGGACAAAAGTCGGTGGCAGCAAGGCAATGTCTTCAGTTGTA<br>GTGTAATGCATGAAGCACTCCACAATCATTACACCCAAAAATCCCTGAGCCTGTCC<br>CCGGGCGGAGGTTCAGATTCATGGCAGGAGGAAGTTATAAAACTGTGCGGGCGCGA<br>GTTGGTGAGGGCGCAGATCGCAATCTGTGGAAAGAGTACGGGAGGTGGCGAAGAGG<br>GTGGTGGAGAAGAGGGAGGAGGTCGACAACTGTATTCCGCGCTCGCGAACAAGTGT<br>TGCCACGTTGGCTGCACCAAACGAAGCCTGGCTCGATTTTGC |
| 488 | GACAAGACACACACTTGTCCACCTTGCCCGGCTCCCGAGGCGGCAGGAGGACCAAG<br>CGTTTTTCTGTTCCCTCCCAAACCAAAGGATACGCTTATGATCTCTCGAACGCCGG<br>AAGTTACTTGCGTAGTAGTTGATGTCTCCCATGAAGATCCCGAAGTGAAGTTCAAC<br>TGGTATGTAGATGGTGTGGAAGTTCATAACGCGAAAACCAAACCACGCGAAGAACA<br>GTATAACAGTACTTATCGGGTTGTTTCAGTACTCACGGTGCTCCATCAAGACTGGC<br>TTAATGGAAAGGAGTATAAATGTAAGGTAAGTAACAAGGCATTGGCGGCTCCCATC<br>GAGAAGACAATCTCCAAAGCAAAAGGGCAACCACGGGAGCCTCAGGTGTATACGTT<br>GCCGCCCAGCAGAGATGAACTTACTAAGAATCAGGTGAGTCTCACTTGTCTCGTCA<br>AGGGCTTCTATCCCAGCGATATAGCCGTAGAATGGGAGAGTAACGGTCAGCCGGAG<br>AACAACTACAAAACAACCCCGCCTGTTTTGGACTCCGATGGGAGTTTTTTTCTCTA<br>CAGCAAACTCACGGTAGACAAAAGCAGGTGGCAGCAGGGCAATGTTTTCAGTTGCT<br>CTGTTCTCCACGAAGCCCTCCACTCCCACTATACTCAGAAGTCTCTGAGTCTCTCA<br>CCAGGGGGAGGTAGCGATAGCTGGCAGGAGGAAGTGATCAAGTTGTGCGGGCGCGA<br>ACTCGTGCGGGCACAAATTGCTATATGCGGTAAAAGTACGGGAGGTGGAGAGGAGG<br>GTGGAGGTGAAGAAGGCGGTGGTAGACAATTGTATAGTGCGCTCGCCAACAAGTGT<br>TGTCATGTCGGGTGTACGAAACGGTCCTTGGCGCGGTTTTGC |
| 489 | GACAAGACACATACTTGTCCACCATGTCCCGCCCCAGAAGCTGCGGGAGGACCATC<br>AGTTTTTTGTTCCCCCCGAAACCGAAGGATACCCTCATGATAAGTCGAACGCCCG<br>AAGTCACTTGCGTGGTGGTTGATGTTAGCCACGAGGACCCAGAAGTGAAGTTCAAC<br>TGGTACGTGGACGGGGTCGAAGTTCATAATGCGAAAACAAAGCCTCGCGAGGAACA<br>GTACAACTCTACATACAGGGTTGTGTCTGTTTTGACAGTCTTGCACCAAGATTGGC<br>TCAACGGGAAGGAATATAAGTGTAAGGTAAGCAATAAAGCACTGGCGGCCCCGATC<br>GAAAAAACGATATCCAAGGCCAAGGGCCAGCCCCGAGAGCCTCAGGTATATACTCT<br>GCCGCCAAGCCGGGATGAACTGACTAAAAACCAGGTCTCTTTGACTTGTCTTGTCA<br>AGGGATTTTACCCAAGTGACATTGCGGTAGAGTGGGAAAGCAACGGTCAACCAGAA<br>AACAATTACAAGACGACACCGCCGGTACTCGACTCAGATGGATCCTTTTTCCTGTA<br>TAGCAAGCTGACAGTGGACAAGTCCCGGTGGCAGCAAGGGAACGTATTTTCATGCA<br>GCGTGATGCATGAGGCTCTTCACAACCATTACACACAGAAAAGTCTGTCATTGAGC<br>CCTGGCGGCGGGAGCGATTCTTGGCAAGAAGAAGTTATAAAACTTTGCGGTCGAGA<br>GCTGGTTCGGGCACAAATTGCTATCTGCGGAAAATCTACAGGAGGAGGCGAGGAGG<br>GAGGGGGCGAAGAAGGCGGGGGGAGACAGTTGTACAGTGCGCTCGCTAACAAGTGT<br>TGCCACGTCGGTTGCACAAAGAGATCCCTGGCTCAATTCTGT |
| 490 | GATAAAACTCACACCTGTCCCCCGTGTCCCGCACCAGAAGCGGCCGGTGGTCCCTC<br>CGTTTTTCTCTTCCCTCCTAAACCTAAGGACACACTTATGATTAGCAGAACTCCAG<br>AAGTTACGTGCGTAGTCGTTGACGTTAGTCATGAAGATCCTGAGGTTAAGTTCAAC<br>TGGTACGTAGACGGAGTAGAGGTCCACAACGCCAAGACGAAACCCCGAGAAGAGCA<br>GTATAATTCTACCTATCGAGTTGTTTCAGTATTGACGGTGCTTCACCAAGATTGGC<br>TGAATGGCAAAGAGTATAAGTGCAAGGTAAGCAACAAAGCACTCGCGGCTCCTATC<br>GAGAAAACTATTTCCAAAGCTAAGGGCCAGCCTCGCGAACCACAAGTCTATACCCT<br>GCCACCGAGTCGGGACGAACTCACCAAGAACCAAGTGTCTCTTACTTGCCTCGTTA<br>AAGGTTTTTATCCCAGCGACATAGCCGTCGAATGGGAGTCCAATGGCCAACCTGAG<br>AACAACTATAAAACTACCCCTCCTGTACTTGATAGCGACGGAAGTTTTTTCCTCTA<br>TTCAAAACTCACAGTTGATAAGTCTCGATGGCAACAGGGCAACGTCTTCTCTTGCA<br>GTGTGTTGCATGAAGCTCTGCACTCTCATTACACAGAAGAGTTTGTCTCTCAGT<br>CCAGGTGGCGGCTCAGATAGCTGGCAGGAAGAAGTAATCAAGTTGTGCGGCAGGGA<br>ACTGGTAAGGGCACAGATAGCCATTTGTGGAAAATCTACGGGTGGCGGTGAGGAAG |

TABLE 9-continued

Nucleotide Sequences Encoding Fusion Proteins and Peptide Components

| SEQ ID NO: | Sequence |
|---|---|
| | GCGGCGGAGAAGAAGGGGGAGGTCGGCAGCTGTATAGTGCACTCGCAAACAAGTGC<br>TGCCATGTCGGGTGCACCAAGCGATCCCTTGCCCAGTTTTGC |
| 491 | GATAAGACGCACACATGCCCACCCTGTCCTGCGCCTGAAGCCGCGGGGGGACCCAG<br>CGTTTTTCTCTTCCCGCCGAAACCGAAAGACACACTTATGATCAGCCGGACTCCCG<br>AGGTTACCTGCGTGGTGGTAGATGTATCTCACGAGGATCCCGAGGTCAAATTCAAC<br>TGGTACGTTGATGGGGTTGAAGTTCATAATGCCAAAACGAAGCCAAGAGAAGAGCA<br>GTATAACTCCACATATAGAGTTGTTTCCGTCTTGACTGTTCTTCACCAAGATTGGC<br>TGAATGGGAAGGAGTACAAATGTAAAGTTAGCAACAAGGCACTCGCCGCTCCCATT<br>GAAAAAACTATAAGCAAAGCTAAGGGCCAACCGCGCGAACCACAGGTCTACACGTT<br>GCCGCCCTCTAGGGACGAACTCACGAAGAATCAGGTTTCCCTTACCTGCCTCGTTA<br>AAGGATTCTACCCCTCTGACATAGCGGTTGAATGGGAGAGCAACGGTCAGCCTGAG<br>AACAACTACAAAACGACGCCTCCGGTGTTGGATTCCGACGGTAGTTTTTTCCTCTA<br>TAGTAAGCTGACAGTGGATAAATCTCGGTGGCAGCAAGGGAATGTATTCTCCTGTT<br>CAGTCCTGCATGAAGCCCTCCACTCCCATTATACACAGAAATCTCTTTCTCTGAGT<br>CCCGGTAAAGGTGGGAGTGACTCTTGGCAGGAAGAGGTAATTAAGTTGTGTGGAAG<br>GGAGCTGGTAAGAGCACAGATTGCCATCTGTGGCAAATCCACGGGCGGCGAAGGTG<br>AGGGGGGTGAGGGGGAAGGGGGGTCCAGACAACTGTATTCTGCTCTGGCGAATAAG<br>TGTTGCCATGTAGGGTGCACTAAACGGTCCTTGGCGCAGTTCTGT |
| 492 | GATAAAACTCATACGTGCCCACCTTGCCCCGCACCGGAGGCTGCTGGAGGACCCTC<br>TGTCTTCCTGTTCCCGCCGAAGCCTAAAGACACATTGATGATCAGTCGAACACCGG<br>AAGTCACCTGTGTAGTGGTTGATGTGAGCCATGAGGACCCTGAAGTAAAATTTAAC<br>TGGTATGTTGATGGCGTAGAAGTACACAACGCGAAGACTAAACCAAGGGAAGAGCA<br>ATACAACTCTACCTATAGGGTCGTTAGCGTACTGACTGTGCTTCACCAAGACTGGC<br>TTAACGGGAAGGAGTACAAGTGCAAAGTGAGCAATAAGGCCCTCGCCGCGCCTATC<br>GAGAAAACCATTTCCAAAGCCAAGGGTCAACCAAGGGAGCCTCAGGTTTACACCCT<br>GCCCCCTTCAAGGGATGAGTTGACAAAAAACCAGGTAAGTCTGACGTGTCTCGTTA<br>AGGGATTCTACCCGTCAGATATCGCGGTAGAGTGGGAGCAACGGTCAGCCAGAA<br>AATAATTACAAAACAACACCTCCAGTTTTGGACTCTGATGGGAGTTTTTTCTTTA<br>TTCTAAGTTGACAGTGGATAAGTCACGCTGGCAACAGGGGAACGTATTTAGCTGCT<br>CAGTACTTCATGAAGCGTTGCATTCTCACTACACACAGAAGAGCCTCTCCTTGAGT<br>CCCGGAGGTGGCTCTGATTCTTGGCAGGAGGAGGTAATAAAACTTTGTGGTAGAGA<br>ACTGGTTCGCGCTCAGATAGCTATTTGTGGAAAATCCACTGGCGGTGAAGGTGAAG<br>GTGGAGAAGGAGAGGGCGGAAGCCGGCAGTTGTACTCTGCCCTGGCTAATAAGTGC<br>TGTCACGTGGGCTGCACTAAGCGGAGCTTGGCAAGATTTTGC |
| 493 | GATAAAACTCATACCTGTCCACCTTGTCCTGCGCCTGAGGCAGCTGGAGGGCCTAG<br>CGTGTTCCTGTTCCCCCCCAAACCCAAAGACACGCTCATGATTAGCCGAACCCCTG<br>AAGTGACCTGCGTTGTTGTGGACGTAAGCCACGAAGACCCCGAAGTTAAGTTTAAT<br>TGGTACGTCGACGGTGTTGAGGTTCATAACGCGAAGACTAAGCCGAGAGAGGAGCA<br>ATATAACAGCACCTACCGCGTAGTCTCAGTTCTTACCGTGCTCCACCAGGACTGGC<br>TTAACGGGAAGGAATACAAATGCAAAGTTTCCAACAAAGCCTTGGCAGCCCCAATA<br>GAGAAGACAATATCTAAGGCGAAAGGCCAACCGCGGGAACCGCAAGTTTATACCCT<br>CCCGAGCTGACGGATGAGCTGACAAAAAATCAGGTTTCCCTCACTTGTCTGGTCA<br>AGGGATTTTATCCTTCAGACATAGCCGTTGAATGGGAGAGTAATGGGCAGCCGGAG<br>AATAATTACAAGACCACCCCCCGGTGTTGGACAGCGACGGTTCCTTCTTTCTCTA<br>TTCTAAACTTACCGTCGACAAATCACGGTGGCAACAAGGAAATGTATTCTCATGCA<br>GTGTATTGCACGAAGCTCTGCACTCTCATTACACCCAAAAATCCCTCTCTCTCAGC<br>CCTGGCGGTGGATCTGATTCTTGGCAGGAAGAGGTGATTAAACTGTGTGGGCGAGA<br>GCTTGTCCGAGCTCAGATCGCTATTTGTGGCAAGAGTACCGGAGGCGAGGGTGAGG<br>GAGGCGAAGGCGAGGGCGGAAGCCGGCAACTCTATAGCGCACTCGCTAATAAATGT<br>TGTCATGTCGGCTGCACGAAGCGCTCACTGGCGCAGTTCTGC |
| 499 | GATAAAACCCATACGTGTCCTCCATGCCCAGCTCCCGAGCTGCTCGGTGGTCCTTC<br>AGTGTTCCTCTTCCCCCAAAGCCGAAGGACACGCTCATGATTAGTCGAACGCCAG<br>AGGTGACATGTGTGGTCGTTGATGTTTCCCATGAGGATCCGGAAGTTAAGTTCAAC<br>TGGTACGTAGATGGCGTGGAGGTTCACAATGCAAAAACCAAGCCCCGCGAGGAGCA<br>GTATAACTCAACCTACAGAGTAGTATCTGTGCTCACGGTCTTGCATCAGGATTGGT<br>TGAACGGGAAGGAATACAAGTGTAAAGTAAGTAATAAGGCACTGCCGGCCCCCATA<br>GAAAAAACTATCAGCAAAGCTAAAGGTCAGCCGCGGGAGCCACAAGTTTACACTCT<br>TCCTCCTAGTAGAGACGAGCTGACGAAGAATCAAGTTTCTTTGACTTGTCTCGTGA<br>AGGGATTCTACCCAAGCGATATAGCTGTAGAGTGGGAAAGCAACGGACAACCAGAA<br>AATAACTACAAGACTACACCCCCGTTCTCGATTCTGATGGCTCATTCTTCTTGTA<br>CTCAAAATTGACAGTTGACAAATCTCGATGGCAGCAGGGTAACGTATTTAGTTGCT<br>CTGTTATGCACGAAGCGTTGCATAACCACTACACACAGAAGTCATTGTCACTGAGC<br>CCAGGAAAAGGTGGTGGCGGGTCCGGCGGTGGAGGTAGCGGTGGCGGGGGCTCCCA<br>GCTTTATAGTGCCCTTGCAAACAAATGTTGCCACGTCGGATGTACGAAGCGCAGTT<br>TGGCGAGATTCTGTGGAGGGGCGGATCCGGAGGCGGGGGGTCCGGAGGAGGAGGT<br>AGCTCATGGATGAAGAGGTAATAAAACTGTGCGGACGCGAGCTTGTCAGGGCCCA<br>AATCGCAATTTGTGGCATGAGCACATGGAGT |

TABLE 9-continued

Nucleotide Sequences Encoding Fusion Proteins and Peptide Components

| SEQ ID NO: | Sequence |
|---|---|
| 532 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTAAGGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGAGAAGGGGGCGGAAGGCAGCTTTACTCTGCTCTGGCTAACAAG<br>TGTTGTCACGTTGGGTGTACCAAGCGGTCCCTTGCGCAATTCTGC |
| 533 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTAAGGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGAGAAGGGGGCGGAAGGCAGCTTTACTCTGCTCTGGCTAACAAG<br>TGTTGTCAAGTTGGGTGTACCAAGCGGTCCCTTGCGCAATTCTGC |
| 534 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTAAGGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGAGAAGGGGGCGGAAGGCAGCTTTACTCTGCTCTGGCTAACAAG<br>TGTTGTCACGTTGGGTGTACCAAGCAATCCCTTGCGCAATTCTGC |
| 535 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTAAGGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGAGAAGGGGGCGGAAGGCAGCTTTACTCTGCTCTGGCTAACAAG<br>TGTTGTCAAGTTGGGTGTACCAAGCAATCCCTTGCGCAATTCTGC |
| 536 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG |

TABLE 9-continued

Nucleotide Sequences Encoding Fusion Proteins and Peptide Components

| SEQ ID NO: | Sequence |
|---|---|
| | AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTAAGGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGATCTGGGGGCGGAAGGCAGCTTTACTCTGCTCTGGCTAACAAG<br>TGTTGTCACGTTGGGTGTACCAAGCGGTCCCTTGCGCAATTCTGC |
| 537 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTAAGGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGATCTGGGGGCGGAAGGCAGCTTTACTCTGCTCTGGCTAACAAG<br>TGTTGTCAAGTTGGGTGTACCAAGCGGTCCCTTGCGCAATTCTGC |
| 538 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTAAGGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGATCTGGGGGCGGAAGGCAGCTTTACTCTGCTCTGGCTAACAAG<br>TGTTGTCACGTTGGGTGTACCAAGCAATCCCTTGCGCAATTCTGC |
| 539 | GATAAAACCCACACTTGCCCACCTTGCCCTGCGCCGGAAGCCGCCGGAGGACCTAG<br>TGTTTTCCTCTTTCCCCCTAAGCCCAAAGACACGTTGATGATCTCTCGGACACCGG<br>AAGTAACTTGTGTCGTTGTGGATGTGTCACATGAGGATCCCGAGGTGAAATTTAAT<br>TGGTACGTTGACGGCGTGGAGGTGCATAACGCAAAGACTAAACCACGCGAGGAGCA<br>GTATAATTCTACATACCGGGTTGTCTCAGTTCTCACAGTTCTTCATCAGGATTGGT<br>TGAATGGAAAGGAGTACAAATGCAAAGTGTCCAACAAAGCGCTTGCTGCGCCGATT<br>GAAAAGACGATTTCAAAGGCAAAAGGGCAGCCCCGCGAACCCCAAGTATATACTTT<br>GCCTCCCTCACGCGATGAACTGACTAAGAACCAGGTGAGCCTGACTTGTTTGGTTA<br>AGGGTTTTTATCCAAGTGACATTGCTGTTGAATGGGAGTCCAATGGCCAGCCTGAG<br>AATAACTACAAAACGACACCTCCTGTACTTGACAGCGACGGCTCCTTTTTTCTTTA<br>TTCAAAACTCACAGTGGACAAATCCAGGTGGCAGCAGGGTAACGTCTTTTCTTGCA<br>GCGTGCTCCACGAAGCTTTGCATTCACATTATACGCAAAAATCCTTGTCATTGTCC<br>CCAGGTAAGGGCGGAAGCGACTCATACCAAGAAGAAGTCATTAAACTTTGTGGACG<br>GGAGCTGGTTAGGGCACAGATTGCTATTTGTGGTAAGTCTACGGGAGGAGAAGGCT<br>CTGGAGGCGAAGGATCTGGGGGCGGAAGGCAGCTTTACTCTGCTCTGGCTAACAAG<br>TGTTGTCAAGTTGGGTGTACCAAGCAATCCCTTGCGCAATTCTGC |

In some embodiments, the vector comprises a polynucleotide sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or 99% identical to a sequence recited in Table 10, below. In some embodiments, the vector comprises a polynucleotide sequence that comprises or consists of a sequence recited in Table 10, below.

TABLE 10

Nucleotide Sequences Encoding Fusion Proteins and Peptide Components

| SEQ ID NO: | Sequence |
|---|---|
| 194 | ATGGAGACTGACACACTCCTCCTTTGGGTTTTGCTGTTGTGGGTGCCTGGATCTAC<br>TGGCGACAAGACCCATACATGTCCGCCTTGTCCTGCGCCTGAGGCAGCAGGCGGAC<br>CATCAGTCTTCTTGTTTCCCCCCAAGCCGAAGGACACCCTTATGATCTCACGCACC<br>CCCGAAGTAACTTGTGTAGTCGTTGATGTCTCACACGAAGACCCGGAAGTAAAGTT<br>TAATTGGTATGTCGATGGTGTTGAGGTCCACAACGCTAAAACGAAACCGCGGGAAG<br>AACAATACAACTCCACATATCGAGTAGTCTCCGTCCTGACTGTTCTTCACCAGGAC<br>TGGCTGAATGGTAAAGAATACAAATGTAAAGTGAGTAACAAGGCCCTTGCAGCACC<br>CATCGAGAAGACGATATCCAAAGCCAAGGGGCAACCGCGCGAGCCACAAGTTTACA<br>CGCTCCCACCCTCAAGAGACGAACTCACCAAAAATCAAGTGTCCCTGACATGTCTG<br>GTGAAAGGATTCTATCCCAGCGACATAGCTGTAGAATGGGAGAGTAATGGCCAACC<br>CGAAAACAATTACAAAACTACCCCCCCGGTTTTGGATAGTGATGGTTCATTCTTCC<br>TCTATAGTAAACTTACCGTGGATAAGTCTCGGTGGCAGCAGGGGAACGTGTTTAGC<br>TGTTCAGTCCTCCATGAGGCACTCCATAGTCACTATACGCAAAAGTCATTGTCCCT<br>TTCTCCGGGCAAGGGCGGGTCAGACTCCTGGCAGGAAGAGGTAATTAAGCTTTGTG<br>GGCGAGAACTCGTTAGGGCACAGATAGCAATCTGCGGGAAAAGTACAGCTTCCGAT<br>GCTGCCGGGGCTGACGCCAATGCGGGAGCACGCCAGCTCTACTCAGCCCTCGCCAA<br>CAAGTGTTGTCATGTAGGTTGCACCAAAAGAAGTCTGGCACAGTTTTGC |
| 195 | ATGGAAACAGACACTCTTCTTTTGTGGGTCTTGTTGCTCTGGGTCCCTGGCTCAAC<br>AGGCGACAAGACGCATACTTGTCCTCCCTGCCCAGCTCCCGAAGCGGCTGGGGGGC<br>CCTCTGTCTTTCTGTTTCCGCCTAAGCCCAAGGACACGCTCATGATAAGTCGCACT<br>CCGGAAGTCACCTGTGTTGTCGTCGATGTTAGCCATGAAGATCCAGAGGTGAAATT<br>TAACTGGTACGTCGACGGAGTGGAGGTTCACAATGCTAAAACCAAACCGCGAGAAG<br>AGCAATACAATTCCACGTATAGGGTCGTCTCCGTCCTGACAGTACTCCATCAGGAT<br>TGGCTGAATGGAAAAGAATACAAGTGCAAGGTTTCCAATAAAGCCTTGGCCGCACC<br>TATTGAGAAAACGATATCAAAAGCTAAGGGACAACCTCGGGAGCCGCAAGTATATA<br>CACTCCCCCCTTCTAGGGACGAACTGACAAAAAACCAAGTTAGTCTGACTTGTCTT<br>GTGAAAGGTTTTTACCCGAGTGATATAGCCGTAGAATGGGAGAGCAATGGCCAGCC<br>CGAAAACAATTACAAAACAACTCCCCCAGTATTGGACAGTGACGGGTCATTTTTTT<br>TGTATTCTAAATTGACCGTAGACAAGTCACGCTGGCAACAAGGGAATGTATTTAGC<br>TGTTCCGTCCTTCATGAGGCGCTCCATAGCCATTACACTCAGAAGTCTTTGTCACT<br>GTCACCGGGCAAGGGTGGTTCTGATTCATGGCAAGAGGAAGTGATTAAGCTGTGCG<br>GTCGGGAGTTGGTAAGAGCTCAAATTGCGATTTGTGGCAAGAGCACTGCGTCCGAT<br>GCCGCAGGTGCTAATGCCGACGCCGGTGCGAGACAGCTTTATTCTGCGCTGGCCAA<br>CAAGTGCTGCCACGTCGGATGCACCAAACGGAGCCTTGCTCAGTTTTGC |
| 196 | ATGGAAACCGACACCCTGCTTCTCTGGGTGCTGCTGCTCTGGGTACCAGGGTCTAC<br>AGGTGACAAAACTCATACTTGTCCACCATGCCCAGCCCCCGAGGCGGCTGGCGGCC<br>CCAGCGTATTCCTTTTCCCCCCAAAACCTAAGGACACGCTTATGATATCTAGAACC<br>CCGGAGGTCACATGTGTCGTCGTAGACGTAAGTCACGAAGATCCTGAAGTCAAGTT<br>TAACTGGTACGTCGATGGAGTCGAGGTCCATAATGCTAAAACGAAGCCTCGCGAAG<br>AACAGTATAATTCTACCTATCGCGTAGTCTCTGTCCTCACCGTCTTGCATCAAGAC<br>TGGTTGAACGGCAAGGAGTACAAGTGTAAGGTTTCAAACAAAGCCCTTGCCGCGCC<br>GATAGAGAAAACAATTAGCAAAGCGAAGGGGCAGCCGAGAGAGCCGCAAGTGTATA<br>CCCTTCCTCCTAGTAGAGACGAGTTGACCAAAAACCAGGTGTCACTTACATGCCTC<br>GTGAAAGGCTTCTACCCGAGTGATATTGCAGTCGAGTGGGAATCCAACGGCCAGCC<br>CGAGAATAACTACAAAACGACGCCGCCCGTACTGGACAGTGATGGAAGTTTTTTTT<br>TGTACTCAAAACTCACGGTTGACAAAAGTCGGTGGCAGCAAGGGAACGTTTTTAGC<br>TGCTCTGTCCTCCATGAAGCACTCCATTCTCATTATACCCAGAAGTCTCTGTCTCT<br>CTCCCCTGGTAAGGGAGGTTCTGACAGTTGGCAGGAAGAGGTAATAAAACTCTGCG<br>GTCGAGAGCTTGTTCGAGCACAAATTGCTATATGTGGAAAATCTACCGCTTCAGAC<br>GCCGCCGGAGCTGATGCGGATGCCGGGGCTCGCCAGCTCTATAGCGCCTTGGCCAA<br>CAAATGTTGTCACGTTGGCTGCACGAAGCGCTCCCTGGCTCAGTTTTGC |
| 197 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAGGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATGGCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCGAAGCGGAAGCTGGTGCAAGGCAGCTTTACTCTGCTCTGGCTAA<br>CAAGTGTTGTCACGTTGGGTGTACCAAGCGGTCCCTTGCGCAATTCTGC |
| 198 | ATGGAGACTGATACACTTCTTCTCTGGGTCCTCCTCCTCTGGGTTCCAGGCTCAAC<br>AGGTGATAAAACTCATACTTGCCCCCCCTGCCCCGCGCCTGAAGCTGCAGGGGGGC |

TABLE 10-continued

Nucleotide Sequences Encoding Fusion Proteins and Peptide Components

| SEQ ID NO: | Sequence |
|---|---|
|  | CATCAGTCTTCTTGTTTCCACCAAAACCTAAGGATACTCTCATGATTAGCCGGACC<br>CCTGAGGTGACATGTGTTGTGGTCGATGTATCTCATGAAGATCCCGAAGTAAAATT<br>TAACTGGTACGTAGACGGGGTTGAAGTTCATAACGCGAAAACGAAACCTCGGGAGG<br>AGCAATATAATAGCACGTATAGAGTTGTTTCAGTCCTTACAGTTCTCCACCAAGAC<br>TGGCTGAATGGCAAGGAGTATAAGTGTAAAGTATCCAATAAAGCCTTGGCTGCGCC<br>AATCGAGAAGACGATCAGCAAAGCCAAAGGTCAGCCTCGCGAACCGCAGGTCTATA<br>CATTGCCCCCTTCACGCGACGAACTCACGAAAAATCAAGTCTCTTTGACTTGCCTT<br>GTGAAAGGCTTCTACCCCTCCGATATTGCCGTCGAATGGGAAAGCAATGGACAGCC<br>GGAAAATAATTACAAAACGACACCCCCGTGTTGGATTCCGATGGGTCCTTCTTCC<br>TCTATTCCAAGCTGACGGTCGATAAGTCTCGATGGCAGCAGGGAAATGTCTTCTCT<br>TGCTCCGTCCTTCATGAGGCATTGCACAGCCATTATACTCAAAAGAGTCTCTCT<br>GTCTCCAGGCAAAGGGGGTTCCGACTCTTGGCAAGAAGAGGTCATAAAACTGTGCG<br>GCCGGGAGCTCGTCAGAGCGCAGATCGCTATATGTGGAAAATCCACCGCGAGTGAC<br>GCAGCAGGTGCACAAGCCGACGCAGGAGCTAGGCAACTGTACTCAGCCCTTGCCAA<br>TAAGTGTTGTCACGTAGGTTGTACTAAACGCTCCCTGGCACAATTTTGT |
| 199 | ATGGAAACCGATACCTTGCTCCTTTGGGTTCTGCTCCTTTGGGTCCCTGGAAGTAC<br>AGGGGATAAGACACACACGTGCCCACCCTGCCCTGCCCCAGAGGCAGCCGGAGGTC<br>CTAGTGTGTTTCTGTTCCCCCCAAAGCCCAAGGACACCCTTATGATATCTAGGACA<br>CCAGAAGTTACGTGCGTCGTTGTGGACGTTAGCCACGAAGACCCAGAAGTGAAGTT<br>TAATTGGTACGTTGATGGAGTCGAAGTGCACAATGCAAAAACAAAACCACGAGAAG<br>AGCAGTATAACAGTACTTATAGAGTAGTCAGCGTCCTTACTGTATTGCATCAGGAT<br>TGGCTGAATGGGAAGGAATATAAATGTAAGGTTAGCAATAAAGCCCTTGCGGCTCC<br>TATCGAGAAAACTATTAGCAAAGCAAAGGGCCAACCCCGAGAGCCCCAAGTTTATA<br>CACTGCCACCCAGTCGAGATGAGCTGACTAAAAATCAAGTATCCCTGACCTGCTTG<br>GTTAAGGGGTTTTATCCTAGTGACATCGCGGTTGAGTGGGAATCCAACGGCCAACC<br>GGAGAATAATTACAAAACCACGCCACCTGTATTGGATTCCGATGGTAGCTTCTTTC<br>TCTATAGTAAACTTACAGTCGATAAGTCAAGATGGCAGCAGGGAAACGTATTTTCA<br>TGCTCAGTTCTGCATGAGGCCTTGCACTCCCATTACACTCAAAAATCACTGAGCCT<br>CAGTCCTGGTAAGGGTGGCTCTGACTCATGGCAGGAGGAAGTAATCAAGCTGTGTG<br>GGAGGGAATTGGTAAGGGCTCAGATTGCAATTTGTGGAAAGAGCACAGCGTCTGAC<br>GCTGCAGGTGCCGACGCACAGGCGGGCGCGAGGCAGCTCTACAGTGCTCTTGCGAA<br>CAAGTGTTGTCATGTAGGTTGCACGAAACGAAGTTTGGCGCAATTCTGT |
| 200 | ATGGAGACTGACACTCTCCTTCTTTGGGTGCTGTTGCTCTGGGTTCCCGGAAGCAC<br>GGGGGATAAAACACACACCTGCCCCCCTTGCCCAGCACCTGAAGCAGCGGGTGGTC<br>CCAGCGTTTTTCTTTTCCCCCCTAAGCCAAAGGACACGCTCATGATAAGTCGCACC<br>CCGGAGGTCACCTGCGTCGTTGTTGACGTATCACATGAAGATCCTGAGGTGAAGTT<br>TAATTGGTACGTAGATGGTGTTGAGGTCCACAACGCAAAGACGAAACCGAGGGAAG<br>AACAGTACAACAGTACTTATCGCGTAGTCTCCGTTCTGACTGTCCTGCATCAAGAT<br>TGGTTGAACGGGAAGGAGTACAAGTGCAAAGTTAGTAACAAGGCTCTCGCGGCCCC<br>AATTGAGAAGACGATATCCAAAGCGAAAGGACAGCCGAGAGAGCCCCAAGTCTACA<br>CTCTGCCCCCTTCCAGGGATGAGCTCACCAAAAATCAGGTCAGTCTCACGTGCCTG<br>GTTAAGGGATTCTACCCAAGTGATATAGCAGTTGAATGGGAGTAACGGCCAGCC<br>CGAGAACAACTATAAAACTACACCGCCCGTTCTTGATTCCGATGGGTCTTTCTTCC<br>TTTATAGTAAGCTCACCGTTGATAAGTCCCGATGGCAGCAAGGTAATGTCTTCTCA<br>TGTTCAGTTCTTCATGAAGCCCTGCATTCCCATTATACACAAAAGAGCTTGTCCTT<br>GTCACCGGGCAAAGGCGGTAGCGATTCTTGGCAAGAAGAAGTTATAAAGTTGTGCG<br>GTAGGGAACTGGTACGCGCTCAAATAGCTATATGCGGTAAGTCTACTGCTTCAGAT<br>GCGGCTGGCGCACAGGCACAGGCCGGTGCTAGACAACTCTATAGTGCGCTGGCCAA<br>CAAGTGCTGCCATGTGGGGTGTACAAAACGGAGTCTTGCCCAGTTTTGT |
| 201 | ATGGAAACTGACACGCTTTTGCTTTGGGTCCTCCTTCTTTGGGTTCCCGGCTCTAC<br>TGGAGACAAAACTCATACATGCCCCCCATGCCCAGCACCCGAAGCGGCCGGAGGTC<br>CGTCTGTCTTTCTGTTTCCGCCGAAACCTAAAGATACGTTGATGATTAGCAGAACC<br>CCTGAGGTAACATGTGTGGTAGTCGATGTCTCCCATGAGGACCCCGAGGTAAAGTT<br>CAATTGGTATGTTGACGGCGTCGAAGTCCATAACGCAAAAACGAAGCCCCGAGAGG<br>AGCAATATAACTCTACCTATCGCGTTGTTTCTGTTTTGACTGTGTTGCACCAGGAT<br>TGGCTCAACGGCAAGGAATACAAATGTAAAGTGTCCAACAAGGCCCTTGCTGCACC<br>TATCGAAAAACGATTAGTAAGGCAAAGGGACAACCGCGCGAACCACAGGTATATA<br>CTTTGCCGCCTAGCAGAGATGAACTCACCAAGAATCAAGTTTCCTTACCTGTTTG<br>GTTAAAGGATTTTACCCGTCTGACATAGCTGTTGAATGGGAGAGCAATGGTCAGCC<br>GGAAAATAATTATAAAACCACCCCGCCAGTATTGGATTCAGATGGGTCCTTTTTCT<br>TGTATTCTAAACTTACCGTGGATAAGTCTAGGTGGCAACAGGGAAACGTCTTTTCA<br>TGTAGTGTACTTCATGAAGCCCTCCATAGTCACTACACGCAGAAATCCTTGTCTCT<br>TAGTCCGGGTGAAGGTGGGTCTGATTCCTGGCAGGAAGAGGTGATAAAGCTCTGTG<br>GTCGGGAACTTGTTAGGGCGCAGATCGCTATTTGCGGCAAATCTACAGCATCAGAT<br>GCCGCCGGAGCTGATGCAACGCAGGAGCGAGGCAGCTGTACTCCGCACTTGCTAA<br>CAAGTGTTGCCATGTCGGCTGCACCAAGAGGAGTCTTGCTCAATTCTGC |
| 202 | ATGGAAACCGACACCCTCCTTCTTTGGGTCTTGCTGCTTTGGGTTCCTGGTTCTAC<br>TGGAGATAAGACCCATACATGCCCGCCATGTCCCGCACCCGAGGCAGCGGGTGGAC<br>CCTCTGTCTTTCTGTTCCCTCCAAAGCCAAAAGATACCCTGATGATTAGCCGAACC<br>CCGGAGGTGACTTGTGTCGTAGTAGATGTCAGTCACGAGGATCCCGAAGTAAAGTT |

TABLE 10-continued

Nucleotide Sequences Encoding Fusion Proteins and Peptide Components

| SEQ ID NO: | Sequence |
|---|---|
| | TAATTGGTATGTGGACGGTGTGGAGGTACATAACGCTAAGACGAAACCCCGAGAGG<br>AACAATACAACTCTACGTACAGGGTCGTCTCAGTGCTCACGGTCCTGCACCAGGAC<br>TGGCTTAATGGGAAGGAATATAAATGCAAAGTCTCTAATAAGGCGCTTGCTGCACC<br>TATTGAAAAAACGATTTCTAAGGCGAAGGGACAACCCCGGGAGCCACAAGTCTACA<br>CCCTTCCTCCAAGCAGAGATGAGCTTACGAAAAATCAAGTGTCTCTTACGTGCCTC<br>GTAAAGGGCTTTTACCCATCCGACATTGCGGTGGAGTGGGAATCAAACGGGCAGCC<br>GGAAAATAACTACAAAACAACGCCGCCTGTATTGGATTCCGACGGCTCTTTCTTCC<br>TTTACAGCAAACTGACAGTCGATAAATCCAGATGGCAACAAGGGAACGTTTTTTCA<br>TGTTCCGTTCTGCATGAAGCCCTTCACAGTCATTACACCCAAAAGTCACTTTCACT<br>TTCACCGGGCGAGGGGGGGTCAGACTCCTGGCAAGAGGAAGTTATAAAGTTGTGCG<br>GCAGGGAACTGGTTAGAGCGCAGATAGCGATTTGCGGAAAATCTACTGCGAGTGAT<br>GCTGCGGGAGCGAATGCGGACGCCGGGGCCCGACAGCTCTATTCCGCACTCGCCAA<br>TAAGTGCTGCCATGTTGGTTGTACGAAGAGAAGTCTTGCACAATTTTGC |
| 203 | ATGGAAACAGACACGCTGCTTTTGTGGGTACTGTTGCTTTGGGTCCCAGGATCCAC<br>AGGTGATAAGACACATACATGCCCCCCCTGCCCGGCTCCCGAAGCTGCCGGGGGAC<br>CGTCAGTGTTTTTGTTTCCGCCCAAGCCGAAGGATACTTTGATGATTAGTCGGACA<br>CCAGAAGTGACATGTGTTGTCGTTGACGTGAGTCACGAGGATCCCGAGGTCAAGTT<br>CAACTGGTACGTTGATGGGGTTGAAGTTCACAACGCTAAAACGAAACCCCGCGAAG<br>AGCAGTATAACTCCACTTACCGGGTCGTCAGTGTCCTGACGGTCTTGCACCAGGAC<br>TGGCTGAATGGAAAGGAATACAAGTGTAAAGTTTCCAATAAAGCACTGGCCGCCCC<br>GATCGAAAAAACAATTTCCAAAGCTAAGGGACAGCCCAGGGAACCGCAAGTTTATA<br>CTCTTCCACCCTCCCGGGATGAACTGACCAAAAACCAAGTGCTTTTGACGTGCCTC<br>GTAAAGGGCTTCTACCCGTCAGACATAGCTGTCGAATGGGAGTCTAATGGACAGCC<br>GGAAAACAATTATAAGACTACACCGCCGGTGCTTGATAGTGATGGAAGTTTCTTTT<br>TGTACTCCAAACTTACGGTCGATAAAAGCCGGTGGCAGCAGGGAAACGTATTCAGT<br>TGTAGCGTTCTGCATGAAGCTCTTCATTCTCACTACACCCAGAAGTCTCTGTCTCT<br>GAGCCCCGGAGAGGGTGGATCTGATTCTTGGCAGGAAGAAGTGATAAAGTTGTGCG<br>GCCGGGAATTGGTACGCGCCCAGATAGCCATTTGCGGGAAGTCTACGGCGAGTGAC<br>GCAGCAGGTGCTGACGCGGACGCTGGTGCTAGACAGCTGTATTCTGCCCTGGCTAA<br>TAAGTGTTGCCACGTTGGCTGCACCAAGAGATCCCTGGCCCAATTCTGT |
| 204 | ATGGAAACTGACACTTTGCTGTTGTGGGTCCTCCTGTTGTGGGTCCCCGGAAGTAC<br>AGGAGACAAGACACATACTTGTCCCCCCTGCCCAGCTCCAGAAGCTGCCGGAGGGC<br>CGTCAGTCTTCCTTTTCCCTCCAAAACCTAAGGATACGCTTATGATTTCTCGAACG<br>CCAGAGGTTACGTGTGTAGTCGTGGACGTTTCCCACGAGGATCCTGAGGTCAAGTT<br>TAACTGGTATGTAGACGGGGTTGAGGTCCATAATGCCAAGACAAAGCCGCGCGAGG<br>AACAATACAACAGTACATATAGGGTGGTGAGCGTCCTCACAGTCTTGCATCAAGAT<br>TGGCTCAACGGCAAAGAGTACAAATGTAAGGTTAGCAACAAAGCCCTCGCTGCTCC<br>CATCGAAAAGACGATTTCTAAGGCGAAGGGCCAACCACGAGAACCCAAGTATATA<br>CTCTTCCCCCTTCACGGGACGAGCTGACCAAAAACCAGGTATCCTTGACTTGCCTG<br>GTCAAAGGATTTTACCCCTCTGATATTGCGGTCGAGTGGGAGAGTAATGGGCAACC<br>AGAAAATAATTATAAAACGACCCCCCGGTACTCGACAGTGATGGGTCTTTTTTCC<br>TGTATTCTAAGCTTACGGTTGATAAGTCTAGATGGCAGCAAGGGAATGTCTTCTCA<br>TGTAGTGTTCTGCATGAAGCACTTCATTCTCACTATACTCAGAAATCTCTTTCCCT<br>TAGTCCGGGAGAAGGTGGGAGCGATAGTTGGCAAGAGGAGGTGATAAAACTGTGTG<br>GTCGGGAGCTGGTGAGAGCCCAAATAGCTATCTGCGGCAAATCAACAGCAAGTGAT<br>GCGGCAGGAGCGGAAGCGGAGGCGGGAGCGCGGCAATTGTATAGTGCCCTTGCTAA<br>TAAATGCTGTCACGTTGGGTGTACTAAACGATCTCTTGCTCAATTCTGC |
| 205 | ATGGAGACGGATACGTTGTTGCTTTGGGTCCTCCTGTTGTGGGTGCCCGGCTCTAC<br>CGGTGATAAAACCCATACATGTCCTCCGTGTCCCGCTCCAGAAGCCGCTGGCGGGC<br>CATCTGTGTTTTTGTTCCCCCCCAAGCCTAAGGATACGTTGATGATCAGCAGGACC<br>CCGGAGGTTACATGCGTAGTAGTTGACGTTTCTCATGAAGACCCAGAAGTAAAATT<br>TAACTGGTATGTCGATGGCGTCGAAGTACATAATGCTAAAACTAAGCCCAGGGAAG<br>AGCAATACAATTCAACGTACCGAGTTGTGAGTGTCCTTACGGTCCTGCACCAAGAC<br>TGGTTGAACGGCAAAGAGTACAAATGCAAAGTGTCTAACAAGGCATTGGCCGCGCC<br>TATAGAAAAGACCATTAGCAAAGCAAAAGGGCAGCCTCGGGAACCCCAGGTCTACA<br>CGCTGCCACCTTCCCGAGATGAATTGACGAAAAACCAGGTCTCTTTGACCTGCTTG<br>GTTAAAGGCTTCTACCCAAGCGACATTGCAGTGGAGTGGGAGTCTAACGGGCAACC<br>CGAAAACAACTATAAGACGACTCCCCCTGTTCTTGATTCTGATGGGAGTTTTTTTC<br>TGTACAGTAAGTTGACAGTGGATAAATCAAGATGGCAGCAAGGTAATGTCTTCTCT<br>TGTTCAGTGCTTCACGAAGCATTGCATTCTCACTACACAAAAGTCTTTGTCCTT<br>GTCTCCAGGTGAAGGCGGTAGCGATTCATGGCAAGAAGAAGTCATTAAGCTGTGTG<br>GAAGGGAACTGGTTAGGGCCCAAATTGCGATATGTGGAAAGTCTACGGCGAGTGAT<br>GCGGCCGGTGCTCAAGCGGATGCGGGTGCTAGACAGTTGTACTCAGCCCTTGCGAA<br>CAAATGTTGTCACGTTGGCTGTACGAAACGCAGCCTTGCTCAATTCTGC |
| 206 | ATGGAAACTGACACCCTTCTGCTCTGGGTACTCTTGTTGTGGGTCCCCGGCAGTAC<br>AGGCGATAAAACTCACACATGCCCCCCATGCCCAGCACCGGAAGCTGCCGGAGGAC<br>CGTCTGTATTCCTCTTTCCGCCCAAACCTGAAGACACGTTGATGATTTCTCGGACT<br>CCCGAGGTAACTTGTGTCGTGGTCGACGTCTCACACGAGGACCCGGAGGTCAAATT<br>TAACTGGTATGTCGATGGGGTGGAGGTCCATAATGCTAAGACGAAGCCCAGAGAAG<br>AACAGTATAACTCTACTTATAGAGTTGTAAGCGTGCTCACTGTATTGCACCAGGAC |

TABLE 10-continued

Nucleotide Sequences Encoding Fusion Proteins and Peptide Components

| SEQ ID NO: | Sequence |
|---|---|
| | TGGCTCAACGGGAAAGAATATAAGTGTAAGGTCTCAAACAAAGCTCTCGCAGCCCC<br>GATAGAGAAAACAATATCTAAGGCCAAGGGCCAACCGCGCGAGCCGCAGGTTTATA<br>CACTTCCACCCTCCCGCGATGAGCTGACCAAGAACCAGGTCTCTCTCACCTGTCTC<br>GTAAAGGGCTTTTATCCCTCCGACATTGCAGTGGAGTGGGAATCAAACGGCCAGCC<br>GGAAAATAATTACAAGACCACTCCTCCCGTCCTCGACTCCGATGGGTCATTTTTCC<br>TGTACAGTAAGCTCACCGTTGATAAGTCAAGGTGGCAGCAGGGCAACGTGTTTAGC<br>TGTAGTGTTCTGCATGAGGCGCTCCACAGTCACTACACCCAGAAAAGTCTGAGCCT<br>TTCCCCAGGTGAGGGTGGTAGCGATAGCTGGCAGGAGGAAGTAATTAAACTCTGCG<br>GTAGAGAATTGGTAAGGGCCCAAATTGCCATCTGCGGAAAGAGCACCGCATCAGAT<br>GCTGCGGGCGCGGATGCGCAGGCTGGTGCTAGGCAACTCTACTCTGCCCTGGCGAA<br>TAAATGTTGCCACGTCGGTTGCACGAAACGAAGTTTGGCTCAATTTTGC |
| 207 | ATGGAAACGGACACACTTCTCTTGTGGGTTCTTCTGCTCTGGGTTCCCGGCAGTAC<br>AGGCGACAAAACACATACATGCCCCCCTTGCCCGGCTCCCGAGGCCGCCGGTGGTC<br>CTAGCGTCTTTCTTTTCCCTCCCAAACCCAAAGACACACTTATGATTAGCAGAACT<br>CCCGAGGTAACATGTGTGGTCGTAGACGTAAGTCACGAAGATCCCGAAGTTAAATT<br>CAACTGGTACGTTGATGGTGTGGAAGTTCATAATGCAAAAACCAAACCGCGAGAGG<br>AACAGTATAACTCTACCTACCGCGTGGTCTCAGTGCTGACTGTCCTGCATCAGGAC<br>TGGCTCAACGGGAAGGAATATAAGTGCAAAGTGAGTAATAAGGCCCTTGCAGCTCC<br>CATAGAAAAGACGATATCAAAGGCTAAAGGACAGCCGAGGGAGCCACAGGTGTACA<br>CTTTGCCTCCGAGTAGAGATGAACTCACTAAAAACCAAGTAAGTTTGACATGCCTG<br>GTCAAAGGTTTTTACCCCAGTGATATAGCGGTTGAGTGGGAGTCCAATGGGCAACC<br>GGAGAACAACTATAAGACTACTCCACCTGTCCTGGATAGCGATGGAAGTTTTTTTC<br>TTTACTCAAAGCTGACGGTGGATAAGAGTCGATGGCAGCAGGGCAATGTGTTTAGC<br>TGTTCTGTGCTTCACGAAGCACTTCACTCTCATTATACCCAGAAGTCATTGAGCCT<br>TTCCCCTGGTGAAGGAGGGTCAGATTCCTGGCAGGAGGAGGTTATAAAGCTGTGTG<br>GCCGGGAACTCGTGCGAGCTCAAATTGCGATCTGTGGAAAATCCACCGCTAGTGAT<br>GCGGCGGGAGCACAAGCTCAAGCGGGCGCTCGACAACTTTATAGCGCTTTGGCTAA<br>TAAGTGCTGCCATGTGGGTTGTACAAAGCGCAGCCTCGCTCAATTTTGC |
| 208 | ATGGAAACAGACACTCTCCTCCTGTGGGTACTTCTCTTGTGGGTACCAGGATCCAC<br>CGGGGATAAGACGCACACTTGCCCTCCTTGCCCGGCACCCGAAGCCGCTGGTGGGC<br>CTAGTGTATTCCTGTTCCCCCCGAAGCCGAAGGATACTCTTATGATTTCACGCACG<br>CCCGAGGTTACATGCGTAGTAGTGGACGTATCTCACGAAGATCCCGAAGTCAAGTT<br>CAATTGGTATGTCGACGGAGTAGAAGTTCACAACGCAAAGACAAAACCGCGGGAAG<br>AGCAATACAACTCCACGTACCGCGTCGTTTCTGTTCTTACGGTCTTGCACCAGGAC<br>TGGCTCAATGGCAAGGAGTATAAGTGCAAGGTATCCAACAAGGCCCTTGCCGCACC<br>TATTGAAAAGACTATCAGCAAGGCCAAGGGACAGCCAAGGGAGCCTCAAGTCTACA<br>CGCTCCCGCCTAGTAGAGACGAGTTGACAAAGAATCAAGTGAGTTTGACTTGTCTG<br>GTTAAAGGTTTTTACCCGTCAGATATTGCAGTAGAATGGGAATCTAACGGACAACC<br>CGAAAACAACTATAAAACGACGCCTCCTGTGTTGGATTCAGATGGGTCATTTTTTC<br>TCTACTCAAAGCTCACGGTAGATAAATCAAGATGGCAACAAGGCAATGTATTTTCC<br>TGCTCCGTGCTCCACGAGGCTCTGCACAGCCATTATACGCAAAAGAGTCTGTCTTT<br>GAGCCCAGGTGAGGGTGGCTCCGATTCCTGGCAGGAGGAAGTAATTAAGTTGTGCG<br>GCAGGGAACTTGTTCGCGCACAAATAGCCATTTGTGGTCAGAGCACAGCATCAGAT<br>GCCGCCGGAGCCGACGCCAACGCAGGTGCCCGCCAACTTTATTCTGCCCTCGCAAA<br>CAAATGCTGCCACGTCGGCTGCACGAAGAGGAGCCTCGCCCAATTTTGC |
| 209 | ATGGAAACAGACACGCTGCTCCTCTGGGTGTTGCTTCTCTGGGTGCCTGGCAGTAC<br>AGGTGATAAGACCCATACGTGCCCGCCATGTCCAGCCCCCGAGGCAGCCGGAGGTC<br>CTTCCGTTTTCCTTTTCCCCCCTAAGCCCAAGGACACTCTGATGATCTCCCGGACG<br>CCTGAAGTCACTTGCGTAGTCGTAGACGTTTCACATGAGGATCCAGAAGTTAAATT<br>TAACTGGTACGTCGATGGCGTCGAGGTCCATAACGCGAAAACCAAGCCCAGGGAGG<br>AACAATATAACTCCACCTATAGGGTCGTGAGTGTGCTCACCGTTTTGCACCAAGAC<br>TGGCTCAACGGGAAAGAGTACAAATGTAAAGTTTCAAATAAGGCTTTGGCCGCCCC<br>AATAGAGAAGACTATATCCAAGGCTAAGGGACAGCCTCGAGAACCGCAGGTATATA<br>CGCTTCCTCCGTCTAGGGATGAACTCACAAAAAACCAGGTTTCTTTGACCTGCTTG<br>GTAAAGGGATTTTATCCCTCCGACATTGCGGTCGAATGGGAGAGCAACGGACAGCC<br>GGAAAACAATTACAAAACGACACCCCGGTTTTGGACTCTGATGGAAGCTTCTTCC<br>TCTATAGTAAGTTGACCGTAGACAAGTCTCGCTGGCAGCAGGGAAACGTCTTCAGT<br>TGCTCAGTTCTCCATGAGGCGTTGCATAGTCACTATACACAGAGAGTCTTAGTTT<br>GTCTCCAGGAGAAGGAGGTTCTGATTCTTGGCAAGAGGAGGTAATCAAATTGTGTG<br>GCCGAGAACTTGTTAGAGCTCAGATAGCCATCTGCGGACAGTCTACGGCGTCCGAT<br>GCGGCCGGAGCTAATGCTGACGCAGGTGCGCGACAGCTGTACTCCGCACTGGCGAA<br>TAAGTGCTGCCACGTGGGATGCACTAAGCGGTCTCTCGCGCAATTCTGT |
| 210 | ATGGAGACCGACACTCTTTTGCTCTGGGTGCTGTTGCTGTGGGTTCCAGGTTCAAC<br>GGGAGATAAAACCCACACCTGTCCACCATGCCCGGCGCCGGAAGCCGCCGGGGGAC<br>CCAGCGTATTTCTTTTCCCCCCAAGCCCAAAGACACGCTGATGATTTCACGAACG<br>CCGGAGGTGACTTGCGTGGTAGTGGACGTCTCCCATGAGGATCCCGAAGTTAAATT<br>TAATTGGTATGTAGATGGTGTTGAGGTCCATAATGCTAAAACAAAGCCGCGGGAAG<br>AGCAATATAACTCCACCTATAGAGTGGTCTCTGTACTCACTGTCCTGCACCAGGAT<br>TGGCTGAATGGGAAAGAGTACAAGTGTAAAGTTAGCAACAAAGCGCTCGCCGCGCC<br>TATCGAAAAAACGATTTCCAAAGCAAAGGGCCAACCACGAGAACCCCAGGTTTACA |

TABLE 10-continued

Nucleotide Sequences Encoding Fusion Proteins and Peptide Components

| SEQ ID NO: | Sequence |
|---|---|
|  | CCCTGCCACCCAGTCGAGATGAACTCACTAAGAATCAGGTGTCCCTTACATGCCTC<br>GTCAAGGGATTCTATCCGAGCGATATAGCGGTGGAATGGGAGAGTAACGGTCAACC<br>CGAAAATAACTATAAAACCACTCCGCCGGTACTCGATTCTGACGGTTCCTTCTTTC<br>TTTATTCCAAACTGACTGTAGACAAATCACGGTGGCAGCAGGGCAACGTGTTTAGC<br>TGCTCTGTACTCCATGAGGCCTTGCATTCTCATTATACTCAAAAGAGTCTGAGTCT<br>GAGTCCAGGTGAAGGGGGTTCCGATTCATGGCAAGAGGAAGTCATTAAACTCTGCG<br>GAAGGGAACTTGTAAGAGCACAAATCGCGATTTGTGGGCAATCTACCGCATCCGAC<br>GCGGCTGGAGCAGATGCAGATGCCGGAGCGAGGCAGCTGTATTCAGCATTGGCTAA<br>CAAATGTTGCCATGTTGGATGTACGAAGAGATCACTTGCACAGTTCTGT |
| 211 | ATGGAAACTGACACCCTCCTTCTCTGGGTACTGCTCTTGTGGGTTCCAGGCTCTAC<br>TGGCGATAAGACTCATACCTGCCCGCCCTGTCCCGCACCCGAGGCTGCCGGAGGGC<br>CATCAGTGTTCCTTTTCCCACCAAAGCCGAAGGATACACTTATGATCAGCAGGACA<br>CCCGAAGTGACCTGTGTAGTCGTAGACGTGTCCCACGAAGACCCCGAAGTAAAATT<br>TAATTGGTATGTCGATGGCGTAGAGGTCCACAACGCGAAAACGAAACCCCGCGAAG<br>AACAATATAATTCCACATACCGAGTTGTCAGCGTCCTCACTGTTCTCCATCAGGAC<br>TGGCTGAATGGGAAGGAATATAAGTGCAAGGTCTCAAACAAGGCGCTGGCGGCCCC<br>CATAGAGAAAACGATTTCTAAGGCCAAAGGACAGCCACGGGAACCGCAGGTCTATA<br>CGCTCCCACCTAGTAGGGATGAGTTGACCAAGAATCAGGTATCCCTCACATGTCTC<br>GTCAAGGGATTCTATCCCAGCGACATAGCCGTGGAGTGGGAATCTAACGGTCAACC<br>TGAGAATAACTATAAAACAACCCCCCGGTCCTCGACTCCGATGGTAGCTTCTTTC<br>TGTATTCCAAACTGACGGTAGATAAAAGCCGATGGCAACAGGGTAACGTCTTTAGT<br>TGTTCTGTATTGCACGAGGCGCTCCATAGTCACTACACACAGAAGTCTTTGAGCCT<br>CTCACCTGGGGAGGGGGGTAGCGATTCTTGGCAGGAGGAAGTGATCAAACTGTGCG<br>GCAGGGAACTGGTCAGAGCACAGATAGCAATATGCGGTCAGAGTACGGCCTCTGAC<br>GCCGCCGGTGCGGAGGCTGAGGCAGGGCGAGACAGCTCTACAGCGCTCTTGCAAA<br>TAAGTGTTGTCACGTGGGGTGCACAAAGAGATCCTTGGCGCAATTTTGT |
| 212 | ATGGAAACCGATACATTGCTTTTGTGGGTCTTGTTGCTGTGGGTGCCCGGTTCTAC<br>TGGTGATAAGACCCACACATGTCCGCCATGTCCAGCCCCAGAGGCAGCAGGGGGCC<br>CGTCCGTATTCTTGTTTCCCCCGAAACCCAAAGATACCCTTATGATTAGTCGAACT<br>CCAGAAGTCACGTGTGTGGTGGTGGACGTATCCCACGAGGACCCCGAAGTGAAATT<br>CAATTGGTATGTGGACGGGGTGGAAGTCCATAACGCTAAGACGAAGCCCAGAGAGG<br>AGCAGTACAATTCTACCTATCGGGTTGTATCTGTGCTTACTGTTCTCCATCAAGAT<br>TGGCTGAACGGGAAGGAATACAAATGTAAAGTTAGTAACAAAGCATTGGCAGCTCC<br>TATCGAAAAGACGATAAGCAAGGCTAAAGGTCAACCCCGAGAGCCTCAGGTCTACA<br>CTTTGCCGCCCTCCAGGGATGAGCTTACCAAGAACCAAGTGAGCTTGACGTGTCTC<br>GTGAAGGGATTCTACCCATCAGATATAGCGGTAGAATGGGAGTCTAATGGGCAGCC<br>CGAGAACAACTATAAGACCACCCCTCCCGTTCTTGACTCCGACGGTTCCTTTTTCT<br>TGTACTCCAAACTCACGGTCGACAAGTCTAGGTGGCAGCAAGGCAATGTTTTCAGT<br>TGTTCCGTGCTGCACGAAGCTCTTCATTCTCACTATACGCAAAAAAGCCTGAGTCT<br>TTCACCTGGAGAGGGGGGTTCCGATTCTTGGCAGGAAGAAGTCATTAAGCTGTGCG<br>GCAGAGAACTTGTGCGCGCACAAATTGCTATTTGTGGACAGTCAACTGCATCTGAC<br>GCCGCTGGAGCCCAAGCGGACGCAGGGGCAAGGCAGCTTTATTCAGCGCTTGCGAA<br>TAAGTGTTGCCATGTGGGTTGCACGAAACGAAGCCTGGCGCAATTTTGT |
| 213 | ATGGAGACTGATACATTGTTGCTTTGGGTACTCTTGCTTTGGGTGCCCGGAAGTAC<br>AGGGGATAAGACACATACATGTCCTCCCTGTCCCGCTCCGGAGGCAGCCGGTGGGC<br>CTTCAGTTTTCTTGTTTCCGCCGAAGCCTAAGGACACGTTGATGATATCCCGAACA<br>CCAGAGGTCACATGCGTCGTCGTGGACGTCTCACACGAGGACCCTGAAGTGAAATT<br>CAACTGGTATGTAGACGGGGTCGAAGTTCACAATGCGAAAACTAAACCTCGCGAGG<br>AGCAATATAACTCAACATACCGCGTAGTGTCCGTCTTGACTGTCCTTCATCAGGAT<br>TGGCTGAATGGTAAAGAATATAAATGTAAAGTTTCTAATAAAGCGCTTGCGGCACC<br>CATTGAGAAGACAATTTCCAAAGCCAAAGGCCAACCCCGAGAGCCTCAGGTATATA<br>CGCTGCCTCCGTCTCGAGATGAGTTGACAAAAAATCAAGTCAGCTTGACTTGTCTT<br>GTAAAGGGGTTCTATCCGTCAGACATAGCAGTGGAGTGGGAATCCAACGGGCAACC<br>AGAAAATAATTACAAAACCACTCCGCCCGTGCTTGACTCAGATGGGAGCTTCTTCC<br>TTTATAGCAAACTTACGGTAGATAAATCCAGATGGCAGCAAGGCAACGTATTCAGC<br>TGTAGTGTGCTGCATGAAGCGCTTCACTCCCATTATACTCAAAAATCTCTTTCTCT<br>GTCACCGGGCGAGGGCGGAAGTGATAGTTGGCAGGAAGAGGTCATCAAGCTCTGTG<br>GGAGAGAGCTTTGTACGCGCTCAGATTGCTATATGCGGCCAGTCAACTGCAAGCGAT<br>GCAGCGGGTGCCGATGCCCAAGCGGGGGCACGGCAACTCTACTCAGCCCTCGCGAA<br>TAAATGTTGTCATGTAGGGTACTAAGAGAAGCCTCGCGCAATTTTGT |
| 214 | ATGGAAACTGATACTCTTCTTTTGTGGGTACTGTTGTTGTGGGTCCCAGGAAGTAC<br>CGGCGATAAAACGCATACTTGCCCGCCGTGCCCAGCACCTGAGGCAGCCGGCGGCC<br>CTAGTGTCTTCTTGTTCCCGCCAAGCCCAAGGATACACTCATGATCTCCCGAACG<br>CCAGAGGTCACATGCGTAGTTGTTGACGTTTCCCATGAGGACCCTGAAGTGAAATT<br>TAACTGGTACGTCGACGGCGTTGAGGTTCACAACGCTAAGACTAAGCCAAGAGAGG<br>AACAGTACAATTCAACTTATAGAGTGGTGTCTGTATTGACAGTTCTCCATCAGGAT<br>TGGCTGAACGGAAAAGAATATAAGTGCAAGGTCTCAAATAAGGCGCTCGCTGCACC<br>CATAGAAAAACCATATCAAAAGCGAAGGGGCAACCAAGAGAACCCAGGTGTACA<br>CGCTCCCCCCGTCCAGAGATGAACTCACGAAGAATCAAGTGTCACTCACATGTCTT<br>GTAAAGGGGTTCTACCCCTCTGATATTGCCGTAGAATGGGAAAGCAACGGACAGCC |

TABLE 10-continued

Nucleotide Sequences Encoding Fusion Proteins and Peptide Components

| SEQ ID NO: | Sequence |
|---|---|
|  | CGAGAATAACTACAAGACGACACCGCCAGTTCTTGATTCTGACGGAAGCTTTTTCC<br>TCTATTCAAAATTGACCGTTGACAAGTCCCGATGGCAACAGGGCAACGTTTTCTCA<br>TGCTCCGTCCTTCACGAAGCCTTGCATTCCCACTATACGCAGAAGAGTCTCTCTTT<br>GAGCCCCGGAGAGGGAGGCAGTGATTCATGGCAAGAGGAAGTGATCAAACTTTGCG<br>GCAGAGAATTGGTTAGAGCCCAGATTGCCATTTGTGGACAAAGTACGGCCTCAGAT<br>GCTGCGGGGCACAAGCTCAGGCGGGCGCACGCCAGTTGTACAGTGCTCTGGCGAA<br>TAAGTGCTGCCACGTTGGTTGCACCAAGCGATCCTTGGCGCAATTTTGC |
| 215 | ATGGAAACAGATACGCTCCTTTTGTGGGTACTGTTGTTGTGGGTGCCCGGCTCTAC<br>GGGCGACAAGACTCATACTTGTCCGCCCTGCCCCGCTCCTGAGGCTGCCGGAGGCC<br>CTTCAGTATTCTTGTTTCGCCGAAACCGAAGGATACCTTGATGATTAGTAGGACA<br>CCGGAAGTCACCTGCGTAGTGGTGGACGTAAGCCACGAAGATCCCGAAGTAAAGTT<br>TAATTGGTATGTTGATGGCGTAGAGGTGCATAATGCGAAAACCAAACCTAGGGAGG<br>AACAGTACAATAGTACTTACCGCGTAGTGTCAGTGCTTACCGTGCTGCATCAGGAC<br>TGGCTTAATGGGAAGGAATACAAATGTAAAGTATCCAATAAAGCGCTGGCGGCTCC<br>CATCGAGAAAACGATCTCAAAAGCCAAAGGACAACCACGGGAACCGCAGGTCTATA<br>CTCTGCCACCTTCAAGAGACGAACTTACCAAGAACCAAGTCTCATTGACGTGCTTG<br>GTAAAAGGTTTTTATCCGTCTGACATCGCTGTTGAATGGGAGTCTAACGGCCAGCC<br>GGAGAACAATTACAAAACAACTCCACCAGTCTTGGATTCAGATGGGTCTTTTTTTT<br>TGTATTCAAAGCTTACCGTTGACAAAAGCCGCTGGCAACAAGGAAACGTTTTCAGC<br>TGCAGTGTGCTGCACGAAGCGCTCCACAGTCATTATACCCAGAAATCTTTGAGCCT<br>GTCTCCAGGGGAAGGTGGGAGTGACTCTTGGCAAGAAGAGGTTATCAAACTTTGCG<br>GGCGGGAGCTGGTAAGGGCCCAAATTGCAATATGCGGCAAAAGTACTGCATCTGAT<br>GCCGCTGGGGCCGATGCTAACGCGGGCGCAAGACAACTTTATAGCGCGTTGGCGAA<br>CAAATGCTGTCATGTGGGATGCACCAAACAAAGTTTGGCGCAATTTTGT |
| 216 | ATGGAAACCGATACCTTGCTGCTTTGGGTGCTCTTGCTGTGGGTTCCCGGTTCCAC<br>GGGTGATAAAACTCACACGTGTCCGCCATGCCCCGCACCTGAAGCGGCGGGTGGTC<br>CGAGCGTGTTTTTGTTTCCGCCTAAGCCCAAGGATACCCTGATGATTAGTCGGACA<br>CCCGAAGTAACATGTGTCGTCGTGGATGTAAGTCACGAGGATCCCGAAGTGAAATT<br>CAACTGGTATGTGGATGGAGTTGAAGTCCATAATGCGAAAACAAAACCGAGAGAGG<br>AACAGTACAACTCAACATACCGGGTGGTAAGTGTACTGACGGTACTCCACCAGGAC<br>TGGCTGAATGGTAAGGAGTACAAATGCAAAGTTTCAAATAAGGCGCTCGCTGCCCC<br>CATCGAGAAACCATTAGTAAGGCTAAAGGTCAACCTAGGGAGCCACAAGTATATA<br>CATTGCCGCCTTCTAGAGATGAGCTGACCAAAAACCAGGTCAGCCTGACCTGTTTG<br>GTGAAAGGCTTCTATCCAAGCGACATTGCTGTCGAGTGGGAGTCAAATGGGCAGCC<br>GGAAAATAACTATAAAACGACTCCTCCTGTTCTCGACTCCGATGGTTCATTCTTCC<br>TCTACTCAAAGCTTACCGTGGATAAATCCAGGTGGCAACAAGGTAACGTGTTCTCA<br>TGTTCCGTTCTGCACGAAGCACTGCATTCCCATTATACACAAAAATCCCTGAGCCT<br>CTCACCTGGGGAGGGCGGAAGCGATAGTTGGCAAGAGGAAGTAATAAAGCTGTGTG<br>GCAGGGAACTCGTAAGGGCTCAGATTGCGATATGTGGAAAAAGCACTGCTTCTGAC<br>GCCGCAGGGGCCAACGCAGATGCTGGCGCCCGACAACTCTATTCTGCGCTTGCGAA<br>CAAGTGTTGTCATGTAGGATGTACCAAGCAAAGCCTTGCTCAGTTCTGT |
| 217 | ATGGAGACCGATACACTCTTGCTCTGGGTCCTTCTTCTTTGGGTTCCAGGCTCCAC<br>AGGAGACAAAACCCACACTTGTCCGCCCTGTCCCGCTCCGGAGGCTGCAGGCGGCC<br>CAAGTGTGTTTCTTTTCCCCCAAAGCCGAAAGACACCTTGATGATATCCCGCACA<br>CCCGAAGTGACTTGCGTTGTCGTCGACGTGTCTCATGAGGACCCAGAAGTCAAGTT<br>TAATTGGTACGTTGATGGCGTGGAAGTTCACAATGCGAAAACTAAGCCCAGAGAGG<br>AGCAATATAACTCAACCTACCGGGTGGTAAGTGTTCTGACAGTTCTCCACCAGGAC<br>TGGTTGAACGGAAAAGAATACAAATGCAAAGTGAGTAACAAAGCCCTGGCTGCCCC<br>TATCGAAAAGACCATATCCAAAGCGAAGGGCCAGCCACGGGAACCGCAAGTATATA<br>CACTTCCACCATCTAGAGATGAGCTTACAAAGAACCAGGTGTCCCTTACCTGCCTT<br>GTCAAAGGCTTCTATCCCTCTGACATCGCAGTGGAGTGGGAGTCCAACGGACAACC<br>AGAGAACAACTATAAGACAACGCCGCCAGTACTGGATTCAGATGGTTCATTCTTCT<br>TGTATTCTAAACTGACTGTTGATAAATCCCGATGGCAGCAGGGCAACGTTTTTAGT<br>TGTAGTGTTCTGCACGAAGCCCTTCATTCCCATTATACACAAAAATCTCTTTCCCT<br>CAGCCCAGGCGAGGGAGGAAGTGACAGTTGGCAAGAGGAGGTGATAAAGCTCTGTG<br>GGAGGGAGCTGGTACGCGCACAGATTGCAATCTGCGGAAAGAGCACAGCAAGCGAT<br>GCTGCTGGGGCCGATGCCGATGCTGGCGCTCGACAATTGTATTCAGCTCTTGCTAA<br>CAAATGCTGTCACGTAGGATGCACTAAACAGAGCCTTGCTCAATTTTGT |
| 218 | ATGGAAACCGACACTCTTCTGCTGTGGGTTCTTCTCCTGTGGGTGCCTGGATCAAC<br>CGGAGATAAGACCCACACATGTCCACCATGCCCAGCCCCAGAAGCGGCAGGTGGTC<br>CTTCTGTGTTTCTCTTTCCTCCCAAACCGAAAGATACTCTGATGATAAGCCGGACC<br>CCAGAAGTTACGTGCGTTGTAGTAGACGTGTCTCACGAGGACCCAGAAGTGAAGTT<br>TAACTGGTATGTCGACGGTGTAGAAGTTCATAATGCGAAAACAAAGCCCAGGGAAG<br>AACAATATAATTCAACGTACCGGGTCGTTTCCGTGCTGACAGTTCTGCACCAAGAT<br>TGGCTCAACGGGAAAGAGTACAAATGCAAGTATCAAATAAGGCCTTGGCTGCGCC<br>GATTGAAAAGACGATTTCCAAAGCAAGGGCCAGCCAAGGGAACCCCAGGTCTATA<br>CCCTCCCTCCTAGCAGAGATGAACTTACAAAAAACCAAGTCTCCCTCACCTGCCTG<br>GTCAAAGGATTCTATCCCTCAGATATAGCAGTAGAATGGGAAAGTAACGGGCAGCC<br>CGAAACAATTATAAGACCACTCCTCCAGTACTCGATTCAGACGGTAGCTTCTTTC<br>TGTATTCCAAGCTGACCGTAGATAAAAGTAGGTGGCAGCAAGGTAATGTCTTCTCA |

TABLE 10-continued

Nucleotide Sequences Encoding Fusion Proteins and Peptide Components

| SEQ ID NO: | Sequence |
|---|---|
| | TGTAGTGTACTTCATGAGGCGTTGCATTCCCATTACACGCAAAAGTCTTTGAGTCT<br>CAGTCCGGGTGAAGGAGGTAGCGATTCTTGGCAGGAAGAAGTAATTAAGCTGTGCG<br>GCCGGGAGCTCGTCAGGGCTCAGATAGCTATATGCGGCAAGAGCACGGCCAGTGAT<br>GCTGCTGGTGCAGAGGCTGAAGCAGGTGCCAGGCAGTTGTACAGCGCACTCGCTAA<br>TAAGTGTTGCCACGTGGGGTGTACAAAGCAATCTTTGGCACAATTCTGT |
| 219 | ATGGAGACTGATACTTTGCTGCTGTGGGTTCTCCTTCTTTGGGTCCCAGGTTCCAC<br>AGGAGATAAGACCCATACTTGTCCTCCGTGCCCGGCACCAGAGGCTGCGGGTGGCC<br>CATCCGTTTTCCTGTTTCCGCCAAAGCCTAAGGATACTCTGATGATTTCACGCACA<br>CCCGAAGTGACCTGCGTGGTGGTCGACGTATCTCACGAAGACCCAGAGGTAAAATT<br>CAATTGGTACGTGGACGGCGTCGAGGTTCATAACGCGAAAACTAAGCCGAGAGAAG<br>AGCAGTACAACTCTACGTATCGCGTGGTGTCCGTACTGACAGTATTGCATCAGGAC<br>TGGTTGAATGGCAAGGAGTATAAGTGCAAGGTATCTAATAAGGCATTGGCTGCCCC<br>AATAGAGAAAACGATCAGCAAAGCAAAGGGGCAGCCGCGCGAGCCGCAGGTATATA<br>CACTTCCACCATCACGGGATGAGTTGACGAAAAATCAAGTCTCTCTCACATGTCTG<br>GTAAAAGGTTTCTATCCTTCTGATATCGCCGTGGAATGGGAAAGCAACGGCCAACC<br>CGAAAACAACTATAAGACGACGCCGCCGGTACTCGACAGCGACGGAAGCTTTTTCT<br>TGTATTCCAAGTTGACAGTGGACAAGTCTCGATGGCAGCAAGGAAACGTGTTCTCA<br>TGTTCTGTTCTTCACGAAGCCCTTCATAGCCATTATACTCAGAAATCTCTCTCACT<br>CTCCCCAGGTGAAGGGGAAGTGACTCTTGGCAAGAAGAAGTCATTAAGCTTTGCG<br>GTCGAGAATTGGTTCGGGCTCAAATAGCTATTTGTGGCAAGTCCACGGCAAGTGAT<br>GCAGCGGGGCTCAGGCAGACGCGGGCGCAAGGCAGCTTTATTCCGCACTTGCAAA<br>TAAGTGCTGTCACGTCGGATGTACTAAACAATCACTTGCACAATTCTGC |
| 220 | ATGGAGACCGACACACTTCTCCTCTGGGTCCTGCTCCTTTGGGTGCCAGGCAGTAC<br>AGGTGACAAGACACATACATGTCCCCCATGCCCTGCACCCGAAGCTGCTGGGGGGC<br>CCAGCGTGTTCCTGTTTCCGCCAAGCCCAAGGACACATTGATGATTAGTAGAACC<br>CCAGAGGTAACTTGTGTTGTGGTCGATGTGTCACATGAAGACCCCGAGGTAAAGTT<br>TAACTGGTATGTGGATGGGGTAGAGGTACATAATGCAAAAACCAAGCCGCGGGAGG<br>AGCAGTATAATTCAACCTATCGAGTCGTGTCAGTCTTGACCGTGCTCCACCAGGAC<br>TGGCTTAACGGTAAGGAGTATAAATGCAAAGTCAGTAATAAGGCATTGGCCGCCCC<br>CATTGAGAAGACCATCAGTAAAGCTAAGGGGCAACCTAGAGAGCCACAGGTTTACA<br>CCCTCCCTCCCTCCCGGGATGAACTCACCAAAAACCAGGTGTCCCTTACTTGTTTG<br>GTAAAGGGCTTTTATCCTTCTGATATTGCTGTTGAATGGGAGTCTAACGGGCAACC<br>TGAAAATAACTACAAAACAACTCCCCCCGTTCTGGACTCTGATGGGTCATTCTTCC<br>TTTATTCAAAATTGACAGTTGATAAGAGTAGATGGCAACAAGGCAACGTATTTTCA<br>TGTTCTGTGCTCCACGAGGCTCTCCATTCCCACTACACACAGAAAAGTCTCTCACT<br>GTCCCCAGGAGAGGGCGGGAGCGACTCTTGGCAGGAAGAAGTAATCAAGTTGTGTG<br>GCAGGGAACTCGTACGCGCTCAGATTGCAATATGCGGGAAATCCACGGCAAGTGAC<br>GCTGCCGGGCCGACGCGCAAGCAGGGGCACGGCAGCTTTACTCCGCCCTCGCAAA<br>TAAATGTTGTCATGTGGGATGCACTAAACAGTCCCTTGCCCAGTTTTGC |
| 221 | ATGGAGACAGATACACTGCTTCTGTGGGTGCTCTTGCTTTGGGTCCCCGGTTCCAC<br>AGGCGATAAAACCCATACCTGTCCACCATGCCCCGCGCCAGAGGCAGCGGGTGGTC<br>CAAGCGTTTTCCTTTTTCCACCGAAACCAAAAGATACACTTATGATATCAAGGACC<br>CCCGAGGTAACGTGCGTCGTAGTTGACGTTTCTCACGAAGATCCCGAGGTGAAATT<br>CAATTGGTACGTAGATGGTGTAGAGGTACACAATGCGAAGACAAAACCGCGGGAAG<br>AGCAGTATAATAGCACATACAGAGTCGTGAGCGTCCTCACCGTACTTCACCAAGAT<br>TGGCTGAATGGAAAGGAGTACAAATGTAAGGTAAGTAATAAAGCACTTGCGGCCCC<br>CATCGAGAAAACTATCAGTAAAGCAAAGGGCAACCACGAGAACCCCAGGTCTACA<br>CTTTGCCACCATCACGGGATGAACTGACAAAAAATCAGGTGTCACTCACTTGCCTT<br>GTTAAAGGGTTCTATCCTAGTGACATAGCGGTAGAATGGGAGTCTAACGGGCAGCC<br>TGAGAACAATTATAAAACTACGCCCCCTGTTCTTGATTCCGATGGATCATTTTTTC<br>TCTACTCCAAACTCACCGTAGACAAATCCCGCTGGCAGCAGGGCAACGTGTTTAGT<br>TGCAGCGTTCTTCACGAAGCACTTCACTCACATTACACACAAAAGTCCCTGAGCTT<br>GAGTCCTGGGGAGGGTGGATCTGATTCTTGGCAGGAAGAAGTTATAAAACTTTGTG<br>GCAGAGAGTTGGTCCGCGCACAAATCGCCATATGTGGTAAAAGCACAGCGTCTGAC<br>GCGGCGGGAGCGCAAGCCCAGGCGGGGCTCGGCAACTCTACTCAGCCCTGGCTAA<br>CAAGTGCTGTCACGTGGGATGCACTAAACAAAGTCTGGCGCAGTTCTGC |
| 222 | ATGGAGACCGATACGTTGCTGTTGTGGGTTTTGTTGCTGTGGGTACCTGGATCTAC<br>AGGTGACAAAACCCATACGTGTCCCCCGTGTCCGGCTCAGAGGCTGCGGGAGGAC<br>CGTCTGTGTTCTTGTTCCCGCCAAGCCTAAAGATACGCTGATGATTAGTCGGACC<br>CCCGAGGTGACCTGCGTGGTAGTAGACGTATCTCATGAAGATCCGGAAGTAAAGTT<br>TAACTGGTACGTAGACGGCGTCGAGGTACATAATGCCAAGACGAAACCCAGAGAAG<br>AGCAATATAATAGCACTTATCGAGTTGTAAGCGTATTGACGGTCCTTCACCAGGAC<br>TGGTTGAACGGCAAAGAGTACAAATGTAAGGTATCCAATAAAGCATTGGCTGCGCC<br>AATTGAAAAGACAATTTCCAAAGCGAAGGGGCAACCTCGAGAGCCGCAAGTCTACA<br>CGCTGCCACCGAGTAGGGATGAATTGACTAAGAATCAGGTGAGTCTCACGTGTCTC<br>GTGAAGGGGTTTTACCCCAGTGATATTGCGGTAGAATGGGAGTCCAACGGTCAGCC<br>AGAAAATAATTATAAAACAACGCCCCTGTATTGGATTCTGACGGGAGCTTTTTCC<br>TGTACTCAAAACTCACCGTAGATAAGAGTCGCTGGCAACAGGGCAACGTATTCTCA<br>TGTAGCGTTCTGCACGAGGCGCTGCACTCTCACTACACACGAAGAGTTTGAGTTT<br>GTCCCCTGGCGAAGGAGGTTCTGATTCCTGGCAGGAGGAGGTGATTAAGCTGTGTG |

TABLE 10-continued

Nucleotide Sequences Encoding Fusion Proteins and Peptide Components

| SEQ ID NO: | Sequence |
|---|---|
|  | GCCGCGAATTGGTGAGGGCTCAAATTGCTATTTGCGGACAGAGCACAGCGTCCGAT<br>GCCGCCGGCGCAGATGCTAATGCCGGTGCAAGGCAACTGTACTCCGCTCTCGCCAA<br>TAAGTGTTGTCATGTCGGCTGCACCAAGCAATCCCTGGCCCAGTTTTGC |
| 223 | ATGGAGACAGATACGCTCTTGCTGTGGGTACTCCTCCTCTGGGTCCCAGGCTCAAC<br>GGGCGACAAGACTCACACTTGTCCCCCATGTCCAGCACCGGAAGCTGCCGGCGGTC<br>CCTCAGTTTTCCTTTTCCCCCCCAAACCCAAGGACACCCTTATGATTTCAAGGACA<br>CCAGAGGTAACGTGCGTAGTGGTGGACGTCAGTCATGAAGACCCAGAGGTAAAGTT<br>TAACTGGTACGTGGATGGGGTAGAGGTTCATAATGCTAAAACAAAACCACGCGAGG<br>AACAGTACAATAGTACGTATAGAGTGGTCTCCGTTCTTACGGTGCTGCATCAGGAC<br>TGGCTGAACGGAAAAGAGTACAAGTGTAAGGTTAGCAATAAGGCGCTGGCGGCCCC<br>AATCGAAAAGACGATTTCTAAGGCCAAAGGCCAGCCAAGGGAGCCACAAGTATATA<br>CCCTTCCCCCTTCCCGAGATGAGCTGACTAAGAATCAAGTCAGTCTCACCTGCCTT<br>GTCAAAGGGTTCTACCCATCCGATATTGCTGTTGAATGGGAGTCTAATGGCCAGCC<br>GGAGAACAATTACAAGACAACTCCGCCTGTATTGGATTCCGACGGGTCTTTTTTCC<br>TCTATTCAAAACTCACAGTAGACAAAAGTCGATGGCAGCAAGGTAACGTGTTTTCT<br>TGCTCTGTGTTGCATGAAGCACTTCATTCTCATTATACTCAAAAATCATTGAGCCT<br>CAGTCCAGGCGAAGGGGTAGTGACTCATGGCAGGAGGAGGTAATCAAGCTTTGCG<br>GACGAGAGTTGGTCAGGGCCCAGATAGCTATTTGTGGTCAGTCCACGGCGAGTGAC<br>GCAGCAGGGGCGAATGCCGATGCAGGAGCAAGACAACTGTATTCTGCTCTGGCCAA<br>CAAGTGTTGTCATGTAGGGTGTACTAAACAAAGTCTCGCCCAGTTCTGC |
| 224 | ATGGAAACGGATACGCTGTTGTTGTGGGTCTTGCTCCTGTGGGTCCCCGGATCCAC<br>AGGTGATAAAACCCACACCTGTCCCCCATGTCCGGCTCCCGAAGCAGCGGGGGCC<br>CTTCAGTTTTTCTCTTTCCCCCCAAACCGAAAGACACGCTGATGATTAGCAGAACT<br>CCAGAGGTTACCTGTGTAGTTGTGGACGTTTCACACGAGGATCCCGAGGTTAAATT<br>CAACTGGTATGTGGACGGCGTCGAAGTGCATAATGCAAAAACAAAGCCCCGGGAAG<br>AACAATATAATAGTACCTATAGGGTCGTTTCCGTACTGACCGTACTTCATCAAGAT<br>TGGCTCAATGGGAAGGAATACAAATGTAAAGTGAGTAATAAAGCCCTGGCGGCACC<br>GATCGAAAAAACCATTTCAAAGGCTAAGGGACAACCGCGCGAACCTCAGGTCTATA<br>CCTTGCCCCCTTCACGCGACGAGCTTACGAAGAATCAGGTAAGCCTTACTTGTCTT<br>GTCAAGGGTTTTTACCCCAGCGACATAGCTGTCGAGTGGGAATCCAATGGCCAACC<br>GGAGAATAATTACAAAACTACCCCTCCTGTTCTTGATAGCGACGGAAGCTTCTTCT<br>TGTATTCCAAACTCACAGTAGATAAAAGTAGGTGGCAGCAGGGCAATGTATTTTCT<br>TGCAGCGTCCTGCATGAAGCACTGCATAGCCATTATACTCAAAAGTCCCTGTCTTT<br>GTCTCCTGGAGAGGGCGGAAGCGATTCTTGGCAAGAGGAAGTTATTAAGCTGTGCG<br>GGCGCGAACTTGTGAGGGCTCAAATAGCGATATGTGGTCAGAGCACCGCTAGCGAT<br>GCGGCTGGTGCAGACGCCGATGCCGGTGCTAGGCAACTTTACAGTGCACTTGCGAA<br>TAAGTGCTGTCACGTCGGATGTACTAAACAAGCCTCGCCCAGTTCTGC |
| 225 | ATGGAAACGGATACTCTTCTTTTGTGGGTTCTTCTTCTGTGGGTACCAGGAAGTAC<br>TGGTGATAAAACACATACTTGCCCTCCTTGTCCGGCTCCCGAAGCCGCAGGTGGAC<br>CTTCCGTCTTTCTTTTCCCACCCAAACCTAAAGACACTTTGATGATTAGCCGGACC<br>CCCGAGGTAACCTGTGTCGTAGTTGACGTTTCCCATGAAGACCCCGAAGTTAAGTT<br>CAACTGGTATGTCGACGGCGTCGAGGTGCACAACGCGAAGACTAAGCCAAGAGAGG<br>AGCAATACAATTCAACTTACAGGGTCGTGTCCGTCTTGACAGTGCTTCATCAAGAC<br>TGGCTTAATGGAAAGGAATACAAATGTAAAGTCTCCAACAAGGCTCTCGCAGCGCC<br>CATTGAGAAAACGATATCCAAAGCGAAGGGTCAACCAAGAGAACCCCAGGTTTACA<br>CCCTCCCCCCTAGTCGGGACGAGCTTACGAAGAACCAGGTCAGTTTGACATGCCTG<br>GTGAAAGGCTTCTATCCGTCAGACATCGCCGTAGAGTGGGAAAGCAACGGGCAACC<br>CGAGAACAACTATAAGACGACTCCCCCGGTGTTGGATAGCGATGGCTCTTTCTTCC<br>TGTACTCTAAGCTGACCGTAGATAAATCAGGTGGCAACAGGGGAACGTGTTTTCA<br>TGCTCAGTGCTCCATGAAGCCCTCCATTCACACTATACACAAAAGTCTTTGTCACT<br>GTCCCCCGGTGAAGGCGGCAGTGATAGCTGGCAAGAAGAAGTCATAAAGCTCTGTG<br>GTCGCGAGCTTGTTAGGGCCCAAATTGCGATCTGTGGTCAGTCAACGGCTTCTGAC<br>GCCGCCGGAGCGGAAGCCGAGGCGGGTGCTCGGCAATTGTATTCAGCACTGGCGAA<br>CAAATGTTGCCATGTTGGTTGTACTAAACAAAGCCTGGCCCAGTTTTGC |
| 226 | ATGGAGACCGATACCTTGTTGCTGTGGGTGCTTCTTCTCTGGGTTCCGGGATCTAC<br>AGGAGACAAGACTCACACTTGTCACCCTGTCCAGCACCTGAAGCCGCTGGTGGAC<br>CATCTGTCTTTCTGTTCCCCCCTAAACCAAAGGATACACTTATGATCAGCAGAACA<br>CCTGAAGTCACATGCGTTGTGGTAGACGTTTCCCACGAGGATCCTGAAGTGAAGTT<br>TAACTGGTACGTGGATGGCGTTGAGGTTCATAATGCCAAGACGAAACCTCGGGAGG<br>AGCAGTATAATTCTACTTATAGGGTGGTAAGCGTACTGACAGTCCTCCATCAAGAC<br>TGGTTGAACGGGAAGGAATACAAGTGTAAAGTTTCCAACAAAGCTCTGGCGGCGCC<br>TATAGAAAAGACAATATCAAAAGCGAAAGGCAACCCAGAGAGCCTCAAGTATATA<br>CATTGCCCCCTAGCAGAGACGAATTGACGAAAAATCAGGTCTCTCTCACGTGCCTC<br>GTGAAGGGCTTCTATCCTAGTGATATAGCTGTGGAATGGGAATCCAATGGACAGCC<br>AGAAAACAACTACAAGACCACGCCCCCGTCTTGGATTCCGACGGGTCATTCTTCC<br>TGTACAGCAAGCTGACTGTCGACAAGAGTCGATGGCAACAGGGCAACGTCTTTAGC<br>TGCAGCGTCCTGCACGAAGCTCTGCATAGTCATTACACCCAAAAGTCCCTTTCTCT |

TABLE 10-continued

Nucleotide Sequences Encoding Fusion Proteins and Peptide Components

| SEQ ID NO: | Sequence |
|---|---|
|  | CTCCCCTGGTGAAGGCGGTTCCGATTCATGGCAAGAAGAAGTAATTAAGCTCTGTG<br>GACGAGAGCTTGTCCGAGCACAAATTGCGATCTGCGGGCAGAGTACCGCATCTGAC<br>GCTGCTGGCGCGCAGGCAGATGCGGGTGCACGGCAGCTTTATTCAGCTCTCGCCAA<br>CAAGTGTTGTCATGTGGGGTGTACAAAGCAGAGCCTTGCCCAGTTTTGT |
| 227 | ATGGAAACGGACACACTGCTGCTTTGGGTTCTCTTGCTGTGGGTCCCAGGCTCTAC<br>AGGGGATAAGACCCATACGTGTCCCCCTTGCCCTGCACCCGAGGCGGCTGGGGGCC<br>CTTCCGTATTCTTGTTTCCTCCTAAGCCCAAAGATACCTTGATGATAAGTCGAACG<br>CCAGAAGTGACTTGCGTTGTTGTGGATGTCTCCCACGAGGATCCAGAAGTCAAATT<br>TAACTGGTATGTCGATGGGGTCGAAGTGCATAATGCTAAAACGAAACCCAGAGAGG<br>AACAATACAATTCAACATACCGCGTAGTCAGTGTTCTTACTGTGCTCCATCAGGAT<br>TGGCTCAATGGGAAAGAATACAAGTGTAAAGTCTCAAATAAAGCATTGGCGGCCCC<br>TATAGAGAAGACCATAAGCAAGGCTAAAGGTCAGCCTAGGGAGCCTCAAGTATATA<br>CCTTGCCTCCTAGCAGAGATGAGTTGACCAAGAACCAGGTCAGCCTCACATGCCTG<br>GTGAAAGGGTTTTACCCATCTGATATTGCCGTCGAGTGGGAAAGTAATGGGCAGCC<br>AGAGAACAACTACAAGACGACACCACCGGTACTGGATAGTGACGGAAGTTTTTTC<br>TTTACAGTAAGCTCACAGTCGACAAAAGCCGGTGGCAACAAGGAAATGTATTTTCA<br>TGTAGCGTACTTCATGAAGCCCTCCACTCTCATTACACGCAGAAGTCACTTTCACT<br>TAGTCCGGGTGAGGGTGGAAGCGATAGCTGGCAAGAGGAGGTTATCAAGCTCTGTG<br>GACGAGAACTCGTGAGAGCGCAAATTGCAATCTGCGGGCAGAGCACGGCGAGTGAT<br>GCGGCCGGGCGGACGCGCAAGCAGGAGCACGACAACTTTATAGTGCTTTGGCTAA<br>TAAATGTTGCCACGTTGGATGTACTAAACAGAGCTTGGCACAGTTTTGC |
| 228 | ATGGAGACTGATACACTGCTTCTGTGGGTATTGTTGTTGTGGGTCCCCGGTTCCAC<br>AGGTGATAAAACGCACACTTGTCCGCCATGTCCGGCACCTGAGGCAGCGGGAGGAC<br>CGTCCGTGTTTCTGTTTCCCCCTAAACCAAAGGACACGCTGATGATCAGCCGAACA<br>CCTGAAGTAACATGCGTGGTCGTTGACGTGTCTCACGAGGATCCAGAAGTAAAGTT<br>CAATTGGTATGTTGACGGAGTTGAAGTACATAATGCTAAGACTAAACCCCGCGAAG<br>AACAATATAATTCTACGTACAGAGTTGTATCCGTGCTCACGGTACTTCACCAAGAT<br>TGGCTTAACGGGAAGAATATAAGTGTAAGGTCTCAAATAAGGCCCTGGCTGCTCC<br>GATCGAAAAAACGATATCAAAGGCAAAGGGTCAACCTCGGGAGCCTCAAGTATATA<br>CCCTCCCCCCATCTAGGGATGAGCTGACAAAGAACCAAGTTTCACTGACCTGTCTC<br>GTAAAGGGTTTCTATCCTTCTGACATCGCAGTTGAATGGGAGTCCAACGGCCAACC<br>AGAGAACAACTATAAGACGACACCCCCGTGTTGGACAGTGACGGAAGTTTTTTCC<br>TGTACTCCAAGCTGACGGTTGATAAAAGTAGATGGCAACAAGGAAATGTTTTCAGT<br>TGTTCTGTGTTGCACGAGGCCCTCCACTCACACTATACCCAAAAAGTTTGTCTCT<br>GAGTCCCGGTGAAGGCGGGAGCGATTCATGGCAGGAGGAAGTAATCAAACTTTGTG<br>GGCGAGAACTGGTCAGGGCGCAAATAGCGATATGTGGGCAAAGCACAGCTTCAGAT<br>GCAGCCGGTGCTCAAGCTCAGGCTGGAGCTCGACAGCTTTATAGCGCCTTGGCTAA<br>TAAATGTTGTCACGTTGGCTGTACGAAGCAGAGCCTGGCACAGTTCTGC |
| 229 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCGAAGCGGAAGCTGGTGCAAGGCAGCTTTACTCTGCTCTGGCTAA<br>CAAGTGTTGTCACGTTGGGTGTACCAAGCGGTCCCTTGCGCAATTCTGC |
| 230 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATTTCAAGAAGAAGTCATTAAACTTTGTG<br>GACGGGAGCTGGTTAGGGCACAGATTGCTATTTGTGGTAAGTCTACGGCTAGTGAC |

TABLE 10-continued

Nucleotide Sequences Encoding Fusion Proteins and Peptide Components

| SEQ ID NO: | Sequence |
|---|---|
| | GCAGCGGGCGCCGAAGCGGAAGCTGGTGCAAGGCAGCTTTACTCTGCTCTGGCTAA<br>CAAGTGTTGTCACGTTGGGTGTACCAAGCGGTCCCTTGCGCAATTCTGC |
| 231 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCACTTCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCGAAGCGGAAGCTGGTGCAAGGCAGCTTTACTCTGCTCTGGCTAA<br>CAAGTGTTGTCACGTTGGGTGTACCAAGCGGTCCCTTGCGCAATTCTGC |
| 232 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCAATTCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCGAAGCGGAAGCTGGTGCAAGGCAGCTTTACTCTGCTCTGGCTAA<br>CAAGTGTTGTCACGTTGGGTGTACCAAGCGGTCCCTTGCGCAATTCTGC |
| 233 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATGGCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCGAAGCGGAAGCTGGTGCAAGGCAGCTTTACTCTGCTCTGGCTAA<br>CAAGTGTTGTTACGTTGGGTGTACCAAGCGGTCCCTTGCGCAATTCTGC |
| 234 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATGGCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCGAAGCGGAAGCTGGTGCAAGGCAGCTTTACTCTGCTCTGGCTAA<br>CAAGTGTTGTCTTGTTGGGTGTACCAAGCGGTCCCTTGCGCAATTCTGC |

TABLE 10-continued

Nucleotide Sequences Encoding Fusion Proteins and Peptide Components

| SEQ ID NO: | Sequence |
|---|---|
| 235 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATGGCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCAAGCGGAAGCTGGTGCAAGGCAGCTTTACTCTGCTCTGGCTAA<br>CAAGTGTTGTCAAGTTGGGTGTACCAAGCGGTCCCTTGCGCAATTCTGC |
| 236 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATGGCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCAAGCGGAAGCTGGTGCAAGGCAGCTTTACTCTGCTCTGGCTAA<br>CAAGTGTTGTAAAGTTGGGTGTACCAAGCGGTCCCTTGCGCAATTCTGC |
| 237 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGCGGAAGCGACTCATACCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCAAGCGGAAGCTGGTGCAAGGCAGCTTTACTCTGCTCTGGCTAA<br>CAAGTGTTGTTACGTTGGGTGTACCAAGCGGTCCCTTGCGCAATTCTGC |
| 238 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGCGGAAGCGACTCATACCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCAAGCGGAAGCTGGTGCAAGGCAGCTTTACTCTGCTCTGGCTAA<br>CAAGTGTTGTAAAGTTGGGTGTACCAAGCGGTCCCTTGCGCAATTCTGC |

TABLE 10-continued

Nucleotide Sequences Encoding Fusion Proteins and Peptide Components

| SEQ ID NO: | Sequence |
|---|---|
| 239 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTGAAGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGAGAAGGGGGCGGAAGACAGCTTTACTCTGCTCTGGCTAA<br>CAAGTGTTGTTACGTTGGGTGTACCAAGCGGTCCCTTGCGCAATTCTGC |
| 240 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTGAAGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGAGAAGGGGGCGGAAGACAGCTTTACTCTGCTCTGGCTAA<br>CAAGTGTTGTAAAGTTGGGTGTACCAAGCGGTCCCTTGCGCAATTCTGC |
| 241 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTGAAGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGATCTGGGGCGGAAGACAGCTTTACTCTGCTCTGGCTAA<br>CAAGTGTTGTTACGTTGGGTGTACCAAGCGGTCCCTTGCGCAATTCTGC |
| 242 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTGAAGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGATCTGGGGCGGAAGACAGCTTTACTCTGCTCTGGCTAA<br>CAAGTGTTGTAAAGTTGGGTGTACCAAGCGGTCCCTTGCGCAATTCTGC |

TABLE 10-continued

Nucleotide Sequences Encoding Fusion Proteins and Peptide Components

| SEQ ID NO: | Sequence |
|---|---|
| 243 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCGAAGCGGAAGCTGGTGCAAGGCAGCTTTACTCTGCTCTGGCTAA<br>CAAGTGTTGTTACGTTGGGTGTACCAAGCAATCCCTTGCGCAATTCTGC |
| 244 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGCTAGTGAC<br>GCAGCGGGCGCCGAAGCGGAAGCTGGTGCAAGGCAGCTTTACTCTGCTCTGGCTAA<br>CAAGTGTTGTAAAGTTGGGTGTACCAAGCAATCCCTTGCGCAATTCTGC |
| 245 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCAAGGAGAAGGGGCGGAAGACAGCTTTACTCTGCTCTGGCTAA<br>CAAGTGTTGTTACGTTGGGTGTACCAAGCAATCCCTTGCGCAATTCTGC |
| 246 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCAAGGAGAAGGGGCGGAAGACAGCTTTACTCTGCTCTGGCTAA<br>CAAGTGTTGTAAAGTTGGGTGTACCAAGCAATCCCTTGCGCAATTCTGC |

TABLE 10-continued

Nucleotide Sequences Encoding Fusion Proteins and Peptide Components

| SEQ ID NO: | Sequence |
|---|---|
| 247 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCAAGGATCTGGGGCGGAAGACAGCTTTACTCTGCTCTGGCTAA<br>CAAGTGTTGTTACGTTGGGTGTACCAAGCAATCCCTTGCGCAATTCTGC |
| 248 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCAAGGATCTGGGGGCGGAAGACAGCTTTACTCTGCTCTGGCTAA<br>CAAGTGTTGTAAAGTTGGGTGTACCAAGCAATCCCTTGCGCAATTCTGC |
| 381 | ATGGAGACGGACACTTTGCTGCTTTGGGTACTGCTGCTTTGGGTTCCTGGATCTAC<br>TGGCGATAAAACACACACGTGTCCCCCCTGCCCGGCTCCAGAGGCGGCTGGTGGTC<br>CCAGCGTATTCTTGTTTCCTCCCAAACCTAAGGATACGCTCATGATATCCCGCACC<br>CCAGAAGTTACGTGTGTAGTCGTCGACGTCAGTCACGAAGATCCAGAGGTCAAATT<br>TAACTGGTATGTCGACGGAGTAGAGGTCCACAATGCGAAAACCAAGCCCAGAGAAG<br>AGCAGTACAACTCCACGTATCGCGTCGTCTCCGTCCTCACCGTACTCCATCAAGAT<br>TGGCTGAATGGGAAGAGTATAAATGCAAAGTATCTAACAAGGCTCTGCCAGCTCC<br>GATAGAAAAGACTATATCAAAGGCCAAGGGGCAGCCAAGGGAGCCTCAAGTCTATA<br>CTTTGCCCCCATCTCGGGATGAGCTTACGAAAAACCAGGTCAGCCTTACCTGTCTT<br>GTTAAAGGTTTTTATCCGAGTGACATCGCAGTGGAATGGGAATCTAATGGTCAACC<br>TGAAAACAATTACAAAACCACACCGCCAGTATTGGACAGCGATGGTAGTTTTTTC<br>TTTACTCAAAACTGACTGTAGATAAAAGCAGATGGCAGCAGGGCAATGTCTTTTCA<br>TGTAGCGTTATGCATGAGGCTCTTCACAACCACTATACCCAAAAGTCATTGTCTCT<br>TAGTCCCGGAAAGGGCGGAAGTGATTCTTGGAAGGAGGAGGTAATCAAGTTGTGCG<br>GGCGAGAGTTGGTACGGGCACAGATCGCGATATGCGGAAAATCCACAGGTGGGGGC<br>GAAGGAGGAGGTGAGGGTGGAGGTGAAGGACGACAGTTGTATTCCGCCTTGGCAAA<br>CAAGTGTTGCCATGTGGGTTGCACAAAACGCAGTCTTGCCCGCTTCTGT |
| 382 | ATGGAGACCGATACGCTGTTGCTGTGGGTATTGCTTCTCTGGGTGCCCGGCTCAAC<br>TGGGGATAAGACACATACATGCCCTCCCTGTCCGGCTCCAGAGGCAGCCGGGGGTC<br>CATCAGTCTTCCTTTTTCCGCCTAAACCTAAGGATACACTGATGATCTCTCGAACA<br>CCGGAGGTCACTTGTGTTGTCGTTGACGTATCACATGAGGATCCCGAAGTAAAGTT<br>CAACTGGTATGTCGATGGTGTGGAGGTTCATAATGCTAAAACTAAACCACGGGAGG<br>AGCAATATAATTCCACATATAGGGTCGTGAGCGTGTTGACGGTGCTTCATCAAGAC<br>TGGCTTAATGGGAAGGAATATAAATGCAAAGTGTCAAATAAAGCACTTCCTGCGCC<br>AATCGAGAAAACAATTAGTAAGGCAAAGGGGCAGCCGCGAGAACCTCAGGTGTACA<br>CCTTGCCGCCTTCTAGAGACGAGCTCACAAAGAACCAAGTTTCCCTGACTTGCCTC<br>GTTAAGGGGTTTTATCCGTCCGATATAGCCGTGGAGTGGGAGTCAAACGGCCAACC<br>GGAAAATAATTACAAAACGACACCCCCAGTATTGGATAGTGACGGCTCTTTTTTCC<br>TTTATTCTAAGCTGACTGTGGACAAAAGCCGCTGGCAGCAGGGCAATGTCTTTTCA<br>TGCAGCGTAATGCATGAAGCCCTGCACAACCACTACACGCAAAAATCCCTTTCCTT<br>GTCACCCGGCAAGGGCGGCTCTGACTCCTGGAAAGAGGAAGTTATAAAACTCTGTG<br>GCCGAGAACTTGTTCGAGCTCAAATCGCGATTTGTGGTAAGTCAACGGGTGGGGGC<br>GAAGGTGGAGGCGAGGGTGGGGAGAAGGAGGAGGCCAGTTGTACTCAGCTCTTGC<br>AAATAAGTGTTGCCACGTTGGTTGTACGAAGCGGAGCCTTGCTCGCTTCTGC |

TABLE 10-continued

Nucleotide Sequences Encoding Fusion Proteins and Peptide Components

| SEQ ID NO: | Sequence |
|---|---|
| 383 | ATGGAAACTGATACTCTTCTGCTGTGGGTCCTGCTGCTGTGGGTTCCAGGATCTAC<br>TGGAGACAAAACACATACTTGTCCGCCTTGCCCGGCACCCGAAGCGGCCGGCGGAC<br>CCAGTGTCTTTCTCTTCCCACCCAAACCGAAAGACACTCTGATGATTTCCAGGACG<br>CCTGAAGTGACCTGCGTTGTAGTTGATGTATCACACGAGGATCCCGAGGTCAAGTT<br>CAATTGGTATGTAGATGGGGTGGAGGTCCATAATGCAAAGACGAAGCCACGGGAGG<br>AACAGTACAACTCTACGTACAGAGTTGTCAGTGTTTTGACCGTCCTTCATCAGGAT<br>TGGCTGAACGGTAAAGAATATAAATGCAAGGTTAGCAATAAAGCTTTGCCCGCCCC<br>TATAGAGAAAACGATCAGTAAGGCGAAGGGGCAGCCTAGGGAACCCCAGGTATATA<br>CCTTGCCGCCAAGTCGAGATGAGCTGACGAAGAACCAAGTGAGTCTGACATGCCTC<br>GTGAAGGGCTTCTATCCGAGCGATATCGCTGTCGAATGGGAGGCAATGGGCAGCC<br>TGAGAATAACTATAAAACAACGCCACCCGTCCTCGACTCCGATGGCTCATTCTTCC<br>TGTACAGTAAACTTACAGTAGATAAGAGTAGATGGCAGCAGGGTAACGTCTTTAGT<br>TGCTCCGTGATGCACGAGGCATTGCACAATCATTACACTCAAAAATCTCTGTCCCT<br>GAGTCCGGGCAAAGGCGGTTCAGATAGCTGGATGGAGGAGGTCATAAAGCTTTGTG<br>GACGAGAACTCGTTCGCGCCCAGATAGCTATTTGTGGGAAATCAACCGGGGGTGGA<br>GAAGGTGGCGGAGAAGGGGGAGGCGAAGGGCGCCAACTGTATTCTGCATTGGCTAA<br>TAAGTGCTGTCACGTAGGATGTACAAAAAGGTCTCTGGCGAGATTCTGC |
| 384 | ATGGAGACCGACACCCTCTTGTTGTGGGTTCTCCTCTTGTGGGTGCCCGGCAGTAC<br>TGGAGACAAGACGCACACTTGTCCACCTTGCCCTGCGCCGGAAGCTGCTGGAGGCC<br>CCAGTGTCTTTTTGTTCCCGCCCAAACCGAAGGACACTTTGATGATAAGTCGCACG<br>CCCGAGGTTACCTGTGTGGTTGTCGATGTCTCACACGAAGATCCGGAGGTGAAGTT<br>TAATTGGTATGTAGATGGCGTGGAGGTTCATAACGCCAAAACGAAACCCAGAGAAG<br>AACAATATAACAGTACATATCGAGTAGTATCCGTTCTCACTGTCCTGCATCAAGAC<br>TGGTTGAACGGGAAGGAATATAAGTGCAAGGTGAGCAATAAAGCACTCCCGGCCCC<br>AATCGAAAAGACCATCAGCAAAGCGAAGGGGCAACCTCGAGAACCCCAGGTATATA<br>CGCTCCCCCCTAGTCGGGATGAACTTACTAAAAATCAGGTTAGCCTCACTTGCCTT<br>GTTAAAGGGTTCTATCCCAGTGATATTGCCGTCGAATGGGAATCAAACGGGCAGCC<br>GGAAAATAACTACAAGACAACCCCTCCTGTGCTCGATAGCGATGGCTCTTTTTTCC<br>TCTACAGCAAACTTACCGTTGATAAGAGCCGGTGGCAACAAGGTAATGTTTTCTCC<br>TGCTCCGTTATGCATGAAGCACTCCATAACCATTATACCCAAAAAAGCCTGTCACT<br>TAGTCCGGGTAAAGGAGGTAGTGATTCTTGGCAGGAGGAGGTAATCAAACTTTGTG<br>GGAGGGAGCTGGTACGAGCTCAGATTGCTATATGTGGAAAAAGCACGGGCGGAGGA<br>GAAGGAGGTGGCGAAGGCGGGGGTGAAGGTCGGCAACTCTACTCCGCTCTCGCTAA<br>TAAGTGCTGCCACGTCGGGTGTACGAAGCGCTCCCTGGCGCGATTCTGC |
| 385 | ATGGAAACAGATACCCTCCTCCTCTGGGTCCTTCTTCTTTGGGTGCCTGGCTCAAC<br>TGGAGATAAAACGCACACGTGTCCGCCCTGCCCAGCGCCTGAAGCCGCAGGCGGGC<br>CGTCCGTCTTCCTCTTTCCTCCAAAACCCAAAGACACACTTATGATCAGTAGGACC<br>CCAGAGGTAACCTGCGTCGTGGTCGACGTTTCCCATGAAGACCCAGAGGTCAAGTT<br>CAACTGGTACGTCGACGGTGTCGAAGTACATAATGCTAAAACGAAGCCTCGGGAAG<br>AGCAGTACAACTCTACCTACCGCGTCGTTTCCGTACTCACCGTACTTCACCAGGAC<br>TGGCTTAACGGTAAAGAGTATAAATGCAAAGTATCTAATAAGGCTCTCGCCGCGCC<br>GATTGAGAAGACAATTTCAAAGGCCAAGGGGCAGCCGCGGGAGCCCCAAGTGTATA<br>CCTTGCCCCCGTCCCGAGATGAGCTGACTAAAAACCAAGTAAGCTTGACTTGCTTG<br>GTCAAAGGCTTCTACCCTTCCGATATAGCTGTCGAATGGGAGTCAAATGGCCAACC<br>AGAGAACAATTATAAAACTACACCCCGGTCTTGGATTCTGATGGCTCATTTTTTC<br>TCTATTCTAAACTGACCGTGGATAAGTCTCGCTGGCAGCAAGGTAACGTGTTCAGT<br>TGCTCTGTTCTTCACGAAGCACTGCACAGTCATTACACTCAGAAGAGTCTTAGCCT<br>GAGCCCTGGTAAAGGGGTTCTGATTCCTGGCAGGAGGAAGTAATAAAACTCTGTG<br>GCCGGGAGTTGGTACGGGCGCAGATTGCGATATGCGGTAAGAGCACCGGCGGAGGC<br>GAAGGCGGTGGGGAAGGAGGAGGAGAAGGGAGACAACTCTATTCCGCATTGGCAAA<br>TAAGTGCTGCCACGTCGGGTGTACCAAACGATCCCTTGCACGGTTCTGT |
| 386 | ATGGAGACGGACACCCTCCTTCTCTGGGTTTTGCTCCTTTGGGTCCCTGGTTCCAC<br>TGGAGATAAGACCCATACGTGCCCCCCTTGCCCTGCGCCTGAGGCAGCGGGTGGCC<br>CATCAGTCTTTTTGTTCCCGCCCAAGCCAAAGGACACCCTCATGATTAGTAGAACA<br>CCGGAGGTTACGTGCGTCGTAGTGGATGTCAGCCACGAGGATCCCGAGGTTAAGTT<br>TAACTGGTACGTTGATGGGGTTGAGGTCCATAATGCGAAGACTAAGCCGAGAGAGG<br>AACAGTACAATTCCACGTATAGAGTTGTCTCTGTACTGACTGTGCTGCATCAAGAT<br>TGGCTTAACGGTAAGGAGTACAAGTGCAAAGTCTCTAATAAGGCTCTTCCTGCACC<br>CATTGAGAAACTATAAGCAAAGCAAAAGGTCAACCTCGCGAACCTCAGGTGTACA<br>CACTGCCACCCTCTAGGGACGAGCTTACCAAAAATCAAGTATCTCTTACCTGCCTT<br>GTGAAAGGGTTTTATCCCTCAGATATTGCGGTTGAGTGGGAGTCTAACGGACAACC<br>TGAGAACAACTATAAGACTACTCCCCGGTGCTTGATTCAGACGGGAGTTTTTTTT<br>TGTATAGCAAACTTACCGTCGACAAAAGCCGGTGGCAACAGGGCAATGTATTCAGT<br>TGTTCTGTAATGCATGAAGCTTTGCATAATCATTACACCCAAAAGAGTCTTTCCCT<br>GTCTCCTGGAAAAGGGGGGTCAGACTCCTGGATGGAGGAGGTGATCAAACTGTGTG<br>GGAGAGAGCTCGTCCGGGCTCAGATAGCTATATGCGGCAAGTCTACGGGTGGGGA<br>GAGGGCGGAGGAGAGGGCCGTGGAGAAGGAGGCGGCCAACTCTACAGCGCTCTGGC<br>CAATAAATGTTGTCATGTCGGGTGTACTAAGCGCTCACTGGCACGCTTTTGC |

TABLE 10-continued

Nucleotide Sequences Encoding Fusion Proteins and Peptide Components

| SEQ ID NO: | Sequence |
|---|---|
| 387 | ATGGAAACCGACACCCTTTTGTTGTGGGTATTGCTGTTGTGGGTTCCCGGTAGCAC<br>GGGGGACAAGACGCATACATGCCCGCCATGCCCGGCCCCCGAAGCTGCTGGGGGAC<br>CATCCGTATTCCTCTTCCCTCCCAAACCAAAAGACACGTTGATGATAAGTAGAACA<br>CCAGAGGTAACGTGCGTGGTTGTCGATGTTTCCCACGAAGATCCGGAGGTAAAATT<br>CAATTGGTATGTAGATGGGGTGGAAGTGCACAATGCCAAAACAAAGCCGCGAGAAG<br>AACAATACAATAGTACTTACCGGGTTGTGAGCGTGCTCACGGTGTTGCACCAAGAC<br>TGGCTCAACGGCAAGGAATACAAGTGCAAAGTATCTAATAAAGCTCTGCCTGCGCC<br>GATAGAGAAGACCATCAGTAAGGCCAAAGGGCAGCCCCGAGAGCCGCAAGTTTACA<br>CTCTTCCTCCGAGCAGAGATGAATTGACCAAGAACCAAGTAAGTTTGACGTGCCTG<br>GTGAAGGGCTTCTACCCCTCAGACATTGCGGTGGAGTGGGAAAGTAATGGTCAACC<br>GGAAAACAACTACAAGACCACGCCGCCCGTCCTCGACTCCGATGGGTCTTTCTTTC<br>TTTATTCAAAGTTGACAGTAGATAAGTCAAGGTGGCAGCAAGGTAACGTGTTTAGT<br>TGTAGTGTAATGCACGAGGCCCTGCATAATCATTATACCCAAAAGAGTTTGAGCCT<br>CTCCACCAGGAAAAGGCGGATCAGACAGCTGGCAGGAGGAGGTAATTAAATTGTGTG<br>GACGGGAGTTGGTCAGGGCGCAAATAGCCATCTGCGGTAAGAGCACGGGTGGAGGA<br>GAGGGTGGAGGGGAAGGTGGGGGAGAAGGCGGCGGGCAGCTCTATTCTGCACTCGC<br>CAACAAGTGTTGTCACGTCGGATGCACAAAGAGATCTCTTGCTCGATTCTGC |
| 388 | ATGGAGACTGATACTCTTTTGTTGTGGGTACTGCTCCTGTGGGTTCCAGGCTCCAC<br>AGGAGACAAAACACACACCTGTCCGCCTTGCCCGGCTCCTGAAGCCGCGGGTGGCC<br>CTAGTGTGTTTTTGTTTCCGCCGAAACCTAAGGATACCCTCATGATAAGCCGGACG<br>CCCGAGGTTACCTGTGTCGTGGTCGATGTTAGTCATGAGGATCCAGAAGTCAAGTT<br>TAATTGGTACGTCGACGGCGTTGAAGTCCACAATGCAAAAACTAAACCGCGAGAAG<br>AACAGTACAACTCCACCTACAGAGTTGTCTCAGTTTTGACAGTTCTCCATCAGGAT<br>TGGCTCAATGGAAAGGAATATAAGTGCAAGGTCAGCAATAAAGCGCTTGCCGCCCC<br>TATAGAGAAGACCATTAGCAAGGCGAAAGGACAGCCCCGCGAGCCCCAGGTCTATA<br>CGCTGCCTCCTAGCAGAGATGAGCTCACGAAAAATCAGGTCAGCTTGACATGCTTG<br>GTGAAGGGCTTCTACCCCAGTGACATCGCAGTTGAATGGGAGAGCAACGGCCAACC<br>TGAGAACAACTACAAAACAACGCCCCCGGTTCTTGACAGCGATGGGTCCTTCTTTC<br>TTTACTCTAAGCTTACAGTTGATAAAAGCAGGTGGCAGCAGGGGAATGTGTTCTCA<br>TGTTCCGTACTGCATGAGGCTCTGCATTCTCACTACACCCAAAAAAGCCTTAGCCT<br>GAGCCCCGGTAAGGGAGGTAGTGACTCATGGCAAGAGGAAGTGATTAAGCTCTGCG<br>GCCGGGAGTTGGTGAGAGCCCAAATCGCCATTTGCGGTAAAAGTACCGGAGGGGGC<br>GAGGGAGGAGGCGAAGGTGGAGGTGAAGGAGGTGGACAGTTGTACTCAGCTCTTGC<br>AAATAAATGTTGTCATGTTGGTTGCACGAAAAGATCTCTTGCGAGGTTCTGT |
| 389 | ATGGAGACTGACACTCTTTTGTTGTGGGTGCTTCTTCTGTGGGTACCTGGATCCAC<br>TGGGGATAAGACGCATACTTGTCCACCGTGCCCCGCACCGGAAGCGGCTGGTGGTC<br>CATCAGTTTTTCTGTTCCCACCGAAACCTAAGGACACGTTGATGATATCACGGACA<br>CCAGAGGTTACGTGCGTAGTGGTGGATGTGAGCCACGAGGATCCAGAAGTTAAATT<br>TAATTGGTACGTAGATGGAGTGGAGGTTCATAATGCGAAGACAAAGCCTCGCGAGG<br>AACAGTATAATTCCACCTATCGCGTCGTATCTGTGCTTACGGTACTTCACCAAGAC<br>TGGTTGAACGGTAAGGAATATAAATGCAAGGTTTCCAATAAAGCACTTCCTGCGCC<br>AATTGAGAAGACAATATCCAAAGCTAAAGGTCAACCCAGGGAACCGCAAGTCTACA<br>CTCTCCCCCCGTCTCGCGATGAATTGACGAAGAACCAGGTTAGTCTCACCTGCCTG<br>GTCAAGGGGTTTTACCCCTCTGACATAGCTGTAGAATGGGAGTCTAATGGACAGCC<br>AGAGAACAATTACAAAACGACCCCCCGGTCCTCGATTCTGATGGGAGTTTTTTTC<br>TTTATTCAAAATTGACTGTCGATAAGTCAAGATGGCAACAGGGTAACGTATTTTCT<br>TGCAGTGTTATGCATGAAGCATTGCACAACCACTATACACAAAAATCATTGAGTTT<br>GAGTCCCGGTAAAGGGGAAGCGACTCATGGATGGAAGAAGTAATCAAGCTGTGCG<br>GGCGAGAGCTTGTGCGAGCTCAGATAGCAATCTGTGGTAAGTCTACAGGTGGAGAG<br>GGTGGCGGTGAAGAAGGCGGGGAGAGGGAGGCCAGCTTTATTCTGCCCTGGCTAA<br>CAAGTGCTGTCACGTTGGATGCACGAAGCGCTCCCTGGCCCGATTCTGC |
| 390 | ATGGAAACCGATACATTGCTTTTGTGGGTCCTCCTTCTTTGGGTTCCTGGCTCTAC<br>AGGCGATAAGACGCATACTTGTCCCCCATGTCCCGCTCCGGAAGCCGCTGGCGGCC<br>CCTCCGTTTTTCTGTTCCCGCCGAAACCGAAAGACACCCTGATGATATCACGCACT<br>CCCGAGGTCACTTGCGTGGTAGTCGATGTTAGTCATGAAGATCCTGAGGTCAAATT<br>CAATTGGTATGTAGATGGCGTTGAGGTACACAACGCGAAGACAAAACCCCGAGAAG<br>AACAGTATAACTCAACCTACCGCTAGTTTCAGTTCTTACCGTACTGCACCAAGAC<br>TGGTTGAACGGTAAGAGTACAAATGTAAAGTCAGCAATAAAGCTTTGCCAGCACC<br>TATCGAAAAACCATCAGTAAGGCCAAGGGTCAACCCAGGGAGCCGCAAGTGTACA<br>CTCTTCCCCCTAGCAGGGATGAATTGACCAAGAATCAGGTCTCTTTGACGTGCCTC<br>GTTAAGGGTTTCTATCCCAGCGATATAGCCGTAGAATGGGAGTCTAACGGTCAGCC<br>AGAAAATAACTATAAGACAACCCCGCCTGTTTTGGATTCCGACGGCTCTTTTTTTC<br>TCTACTCTAAGTTGACCGTTGATAAGAGCAGATGGCAGCAGGGAAACGTATTTCT<br>TGTTCCGTGATGCACGAAGCCCTGCACAATCACTATACGCAAAAGTCTCTGAGCTT<br>GAGTCCGGGTAAAGGCGGTTCTGACTCCTGGCAGGAGGAAGTCATAAAACTCTGCG |

TABLE 10-continued

Nucleotide Sequences Encoding Fusion Proteins and Peptide Components

| SEQ ID NO: | Sequence |
|---|---|
| | GAAGAGAGCTCGTAAGGGCGCAAATCGCTATTTGTGGTAAGAGCACCGGTGGGGAA<br>GGAGGCGGTGAAGAGGGTGGCGGCGAGGGTGGGCAATTGTATTCCGCGCTTGCCAA<br>TAAATGTTGTCACGTAGGCTGCACAAAGCGAAGTCTCGCTAGGTTCTGC |
| 391 | ATGGAAACCGACACCTTGCTTTTGTGGGTGCTCTTGCTGTGGGTTCCGGGGAGCAC<br>TGGCGACAAGACCCACACATGTCCCCCGTGTCCGGCACCAGAAGCAGCGGGGGGAC<br>CGTCAGTATTCTTGTTTCCACCGAAGCCCAAAGACACATTGATGATTTCACGAACT<br>CCTGAAGTTACCTGTGTGGTTGTAGATGTATCACACGAAGACCCAGAAGTCAAATT<br>CAATTGGTATGTCGACGGGGTTGAAGTTCACAATGCGAAGACGAAGCCCCGGGAGG<br>AACAGTACAACAGCACGTACAGGGTTGTGAGCGTTCTTACTGTATTGCACCAGGAT<br>TGGCTCAACGGCAAGGAGTATAAATGTAAAGTTTCTAATAAGGCTCTTCCTGCCCC<br>AATTGAAAAGACGATATCTAAAGCGAAGGGCCAACCACGGGAACCTCAGGTGTACA<br>CACTTCCGCCTAGCAGGGATGAGTTGACCAAGAATCAAGTCTCTTTGACGTGCCTG<br>GTCAAGGGGTTTTACCCATCAGATATCGCCGTCGAATGGGAGTCAAACGGACAACC<br>CGAAAATAACTATAAAACTACTCCACCAGTTCTGGATAGCGACGGCTCATTTTTTC<br>TGTATTCAAAGCTCACTGTAGACAAGTCTAGGTGGCAGCAGGGTAATGTCTTCTCC<br>TGCTCAGTAATGCATGAGGCTCTTCACAACCACTATACTCAAAAGAGCCTTTCCCT<br>GTCACCTGGCGGTGGAAGCGACTCATGGATGGAGGAGGTAATAAAGCTCTGCGGAA<br>GAGAACTGGTACGCGCACAAATCGCAATTTGTGGTAAGAGTACTGGCGGGGAAGGA<br>GGTGGGGAAGAAGGGGGCGGTGAGGGCGGACAGCTCTATTCTGCACTTGCAAACAA<br>ATGTTGCCACGTGGGATGTACTAAGCGAAGCCTTGCAAGATTCTGC |
| 392 | ATGGAGACCGACACACTGTTGCTGTGGGTACTCCTCCTGTGGGTGCCAGGAAGCAC<br>GGGCGATAAAACCCACACATGCCCTCCATGCCCTGCTCCAGAGGCCGCCGGTGGGC<br>CATCAGTTTTCTTGTTTCCGCCTAAACCAAAGGACACGCTTATGATCTCCAGGACC<br>CCCGAAGTTACGTGTGTGGTGGTTGATGTTAGTCACGAGGACCCGGAAGTCAAGTT<br>CAACTGGTACGTTGATGGTGTAGAGGTGCACAATGCAAAGACGAAGCCACGCGAAG<br>AACAATACAACAGCACATATCGAGTTGTGAGCGTACTCACGGTACTGCATCAGGAC<br>TGGCTGAACGGTAAAGAATACAAATGTAAAGTCTCCAATAAGGCACTTCCTGCGCC<br>GATAGAAAAACGATCAGTAAGGCCAAGGGCCAACCCCGAGAACCACAGGTATATA<br>CGCTCCCACCGTCACGAGACGAGTTGACAAAAAATCAGGTCTCCCTGACTTGCCTC<br>GTGAAAGGTTTTTATCCCTCAGATATTGCTGTTGAGTGGGAAAGCAATGGGCAGCC<br>AGAGAATAATTATAAGACGACTCCTCCGGTTTTGGATTCCGACGGTAGTTTTTTCT<br>TGTATAGTAAGCTTACTGTAGACAAGTCAAGATGGCAACAAGGTAATGTGTTCTCT<br>TGCTCAGTTATGCATGAAGCTCTTCATAACCATTACACGCAAAAGAGTCTCAGTCT<br>GAGCCCCGGTGGCGGTAGCGACAGTTGGCAGGAAGAGGTGATTAAGTTGTGCGGTC<br>GCGAGCTCGTTCGGGCCCAAATTGCAATCTGCGGAAAATCTACGGGCGGAGAGGGC<br>GGGGGTGAGGAGGGTGGGGGTGAAGGTGGGCAGCTCTATAGCGCCCTTGCGAATAA<br>ATGTTGTCACGTCGGATGCACAAAGAGGTCCCTCGCCAGGTTCTGC |
| 393 | ATGGAAACTGACACACTGTTGCTGTGGGTGCTGCTCCTTTGGGTACCCGGATCAAC<br>CGGGGATAAGACCCACACTTGCCCCCCTTGCCCTGCCCCCGAAGCGGCCGGAGGTC<br>CTTCAGTATTTTTGTTTCCACCGAAACCCAAAGATACTTTGATGATATCAAGAACT<br>CCTGAAGTCACCTGCGTGGTAGTTGACGTATCTCATGAGGATCCCGAGGTGAAGTT<br>CAATTGGTACGTCGATGGCGTCGAGGTTCATAACGCTAAGACTAAGCCGAGGGAAG<br>AGCAATATAATTCCACTTATAGGGTGGTGTCCGTCTTGACTGTTTTGCACCAGGAT<br>TGGTTGAACGGGAAAGAGTACAAATGTAAGGTGAGTAATAAAGCTTTGGCTGCTCC<br>CATCGAAAAGACAATAAGCAAGGCCAAGGGGCAACCTCGGGAGCCGCAGGTGTACA<br>CCCTTCCTCCCAGTAGAGACGAACTGACAAAAAACCAGGTGTCCCTGACCTGCCTT<br>GTGAAGGGGTTTTACCCGAGCGACATAGCGGTTGAATGGGAGAGCAACGGGCAACC<br>CGAGAACAACTACAAAACTACACCGCCTGTCCTGGACTCCGATGGAAGCTTCTTCC<br>TCTACTCCAAACTGACCGTGGACAAAAGCAGATGGCAACAAGGAAACGTATTCTCA<br>TGCTCAGTAATGCACGAAGCATTGCACAATCACTACACCCAAAAGTCCCTCTCACT<br>CTCCCCTGGTAAGGGCGGATCAGACTCATGGCAAGAGGAGGTAATTAAGTTGTGCG<br>GGAGGGAGCTCGTCCGCGCGCAAATAGCCATTTGTGGCAAGTCCACTGGAGGAGGC<br>GAGGGTGGAGGAGAGGGTGGTGGGGAGGGCAGGCAACTCTACAGTGCGCTCGCCAA<br>TAAATGCTGCCATGTTGGGTGCACGAAGCGCAGTCTCGCACAATTCTGC |
| 394 | ATGGAGACCGACACTCTGCTGCTCTGGGTACTCTTGCTGTGGGTGCCTGGGTCTAC<br>TGGGGATAAGACCCACACGTGTCCTCCATGTCCGGCACCGGAGGCTGCTGGCGGGC<br>CTTCTGTATTCCTCTTCCCACCCAAGCCAAAAGACACATTGATGATATCAAGGACG<br>CCGGAAGTCACCTGTGTTGTTGTGGACGTTTCCCATGAAGACCCAGAGGTAAAATT<br>CAATTGGTATGTGGACGGCGTAGAGGTTCACAACGCCAAAACCAAACCCCGAGAGG<br>AACAGTATAATAGCACATATCGAGTAGTATCTGTTCTCACAGTGCTCCATCAAGAC<br>TGGCTTAATGGTAAAGAGTATAAATGCAAAGTTTCCAATAAAGCCCTCGCTGCACC<br>GATCGAGAAGACAATCAGTAAAGCGAAGGGCCAGCCTCGGGAACCGCAGGTGTATA<br>CTCTTCCACCCTCAAGAGACGAGCTCACTAAAAACCAAGTTTCATTGACATGCCTC<br>GTCAAAGGTTTCTACCCATCAGACATCGCGGTCGAATGGGAAAGTAATGGGCAGCC<br>GGAAAACAACTATAAAACGACGCCGCCCGTCTTGGATTCTGATGGTTCATTTTTTC<br>TTTACTCTAAATTGACCGTCGATAAAAGTAGGTGGCAACAAGGAAATGTTTTTTCC<br>TGCTCCGTCCTGCATGAAGCGTTGCACAGTCACTATACCCAGAAGAGTCTTTCTTT<br>GTCACCCGGAAAAGGCGGTTCAGATTCATGGCAGGAAGAAGTAATTAAACTCTGTG |

TABLE 10-continued

Nucleotide Sequences Encoding Fusion Proteins and Peptide Components

| SEQ ID NO: | Sequence |
|---|---|
| | GCCGCGAGCTTGTTAGGGCGCAGATAGCCATATGTGGTAAAAGCACCGGAGGAGGT GAAGGCGGAGGCAAGGAGGTGGGGAAGGAAGACAATTGTATTCTGCACTTGCAAA TAAATGCTGTCATGTGGGGTGCACGAAACGCAGTCTTGCACAATTTTGT |
| 395 | ATGGAAACCGATACGCTGCTTCTTTGGGTTCTTCTCCTCTGGGTTCCAGGGTCCAC CGGCGACAAAACCCATACCTGCCCCCCTTGCCCTGCACCAGAAGCGGCGGGAGGAC CTAGCGTTTTTCTTTTTCCTCCGAAACCGAAAGATACCCTCATGATATCAAGAACA CCTGAGGTTACTTGCGTTGTCGTGGACGTGAGTCACGAAGACCCCGAGGTGAAGTT CAACTGGTATGTAGATGGAGTGGAGGTCCATAATGCAAAAACGAAACCGAGAGAAG AACAATACAACTCTACATATCGAGTCGTGTCAGTACTCACGGTTTTGCATCAAGAT TGGCTGAACGGTAAGGAGTACAAGTGTAAGGTTAGCAACAAGGCTCTCGCGGCGCC GATAGAAAAGACTATAAGTAAAGCAAAAGGCCAGCCCAGAGAACCTCAAGTTTACA CTCTGCCTCCCAGCAGAGATGAACTGACTAAAAATCAGGTTTCATTGACCTGTCTC GTCAAGGGTTTTTATCCAAGCGACATAGCAGTTGAATGGGAAAGCAACGGTCAACC AGAAAATAATTACAAAACCACTCCACCAGTCTTGGACTCTGACGGATCCTTCTTTC TCTATTCAAAATTGACGGTGGATAAATCTAGGTGGCAGCAAGGCAACGTCTTCTCT TGTAGCGTTATGCATGAGGCGCTGCACAACCACTACACACAAAAGTCTCTTAGTTT GAGCCCGGCGGCGGAAGCGACTCTTGGCAAGAGGAAGTGATAAAACTCTGTGGTC GAGAATTGGTACGCGCGCAGATCGCTATCTGCGGCAAGTCCACAGGGGGAGGGGAA GGTGGCGGGGAAGGTGGTGGCGAGGGCAGGCAGTTGTATAGTGCACTTGCCAACAA GTGCTGCCATGTGGGGTGCACCAAGCGCAGTTTGGCACGGTTCTGC |
| 396 | ATGGAAACGGACACCCTTCTGCTCTGGGTACTGCTGCTCTGGGTTCCTGGTTCTAC CGGTGATAAAACTCACACTTGTCCCCCGTGTCCGGCACCAGAAGCCGCAGGAGGGC CATCTGTCTTTCTTTTTCCCCCAAAACCCAAGGATACACTGATGATCTCCCGCACT CCCGAAGTTACTTGTGTCGTAGTAGACGTTTCTCACGAGGACCCAGAGGTGAAATT CAATTGGTATGTTGACGGAGTAGAGGTGCATAATGCCAAGACAAAGCCCCGAGAGG AACAATACAATTCAACCTACAGAGTAGTGTCCGTTCTTACGGTTCTCCATCAGGAT TGGCTCAACGGTAAGGAATATAAGTGCAAGGTAAGCAACAAAGCGCTGGCCGCACC CATTGAGAAAACCATTTCAAAAGCTAAAGGCCAACCCCGCGAACCACAAGTTTATA CTCTCCCCCCAAGTCGCGATGAACTTACAAAAAATCAAGTCTCATTGACGTGCTTG GTCAAAGGCTTCTACCCGAGCGATATCGCTGTTGAATGGGAGTCTAATGGACAACC GGAAAATAACTATAAAACTACACCCCCAGTCCTCGATTCAGACGGCAGCTTCTTCC TGTATTCAAAACTGACGGTTGACAAATCACGCTGGCAACAGGGTAACGTTTTTTCC TGTAGCGTTCTTCATGAAGCCTTGCACAGTCACTACACCCAGAAGTCCCTTAGCTT GTCACCTGGCGGGGTTCAGACTCTTGGCAGGAGGAGGTAATCAAACTGTGCGGAA GAGAACTGGTGAGGGCTCAGATTGCAATTTGTGGGAAGAGCACGGGTGGCGGTGAA GGAGGTGGCGAGGGCGGAGGAGAGGGGAGGCAACTCTACAGTGCGTTGGCTAATAA ATGCTGTCACGTCGGCTGTACTAAGAGAAGCCTCGCCAGATTTTGC |
| 397 | ATGGAAACAGATACTTTGTTGCTGTGGGTACTCCTCCTCTGGGTACCTGGGAGCAC CGGGGACAAGACGCATACTTGCCCTCCGTGCCCTGCACCAGAAGCCGCTGGTGGCC CATCTGTGTTTTTGTTCCCCCCTAAGCCAAAAGACACATTGATGATTTCACGAACT CCAGAAGTGACTTGCGTAGTTGTTGACGTATCACACGAAGACCCCGAGGTTAAATT TAATTGGTATGTGGACGGGGTCGAGGTGCATAACGCCAAAACCAAACCCCGGGAGG AACAATATAACTCTACGTATCGGGTCGTATCTGTGTTGACCGTCCTTCACCAAGAT TGGTTGAACGGCAAGGAATATAAGTGTAAAGTGTCTAATAAAGCATTGGCTGCCCC GATAGAAAAGACGATCTCTAAAGCCAAGGGCCAACCCAGAGAGCCTCAAGTATATA CTCTCCCACCGAGTCGAGATGAGCTCACTAAGAACCAGGTGTCACTCACGTGTCTG GTTAAAGGATTTTACCCTAGTGATATAGCCGTCGAGTGGGAATCAAATGGGCAGCC GGAGAATAACTATAAGACCACGCCTCCAGTTCTCGATTCCGATGGTAGCTTTTTCC TTTACTCTAAACTTACGGTCGACAAGTCCAGGTGGCAACAGGGCAATGTATTTTCT TGCTCCGTCATGCACGAGGCTTTGCACAACCATTACACGCAAAAGTCACTGTCCCT GTCTCCTGGAGGCGGTTCTGACAGTTGGCAGGAGGAGGTAATCAAATTGTGTGGGC GGGAGTTGGTTAGGGCGCAAATTGCTATTTGCGGCAAAAGTACTGGGGCGGTGAA GGCGGAGGCGAGGAGGAGGAGAAGGTCGACAACTGTATTCTGCCTTGGCGAACAA ATGCTGTCACGTCGGCTGTACGAAACGGTCTTTGGCCCAGTTTTGT |
| 398 | ATGGAAACTGACACTCTTCTGTTGTGGGTCCTTCTGCTGTGGGTTCCTGGCTCTAC TGGAGATAAGACACACACTTGTCCGCCATGCCCTGCGCCGGAAGCGGCGGGAGGAC CGTCCGTTTTCCTGTTCCCTCCCAAACCCAAAGACACGTTGATGATTAGTCGCACG CCAGAAGTTACGTGCGTTGTCGTAGATGTATCCACGAAGACCCCGAGGTGAAGTT CAATTGGTATGTAGATGGGGTGGAGGTCCATAACGCTAAGACCAAACCACGCGAGG AACAATATAATTCTACGTACCGCGTAGTGAGCGTTCTCACAGTTCTTCACCAGGAT TGGCTTAACGGCAAGGAGTATAAGTGTAAGGTGTCTAATAAGGCCTTGGCTGCCCC GATCGAAAAAACGATAAGTAAAGCAAAGGGTCAACCTAGAGAACCCAAGTGTACA CTCTCCCGCCATCACGGGATGAATTGACTAAGAACCAAGTGTCACTCACGTGTCTT GTAAAGGGCTTCTACCCATCCGATATAGCCGTTGAGTGGGAATCCAATGGTCAGCC AGAGAACAACTATAAGACAACTCCGCCCGTACTTGATAGTGACGGTTCCTTTTTCC TTTACAGTAAATTGACGGTAGATAAGTCTCGCTGGCAGCAAGGAAACGTCTTTTCT TGTTCAGTGCTTCATGAGGCGCTTCACTCACACTATACTCAGAAGAGTTTGAGTTT GTCTCCAGGTGGAGGCAGCGACTCATGGCAAGAGGAAGTAATCAAACTGTGTGGTC |

TABLE 10-continued

Nucleotide Sequences Encoding Fusion Proteins and Peptide Components

| SEQ ID NO: | Sequence |
| --- | --- |
|  | GCGAATTGGTACGAGCACAGATCGCGATCTGCGGGAAATCAACAGGTGGCGGCGAA<br>GGCGGCGGGGAAGGCGGCGGCGAAGGTAGGCAACTTTACTCAGCCCTTGCGAACAA<br>ATGTTGCCACGTAGGCTGTACTAAGAGAAGTCTCGCCCAGTTTTGC |
| 399 | ATGGAGACAGATACCCTTCTGTTGTGGGTCCTTCTGCTTTGGGTGCCGGGAAGTAC<br>AGGCGACAAGACTCATACCTGCCCCCCTTGTCCAGCACCAGAAGCAGCTGGCGGGC<br>CAAGCGTGTTCCTGTTTCCACCTAAGCCCAAAGATACGTTGATGATCAGCCGCACC<br>CCGGAAGTAACCTGTGTAGTAGTAGATGTGTCCCACGAAGACCCCGAAGTAAAGTT<br>TAATTGGTACGTCGATGGTGTCGAAGTACATAACGCTAAAACGAAGCCCCGAGAAG<br>AGCAGTACAACAGTACTTACAGAGTAGTTTCTGTTCTTACAGTGCTGCATCAGGAT<br>TGGCTGAACGGGAAGGAGTATAAATGTAAAGTCTCAAACAAGGCACTTGCGGCACC<br>AATAGAGAAGACAATATCTAAGGCCAAAGGGCAGCCTAGAGAGCCACAAGTATATA<br>CGCTGCCCCCCAGCAGGGACGAGCTGACAAAGAACCAAGTGTCACTGACCTGCCTT<br>GTTAAGGGCTTCTATCCGAGTGATATTGCTGTTGAATGGGAAAGTAACGGACAGCC<br>GGAGAACAACTATAAAACTACTCCACCCGTGTTGGATAGTGACGGTAGCTTTTTTC<br>TGTACTCCAAGTTGACGGTAGACAAAAGTCGGTGGCAGCAGGGGAACGTATTTTCT<br>TGTTCTGTCATGCACGAAGCTCTTCACAATCACTATACGCAGAAGTCCCTCTCTCT<br>CTCTCCTGGGAAGGGTGGTTCCGACAGCTGGCAGGAGGAGGTCATTAAACTGTGTG<br>GTAGAGAGCTGGTACGGGCTCAAATTGCAATTTGTGGTAAGAGTACTGGCGGTGGC<br>GAGGAAGGGGGTGGGGAGGAGGCGGAGGTAGGCAGCTCTACTCTGCTCTCGCCAA<br>CAAGTGTTGTCACGTCGGGTGTACTAAAAGATCACTTGCCCGCTTTTGT |
| 400 | ATGGAAACCGATACCCTGCTCTTGTGGGTCCTCCTGCTTTGGGTCCCAGGTTCCAC<br>AGGCGACAAAACACATACATGCCCGCCGTGTCCGGCGCCTGAAGCAGCAGGAGGCC<br>CCAGTGTATTCCTTTTCCCTCCAAAGCCAAAAGATACGTTGATGATATCTAGGACA<br>CCTGAGGTTACCTGCGTCGTAGTGGACGTATCCCACGAAGACCCAGAAGTCAAGTT<br>TAACTGGTATGTGGACGGAGTGGAGGTACACAATGCAAAGACAAAGCCGCGAGAGG<br>AACAATATAATTCCACCTATAGAGTCGTGTCAGTCCTTACGGTCTTGCACCAGGAC<br>TGGCTCAATGGTAAGGAGTATAAGTGCAAAGTATCAAACAAAGCTCTCGCAGCGCC<br>CATCGAAAAGACCATCAGCAAAGCTAAGGGCCAGCCAAGAGAGCCTCAAGTGTACA<br>CGTTGCCGCCTTCAAGGGACGAGCTCACTAAAAATCAGGTATCACTTACGTGTCTT<br>GTCAAAGGGTTTTATCCTTCCGACATCGCGGTTGAATGGGAGAGCAATGGACAGCC<br>GGAGAATAATTATAAAACGACGCCGCCGGTCCTTGACAGCGATGGTTCATTTTTCC<br>TTTACTCAAAGCTGACGGTTGATAAGTCTAGGTGGCAGCAGGGGAACGTCTTTTCC<br>TGTAGTGTACTTCATGAGGCGCTCCATTCTCATTACACTCAGAAGTCACTGAGCCT<br>TTCACCCGGCAAAGGTGGATCAGACTCCTGGCAAGAAGAGGTAATCAAACTCTGTG<br>GGAGGGAACTCGTTCGAGCCCAGATTGCAATCTGTGGGAAAAGCACAGGCGGAGGG<br>GAAGAAGGGGGTGGCGAAGAAGGTGGGGCAGGCAGCTCTATTCAGCTCTTGCCAA<br>CAAATGCTGTCATGTAGGCTGCACAAAGCGATCACTGGCGAGATTCTGT |
| 401 | ATGGAAACCGACACCCTGCTGCTCTGGGTTCTTCTCCTCTGGGTTCCCGGCTCAAC<br>CGGAGATAAAACTCATACTTGCCCCACCCTGCCCGGCTCCCGAGGCAGCAGGTGGAC<br>CCTCAGTATTTTTGTTCCCTCCGAAACCTAAAGATACACTTATGATTAGCCGGACC<br>CCTGAGGTAACGTGTGTGGTGGTTGACGTAAGTCATGAAGATCCAGAAGTAAAGTT<br>TAACTGGTACGTAGACGGTGTGGAGGTACATAATGCGAAGACAAAACCACGAGAGG<br>AACAGTATAACTCTACCTACCGCGTAGTAAGCGTACTTACTGTGCTCCACCAAGAC<br>TGGCTTAACGGGAAGAGTATAAGTGTAAAGTCAGTAATAAAGCACTGGCCGCCCC<br>GATCGAAAAAACAATCAGCAAGGCCAAAGGACAACCAAGGGAGCCTCAGGTCTATA<br>CTCTTCCCCCGAGTAGGGATGAGCTTACCAAGAACCAGGTGTCTCTGACATGCCTT<br>GTCAAGGGATTTTACCCGAGTGACATAGCCGTAGAATGGGAGTCAAACGGCCAACC<br>TGAAAACAACTATAAGACCACGCCTCCCGTACTCGACTCAGATGGAAGCTTTTTCC<br>TCTATAGCAAGCTGACCGTCGACAAAAGTAGGTGGCAACAGGGAAACGTCTTTAGT<br>TGTTCCGTCATGCACGAAGCTTTGCATAACCATTACACCCAGAAGAGTCTTTCCCT<br>TTCCCCTGGCAAGGGGGCTCCGACTCCTGGCAAGAGGAAGTAATCAAACTGTGTG<br>GGCGCGAGCTTGTCCGCGCGCAAATAGCCATTTGCGGAAAAAGTACTGGAGGAGGA<br>GAGGAAGGCGGCGGCGAGGAAGGTGGGGCAGGCAGCTGTACAGTGCCTTGGCTAA<br>CAAGTGCTGCCATGTCGGCTGTACGAAAAGGTCTCTTGCTCAATTCTGT |
| 402 | ATGGAAACTGATACTCTTCTCCTTTGGGTGCTCCTCCTCTGGGTTCCCGGGTCCAC<br>AGGCGATAAGACACATACCTGTCCACCCTGCCCAGCACCTGAAGCTGCAGGCGGCC<br>CCAGCGTATTCCTGTTTCCTCCGAAGCCGAAAGACACACTTATGATTTCCCGGACG<br>CCTGAGGTAACTTGCGTCGTAGTAGATGTGTCTCACGAAGACCCCGAGGTGAAATT<br>CAACTGGTACGTTGATGGTGTGGAAGTTCATAATGCGAAAACTAAACCACGAGAGG<br>AGCAATATAACTCAACTTATAGAGTTGTGAGCGTCTTGACGGTACTGCACCAGGAC<br>TGGCTGAATGGCAAAGAGTACAAATGCAAAGTCTCAAATAAGGCGTTGGCGGCTCC<br>CATAGAGAAAACTATCAGCAAAGCCAAGGGTCAACCTCGGGAGCCACAAGTGTATA<br>CTCTTCCGCCTAGTCGCGACGAGCTCACAAAGAATCAGGTGAGTCTTACTTGTTTG<br>GTTAAGGGTTTCTACCCCAGTGACATTGCGGTCGAGTGGGAAGTAACGGACAGCC<br>TGAAACAACTATAAAACAACGCCTCCAGTACTCGATTCAGATGGTTCATTCTTTC<br>TTTATTCCAAACTCACAGTCGACAAGAGTAGATGGCAACAAGGGAACGTGTTTAGC |

TABLE 10-continued

Nucleotide Sequences Encoding Fusion Proteins and Peptide Components

| SEQ ID NO: | Sequence |
|---|---|
| | TGTAGCGTACTCCATGAGGCACTCCACTCTCACTATACCCAAAAGTCTCTCAGCTT<br>GTCACCCGGAAAAGGCGGTTCTGACAGTTGGCAAGAGGAAGTGATTAAATTGTGTG<br>GGCGGGAACTTGTGAGGGCTCAAATCGCGATTTGCGGCAAGTCCACTGGTGGCGGC<br>GAGGAAGGAGGAGGTGAAGAAGGAGGAGGTAGGCAACTGTATTCAGCGTTGGCGAA<br>TAAATGCTGCCATGTTGGATGTACTAAACGGAGCCTTGCTCAGTTCTGC |
| 403 | ATGGAAACTGACACCTTGTTGCTTTGGGTATTGCTTCTGTGGGTTCCGGGTAGCAC<br>GGGTGATAAAACGCATACTTGCCCTCCTTGCCCGGCACCTGAAGCTGCCGGAGGTC<br>CTTCCGTGTTCCTGTTCCCACCTAAGCCAAAAGACACACTTATGATTTCTCGCACA<br>CCAGAAGTAACGTGCGTCGTAGTTGACGTCTCCCATGAAGACCCGGAGGTAAAATT<br>TAATTGGTACGTCGACGGGGTAGAAGTTCATAACGCAAAGACTAAACCACGAGAAG<br>AGCAATACAACTCTACATACAGAGTAGTAAGCGTTCTCACCGTTCTTCATCAAGAT<br>TGGCTCAACGGAAAGGAGTATAAGTGTAAGGTGTCCAATAAAGCGTTGGCCGCACC<br>AATCGAAAAGACCATAAGCAAAGCCAAAGGCCAACCCCGCGAACCGCAGGTGTACA<br>CACTTCCCCCGTCCAGGGATGAATTGACAAAAAACCAAGTTTCCCTCACGTGTCTC<br>GTCAAGGGATTCTACCCGAGTGATATCGCAGTTGAATGGGAAAGCAATGGTCAGCC<br>CGAGAATAACTACAAGACTACTCCCCCTGTGTTGGACTCAGACGGCTCATTCTTCC<br>TCTACAGTAAGTTGACTGTGGACAAAAGTCGGTGGCAGCAAGGCAATGTCTTCAGT<br>TGTAGTGTAATGCATGAAGCACTCCACAATCATTACACCCAAAAATCCCTGAGCCT<br>GTCCCCGGGCGGAGGTTCAGATTCATGCAGGAGGAAGTTATAAAACTGTGCGGGC<br>GCGAGTTGGTGAGGGCGCAGATCGCAATCTGTGGAAAGAGTACGGGAGGTGGCGAA<br>GAGGGTGGTGGAGAAGAGGGAGGAGGTCGACAACTGTATTCCGCGCTCGCGAACAA<br>GTGTTGCCACGTTGGCTGCACCAAACGAAGCCTGGCTCGATTTTGC |
| 404 | ATGGAGACTGACACCCTTCTCCTCTGGGTCCTCTTGCTTTGGGTCCCTGGCTCTAC<br>TGGTGACAAGACACACACTTGTCCACCTTGCCCGGCTCCCGAGGCGGCAGGAGGAC<br>CAAGCGTTTTTCTGTTCCCTCCCAAACCAAAGGATACGCTTATGATCTCTCGAACG<br>CCGGAAGTTACTTGCGTAGTAGTTGATGTCTCCCATGAAGATCCCGAAGTGAAGTT<br>CAACTGGTATGTAGATGGTGTGGAAGTTCATAACGCGAAAACCAAACCACGCGAAG<br>AACAGTATAACAGTACTTATCGGGTTGTTTCAGTACTCACGGTGCTCCATCAAGAC<br>TGGCTTAATGGAAAGGAGTATAAATGTAAGGTAAGTAACAAGGCATTGGCGGCTCC<br>CATCGAGAAGACAATCTCAAAGCAAAAGGGCAACCACGGGAGCCTCAGGTGTATA<br>CGTTGCCGCCCAGCAGAGATGAACTTACTAAGAATCAGGTGAGTCTCACTTGTCTC<br>GTCAAGGGCTTCTATCCCAGCGATATAGCCGTAGAATGGGAGAGTAACGGTCAGCC<br>GGAGAACAACTACAAAACAACCCCGCCTGTTTTGGACTCCGATGGGAGTTTTTTTC<br>TCTACAGCAAACTCACGGTAGACAAAAGCAGGTGGCAGCAGGGCAATGTTTTCAGT<br>TGCTCTGTTCTCCACGAAGCCCTCCACTCCCACTATACTCAGAAGTCTCTGAGTCT<br>CTCACCAGGGGGAGGTAGCGATAGCTGGCAGGAGGAAGTGATCAAGTTGTGCGGGC<br>GCGAACTCGTGCGGGCACAAATTGCTATATGCGGTAAAAGTACGGGAGGTGGAGAG<br>GAGGGTGGAGGTGAAGAAGGCGGTGGTAGACAATTGTATAGTGCGCTCGCCAACAA<br>GTGTTGTCATGTCGGGTGTACGAAACGGTCCTTGGCGCGGTTTTGC |
| 405 | ATGGAAACTGACACACTTCTTCTGTGGGTACTCTTGTTGTGGGTTCCGGGCTCAAC<br>GGGTGACAAGACACATACTTGTCCACCATGTCCCGCCCCAGAAGCTGCGGGAGGAC<br>CATCAGTTTTTTTGTTCCCCCCGAAACCGAAGGATACCCTCATGATAAGTCGAACG<br>CCCGAAGTCACTTGCGTGGTGGTTGATGTTAGCCACGAGGACCCAGAAGTGAAGTT<br>CAACTGGTACGTGGACGGGGTCGAAGTTCATAATGCGAAAACAAAGCCTCGCGAGG<br>AACAGTACAACTCTACATACAGGGTTGTGTCTGTTTTGACAGTCTTGCACCAAGAT<br>TGGCTCAACGGGAAGGAATATAAGTGTAAGGTAAGCAATAAAGCACTGGCGGCCCC<br>GATCGAAAAAACGATATCCAAGGCCAAGGGCCAGCCCCGAGAGCCTCAGGTATATA<br>CTCTGCCGCCAAGCCGGGATGAACTGACTAAAAACCAGGTCTCTTTGACTTGTCTT<br>GTCAAGGGATTTTACCCAAGTGACATTGCGGTAGAGTGGGAAAGCAACGGTCAACC<br>AGAAAACAATTACAAGACGACACCGCCGGTACTCGACTCAGATGGATCCTTTTTCC<br>TGTATAGCAAGCTGACAGTGGACAAGTCCCGGTGGCAGCAAGGGAACGTATTTTCA<br>TGCAGCGTGATGCATGAGGCTCTTCACAACCATTACACACAGAAAAGTCTGTCATT<br>GAGCCCTGGCGGCGGGAGCGATTCTTGGCAAGAAGAAGTTATAAAACTTTGCGGTC<br>GAGAGCTGGTTCGGGCACAAATTGCTATCTGCGGAAAATCTACAGGAGGAGGCGAG<br>GAGGGAGGGGGCGAAGAAGGCGGGGGAGACAGTTGTACAGTGCGCTCGCTAACAA<br>GTGTTGCCACGTCGGTTGCACAAAGAGATCCCTGGCTCAATTCTGT |
| 406 | ATGGAGACAGATACTCTCTTGCTGTGGGTGCTGCTCTTGTGGGTTCCTGGAAGTAC<br>CGGTGATAAAACTCACACCTGTCCCCGTGTCCCGCACCAGAAGCGGCCGGTGGTC<br>CCTCCGTTTTTCTCTTCCCTCCTAAACCTAAGGACACACTTATGATTAGCAGAACT<br>CCAGAAGTTACGTGCGTAGTCGTTGACGTTAGTCATGAAGATCCTGAGGTTAAGTT<br>CAACTGGTACGTAGACGGGAGTAGAGGTCACAACGCCAAGACGAAACCCCGAGAAG<br>AGCAGTATAATTCTACCTATCGAGTTGTTTCAGTATTGACGGTGCTTCACCAAGAT<br>TGGCTGAATGGCAAAGAGTATAAGTGCAAGGTAAGCAACAAAGCACTCGCGGCTCC<br>TATCGAGAAAACTATTTCCAAAGCTAAGGGCCAGCCTCGCGAACCACAAGTCTATA<br>CCCTGCCACCGAGTCGGGACGAACTCACCAAGAACCAAGTGTCTCTTACTTGCCTC<br>GTTAAAGGTTTTTATCCCAGCGACATAGCCGTCGAATGGGAGTCCAATGGCCAACC<br>TGAGAACAACTATAAACTACCCCTCCTGTACTTGATAGCGACGGAAGTTTTTTCC<br>TCTATTCAAAACTCACAGTTGATAAGTCTCGATGGCAACAGGGCAACGTCTTCTCT<br>TGCAGTGTGTTGCATGAAGCTCTGCACTCTCATTACACACAGAAGAGTTTGTCTCT<br>CAGTCCAGGTGGCGGCTCAGATAGCTGGCAGGAAGAAGTAATCAAGTTGTGCGGCA |

TABLE 10-continued

Nucleotide Sequences Encoding Fusion Proteins and Peptide Components

| SEQ ID NO: | Sequence |
|---|---|
| | GGGAACTGGTAAGGGCACAGATAGCCATTTGTGGAAAATCTACGGGTGGCGGTGAG<br>GAAGGCGGCGGAGAAGAAGGGGGAGGTCGGCAGCTGTATAGTGCACTCGCAAACAA<br>GTGCTGCCATGTCGGGTGCACCAAGCGATCCCTTGCCCAGTTTTGC |
| 407 | ATGGAGACGGACACTCTTCTCCTGTGGGTTCTCCTCTTGTGGGTTCCAGGATCTAC<br>CGGCGATAAGACGCACACATGCCCACCCTGTCCTGCGCCTGAAGCCGCGGGGGGAC<br>CCAGCGTTTTTCTCTTCCCGCCGAAACCGAAAGACACACTTATGATCAGCCGGACT<br>CCCGAGGTTACCTGCGTGGTGGTAGATGTATCTCACGAGGATCCCGAGGTCAAATT<br>CAACTGGTACGTTGATGGGGTTGAAGTTCATAATGCCAAAACGAAGCCAAGAGAAG<br>AGCAGTATAACTCCACATATAGAGTTGTTTCCGTCTTGACTGTTCTTCACCAAGAT<br>TGGCTGAATGGGAAGGAGTACAAATGTAAAGTTAGCAACAAGGCACTCGCCGCTCC<br>CATTGAAAAAACTATAAGCAAAGCTAAGGGCCAACCGCGCGAACCACAGGTCTACA<br>CGTTGCCGCCCTCTAGGGACGAACTCACGAAGAATCAGGTTTCCCTTACCTGCCTC<br>GTTAAAGGATTCTACCCCTCTGACATAGCGGTTGAATGGGAGAGCAACGGTCAGCC<br>TGAGAACAACTACAAAACGACGCCTCCGGTGTTGGATTCCGACGGTAGTTTTTTCC<br>TCTATAGTAAGCTGACAGTGGATAAATCTCGGTGGCAGCAAGGGAATGTATTCTCC<br>TGTTCAGTCCTGCATGAAGCCCTCCACTCCCATTATACACAGAAATCTCTTTCTCT<br>GAGTCCCGGTAAAGGTGGGAGTGACTCTTGGCAGGAAGAGGTAATTAAGTTGTGTG<br>GAAGGGAGCTGGTAAGAGCACAGATTGCCATCTGTGGCAAATCCACGGGCGGCGAA<br>GGTGAGGGGGGTGAGGGGGAAGGGGGGTCCAGACAACTGTATTCTGCTCTGGCGAA<br>TAAGTGTTGCCATGTAGGGTGCACTAAACGGTCCTTGGCGCAGTTCTGT |
| 408 | ATGGAGACTGACACACTGCTCCTCTGGGTCCTTTTGCTCTGGGTTCCGGGGTCCAC<br>CGGTGATAAAACTCATACGTGCCCACCTTGCCCCGCACCGGAGGCTGCTGGAGGAC<br>CCTCTGTCTTCCTGTTCCCGCCGAAGCCTAAAGACACATTGATGATCAGTCGAACA<br>CCGGAAGTCACCTGTGTAGTGGTTGATGTGAGCCATGAGGACCCTGAAGTAAAATT<br>TAACTGGTATGTTGATGGCGTAGAAGTACACAACGCGAAGACTAAACCAAGGGAAG<br>AGCAATACAACTCTACCTATAGGGTCGTTAGCGTACTGACTGTGCTTCACCAAGAC<br>TGGCTTAACGGGAAGGAGTACAAGTGCAAAGTGAGCAATAAGGCCCTCGCCGCGCC<br>TATCGAGAAAACCATTTCCAAAGCCAAGGGTCAACCAAGGGAGCCTCAGGTTTACA<br>CCCTGCCCCCTTCAAGGGATGAGTTGACAAAAAACCAGGTAAGTCTGACGTGTCTC<br>GTTAAGGGATTCTACCCGTCAGATATCGCGGTAGAGTGGGAGAGCAACGGTCAGCC<br>AGAAAATAATTACAAAACAACACCTCCAGTTTTGGACTCTGATGGGAGTTTTTTTC<br>TTTATTCTAAGTTGACAGTGGATAAGTCACGCTGGCAACAGGGGAACGTATTTAGC<br>TGCTCAGTACTTCATGAAGCGTTGCATTCTCACTACACACAGAAGAGCCTCTCCTT<br>GAGTCCCGGAGGTGGCTCTGATTCTTGGCAGGAGGAGGTAATAAAACTTTGTGGTA<br>GAGAACTGGTTCGCGCTCAGATAGCTATTTGTGGAAAATCCACTGGCGGTGAAGGT<br>GAAGGTGGAGAAGGAGAGGCGGAAGCCGGCAGTTGTACTCTGCCCTGGCTAATAA<br>GTGCTGTCACGTGGGCTGCACTAAGCGGAGCTTGGCAAGATTTTGC |
| 409 | ATGGAAACCGACACGCTGCTGCTGTGGGTGCTGTTGTTGTGGGTTCCAGGCTCAAC<br>TGGCGATAAAACTCATACCTGTCCACCTTGTCCTGCGCCTGAGGCAGCTGGAGGGC<br>CTAGCGTGTTCCTGTTCCCCCCCAAACCCAAAGACACGCTCATGATTAGCCGAACC<br>CCTGAAGTGACCTGCGTTGTTGTGGACGTAAGCCACGAAGACCCCGAAGTTAAGTT<br>TAATTGGTACGTCGACGGTGTTGAGGTTCATAACGCGAAGACTAAGCCGAGAGAGG<br>AGCAATATAACAGCACCTACCGCGTAGTCTCAGTTCTTACCGTGCTCCACCAGGAC<br>TGGCTTAACGGGAAGGAATACAAATGCAAAGTTTCCAACAAAGCCTTGGCAGCCCC<br>AATAGAGAAGACAATATCTAAGGCGAAAGGCCAACCGCGGGAACCGCAAGTTTATA<br>CCCTCCCACCGAGCAGGGATGAGCTGACAAAAAATCAGGTTTCCCTCACTTGTCTG<br>GTCAAGGGATTTTATCCTTCAGACATAGCCGTTGAATGGGAGAGTAATGGGCAGCC<br>GGAGAATAATTACAAGACCACCCCCCGGTGTTGGACAGCGACGGTTCCTTCTTTC<br>TCTATTCTAAACTTACCGTCGACAAATCACGGTGGCAACAAGGAAATGTATTCTCA<br>TGCAGTGTATTGCACGAAGCTCTGCACTCTCATTACACCCAAAAATCCCTCTCTCT<br>CAGCCCTGGCGGTGGATCTGATTCTTGGCAGGAAGAGGTGATTAAACTGTGTGGGC<br>GAGAGCTTGTCCGAGCTCAGATCGCTATTTGTGGCAAGAGTACCGGAGGCGAGGGT<br>GAGGGAGGCGAAGGCGAGGCGGAAGCCGGCAACTCTATAGCGCACTCGCTAATAA<br>ATGTTGTCATGTCGGCTGCACGAAGCGCTCACTGGCGCAGTTCTGC |
| 500 | ATGGAAACTGATACCCTGTTGTTGTGGGTCCTTTTGCTTTGGGTTCCAGGCAGCAC<br>CGGAGATAAAACCCATACGTGTCCTCCATGCCCAGCTCCCGAGCTGCTCGGTGGTC<br>CTTCAGTGTTCCTCTTCCCCCCAAAGCCGAAGGACACGCTCATGATTAGTCGAACG<br>CCAGAGGTGACATGTGTGGTCGTTGATGTTTCCCATGAGGATCCGGAAGTTAAGTT<br>CAACTGGTACGTAGATGGCGTGGAGGTTCACAATGCAAAACCAAGCCCCGCGAGG<br>AGCAGTATAACTCAACCTACAGAGTAGTATCTGTGCTCACGGTCTTGCATCAGGAT<br>TGGTTGAACGGGAAGGAATACAAGTGTAAAGTAAGTAATAAGGCACTGCCGGCCCC<br>CATAGAAAAACTATCAGCAAAGCTAAAGGTCAGCCGCGGGAGCCACAAGTTTACA<br>CTCTTCCTCCTAGTAGAGACGAGCTGACGAAGAATCAAGTTTCTTTGACTTGTCTC<br>GTGAAGGGATTCTACCCAAGCGATATAGCTGTAGAGTGGGAAAGCAACGGACAACC<br>AGAAAATAACTACAAGACTACACCCCCCGTTCTCGATTCTGATGGCTCATTCTTCT<br>TGTACTCAAAATTGACAGTTGACAAATCTCGATGGCAGCAGGGTAACGTATTTAGT<br>TGCTCTGTTATGCACGAAGCGTTGCATAACCACTACACACAGAAGTCATTGTCACT<br>GAGCCCAGGAAAAGGTGGTGGCGGGTCCGGCGGTGGAGGTAGCGGTGGCGGGGCT<br>CCCAGCTTTATAGTGCCCTTGCAAACAAATGTTGCCACGTCGGATGTACGAAGCGC<br>AGTTTGGCGAGATTCTGTGGAGGGGGCGGATCCGGAGGCGGGGGGTCCGGAGGAGG |

TABLE 10-continued

Nucleotide Sequences Encoding Fusion Proteins and Peptide Components

| SEQ ID NO: | Sequence |
|---|---|
| | AGGTAGCTCATGGATGGAAGAGGTAATAAAACTGTGCGGACGCGAGCTTGTCAGGG<br>CCCAAATCGCAATTTGTGGCATGAGCACATGGAGT |
| 540 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGAGAAGGGGCGGAAGGCAGCTTTACTCTGCTCTGGCTAA<br>CAAGTGTTGTCACGTTGGGTGTACCAAGCGGTCCCTTGCGCAATTCTGC |
| 541 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGAGAAGGGGCGGAAGGCAGCTTTACTCTGCTCTGGCTAA<br>CAAGTGTTGTCAAGTTGGGTGTACCAAGCGGTCCCTTGCGCAATTCTGC |
| 542 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGAGAAGGGGCGGAAGGCAGCTTTACTCTGCTCTGGCTAA<br>CAAGTGTTGTCACGTTGGGTGTACCAAGCAATCCCTTGCGCAATTCTGC |
| 543 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGAGAAGGGGCGGAAGGCAGCTTTACTCTGCTCTGGCTAA<br>CAAGTGTTGTCAAGTTGGGTGTACCAAGCAATCCCTTGCGCAATTCTGC |

TABLE 10-continued

Nucleotide Sequences Encoding Fusion Proteins and Peptide Components

| SEQ ID NO: | Sequence |
|---|---|
| 544 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGACTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGAGGAGAA<br>GGCTCTGGAGGCGAAGGATCTGGGGCGGAAGGCAGCTTTACTCTGCTCTGGCTAA<br>CAAGTGTTGTCACGTTGGGTGTACCAAGCGGTCCCTTGCGCAATTCTGC |
| 545 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGATCTGGGGGCGGAAGGCAGCTTTACTCTGCTCTGGCTAA<br>CAAGTGTTGTCAAGTTGGGTGTACCAAGCGGTCCCTTGCGCAATTCTGC |
| 546 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGATCTGGGGGCGGAAGGCAGCTTTACTCTGCTCTGGCTAA<br>CAAGTGTTGTCACGTTGGGTGTACCAAGCAATCCCTTGCGCAATTCTGC |
| 547 | ATGGAAACGGATACGCTGTTGTTGTGGGTTCTGCTCTTGTGGGTGCCAGGGAGCAC<br>AGGTGATAAAACCCACACTTGCCCACCTTGCCCTGCGCCGGAAGCCGCCGGAGGAC<br>CTAGTGTTTTCCTCTTTCCCCCTAAGCCCAAAGACACGTTGATGATCTCTCGGACA<br>CCGGAAGTAACTTGTGTCGTTGTGGATGTGTCACATGAGGATCCCGAGGTGAAATT<br>TAATTGGTACGTTGACGGCGTGGAGGTGCATAACGCAAAGACTAAACCACGCGAGG<br>AGCAGTATAATTCTACATACCGGGTTGTCTCAGTTCTCACAGTTCTTCATCAGGAT<br>TGGTTGAATGGAAAGGAGTACAAATGCAAAGTGTCCAACAAAGCGCTTGCTGCGCC<br>GATTGAAAAGACGATTTCAAAGGCAAAAGGGCAGCCCCGCGAACCCCAAGTATATA<br>CTTTGCCTCCCTCACGCGATGAACTGACTAAGAACCAGGTGAGCCTGACTTGTTTG<br>GTTAAGGGTTTTTATCCAAGTGACATTGCTGTTGAATGGGAGTCCAATGGCCAGCC<br>TGAGAATAACTACAAAACGACACCTCCTGTACTTGACAGCGACGGCTCCTTTTTTC<br>TTTATTCAAAACTCACAGTGGACAAATCCAGGTGGCAGCAGGGTAACGTCTTTTCT<br>TGCAGCGTGCTCCACGAAGCTTTGCATTCACATTATACGCAAAAATCCTTGTCATT<br>GTCCCCAGGTAAGGGCGGAAGCGACTCATACCAAGAAGAAGTCATTAAACTTTGTG<br>GACGGGAGCTGGTTAGGGCACAGATTGCTATTTGTGGTAAGTCTACGGGAGGAGAA<br>GGCTCTGGAGGCGAAGGATCTGGGGGCGGAAGGCAGCTTTACTCTGCTCTGGCTAA<br>CAAGTGTTGTCAAGTTGGGTGTACCAAGCAATCCCTTGCGCAATTCTGC |

In some embodiments, any of the nucleotide sequences shown in Table 10 further comprise additional nucleotide sequence on their 5' and/or 3' ends. In some embodiments, any of the nucleotide sequences shown in Table 10 further comprise the nucleotide sequence ACGGGACC-GATCCAGCCTCCGGACTCTAGAGCCACC (SEQ ID NO: 494) on their 5' ends and/or any of the nucleotide sequences shown in Table 10 further comprise the nucleotide sequence TGATAAACCGGTTAGTAATGAGTTTGA-TATCTCGAC (SEQ ID NO: 495) on their 3' ends.

A variety of host cells and expression vector systems can be utilized to express the fusion proteins described herein. Such expression systems represent vehicles by which the coding sequences of interest can be produced and subsequently purified, but also represent cells which can, when transformed or transfected with the appropriate nucleotide coding sequences, express a fusion protein described herein in situ. These include but are not limited to microorganisms such as bacteria (e.g., E. coli and B. subtilis) transformed with, e.g., recombinant bacteriophage DNA, plasmid DNA or cosmid DNA expression vectors containing fusion protein coding sequences; yeast (e.g., Saccharomyces Pichia) transformed with, e.g., recombinant yeast expression vectors containing fusion protein coding sequences; insect cell systems infected with, e.g., recombinant virus expression vectors (e.g., baculovirus) containing fusion protein coding sequences; plant cell systems (e.g., green algae such as Chlamydomonas reinhardtii) infected with, e.g., recombinant virus expression vectors (e.g., cauliflower mosaic virus, CaMV; tobacco mosaic virus, TMV) or transformed with, e.g., recombinant plasmid expression vectors (e.g., Ti plasmid) containing fusion protein coding sequences; or mammalian cell systems (e.g., COS (e.g., COS1 or COS), CHO, BHK, MDCK, HEK 293, NS0, PER.C6, VERO, CRL7030, HsS78Bst, HeLa, and NIH 3T3, HEK-293T, HepG2, SP210, R1.1, B-W, L-M, BSC1, BSC40, YB/20, and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, cells for expressing the fusion proteins described herein are human cells, e.g., human cell lines. In certain embodiments, a mammalian expression vector is pOptiVEC™ or pcDNA3.3. In certain embodiments, bacterial cells such as Escherichia coli, or eukaryotic cells (e.g., mammalian cells), are used for the expression of a fusion protein. For example, mammalian cells such as CHO or HEK293 cells, in conjunction with a vector such as the major intermediate early gene promoter element from human cytomegalovirus is an effective expression system for fusion proteins disclosed herein.

In bacterial systems, a number of expression vectors can be advantageously selected depending upon the use intended for the fusion protein being expressed. For example, when a large quantity of a fusion protein is to be produced, vectors which direct the expression of high levels of fusion protein products that are readily purified can be desirable. Such vectors include, but are not limited to, the E. coli expression vector pUR278 (Ruether U & Mueller-Hill B (1983) EMBO J 2:1791-1794), in which the fusion protein coding sequence can be ligated individually into the vector in frame with the lac Z coding region so that a fusion protein is produced; pIN vectors (Inouye S & Inouye M (1985) Nuc Acids Res 13:3101-3109; Van Heeke G & Schuster S M (1989) J Biol Chem 24:5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV), for example, can be used as a vector to express foreign genes. The virus grows in Spodoptera frugiperda cells. The fusion protein coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the fusion protein coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the fusion protein molecule in infected hosts (see, e.g., Logan J & Shenk T (1984) PNAS 81(12):3655-9, which is herein incorporated by reference in its entirety). Specific initiation signals can also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al. (1987) Methods Enzymol. 153:516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2, SP210, R1.1, B-W, L-M, BSC1, BSC40, YB/20, BMT10, and HsS78Bst cells.

For long-term, high-yield production of recombinant proteins, stable expression cells can be generated. For example, cell lines which stably express a fusion protein described herein can be engineered.

In certain embodiments, rather than using expression vectors which contain viral origins of replication, host cells can be transformed with a polynucleotide (e.g., DNA or RNA) controlled by appropriate transcriptional regulatory elements (e.g., promoter, enhancer, sequences, transcription terminators, polyadenylation sites, etc.), and a selectable marker. Following the introduction of polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express a fusion protein described herein or a fragment thereof.

A number of selection systems can be used, including but not limited to the herpes simplex virus thymidine kinase (Wigler M et al. (1977) Cell 11(1):223-32), hypoxanthine-guanine phosphoribosyltransferase (Szybalska E H & Szybalski W (1962) PNAS 48(12):2026-2034) and adenine phosphoribosyltransferase (Lowy I et al. (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al. (1980) PNAS 77(6):3567-70; O'Hare K et al. (1981) PNAS 78:1527-31); gpt, which confers resistance to mycophenolic acid (Mulligan R C & Berg P (1981) PNAS 78(4):2072-6); neo, which confers resistance to the aminoglycoside G-418 (Wu G Y & Wu C H (1991) Biotherapy 3:87-95; Tolstoshev P (1993) Ann Rev Pharmacol Toxicol 32:573-596; Mulligan R C (1993) Science 260:926-932; Morgan R A & Anderson W F (1993) Ann Rev Biochem 62:191-217; Nabel G J & Felgner P L (1993) Trends Biotechnol 11(5):211-5); and hygro, which confers resistance to hygromycin (Santerre R F et al. (1984) Gene 30(1-3):147-56), all of which are herein incorporated by reference in their entireties. Methods commonly known in the art of recombinant DNA technology can be routinely applied to select the desired recombinant clone and such methods are described, for example, in Ausubel F M et al. (eds.), Current Protocols in Molecular Biology, John Wiley & Sons, NY (1993); Kriegler M, Gene Transfer and Expression, A Laboratory Manual, Stockton Press, NY (1990); and in Chapters 12 and 13, Dracopoli N C et al. (eds.), Current Protocols in Human Genetics, John Wiley & Sons, NY (1994); Colbere-Garapin F et al. (1981) *J Mol Biol* 150:1-14, all of which are herein incorporated by reference in their entireties.

Pharmaceutical Compositions

The present disclosure provides pharmaceutical compositions comprising the fusion proteins or component peptides described herein or the nucleic acid molecules, or the expression vectors that encode them. The pharmaceutical compositions described herein are formulated with suitable carriers, excipients, and other agents that provide improved transfer, delivery, tolerance, and the like. A multitude of appropriate formulations can be found in the formulary known to all pharmaceutical chemists: *Remington's Pharmaceutical Sciences*, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also, Powell et al., "Compendium of excipients for parenteral formulations" PDA (1998) *J Pharm Sci Technol* 52:238-311.

The dose of the fusion proteins or component peptides described herein or the nucleic acid molecules, or the expression vectors that encode them administered to a patient may vary depending upon the age and the size of the patient, target disease, conditions, route of administration, and the like. The preferred dose is typically calculated according to body weight or body surface area. Depending on the severity of the condition, the frequency and the duration of the treatment can be adjusted. Effective dosages and schedules for administering the fusion proteins or component peptides described herein or the nucleic acid molecules, or the expression vectors that encode them may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition disclosed herein, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Any pharmaceutical composition described herein can be delivered subcutaneously or intravenously with a standard needle and syringe. In addition, with respect to subcutaneous delivery, a pen delivery device readily has applications in delivering a pharmaceutical composition disclosed herein. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see, Langer, supra; Sefton, 1987, *CRC Crit. Ref Biomed. Eng.* 14:201). In another embodiment, polymeric materials can be used; see, *Medical Applications of Controlled Release*, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, *Science* 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending, or emulsifying any of the fusion proteins described herein in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid fusion protein contained is generally about 5 to about 500 mg per dosage form in a unit dose; especially in the form of injection, it is preferred that the aforesaid fusion protein is contained in about 5 to about 100 mg and in about 10 to about 250 mg for the other dosage forms.

Therapeutic Uses
Monotherapy

The present disclosure provides methods of enhancing a relaxin-2-related activity in a primary cell, comprising contacting the primary cell with a fusion protein or component peptide described herein. In some embodiments, contacting the primary cell with the fusion protein or component peptide results in enhanced relaxin-2 activity in the cell, e.g., as described above. In some embodiments, contacting the primary cell with the fusion protein or component peptide results in activation of the relaxin-2 receptor (RFXP1) on a cell surface. Activation of RXFP1 on the cell surface can lead to cellular responses, including but not limited to, the elevation of cAMP levels, vasodilation, the expression of angiogenic factors, including VEGF, the expression of MMPs, and collagen degradation. In some embodiments, the cell is selected from the group consisting of endothelial cells, vascular smooth muscle cells, other vascular cells, cardiomyocytes, other cardiac cells, and fibroblasts. In some embodiments, the primary cell is within a subject, as described below.

In certain embodiments, the present disclosure provides methods for activating RXFP1 on a cell surface, comprising administering an effective amount of the fusion proteins or component peptides described herein or the nucleic acid molecules, or the expression vectors that encode them to a subject in need thereof, thereby activating RXFP1 on the surface of the cell. Activation of RXFP1 on the cell surface can lead to cellular responses, including but not limited to, the elevation of cAMP levels, vasodilation, the expression of angiogenic factors, including VEGF, the expression of MMPs, and collagen degradation. In some embodiments, the cell is selected from the group consisting of endothelial cells, vascular smooth muscle cells, other vascular cells, cardiomyocytes, other cardiac cells, and fibroblasts.

This disclosure also provides methods for treating various relaxin-2 associated diseases. As used herein, the term "relaxin-2-associated disease," is a disease or disorder that is caused by, or associated with, relaxin-2 protein production or relaxin-2 protein activity. The term "relaxin-2-associated disease" includes a disease, disorder or condition that would benefit from an increase in relaxin-2 protein activity. As used herein, the term "relaxin-2-associated disorder" has the same meaning as "relaxin-2-associated disease."

In certain embodiments, the relaxin-2-associated disease or disorder is selected from the group consisting of kidney diseases, fibrotic diseases, and cardiovascular diseases. In certain embodiments, the relaxin-2-associated disease or disorder is pulmonary hypertension.

There are five groups of pulmonary hypertension as defined by the World Health Organization (WHO). Group 1 is pulmonary arterial hypertension (PAH), the diagnosis of which requires right heart catheterization (RHC) to demonstrate a mean pulmonary arterial (PA) pressure (mPAP) ≥20 mm Hg at rest and a pulmonary vascular resistance (PVR) of 2 Wood units. Additional criteria to meet Group 1 PAH includes: a mean pulmonary capillary wedge pressure (PCWP) ≤15 mm Hg, chronic lung diseases (CLDs) and other causes of hypoxemia are mild or absent; venous thromboembolic disease and PA obstructions are absent; and certain miscellaneous disorders are absent, including systemic disorders (e.g., sarcoidosis, chronic renal insufficiency), hematologic disorders (e.g., myeloproliferative diseases and chronic hemolytic anemias), and metabolic disorders (e.g., glycogen storage disease). Group 1 also includes PAH due to an unknown mechanism (idiopathic PAH) and heritable genetic defects (heritable PAH); PAH developed from drugs and toxins; PAH associated with systemic disorders such as connective tissue diseases, human immuno-deficiency virus (HIV) infection, congenital heart disease, and schistosomiasis; PAH with overt features of venous/capillary involvement; and persistent PH of the newborn.

Group 2 is PH due to left heart disease (PH-LHD), which may be diagnosed clinically when there is sufficient LHD on echocardiography (with or without other confirmatory testing) to explain PH. For patients in whom RHC is performed, an mPAP ≥20 mmHg, PCWP ≥15 mmHg, and a normal or reduced cardiac output is consistent with a hemodynamic diagnosis of LHD-PH. Important adjunct information is the presence of left atrial (LA) enlargement on an echocardiogram and a left heart catheterization (LHC) to confirm an elevated left ventricular end-diastolic pressure. Once PH-LHD is confirmed, patients should be allocated into one of the following categories: PH-LHD due to heart failure with preserved or reduced ejection fraction (group 2.1), heart failure with reduced ejection fraction (group 2.2), valvular heart disease, or congenital or acquired conditions leading to postcapillary PH (group 2.3; e.g., restrictive cardiomyopathy, constrictive pericarditis, LA myxoma, congenital or acquired inflow/outflow tract obstruction, and congenital cardiomyopathies). There are two subgroups of Group 2 PH that patients can be distinguished into: those who have combined pre- and postcapillary PH (CpcPH) and those who have isolated postcapillary hypertension (IpcPH).

Group 3 is PH due to chronic lung disease and/or hypoxemia, which is the diagnosis of PH due to CLD and/or hypoxemia made by demonstration of PH on RHC or echocardiogram and evidence of moderate to severe lung dysfunction and/or hypoxemia. Patients are allocated into PH due to obstructive lung disease (group 3.1), restrictive lung disease (group 3.2), mixed obstructive and restrictive lung disease (group 3.3), PH associated with hypoventilation (group 3.4) hypoxia without lung disease (group 3.5), or PH due to developmental disorders (group 3.6). In some cases, Group 3 PH may be due to COPD, interstitial lung disease, or obstructive sleep apnea.

Group 4 is PH due to pulmonary artery obstructions and includes mostly patients with chronic thromboembolic PH (CTEPH; group 4.1) as well as PH due to PA obstructions (group 4.2, e.g., benign or malignant tumors, arteritis in the absence of CTD, congenital PA stenosis, parasites).

Group 5 is PH due to multifactorial mechanisms and include patients with PH who do not clearly fit into Group 1 through 4. Group 5 PH can be further classified into those that have: hematologic disorders such as chronic hemolytic anemia (e.g., sickle cell disease, beta thalassemia, or spherocytosis) and myeloproliferative disorders; systemic or metabolic disorders including sarcoidosis, pulmonary Langerhans histiocytosis X, and neurofibromatosis; metabolic disorders including Gaucher disease and glycogen storage disease; chronic renal failure and PH associated with hemodialysis; pulmonary tumor thrombotic microangiopathy; and fibrosing mediastinitis.

In certain embodiments, the relaxin-2-associated disease or disorder is pulmonary hypertension, including, any of the WHO defined Group 1, Group 2, Group 3, Group 4, and Group 5 PH.

In certain embodiments, the relaxin-2-associated disease or disorder is pulmonary hypertension, including, but not limited to, pulmonary arterial hypertension (PAH), pulmonary hypertension due to left heart disease (PH-LHD), combined precapillary and postcapillary pulmonary hypertension (CpcPH), and isolated postcapillary pulmonary hypertension (IpcPH). In certain embodiments, the relaxin-2-associated disease or disorder is pulmonary arterial hypertension (PAH). In certain embodiments, the relaxin-2-associated disease or disorder is pulmonary hypertension due to left heart disease (PH-LHD). In certain embodiments, the relaxin-2-associated disease or disorder is combined precapillary and postcapillary pulmonary hypertension (CpcPH). In certain embodiments, the relaxin-2-associated disease or disorder is isolated postcapillary pulmonary hypertension (IpcPH).

In certain embodiments, the relaxin-2-associated disease or disorder is a Group 2 pulmonary hypertension. In certain embodiments, the relaxin-2-associated disease or disorder is isolated postcapillary pulmonary hypertension (IpcPH). IpcPH includes characteristics such as right ventricular dysfunction; thickening and stiffening of left ventricle (LHD); and compromised kidney function. In certain embodiments, the relaxin-2-associated disease or disorder is selected from the group consisting of right ventricular dysfunction; thickening and stiffening of left ventricle (LHD); and compromised kidney function. In certain embodiments, the relaxin-2-associated disease or disorder is combined pre- and postcapillary pulmonary hypertension (CpcPH). CpcPH includes characteristics such as pulmonary artery narrowing, thickening, stiffening, and/or fibrotic remodeling; right ventricular dysfunction; thickening and stiffening of left ventricle (LHD); and compromised kidney function. In certain embodiments, the relaxin-2-associated disease or disorder is selected from the group consisting of pulmonary artery narrowing, thickening, stiffening, and/or fibrotic remodeling; right ventricular dysfunction; thickening and stiffening of left ventricle (LHD); and compromised kidney function.

In certain embodiments, the relaxin-2-associated disease or disorder is heart failure, including, but not limited to, heart failure with preserved ejection fraction (HFpEF), and heart failure with reduced ejection fraction (HFrEF). In certain embodiments, the relaxin-2-associated disease or disorder is heart failure with preserved ejection fraction (HFpEF). In certain embodiments, the relaxin-2-associated disease or disorder is heart failure with reduced ejection fraction (HFrEF).

In certain embodiments, the relaxin-2-associated disease or disorder is heart disease, including, but not limited to, valvular heart disease.

In certain embodiments, the relaxin-2-associated disease or disorder is Group 2 PH (CpcPH or IpcPH) with heart failure with preserved ejection fraction (HFpEF). In certain embodiments, the relaxin-2-associated disease or disorder is CpcPH with HFpEF. In certain embodiments, the relaxin-2-associated disease or disorder is IpcPH with HFpEF. In certain embodiments, the HFpEF is defined as signs and symptoms of New York Heart Association (NYHA) class II-III heart failure and LVEF ≥50% and at least one of (i) Heart Failure Association-Pre-test assessment, Echocardiography and natriuretic peptide score, Functional testing in cases of uncertainty, Final etiology (HFA-PEFF) score ≥5 points; and/or (ii) HFA-PEFF score 2-4 points and abnormal diastolic stress testing or invasive hemodynamic measurements. In certain embodiments, the relaxin-2-associated disease or disorder is CpcPH with NYHA class II-III heart failure and LVEF ≥50% and at least one of (i) HFA-PEFF score ≥5 points; and/or (ii) HFA-PEFF score 2-4 points and abnormal diastolic stress testing or invasive hemodynamic measurements. In certain embodiments, the relaxin-2-associated disease or disorder is IpcPH with NYHA class II-III heart failure and LVEF ≥50% and at least one of (i) HFA-PEFF score ≥5 points; and/or (ii) HFA-PEFF score 2-4 points and abnormal diastolic stress testing or invasive hemodynamic measurements.

In certain embodiments, the relaxin-2-associated disease or disorder is Group 2 PH (CpcPH or IpcPH) with heart failure with mid-range ejection fraction (HFmrEF). In certain embodiments, the relaxin-2-associated disease or disorder is CpcPH with HFmrEF. In certain embodiments, the relaxin-2-associated disease or disorder is IpcPH with HFmrEF. In certain embodiments, HFmrEF is defined as signs and symptoms of New York Heart Association (NYHA) class II-III heart failure and LVEF 40% to 49%. In certain embodiments, the relaxin-2-associated disease or disorder is CpcPH with NYHA class II-III heart failure and LVEF 40% to 49%. In certain embodiments, the relaxin-2-associated disease or disorder is IpcPH with NYHA class II-III heart failure and LVEF 40% to 49%.

In certain embodiments, the relaxin-2-associated disease or disorder is Group 2 PH (CpcPH or IpcPH) with heart failure with reduced ejection fraction (HFrEF). In certain embodiments, the relaxin-2-associated disease or disorder is CpcPH with HFrEF. In certain embodiments, the relaxin-2-associated disease or disorder is IpcPH with HFrEF.

In certain embodiments, CpcPH is based on right heart catheterization (RHC) performed showing pulmonary vascular resistance (PVR) ≥3 Wood units, mPAP of >20 mm Hg, PCWP >15 mm Hg or PCWP >12 mm Hg and ≤14 mm Hg with evidence on left atrial volume index (LAVI) on echocardiography of ≥34 mL/m$^2$. In certain embodiments, IpcPH is based on RHC performed showing PVR <3 Wood units, mPAP of >20 mm Hg, PCWP >15 mm Hg or PCWP >12 mm Hg and ≤14 mm Hg with evidence on left atrial volume index (LAVI) on echocardiography of ≥34 mL/m².

In certain embodiments, the relaxin-2-associated disease or disorder is a cardiovascular disease associated with pregnancy, including, but not limited to, preeclampsia, post-partum hypertension, post-partum cardiomyopathy, pregnancy induced heart failure, and maternal hypertension complicating the puerperium.

In certain embodiments, the relaxin-2-associated disease or disorder is kidney disease. In certain embodiments, the relaxin-2-associated disease or disorder is chronic kidney disease. In certain embodiments, the relaxin-2-associated disease or disorder is hypertensive kidney disease.

In certain embodiments, the relaxin-2-associated disease or disorder is joint disease. In certain embodiments, the relaxin-2-associated disease or disorder is frozen shoulder (also known as adhesive capsulitis).

Administration of the compositions according to the methods described herein may result in a reduction of the severity, signs, symptoms, or markers of a relaxin-2-associated disease or disorder in a patient with a relaxin-2-associated disease or disorder. By "reduction" in this context is meant a statistically significant decrease in such level. The reduction (absolute reduction or reduction of the difference between the elevated level in the subject and a normal level) can be, for example, at least about 20%, 25%, 30%, 35%, 40%, 45%, 50%, 55%, 60%, 65%, 70%, 75%, 80%, 85%, 90%, or 95%, or to below the level of detection of the assay used.

In certain embodiments, administration of the compositions according to the methods described herein results in pulmonary vasodilation in the patient. In certain embodiments, administration of the compositions according to the methods described herein results in an anti-inflammatory effect in the patient. In certain embodiments, administration of the compositions according to the methods described herein results in an anti-fibrotic effect in the patient. In certain embodiments, administration of the compositions according to the methods described herein results in right ventricular remodeling in the patient. In certain embodiments, administration of the compositions according to the methods described herein results in peripheral vasodilation in the patient. In certain embodiments, administration of the compositions according to the methods described herein results in cardiac relaxation in the patient. In certain embodiments, administration of the compositions according to the methods described herein results in left ventricular remodeling in the patient. In certain embodiments, administration of the compositions according to the methods described herein results in improvement in kidney function in the patient.

In certain embodiments, administration of the compositions according to the methods described herein results in increased renal plasma flow. In certain embodiments, administration of the compositions according to the methods described herein results in increased renal plasma flow that persists after 1 week, 2 weeks, 3 weeks, 4 weeks, 5 weeks, or 1 month, after a single administration. In certain embodiments, the increase in the renal plasma flow in the subject is maintained by at least about 30%, at least about 40%, at least about 50%, at least about 60%, at least about 70%, at least about 75%, at least about 80%, at least about 85%, at least about 90%, or at least about 95% 1 week, 2 weeks, 3 weeks, 4 weeks, 5 weeks, or 1 month after a single administration. In certain embodiments, administration of the compositions according to the methods described herein results in increased renal plasma flow that persists after 1 week, 2 weeks, 3 weeks, 4 weeks, 5 weeks, or 1 month, after a single administration to a human. In certain embodiments, the increase in the renal plasma flow in the subject is maintained by at least about 30%, at least about 40%, at least about 50%, at least about 60%, at least about 70%, at least about 75%, at least about 80%, at least about 85%, at least about 90%, or at least about 95% 1 week, 2 weeks, 3 weeks, 4 weeks, 5 weeks, or 1 month after a single administration to a human.

Combination Therapies and Formulations

The present disclosure also provides compositions and therapeutic formulations comprising the fusion proteins or component peptides described herein or the nucleic acid molecules, or the expression vectors that encode them in combination with one or more additional therapeutically active components (i.e., therapeutic agents), and methods of treatment comprising administering such combinations to subjects in need thereof.

Exemplary additional therapeutic agents include any therapeutic agents that may be used for the treatment of any relaxin-2-related disorders described herein. Exemplary additional therapeutic agents that may be combined with or administered in combination with the fusion proteins or component peptides described herein or the nucleic acid molecules, or the expression vectors that encode them include, but are not limited to any one or more of: angiotensin II receptor blockers, e.g., azilsartan, candesartan, eprosartan, losartan; ACE inhibitors, e.g., lisinopril, benazepril, captopril, enalapril, moexipril, perindopril, quinapril, trandolapril; calcium channel blockers, e.g., amlodipine, amlodipine and benazepril, amlodipine and valsartan, sacubitril and valsartan, diltiazem, felodipine, isradipine, nicardipine, nimodipine, nisoldipine, verapamil; diuretics, e.g., chlorthalidone, hydrochlorothiazide, metolazone, indapamide, torsemide, furosemide, bumetanide, amiloride, triamterene, spironolactone, eplerenone; aldosterone antagonists, e.g., spironolactone, eplerenone; digoxin, e.g., lanoxin; beta blockers, e.g., carvedilol, metoprolol, bisoprolol; activin signaling inhibitors, e.g., sotatercept; sodium/glucose cotransporter 2 (SGLT2) inhibitors, e.g., empagliflozin, dapagliflozin, bexagliflozin, canagliflozin, ertugliflozin, ipragliflozin, luseogliflozin, remogliflozin etabonate sergliflozin etabonate, sotagliflozin, tofogliflozin, henagliflozin, janagliflozin, mizagliflozin, velagliflozin proline hydrate, enavogliflozin; and glucagon-like peptide-1 (GLP-1) receptor agonists, e.g., exenatide, liraglutide, albiglutide, dulaglutide, lixisenatide, semaglutide, and tirzepatide.

In some embodiments, the additional therapeutic agents that may be combined with or administered in combination with the fusion proteins or component peptides described herein or the nucleic acid molecules, or the expression vectors that encode them include, but are not limited to any one or more of: sotatercept, empagliflozin, dapagliflozin, sacubitril, valsartan, semaglutide, dulaglutide, and tirzepatide.

In some embodiments, the additional therapeutic agents are drugs effective in treating fibrosis, including but not limited to, small molecule drugs and antibodies. Exemplary anti-fibrosis drugs include, but are not limited to, TGF-β inhibitors, e.g., small molecules such as hydronidone, distiertide, or antibodies such as fresolimumab, PDGF or VEGF antagonist, e.g., small molecules such as imatinib, nilotinib, or any drugs that target extracellular factors that are involved in the pathogenesis of fibrosis. The description of exemplary drugs for fibrosis can be found, e.g., Li et al., "Drugs and Targets in Fibrosis, Frontiers in Pharm." 8: Article 855 (2007), incorporated herein by reference.

The additional therapeutically active component(s) may be administered just prior to, concurrent with, or shortly after the administration of the fusion proteins or component peptides described herein or the nucleic acid molecules, or the expression vectors that encode them.

The present disclosure provides pharmaceutical compositions in which the fusion proteins or component peptides described herein or the nucleic acid molecules, or the expression vectors that encode them is co-formulated with one or more of the additional therapeutically active component(s) as described elsewhere herein.

Administration Regimens

In some embodiments, multiple doses of the fusion proteins or component peptides described herein or the nucleic acid molecules, or the expression vectors that encode them may be administered to a subject over a defined time course. The methods according to this aspect of the disclosure comprise sequentially administering to a subject multiple doses of the fusion proteins or component peptides described herein or the nucleic acid molecules, or the expression vectors that encode them. As used herein, "sequentially administering" means that each dose of the fusion proteins or component peptides described herein or the nucleic acid molecules, or the expression vectors that encode them is administered to the subject at a different point in time, e.g., on different days separated by a predetermined interval (e.g., hours, days, weeks, or months). The present disclosure provides methods which comprise sequentially administering to the patient a single initial dose of a fusion proteins or component peptides described herein or the nucleic acid molecules, or the expression vectors that encode them, followed by one or more secondary doses of the fusion proteins or component peptides described herein or the nucleic acid molecules, or the expression vectors that encode them, and optionally followed by one or more tertiary doses of the fusion proteins or component peptides described herein or the nucleic acid molecules, or the expression vectors that encode them.

The terms "initial dose," "secondary doses," and "tertiary doses," refer to the temporal sequence of administration of the fusion proteins or component peptides described herein or the nucleic acid molecules, or the expression vectors that encode them. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the fusion proteins or component peptides described herein or the nucleic acid molecules, or the expression vectors that encode them, but generally may differ from one another in terms of frequency of administration. In certain embodiments, however, the amounts of fusion proteins or component peptides described herein or the nucleic acid molecules, or the expression vectors that encode them contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of fusion proteins or component peptides described herein or the nucleic acid molecules, or the expression vectors that encode them, which is administered to a patient prior to the administration of the very next dose in the sequence with no intervening doses.

In one embodiment, each secondary and/or tertiary dose is administered 4 weeks after the immediately preceding dose. In one embodiment, a dose of the fusion protein or component peptide described herein, or the nucleic acid molecules, or the expression vectors that encode them, is administered to a patient once every 4 weeks (Q4W).

The methods according to this aspect of the disclosure may comprise administering to a patient any number of secondary and/or tertiary doses of fusion proteins or component peptides described herein or the nucleic acid molecules, or the expression vectors that encode them. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In one embodiment, one or more of the fusion proteins or component peptides described herein or the nucleic acid molecules, or the expression vectors that encode them are administered to a subject as a weight-based dose. A "weight-based dose" (e.g., a dose in mg/kg) is a dose of the protein or peptides that will change depending on the subject's weight.

In another embodiment, one or more of the fusion proteins or component peptides described herein or the nucleic acid molecules, or the expression vectors that encode them, is administered to a subject as a fixed dose. A "fixed dose" (e.g., a dose in mg) means that one dose of the fusion proteins or component peptides described herein or the nucleic acid molecules, or the expression vectors that encode them is used for all subjects regardless of any specific subject-related factors, such as weight. In one particular embodiment, a fixed dose of fusion proteins or component peptides described herein or the nucleic acid molecules, or the expression vectors that encode them is based on a predetermined weight or age.

In general, a suitable dose of the fusion proteins or component peptides described herein or the nucleic acid molecules, or the expression vectors that encode them can be in the range of about 0.001 to about 200.0 milligram per kilogram body weight of the recipient, generally in the range of about 1 to 50 mg per kilogram body weight. In certain embodiments, the fusion proteins or component peptides described herein or the nucleic acid molecules, or the expression vectors that encode them are administered in the range of about 0.001 mg/kg to about 200 mg/kg. In certain embodiments, the fusion proteins or component peptides described herein or the nucleic acid molecules, or the expression vectors that encode them are administered in the range of 0.001 mg/kg to 200 mg/kg. In certain embodiments, the fusion proteins or component peptides described herein or the nucleic acid molecules, or the expression vectors that encode them are administered in the range of about 0.01 mg/kg to about 100 mg/kg. In certain embodiments, the fusion proteins or component peptides described herein or the nucleic acid molecules, or the expression vectors that encode them are administered in the range of 0.01 mg/kg to 100 mg/kg. In certain embodiments, the fusion proteins or component peptides described herein or the nucleic acid molecules, or the expression vectors that encode them are administered in the range of about 0.1 mg/kg to about 20 mg/kg. In certain embodiments, the fusion proteins or component peptides described herein or the nucleic acid molecules, or the expression vectors that encode them are administered in the range of 0.1 mg/kg to 20 mg/kg. In certain embodiments, the fusion proteins or component peptides described herein or the nucleic acid molecules, or the expression vectors that encode them are administered in the range of about 1 mg/kg to about 50 mg/kg. In certain embodiments, the fusion proteins or component peptides described herein or the nucleic acid molecules, or the expression vectors that encode them are administered in the range of 1 mg/kg to 50 mg/kg. For example, the fusion proteins or component peptides described herein or the nucleic acid molecules, or the expression vectors that encode them can be administered at about 0.1 mg/kg, about 0.2 mg/kg, about 0.3 mg/kg, about 0.5 mg/kg, about 1 mg/kg, about 1.5 mg/kg, about 2 mg/kg, about 3 mg/kg, about 5 mg/kg, about 10 mg/kg, about 15 mg/kg, about 20 mg/kg, about 25 mg/kg, about 30 mg/kg, about 40 mg/kg, about 50 mg/kg per single dose. In certain embodiments, the fusion proteins or component peptides described herein or the nucleic acid molecules, or the expression vectors that encode them can be administered at 0.1 mg/kg, 0.2 mg/kg, 0.3 mg/kg, 0.5 mg/kg, 1 mg/kg, 1.5 mg/kg, 2 mg/kg, 3 mg/kg, 5 mg/kg, 10 mg/kg, 15 mg/kg, 20 mg/kg, 25 mg/kg, 30 mg/kg, 40 mg/kg, 50 mg/kg per single dose. Values and ranges intermediate to the recited values are also intended to be part of this disclosure.

In certain embodiments, the fusion proteins or component peptides described herein or the nucleic acid molecules, or the expression vectors that encode them are administered at about 0.3 mg/kg. In certain embodiments, the fusion proteins or component peptides described herein or the nucleic acid molecules, or the expression vectors that encode them are administered at 0.3 mg/kg. In certain embodiments, the fusion proteins or component peptides described herein or the nucleic acid molecules, or the expression vectors that encode them are administered at about 1 mg/kg. In certain embodiments, the fusion proteins or component peptides described herein or the nucleic acid molecules, or the expression vectors that encode them are administered at 1 mg/kg. In certain embodiments, the fusion proteins or component peptides described herein or the nucleic acid molecules, or the expression vectors that encode them are administered at about 3 mg/kg. In certain embodiments, the fusion proteins or component peptides described herein or the nucleic acid molecules, or the expression vectors that encode them are administered at 3 mg/kg. In certain embodiments, the fusion proteins or component peptides described herein or the nucleic acid molecules, or the expression vectors that encode them are administered at about 10 mg/kg. In certain embodiments, the fusion proteins or component peptides described herein or the nucleic acid molecules, or the expression vectors that encode them are administered at 10 mg/kg.

In some embodiments, one or more of the fusion proteins or component peptides described herein or the nucleic acid molecules, or the expression vectors that encode them is administered as a fixed dose of between about 10 mg to about 2500 mg. In some embodiments, one or more of the fusion proteins or component peptides described herein or the nucleic acid molecules, or the expression vectors that encode them is administered as a fixed dose of between 10 mg to 2500 mg. In some embodiments, one or more of the fusion proteins or component peptides described herein or the nucleic acid molecules, or the expression vectors that encode them is administered as a fixed dose of between about 100 mg to about 1500 mg. In some embodiments, one or more of the fusion proteins or component peptides described herein or the nucleic acid molecules, or the expression vectors that encode them is administered as a fixed dose of between 100 mg to 1500 mg. In some embodiments, the fusion proteins or component peptides described herein or the nucleic acid molecules, or the expression vectors that encode them are administered as a fixed dose of about 10 mg, about 15 mg, about 20 mg, 25 mg, about 30 mg, about 50 mg, about 75 mg, about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1500 mg, about 2000 mg, or about 2500 mg. In some embodiments, the fusion proteins or component peptides described herein or the nucleic acid molecules, or the expression vectors that encode them are administered as a fixed dose of 10 mg, 15 mg, 20 mg, 25 mg, 30 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1500 mg, 2000 mg, or 2500 mg. Values and ranges intermediate to the recited values are also intended to be part of this disclosure.

In some embodiments, the fusion proteins or component peptides described herein or the nucleic acid molecules, or the expression vectors that encode them are administered as a fixed dose of about 150 mg. In some embodiments, the fusion proteins or component peptides described herein or the nucleic acid molecules, or the expression vectors that encode them are administered as a fixed dose of 150 mg. In some embodiments, the fusion proteins or component peptides described herein or the nucleic acid molecules, or the expression vectors that encode them are administered as a fixed dose of at least 150 mg. In some embodiments, the fusion proteins or component peptides described herein or the nucleic acid molecules, or the expression vectors that encode them are administered as a fixed dose of about 300 mg. In some embodiments, the fusion proteins or component peptides described herein or the nucleic acid molecules, or the expression vectors that encode them are administered as a fixed dose of 300 mg. In some embodiments, the fusion proteins or component peptides described herein or the nucleic acid molecules, or the expression vectors that encode them are administered as a fixed dose of about 600 mg. In some embodiments, the fusion proteins or component peptides described herein or the nucleic acid molecules, or the expression vectors that encode them are administered as a fixed dose of 600 mg.

In some embodiments, the fusion proteins or component peptides described herein or the nucleic acid molecules, or the expression vectors that encode them are administered by intravenous administration. In some embodiments, the fusion proteins or component peptides described herein or the nucleic acid molecules, or the expression vectors that encode them are administered by subcutaneous administration.

In some embodiments, the fusion proteins or component peptides described herein or the nucleic acid molecules, or the expression vectors that encode them are administered by intravenous infusion. In some embodiments, the fusion proteins or component peptides described herein or the nucleic acid molecules, or the expression vectors that encode them are administered by intravenous infusion over a duration of 1 minute, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 minutes, 2 hours, 3 hours, 4 hours, or more. In some embodiments, the fusion proteins or component peptides described herein or the nucleic acid molecules, or the expression vectors that encode them are administered by intravenous infusion over 30 minutes. In some embodiments, the fusion proteins or component peptides described herein or the nucleic acid molecules, or the expression vectors that encode them are administered by intravenous infusion over 60 minutes. In some embodiments, the fusion proteins or component peptides described herein or the nucleic acid molecules, or the expression vectors that encode them are administered by intravenous infusion over 30 to 60 minutes.

In some embodiments, the fusion proteins or component peptides described herein or the nucleic acid molecules, or the expression vectors that encode them are administered intravenously at a dose of about 0.3 mg/kg once every 4 weeks. In some embodiments, the fusion proteins or component peptides described herein or the nucleic acid molecules, or the expression vectors that encode them are administered intravenously at a dose of 0.3 mg/kg once every 4 weeks. In certain embodiments, the fusion proteins or component peptides described herein or the nucleic acid molecules, or the expression vectors that encode them are administered at about 0.3 mg/kg once every 4 weeks. In certain embodiments, the fusion proteins or component peptides described herein or the nucleic acid molecules, or the expression vectors that encode them are administered at 0.3 mg/kg once every 4 weeks. In certain embodiments, the fusion proteins or component peptides described herein or the nucleic acid molecules, or the expression vectors that encode them are administered at about 1 mg/kg once every 4 weeks. In certain embodiments, the fusion proteins or component peptides described herein or the nucleic acid molecules, or the expression vectors that encode them are administered at 1 mg/kg once every 4 weeks. In certain embodiments, the fusion proteins or component peptides described herein or the nucleic acid molecules, or the expression vectors that encode them are administered at about 3 mg/kg once every 4 weeks. In certain embodiments, the fusion proteins or component peptides described herein or the nucleic acid molecules, or the expression vectors that encode them are administered at 3 mg/kg once every 4 weeks. In certain embodiments, the fusion proteins or component peptides described herein or the nucleic acid molecules, or the expression vectors that encode them are administered at about 10 mg/kg once every 4 weeks. In certain embodiments, the fusion proteins or component peptides described herein or the nucleic acid molecules, or the expression vectors that encode them are administered at 10 mg/kg once every 4 weeks.

In some embodiments, the fusion proteins or component peptides described herein or the nucleic acid molecules, or the expression vectors that encode them are administered at a dose of about 150 mg once every 4 weeks. In some embodiments, the fusion proteins or component peptides described herein or the nucleic acid molecules, or the expression vectors that encode them are administered at a dose of 150 mg once every 4 weeks. In some embodiments, the fusion proteins or component peptides described herein or the nucleic acid molecules, or the expression vectors that encode them are administered at a dose of at least 150 mg once every 4 weeks. In some embodiments, the fusion proteins or component peptides described herein or the nucleic acid molecules, or the expression vectors that encode them are administered as a fixed dose of about 150 mg once every 4 weeks. In some embodiments, the fusion proteins or component peptides described herein or the nucleic acid molecules, or the expression vectors that encode them are administered as a fixed dose of 150 mg once every 4 weeks. In some embodiments, the fusion proteins or component peptides described herein or the nucleic acid molecules, or the expression vectors that encode them are administered as a fixed dose of at least 150 mg once every 4 weeks. In some embodiments, the fusion proteins or component peptides described herein or the nucleic acid molecules, or the expression vectors that encode them are administered as a fixed dose of about 300 mg once every 4 weeks. In some embodiments, the fusion proteins or component peptides described herein or the nucleic acid molecules, or the expression vectors that encode them are administered as a fixed dose of 300 mg once every 4 weeks. In some embodiments, the fusion proteins or component peptides described herein or the nucleic acid molecules, or the expression vectors that encode them are administered as a fixed dose of about 600 mg once every 4 weeks. In some embodiments, the fusion proteins or component peptides described herein or the nucleic acid molecules, or the expression vectors that encode them are administered as a fixed dose of 600 mg once every 4 weeks.

In some embodiments, the fusion proteins or component peptides described herein or the nucleic acid molecules, or the expression vectors that encode them are administered subcutaneously at a dose of about 150 mg once every 4 weeks. In some embodiments, the fusion proteins or component peptides described herein or the nucleic acid molecules, or the expression vectors that encode them are administered subcutaneously at a dose of 150 mg once every 4 weeks. In some embodiments, the fusion proteins or component peptides described herein or the nucleic acid molecules, or the expression vectors that encode them are administered subcutaneously at a dose of at least 150 mg once every 4 weeks. In some embodiments, the fusion proteins or component peptides described herein or the nucleic acid molecules, or the expression vectors that encode them are administered as a fixed dose subcutaneously of about 150 mg once every 4 weeks. In some embodiments, the fusion proteins or component peptides described herein or the nucleic acid molecules, or the expression vectors that encode them are administered as a fixed dose subcutaneously of 150 mg once every 4 weeks. In some embodiments, the fusion proteins or component peptides described herein or the nucleic acid molecules, or the expression vectors that encode them are administered as a fixed dose subcutaneously of at least 150 mg once every 4 weeks. In some embodiments, the fusion proteins or component peptides described herein or the nucleic acid molecules, or the expression vectors that encode them are administered as a fixed dose subcutaneously of about 300 mg once every 4 weeks. In some embodiments, the fusion proteins or component peptides described herein or the nucleic acid molecules, or the expression vectors that encode them are administered as a fixed dose subcutaneously of 300 mg once every 4 weeks. In some embodiments, the fusion proteins or component peptides described herein or the nucleic acid molecules, or the expression vectors that encode them are administered as a fixed dose subcutaneously of about 600 mg once every 4 weeks. In some embodiments, the fusion proteins or component peptides described herein or the nucleic acid molecules, or the expression vectors that encode them are administered as a fixed dose subcutaneously of 600 mg once every 4 weeks.

In some embodiments, the fusion proteins or component peptides described herein or the nucleic acid molecules, or the expression vectors that encode them are administered intravenously at a dose of about 0.3 mg/kg once every 1 month. In some embodiments, the fusion proteins or component peptides described herein or the nucleic acid molecules, or the expression vectors that encode them are administered intravenously at a dose of 0.3 mg/kg once every 1 month. In certain embodiments, the fusion proteins or component peptides described herein or the nucleic acid molecules, or the expression vectors that encode them are administered at about 0.3 mg/kg once every 1 month. In certain embodiments, the fusion proteins or component peptides described herein or the nucleic acid molecules, or the expression vectors that encode them are administered at 0.3 mg/kg once every 1 month. In certain embodiments, the fusion proteins or component peptides described herein or the nucleic acid molecules, or the expression vectors that encode them are administered at about 1 mg/kg once every 1 month. In certain embodiments, the fusion proteins or component peptides described herein or the nucleic acid molecules, or the expression vectors that encode them are administered at 1 mg/kg once every 1 month. In certain embodiments, the fusion proteins or component peptides described herein or the nucleic acid molecules, or the expression vectors that encode them are administered at about 3 mg/kg once every 1 month. In certain embodiments, the fusion proteins or component peptides described herein or the nucleic acid molecules, or the expression vectors that encode them are administered at 3 mg/kg once every 1 month. In certain embodiments, the fusion proteins or component peptides described herein or the nucleic acid molecules, or the expression vectors that encode them are administered at about 10 mg/kg once every 1 month. In certain embodiments, the fusion proteins or component peptides described herein or the nucleic acid molecules, or the expression vectors that encode them are administered at 10 mg/kg once every 1 month.

In some embodiments, the fusion proteins or component peptides described herein or the nucleic acid molecules, or the expression vectors that encode them are administered at a dose of about 150 mg once every 1 month. In some embodiments, the fusion proteins or component peptides described herein or the nucleic acid molecules, or the expression vectors that encode them are administered at a dose of 150 mg once every 1 month. In some embodiments, the fusion proteins or component peptides described herein or the nucleic acid molecules, or the expression vectors that encode them are administered at a dose of at least 150 mg once every 1 month. In some embodiments, the fusion proteins or component peptides described herein or the nucleic acid molecules, or the expression vectors that encode them are administered as a fixed dose of about 150 mg once every 1 month. In some embodiments, the fusion proteins or component peptides described herein or the nucleic acid molecules, or the expression vectors that encode them are administered as a fixed dose of 150 mg once every 1 month. In some embodiments, the fusion proteins or component peptides described herein or the nucleic acid molecules, or the expression vectors that encode them are administered as a fixed dose of at least 150 mg once every 1 month. In some embodiments, the fusion proteins or component peptides described herein or the nucleic acid molecules, or the expression vectors that encode them are administered as a fixed dose of about 300 mg once every 1 month. In some embodiments, the fusion proteins or component peptides described herein or the nucleic acid molecules, or the expression vectors that encode them are administered as a fixed dose of 300 mg once every 1 month. In some embodiments, the fusion proteins or component peptides described herein or the nucleic acid molecules, or the expression vectors that encode them are administered as a fixed dose of about 600 mg once every 1 month. In some embodiments, the fusion proteins or component peptides described herein or the nucleic acid molecules, or the expression vectors that encode them are administered as a fixed dose of 600 mg once every 1 month.

In some embodiments, the fusion proteins or component peptides described herein or the nucleic acid molecules, or the expression vectors that encode them are administered subcutaneously at a dose of about 150 mg once every 1 month. In some embodiments, the fusion proteins or component peptides described herein or the nucleic acid molecules, or the expression vectors that encode them are administered subcutaneously at a dose of 150 mg once every 1 month. In some embodiments, the fusion proteins or component peptides described herein or the nucleic acid molecules, or the expression vectors that encode them are administered subcutaneously at a dose of at least 150 mg once every 1 month. In some embodiments, the fusion proteins or component peptides described herein or the nucleic acid molecules, or the expression vectors that encode them are administered as a fixed dose subcutaneously of about 150 mg once every 1 month. In some embodiments, the fusion proteins or component peptides described herein or the nucleic acid molecules, or the expression vectors that encode them are administered as a fixed dose subcutaneously of 150 mg once every 1 month. In some embodiments, the fusion proteins or component peptides described herein or the nucleic acid molecules, or the expression vectors that encode them are administered as a fixed dose subcutaneously of at least 150 mg once every 1 month. In some embodiments, the fusion proteins or component peptides described herein or the nucleic acid molecules, or the expression vectors that encode them are administered as a fixed dose subcutaneously of about 300 mg once every 1 month. In some embodiments, the fusion proteins or component peptides described herein or the nucleic acid molecules, or the expression vectors that encode them are administered as a fixed dose subcutaneously of 300 mg once every 1 month. In some embodiments, the fusion proteins or component peptides described herein or the nucleic acid molecules, or the expression vectors that encode them are administered as a fixed dose subcutaneously of about 600 mg once every 1 month. In some embodiments, the fusion proteins or component peptides described herein or the nucleic acid molecules, or the expression vectors that encode them are administered as a fixed dose subcutaneously of 600 mg once every 1 month.

Kits

Any of the compositions described herein may be comprised in a kit. In a non-limiting example, the kit comprises one or more of the fusion proteins or component peptides described herein or the nucleic acid molecules, or the expression vectors that encode them.

The kit may further include reagents or instructions for using the fusion proteins or component peptides described herein or the nucleic acid molecules, or the expression vectors that encode them in a subject. It may also include one or more buffers.

The components of the kits may be packaged either in aqueous media or in lyophilized form. The container means of the kits will generally include at least one vial, test tube, flask, bottle, syringe, or other container means, into which a component may be placed, and preferably, suitably aliquoted. Where there is more than one component in the kit (labeling reagent and label may be packaged together), the kit also will generally contain a second, third, or other additional container into which the additional components may be separately placed. The kits may also comprise a second container means for containing a sterile, pharmaceutically acceptable buffer and/or other diluent. However, various combinations of components may be comprised in a vial. The kits of the present disclosure also typically include a means for containing the fusion proteins or component peptides described herein or the nucleic acid molecules, or the expression vectors that encode them, and any other reagent containers in close confinement for commercial sale.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The examples of the present disclosure are offered by way of illustration and explanation, and are not intended to limit the scope of the present disclosure. The results described in each Example are reflective of the particular conditions outlined in the experiments described therein.

Example 1. Heparin Chromatography for Relaxin-2 Fusion Protein Analogs

Heparin chromatography is a method that can be used at early candidate screening to better understand a molecule's propensity to interact with elements of the vasculature when dosed in patients. Heparin and heparin sulfate proteoglycans are negatively charged polysaccharides present in vasculature and in tissues, of which positively charged molecules may bind at physiological pH (i.e., pI >7.4). Here, heparin chromatography was employed to screen for candidates/variants with reduced heparin binding, which is predictive of good PK properties. Materials used for the heparin chromatography are provided in Table 11.

TABLE 11

| Materials | | |
|---|---|---|
| Item | Vendor | Cat No. |
| POROS ™ Heparin 2.1 × 30 mm Column | Thermo Fisher | 4333411 |

Methods

Mobile Phase A (Binding): 20 mM Tris pH 7.4; Mobile Phase B (Elution): 20 mM Tris pH 7.4+1M NaCl; Injection: 10 μg; Detection: 220 nm.

1. Equilibrated heparin column using mobile phase A for 10 minutes at 0.5 mL/min prior to analysis.
2. Diluted samples for analysis to 1 mg/mL with 20 mM Tris pH 7.4 to minimize ionic strength.
3. Ran the Heparin Chromatography method on the Agilent HPLC, using gradient shown in Table 12, below:

TABLE 12

| HPLC Gradient | | | |
|---|---|---|---|
| Time (min) | Flow (mL/min) | % A | % B |
| 0 | 0.5 | 100 | 0 |
| 1 | 0.5 | 100 | 0 |
| 6 | 0.5 | 50 | 50 |
| 6.5 | 0.5 | 50 | 50 |
| 7 | 0.5 | 0 | 100 |
| 8 | 0.5 | 0 | 100 |
| 8.5 | 0.5 | 100 | 0 |
| 10 | 0.5 | 100 | 0 |

4. Included a positive control (no Heparin binding, Human IgG pool) and negative control (SE301 or AT1R).
5. Analyzed samples for retention time and reported relative retention time compared to the positive control (i.e., RT sample/RT positive control).
6. Calculated the approximate concentration of NaCl needed to elute using the following calculation:

$$[NaCl]_i = (RT sampl - 1) * 100$$

The results of the calculation are shown in Table 13.

TABLE 13

| Retention Time, Relative Retention Time, and NaCl Concentration for Samples | | | |
|---|---|---|---|
| Sample | RT | RRT | [NaCl] |
| Positive Control | 1.5 | N/A | 50 |
| Negative Control | 3.5 | 2.3 | 250 |
| Sample | 2.0 | 1.3 | 100 |

Results

Table 14 shows the results of the heparin chromatography for a variety of relaxin-2 analog fusion proteins.

TABLE 14

Heparin Chromatography

| Sample | Theoretical pI | Heparin Chromatography RT | ~[NaCl] (mM) at elution |
|---|---|---|---|
| IgG | N/A | 2.0 | 20 |
| Prior fusion protein | 8.5 (9.4*) | 4.6 | 278 |
| SEQ ID NO: 300 | 8.2 | 3.9 | 208 |
| SEQ ID NO: 302 | 7.9 | 3.3 | 152 |
| SEQ ID NO: 303 | 7.9 | 3.4 | 163 |
| SEQ ID NO: 305 | 7.6 | 2.7 | 91 |
| SEQ ID NO: 306 | 7.6 | 2.8 | 99 |
| SEQ ID NO: 308 | 7.2 | 2.4 | 62 |
| SEQ ID NO: 309 | 7.2 | 2.5 | 70 |
| SEQ ID NO: 310 | 6.8 | 2.2 | 39 |
| SEQ ID NO: 311 | 6.8 | 2.2 | 43 |
| SEQ ID NO: 359 | 8.4 | 3.6 | 183 |
| SEQ ID NO: 360 | 8.3 | 3.2 | 140 |

*Experimentally determined using imaged capillary isoelectric focusing.

IgG is from Jackson ImmunoResearch (Catalog #009-000-003). The "Prior fusion protein" is a LALA IgG-RelB-Linker-RelA fusion with a theoretical pI of 8.5, but an experimentally determined pI of 9.4. Its linker protein comprises only one acidic amino acid. SEQ ID NOs: 300, 302, 303, 305, 306, and 308-311 have linker proteins comprising at least two acidic amino acids as well as LALA IgG (SEQ ID NO: 77 or 81). The final two fusion proteins have linker proteins comprising only one acidic amino acid and have higher theoretical pI's. As shown in Table 14, above, there is a correlation between lower pI and lower non-specific binding found through heparin chromatography.

Example 2. Low pI Relaxin-2 Fusion Protein Analogs Tend to have Decreased Self Association as Measured by Affinity-Capture Self-Interaction Nanoparticle Spectroscopy (AC-SINS)

Understanding a molecule's propensity to self-associate is critical when evaluating biophysical properties of a development candidate. There are numerous ways to evaluate a molecule's propensity to self-associate, concentrating the molecule to high concentrations and evaluating by SEC (% Monomer) or measuring changes in turbidity (OD 340 nm), using DLS to calculate the second virial coefficient ($B_{22}$) or self-interaction coefficient ($k_d$), or using AC-SINS ($\Delta\lambda_{max}$). All three of these methods provide useful information but use different amounts of material to perform the evaluation. AC-SINS has emerged as a high throughput method for evaluating self-association using minimal material but still giving locally high concentrations by using affinity capture on gold nanoparticles. In short, gold nanoparticles are pre-coated with anti-human antibodies (Fc, Fab and H+L), which when incubated with target antibodies in dilute solutions, capture and concentrate in solution the antibody of interest. When the immobilized molecules of interest interact, the inter-particle distances decrease between gold nanoparticles, leading to increased plasmon wavelengths (i.e., red shift) that can be quantified using UV-VIS spectroscopy. Materials used for the spectroscopy are provided in Table 15.

TABLE 15

Materials

| Item | Vendor | Cat No. |
|---|---|---|
| 1M sodium acetate pH 4.3 | Molecular Dimensions | MD2-019-PH |
| 1x DPBS | Gibco | 14190-136 |
| Panitumumab (Low Assoc Ctrl) | MyBioSource | MBS156169 |
| Ipilimumab (Med Assoc Ctrl) | MyBioSource | MBS156153 |
| Ganitumab (High Assoc Ctrl) | MyBioSource | MBS156142 |
| 20 nm gold nanoparticles | Ted Pella | 15705 |
| PEG methyl ether thiol (2kDa) | Sigma | 729140 |
| Goat anti-Human IgG, Fcγ | Jackson ImmunoResearch | 109-005-098 |
| Goat non-specific mAb | Jackson ImmunoResearch | 005-000-003 |
| Zeba Desalting Columns 40K 5 mL | Thermo Fisher | 87770 |
| Zeba Desalting Columns 40K 2 mL | Thermo Fisher | 87768 |
| Zeba Desalting Columns 40K 0.5 mL | Thermo Fisher | 87766 |
| Costar 384-well Polystyrene plates | Fisher Scientific | 12-565-506 |
| 96-well Polypropylene plates | Grenier Bio-One | 652230P |

Methods

Preparing Buffer Solutions: To prepare 20 mM sodium acetate pH 4.3, 2 mL 1M sodium acetate pH 4.3 stock was diluted to 100 mL with MilliQ water. pH was measured 4.3±0.1 and the solution was sterile filtered. The solution remained stable at room temperature for 1 month. To 1 g PEG methyl ether thiol, was added 10 mL MilliQ water. This was vortexed briefly to suspend solids, making a 50 mM solution. To prepare a 10 µM solution for final dilution, the dilution scheme below was followed:
  a. Dilute 50 mM stock to 1 mM (20 µL 50 mM stock+980 µL MilliQ water)
  b. Dilute 1 mM step to 100 µM (10 µL 1 mM stock+90 µL MilliQ water)
  c. Dilute 100M step to 10 µM (100 µL 100 µM stock+900 µL MilliQ water)
  d. Volumes can be scaled according to number of samples to assay
  e. Remaining 50 mM stock should be aliquoted and kept at −20° C. until needed Preparing Gold NanoParticle Solution: Goat anti-human Fc IgG antibody (capture) and goat IgG antibody (non-capture) were buffer exchanged into 20 mM sodium acetate, pH 4.3. After buffer exchange, concentrations were normalized to 0.4 mg/mL for both antibodies. A 4:1 volume ratio mixture of capture (anti-Fc):non-capture (Goat IgG) solution was prepared for 80% capture capacity coating solution to be used to incubate gold nanoparticles (AuNPs).

A 9:1 volume ratio of AuNPs:coating solution was made. The solution was incubated at room temperature, overnight in the dark. After incubation, thiolated PEG was added to 0.1 µM final concentration from the diluted 10 µM stock to block empty sites on the AuNPs (i.e., 5 mL solution of AuNPs, add 50 µL 10 µM stock) and incubated at RT for one hour in the dark.

Preparing AuNP Solution: 2 mL of coated AuNP solution was centrifuged at 20,000×g for 15 minutes to sediment the AuNPs and 1800 µL supernatant was carefully removed using a 1 mL pipette. The pelleted AuNPs were gently resuspended using a 200 µL pipette to generate a 10× concentrated stock of coated AuNPs.

Preparing Target Antibody Solution (either method follows this): For each sample analyzed, 10 µL of AuNP concentrate was incubated with 100 µL antibody test solution (normalize to 0.05 mg/mL) at room temperature in the dark for 2 hours in a 96-well polypropylene plate. Two blank solutions were prepared with 10 μL 10× AuNP concentrated to 100 μL PBS for purposes of blanking the assay and determining wavelength shift upon addition of test antibody. Ganitumab was included as a positive control (high association, red shift) and Panitumumab as a negative control (no association, no UV shift). Each sample was prepared in duplicate for analysis. After the 2-hour incubation, 100 μL of resulting solution was transferred to a UV transparent polystyrene plate (384-well format). Two blank solutions were transferred to properly assess wavelength shift, then add duplicate standards and samples for analysis. The plate was then centrifuged for 1 minute at 1000× g to level the solutions in the wells. Absorbance data were collected from 510 to 570 nm in 2 nm steps to determine wavelength shifts for each sample relative to AuNPs alone.

Results

The results from ASCINS are shown below in Table 16.

TABLE 16 pI Variants Have Decreased Self- Association Propensity

| Sample | Isoelectric Point (Calculated) | Δλmax |
| --- | --- | --- |
| Prior fusion protein (Control) | 8.5 | 15.2 |
| Prior fusion protein (LALA) | 8.5 | 15.9 |
| SEQ ID NO: 300 | 8.2 | 7.5 |
| SEQ ID NO: 301 | 7.9 | 1.2 |
| SEQ ID NO: 302 | 7.9 | 7.0 |
| SEQ ID NO: 303 | 7.9 | 6.7 |
| SEQ ID NO: 305 | 7.6 | 1.8 |
| SEQ ID NO: 306 | 7.6 | 1.9 |
| SEQ ID NO: 308 | 7.2 | −0.6 |
| SEQ ID NO: 309 | 7.2 | −0.4 |
| SEQ ID NO: 310 | 6.8 | 0.4 |
| SEQ ID NO: 311 | 6.8 | 0.4 |
| SEQ ID NO: 359 | 8.4 | 10.1 |
| SEQ ID NO: 360 | 8.3 | 6.1 |

As shown in Table 16, above, fusion proteins with low pI also have a tendency to show low self-aggregation.

Example 3. Relaxin-2 Fusion Protein Analogs Induce cAMP Response in RXFP1 Transfected Cells This Example provides data relating to the potency of various relaxin-2 fusion protein analogs described herein. Potency of the fusion protein analogs were assayed by testing their ability to activate RXFP1 by measuring cAMP signaling.

Methods

HEK293 cells were seeded into a 96-well tissue culture plate followed by transient co-transfection with a human RXFP1 and a pGloSensor-22F plasmid. Transfected cells were stimulated by relaxin-2 or fusion protein analogs thereof, inducing Gs-mediated cAMP signaling. cAMP is assayed using the activity of the GloSensor biosensor, which is a mutant luciferase fused to a cAMP binding domain, leading to a production of light in the presence of its substrate luciferin. This readout of relative luminescent units (RLU) is used a proxy for cAMP response.

Reagents 96-well tissue-culture treated plates. White with clear bottom. (Corning #3610)
HEK293 cells (ATCC CRL-1573)
Poly-D-lysine (Gibco A3890401)
DPBS (No calcium, no magnesium; Gibco 14190250)
DMEM (High glucose with L-glutamine and Sodium Pyruvate; Gibco 11995065)
TrypLE Express (Gibco 12605010)
FBS (HyClone™, Australian origin; Cytiva SH30084)
Penicillin-Streptomycin (Gibco 15140122)
$CO_2$-independent media (Gibco 18045088)
Opti-MEM™ I Reduced Serum media (Gibco 31985062)
pGloSensor™-22F cAMP plasmid (Promega Cat. #E2301)
D-luciferin, Potassium Salt (GoldBio LUCK-1G)
FuGENE HD transfection reagent (Promega #E2311)
Reservoirs (Corning/Axygen RES-V-25-SI)
Relaxin-2 (R&D Biosystems 6586-RN-025)
RXFP1-containing plasmid (pcDNA5/FRT/TO-human RXFP1, full-length)
Forskolin (Sigma F6886)
Plate reader capable of reading luminescence (CLARIOstar Plus)

Reagent Preparation

D-luciferin, Potassium Salt: D-luciferin was reconstituted in 10 mM HEPES, pH 7.5 at 25 mg/mL (78.5 mM; MW=318.4). This was aliquoted into single-use aliquots of ~200-500 μL in sterile microfuge tubes and stored at −80° C.

Relaxin-2 peptide: Relaxin-2 peptides or relaxin-2 fusion protein analogs were reconstituted at 0.1 mg/mL in sterile DPBS (MW=5,986 Da, ε=12,865 $M^{-1}$ $cm^{-1}$) and measured at $A_{280}$ to determine final concentration. Aliquots were stored at −20° C.

Forskolin: Forskolin was reconstituted in 100% DMSO at 5 mM (2.05 mg/mL, MW=410.5). Aliquots were stored at −20° C.

cAMP assay media: $CO_2$-independent media was pre-warmed to 37° C. using the bead bath. A single aliquot of D-luciferin was thawed and added at 5% final concentration (e.g., 4.75 mL cAMP assay media+250 μL of D-luciferin stock; gives 1.25 mg/mL or 3.93 mM final D-luciferin). This was used within the same day or discarded.

Cell Culture and Maintenance

HEK293 cells (ATCC CRL-1573) were cultured in DMEM+10% FBS, 1% (1× or 10 U/mL) Pen-Strep in a humidified $CO_2$ incubator at 37 C, 5% $CO_2$ until 80-100% confluency. Cells were typically split 1:6 for 3 days and maintained in a sterile T-75 tissue culture flask.

cAMP Signaling Assay Protocol

This protocol was adapted from the GloSensor cAMP assay by Promega.

Raw data was exported to Excel using the MARS data analysis software that is opened following a run on the CLARIOstar plate reader. These values are measured in RLU, or relative luminescence units.

As shown in Table 17, all of the low pI relaxin-2 fusion protein analogs were able to induce a cAMP response in RXFP1 transfected cells.

TABLE 17 cAMP Response in RXFP1 Transfected HEK293 Cells

| Agonist | $PEC_{50}$ | $EC_{50}$ in nM |
| --- | --- | --- |
| Relaxin | 10.38 | 0.042 |
| Prior fusion protein (Control) | 9.51 | 0.31 |
| Prior fusion protein (LALA) | 9.49 | 0.33 |
| SEQ ID NO: 300 | 8.66 | 2.17 |
| SEQ ID NO: 301 | 8.10 | 7.87 |
| SEQ ID NO: 302 | 8.62 | 2.41 |
| SEQ ID NO: 303 | 8.72 | 1.90 |
| SEQ ID NO: 305 | 7.83 | 14.7 |

TABLE 17-continued cAMP Response in RXFP1 Transfected HEK293 Cells

| Agonist | PEC$_{50}$ | EC$_{50}$ in nM |
|---|---|---|
| SEQ ID NO: 306 | 7.75 | 17.7 |
| SEQ ID NO: 308 | 7.25 | 56.7 |
| SEQ ID NO: 309 | 7.18 | 65.8 |
| SEQ ID NO: 310 | 6.76 | 173.3 |
| SEQ ID NO: 311 | 7.02 | 96.2 |
| SEQ ID NO: 359 | 9.37 | 0.42 |
| SEQ ID NO: 360 | 8.84 | 1.46 |

Example 4. In Vitro Characteristics of Relaxin-2 Fusion Protein Analogs

This Example provides in vitro characteristics of various relaxin-2 fusion protein analogs described herein.

Methods

Heparin chromatography: heparin chromatography was performed to understand the propensity of a relaxin-2 fusion protein analog to interact with elements of the vasculature and/or rapidly distribute into tissues when dosed in patients. Analogs that were found to bind heparin weakly may be predictive of good pharmnacokinetic properties. Briefly, a heparin column was equilibrated using mobile phase A (20 mM Tris pH 7.4) for 10 minutes at 0.5 mL/min prior to analysis. 10 µg per sample was run using the Heparin Chromatography method on an Agilent HPLC using 280 nm detection, using gradient shown in Table 18, below (mobile phase B: 20 mM Tris pH 7.4, 1 M NaCl).

TABLE 18

HPLC Gradient

| Time (min) | Flow (mL/min) | % A | % B |
|---|---|---|---|
| 0 | 0.5 | 100 | 0 |
| 6 | 0.5 | 50 | 50 |
| 7 | 0.5 | 0 | 100 |
| 8 | 0.5 | 0 | 100 |
| 8.5 | 0.5 | 100 | 0 |
| 10 | 0.5 | 100 | 0 |

A positive control (no Heparin binding, pembrolizumab) and negative control (mild Heparin binding, adalimumab) was included, and samples were analyzed for retention time and relative retention time compared to the positive control (i.e., RT sample/RT positive control). The approximate concentration of NaCl needed to elute was calculated using the following calculation:

$$[NaCl] = (RT\ sample) * 100$$

The results of the calculation are shown in Table 19.

TABLE 19

Retention Time and NaCl Concentration for Samples

| Sample | RT | [NaCl] |
|---|---|---|
| Positive Control | 1.5 | 150 |
| Negative Control | 3.5 | 350 |
| Sample | 2.0 | 200 |

Hydrophobic Interaction Chromatography (HIC): HIC is a chromatography method that separates molecules based on their hydrophobicity. To a butyl HIC column pre-equilibrated with high ammonium sulfate buffer, 10 g of protein was injected. The protein was eluted with a gradient from high salt concentration to low salt concentration over ten minutes. Samples were compared for hydrophobicity based on retention time, with high retention time indicative of high hydrophobicity and low retention time indicative of low hydrophobicity. Retention times were converted to approximate salt concentration at elution and compared against high and low hydrophobicity standards.

Size exclusion chromatography (SEC): SEC is a liquid chromatography method used to determine levels of monomeric and multimeric species in solution for a given analyte. SEC was used to assess the presence of fusion protein aggregates. Samples were prepared and added to a 1.7 µm particle SEC column with an aqueous mobile phase comprised of 25 mM potassium phosphate and 0.5M potassium chloride pH 8.0. Once elution of sample was verified, the method was capable of quantifying levels of soluble aggregate species in the sample, with high resolution between peaks of monomer and high molecular weight (HMW) species. Percentage of monomer (i.e., % monomer) and other species (e.g., HMW species, low molecular weight species) was calculated by integrating the corresponding elution curve to determine the percent area.

Capillary isoelectric focusing (cIEF): Imaged cIEF was used to separate differentially charged molecules (i.e., relaxin-2 fusion protein analogs) using electrophoretic mobility in an ampholyte solution to determine their isoelectric points (pI). Molecules were loaded to a capillary and separated based on their pI by allowing molecules to migrate along an electrical field until the molecules reached the pH corresponding to their pI. UV absorption of the whole capillary was measured throughout the separation, which allowed for real-time observation as well as final quantification.

Baculovirus Particle (BVP) ELISA: BVP ELISA was employed to understand the propensity of a relaxin-2 fusion protein analog for non-specific or non-target interactions. BVPs are empty viral capsids with no viral genome, but in the process of production, budding off from the cell membrane allows them to take components of the cell membrane along with them. Thus, the BVPs possess a highly diverse cell surface with many moieties present, which mimic what the molecule of interest (i.e., relaxin-2 fusion protein analog) may encounter in vivo. Briefly, BVPs are coated on a plate by adding 25 µL of BVP solution to each well. BVP solution was made by diluting BVP stock (Medna Scientific; Cat. No. E3001) to 1×10$^6$ PFU/mL with 0.1 M carbonate buffer, pH 9.6. Following overnight incubation at 5° C., BVP solution was blotted from wells and wells were washed three times with PBST. Plates were blocked with 100 µL/well of 1×BSA in PBS blocking buffer (Cepham Life Sciences; Cat. No. 10615). Plates were incubated at 25° C. on a plate shaker for 1 hour. Blocking solution was blotted from wells and wells were washed three times with PBST. Samples (i.e., relaxin-2 fusion protein analogs) were prepared in duplicate to cover dilution range from 3 µM to 0.1 nM and added to plates. Plates were incubated at 25° C. for 1 hour, after which the wells were blotted and washed three times with PBST. 25 µL/well of 1:10,000 diluted detection monoclonal antibody (Peroxidase AffiniPure Goat Anti-Human IgG, Fcγ fragment specific; Jackson ImmunoResearch; Cat. No. 50-194-1564) was added, and plates were incubated at 25° C. for 1 hour, after which the wells were blotted and washed three times with PBST. 1-Step™ Ultra TMB-ELISA Substrate Solution (Life Technologies; Cat. No. 34029) was then added. After about 2 minutes, 25 µL 2N HCl was added to quench the reaction, and a plate reader was used to analyze the plate at 450 nm with correction at 570 nm.

Potency assay: HEK293 cells were seeded into a 96-well tissue culture plate followed by transient co-transfection with a human RXFP1 and a pGloSensor-22F plasmid. Transfected cells were stimulated by relaxin-2 or fusion protein analogs thereof, inducing Gs-mediated cAMP signaling. cAMP is assayed using the activity of the GloSensor biosensor, which is a mutant luciferase fused to a cAMP binding domain, leading to a production of light in the presence of its substrate luciferin. This readout of relative luminescent units (RLU) is used as a proxy for cAMP response.

cAMP Signaling Assay Protocol: this protocol is adapted from the GloSensor cAMP assay by Promega. Raw data was exported to Excel using the MARS data analysis software that is opened following a run on the CLARIOstar plate reader. These values are measured in RLU, or relative luminescence units.

Affinity-Capture Self-Interaction Nanoparticle Spectroscopy (AC-SINS): AC-SINS was performed to understand the propensity of a molecule (i.e., relaxin-2 fusion protein analog) to self-associate. Briefly, gold nanoparticles were pre-coated with anti-human antibodies (Fc, Fab and H+L), which when incubated with target antibodies in dilute solutions, capture and concentrate in solution the antibody of interest. When the immobilized molecules of interest interact, the inter-particle distances decrease between gold nanoparticles, leading to increased plasmon wavelengths (i.e., red shift) that can be quantified using UV-VIS spectroscopy. Materials used for the spectroscopy are provided in Table 20.

TABLE 20

Materials for AC-SINS

| Item | Vendor | Cat No. |
|---|---|---|
| 1M sodium acetate pH 4.3 | Molecular Dimensions | MD2-019-PH |
| 1x DPBS | Gibco | 14190-136 |
| Panitumumab (Low Assoc Ctrl) | MyBioSource | MBS156169 |
| Ipilimumab (Med Assoc Ctrl) | MyBioSource | MBS156153 |
| Ganitumab (High Assoc Ctrl) | MyBioSource | MBS156142 |
| 20 nm gold nanoparticles | Ted Pella | 15705 |
| PEG methyl ether thiol (2kDa) | Sigma | 729140 |
| Goat anti-Human IgG, Fcγ | Jackson ImmunoResearch | 109-005-098 |
| Goat non-specific mAb | Jackson ImmunoResearch | 005-000-003 |
| Zeba Desalting Columns 40K 5 mL | Thermo Fisher | 87770 |
| Zeba Desalting Columns 40K 2 mL | Thermo Fisher | 87768 |
| Zeba Desalting Columns 40K 0.5 mL | Thermo Fisher | 87766 |
| Costar 384-well Polystyrene plates | Fisher Scientific | 12-565-506 |
| 96-well Polypropylene plates | Grenier Bio-One | 652230P |

Goat anti-human Fc IgG antibody (capture) and goat IgG antibody (non-capture) were buffer exchanged into 20 mM sodium acetate, pH 4.3. After buffer exchange, concentrations were normalized to 0.4 mg/mL for both antibodies. A 4:1 volume ratio mixture of capture (anti-Fc):non-capture (Goat IgG) solution was prepared for 80% capture capacity coating solution to be used to incubate gold nanoparticles (AuNPs). A 9:1 volume ratio of AuNPs:coating solution was made. The solution was incubated at room temperature, overnight in the dark. After incubation, thiolated PEG was added to 0.1 µM final concentration from the diluted 10 µM stock to block empty sites on the AuNPs (i.e., 5 mL solution of AuNPs, add 50 µL 10 µM stock) and incubated at RT for one hour in the dark.

2 mL of coated AuNP solution was centrifuged at 20,000×g for 15 minutes to sediment the AuNPs and 1800 µL supernatant was carefully removed using a 1 mL pipette. The pelleted AuNPs were gently resuspended using a 200 µL pipette to generate a 10× concentrated stock of coated AuNPs. For each sample analyzed, 5 µL of AuNP concentrate was incubated with 45 L antibody test solution (normalized to 0.05 mg/mL) at room temperature in the dark for 2 hours in a 384-well polypropylene plate. After the 2-hour incubation, absorbance data was collected from 450 nm to 650 nm in 1 nm steps to determine wavelength shifts for each sample relative to AuNPs alone.

Nanoscale Differential Scanning Fluorimetry (NanoDSF): NanoDSF was performed using the NanoTemper Prometheus Panta to investigate the conformational stability of a relaxin-2 protein fusion analog. Conformational stability was measured by applying a thermal ramp to a solution containing the molecule of interest, measuring the intrinsic fluorescence, backscattering, and using dynamic light scattering (DLS) to provide various thermal stability parameters, including the temperature at which fusion protein unfolding begins ($T_{onset}$), the temperature at which half of the fusion protein in a given sample is unfolded ($T_m1$), and the temperature at which fusion protein aggregation begins ($T_{agg}$).

Sequences: Sequences of relaxin-2 fusion protein analogs are described throughout the present disclosure. SEQ ID NOs: 496, 497, and 501 are set forth below:

(SEQ ID NO: 496)
DKTHTCPPCPAPEAAGGPSVFLFPPKPKDTLMISRTPEVTCVVVDVSH

EDPEVKFNWYVDGVEVHNAKTKPREEQYNSTYRVVSVLTVLHQDWLNG

KEYKCKVSNKALAAPIEKTISKAKGQPREPQVYTLPPSRDELTKNQVS

LTCLVKGFYPSDIAVEWESNGQPENNYKTTPPVLDSDGSFFLYSKLTV

DKSRWQQGNVFSCSVLHEALHSHYTQKSLSLSPGKGGSDSWKEEVIKL

CGRELVRAQIAICGKSTASDAAGANANAGARQLYSALANKCCHVGCTK

RSLARFC;

(SEQ ID NO: 497)
DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVS

LTCLVKGFYPSDIAVEWESNGQPENNYKTTPPVLDSDGSFFLYSKLTV

DKSRWQQGNVFSCSVMHEALHNHYTQKSLSLSPGKGGGGSGGGGSGGG

GSQLYSALANKCCHVGCTKRSLARFCGGGGSGGGGSGGGGSSWMEEVI

KLCGRELVRAQIAICGMSTWS;
and (SEQ ID NO: 501)
MPRLFFFHLLGVCLLLNQFSRAVADSWMEEVIKLCGRELVRAQIAICG

MSTWSKRSLSQEDAPQTPRPVAEIVPSFINKDTETINMMSEFVANLPQ

ELKLTLSEMQPALPQLQQHVPVLKDSSLLFEEFKKLIRNRQSEAADSS

PSELKYLGLDTHSRKKRQLYSALANKCCHVGCTKRSLARFC.

Results

The results are shown below in Tables 21, 22, and 23.

TABLE 21

In vitro Characteristics of Relaxin-2 Fusion Protein Analogs.

| Sample | Heparin Binding RT[1] | Heparin Binding [NaCl] (mM)[2] | cIEF Isoelectric Point (pI) | BVP ELISA Normalized Score | Potency[3] (nM) | AC-SINS Δλmax | NanoDSF $T_{onset}$ (°C.) | NanoDSF $T_m1$ (°C.) |
|---|---|---|---|---|---|---|---|---|
| Wild-type human relaxin-2 | ND | ND | 9.4 | N/A | 0.1 | N/A | N/A | N/A |
| SEQ ID NO: 497 | ND | ND | 9.0 | 28 | 0.3 | 7 | 61.4 | 68.9 |
| SEQ ID NO: 496 | 4.75 | 400 | 9.1 | 34 | 0.2 | 14 | 59.7 | 68.4 |
| SEQ ID NO: 361 | 3.88 | 330 | 8.9 | 2 | 2.5 | 8 | 60.5 | 70.4 |
| SEQ ID NO: 362 | NT | NT | ND | ND | 12.3 | 1 | 63.3 | 70.7 |
| SEQ ID NO: 363 | 3.32 | 280 | 8.5 | 1 | 2.9 | 7 | 62.8 | 70.6 |
| SEQ ID NO: 304 | 3.43 | 290 | 8.5 | 1 | 2.5 | 7 | 61.6 | 70.6 |
| SEQ ID NO: 364 | 2.71 | 230 | 7.9 | 1 | 16.0 | 2 | 62.9 | 70.9 |
| SEQ ID NO: 307 | 2.79 | 240 | 7.9 | 1 | 15.8 | 2 | 63.0 | 71.0 |
| SEQ ID NO: 365 | 2.42 | 210 | 7.5 | 1 | 60.3 | 0 | 63.9 | 71.1 |
| SEQ ID NO: 366 | 2.5 | 210 | 7.1 | 1 | 62.8 | 0 | 63.6 | 71.2 |
| SEQ ID NO: 367 | 2.19 | 190 | 7.1 | 1 | 140.0 | 0 | 62.4 | 71.0 |
| SEQ ID NO: 368 | 2.23 | 190 | ND | 1 | 101.2 | 0 | 62.8 | 70.8 |
| SEQ ID NO: 369 | 3.63 | 310 | ND | 1 | 0.5 | 10 | 62.9 | 70.8 |
| SEQ ID NO: 370 | 3.2 | 270 | ND | 1 | 1.8 | 6 | 63.0 | 71.2 |
| SEQ ID NO: 313 | 2.7 | 230 | 8.0 | 1 | 4.2 | 5 | 63.0 | 69.9 |
| SEQ ID NO: 315 | 3 | 250 | 8.0 | 1 | 3.3 | 11 | 61.9 | 69.3 |
| SEQ ID NO: 317 | 2.5 | 210 | 7.5 | 1 | 8.0 | 7 | 61.9 | 69.7 |
| SEQ ID NO: 319 | 3.1 | 260 | 8.0 | 1 | 5.8 | 4 | 62.6 | 69.6 |
| SEQ ID NO: 321 | 2.6 | 220 | 7.4 | 1 | 10.2 | 3 | 62.3 | 69.9 |
| SEQ ID NO: 323 | 3 | 250 | 7.4 | ND | ND | ND | ND | ND |
| SEQ ID NO: 325 | 2.3 | 200 | 7.1 | 1 | 23.4 | 4 | 60.9 | 69.9 |
| SEQ ID NO: 326 | 2.6 | 220 | 7.5 | 1 | 18.9 | 4 | 62.3 | 70.1 |
| SEQ ID NO: 327 | 2.8 | 240 | 7.5 | ND | 9.3 | 7 | 60.9 | 69.2 |
| SEQ ID NO: 328 | 2.3 | 200 | 7.1 | 1 | 41.9 | 5 | 61.4 | 69.9 |
| SEQ ID NO: 84 | 3.1 | 260 | 8.5 | 2 | 1.9 | 8 | 61.1 | 69.3 |
| SEQ ID NO: 85 | 3.1 | 260 | 8.5 | 2 | 2.0 | 9 | 60.8 | 69.4 |
| SEQ ID NO: 86 | 2.8 | 240 | 7.9 | 3 | 4.0 | 5 | 60.4 | 69.6 |
| SEQ ID NO: 87 | 2.8 | 240 | 7.9 | 2 | 5.2 | 6 | 62.0 | 69.7 |
| SEQ ID NO: 88 | 3.1 | 260 | 8.5 | 10 | 1.4 | 9 | 60.6 | 69.5 |
| SEQ ID NO: 89 | 3.1 | 260 | 8.4 | 3 | 2.5 | 9 | 60.1 | 69.4 |
| SEQ ID NO: 90 | 3.5 | 300 | 8.8 | 4 | 0.6 | 15 | 60.8 | 69.4 |
| SEQ ID NO: 91 | 2.7 | 230 | 7.4 | 1 | 3.9 | 8 | 61.1 | 69.6 |
| SEQ ID NO: 92 | 2.7 | 230 | 7.4 | 1 | 4.3 | 9 | 61.1 | 69.6 |

TABLE 21-continued

In vitro Characteristics of Relaxin-2 Fusion Protein Analogs.

| Sample | Heparin Binding | | cIEF | BVP ELISA | | AC- | NanoDSF | |
|---|---|---|---|---|---|---|---|---|
| | RT[1] | [NaCl] (mM)[2] | Isoelectric Point (pI) | Normalized Score | Potency[3] (nM) | SINS Δλmax | $T_{onset}$ (° C.) | $T_m1$ (° C.) |
| SEQ ID NO: 93 | 2.4 | 200 | 7.0 | 1 | 11.1 | 5 | 60.7 | 69.5 |
| SEQ ID NO: 94 | 2.5 | 210 | 7.0 | 2 | 12.2 | 5 | 59.8 | 69.5 |
| SEQ ID NO: 95 | 2.7 | 230 | 7.4 | 3 | 6.8 | 6 | 59.7 | 69.4 |
| SEQ ID NO: 96 | 2.8 | 240 | 7.4 | 3 | 9.9 | 7 | 60.3 | 69.3 |
| SEQ ID NO: 97 | 3.1 | 260 | 8.0 | 5 | 1.3 | 13 | 60.4 | 69.2 |
| SEQ ID NO: 98 | 2.6 | 220 | 7.0 | 2 | 8.8 | 6 | 61.6 | 69.5 |
| SEQ ID NO: 99 | 2.6 | 220 | 7.0 | 1 | 9.4 | 8 | 60.6 | 69.3 |
| SEQ ID NO: 100 | 2.3 | 200 | 6.8 | 1 | 28.7 | 4 | 60.7 | 69.5 |
| SEQ ID NO: 101 | 2.3 | 200 | 6.8 | 1 | 29.4 | 3 | 62.1 | 69.7 |
| SEQ ID NO: 102 | 2.6 | 220 | 7.0 | 1 | 7.5 | 8 | 61.7 | 69.6 |
| SEQ ID NO: 103 | 2.6 | 220 | 7.0 | 2 | 12.2 | 6 | 61.3 | 69.6 |
| SEQ ID NO: 104 | 2.9 | 250 | 7.4 | 3 | 2.8 | 11 | 61.5 | 69.5 |
| SEQ ID NO: 106 | 2.5 | 210 | 7.1 | 2 | 14.0 | 4 | 60.4 | 69.4 |
| SEQ ID NO: 108 | 2.3 | 200 | 6.8 | 1 | 35.2 | 2 | 61.0 | 69.5 |
| SEQ ID NO: 110 | 2.5 | 210 | 7.0 | 2 | 17.2 | 4 | 60.5 | 69.5 |
| SEQ ID NO: 111 | 2.8 | 240 | 7.4 | 2 | 3.5 | 6 | 60.4 | 69.6 |
| SEQ ID NO: 112 | 2.4 | 200 | 6.8 | 1 | 24.8 | 3 | 60.9 | 69.5 |
| SEQ ID NO: 113 | 2.3 | 200 | 6.8 | 2 | 26.0 | 2 | 60.2 | 69.4 |
| SEQ ID NO: 116 | 2.3 | 200 | 6.8 | 1 | 25.9 | 3 | 60.6 | 69.5 |
| SEQ ID NO: 117 | 2.4 | 200 | 6.8 | 1 | 31.2 | 2 | 60.9 | 69.7 |
| SEQ ID NO: 118 | 2.7 | 230 | 7.1 | 2 | 10.1 | 5 | 60.5 | 69.5 |

[1]Retention time.
[2]Concentration of NaCl in mM at peak elution from column.
[3]Potency based on transient hRXFP1 assay described above.
ND—not determined.
N/A—not applicable.

TABLE 22

In vitro Characteristics of Relaxin-2 Fusion Protein Analogs.

| Sample | Heparin binding | HIC | SEC | NanoDSF | | | Potency[1] (nM) | Calculated | |
|---|---|---|---|---|---|---|---|---|---|
| | [NaCl] (mM)[2] | [Salt] (mM) | Monomer (%) | $T_{onset}$ (° C.) | $T_m1$ (° C.) | Tagg (° C.) | | isoelectric point (pI) | CIEF pI |
| SEQ ID NO: 87 | 217 | 620 | ND | 59 | 69 | 71 | 8.5 | 8 | 7.6 |
| SEQ ID NO: 119 | 225 | 630 | 95.6 | 60 | 70 | 81 | 4.9 | 8 | 7.6 |
| SEQ ID NO: 120 | 225 | 630 | 95.5 | 60 | 70 | 84 | 4.8 | 8 | 7.6 |
| SEQ ID NO: 121 | 225 | 640 | 95.8 | 60 | 70 | 80 | 5.5 | 8 | 7.6 |
| SEQ ID NO: 122 | 225 | 650 | 95.2 | 60 | 69 | 80 | 6.5 | 8 | 7.6 |

TABLE 22-continued

In vitro Characteristics of Relaxin-2 Fusion Protein Analogs.

| Sample | Heparin binding [NaCl] (mM)[2] | HIC [Salt] (mM) | SEC Monomer (%) | NanoDSF $T_{onset}$ (° C.) | NanoDSF $T_m1$ (° C.) | NanoDSF Tagg (° C.) | Potency[1] (nM) | Calculated isoelectric point (pI) | CIEF pI |
|---|---|---|---|---|---|---|---|---|---|
| SEQ ID NO: 123 | 200 | 480 | 93.4 | 60 | 69 | 91 | 11.7 | 8 | 7.6 |
| SEQ ID NO: 124 | 192 | 560 | 95.1 | 60 | 69 | 77 | 20.8 | 8 | 7.6 |
| SEQ ID NO: 125 | 192 | 650 | 95.7 | 60 | 69 | 84 | 11.1 | 8 | 7.6 |
| SEQ ID NO: 126 | 267 | 710 | 95.8 | 61 | 69 | 84 | 8.3 | 8.5 | 8 |
| SEQ ID NO: 127 | 158 | 460 | 94.6 | 60 | 69 | 92 | 32 | 7.1 | 6.7 |
| SEQ ID NO: 128 | 233 | 670 | 96.2 | 59 | 69 |  | 23.2 | 7.5 | 7.1 |
| SEQ ID NO: 129 | 167 | 500 | 89.4 | 59 | 69 | 76 | 42.4 | 7.1 | 6.7 |
| SEQ ID NO: 130 | 250 | 710 | 83.4 | 58 | 68 | 76 | 24.6 | 7.5 | 7.1 |
| SEQ ID NO: 131 | 200 | 500 | 91.9 | 59 | 69 | 76 | 16.4 | 7.5 | 7.1 |
| SEQ ID NO: 132 | 283 | 710 | 86 | 59 | 69 | 76 | 11.2 | 8.1 | 7.6 |
| SEQ ID NO: 133 | 183 | 480 | 86.7 | 60 | 69 | 74 | 30.6 | 7.5 | 7.1 |
| SEQ ID NO: 134 | 250 | 690 | 91.4 | 60 | 69 | 74 | 21.6 | 8 | 7.6 |
| SEQ ID NO: 135 | 192 | 520 | 86 | 60 | 69 | 73 | 29.5 | 7.5 | 7.1 |
| SEQ ID NO: 136 | 258 | 730 | 90.2 | 59 | 69 | 32 | 17.6 | 8 | 7.6 |
| SEQ ID NO: 137 | 217 | 520 | 89.2 | 59 | 69 | 76 | 11.4 | 8 | 7.6 |
| SEQ ID NO: 138 | 292 | 730 | 94.8 | 60 | 69 |  | 7.5 | 8.6 | 8 |

[1]Potency based on transient hRXFP1 assay described above.
[2]Concentration of NaCl in mM at peak elution from column.
ND—not determined.

TABLE 23

In vitro Characteristics of Relaxin-2 Fusion Protein Analogs.

| Sample | Heparin binding [NaCl] (mM)[2] | SEC Monomer (%) | NanoDSF $T_{onset}$ (° C.) | NanoDSF $T_m$ (° C.) | NanoDSF $T_{agg}$ (° C.) | Potency[1] (nM) | Calculated isoelectric point (pI) |
|---|---|---|---|---|---|---|---|
| SEQ ID NO: 516 | 275 | 86.8 | 52 | 65 | 51 | 5.6 ± 5.2 (n = 2) | 7.62 |
| SEQ ID NO: 517 | 217 | 93.5 | 59 | 69 | 73 | 15.5 ± 17 (n = 2) | 7.61 |
| SEQ ID NO: 518 | 208 | 92.9 | 59 | 69 | 73 | 15.8 ± 14 (n = 2) | 7.16 |
| SEQ ID NO: 519 | 183 | 93.9 | 59 | 69 | 73 | 38.1 ± 37 (n = 2) | 7.14 |
| SEQ ID NO: 520 | 258 | 90.4 | 60 | 68 | 62 | 4.9 ± 4.7 (n = 2) | 7.97 |
| SEQ ID NO: 521 | 242 | 94.6 | 59 | 69 | 73 | 3.3 ± 3.6 (n = 2) | 7.97 |
| SEQ ID NO: 522 | 242 | 91.9 | 60 | 70 | 73 | 6.5 ± 6.8 (n = 2) | 7.62 |
| SEQ ID NO: 523 | 217 | 94.9 | 60 | 69 | 73 | 9.3 ± 8.9 (n = 2) | 7.61 |

[1]Potency based on transient hRXFP1 assay described above.
[2]Concentration of NaCl in mM at peak elution from column.
ND— not determined.

All samples in Tables 21, 22, and 23 are LALA PA LS IgG-RelB-Linker-RelA fusions containing the LALA PA LS IgG (SEQ ID NO: 79 or 83) except for wild-type human relaxin-2 and SEQ ID NO: 497. As shown in Tables 21, 22 and 23, above, there is a correlation between lower pI and lower non-specific binding found through heparin chromatography.

Confirmatory AC-SINS and BVP ELISA assays, and additional cAMP potency assays were performed on a subset of relaxin-2 fusion protein analogs, with results shown in Table 24.

detected by size exclusion chromatography. In addition, based on non-reducing capillary electrophoresis samples (CE-SDS NR), no significant fragmentation was observed for any stresses in any of the tested samples.

The formation of stress induced post translational modifications (PTMs) was also tested. Stresses included incubation at 40° C. for 4 weeks, room temperature and high pH (Tris buffer pH 8) for 2 weeks, room temperature and low pH (glycine buffer pH 3) for 2 weeks and room temperature oxidative stress (0.02% hydrogen peroxide) for 24 hours. SEQ ID NO: 313 and SEQ ID NO: 87 did not show any

TABLE 24

Additional Potency Assays for Relaxin-2 Fusion Protein Analogs.

| Sample | pI | ACSINS (nm) | BVP ELISA | THP1 (endogenous RXFP1) CAMP EC50 (nM) (n) | Transient HEK293 hRXFP1cAMP EC50 (nM) (n) | Transient HEK293 rRXFP1cAMP EC50 (nM) (n) |
|---|---|---|---|---|---|---|
| Wild-type human relaxin-2 | ND | ND | ND | 0.2 ± 0.2 (7) | 0.039 ± 0.015 (3) | 0.122 ± 0.07 (3) |
| SEQ ID NO: 497 | ND | 28 | 7 | ND | 0.3** | 0.95 ± 0.10 (2) |
| SEQ ID NO: 496 | 9.1 | 14 | 34 | 2.0 ± 1.3 (4) | 0.19 ± 0.15 (2) | 1.15 ± 0.23 (2) |
| SEQ ID NO: 367 | 7 | 0 | 1 | ND | ~150 | ND |
| SEQ ID NO: 313 | 7.9 | 3 | 2 | 49 ± 9 (4) | 10.0 ± 4.27 (3) | 15.1 ± 2.17 (3) |
| SEQ ID NO: 317 | 7.5 | 7 | 1 | 63 ± 3 (3) | 38.2 (1) | 31.2 ± 11.1 (3) |
| SEQ ID NO: 86 | 7.9 | 5 | 3 | 30 ± 20 (3) | 7.46 ± 3.32 (3) | 24.5 ± 18.8 (3) |
| SEQ ID NO: 87 | 7.9 | 6 | 2 | 25 ± 12 (4) | 8.70 ± 4.40 (3) | 10.3 ± 3.45 (3) |
| SEQ ID NO: 90 | 8.8 | 15 | 4 | 4.4 ± 0.9 (2) | 0.6 + 0.5 (3) + I:BC | ND |
| SEQ ID NO: 91 | 7.4 | 8 | 1 | 30 ± 20 (3) | 10.2 ± 5.86 (3) | 12.4 ± 3.07 (3) |
| SEQ ID NO: 93 | 7 | 5 | 2 | 90 ± 10 (2) | 19.1 ± 4.80 (3) | 21.3 ± 9.59 (2) |
| SEQ ID NO: 95 | 7.4 | 6 | 3 | 26 ± 4 (4) | 10.9 ± 5.26 (3) | 13.5 ± 0.98 (2) |
| SEQ ID NO: 98 | 7 | 6 | 1 | 100 ± 40 (2) | 21.5 ± 13.5 (3) | 29.1 ± 5.71 (2) |
| SEQ ID NO: 104 | 7.4 | 11 | 3 | 11 ± 2 (3) | 6.17 ± 2.21 (3) | 6.74 ± 0.73 (2) |
| SEQ ID NO: 111 | 7.4 | 6 | 3 | 80 ± 50 (2) | 5.94 ± 1.32 (3) | 6.74 ± 4.57 (2) |
| SEQ ID NO: 118 | 7.1 | 5 | 2 | 200 ± 100 (2) | 25.0 ± 6.20 (3) | 20.3 ± 1.12 (2) |

ND—not determined.

A subset of relaxin-2 fusion protein analog (SEQ ID NO: 496, SEQ ID NO: 313, SEQ ID NO: 87, SEQ ID NO: 90, SEQ ID NO: 95, and SEQ ID NO: 104) samples was tested under various developability assessments. Under high concentration stress (target concentration of about 100 mg/mL), none of the samples showed loss of protein concentration based on UV. Thermal stress induced increased turbidity/opalescence for all samples tested. Agitation stress had no effect on SEQ ID NO: 313 and SEQ ID NO: 104 samples. Under chemical stress (target concentration of about 5 mg/mL), SEQ ID NO: 496 and SEQ ID NO: 90 samples showed reduction in concentration for all chemical stresses tested, while SEQ ID NO: 313, SEQ ID NO: 87, SEQ ID NO: 95, and SEQ ID NO: 104 samples appeared stable. All samples showed oxidation induced reduction in concentration, with SEQ ID NO: 496 and SEQ ID NO: 90 oxidized samples showing elevated high molecule weight species stress induced modifications; SEQ ID NO: 90 and SEQ ID NO: 95 showed aspartic acid isomerization in the linker region; SEQ ID NO: 496 showed asparagine deamidation in the linker region; and SEQ ID NO: 95 and SEQ ID NO: 104 showed aspartic acid isomerization in the relaxin sequences.

During manufacturability assessments, color change and aggregation were observed with multiple molecules under certain stress conditions, which is common in oxidized proteins. The color change is typically driven by tryptophan oxidation, which drives a change in absorbance at 320 nm and 365 nm (Ambrogelly (2021) Antibodies 10(2):21). In order to probe light sensitivity of relaxin-2 fusion protein analogs SEQ ID NO: 522 and SEQ ID NO: 523, a light box was created using a tabletop 25° C. incubator with a transparent glass door. A photometer was attached to the inside of the incubator, a rectangular LED with an adjustable light intensity switch was placed on the outside of the incubator, and the light intensity was adjusted to 1000 lux, which is similar to the light intensity in standard manufacturing suite rooms. Samples were placed in transparent glass vials with 200 μL glass inserts to allow for maximum surface area for light exposure, while maintaining minimal sample volume requirements. Relaxin-2 fusion protein analogs SEQ ID NO: 522 and SEQ ID NO: 523 were incubated at 25° C., 1000 lux for 7 or 14 days. Samples were also subjected to thermal stress via incubation at 40° C. for 7 or 14 days. After light or heat exposure, samples were evaluated using size exclusion high-performance liquid chromatography (SEC) to assess aggregate formation and CE-SDS to assess purity. As shown in Table 25, under these conditions, SEQ ID NO: 522 and SEQ ID NO: 523 are both resistant to thermal and light stress as assessed by aggregate formation and purity.

TABLE 25

Light and Heat Stress Stability of Relaxin-2 Fusion Protein Analogs.

| Sample | Condition | SEC Monomer (%) | SEC HMW (%) | CE-SDS Reduced purity (%) | CE-SDS Non-reduced purity (%) |
|---|---|---|---|---|---|
| SEQ ID NO: 522 | Control (unstressed) | 96.2 | 3.8 | 99.5 | 90.4 |
| | Light (7 days) | 95.5 | 4.5 | 99.5 | 90.4 |
| | Light (14 days) | 95.7 | 4.3 | 99.5 | 90.6 |
| | 40° C. (7 days) | 95.6 | 4.4 | 99.5 | 90.1 |
| | 40° C. (14 days) | 95.2 | 4.8 | 99.5 | 89.9 |
| SEQ ID NO: 523 | Control (unstressed) | 90.6 | 9.4 | 99.5 | 94.7 |
| | Light (7 days) | 90.1 | 9.9 | 99.5 | 94.4 |
| | Light (14 days) | 90.5 | 9.5 | 99.5 | 94.6 |
| | 40° C. (7 days) | 90.4 | 9.6 | 99.5 | 94.7 |
| | 40° C. (14 days) | 90.3 | 9.7 | 99.5 | 94.9 |

Figure 1C:
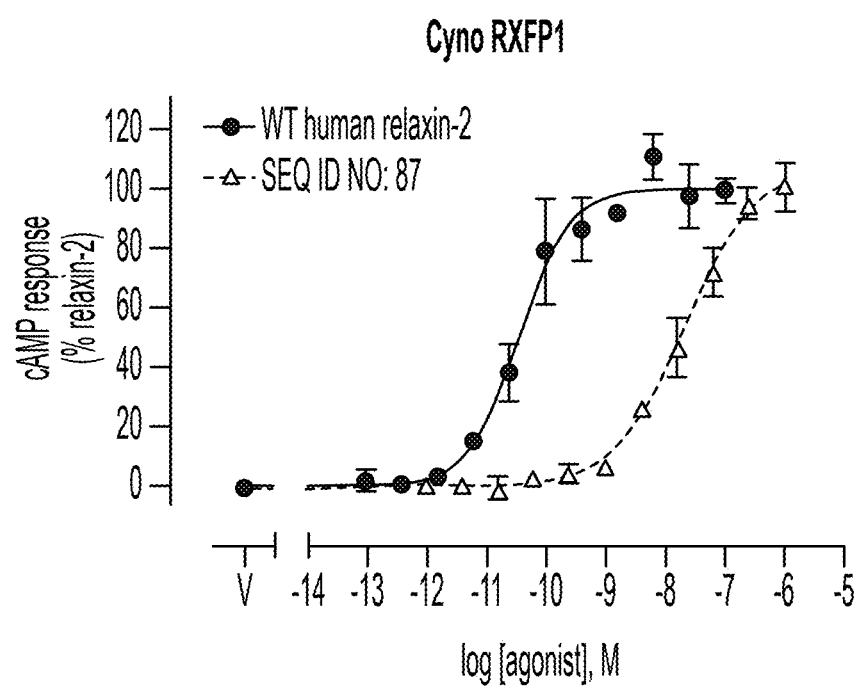

A separate study was performed to investigate the in vitro potency of SEQ ID NO: 87 as compared to wild-type (WT) human relaxin-2, using mammalian cell systems that either transiently, stably, or endogenously expressed human RXFP1 or orthologs from cynomolgus monkey and rat. Table 26 shows a summary of cAMP response induced by SEQ ID NO: 87 and wild-type human relaxin-2 on HEK293 cells transiently expressing human, monkey, and rat RXFP1. As shown in Table 26 and FIGS. 1A-1C, the average EC50 for SEQ ID NO: 87 for human (FIG. 1A), rat (FIG. 1B), and monkey (FIG. 1C) RXFP1 was 10±4 nM, 10±9 nM, and 30±20 nM, respectively.

TABLE 26

Summary of cAMP Response in Cells Transiently Expressing RXFP1.

| | Wild-type human relaxin-2 $EC_{50}$ | | SEQ ID NO: 87 $EC_{50}$ | |
|---|---|---|---|---|
| | nM Mean ± SD (n) | ng/ml Mean ± SD (n) | nM Mean ± SD (n) | ng/ml Mean ± SD (n) |
| Human RXFP1 in HEK293 | 0.05 ± 0.02 (6) | 0.3 ± 0.1 (6) | 10 ± 4 (6) | 800 ± 300 (6) |
| Rat RXFP1 in HEK293 | 0.1 ± 0.02 (3) | 0.6 ± 0.1 (3) | 30 ± 20 (3) | 2000 ± 1000 (3) |
| Cynomolgus monkey RXFP1 in HEK293 | 0.04 ± 0.01 (3) | 0.2 ± 0.1 (3) | 10 ± 9 (3) | 800 ± 600 (3) |

To test the selectivity of SEQ ID NO: 87, CHO-K1 cells stably expressing human RXFP1 or human RXFP2 were used. As shown in Table 27, the $EC_{50}$ for SEQ ID NO: 87 for human RXFP1 was 40±20 nM, and for human RXFP2, was ~100-fold less potent ($EC_{50}$ of >2000 nM), demonstrating that SEQ ID NO: 87 is selective for RXFP1.

TABLE 27

Summary of cAMP Response in Cells Stably or Endogenously Expressing RXFP1.

| | Wild-type human relaxin-2 $EC_{50}$ | | SEQ ID NO: 87 $EC_{50}$ | |
|---|---|---|---|---|
| | nM Mean ± SD (n) | ng/mL Mean ± SD (n) | nM Mean ± SD (n) | ng/ml Mean ± SD (n) |
| Human RXFP1 (stable) in CHO-K1 | 0.2 ± 0.1 (4) | 1 ± 0.6 (4) | 40 ± 20 (4) | 2000 ± 1000 (4) |
| Human RXFP2 (stable) in CHO-K1 | 10 ± 10 (4) | 90 ± 60 (4) | >2000 (4) | >$10^6$ (4) |

TABLE 27-continued

Summary of cAMP Response in Cells Stably or Endogenously Expressing RXFP1.

|  | Wild-type human relaxin-2 $EC_{50}$ | | SEQ ID NO: 87 $EC_{50}$ | |
|---|---|---|---|---|
|  | nM Mean ± SD (n) | ng/mL Mean ± SD (n) | nM Mean ± SD (n) | ng/ml Mean ± SD (n) |
| THP-1 (endogenous RXFP1) | 0.07 ± 0.03 (5) | 0.4 ± 0.2 (5) | 10 ± 6 (5) | 900 ± 400 (5) |

In some cases, transient or stable ectopic expression of proteins in cells can result in over-expression of targets, which may impact the potency and efficacy of test articles. To address this, the potency of SEQ ID NO: 87 was tested in the human leukemia monocytic cell line, THP-1, which endogenously expressed RXFP1. As shown in Table 27, the EC50 for SEQ ID NO:87 was found to be 10±6 nM, consistent with what was found in the in vitro RXFP1 potency assays described above.

Figure 2A:
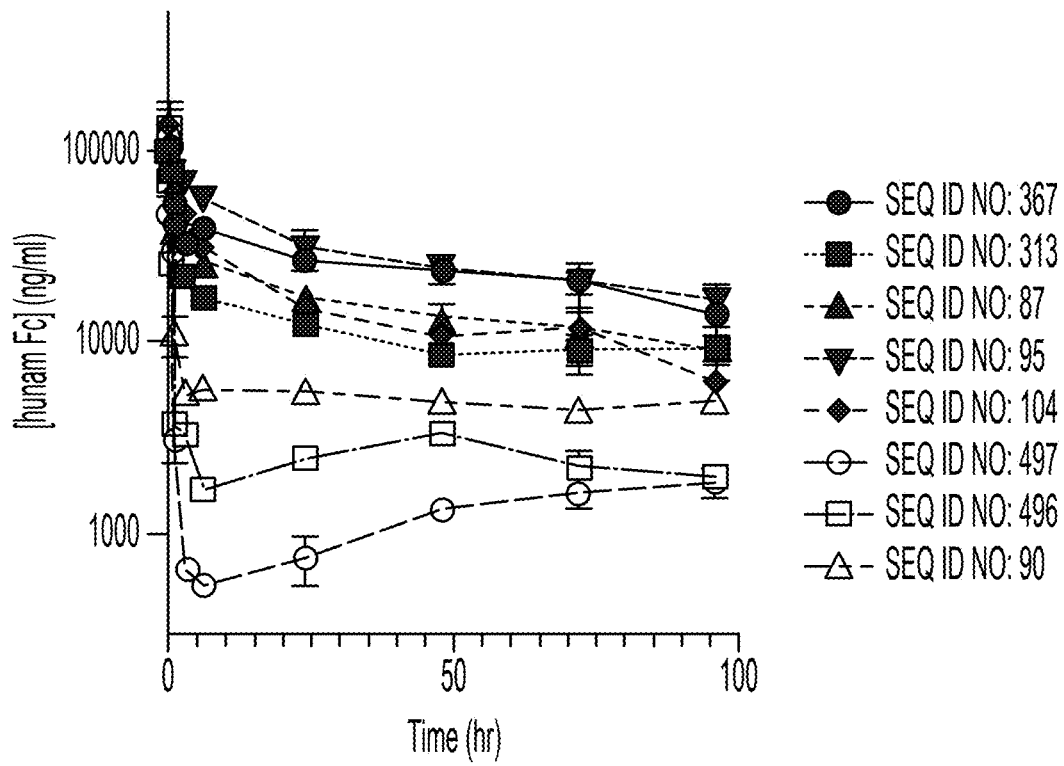
FIGS. 2A-2C are graphs depicting the pharmacokinetic (PK) values obtained by measuring the concentration of the various relaxin-2 fusion protein analogs (using human Fc levels as a proxy) as indicated in the serum of rats following a 5 mg/kg intravenous (IV) injection of the respective protein analog over time.

Example 5. Pharmacokinetic (PK) and Pharmacodynamic (PD) Properties of Relaxin-2 Fusion Protein Analogs Pharmacokinetic (PK) values were determined by measuring the concentration of a relaxin-2 fusion protein analog in the plasma of rats following a 5 mg/kg intravenous (IV) injection of the respective protein analog over time. PK values were determined for a subset of relaxin-2 fusion protein analog (SEQ ID NO: 496, SEQ ID NO: 497, SEQ ID NO: 367, SEQ ID NO: 313, SEQ ID NO: 87, SEQ ID NO: 95, SEQ ID NO: 90, and SEQ ID NO: 104) samples described herein (FIG. 2A). Rat PK parameters are shown in Table 28, below.

Example 6. Hemodynamics and Renal Blood Flow Effects of Relaxin-2 Fusion Protein Analogs The high isoelectric point (pI) of relaxin and related molecules presents significant pharmacokinetic (PK) and biophysical challenges, reflected in the rapid decline observed in serum concentration for these molecules in the earliest timepoints of the PK curve. Without being bound by any theory, this high clearance phenomenon has been attributed to non-specific binding of high pI molecules to negatively charged heparin proteoglycans in the vasculature and in tissues. These issues were resolved through structure-guided engineering of the relaxin-2 fusion protein analogs to reduce their pI, as shown in Examples 1-5.

To assess the impact of the changes to lower pI, the PK and pharmacodynamic (PD) effects of the relaxin-2 fusion protein analogs were measured in rats. One of the most readily quantifiable activities of relaxin is to produce an observable increase in renal arterial blood flow (RABF) shortly following administration. This is a PD effect that has been shown to be observable in both rats and human patients with administration of serelaxin and can be modeled to establish a PK/PD relationship for test compounds.

TABLE 28

Summary of PK Parameters.

| Parameter | SEQ ID NO: 496 | SEQ ID NO: 313 | SEQ ID NO: 87 | SEQ ID NO: 90 | SEQ ID NO: 95 | SEQ ID NO: 104 | SEQ ID NO: 367 | SEQ ID NO: 497 |
|---|---|---|---|---|---|---|---|---|
| | | | | rat (mL/h or mL) | | | | |
| Clearance CL | 2.76 | 0.69 | 0.52 | 0.29 | 0.32 | 0.52 | 0.356 | ND |
| Central Volume 1 | 6.73 | 11.5 | 11.28 | 13.46 | 9.45 | 16.63 | 15.798 | ND |
| Peripheral Clearance | 28.24 | 16.8 | 8.42 | 32.18 | 1.12 | 2.28 | 12.014 | ND |
| Peripheral Volume | 413.8 | 56.3 | 47.82 | 249.95 | 17.41 | 50.22 | 21.655 | ND |
| Peripheral Clearance 2 | ND | ND | 0.13 | ND | 3.95 | ND | ND | ND |
| Peripheral Volume 2 | ND | ND | 0.11 | ND | 6.07 | ND | ND | ND |

ND—not determined.

Figure 2B:
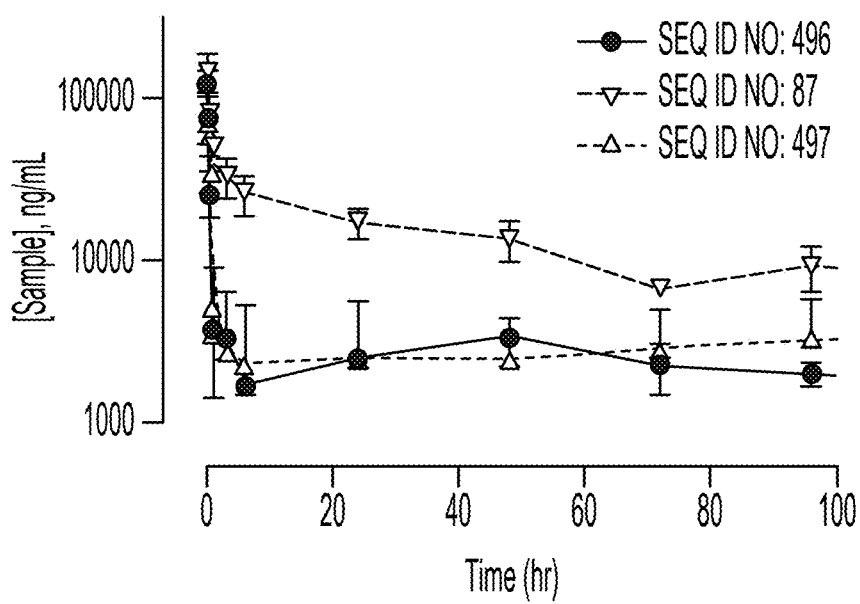

FIG. 2B shows a separate experiment with PK values determined using the same methods described for FIG. 2A, for a subset of relaxin-2 fusion protein analog (SEQ ID NO: 87, SEQ ID NO: 496, and SEQ ID NO: 497) samples described herein.

Figure 2C:
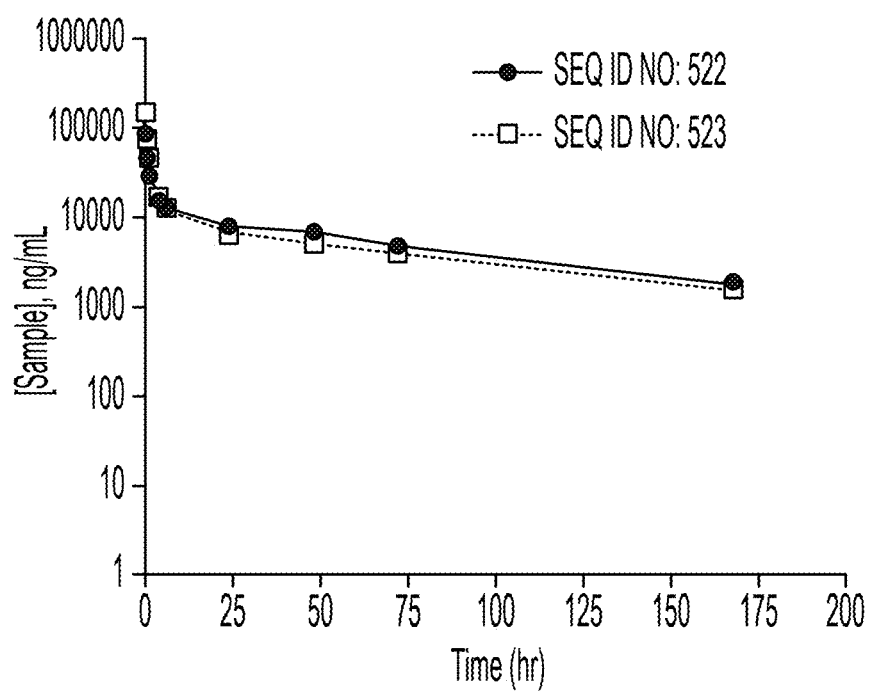

FIG. 2C shows a separate experiment with PK values determined using the same methods described for FIG. 2A, for a subset of relaxin-2 fusion protein analog (SEQ ID NO: 522 and SEQ ID NO: 523) samples described herein.

Naïve male Sprague-Dawley rats (weight range: 0.308-0.399 kg) were anesthetized via 5% isoflurane driven by 100% oxygen in an induction chamber. Once consciousness was lost, animals were removed from the chamber and an endotracheal tube was inserted for mechanical positive-pressure ventilation. The ventilator was connected to a vaporizer that delivered approximately 1-2% isoflurane driven by 100% oxygen for the duration of the experiment. Anesthetic depth was assessed prior to surgery and approximately every 15 minutes during the experimental procedure. Animals were maintained at approximately 37±0.5° C. on a heating pad, and body temperature was monitored throughout the protocol with a rectal temperature probe.

A Millar pressure catheter was placed in the right carotid artery to measure systolic arterial pressure (SAP), diastolic arterial pressure (DAP) and heart rate (HR). Mean arterial pressure (MAP) was calculated. A small incision was made along the linea alba to access the abdominal cavity. The left renal artery was dissected and a doppler flow probe was placed around the artery. Renal artery blood flow (RABF) was continuously monitored throughout the experimental period, and renal vascular resistance (RVR=MAP/RABF) was calculated.

Following an approximately 10-15-minute equilibration period, baseline (BL) measurements were collected for 15 minutes. Individual animals were deemed acceptable for use in the study based on health status, body weight, hemodynamic parameters and renal blood flow. Following BL measurements, rats received a bolus intravenous (IV) administration (Dose 1) of either vehicle (10 mM histidine, 50 mM NaCl, 6.5% trehalose in deionized water pH 6.0) or a relaxin-2 fusion protein analog (test compound). Immediately following the bolus IV dose, rats in each group received a maintenance dose via IV infusion (Dose 2) of the respective test compound over a 180-minute dosing period.

Blood samples were collected prior to Dose 1 (before the end of BL) and at 5 minutes, 1 hour, 2 hours and 3 hours after the start of Dose 2. Samples were obtained from a jugular vein cannula into a K2EDTA tube. Tubes were stored on wet ice until centrifugation in a refrigerated centrifuge. The resultant plasma was frozen on dry ice and stored at −80° C. At the conclusion of the study, rats were euthanized by exsanguination.

Mean values taken from 15-minute blocks during BL and from the 180-minute dose period were used for analysis. Values from each individual animal were pooled to determine an average for each variable for each group (if applicable). Average percent change from baseline values were determined for each variable. The term "dosing period" will describe the period during bolus and maintenance dose infusion (180 minutes) and will be used for the remainder of this report.

In one experiment, the effect on renal blood flow in rats of relaxin-2 fusion protein analogs SEQ ID NO: 313 and SEQ ID NO: 87 were compared to prior fusion protein SEQ ID NO: 496. Table 29 below shows the potency of relaxin-2 fusion protein analogs in recombinant human and rat RXFP1 assays (as described in Example 4).

TABLE 29

Fusion Protein Analogs in Human and Rat RXFP1 Potency Assays

| | HEK293 cells expressed RXFP1 cAMP assay (EC50 (nM) ± SD (n)) | |
|---|---|---|
| | Human RXFP1 | Rat RXFP1 |
| Wild-type human relaxin-2 | 0.04 ± 0.01 (4) | 0.11 ± 0.06 (4) |
| SEQ ID NO: 496 | 0.2 ± 0.2 (3) | 1.2 ± 0.2 (3) |
| SEQ ID NO: 313 | 10 ± 4 (4) | 17 ± 5 (4) |
| SEQ ID NO: 87 | 7 ± 4 (4) | 10 ± 3 (4) |
| SEQ ID NO: 90 | 0.9 ± 0.5 (2) | 3 (1) |

Figure 3:
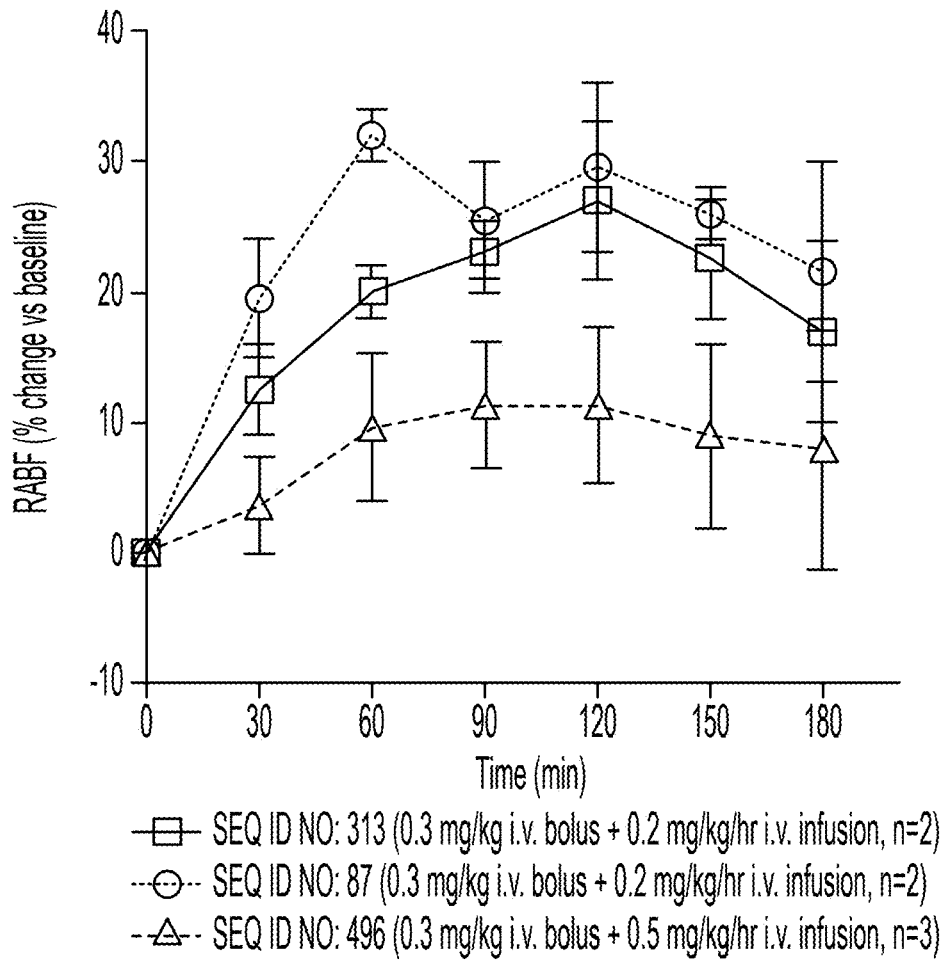
FIG. 3 is a graph depicting the change in renal arterial blood flow (RABF) compared to baseline, over time, in rats administered the various relaxin-2 fusion protein analogs as indicated.

As shown in FIG. 3, administration of SEQ ID NO: 313 and SEQ ID NO: 87 at a bolus intravenous dose of 0.3 mg/kg and intravenous infusion of 0.2 mg/kg/hr caused a greater increase in rat RABF than administration of prior fusion protein SEQ ID NO: 496 at a bolus intravenous dose of 0.3 mg/kg and intravenous infusion of 0.5 mg/kg/hr. As such, despite the reduced in vitro potency observed for SEQ ID NO: 313 and SEQ ID NO: 87, these fusion proteins demonstrate greater increase in rat RABF.

Additional experiments were performed to further evaluate the effect of fusion protein analog SEQ ID NO: 87 and SEQ ID NO: 497 on renal blood flow. In these experiments, the average potency of relaxin-2 fusion protein analogs in recombinant human and rat RXFP1 assays are shown in Table 30, below.

TABLE 30

Fusion Protein Analogs in Human and Rat RXFP1 Potency Assays

| | EC50 for cAMP generation in recombinant RXFP1 assay (nM) | |
|---|---|---|
| | Human RXFP1 | Rat RXFP1 |
| Wild-type human relaxin-2 | 0.04 | 0.1 |
| SEQ ID NO: 496 | 0.2 | 1 |
| SEQ ID NO: 87 | 10 | 35 |
| SEQ ID NO: 497 | 0.3 | 1 |

SEQ ID NO: 87 was infused by cannulated femoral vein using a syringe pump. The dose was infused intravenously (1 ml/kg) as a bolus followed by continuous infusion of PBS at the rate of 0.5 mL/kh/hr to maintain the circulating fluid volume.

Figure 4A:
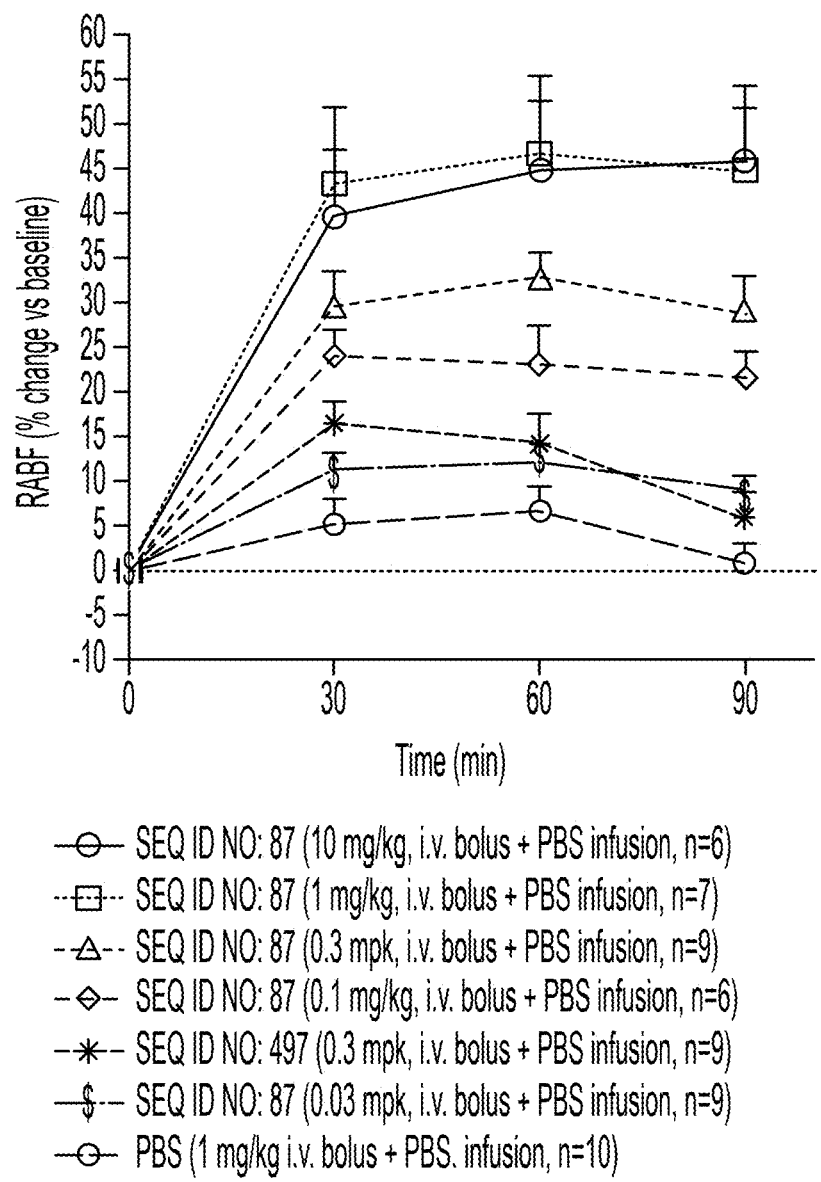
FIGS. 4A and 4B are graphs depicting the changes to RABF (FIG. 4A) and serum levels of fusion protein (FIG. 4B; using human Fc levels as a proxy) in response to dose of SEQ ID NO: 87 or SEQ ID NO: 497 as indicated, over time.
Figure 4B:
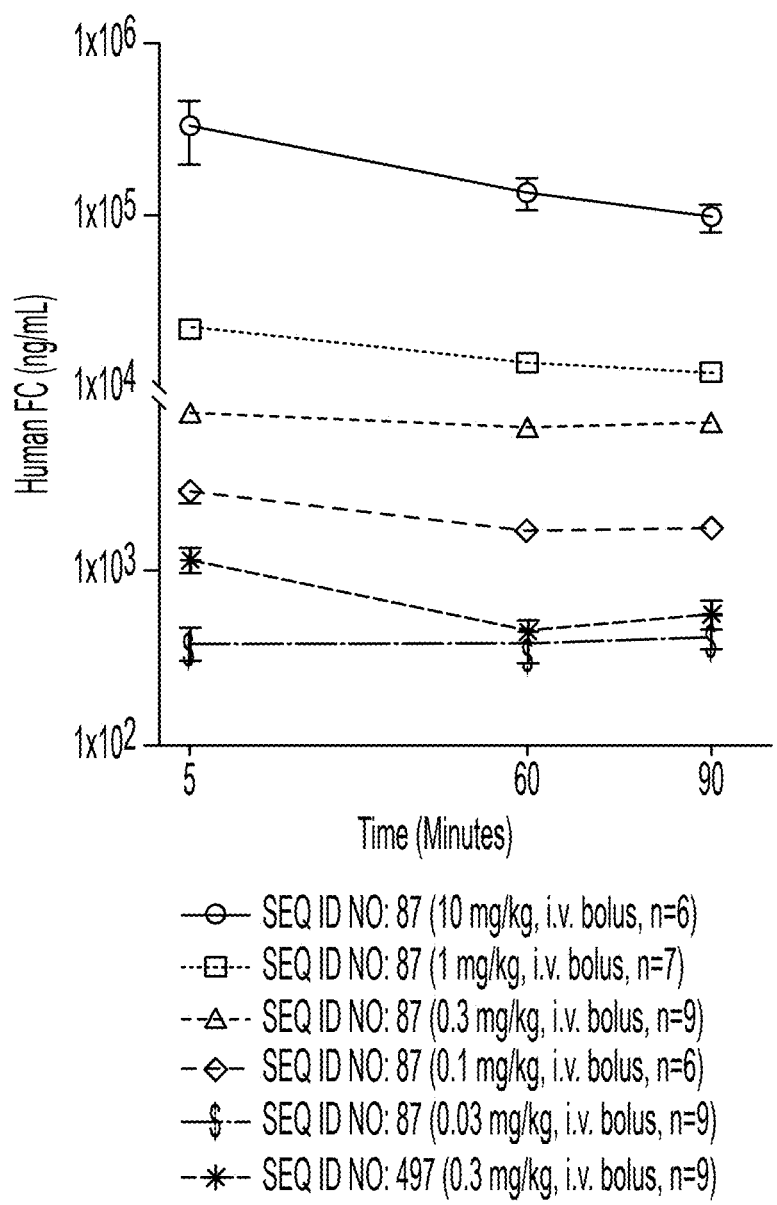

As shown in FIG. 4B, the measured serum concentration (using human Fc levels as proxy) for 0.3 mg/kg SEQ ID NO: 497 was ~10 fold lower than that of 0.3 mg/kg SEQ ID NO: 87. Given the fact that the in vitro potency of SEQ ID NO: 497 in the rat RXFP1 signaling assay was found to be more than 30-fold higher than the in vitro potency of SEQ ID NO: 87 (see, Table 30), one would expect that the two molecules would give at least comparable increases in RABF when administered at the same dose. Instead, the efficacy of SEQ ID NO: 497 was comparable to a dose of SEQ ID NO: 87 that was 10-fold lower (0.03 mg/kg) (FIG. 4A), implying that the efficacy of SEQ ID NO: 87 was more than 10-fold higher than expected based on PK and in vitro potency data. The plasma concentration for 0.03 mg/kg SEQ ID NO: 87 was nearly identical to that for 0.3 mg/kg SEQ ID NO: 497.

Figure 4C:
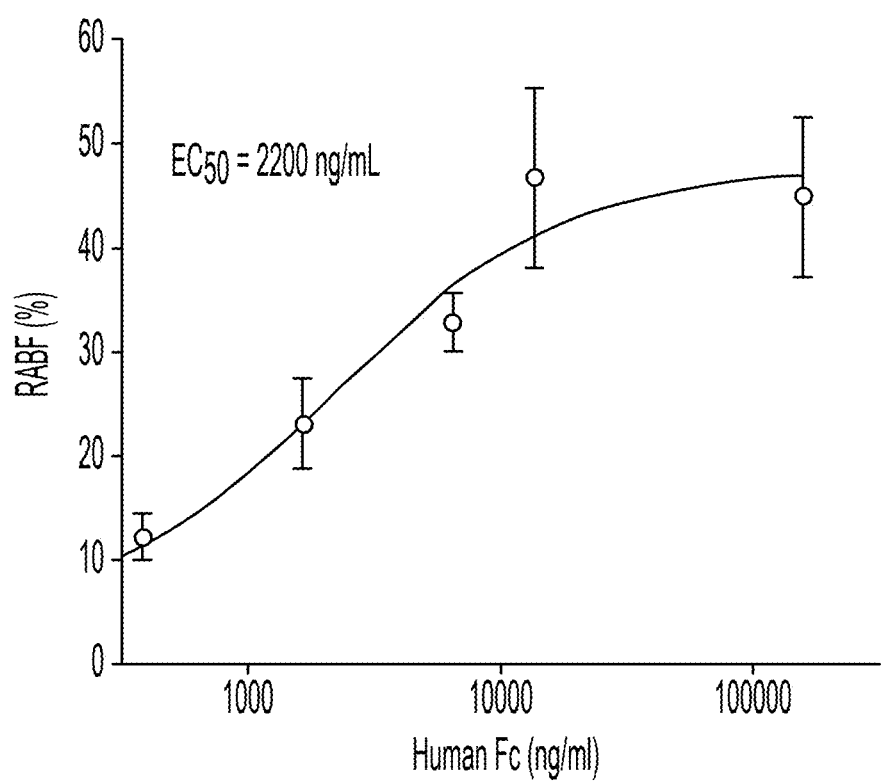
FIG. 4C is a graph depicting serum PK as a function of increase in RABF (baseline subtracted).

The PBS data in FIG. 4A show that there is a small effect on renal blood flow from the volume expansion from the intravenous bolus that returned to baseline by 90 minutes. Using the 90-minute timepoint to fit the dose response for SEQ ID NO: 87 from 0.03 mg/kg to 10 mg/kg, the EC50 for SEQ ID NO: 87 in the rat in vivo was estimated to be ~2200 ng/mL (FIG. 4C) which corresponds to about 34 nM, consistent with the average EC50 for SEQ ID NO: 87 signaling as shown in Table 30.

Figure 5A:
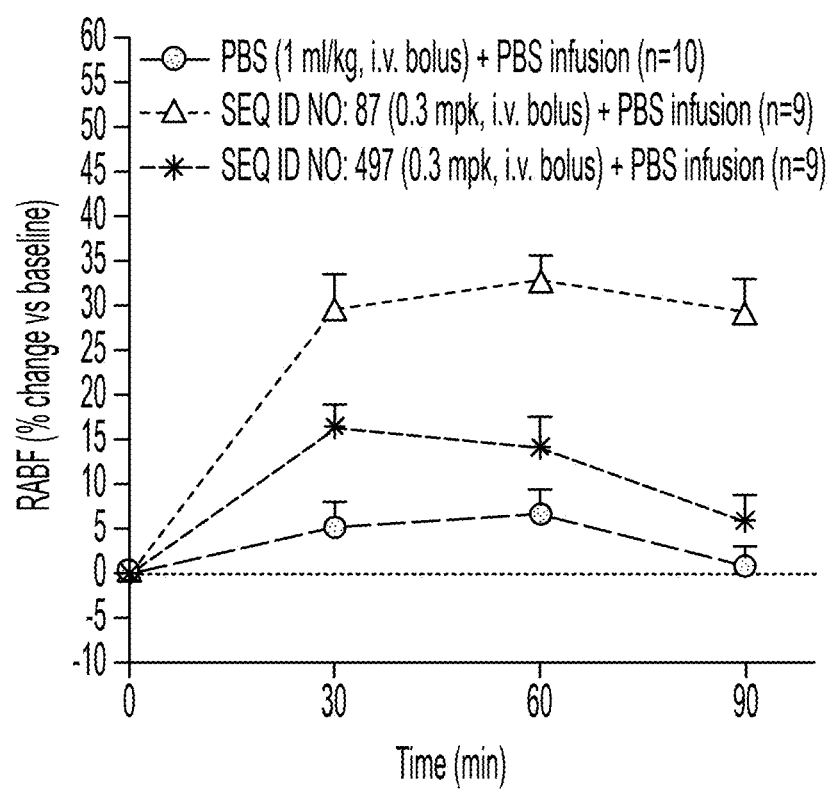
FIGS. 5A and 5B are graphs depicting that a low dose of SEQ ID NO: 87 increases and maintains RABF in treated rats significantly more than SEQ ID NO: 497.
Figure 5B:
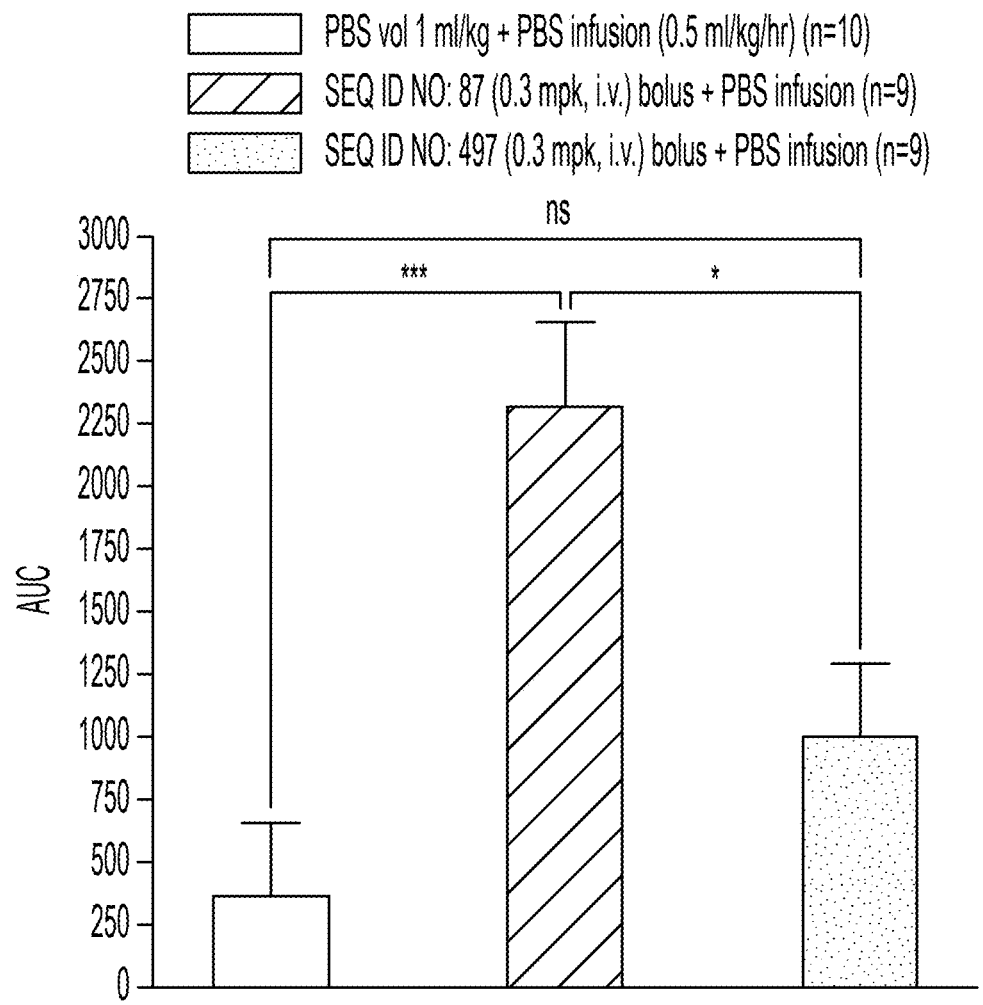

Additionally, as shown in FIGS. 5A and 5B, a low dose of SEQ ID NO: 87 increased and maintained RABF more than SEQ ID NO: 497. At 0.3 mg/kg, infusion of SEQ ID NO: 87 resulted in increased RABF by approximately 25% over baseline, which was maintained over the 90-minute experimental time course. At 0.3 mg/kg, infusion of SEQ ID NO: 497 resulted in increased RABF by approximately 15% over baseline, and RABF levels dropped close to baseline within 90 minutes post-infusion (FIG. 5A). Quantification of the area under the curve (AUC) showed that infusion of SEQ ID NO: 87 significantly increased RABF about 2-fold more than infusion of SEQ ID NO: 497 (FIG. 5B).

Without being bound by any theory, it is hypothesized that the enhanced effect of SEQ ID NO: 87 is due to an increase in distribution of SEQ ID NO: 87 to target tissues well above levels expected from plasma levels because of reduced heparin binding, as well as decreased non-specific cellular uptake, blood clearance and potentially higher bioavailability of SEQ ID NO: 87 compared to the more highly charged SEQ ID NO: 497 molecule.

Example 7. Therapeutic Effect of a Relaxin-2 Fusion Protein Analog in a Rat Pulmonary Arterial Hypertension Model Pulmonary arterial hypertension (PAH) is characterized by a progressive pulmonary vascular remodeling of the distal precapillary arteries that causes a significant increase of the right ventricle (RV) load, ultimately leading to right heart failure and premature death. Using monocrotaline (MCT) rat model as an in vivo PAH model, rats reproducibly develop pulmonary hypertension with a mean pulmonary pressure of ~40 mmHg approximately 4 weeks after single MCT administration. MCT is an 11-membered macrocyclic pyrrolizidine alkaloid derived from the seeds of the *Crotalaria spectabilis* plant. The MCT alkaloid is activated to the reactive pyrrole metabolite dehydromonocrotaline (MCTP) in the liver, a reaction that is highly dependent on cytochrome P-450 (CYP3A4). When administered, MCT induces a syndrome characterized, among other manifestations, by pulmonary hypertension (PH), pulmonary mononuclear vasculitis, and right-ventricular hypertrophy through injury to pulmonary endothelial cells. The therapeutic potential of the SEQ ID NO: 87 relaxin-2 fusion protein analog was evaluated in a rat model of MCT-induced PAH.

On Study Day 1, naïve young (200-240 g) male Sprague Dawley rats in groups 1-5 received a 60 mg/kg dose (1 mL/kg s.c. in 100% DMSO) of MCT. Rats in Group 1 and 4 received anti-mouse CD20 antibody (20 mg/kg, i.p.) on days 8, 9, 10, and 17. Rats in Group 1 and 2 received SEQ ID NO: 87 (10 mg/kg, i.v.) on days 7, 10, 14, 17, 21 and 24. Beginning on study day 8, rats in Group 5 were dosed orally twice daily with sildenafil (positive control, 30 mg/kg, p.o., BID) with the last dose administered on study day 28. Rats in Group 6 were administered DMSO as control. 12 rats were tested in each of Groups 1 to 4, and 10 rats were tested in each of Group 5 and 6.

Cage side observations were done once daily for general health and appearance, mortality and signs of pain or distress. Body weights were recorded pre-dose on study day 0, and weekly throughout the study and on the day of the terminal procedure. On Study Day 28, animals were anesthetized with urethane (1.25 g/kg, i.p.). Blood samples were collected from the Retro-Orbital plexus for PK and biomarker analysis (e.g., N-terminal (NT)-pro hormone BNP (NT-proBNP)). Serum NT pro-BNP was analyzed using Rat NT-proBNP Assay Kit-Meso Scale Discovery, MD, USA (catalog no. K153JKD). Rats were ventilated using RoVent® Jr. Small Animal Ventilator from Kent Scientific Corporation. The mean right ventricular pressure and mean pulmonary artery pressure were measured via a 1.6 French solid-state catheter purchased from Transonic Inc. using an open chest approach. Data were recorded and analyzed using SP200 Pressure System and LabChart software (ADI instruments). The animals were then humanely euthanized via exsanguination while under deep anesthesia. At necropsy, the heart and lungs were collected from each animal for weighing. After weighing, both the right ventricle and lung samples, were fixed in formalin and then stored at room temperature. The brain was also collected and weighed to normalize with the rat body weight. Immunohistochemistry analysis was performed on the formalin fixed lungs and ventricles.

An assay was developed to quantify the presence of SEQ ID NO: 87 in mouse serum samples, coming from both serum and plasma. The assay utilizes a quantitative sandwich enzyme immunoassay, with an affinity-purified polyclonal antibody specific for Human Fc coated to a 96-well plate. Samples containing molecules with Human Fc were added to wells, incubated, and washed before the addition of an enzyme-linked polyclonal antibody specific for Human Fc. After incubation with the enzyme-linked antibody, wells were washed, and the enzyme-substrate was added and allowed to develop before quenching with acid. After quenching with an acid plate, read the plate at 450 and 570 nm within 30 minutes of color change. Values from each animal were pooled to determine an average of each variable for each group (if applicable). The mean right ventricular pressure (mRVP) and mean pulmonary artery pressure (mPAP) were recorded, and Right Ventricular Systolic Pressure (RVSP) was analyzed.

SEQ ID NO: 87 was administered in the MCT-induced PAH model at 10 mg/kg, i.v. twice weekly for 3 weeks with therapeutic dosing initiated one week after MCT injection. To mitigate efficacy reducing anti-drug antibody (ADA) generation to the test article, the study was performed with and without B-cell depletion by injecting anti-mouse CD20 antibody to rats. Cardiac hemodynamics including right ventricular systolic pressure (RVSP) and mean pulmonary arterial pressure (mPAP) were measured using an open chest approach. The Fulton Index, the ratio of right ventricular weight to the weight of the left ventricle and septum, was measured at week 4. Blood samples for serum NT pro-BNP, PK and ADA analysis were collected.

Figure 6A:
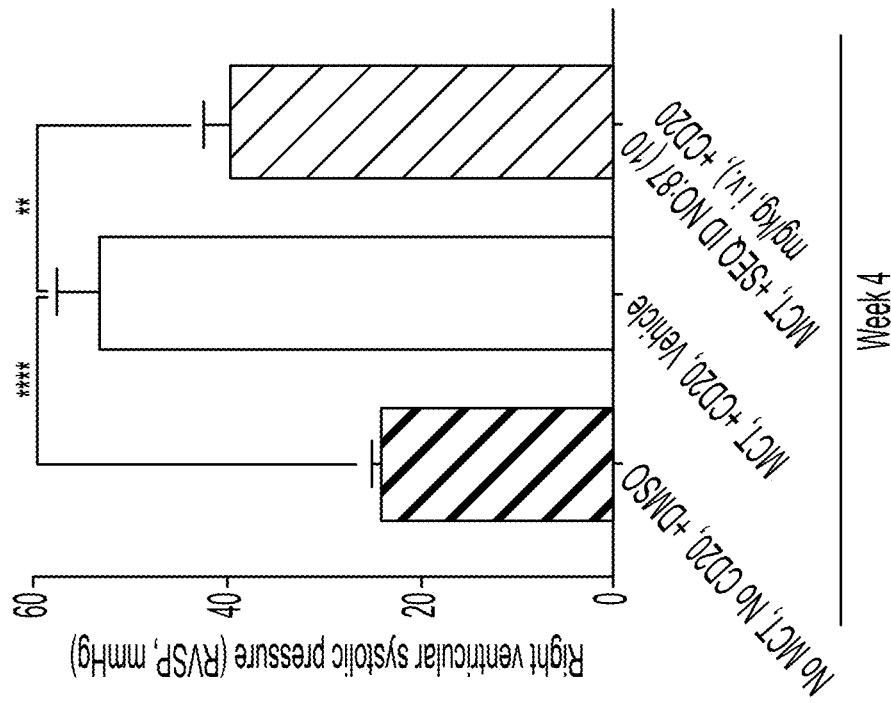
FIGS. 6A and 6B are graphs depicting the effect of SEQ ID NO: 87 on right ventricular systolic pressure (RVSP) following 10 mg/kg intravenous treatment of SEQ ID NO: 87 for three weeks in MCT-induced rats (MCT), with (FIG. 6A) or without (FIG. 6B) B cell depletion using an anti-CD20 antibody (no CD20 or +CD20). Sildenafil was used as a positive control in the non-B cell depleted animals.
Figure 6B:
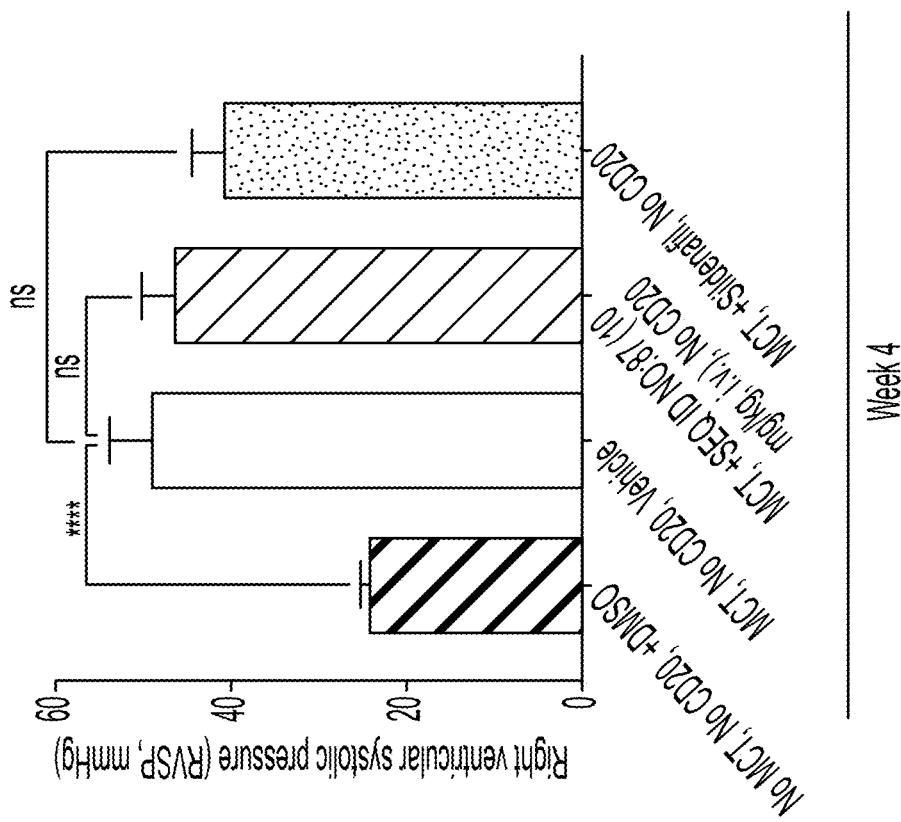
Figure 7A:
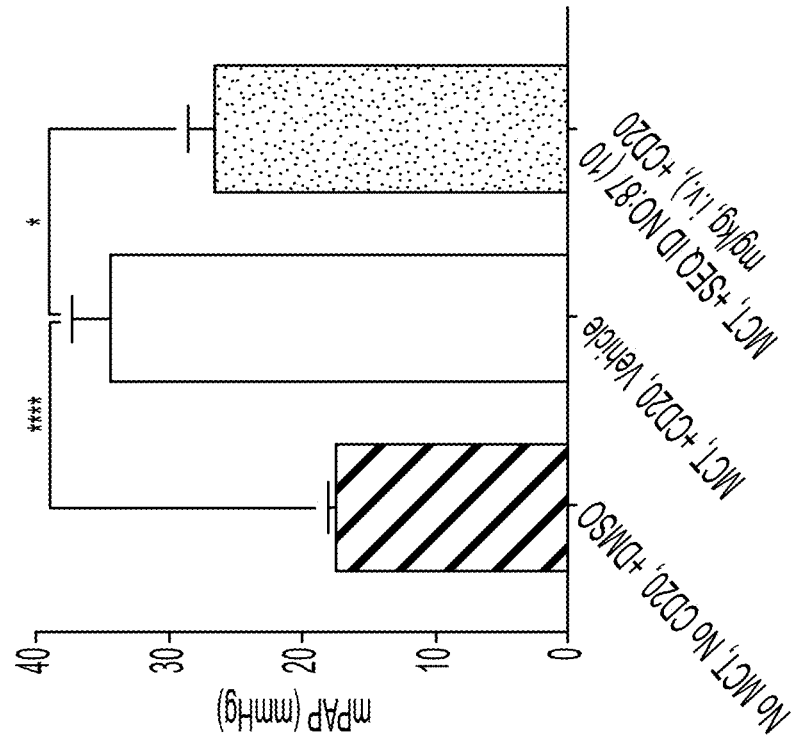
FIGS. 7A and 7B are graphs depicting the effect of SEQ ID NO: 87 on mean pulmonary arterial pressure (mPAP) following 10 mg/kg intravenous treatment of SEQ ID NO: 87 for three weeks in MCT-induced rats (MCT), with (FIG. 7A) or without (FIG. 7B) B cell depletion using an anti-CD20 antibody (no CD20 or +CD20). Sildenafil was used as a positive control in the non-B cell depleted animals.
Figure 7B:
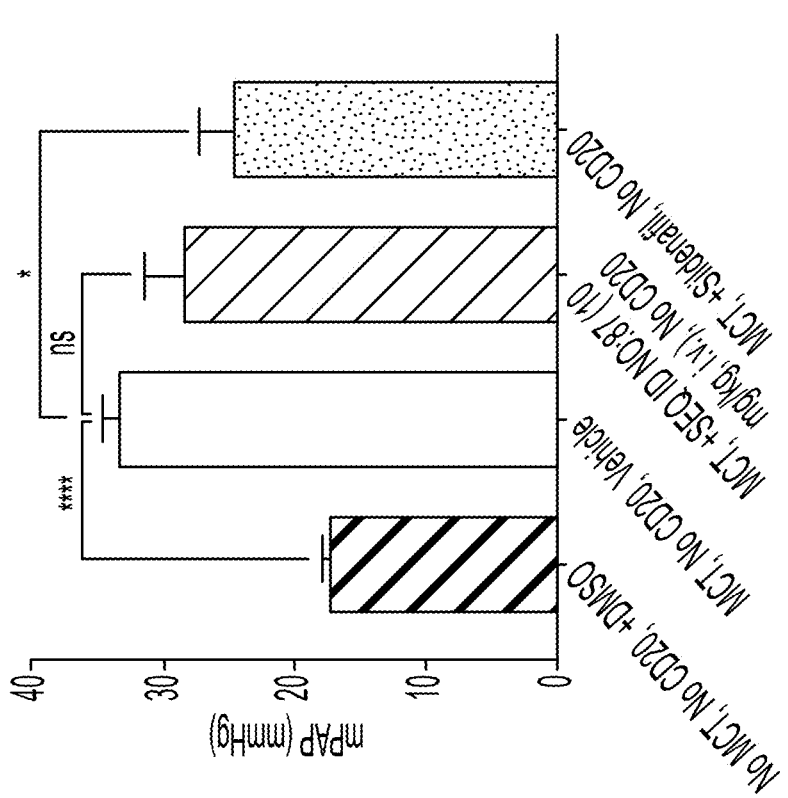
Figure 8B:
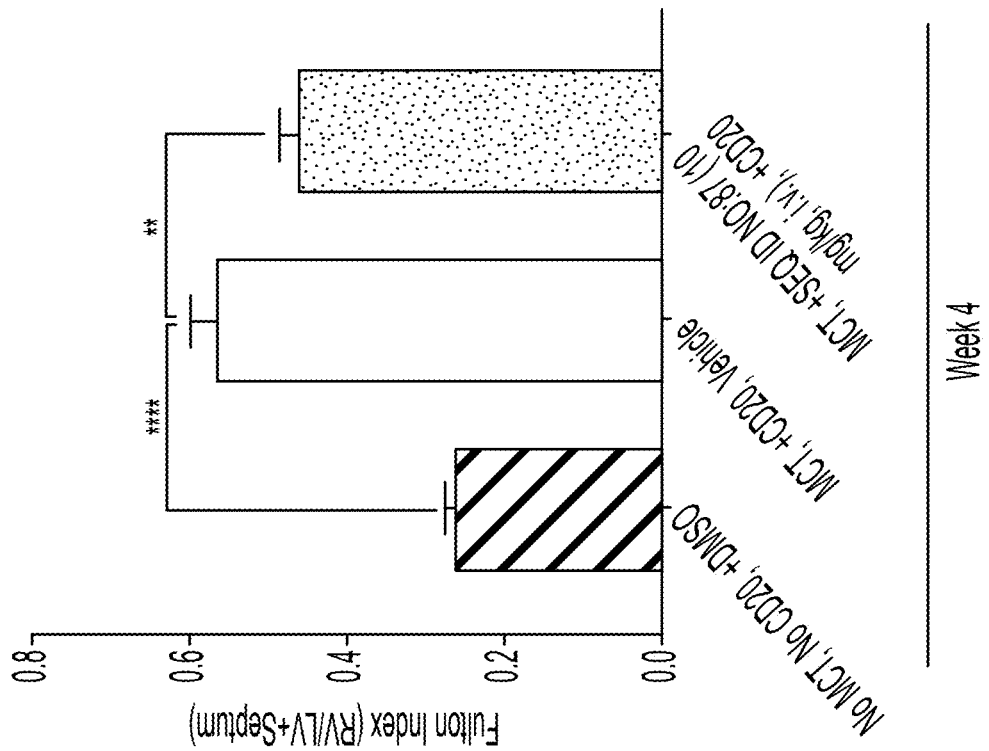
FIGS. 8A and 8B are graphs depicting the effect of SEQ ID NO: 87 on the Fulton Index following 10 mg/kg intravenous treatment of SEQ ID NO: 87 for three weeks in MCT-induced rats (MCT), with (FIG. 8A) or without (FIG. 8B) B cell depletion using an anti-CD20 antibody (no CD20 or +CD20). Sildenafil was used as a positive control in the non-B cell depleted animals.
Figure 8A:
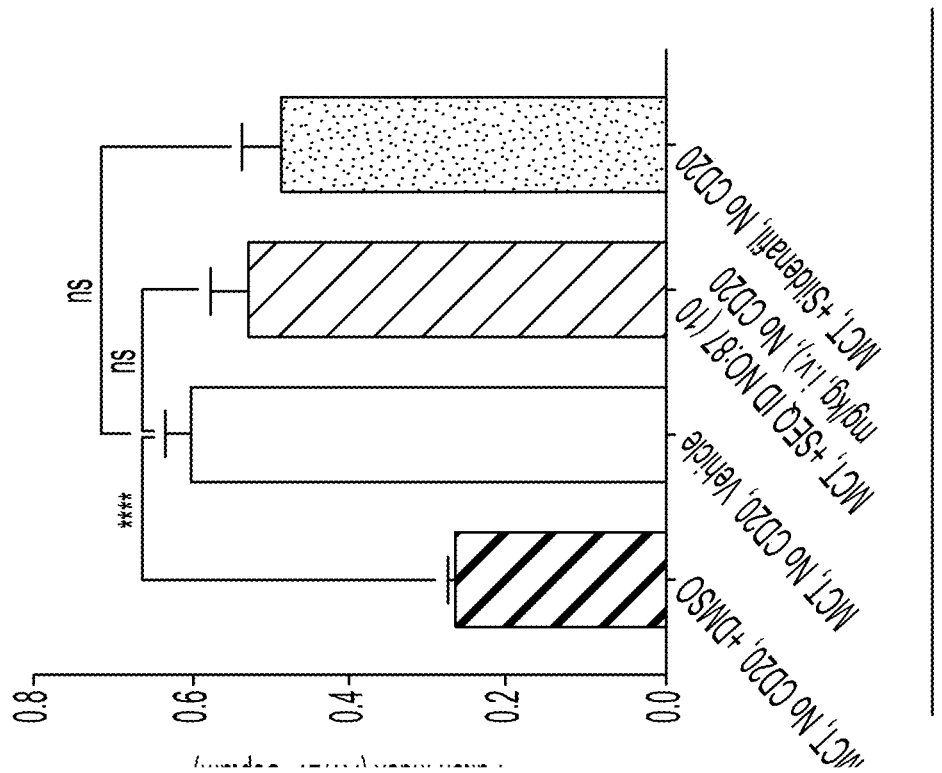
Figure 9A:
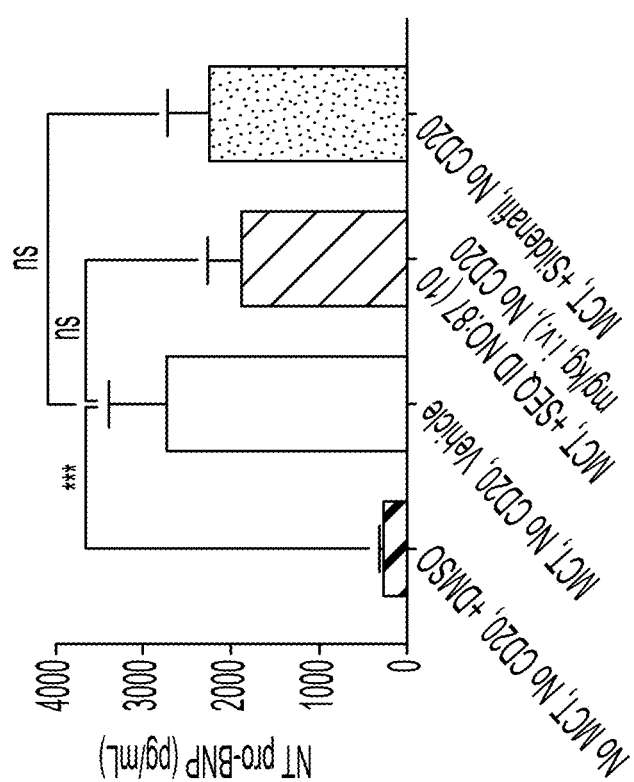
FIGS. 9A and 9B are graphs depicting the effect of SEQ ID NO: 87 on serum NT-pro-BNP levels following 10 mg/kg intravenous treatment of SEQ ID NO: 87 for three weeks in MCT-induced rats (MCT), with (FIG. 9A) or without (FIG. 9B) B cell depletion using an anti-CD20 antibody (no CD20 or +CD20). Sildenafil was used as a positive control in the non-B cell depleted animals.
Figure 9B:
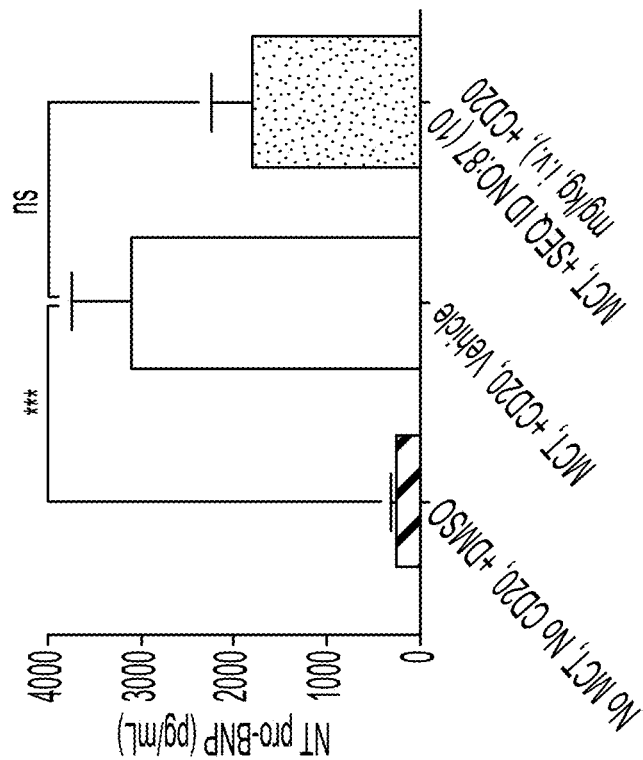

MCT treatment of rats significantly increased RVSP (FIGS. 6A and 6B), mPAP (FIGS. 7A and 7B), Fulton Index value (FIGS. 8A and 8B), and NT-pro-BNP (FIGS. 9A and 9B) while decreasing survival compared to the naïve group (no MCT) over a 4-week period. As shown, rats treated with SEQ ID NO: 87 demonstrated significant improvements in RVSP (FIG. 6B), mPAP (FIG. 7B), and Fulton Index value (FIG. 8B) in rats where B cells were depleted. In addition, there was a clear survival benefit following treatment with SEQ ID NO: 87, with treated rats being the only group showing 100% survival.

Figure 10A:
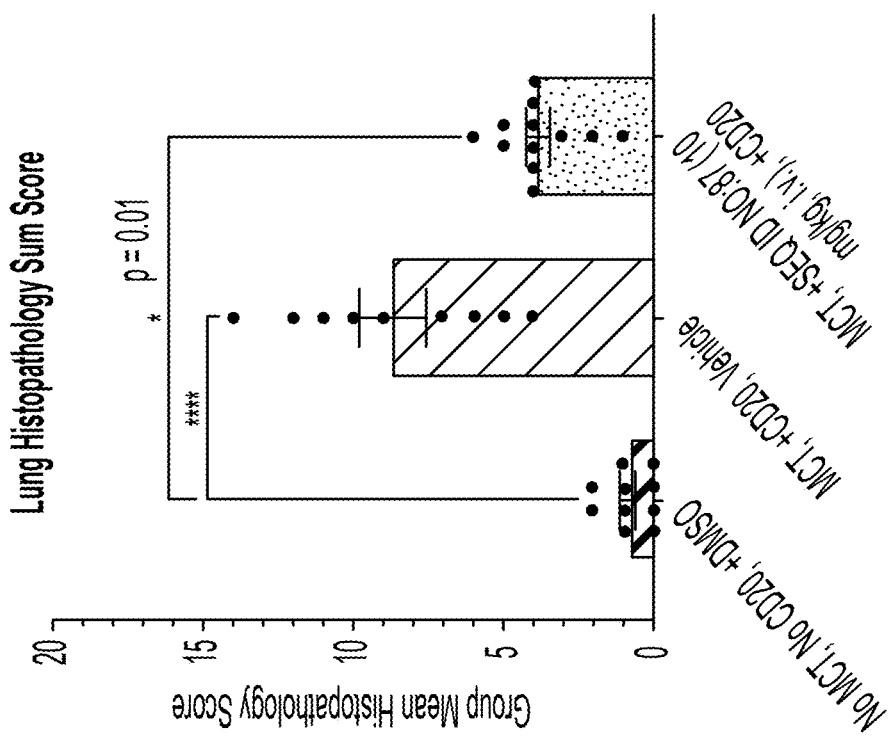
FIGS. 10A and 10B are graphs depicting the results of histopathological analysis of the effect of SEQ ID NO: 87 on lung inflammation (FIG. 10A) and pulmonary arterial muscularization (FIG. 10B) following 10 mg/kg intravenous treatment of SEQ ID NO: 87 for three weeks in MCT-induced rats (MCT), with B cell depletion using an anti-CD20 antibody (+anti-CD20). *: $p<0.05$; : $p<0.01$; **: $p<0.0001$ using a nonparametric 1-way analysis of variance with post hoc Dunn's multiple comparisons tests.
Figure 10B:
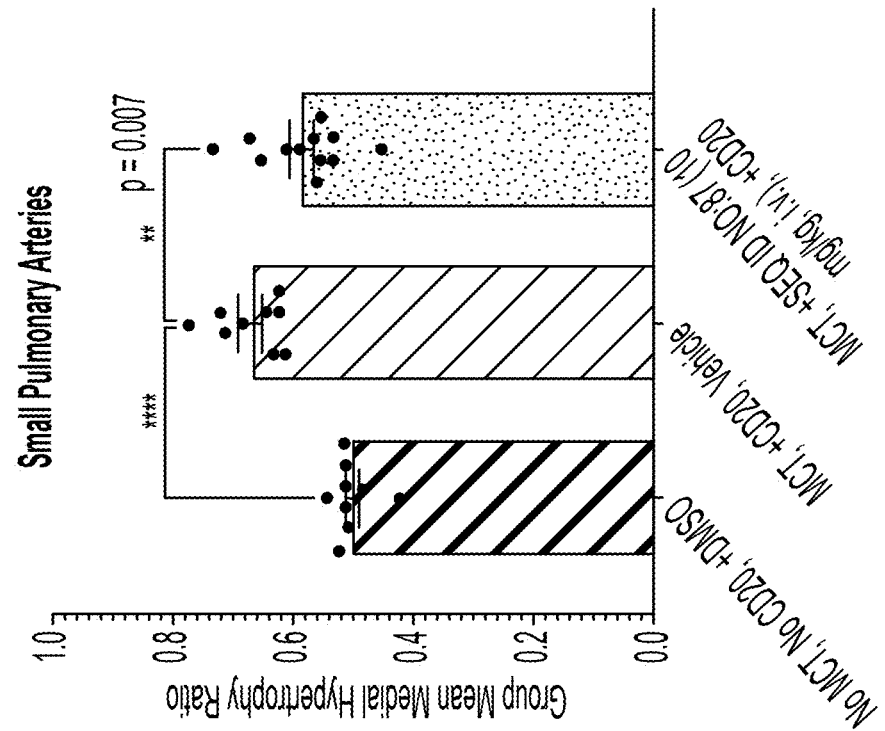

In addition, histopathology analysis revealed that SEQ ID NO: 87 significantly improved lung inflammation and reduced pulmonary arterial muscularization (FIGS. 10A and 10B, respectively). To assess lung inflammation, histopathology analysis was performed on tissues stained using hematoxylin and eosin. The lung histopathology sum score was calculated as the sum scores of parameters analyzed, including pulmonary arterial hypertrophy, vasculitis/necrosis, alveolar histiocytosis, perivascular and interstitial inflammation, hemorrhage, and fibrin deposition. Significant improvement was observed in the overall lung histopathology sum score as well as in the degree of vasculitis/necrosis, hemorrhage, and fibrin deposition in the lung tissues of rats, compared to rats that received vehicle control. To assess pulmonary arterial muscularization, histopathology analysis was performed using tissues stained with an anti-alpha smooth muscle actin (SMA) antibody to quantify muscularization, and Verhoeff stain to stain internal elastic laminae of arterioles. Thickening of the arterial wall, primarily by smooth muscle hypertrophy, was seen at all levels of the pulmonary arterial tree in animals exposed to MCT. This was associated with an increased arterial medial hypertrophy ratio across five vessel sizes quantified. Medial thickening relative to external diameter was best developed in the smallest caliber arteries and arterioles with less dramatic medial hypertrophy seen in the intermediate and larger caliber arteries. Lungs from rats treated with SEQ ID NO: 87 had lower arteriolar, small, and intermediate artery medial hypertrophy ratios than untreated animals. For small caliber arteries, rats treated with SEQ ID NO: 87 had significantly lower ratios than untreated animals.

Figure 11:
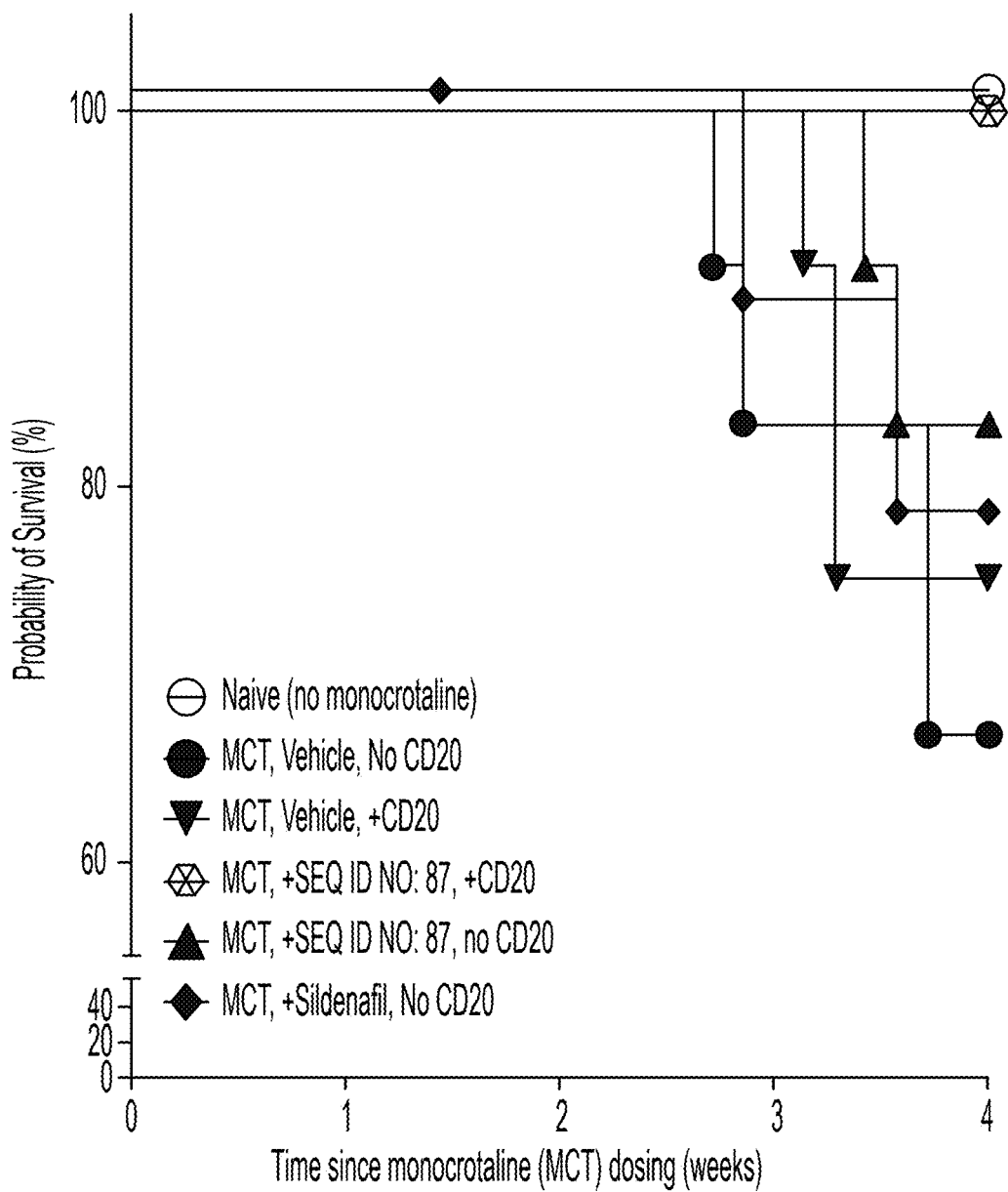
FIG. 11 is a graph depicting the effect of SEQ ID NO: 87 on mortality following 10 mg/kg intravenous treatment of SEQ ID NO: 87 for three weeks in MCT-induced rats (MCT), with or without B cell depletion using an anti-CD20 antibody (no CD20 or +CD20). Sildenafil was used as a positive control in the non-B cell depleted animals.

No mortality was observed in B cell depleted rats treated with SEQ ID NO: 87 compared to the vehicle and sildenafil treated groups (FIG. 11).

Example 8. Anti-Fibrotic Effect of Relaxin-2 Fusion Protein Analogs in a Mouse Model of Kidney Fibrosis This Example describes evaluation of the anti-fibrotic effect of relaxin-2 fusion protein analogs SEQ ID NO: 496, SEQ ID NO: 313, and SEQ ID NO: 87 in a mouse unilateral ureteral obstruction (UUO) model of kidney fibrosis. The UUO model induces renal fibrosis, where the primary feature of UUO is tubular injury because of obstructed urine flow. Furthermore, experimental UUO in rodents is believed to mimic human chronic obstructive nephropathy in an accelerated manner. Renal fibrosis is the common pathway for most forms of progressive renal disease. Because removal of the obstruction is generally not sufficient to reverse fibrosis, model animals may benefit from an accompanying treatment. UUO is a model widely used to study obstructive nephropathy.

An initial study evaluated the effect of SEQ ID NO: 496 and SEQ ID NO: 313. Sixty-five male C57BL/6 mice were used for the study (8-10 weeks of age at initiation). UUO was induced on Day 0 by ligation of a ureter of the left kidney, while the contra-lateral kidney served as a control. The UUO surgery was performed according to a standard procedure under deep anesthesia. Briefly, the kidney and ureter were exposed through midline abdominal incision after removal of hair from abdominal area. The left ureter was completely obstructed with two ligations. The first suture was placed 1 mm below the kidney and the other suture was placed 1 mm below the renal pelvis with silk or prolene suture. The wound was closed with 2 to 3 staples. The animal was returned to its cage and monitored until it started to move. On the day of surgical procedure and for 72 hours post-surgery, animals were provided with pain medication Buprenorphine. A control group (n=5) underwent sham surgery). UUO mouse groups were treated with 10 mg/kg SEQ ID NO: 496 (n=10), 20 mg/kg SEQ ID NO: 496 (n=10), 10 mg/kg SEQ ID NO: 313 (n=10), or 20 mg/kg SEQ ID NO: 313 (n=10). The treatment groups received intravenous injections 2 days before surgery (Day −2) and on Day 2 and Day 5 post-surgery. A positive control group (n=10) received enalapril, an ACE inhibitor medication used to treat high blood pressure, diabetic kidney disease, and heart failure, which was provided through drinking water at 200 mg/L beginning on Day −2 and continued through study termination. A negative control group (n=10) was treated with vehicle (PBS). The study was terminated on Day 7 post-surgery, and fibrosis symptoms as well as in-life parameters were assessed.

No adverse clinical symptoms were developed in any of the animals post-UUO surgery. The animals tolerated treatment with SEQ ID NO: 496, SEQ ID NO: 313, and enalapril well, and 100% survival was recorded. On Day 7 post-surgery, left kidneys were harvested, weighed, and fixed for histology.

All groups with surgically induced UUO showed reduced body weight relative to the sham surgery group. At Day 4 post-surgery, body weights began to trend toward recovery for all UUO groups. Additionally, all UUO groups showed a significant increase in kidney weight relative to the sham surgery group, and there was no statistically significant change in kidney weight across the treatment or control UUO groups.

Figure 12:
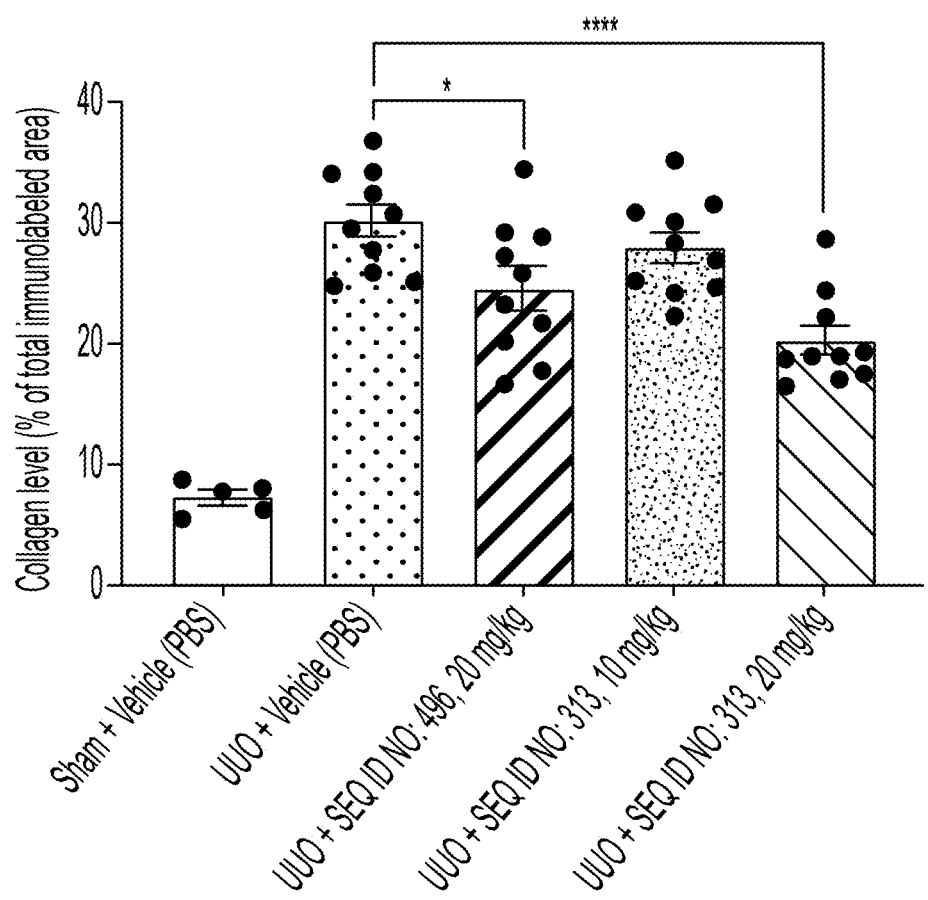
FIG. 12 is a graph depicting the effect of SEQ ID NO: 496 and SEQ ID NO: 313 on collagen deposition in renal parenchyma in a mouse unilateral ureteral obstruction (UUO) model, according to aspects of the present disclosure. Mice underwent UUO surgery and were treated with vehicle (PBS; n=10), 20 mg/kg SEQ ID NO: 496 (n=10), 10 mg/kg SEQ ID NO: 313 (n=10), or 20 mg/kg SEQ ID NO: 313 (n=10). Also shown are control mice that underwent a sham surgery and were treated with vehicle (PBS; n=5). Following treatment, obstructed kidneys were harvested and fixed for histology. Collagen was detected via immunolabeling. Depicted is a quantification of collagen levels as a percentage of total immunolabeled area. *: $p<0.05$; ****: $p<0.0001$.

Histological analysis of kidney sections fixed on Day 7 post-surgery showed a significant increase in collagen deposition in renal parenchyma in all UUO groups relative to the sham surgery group (FIG. 12). Animals treated with SEQ ID NO: 496 and SEQ ID NO: 313 at 20 mg/kg showed significantly reduced collagen deposition relative to the vehicle-treated control group.

Figure 13:
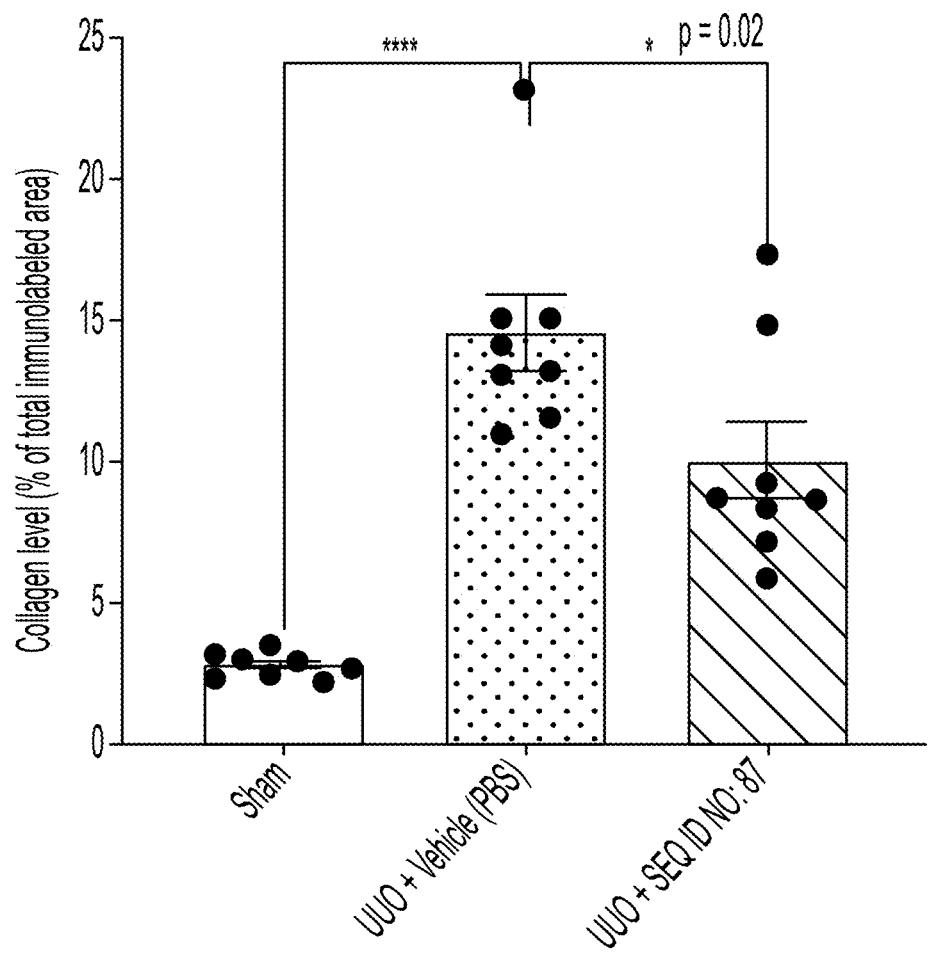
FIG. 13 is a graph depicting the effect of SEQ ID NO: 87 on collagen deposition in kidney cortex in a mouse UUO model, according to aspects of the present disclosure. Mice underwent UUO surgery and were treated with vehicle (PBS; n=8) or 10 mg/kg SEQ ID NO: 87 (n=8). Also shown are control mice that underwent a sham surgery and were treated with vehicle (PBS; n=8). Following treatment, obstructed kidneys were harvested and fixed for histology. Collagen was detected via immunolabeling. Depicted is a quantification of collagen levels as a percentage of total immunolabeled area. ****: $p<0.0001$; *: $p=0.02$.
Figure 14:
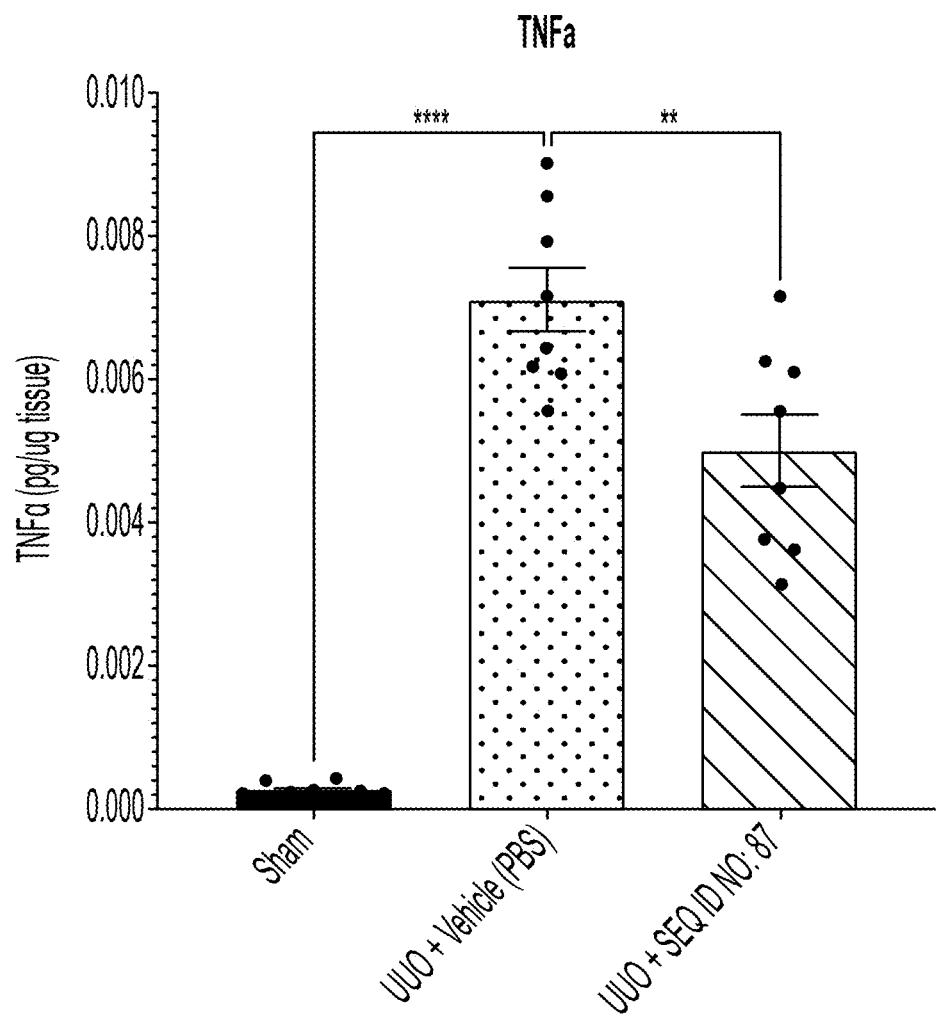
FIG. 14 is a graph depicting the effect of SEQ ID NO: 87 on TNFα levels in kidney cortex in a mouse UUO model, according to aspects of the present disclosure. Mice treated as described for FIG. 13, and TNFα levels were quantified in protein lysates via electrochemiluminescence assay. **: $p<0.0001$; *: $p<0.001$.

The anti-fibrotic effect of SEQ ID NO: 87 was observed following a similar procedure. Mice treated with SEQ ID NO: 87 showed a significant decrease in collagen deposition following UUO induction relative to vehicle-treated mice (FIG. 13). Tissue TNFα levels were evaluated via electrochemiluminescence, and mice treated with SEQ ID NO: 87 also showed a significant decrease in TNFα levels relative to vehicle-treated mice (FIG. 14). Reduction of IL-13 and IL-6 in fibrotic kidney was also observed in the SEQ ID NO: 87-treated mice relative to vehicle treated mice.

Example 9. Effect of Relaxin-2 Fusion Protein Analogs on Isoproterenol-Induced Cardiac Hypertrophy and Fibrosis This Example describes evaluation of the effect of relaxin-2 fusion protein analog SEQ ID NO: 87 on cardiac hypertrophy and fibrosis following isoproterenol challenge. Isoproterenol is a drug that increases heart rate and heart muscle contractions and can lead to cardiac hypertrophy and increased fibrosis.

All animals were treated and cared for in accordance with the Guide for the Care and Use of Laboratory Animals (National Institutes of Health, revised 2011), and protocols were approved by an Institutional Animal Care and Use Committee. Male C57BL/6J mice were obtained at 10-11 weeks of age with body weight ranging between 25 grams and 30 grams. The animals were housed in the vivarium on a conventional 12 hr light/dark cycle. After equilibration housing for 1 week, micro-osmotic minipump implantation was performed on mice. Briefly, mice were anesthetized using 1% to 3% isoflurane given by inhalation through a vaporizer. Osmotic minipumps with a flow rate of 0.25 μl/h were surgically implanted subcutaneously into the subscapular space of mice. Each pump delivered a constant dose (0.25 μl/h) of infused drug (isoproterenol in PBS containing 0.002% ascorbic acid at 15 mg/kg per day) or vehicle (PBS with 0.002% ascorbic acid) for 2 weeks. Postoperative analgesia was achieved with a single dose of meloxicam SR (2.5 mg/kg) during minipump implantation and another single dose of meloxicam SR (2.5 mg/kg) one day after the surgery. Mice were treated with either vehicle or 10 mg/kg of SEQ ID NO: 87 one day before minipump implantation. Mice were then dosed with relaxin-2 fusion protein analog SEQ ID NO: 87 bi-weekly for the duration of the study (total of 14 days). To reduce anti-drug activity, mice were injected intraperitoneally with 20 mg/kg of anti-mouse CD20 to deplete all B cells one day post minipump implantation.

Figure 15:
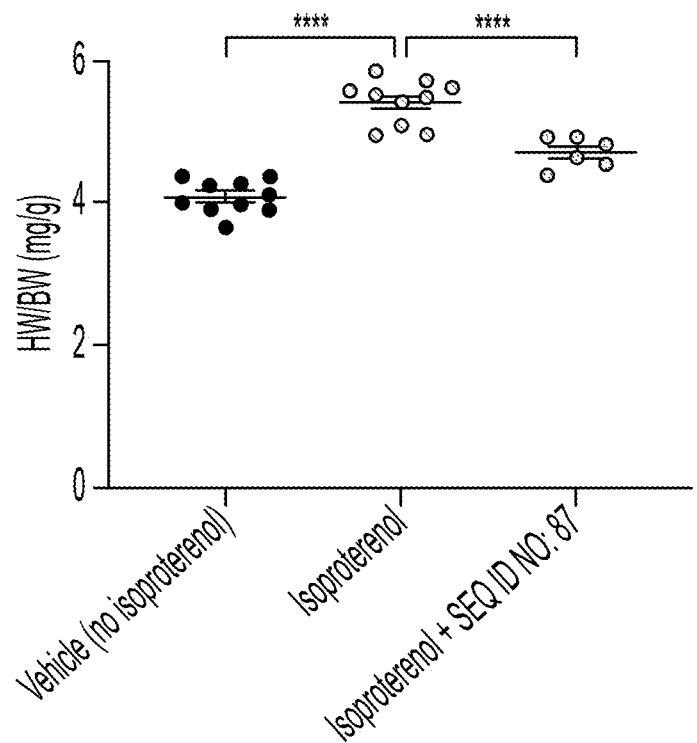
FIG. 15 is a graph depicting the effect of SEQ ID NO: 87 on isoproterenol-induced cardiac hypertrophy, according to aspects of the present disclosure. Mice were treated with vehicle (n=10), isoproterenol (n=10), or isoproterenol and SEQ ID NO: 87 (n=6). Following treatment, body weight and heart rate was measured for each mouse. Depicted is heart weight normalized by body weight (HW/BW) for each group. ****: $p<0.0001$.

After 14 days of incubation, animals were euthanized via $CO_2$ inhalation followed by cervical dislocation. The body weights were measured. Whole hearts were explanted, washed in PBS, dried with paper towel, and weighed. The fresh heart tissues were immediately snap frozen in liquid nitrogen and stored for further collagen content analysis. Tibia was obtained by blunt limb dissection and tibia length was measurement using a digital caliper. Heart weights (HW) were normalized by body weight (BW) and by tibial length (TL). Data (HW/TL, and HW/BW) were analyzed using standard software. As shown in FIG. 15, isoproterenol administration caused a significant increase in cardiac hypertrophy, as measured via normalized heart weight (HW/BW), relative to vehicle treated mice. Coadministration of SEQ ID NO: 87 with isoproterenol significantly attenuated the isoproterenol-induced cardiac hypertrophy.

Figure 16:
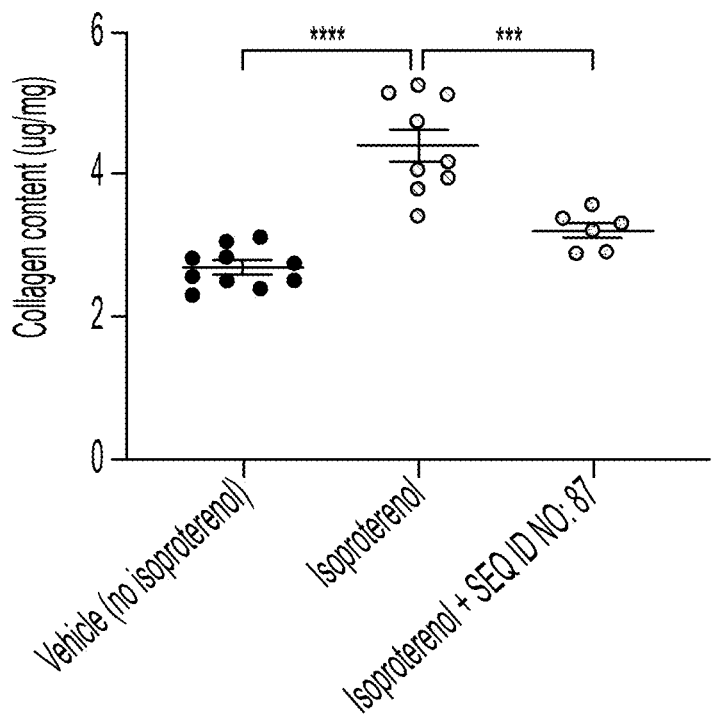
FIG. 16 is a graph depicting the effect of SEQ ID NO: 87 on isoproterenol-induced fibrosis, according to aspects of the present disclosure. Mice were treated as described for FIG. 15, and collagen content was quantified using a hydroxyproline assay. **: $p<0.0001$; *: $p<0.001$.

Collagen content in each heart ventricle was measured via a hydroxyproline assay kit. The snap frozen whole heart ventricle tissues were weighed, chopped, and transferred into screw-capped tubes. Tissue was hydrolysed at 100 mg/ml in 6M HCl and incubated for 20 hrs at 95° C. in a calibrated oven or thermoblock. The hydrolyzed samples were then diluted with 4M HCl before assay analysis. To perform the assay analysis, 35 µl hydrolysate or hydroxyproline standard were mixed with 75 µl assay buffer in each well of a 96-well plate. The plate was incubated 20 minutes at room temperature while shaking. After, 75 µl of detection reagent was added to each well, the plate was mixed well and incubated 60 minutes at 60° C. in an oven or incubator. The plate was cooled down to room temperature, read at 570 nm, and hydroxyproline concentrations of each sample were determined by the standard curve. Data were analyzed using standard software. As shown in FIG. 16, isoproterenol administration caused a significant increase in fibrosis, as measured via collagen content, relative to vehicle treated mice. Coadministration of SEQ ID NO: 87 with isoproterenol significantly attenuated the isoproterenol-induced fibrosis.

Example 10. Evaluating Safety, Tolerability, Pharmacokinetics, and Pharmacodynamics of a Relaxin-2 Fusion Protein Analog This Example describes a double-blind, randomized, placebo-controlled, single ascending dose study being performed to assess the safety, tolerability, pharmacokinetics, pharmacodynamics, and immunogenicity of SEQ ID NO: 87 in healthy subjects.

Study Design

Approximately 48 participants are enrolled in the study. A single ascending dose of SEQ ID NO: 87 or matching placebo (i.e., identical buffer without addition of SEQ ID NO: 87) was administered to study participants via intravenous infusion (IV) or subcutaneous (SC) injection in the doses described below. In each cohort, 6 participants receive SEQ ID NO: 87 and 2 participants receive placebo. Infusions were between 30 and 60 minutes in duration. Cohort A receives 0.3 mg/kg IV of SEQ ID NO: 87 or matching placebo. Cohort B receives 1 mg/kg IV of SEQ ID NO: 87 or matching placebo. Cohort C receives 300 mg SC of SEQ ID NO: 87 or matching placebo. In some cases, Cohort C is dosed concurrently with Cohort B. Cohort D receives 3 mg/kg IV of SEQ ID NO: 87 or matching placebo. Cohort E receives 600 mg SC of SEQ ID NO: 87 or matching placebo. In some cases, Cohort E is dosed concurrently with Cohort D. Cohort F receives 10 mg/kg IV of SEQ ID NO: 87 or matching placebo.

A master randomization schedule and code break envelopes was created, and delivered to the site's unblinded pharmacy before dosing. The active and placebo products are infused through a line that is covered to conceal active from placebo. A printed randomization schedule is generated using a permuted blocked fixed method. The people receiving the treatment(s), the people administering the treatment(s), and the people analyzing the results and data are blinded.

Primary Outcome

The primary outcome of the study is to evaluate the safety and tolerability of SEQ ID NO: 87 after single ascending doses. The primary outcome is assessed by monitoring: 1) the incidence of adverse events (AEs) and serious adverse events (SAEs); 2) changes in clinical laboratory safety parameters including blood test results for hematology, serum chemistry, and coagulation studies; 3) changes in vital signs measurements; and 4) changes in electrocardiogram (ECG) findings. Adverse events are assessed by clinical examination, review of patient data and self-reporting. Adverse events are collected via verbal interview by clinic staff during the study period either in person during confinement or clinic visits or via telephone during remote contacts. Vital signs measurements includes resting heart rate and systolic and diastolic blood pressure (BP) using standard manual or electronic clinical procedures. These procedures are completed using standard nursing practices or, in the case of ECG, the instructions provided by the manufacturer. These individual data are utilized to determine safety by physician assessment. Additionally, the totality of the data presented are also factored into the determination of safety.

Adverse events and serious adverse events are assessed at Screening, Day –1, Day 1, Day 2, Day 3, Day 6, Day 8, Day 15, Day 29, Day 43, and Day 57 post dose administration. Laboratory safety parameters are assessed at Screening, Day –1, Day 1, Day 2, Day 8, Day 15, Day 29, Day 43, and Day 57 post dose administration. Vital signs are assessed at Screening, Day –1, Day 1, Day 2, Day 3, Day 6, Day 8, Day 15, Day 29, Day 43, and Day 57 post dose administration. ECG is performed at Screening, Day –1, Day 1, and Day 2 post dose administration.

Secondary Outcomes

A secondary outcome of the study is to characterize the pharmacokinetic (PK) profile of SEQ ID NO: 87 in healthy participants after single ascending doses of SEQ ID NO: 87. Standard PK parameters are assessed: $C_{max}$, $T_{max}$, AUC-last (AUC from 0 to the last measurable concentration), AUC-inf (AUC from 0 to infinity), $t_{1/2}$, CL (clearance), and Vz (terminal phase volume of distribution). Blood sampling for PK parameter assessment occurs at Predose, End of infusion, 6 hrs, and 12 hrs post dose on Day 1, 24 hrs post dose on Day 2, 48 hours post dose on Day 3, 120 hours post dose on Day 6, 168 hours post dose on Day 8, Day 15, Day 29, Day 43 and Day 57 post dose.

Another secondary outcome of the study is to evaluate the pharmacodynamic (PD) effect of single ascending doses of SEQ ID NO: 87 in healthy participants. The change from baseline to day 2 is assessed in the following PD parameters: renal plasma flow (RPF), as measured by change in plasma para-aminohippurate (PAH) over time; renal blood flow (RBF); and filtration fraction (FF), as calculated by glomerular filtration rate (GFR) divided by RPF. Blood sampling for RPF/GFR assessment occurs on Days 2, 8, and 15 for IV Cohorts A, B and D and on Days 15 and 29 for IV Cohort F. Blood sampling for RPF/GFR assessment occurs on Days 2, 15, and 29 for SC Cohorts C and E.

Subject Eligibility

Participants meet the following criteria to be enrolled in this study:
- is a male or a female of non-childbearing potential between the ages of 18 and 55 years;
- is judged to be in good health based upon medical history, physical examination, vital signs, ECGs, and routine laboratory tests;
- has a body mass index (BMI) between 18 and 32 kg per meter square at screening;
- understands the study procedures and agrees to participate in the study by giving written informed consent; and
- is at least 18 years of age and no more than 55 years of age.

Participants were excluded from the study if any of the following criteria apply:
- is mentally or legally incapacitated, has significant emotional problems at the time of the study, or has a history of significant psychiatric disorders at the discretion of the investigator;
- has any clinically significant physical examination abnormalities observed during the screening visit or would not be a good candidate for participation in the study in the opinion of the investigator;
- has clinically significant abnormal complete blood count, clinical chemistry, or urine analysis at screening or Day −1 (in asymptomatic participants, any abnormal laboratory results, including creatine phosphokinase within 3 times the upper limit of normal with suspected cause due to rigorous physical activities, may be repeated once during the screening period);
- was hospitalized for any reason within 30 days of the screening visit;
- has any history of clinically significant renal, neurologic, gastrointestinal, hepatic, or respiratory disease (note that subjects with fully resolved childhood asthma with no recurrence in adulthood may be enrolled);
- has a history of anaphylaxis or other significant allergy in the opinion of the investigator;
- has a history of clinically significant cardiovascular disease including arrhythmias, conduction abnormalities, or clinically significant abnormal vital signs;
- was previously administered relaxin or relaxin fusion proteins; or
- was dosed in any clinical research study evaluating another investigational drug (including biologics) or therapy (including specific immunotherapy) within 90 days or less than or equal to 5 half-lives (whichever is longer) of an investigational biologic drug, or less than or equal to 4 weeks for other investigational products, before the screening visit.

Partial Results

Figure 17A:
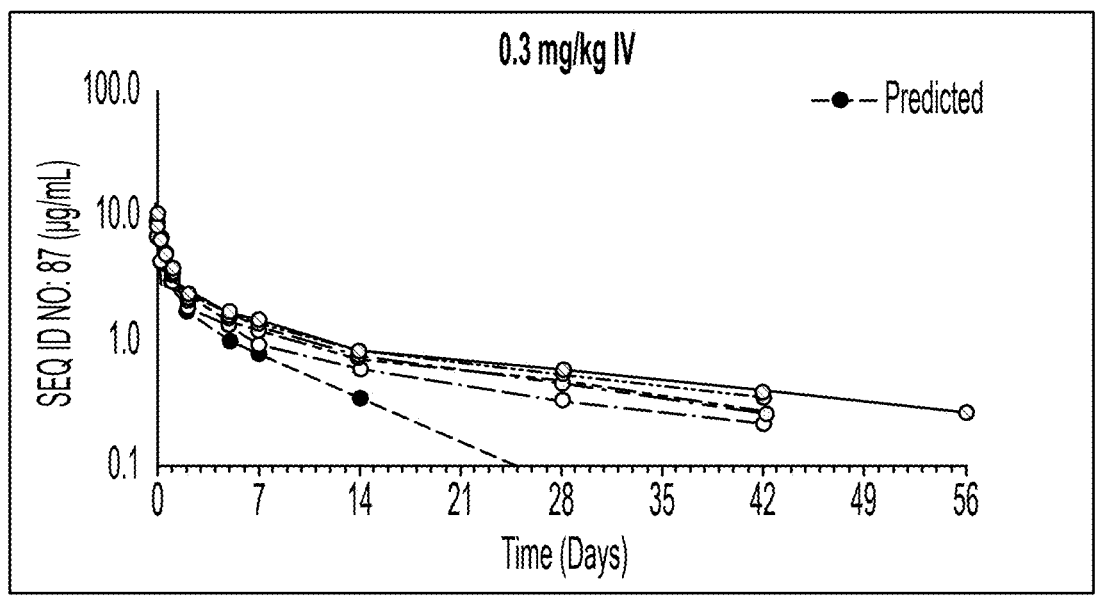
FIGS. 17A and 17B are graphs depicting PK (FIG. 17A) and PD (FIG. 17B) data of healthy human patients administered a single 0.3 mg/kg IV dose of SEQ ID NO: 87.
Figure 17B:
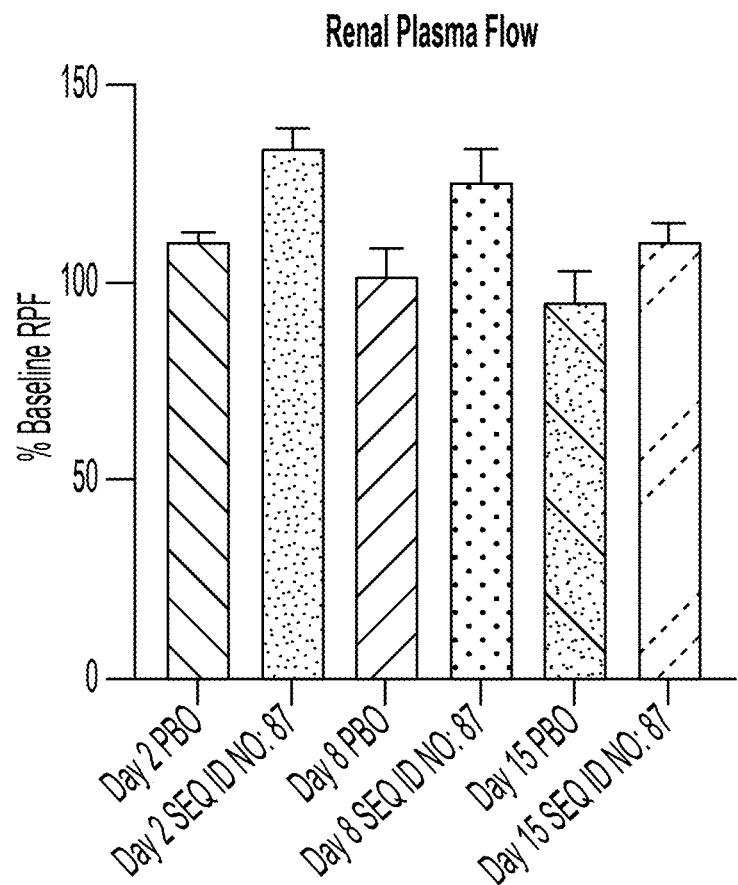

Preliminary PK and PD results were obtained from healthy human patients administered a single 0.3 mg/kg IV dose of SEQ ID NO: 87 (FIGS. 17A and 17B, respectively). As shown in FIG. 17A, SEQ ID NO: 87 demonstrated a desirable PK profile in four individual healthy patients after IV administration and a terminal half-life of 17 days, which is more than double the predicted terminal half-life of 6 days as obtained from simulations in non-human primate models (dashed line). The PD effect of SEQ ID NO: 87 in healthy human patients was investigated by assessing the change from baseline of renal plasma flow (RPF) at days 2, 8, and 15 (FIG. 17B). Briefly, patients were administered a bolus of para-aminohippurate (PAH) and plasma PAH was measured at days 2, 8, and 15. Effective RPF at each time point was calculated by using the formulas:

$$RPF(\text{ml/min}) = \frac{Cl_{PAH\,ml/min}}{\text{extraction ratio}},$$

$$Cl_{PAH\,ml/min} = \frac{\text{rate of } PAH \text{ infusion}}{\text{concentration}_{PAH\,mg/ml}},$$

As shown in FIG. 17B, a single 0.3 mg/kg IV dose of SEQ ID NO: 87 resulted in a substantial increase of at least about 30% in RPF on day 2 post dose compared to patients that received the placebo (PBO), and demonstrated persistence of effect for at least 8 days post dose.

Figure 18:
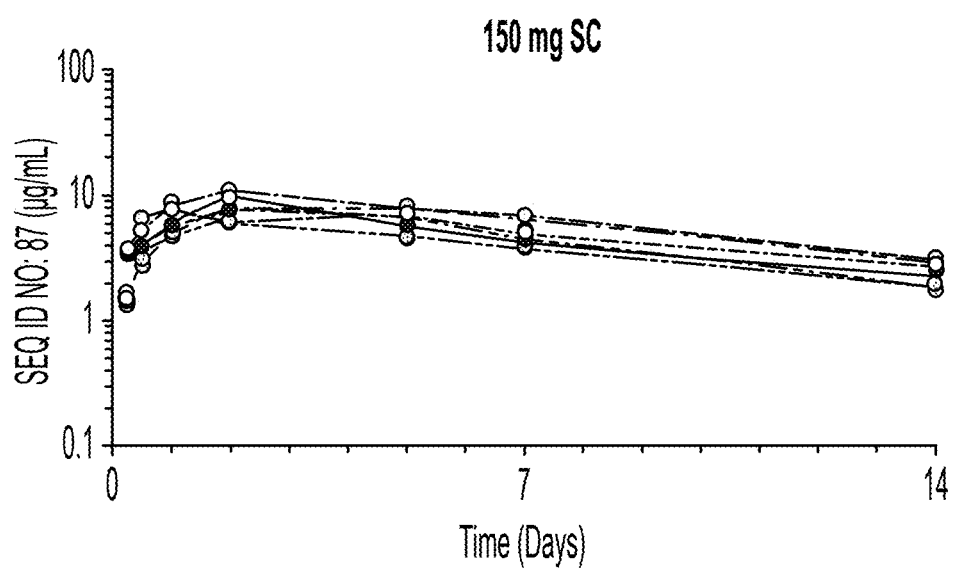
FIG. 18 is a graph depicting PK data of healthy human patients administered a single 150 mg SC dose of SEQ ID NO: 87, showing the concentration of SEQ ID NO: 87 over time in dosed patients.

SEQ ID NO: 87 also demonstrated a desirable PK profile in healthy human patients administered a single 150 mg SC dose (FIG. 18), with terminal half-life not yet determined. Based on the data, SC bioavailability was in the range of 50-60%.

The preliminary data from healthy patients administered SEQ ID NO: 87 by IV and SC, supports a Q4W dosing schedule. The PK data showed low intersubject variability (≤20%) in serum concentrations, and no evidence of immune-mediated drug clearance. SEQ ID NO: 87 was found to be safe and well tolerated with minimal adverse events, and no drug-related SAEs. Expected on target effects were observed (e.g., mild orthostatic tachycardia without BP effect in some subjects), and no infusion or injection site reactions were reported.

Example 11. Single-Dose, Open-Label Study to Evaluate the Safety, Tolerability, and Hemodynamic Effects of a Relaxin-2 Fusion Protein Analog This prophetic Example describes a single-dose, open-label study to evaluate the safety, tolerability, and hemodynamics of SEQ ID NO: 87 in subjects with combined postcapillary and precapillary pulmonary hypertension (CpcPH) or isolated postcapillary pulmonary hypertension (IpcPH) and heart failure with preserved ejection fraction (HFpEF).

Background and Rationale

SEQ ID NO: 87 is a relaxin peptide Fc-fusion biologic that is being developed for the treatment of combined precapillary and postcapillary pulmonary hypertension (CpcPH) and isolated postcapillary pulmonary hypertension (IpcPH). Relaxin is an insulin-like peptide, originally identified as a pregnancy-associated hormone, that has antifibrotic, anti-inflammatory, and vasodilatory properties in both men and women. It produces these effects by binding and activating its G-protein coupled receptor, relaxin family peptide receptor 1 (RXFP1), which then triggers a variety of signaling pathways including cAMP (cyclical adenosine monophosphate), cGMP (cyclical guanosine monophosphate), and MAPKs (mitogen activating protein kinases) as well as altering gene expression of transforming growth factor-beta (TGF-β), MMPs (matrix metalloproteinases), angiogenic growth factors, and endothelin-1 receptors.

Pulmonary hypertension (PH) is a condition that leads to dyspnea, reduced exercise capacity, and hypoxemia and has a high mortality risk. It is defined as a mean pulmonary arterial pressure (mPAP) >20 mm Hg. Because this condition occurs in many different clinical settings, the World Health Organization (WHO) has divided PH into 5 different groups. CpcPH is a subgroup of WHO Group 2 pulmonary hypertension (PH), pH due to left-sided heart disease (PH-LHD). LHD includes the following: heart failure with preserved ejection fraction (EF), defined as heart failure with EF >50% (HFpEF); heart failure with reduced EF, defined as heart failure with EF <40% (HFrEF); and heart failure due to left heart valvular disease (either mitral or aortic valvular disease).

The unique hemodynamics seen in Group 2 PH-LHD that differentiates it from other forms of PH is an elevated pulmonary arterial wedge pressure (PAWP) ≥15 mm Hg. The elevated wedge pressure reflects elevated left atrial pressure and is an indicator of abnormal left ventricular filling consistent with left heart disease. In group 2 PH, the elevation in mPAP may be due to primarily elevated post-capillary pressures due to elevations in PAWP. An additional subgroup of Group 2 PH has elevations in pre-capillary pressures, which are thought to be due to chronic elevations in mPAP leading to remodeling of the pulmonary arterial vasculature, similar to what is seen in pulmonary arterial hypertension (PAH; Group 1 PH). These 2 forms of PH-LHD are known as isolated post-capillary PH (IpcPH), and combined pre- and post-capillary PH (CpcPH).

CpcPH is defined hemodynamically by a pulmonary vascular resistance (PVR) ≥3 Wood units, mean pulmonary artery pressure (mPAP) ≥20 mm Hg, and pulmonary capillary wedge pressure (PCWP) ≥15 mm Hg. In previous clinical trials, native human relaxin (serelaxin) was shown to modulate the hemodynamics of patients with acute heart failure associated with PH (Ponikowski et al. (2014) Eur. Heart J. 35 (7):431-441). In one study, infusion of serelaxin for 20 hours resulted in a rapid and significant decline in mPAP, PVR, and PCWP. In a second trial, infusion of serelaxin for 24 hours in patients with stable heart failure and PH resulted in a sustained and significant increase in cardiac index (CI), and a sustained decrease in PCWP and systemic vascular resistance (SVR) [Group C in Dschietzig, et al. (2009) Ann. N Y Acad. Sci. 1160:387-392]. Clinical risk factors for CpcPH include obesity, hypertension, diabetes, and metabolic syndrome. Right ventricular (RV) dysfunction occurs more frequently in CpcPH than in IpcPH (Lteif, et al. (2021) J. Am. Heart Assoc. 10(11):e020633).

IpcPH is a subtype of Group 2 PH (PH-LHD) where the elevated pulmonary artery pressure is due to passive backflow of elevated pressure from the left atrium and is not associated with major changes in the morphology of the pulmonary arteries and arterioles. It is defined hemodynamically by a PVR <3 Wood units, mPAP ≥20 mm Hg, and PCWP ≥15 mm Hg. Both IpcPH and CpcPH lead to an increase in right ventricular afterload, and this can lead to right heart dysfunction and death (Thenappan (2019) Advances in Pulmonary Hypertension. 18:87-91).

Patients with CpcPH have a worse prognosis than those with IpcPH. The 5-year survival rate for patients with CpcPH is 23% (Ibe et al. (2021) PLoS One. 16(3): e0247987).

In this study, patients with CpcPH or IpcPH with HFpEF will be subjected to right heart catheterization (RHC) and will receive an intravenous (IV) dose of SEQ ID NO: 87. Hemodynamic measurements will be obtained for 8 hours after the dose of SEQ ID NO: 87 to determine the change in PVR and PCWP as well as other hemodynamic assessments over time.

Study Design

Up to 25 participants may be enrolled in the study, across up to 3 cohorts, including a low-dose cohort (cohort A) with at least 2 participants with CpcPH, a cohort at the expected therapeutic dose (cohort B) with at least 6 participants with CpcPH and at least 3 participants with IpcPH, and a high dose cohort (cohort C) with at least 9 participants, including at least 6 participants with CpcPH and at least 3 participants with IpcPH.

During the screening period, participants will undergo assessments to ensure that they are appropriate for participation in the study.

Participants will require a 3-day admission to the clinical unit and then continue to be followed through Day 43. On Day −1, participants will be admitted to the clinical unit and have baseline assessments performed, including an echocardiogram. On Day 1, participants will have a right heart catheter (RHC) placed and baseline hemodynamic measurements will be obtained before dosing with SEQ ID NO: 87. Participants will be administered a dose of SEQ ID NO: 87 via at least a 30-minute intravenous (IV) infusion, and hemodynamic measures, heart rate (HR), and blood pressure (BP) will be obtained over an 8-hour period beginning after the end of the infusion. After the last hemodynamic measure is obtained, the RHC will be removed, and the participant will remain overnight for observation. Participants may be discharged from the clinical unit on Day 2 once all assessments are completed. The participant will return to the clinical unit on Days 8, 15, and 29 postdose for additional follow-up. Participants will return to the clinical unit for an end of study visit on Day 43.

Treatment Plan

Each participant will receive a single open-label intravenous dose of SEQ ID NO: 87, based on a mg/kg body weight calculation (from Day −1), administered via at least a 30-minute infusion. SEQ ID NO: 87 will be administered with the participant in a semirecumbent position.

Up to 25 participants may be enrolled across up to 3 cohorts. Cohort A will enroll at least 2 participants with CpcPH at a proposed dose of 0.3 mg/kg SEQ ID NO: 87. Cohort B will enroll at least 6 participants with CpcPH and at least 3 participants with IpcPH at a dose of 1 mg/kg, and cohort C will enroll at least 6 participants with CpcPH and at least 3 participants with IpcPH at a dose of 3 mg/kg.

Because this is the initial clinical assessment of SEQ ID NO: 87 in patients with CpcPH or IpcPH, and the safety, PK, PD/efficacy, and immunogenicity profile of the compound are still being elucidated in healthy volunteers, this study is designed to have the flexibility to accommodate the inherent dynamic nature of Phase 1 clinical studies and the proposed doses may be adjusted. Participants will not receive a dose higher than 6 mg/kg.

Dosing of the first 2 participants in each cohort will be separated by at least 7 days. After the first 2 participants within a cohort are dosed, no stagger between dosing of participants within a cohort is required.

Study Entry Criteria

Patients who meet the following inclusion criteria will be enrolled in the study:

1. Is a male or a female of non-childbearing potential between the ages of 18 and 80 years. A female of non-childbearing potential is a woman who meets either of the following criteria:
   a. Is in a postmenopausal state defined as no menses for 12 months without an alternative medical cause and follicle-stimulating hormone (FSH) level consistent with postmenopause (≥40 mIU/mL);
   b. Has a documented hysterectomy, bilateral oophorectomy, or salpingectomy.
2. Has one of the following:
   a. Diagnosis of HFmrEF (heart failure with mid-range ejection fraction): defined as signs and symptoms of New York Heart Association (NYHA) class II-III heart failure and left ventricular ejection fraction (LVEF) 40% to 49%;

b. Diagnosis of HFpEF, defined as signs and symptoms of NYHA class II-III heart failure and LVEF ≥50% and at least ONE of the following: i. Heart Failure Association-Pre-test assessment, Echocardiography and natriuretic peptide score, Functional testing in cases of uncertainty, Final etiology (HFA-PEFF) score ≥5 points; ii. HFA-PEFF score 2-4 points AND abnormal diastolic stress testing or invasive hemodynamic measurements.
3. Has demonstrated CpcPH or IpcPH, based on RHC performed within 6 months of or during screening documenting the following:
a. For patients with CpcPH: PVR ≥3 Wood units, or For patients with IpcPH: PVR ≤3 Wood units;
b. mPAP of >20 mm Hg;
c. PCWP >15 mm Hg or PCWP >12 mm Hg and ≤14 mm Hg with evidence on left atrial volume index (LAVI) on echocardiography of ≥34 mL/m².
4. Is receiving chronic medication for heart failure or for any underlying condition, administered at a stable (per investigator) dose for ≥30 days before screening. Diuretics and/or anticoagulants are excepted from this rule but should not be newly started or stopped within 30 days of screening, and a prescribed dose change should not occur within 7 days of screening.
5. Is able to adhere to the study visit schedule and understand and comply with all protocol requirements.
6. Agrees not to participate in any other trials of investigational drugs/devices while enrolled in this study.
7. Understands the study procedures and agrees to participate in the study by giving written informed consent Patients are excluded from the study if any of the following exclusion criteria apply:

8. Has a confirmed diagnosis of PH in WHO Group 1, WHO Group 3, WHO Group 4, or WHO Group 5.
9. Has documented significant lung disease, defined as any of the following:
a. Chronic obstructive pulmonary disease (COPD) with post-bronchodilator forced expiratory volume in the first second (FEV1)<50% predicted;
b. Restrictive lung disease with total lung capacity <60% predicted;
c. More than mild interstitial lung disease (ILD), with forced vital capacity <70% or FEV1 <60% predicted (still appropriate if absence of more than mild ILD, fibrosis, or COPD on computed tomography imaging).
10. Has cardiovascular comorbidities, which include any of the following:
a. Moderate to severe rheumatic heart disease with mitral stenosis;
b. Any history of greater than moderate mitral or aortic regurgitation valvular disease or greater than mild aortic or mitral stenosis. Severe tricuspid regurgitation may be included unless it is due to primary valvular disease, e.g., from endocarditis, carcinoid, or mechanical destruction or pacemaker lead;
c. Acute coronary syndrome, coronary artery bypass graft, or percutaneous coronary intervention within 3 months of screening;
d. Uncontrolled heart rate (HR) (>110 beats per minute [bpm] at screening) from atrial fibrillation or atrial flutter;
e. History of or anticipated heart transplant or ventricular assist device implantation;
f. Anticipated implantation of pacemaker, pacemaker implantation within 14 days of screening, or history of implantable cardioverter defibrillator placement;
g. Occurrence of myocardial infarction within 3 months of screening;
h. History of known pericardial constriction, hypertrophic cardiomyopathy, cardiac sarcoidosis, or amyloid cardiomyopathy and/or infectious or infiltrative myopathy;
i. Uncontrolled systemic hypertension as evidenced by sitting sBP >160 mm Hg or sitting diastolic blood pressure (dBP) >110 mm Hg during screening after a period of rest;
j. Sitting sBP <120 mm Hg or sitting dBP <50 mm Hg during screening;
k. Resting HR of <50 bpm or >115 bpm at screening;
l. Stroke within 90 days of screening;
m. Acutely decompensated heart failure that required hospitalization within 14 days of screening;
n. ECG during screening with heart rate-corrected QT interval (QTc) by Fridericia's method (QTcF) >470 milliseconds (ms) for males or >480 ms for females, or >500 ms if a ventricular conduction defect (right bundle branch block, left bundle branch block, or interventricular conduction delay) is present;
o. Personal or family history of Brugada syndrome;
p. Personal or family history of long QT syndrome unless the participant's ECG shows a normal QTc;
q. Arrhythmogenic right ventricular cardiomyopathy unless the participant has recent cardiac magnetic resonance imaging that shows no evidence of this diagnosis;
r. Any history of mitral or aortic valve replacement or repair (mechanical or biomechanical);
s. Complex congenital heart disease.
11. Was hospitalized for any indication with discharge within 14 days of screening.
12. Received any of the following classes of pulmonary arterial hypertension-specific therapies: endothelin receptor antagonists, prostacyclin analogs, soluble guanylate cyclase stimulators, and PDE5 (phosphodiesterase type 5) inhibitors within 30 days of screening.
13. Received IV inotropes (e.g., dobutamine, dopamine, norepinephrine, vasopressin) within 30 days of screening.
14. Has a known history of chronic liver disease, active hepatitis B infection (positive hepatitis B surface antigen and positive hepatitis B core antibodies), or hepatitis C infection (positive hepatitis C antibodies) at the screening visit. In patients with isolated positive hepatitis B core antibodies, a hepatitis B DNA test will be done to confirm the active hepatitis B. In patients with positive hepatitis C antibodies, hepatitis C RNA will be done to confirm the active hepatitis C.
15. Has HIV infection or HIV seropositivity at the screening visit.
16. Has active tuberculosis, as determined by Quantiferon Gold test and confirmed by chest x-ray.
17. Has any of the following clinical laboratory values before screening as specified:
a. Serum alanine aminotransferase or aspartate aminotransferase levels >3× the upper limit of normal (ULN) or total bilirubin >3×ULN within 30 days of screening;
b. Estimated glomerular filtration rate <15 mL/min/1.73 m² (CKD EPI [Chronic Kidney Disease Epidemiology Collaboration] equation) within 30 days of screening or required renal replacement therapy within 90 days of screening;
c. Glycosylated hemoglobin (HbA1c) >9% within 30 days of screening;

d. Platelet count <50,000/mm³ within 30 days of screening.
18. Has a history of severe allergic or anaphylactic reaction or hypersensitivity to recombinant proteins or excipients in the investigational product.
19. Had major surgery within 60 days of screening. Participants must have completely recovered from any previous surgery before screening.
20. Had a prior heart-lung transplant or has a life expectancy of <12 months.
21. Is pregnant or breastfeeding.
22. Has a history of active malignancy except for fully excised or treated basal cell carcinoma, cervical carcinoma in situ, or ≤2 squamous cell carcinomas of the skin.
23. Has a history of clinically significant (as determined by the investigator) endocrine, hematologic, hepatic, (auto)immune, infectious (requiring chronic antibiotics), metabolic, urologic, pulmonary, neurologic, neuromuscular, dermatologic, psychiatric, renal, and/or another disease that may limit participation in the study.
24. Has body mass index (BMI) <18 kg/m² or ≥40 kg/m2.
25. Has a history of drug or alcohol abuse or has a positive urine drug screen for prohibited drugs.
26. Received any vaccination, including COVID-19 vaccination, within 2 weeks before dosing or plans to receive a vaccine during the study.
27. Was previously administered relaxin or relaxin fusion proteins.
28. Was dosed in any clinical research study evaluating another investigational drug (including biologics) or therapy (including specific immunotherapy) within 90 days or ≤5 half-lives (whichever is longer) of an investigational biologic drug, or ≤4 weeks for other investigational products, before the screening visit.
29. Is mentally or legally incapacitated, has significant emotional problems at the time of the study, or has a history of significant psychiatric disorders at the discretion of the investigator.
30. Has a history of any illness that, in the opinion of the investigator, might confound the results of the study or pose additional risk to the participant.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

The invention claimed is:

1. A fusion protein comprising, from N-terminus to C-terminus:
   a first peptide comprising the amino acid sequence set forth in SEQ ID NO: 1;
   a first linker peptide comprising the amino acid sequence set forth in SEQ ID NO: 21; and
   a second peptide comprising the amino acid sequence set forth in SEQ ID NO: 8.

2. The fusion protein of claim 1, wherein the amino acid sequence of the first peptide is 27, 28, or 29 amino acids in length.

3. The fusion protein of claim 1, wherein the amino acid sequence of the first peptide consists of the amino acid sequence set forth in SEQ ID NO: 1.

4. The fusion protein of claim 1, wherein the amino acid sequence of the first linker peptide is 13, 14, or 15 amino acids in length.

5. The fusion protein of claim 1, wherein the amino acid sequence of the first linker peptide consists of the amino acid sequence set forth in SEQ ID NO: 21.

6. The fusion protein of claim 1, wherein the amino acid sequence of the second peptide is 24 or 25 amino acids in length.

7. The fusion protein of claim 1, wherein the amino acid sequence of the second peptide consists of the amino acid sequence set forth in SEQ ID NO: 8.

8. The fusion protein of claim 1, wherein the amino acid sequence of the second peptide consists of the amino acid sequence set forth in SEQ ID NO: 260.

9. The fusion protein of claim 1, wherein the fusion protein comprises the amino acid sequence set forth in SEQ ID NO: 31.

10. The fusion protein of claim 1, wherein the amino acid sequence of the fusion protein consists of the amino acid sequence set forth in SEQ ID NO: 31.

11. The fusion protein of claim 1, further comprising an IgG Fc polypeptide.

12. The fusion protein of claim 11, wherein the IgG Fc polypeptide comprises the amino acid sequence of a human IgG1 Fc.

13. The fusion protein of claim 11, wherein the IgG Fc polypeptide comprises:

alanine at EU position 329;
alanine at each of EU positions 234 and 235;
alanine at each of EU positions 234, 235, and 329;
leucine and serine at EU positions 428 and 434, respectively; or
alanine, alanine, alanine, leucine, and serine at EU positions 234, 235, 329, 428, and 434, respectively.

14. The fusion protein of claim 11, wherein the IgG Fc polypeptide comprises the amino acid sequence set forth in SEQ ID NO: 79 or 83.

15. The fusion protein of claim 11, wherein the IgG Fc polypeptide is linked to the N-terminus of the first peptide.

16. The fusion protein of claim 15, wherein the IgG Fc polypeptide is linked to the N-terminus of the first peptide via a second linker peptide.

17. The fusion protein of claim 16, wherein the second linker peptide comprises the amino acid sequence GGS or EGGS (SEQ ID NO: 299).

18. The fusion protein of claim 1, wherein the fusion protein comprises the amino acid sequence set forth in SEQ ID NO: 87.

19. A homodimer comprising two fusion proteins of claim 18.

20. The fusion protein of claim 1, wherein the amino acid sequence of the fusion protein consists of the amino acid sequence set forth in SEQ ID NO: 87.

21. A homodimer comprising two fusion proteins of claim 20.

\* \* \* \* \*

```
SEQUENCE LISTING

Sequence total quantity: 558
SEQ ID NO: 1            moltype = AA  length = 27
FEATURE                 Location/Qualifiers
source                  1..27
                        mol_type = protein
                        organism = synthetic construct
SEQUENCE: 1
DSWQEEVIKL CGRELVRAQI AICGKST                                               27

SEQ ID NO: 2            moltype = AA  length = 27
FEATURE                 Location/Qualifiers
source                  1..27
                        mol_type = protein
                        organism = synthetic construct
SEQUENCE: 2
DSWQEEVIKL CGRELVRAQI AICGQST                                               27

SEQ ID NO: 3            moltype = AA  length = 27
FEATURE                 Location/Qualifiers
source                  1..27
                        mol_type = protein
                        organism = synthetic construct
SEQUENCE: 3
DSYQEEVIKL CGRELVRAQI AICGKST                                               27

SEQ ID NO: 4            moltype = AA  length = 27
FEATURE                 Location/Qualifiers
source                  1..27
                        mol_type = protein
                        organism = synthetic construct
SEQUENCE: 4
DSFQEEVIKL CGRELVRAQI AICGKST                                               27

SEQ ID NO: 5            moltype = AA  length = 27
FEATURE                 Location/Qualifiers
source                  1..27
                        mol_type = protein
                        organism = synthetic construct
SEQUENCE: 5
DSLQEEVIKL CGRELVRAQI AICGKST                                               27
```

```
SEQ ID NO: 6              moltype = AA  length = 27
FEATURE                   Location/Qualifiers
source                    1..27
                          mol_type = protein
                          organism = synthetic construct
SEQUENCE: 6
DSIQEEVIKL CGRELVRAQI AICGKST                                              27

SEQ ID NO: 7              moltype = AA  length = 27
FEATURE                   Location/Qualifiers
source                    1..27
                          mol_type = protein
                          organism = synthetic construct
VARIANT                   3
                          note = any amino acid except for M, H, and C
VARIANT                   9
                          note = K, Q, D, E, L, I or Y
VARIANT                   25
                          note = M, K, Q, or N
SEQUENCE: 7
DSXQEEVIXL CGRELVRAQI AICGXST                                              27

SEQ ID NO: 8              moltype = AA  length = 24
FEATURE                   Location/Qualifiers
source                    1..24
                          mol_type = protein
                          organism = synthetic construct
SEQUENCE: 8
QLYSALANKC CHVGCTKRSL AQFC                                                 24

SEQ ID NO: 9              moltype = AA  length = 24
FEATURE                   Location/Qualifiers
source                    1..24
                          mol_type = protein
                          organism = synthetic construct
SEQUENCE: 9
QLYSALANKC CHVGCTKQSL AQFC                                                 24

SEQ ID NO: 10             moltype = AA  length = 24
FEATURE                   Location/Qualifiers
source                    1..24
                          mol_type = protein
                          organism = synthetic construct
SEQUENCE: 10
QLYSALANKC CYVGCTKRSL AQFC                                                 24

SEQ ID NO: 11             moltype = AA  length = 24
FEATURE                   Location/Qualifiers
source                    1..24
                          mol_type = protein
                          organism = synthetic construct
SEQUENCE: 11
QLYSALANKC CLVGCTKRSL AQFC                                                 24

SEQ ID NO: 12             moltype = AA  length = 24
FEATURE                   Location/Qualifiers
source                    1..24
                          mol_type = protein
                          organism = synthetic construct
SEQUENCE: 12
QLYSALANKC CQVGCTKRSL AQFC                                                 24

SEQ ID NO: 13             moltype = AA  length = 24
FEATURE                   Location/Qualifiers
source                    1..24
                          mol_type = protein
                          organism = synthetic construct
SEQUENCE: 13
QLYSALANKC CKVGCTKRSL AQFC                                                 24

SEQ ID NO: 14             moltype = AA  length = 24
FEATURE                   Location/Qualifiers
source                    1..24
                          mol_type = protein
                          organism = synthetic construct
SEQUENCE: 14
QLYSALANKC CYVGCTKQSL AQFC                                                 24

SEQ ID NO: 15             moltype = AA  length = 24
```

```
FEATURE                 Location/Qualifiers
source                  1..24
                        mol_type = protein
                        organism = synthetic construct
SEQUENCE: 15
QLYSALANKC CKVGCTKQSL AQFC                                              24

SEQ ID NO: 16           moltype = AA  length = 24
FEATURE                 Location/Qualifiers
source                  1..24
                        mol_type = protein
                        organism = synthetic construct
VARIANT                 9
                        note = K, Q, D, E, L, I, or Y
VARIANT                 12
                        note = any amino acid except for M, W, and C
VARIANT                 17
                        note = K, Q, D, E, L, I, or Y
VARIANT                 18
                        note = Q, D, E, L, I, Y or R
SEQUENCE: 16
QLYSALANXC CXVGCTXXSL AQFC                                              24

SEQ ID NO: 17           moltype = AA  length = 13
FEATURE                 Location/Qualifiers
source                  1..13
                        mol_type = protein
                        organism = synthetic construct
VARIANT                 8
                        note = D, E, N, or Q
VARIANT                 10
                        note = D, E, N, or Q
SEQUENCE: 17
ASDAAGAXAX AGA                                                          13

SEQ ID NO: 18           moltype = AA  length = 13
FEATURE                 Location/Qualifiers
source                  1..13
                        mol_type = protein
                        organism = synthetic construct
SEQUENCE: 18
ASDAAGADAD AGA                                                          13

SEQ ID NO: 19           moltype = AA  length = 13
FEATURE                 Location/Qualifiers
source                  1..13
                        mol_type = protein
                        organism = synthetic construct
SEQUENCE: 19
ASDAAGADAN AGA                                                          13

SEQ ID NO: 20           moltype = AA  length = 13
FEATURE                 Location/Qualifiers
source                  1..13
                        mol_type = protein
                        organism = synthetic construct
SEQUENCE: 20
ASDAAGADAQ AGA                                                          13

SEQ ID NO: 21           moltype = AA  length = 13
FEATURE                 Location/Qualifiers
source                  1..13
                        mol_type = protein
                        organism = synthetic construct
SEQUENCE: 21
ASDAAGAEAE AGA                                                          13

SEQ ID NO: 22           moltype = AA  length = 13
FEATURE                 Location/Qualifiers
source                  1..13
                        mol_type = protein
                        organism = synthetic construct
SEQUENCE: 22
ASDAAGANAD AGA                                                          13

SEQ ID NO: 23           moltype = AA  length = 13
FEATURE                 Location/Qualifiers
source                  1..13
                        mol_type = protein
```

```
                           -continued organism = synthetic construct
SEQUENCE: 23
ASDAAGAQAD AGA                                                    13

SEQ ID NO: 24            moltype = AA  length = 13
FEATURE                  Location/Qualifiers
source                   1..13
                         mol_type = protein
                         organism = synthetic construct
SEQUENCE: 24
ASDAAGAQAQ AGA                                                    13

SEQ ID NO: 25            moltype = AA  length = 13
FEATURE                  Location/Qualifiers
source                   1..13
                         mol_type = protein
                         organism = synthetic construct
VARIANT                  10
                         note = E or S
SEQUENCE: 25
GGEGSGGEGX GGG                                                    13

SEQ ID NO: 26            moltype = AA  length = 13
FEATURE                  Location/Qualifiers
source                   1..13
                         mol_type = protein
                         organism = synthetic construct
SEQUENCE: 26
GGEGSGGEGE GGG                                                    13

SEQ ID NO: 27            moltype = AA  length = 13
FEATURE                  Location/Qualifiers
source                   1..13
                         mol_type = protein
                         organism = synthetic construct
SEQUENCE: 27
GGEGSGGEGS GGG                                                    13

SEQ ID NO: 28            moltype = AA  length = 65
FEATURE                  Location/Qualifiers
source                   1..65
                         mol_type = protein
                         organism = synthetic construct
SEQUENCE: 28
DSWQEEVIKL CGRELVRAQI AICGKSTASD AAGADANAGA RQLYSALANK CCHVGCTKRS  60
LAQFC                                                             65

SEQ ID NO: 29            moltype = AA  length = 65
FEATURE                  Location/Qualifiers
source                   1..65
                         mol_type = protein
                         organism = synthetic construct
SEQUENCE: 29
DSWQEEVIKL CGRELVRAQI AICGKSTASD AAGANADAGA RQLYSALANK CCHVGCTKRS  60
LAQFC                                                             65

SEQ ID NO: 30            moltype = AA  length = 65
FEATURE                  Location/Qualifiers
source                   1..65
                         mol_type = protein
                         organism = synthetic construct
SEQUENCE: 30
DSWQEEVIKL CGRELVRAQI AICGKSTASD AAGADADAGA RQLYSALANK CCHVGCTKRS  60
LAQFC                                                             65

SEQ ID NO: 31            moltype = AA  length = 65
FEATURE                  Location/Qualifiers
source                   1..65
                         mol_type = protein
                         organism = synthetic construct
SEQUENCE: 31
DSWQEEVIKL CGRELVRAQI AICGKSTASD AAGAEAEAGA RQLYSALANK CCHVGCTKRS  60
LAQFC                                                             65

SEQ ID NO: 32            moltype = AA  length = 65
FEATURE                  Location/Qualifiers
source                   1..65
                         mol_type = protein
                         organism = synthetic construct
```

-continued

```
SEQUENCE: 32
DSWQEEVIKL CGRELVRAQI AICGKSTASD AAGAQADAGA RQLYSALANK CCHVGCTKRS    60
LAQFC                                                                65

SEQ ID NO: 33           moltype = AA  length = 65
FEATURE                 Location/Qualifiers
source                  1..65
                        mol_type = protein
                        organism = synthetic construct
SEQUENCE: 33
DSWQEEVIKL CGRELVRAQI AICGKSTASD AAGADAQAGA RQLYSALANK CCHVGCTKRS    60
LAQFC                                                                65

SEQ ID NO: 34           moltype = AA  length = 65
FEATURE                 Location/Qualifiers
source                  1..65
                        mol_type = protein
                        organism = synthetic construct
SEQUENCE: 34
DSWQEEVIKL CGRELVRAQI AICGKSTASD AAGAQAQAGA RQLYSALANK CCHVGCTKRS    60
LAQFC                                                                65

SEQ ID NO: 35           moltype = AA  length = 65
FEATURE                 Location/Qualifiers
source                  1..65
                        mol_type = protein
                        organism = synthetic construct
SEQUENCE: 35
DSWQEEVIKL CGRELVRAQI AICGQSTASD AAGADANAGA RQLYSALANK CCHVGCTKRS    60
LAQFC                                                                65

SEQ ID NO: 36           moltype = AA  length = 65
FEATURE                 Location/Qualifiers
source                  1..65
                        mol_type = protein
                        organism = synthetic construct
SEQUENCE: 36
DSWQEEVIKL CGRELVRAQI AICGQSTASD AAGANADAGA RQLYSALANK CCHVGCTKRS    60
LAQFC                                                                65

SEQ ID NO: 37           moltype = AA  length = 65
FEATURE                 Location/Qualifiers
source                  1..65
                        mol_type = protein
                        organism = synthetic construct
SEQUENCE: 37
DSWQEEVIKL CGRELVRAQI AICGQSTASD AAGADADAGA RQLYSALANK CCHVGCTKRS    60
LAQFC                                                                65

SEQ ID NO: 38           moltype = AA  length = 65
FEATURE                 Location/Qualifiers
source                  1..65
                        mol_type = protein
                        organism = synthetic construct
SEQUENCE: 38
DSWQEEVIKL CGRELVRAQI AICGQSTASD AAGAEAEAGA RQLYSALANK CCHVGCTKRS    60
LAQFC                                                                65

SEQ ID NO: 39           moltype = AA  length = 65
FEATURE                 Location/Qualifiers
source                  1..65
                        mol_type = protein
                        organism = synthetic construct
SEQUENCE: 39
DSWQEEVIKL CGRELVRAQI AICGQSTASD AAGAQADAGA RQLYSALANK CCHVGCTKRS    60
LAQFC                                                                65

SEQ ID NO: 40           moltype = AA  length = 65
FEATURE                 Location/Qualifiers
source                  1..65
                        mol_type = protein
                        organism = synthetic construct
SEQUENCE: 40
DSWQEEVIKL CGRELVRAQI AICGQSTASD AAGADAQAGA RQLYSALANK CCHVGCTKRS    60
LAQFC                                                                65

SEQ ID NO: 41           moltype = AA  length = 65
FEATURE                 Location/Qualifiers
source                  1..65
```

```
SEQUENCE: 41
DSWQEEVIKL CGRELVRAQI AICGQSTASD AAGAQAQAGA RQLYSALANK CCHVGCTKRS    60
LAQFC                                                               65

SEQ ID NO: 42           moltype = AA  length = 65
FEATURE                 Location/Qualifiers
source                  1..65
                        mol_type = protein
                        organism = synthetic construct
SEQUENCE: 42
DSWQEEVIKL CGRELVRAQI AICGKSTASD AAGADANAGA RQLYSALANK CCHVGCTKQS    60
LAQFC                                                               65

SEQ ID NO: 43           moltype = AA  length = 65
FEATURE                 Location/Qualifiers
source                  1..65
                        mol_type = protein
                        organism = synthetic construct
SEQUENCE: 43
DSWQEEVIKL CGRELVRAQI AICGKSTASD AAGANADAGA RQLYSALANK CCHVGCTKQS    60
LAQFC                                                               65

SEQ ID NO: 44           moltype = AA  length = 65
FEATURE                 Location/Qualifiers
source                  1..65
                        mol_type = protein
                        organism = synthetic construct
SEQUENCE: 44
DSWQEEVIKL CGRELVRAQI AICGKSTASD AAGADADAGA RQLYSALANK CCHVGCTKQS    60
LAQFC                                                               65

SEQ ID NO: 45           moltype = AA  length = 65
FEATURE                 Location/Qualifiers
source                  1..65
                        mol_type = protein
                        organism = synthetic construct
SEQUENCE: 45
DSWQEEVIKL CGRELVRAQI AICGKSTASD AAGAEAEAGA RQLYSALANK CCHVGCTKQS    60
LAQFC                                                               65

SEQ ID NO: 46           moltype = AA  length = 65
FEATURE                 Location/Qualifiers
source                  1..65
                        mol_type = protein
                        organism = synthetic construct
SEQUENCE: 46
DSWQEEVIKL CGRELVRAQI AICGKSTASD AAGAQADAGA RQLYSALANK CCHVGCTKQS    60
LAQFC                                                               65

SEQ ID NO: 47           moltype = AA  length = 65
FEATURE                 Location/Qualifiers
source                  1..65
                        mol_type = protein
                        organism = synthetic construct
SEQUENCE: 47
DSWQEEVIKL CGRELVRAQI AICGKSTASD AAGADAQAGA RQLYSALANK CCHVGCTKQS    60
LAQFC                                                               65

SEQ ID NO: 48           moltype = AA  length = 65
FEATURE                 Location/Qualifiers
source                  1..65
                        mol_type = protein
                        organism = synthetic construct
SEQUENCE: 48
DSWQEEVIKL CGRELVRAQI AICGKSTASD AAGAQAQAGA RQLYSALANK CCHVGCTKQS    60
LAQFC                                                               65

SEQ ID NO: 49           moltype = AA  length = 65
FEATURE                 Location/Qualifiers
source                  1..65
                        mol_type = protein
                        organism = synthetic construct
SEQUENCE: 49
DSWQEEVIKL CGRELVRAQI AICGQSTASD AAGADANAGA RQLYSALANK CCHVGCTKQS    60
LAQFC                                                               65

SEQ ID NO: 50           moltype = AA  length = 65
```

```
FEATURE                 Location/Qualifiers
source                  1..65
                        mol_type = protein
                        organism = synthetic construct
SEQUENCE: 50
DSWQEEVIKL CGRELVRAQI AICGQSTASD AAGANADAGA RQLYSALANK CCHVGCTKQS    60
LAQFC                                                               65

SEQ ID NO: 51           moltype = AA  length = 65
FEATURE                 Location/Qualifiers
source                  1..65
                        mol_type = protein
                        organism = synthetic construct
SEQUENCE: 51
DSWQEEVIKL CGRELVRAQI AICGQSTASD AAGADADAGA RQLYSALANK CCHVGCTKQS    60
LAQFC                                                               65

SEQ ID NO: 52           moltype = AA  length = 65
FEATURE                 Location/Qualifiers
source                  1..65
                        mol_type = protein
                        organism = synthetic construct
SEQUENCE: 52
DSWQEEVIKL CGRELVRAQI AICGQSTASD AAGAEAEAGA RQLYSALANK CCHVGCTKQS    60
LAQFC                                                               65

SEQ ID NO: 53           moltype = AA  length = 65
FEATURE                 Location/Qualifiers
source                  1..65
                        mol_type = protein
                        organism = synthetic construct
SEQUENCE: 53
DSWQEEVIKL CGRELVRAQI AICGQSTASD AAGAQADAGA RQLYSALANK CCHVGCTKQS    60
LAQFC                                                               65

SEQ ID NO: 54           moltype = AA  length = 65
FEATURE                 Location/Qualifiers
source                  1..65
                        mol_type = protein
                        organism = synthetic construct
SEQUENCE: 54
DSWQEEVIKL CGRELVRAQI AICGQSTASD AAGADAQAGA RQLYSALANK CCHVGCTKQS    60
LAQFC                                                               65

SEQ ID NO: 55           moltype = AA  length = 65
FEATURE                 Location/Qualifiers
source                  1..65
                        mol_type = protein
                        organism = synthetic construct
SEQUENCE: 55
DSWQEEVIKL CGRELVRAQI AICGQSTASD AAGAQAQAGA RQLYSALANK CCHVGCTKQS    60
LAQFC                                                               65

SEQ ID NO: 56           moltype = AA  length = 65
FEATURE                 Location/Qualifiers
source                  1..65
                        mol_type = protein
                        organism = synthetic construct
SEQUENCE: 56
DSYQEEVIKL CGRELVRAQI AICGKSTASD AAGAEAEAGA RQLYSALANK CCHVGCTKRS    60
LAQFC                                                               65

SEQ ID NO: 57           moltype = AA  length = 65
FEATURE                 Location/Qualifiers
source                  1..65
                        mol_type = protein
                        organism = synthetic construct
SEQUENCE: 57
DSFQEEVIKL CGRELVRAQI AICGKSTASD AAGAEAEAGA RQLYSALANK CCHVGCTKRS    60
LAQFC                                                               65

SEQ ID NO: 58           moltype = AA  length = 65
FEATURE                 Location/Qualifiers
source                  1..65
                        mol_type = protein
                        organism = synthetic construct
SEQUENCE: 58
DSLQEEVIKL CGRELVRAQI AICGKSTASD AAGAEAEAGA RQLYSALANK CCHVGCTKRS    60
LAQFC                                                               65
```

```
SEQ ID NO: 59          moltype = AA  length = 65
FEATURE                Location/Qualifiers
source                 1..65
                       mol_type = protein
                       organism = synthetic construct
SEQUENCE: 59
DSIQEEVIKL CGRELVRAQI AICGKSTASD AAGAEAEAGA RQLYSALANK CCHVGCTKRS   60
LAQFC                                                              65

SEQ ID NO: 60          moltype = AA  length = 65
FEATURE                Location/Qualifiers
source                 1..65
                       mol_type = protein
                       organism = synthetic construct
SEQUENCE: 60
DSWQEEVIKL CGRELVRAQI AICGKSTASD AAGAEAEAGA RQLYSALANK CCYVGCTKRS   60
LAQFC                                                              65

SEQ ID NO: 61          moltype = AA  length = 65
FEATURE                Location/Qualifiers
source                 1..65
                       mol_type = protein
                       organism = synthetic construct
SEQUENCE: 61
DSWQEEVIKL CGRELVRAQI AICGKSTASD AAGAEAEAGA RQLYSALANK CCLVGCTKRS   60
LAQFC                                                              65

SEQ ID NO: 62          moltype = AA  length = 65
FEATURE                Location/Qualifiers
source                 1..65
                       mol_type = protein
                       organism = synthetic construct
SEQUENCE: 62
DSWQEEVIKL CGRELVRAQI AICGKSTASD AAGAEAEAGA RQLYSALANK CCQVGCTKRS   60
LAQFC                                                              65

SEQ ID NO: 63          moltype = AA  length = 65
FEATURE                Location/Qualifiers
source                 1..65
                       mol_type = protein
                       organism = synthetic construct
SEQUENCE: 63
DSWQEEVIKL CGRELVRAQI AICGKSTASD AAGAEAEAGA RQLYSALANK CCKVGCTKRS   60
LAQFC                                                              65

SEQ ID NO: 64          moltype = AA  length = 65
FEATURE                Location/Qualifiers
source                 1..65
                       mol_type = protein
                       organism = synthetic construct
SEQUENCE: 64
DSYQEEVIKL CGRELVRAQI AICGKSTASD AAGAEAEAGA RQLYSALANK CCYVGCTKRS   60
LAQFC                                                              65

SEQ ID NO: 65          moltype = AA  length = 65
FEATURE                Location/Qualifiers
source                 1..65
                       mol_type = protein
                       organism = synthetic construct
SEQUENCE: 65
DSYQEEVIKL CGRELVRAQI AICGKSTASD AAGAEAEAGA RQLYSALANK CCKVGCTKRS   60
LAQFC                                                              65

SEQ ID NO: 66          moltype = AA  length = 65
FEATURE                Location/Qualifiers
source                 1..65
                       mol_type = protein
                       organism = synthetic construct
SEQUENCE: 66
DSYQEEVIKL CGRELVRAQI AICGKSTGGE GSGGEGEGGG RQLYSALANK CCYVGCTKRS   60
LAQFC                                                              65

SEQ ID NO: 67          moltype = AA  length = 65
FEATURE                Location/Qualifiers
source                 1..65
                       mol_type = protein
                       organism = synthetic construct
SEQUENCE: 67
```

```
DSYQEEVIKL CGRELVRAQI AICGKSTGGE GSGGEGEGGG RQLYSALANK CCKVGCTKRS    60
LAQFC                                                               65

SEQ ID NO: 68           moltype = AA  length = 65
FEATURE                 Location/Qualifiers
source                  1..65
                        mol_type = protein
                        organism = synthetic construct
SEQUENCE: 68
DSYQEEVIKL CGRELVRAQI AICGKSTGGE GSGGEGSGGG RQLYSALANK CCYVGCTKRS    60
LAQFC                                                               65

SEQ ID NO: 69           moltype = AA  length = 65
FEATURE                 Location/Qualifiers
source                  1..65
                        mol_type = protein
                        organism = synthetic construct
SEQUENCE: 69
DSYQEEVIKL CGRELVRAQI AICGKSTGGE GSGGEGSGGG RQLYSALANK CCKVGCTKRS    60
LAQFC                                                               65

SEQ ID NO: 70           moltype = AA  length = 65
FEATURE                 Location/Qualifiers
source                  1..65
                        mol_type = protein
                        organism = synthetic construct
SEQUENCE: 70
DSYQEEVIKL CGRELVRAQI AICGKSTASD AAGAEAEAGA RQLYSALANK CCYVGCTKQS    60
LAQFC                                                               65

SEQ ID NO: 71           moltype = AA  length = 65
FEATURE                 Location/Qualifiers
source                  1..65
                        mol_type = protein
                        organism = synthetic construct
SEQUENCE: 71
DSYQEEVIKL CGRELVRAQI AICGKSTASD AAGAEAEAGA RQLYSALANK CCKVGCTKQS    60
LAQFC                                                               65

SEQ ID NO: 72           moltype = AA  length = 65
FEATURE                 Location/Qualifiers
source                  1..65
                        mol_type = protein
                        organism = synthetic construct
SEQUENCE: 72
DSYQEEVIKL CGRELVRAQI AICGKSTGGE GSGGEGEGGG RQLYSALANK CCYVGCTKQS    60
LAQFC                                                               65

SEQ ID NO: 73           moltype = AA  length = 65
FEATURE                 Location/Qualifiers
source                  1..65
                        mol_type = protein
                        organism = synthetic construct
SEQUENCE: 73
DSYQEEVIKL CGRELVRAQI AICGKSTGGE GSGGEGEGGG RQLYSALANK CCKVGCTKQS    60
LAQFC                                                               65

SEQ ID NO: 74           moltype = AA  length = 65
FEATURE                 Location/Qualifiers
source                  1..65
                        mol_type = protein
                        organism = synthetic construct
SEQUENCE: 74
DSYQEEVIKL CGRELVRAQI AICGKSTGGE GSGGEGSGGG RQLYSALANK CCYVGCTKQS    60
LAQFC                                                               65

SEQ ID NO: 75           moltype = AA  length = 65
FEATURE                 Location/Qualifiers
source                  1..65
                        mol_type = protein
                        organism = synthetic construct
SEQUENCE: 75
DSYQEEVIKL CGRELVRAQI AICGKSTGGE GSGGEGSGGG RQLYSALANK CCKVGCTKQS    60
LAQFC                                                               65

SEQ ID NO: 76           moltype = AA  length = 227
FEATURE                 Location/Qualifiers
source                  1..227
                        mol_type = protein
```

```
                        organism = synthetic construct
SEQUENCE: 76
DKTHTCPPCP APELLGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 77           moltype = AA  length = 227
FEATURE                 Location/Qualifiers
source                  1..227
                        mol_type = protein
                        organism = synthetic construct
SEQUENCE: 77
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 78           moltype = AA  length = 227
FEATURE                 Location/Qualifiers
source                  1..227
                        mol_type = protein
                        organism = synthetic construct
SEQUENCE: 78
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 79           moltype = AA  length = 227
FEATURE                 Location/Qualifiers
source                  1..227
                        mol_type = protein
                        organism = synthetic construct
SEQUENCE: 79
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGK                 227

SEQ ID NO: 80           moltype = AA  length = 226
FEATURE                 Location/Qualifiers
source                  1..226
                        mol_type = protein
                        organism = synthetic construct
SEQUENCE: 80
DKTHTCPPCP APELLGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 81           moltype = AA  length = 226
FEATURE                 Location/Qualifiers
source                  1..226
                        mol_type = protein
                        organism = synthetic construct
SEQUENCE: 81
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 82           moltype = AA  length = 226
FEATURE                 Location/Qualifiers
source                  1..226
                        mol_type = protein
                        organism = synthetic construct
SEQUENCE: 82
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 83           moltype = AA  length = 226
FEATURE                 Location/Qualifiers
source                  1..226
                        mol_type = protein
                        organism = synthetic construct
SEQUENCE: 83
```

```
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPG                 226

SEQ ID NO: 84           moltype = AA  length = 295
FEATURE                 Location/Qualifiers
source                  1..295
                        mol_type = protein
                        organism = synthetic construct
SEQUENCE: 84
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTASD AAGADANAGA RQLYSALANK CCHVGCTKRS LAQFC        295

SEQ ID NO: 85           moltype = AA  length = 295
FEATURE                 Location/Qualifiers
source                  1..295
                        mol_type = protein
                        organism = synthetic construct
SEQUENCE: 85
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTASD AAGANADAGA RQLYSALANK CCHVGCTKRS LAQFC        295

SEQ ID NO: 86           moltype = AA  length = 295
FEATURE                 Location/Qualifiers
source                  1..295
                        mol_type = protein
                        organism = synthetic construct
SEQUENCE: 86
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTASD AAGADADAGA RQLYSALANK CCHVGCTKRS LAQFC        295

SEQ ID NO: 87           moltype = AA  length = 295
FEATURE                 Location/Qualifiers
source                  1..295
                        mol_type = protein
                        organism = synthetic construct
SEQUENCE: 87
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTASD AAGAEAEAGA RQLYSALANK CCHVGCTKRS LAQFC        295

SEQ ID NO: 88           moltype = AA  length = 295
FEATURE                 Location/Qualifiers
source                  1..295
                        mol_type = protein
                        organism = synthetic construct
SEQUENCE: 88
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTASD AAGAQADAGA RQLYSALANK CCHVGCTKRS LAQFC        295

SEQ ID NO: 89           moltype = AA  length = 295
FEATURE                 Location/Qualifiers
source                  1..295
                        mol_type = protein
                        organism = synthetic construct
SEQUENCE: 89
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTASD AAGADAQAGA RQLYSALANK CCHVGCTKRS LAQFC        295

SEQ ID NO: 90           moltype = AA  length = 295
FEATURE                 Location/Qualifiers
```

```
source                  1..295
                        mol_type = protein
                        organism = synthetic construct
SEQUENCE: 90
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTASD AAGAQAQAGA RQLYSALANK CCHVGCTKRS LAQFC        295

SEQ ID NO: 91           moltype = AA  length = 295
FEATURE                 Location/Qualifiers
source                  1..295
                        mol_type = protein
                        organism = synthetic construct
SEQUENCE: 91
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGADANAGA RQLYSALANK CCHVGCTKRS LAQFC        295

SEQ ID NO: 92           moltype = AA  length = 295
FEATURE                 Location/Qualifiers
source                  1..295
                        mol_type = protein
                        organism = synthetic construct
SEQUENCE: 92
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGANADAGA RQLYSALANK CCHVGCTKRS LAQFC        295

SEQ ID NO: 93           moltype = AA  length = 295
FEATURE                 Location/Qualifiers
source                  1..295
                        mol_type = protein
                        organism = synthetic construct
SEQUENCE: 93
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGADADAGA RQLYSALANK CCHVGCTKRS LAQFC        295

SEQ ID NO: 94           moltype = AA  length = 295
FEATURE                 Location/Qualifiers
source                  1..295
                        mol_type = protein
                        organism = synthetic construct
SEQUENCE: 94
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGAEAEAGA RQLYSALANK CCHVGCTKRS LAQFC        295

SEQ ID NO: 95           moltype = AA  length = 295
FEATURE                 Location/Qualifiers
source                  1..295
                        mol_type = protein
                        organism = synthetic construct
SEQUENCE: 95
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGAQADAGA RQLYSALANK CCHVGCTKRS LAQFC        295

SEQ ID NO: 96           moltype = AA  length = 295
FEATURE                 Location/Qualifiers
source                  1..295
                        mol_type = protein
                        organism = synthetic construct
SEQUENCE: 96
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
```

```
DGSFFLYSKL TVDKSRWQQG NVFSCSVLHE ALHSHYTQKS LSLSPGEGGS DSWQEEVIKL   240
CGRELVRAQI AICGKSTASD AAGADAQAGA RQLYSALANK CCHVGCTKRS LAQFC        295

SEQ ID NO: 97           moltype = AA  length = 295
FEATURE                 Location/Qualifiers
source                  1..295
                        mol_type = protein
                        organism = synthetic construct
SEQUENCE: 97
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGAQAQAGA RQLYSALANK CCHVGCTKRS LAQFC        295

SEQ ID NO: 98           moltype = AA  length = 295
FEATURE                 Location/Qualifiers
source                  1..295
                        mol_type = protein
                        organism = synthetic construct
SEQUENCE: 98
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGADANAGA RQLYSALANK CCHVGCTKRS LAQFC        295

SEQ ID NO: 99           moltype = AA  length = 295
FEATURE                 Location/Qualifiers
source                  1..295
                        mol_type = protein
                        organism = synthetic construct
SEQUENCE: 99
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGANADAGA RQLYSALANK CCHVGCTKRS LAQFC        295

SEQ ID NO: 100          moltype = AA  length = 295
FEATURE                 Location/Qualifiers
source                  1..295
                        mol_type = protein
                        organism = synthetic construct
SEQUENCE: 100
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGADADAGA RQLYSALANK CCHVGCTKRS LAQFC        295

SEQ ID NO: 101          moltype = AA  length = 295
FEATURE                 Location/Qualifiers
source                  1..295
                        mol_type = protein
                        organism = synthetic construct
SEQUENCE: 101
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGAEAEAGA RQLYSALANK CCHVGCTKRS LAQFC        295

SEQ ID NO: 102          moltype = AA  length = 295
FEATURE                 Location/Qualifiers
source                  1..295
                        mol_type = protein
                        organism = synthetic construct
SEQUENCE: 102
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGAQADAGA RQLYSALANK CCHVGCTKRS LAQFC        295

SEQ ID NO: 103          moltype = AA  length = 295
FEATURE                 Location/Qualifiers
source                  1..295
                        mol_type = protein
```

```
                        organism = synthetic construct
SEQUENCE: 103
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGADAQAGA RQLYSALANK CCHVGCTKRS LAQFC        295

SEQ ID NO: 104          moltype = AA  length = 295
FEATURE                 Location/Qualifiers
source                  1..295
                        mol_type = protein
                        organism = synthetic construct
SEQUENCE: 104
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGAQAQAGA RQLYSALANK CCHVGCTKRS LAQFC        295

SEQ ID NO: 105          moltype = AA  length = 295
FEATURE                 Location/Qualifiers
source                  1..295
                        mol_type = protein
                        organism = synthetic construct
SEQUENCE: 105
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGADANAGA RQLYSALANK CCHVGCTKQS LAQFC        295

SEQ ID NO: 106          moltype = AA  length = 295
FEATURE                 Location/Qualifiers
source                  1..295
                        mol_type = protein
                        organism = synthetic construct
SEQUENCE: 106
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGANADAGA RQLYSALANK CCHVGCTKQS LAQFC        295

SEQ ID NO: 107          moltype = AA  length = 295
FEATURE                 Location/Qualifiers
source                  1..295
                        mol_type = protein
                        organism = synthetic construct
SEQUENCE: 107
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGADADAGA RQLYSALANK CCHVGCTKQS LAQFC        295

SEQ ID NO: 108          moltype = AA  length = 295
FEATURE                 Location/Qualifiers
source                  1..295
                        mol_type = protein
                        organism = synthetic construct
SEQUENCE: 108
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGAEAEAGA RQLYSALANK CCHVGCTKQS LAQFC        295

SEQ ID NO: 109          moltype = AA  length = 295
FEATURE                 Location/Qualifiers
source                  1..295
                        mol_type = protein
                        organism = synthetic construct
SEQUENCE: 109
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGAQADAGA RQLYSALANK CCHVGCTKQS LAQFC        295
```

```
SEQ ID NO: 110            moltype = AA  length = 295
FEATURE                   Location/Qualifiers
source                    1..295
                          mol_type = protein
                          organism = synthetic construct
SEQUENCE: 110
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGADAQAGA RQLYSALANK CCHVGCTKQS LAQFC        295

SEQ ID NO: 111            moltype = AA  length = 295
FEATURE                   Location/Qualifiers
source                    1..295
                          mol_type = protein
                          organism = synthetic construct
SEQUENCE: 111
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGKSTASD AAGAQAQAGA RQLYSALANK CCHVGCTKQS LAQFC        295

SEQ ID NO: 112            moltype = AA  length = 295
FEATURE                   Location/Qualifiers
source                    1..295
                          mol_type = protein
                          organism = synthetic construct
SEQUENCE: 112
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGADANAGA RQLYSALANK CCHVGCTKQS LAQFC        295

SEQ ID NO: 113            moltype = AA  length = 295
FEATURE                   Location/Qualifiers
source                    1..295
                          mol_type = protein
                          organism = synthetic construct
SEQUENCE: 113
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGANADAGA RQLYSALANK CCHVGCTKQS LAQFC        295

SEQ ID NO: 114            moltype = AA  length = 295
FEATURE                   Location/Qualifiers
source                    1..295
                          mol_type = protein
                          organism = synthetic construct
SEQUENCE: 114
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGADADAGA RQLYSALANK CCHVGCTKQS LAQFC        295

SEQ ID NO: 115            moltype = AA  length = 295
FEATURE                   Location/Qualifiers
source                    1..295
                          mol_type = protein
                          organism = synthetic construct
SEQUENCE: 115
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGEGGS DSWQEEVIKL   240
CGRELVRAQI AICGQSTASD AAGAEAEAGA RQLYSALANK CCHVGCTKQS LAQFC        295

SEQ ID NO: 116            moltype = AA  length = 295
FEATURE                   Location/Qualifiers
source                    1..295
                          mol_type = protein
SEQUENCE: 116
```

```
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGEGGS DSWQEEVIKL  240
CGRELVRAQI AICGQSTASD AAGAQADAGA RQLYSALANK CCHVGCTKQS LAQFC       295

SEQ ID NO: 117            moltype = AA   length = 295
FEATURE                   Location/Qualifiers
source                    1..295
                          mol_type = protein
                          organism = synthetic construct
SEQUENCE: 117
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGEGGS DSWQEEVIKL  240
CGRELVRAQI AICGQSTASD AAGADAQAGA RQLYSALANK CCHVGCTKQS LAQFC       295

SEQ ID NO: 118            moltype = AA   length = 295
FEATURE                   Location/Qualifiers
source                    1..295
                          mol_type = protein
                          organism = synthetic construct
SEQUENCE: 118
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGEGGS DSWQEEVIKL  240
CGRELVRAQI AICGQSTASD AAGAQAQAGA RQLYSALANK CCHVGCTKQS LAQFC       295

SEQ ID NO: 119            moltype = AA   length = 295
FEATURE                   Location/Qualifiers
source                    1..295
                          mol_type = protein
                          organism = synthetic construct
SEQUENCE: 119
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTASD AAGAEAEAGA RQLYSALANK CCHVGCTKRS LAQFC       295

SEQ ID NO: 120            moltype = AA   length = 295
FEATURE                   Location/Qualifiers
source                    1..295
                          mol_type = protein
                          organism = synthetic construct
SEQUENCE: 120
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSFQEEVIKL  240
CGRELVRAQI AICGKSTASD AAGAEAEAGA RQLYSALANK CCHVGCTKRS LAQFC       295

SEQ ID NO: 121            moltype = AA   length = 295
FEATURE                   Location/Qualifiers
source                    1..295
                          mol_type = protein
                          organism = synthetic construct
SEQUENCE: 121
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSLQEEVIKL  240
CGRELVRAQI AICGKSTASD AAGAEAEAGA RQLYSALANK CCHVGCTKRS LAQFC       295

SEQ ID NO: 122            moltype = AA   length = 295
FEATURE                   Location/Qualifiers
source                    1..295
                          mol_type = protein
                          organism = synthetic construct
SEQUENCE: 122
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSIQEEVIKL  240
CGRELVRAQI AICGKSTASD AAGAEAEAGA RQLYSALANK CCHVGCTKRS LAQFC       295

SEQ ID NO: 123            moltype = AA   length = 295
```

```
FEATURE                 Location/Qualifiers
source                  1..295
                        mol_type = protein
                        organism = synthetic construct
SEQUENCE: 123
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTASD AAGAEAEAGA RQLYSALANK CCYVGCTKRS LAQFC       295

SEQ ID NO: 124          moltype = AA  length = 295
FEATURE                 Location/Qualifiers
source                  1..295
                        mol_type = protein
                        organism = synthetic construct
SEQUENCE: 124
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTASD AAGAEAEAGA RQLYSALANK CCLVGCTKRS LAQFC       295

SEQ ID NO: 125          moltype = AA  length = 295
FEATURE                 Location/Qualifiers
source                  1..295
                        mol_type = protein
                        organism = synthetic construct
SEQUENCE: 125
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTASD AAGAEAEAGA RQLYSALANK CCQVGCTKRS LAQFC       295

SEQ ID NO: 126          moltype = AA  length = 295
FEATURE                 Location/Qualifiers
source                  1..295
                        mol_type = protein
                        organism = synthetic construct
SEQUENCE: 126
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTASD AAGAEAEAGA RQLYSALANK CCKVGCTKRS LAQFC       295

SEQ ID NO: 127          moltype = AA  length = 295
FEATURE                 Location/Qualifiers
source                  1..295
                        mol_type = protein
                        organism = synthetic construct
SEQUENCE: 127
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGEGGS DSYQEEVIKL  240
CGRELVRAQI AICGKSTASD AAGAEAEAGA RQLYSALANK CCYVGCTKRS LAQFC       295

SEQ ID NO: 128          moltype = AA  length = 295
FEATURE                 Location/Qualifiers
source                  1..295
                        mol_type = protein
                        organism = synthetic construct
SEQUENCE: 128
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGEGGS DSYQEEVIKL  240
CGRELVRAQI AICGKSTASD AAGAEAEAGA RQLYSALANK CCKVGCTKRS LAQFC       295

SEQ ID NO: 129          moltype = AA  length = 295
FEATURE                 Location/Qualifiers
source                  1..295
                        mol_type = protein
                        organism = synthetic construct
SEQUENCE: 129
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
```

```
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGEGGS DSYQEEVIKL  240
CGRELVRAQI AICGKSTGGE GSGGEGEGGG RQLYSALANK CCYVGCTKRS LAQFC       295

SEQ ID NO: 130           moltype = AA   length = 295
FEATURE                  Location/Qualifiers
source                   1..295
                         mol_type = protein
                         organism = synthetic construct
SEQUENCE: 130
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGEGGS DSYQEEVIKL  240
CGRELVRAQI AICGKSTGGE GSGGEGEGGG RQLYSALANK CCKVGCTKRS LAQFC       295

SEQ ID NO: 131           moltype = AA   length = 295
FEATURE                  Location/Qualifiers
source                   1..295
                         mol_type = protein
                         organism = synthetic construct
SEQUENCE: 131
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGEGGS DSYQEEVIKL  240
CGRELVRAQI AICGKSTGGE GSGGEGSGGG RQLYSALANK CCYVGCTKRS LAQFC       295

SEQ ID NO: 132           moltype = AA   length = 295
FEATURE                  Location/Qualifiers
source                   1..295
                         mol_type = protein
                         organism = synthetic construct
SEQUENCE: 132
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGEGGS DSYQEEVIKL  240
CGRELVRAQI AICGKSTGGE GSGGEGSGGG RQLYSALANK CCKVGCTKRS LAQFC       295

SEQ ID NO: 133           moltype = AA   length = 295
FEATURE                  Location/Qualifiers
source                   1..295
                         mol_type = protein
                         organism = synthetic construct
SEQUENCE: 133
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTASD AAGAEAEAGA RQLYSALANK CCYVGCTKQS LAQFC       295

SEQ ID NO: 134           moltype = AA   length = 295
FEATURE                  Location/Qualifiers
source                   1..295
                         mol_type = protein
                         organism = synthetic construct
SEQUENCE: 134
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTASD AAGAEAEAGA RQLYSALANK CCKVGCTKQS LAQFC       295

SEQ ID NO: 135           moltype = AA   length = 295
FEATURE                  Location/Qualifiers
source                   1..295
                         mol_type = protein
                         organism = synthetic construct
SEQUENCE: 135
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGEGGG RQLYSALANK CCYVGCTKQS LAQFC       295

SEQ ID NO: 136           moltype = AA   length = 295
FEATURE                  Location/Qualifiers
source                   1..295
```

```
                        mol_type = protein
                        organism = synthetic construct
SEQUENCE: 136
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGEGGG RQLYSALANK CCKVGCTKQS LAQFC       295

SEQ ID NO: 137          moltype = AA  length = 295
FEATURE                 Location/Qualifiers
source                  1..295
                        mol_type = protein
                        organism = synthetic construct
SEQUENCE: 137
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGSGGG RQLYSALANK CCYVGCTKQS LAQFC       295

SEQ ID NO: 138          moltype = AA  length = 295
FEATURE                 Location/Qualifiers
source                  1..295
                        mol_type = protein
                        organism = synthetic construct
SEQUENCE: 138
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGSGGG RQLYSALANK CCKVGCTKQS LAQFC       295

SEQ ID NO: 139          moltype = AA  length = 315
FEATURE                 Location/Qualifiers
source                  1..315
                        mol_type = protein
                        organism = synthetic construct
SEQUENCE: 139
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTASD AAGADANAGA RQLYSALANK  300
CCHVGCTKRS LAQFC                                                   315

SEQ ID NO: 140          moltype = AA  length = 315
FEATURE                 Location/Qualifiers
source                  1..315
                        mol_type = protein
                        organism = synthetic construct
SEQUENCE: 140
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTASD AAGANADAGA RQLYSALANK  300
CCHVGCTKRS LAQFC                                                   315

SEQ ID NO: 141          moltype = AA  length = 315
FEATURE                 Location/Qualifiers
source                  1..315
                        mol_type = protein
                        organism = synthetic construct
SEQUENCE: 141
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTASD AAGADADAGA RQLYSALANK  300
CCHVGCTKRS LAQFC                                                   315

SEQ ID NO: 142          moltype = AA  length = 315
FEATURE                 Location/Qualifiers
source                  1..315
                        mol_type = protein
                        organism = synthetic construct
SEQUENCE: 142
METDTLLLWV LLLWVPGSTG DKTHTCPPCP APEAAGGPSV FLFPPKPKDT LMISRTPEVT   60
```

```
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGKGGS DSWQEEVIKL CGRELVRAQI AICGKSTASD AAGAEAEAGA RQLYSALANK    300
CCHVGCTKRS LAQFC                                                     315

SEQ ID NO: 143          moltype = AA   length = 315
FEATURE                 Location/Qualifiers
source                  1..315
                        mol_type = protein
                        organism = synthetic construct
SEQUENCE: 143
METDTLLLWV LLLWVPGSTG DKTHTCPPCP APEAAGGPSV FLFPPKPKDT LMISRTPEVT     60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGKGGS DSWQEEVIKL CGRELVRAQI AICGKSTASD AAGAQADAGA RQLYSALANK    300
CCHVGCTKRS LAQFC                                                     315

SEQ ID NO: 144          moltype = AA   length = 315
FEATURE                 Location/Qualifiers
source                  1..315
                        mol_type = protein
                        organism = synthetic construct
SEQUENCE: 144
METDTLLLWV LLLWVPGSTG DKTHTCPPCP APEAAGGPSV FLFPPKPKDT LMISRTPEVT     60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGKGGS DSWQEEVIKL CGRELVRAQI AICGKSTASD AAGADAQAGA RQLYSALANK    300
CCHVGCTKRS LAQFC                                                     315

SEQ ID NO: 145          moltype = AA   length = 315
FEATURE                 Location/Qualifiers
source                  1..315
                        mol_type = protein
                        organism = synthetic construct
SEQUENCE: 145
METDTLLLWV LLLWVPGSTG DKTHTCPPCP APEAAGGPSV FLFPPKPKDT LMISRTPEVT     60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGKGGS DSWQEEVIKL CGRELVRAQI AICGKSTASD AAGAQAQAGA RQLYSALANK    300
CCHVGCTKRS LAQFC                                                     315

SEQ ID NO: 146          moltype = AA   length = 315
FEATURE                 Location/Qualifiers
source                  1..315
                        mol_type = protein
                        organism = synthetic construct
SEQUENCE: 146
METDTLLLWV LLLWVPGSTG DKTHTCPPCP APEAAGGPSV FLFPPKPKDT LMISRTPEVT     60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGEGGS DSWQEEVIKL CGRELVRAQI AICGKSTASD AAGADANAGA RQLYSALANK    300
CCHVGCTKRS LAQFC                                                     315

SEQ ID NO: 147          moltype = AA   length = 315
FEATURE                 Location/Qualifiers
source                  1..315
                        mol_type = protein
                        organism = synthetic construct
SEQUENCE: 147
METDTLLLWV LLLWVPGSTG DKTHTCPPCP APEAAGGPSV FLFPPKPKDT LMISRTPEVT     60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGEGGS DSWQEEVIKL CGRELVRAQI AICGKSTASD AAGANADAGA RQLYSALANK    300
CCHVGCTKRS LAQFC                                                     315

SEQ ID NO: 148          moltype = AA   length = 315
FEATURE                 Location/Qualifiers
source                  1..315
                        mol_type = protein
                        organism = synthetic construct
SEQUENCE: 148
METDTLLLWV LLLWVPGSTG DKTHTCPPCP APEAAGGPSV FLFPPKPKDT LMISRTPEVT     60
CVVVDVSHED PEVKFNWYVD GVEVHNAKTK PREEQYNSTY RVVSVLTVLH QDWLNGKEYK    120
```

```
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGEGGS DSWQEEVIKL CGRELVRAQI AICGKSTASD AAGADADAGA RQLYSALANK    300
CCHVGCTKRS LAQFC                                                    315

SEQ ID NO: 149          moltype = AA   length = 315
FEATURE                 Location/Qualifiers
source                  1..315
                        mol_type = protein
                        organism = synthetic construct
SEQUENCE: 149
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGEGGS DSWQEEVIKL CGRELVRAQI AICGKSTASD AAGAEAEAGA RQLYSALANK    300
CCHVGCTKRS LAQFC                                                    315

SEQ ID NO: 150          moltype = AA   length = 315
FEATURE                 Location/Qualifiers
source                  1..315
                        mol_type = protein
                        organism = synthetic construct
SEQUENCE: 150
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGEGGS DSWQEEVIKL CGRELVRAQI AICGKSTASD AAGAQADAGA RQLYSALANK    300
CCHVGCTKRS LAQFC                                                    315

SEQ ID NO: 151          moltype = AA   length = 315
FEATURE                 Location/Qualifiers
source                  1..315
                        mol_type = protein
                        organism = synthetic construct
SEQUENCE: 151
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGEGGS DSWQEEVIKL CGRELVRAQI AICGKSTASD AAGADAQAGA RQLYSALANK    300
CCHVGCTKRS LAQFC                                                    315

SEQ ID NO: 152          moltype = AA   length = 315
FEATURE                 Location/Qualifiers
source                  1..315
                        mol_type = protein
                        organism = synthetic construct
SEQUENCE: 152
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGEGGS DSWQEEVIKL CGRELVRAQI AICGKSTASD AAGAQAQAGA RQLYSALANK    300
CCHVGCTKRS LAQFC                                                    315

SEQ ID NO: 153          moltype = AA   length = 315
FEATURE                 Location/Qualifiers
source                  1..315
                        mol_type = protein
                        organism = synthetic construct
SEQUENCE: 153
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGEGGS DSWQEEVIKL CGRELVRAQI AICGQSTASD AAGADANAGA RQLYSALANK    300
CCHVGCTKRS LAQFC                                                    315

SEQ ID NO: 154          moltype = AA   length = 315
FEATURE                 Location/Qualifiers
source                  1..315
                        mol_type = protein
                        organism = synthetic construct
SEQUENCE: 154
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
```

```
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGANADAGA RQLYSALANK   300
CCHVGCTKRS LAQFC                                                   315

SEQ ID NO: 155            moltype = AA  length = 315
FEATURE                   Location/Qualifiers
source                    1..315
                          mol_type = protein
                          organism = synthetic construct
SEQUENCE: 155
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGADADAGA RQLYSALANK   300
CCHVGCTKRS LAQFC                                                   315

SEQ ID NO: 156            moltype = AA  length = 315
FEATURE                   Location/Qualifiers
source                    1..315
                          mol_type = protein
                          organism = synthetic construct
SEQUENCE: 156
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGAEAEAGA RQLYSALANK   300
CCHVGCTKRS LAQFC                                                   315

SEQ ID NO: 157            moltype = AA  length = 315
FEATURE                   Location/Qualifiers
source                    1..315
                          mol_type = protein
                          organism = synthetic construct
SEQUENCE: 157
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGAQADAGA RQLYSALANK   300
CCHVGCTKRS LAQFC                                                   315

SEQ ID NO: 158            moltype = AA  length = 315
FEATURE                   Location/Qualifiers
source                    1..315
                          mol_type = protein
                          organism = synthetic construct
SEQUENCE: 158
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGADAQAGA RQLYSALANK   300
CCHVGCTKRS LAQFC                                                   315

SEQ ID NO: 159            moltype = AA  length = 315
FEATURE                   Location/Qualifiers
source                    1..315
                          mol_type = protein
                          organism = synthetic construct
SEQUENCE: 159
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGAQAQAGA RQLYSALANK   300
CCHVGCTKRS LAQFC                                                   315

SEQ ID NO: 160            moltype = AA  length = 315
FEATURE                   Location/Qualifiers
source                    1..315
                          mol_type = protein
                          organism = synthetic construct
SEQUENCE: 160
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
```

```
LSLSPGEGGS DSWQEEVIKL CGRELVRAQI AICGKSTASD AAGADANAGA RQLYSALANK  300
CCHVGCTKQS LAQFC                                                  315

SEQ ID NO: 161          moltype = AA  length = 315
FEATURE                 Location/Qualifiers
source                  1..315
                        mol_type = protein
                        organism = synthetic construct
SEQUENCE: 161
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGEGGS DSWQEEVIKL CGRELVRAQI AICGKSTASD AAGANADAGA RQLYSALANK  300
CCHVGCTKQS LAQFC                                                  315

SEQ ID NO: 162          moltype = AA  length = 315
FEATURE                 Location/Qualifiers
source                  1..315
                        mol_type = protein
                        organism = synthetic construct
SEQUENCE: 162
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGEGGS DSWQEEVIKL CGRELVRAQI AICGKSTASD AAGADADAGA RQLYSALANK  300
CCHVGCTKQS LAQFC                                                  315

SEQ ID NO: 163          moltype = AA  length = 315
FEATURE                 Location/Qualifiers
source                  1..315
                        mol_type = protein
                        organism = synthetic construct
SEQUENCE: 163
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGEGGS DSWQEEVIKL CGRELVRAQI AICGKSTASD AAGAEAEGA RQLYSALANK   300
CCHVGCTKQS LAQFC                                                  315

SEQ ID NO: 164          moltype = AA  length = 315
FEATURE                 Location/Qualifiers
source                  1..315
                        mol_type = protein
                        organism = synthetic construct
SEQUENCE: 164
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGEGGS DSWQEEVIKL CGRELVRAQI AICGKSTASD AAGAQADAGA RQLYSALANK  300
CCHVGCTKQS LAQFC                                                  315

SEQ ID NO: 165          moltype = AA  length = 315
FEATURE                 Location/Qualifiers
source                  1..315
                        mol_type = protein
                        organism = synthetic construct
SEQUENCE: 165
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGEGGS DSWQEEVIKL CGRELVRAQI AICGKSTASD AAGADAQAGA RQLYSALANK  300
CCHVGCTKQS LAQFC                                                  315

SEQ ID NO: 166          moltype = AA  length = 315
FEATURE                 Location/Qualifiers
source                  1..315
                        mol_type = protein
                        organism = synthetic construct
SEQUENCE: 166
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGEGGS DSWQEEVIKL CGRELVRAQI AICGKSTASD AAGAQAQAGA RQLYSALANK  300
```

```
CCHVGCTKQS LAQFC                                                   315

SEQ ID NO: 167         moltype = AA   length = 315
FEATURE                Location/Qualifiers
source                 1..315
                       mol_type = protein
                       organism = synthetic construct
SEQUENCE: 167
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGADANAGA RQLYSALANK   300
CCHVGCTKQS LAQFC                                                   315

SEQ ID NO: 168         moltype = AA   length = 315
FEATURE                Location/Qualifiers
source                 1..315
                       mol_type = protein
                       organism = synthetic construct
SEQUENCE: 168
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGANADAGA RQLYSALANK   300
CCHVGCTKQS LAQFC                                                   315

SEQ ID NO: 169         moltype = AA   length = 315
FEATURE                Location/Qualifiers
source                 1..315
                       mol_type = protein
                       organism = synthetic construct
SEQUENCE: 169
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGADADAGA RQLYSALANK   300
CCHVGCTKQS LAQFC                                                   315

SEQ ID NO: 170         moltype = AA   length = 315
FEATURE                Location/Qualifiers
source                 1..315
                       mol_type = protein
                       organism = synthetic construct
SEQUENCE: 170
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGAEAEAGA RQLYSALANK   300
CCHVGCTKQS LAQFC                                                   315

SEQ ID NO: 171         moltype = AA   length = 315
FEATURE                Location/Qualifiers
source                 1..315
                       mol_type = protein
                       organism = synthetic construct
SEQUENCE: 171
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGAQADAGA RQLYSALANK   300
CCHVGCTKQS LAQFC                                                   315

SEQ ID NO: 172         moltype = AA   length = 315
FEATURE                Location/Qualifiers
source                 1..315
                       mol_type = protein
                       organism = synthetic construct
SEQUENCE: 172
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSWQEEVIKL CGRELVRAQI AICGQSTASD AAGADAQAGA RQLYSALANK   300
CCHVGCTKQS LAQFC                                                   315
```

```
SEQ ID NO: 173           moltype = AA   length = 315
FEATURE                  Location/Qualifiers
source                   1..315
                         mol_type = protein
                         organism = synthetic construct
SEQUENCE: 173
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGEGGS DSWQEEVIKL CGRELVRAQI AICGQSTASD AAGAQAQAGA RQLYSALANK  300
CCHVGCTKQS LAQFC                                                  315

SEQ ID NO: 174           moltype = AA   length = 315
FEATURE                  Location/Qualifiers
source                   1..315
                         mol_type = protein
                         organism = synthetic construct
SEQUENCE: 174
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSYQEEVIKL CGRELVRAQI AICGKSTASD AAGAEAEAGA RQLYSALANK  300
CCHVGCTKRS LAQFC                                                  315

SEQ ID NO: 175           moltype = AA   length = 315
FEATURE                  Location/Qualifiers
source                   1..315
                         mol_type = protein
                         organism = synthetic construct
SEQUENCE: 175
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSFQEEVIKL CGRELVRAQI AICGKSTASD AAGAEAEAGA RQLYSALANK  300
CCHVGCTKRS LAQFC                                                  315

SEQ ID NO: 176           moltype = AA   length = 315
FEATURE                  Location/Qualifiers
source                   1..315
                         mol_type = protein
                         organism = synthetic construct
SEQUENCE: 176
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSLQEEVIKL CGRELVRAQI AICGKSTASD AAGAEAEAGA RQLYSALANK  300
CCHVGCTKRS LAQFC                                                  315

SEQ ID NO: 177           moltype = AA   length = 315
FEATURE                  Location/Qualifiers
source                   1..315
                         mol_type = protein
                         organism = synthetic construct
SEQUENCE: 177
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSIQEEVIKL CGRELVRAQI AICGKSTASD AAGAEAEAGA RQLYSALANK  300
CCHVGCTKRS LAQFC                                                  315

SEQ ID NO: 178           moltype = AA   length = 315
FEATURE                  Location/Qualifiers
source                   1..315
                         mol_type = protein
                         organism = synthetic construct
SEQUENCE: 178
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTASD AAGAEAEAGA RQLYSALANK  300
CCYVGCTKRS LAQFC                                                  315
```

```
SEQ ID NO: 179          moltype = AA   length = 315
FEATURE                 Location/Qualifiers
source                  1..315
                        mol_type = protein
                        organism = synthetic construct
SEQUENCE: 179
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWQEEVIKL CGRELVRAQI AICGKSTASD AAGAEAEAGA RQLYSALANK   300
CCLVGCTKRS LAQFC                                                    315

SEQ ID NO: 180          moltype = AA   length = 315
FEATURE                 Location/Qualifiers
source                  1..315
                        mol_type = protein
                        organism = synthetic construct
SEQUENCE: 180
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWQEEVIKL CGRELVRAQI AICGKSTASD AAGAEAEAGA RQLYSALANK   300
CCQVGCTKRS LAQFC                                                    315

SEQ ID NO: 181          moltype = AA   length = 315
FEATURE                 Location/Qualifiers
source                  1..315
                        mol_type = protein
                        organism = synthetic construct
SEQUENCE: 181
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWQEEVIKL CGRELVRAQI AICGKSTASD AAGAEAEAGA RQLYSALANK   300
CCKVGCTKRS LAQFC                                                    315

SEQ ID NO: 182          moltype = AA   length = 315
FEATURE                 Location/Qualifiers
source                  1..315
                        mol_type = protein
                        organism = synthetic construct
SEQUENCE: 182
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSYQEEVIKL CGRELVRAQI AICGKSTASD AAGAEAEAGA RQLYSALANK   300
CCYVGCTKRS LAQFC                                                    315

SEQ ID NO: 183          moltype = AA   length = 315
FEATURE                 Location/Qualifiers
source                  1..315
                        mol_type = protein
                        organism = synthetic construct
SEQUENCE: 183
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSYQEEVIKL CGRELVRAQI AICGKSTASD AAGAEAEAGA RQLYSALANK   300
CCKVGCTKRS LAQFC                                                    315

SEQ ID NO: 184          moltype = AA   length = 315
FEATURE                 Location/Qualifiers
source                  1..315
                        mol_type = protein
                        organism = synthetic construct
SEQUENCE: 184
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSYQEEVIKL CGRELVRAQI AICGKSTGGE GSGGEGEGGG RQLYSALANK   300
CCYVGCTKRS LAQFC                                                    315

SEQ ID NO: 185          moltype = AA   length = 315
```

```
FEATURE                 Location/Qualifiers
source                  1..315
                        mol_type = protein
                        organism = synthetic construct
SEQUENCE: 185
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSYQEEVIKL CGRELVRAQI AICGKSTGGE GSGGEGEGGG RQLYSALANK   300
CCKVGCTKRS LAQFC                                                   315

SEQ ID NO: 186          moltype = AA  length = 315
FEATURE                 Location/Qualifiers
source                  1..315
                        mol_type = protein
                        organism = synthetic construct
SEQUENCE: 186
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSYQEEVIKL CGRELVRAQI AICGKSTGGE GSGGEGSGGG RQLYSALANK   300
CCYVGCTKRS LAQFC                                                   315

SEQ ID NO: 187          moltype = AA  length = 315
FEATURE                 Location/Qualifiers
source                  1..315
                        mol_type = protein
                        organism = synthetic construct
SEQUENCE: 187
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGEGGS DSYQEEVIKL CGRELVRAQI AICGKSTGGE GSGGEGSGGG RQLYSALANK   300
CCKVGCTKRS LAQFC                                                   315

SEQ ID NO: 188          moltype = AA  length = 315
FEATURE                 Location/Qualifiers
source                  1..315
                        mol_type = protein
                        organism = synthetic construct
SEQUENCE: 188
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTASD AAGAEAEAGA RQLYSALANK   300
CCYVGCTKQS LAQFC                                                   315

SEQ ID NO: 189          moltype = AA  length = 315
FEATURE                 Location/Qualifiers
source                  1..315
                        mol_type = protein
                        organism = synthetic construct
SEQUENCE: 189
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTASD AAGAEAEAGA RQLYSALANK   300
CCKVGCTKQS LAQFC                                                   315

SEQ ID NO: 190          moltype = AA  length = 315
FEATURE                 Location/Qualifiers
source                  1..315
                        mol_type = protein
                        organism = synthetic construct
SEQUENCE: 190
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGEGGG RQLYSALANK   300
CCYVGCTKQS LAQFC                                                   315

SEQ ID NO: 191          moltype = AA  length = 315
FEATURE                 Location/Qualifiers
```

```
source                  1..315
                        mol_type = protein
                        organism = synthetic construct
SEQUENCE: 191
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGEGGG RQLYSALANK   300
CCKVGCTKQS LAQFC                                                    315

SEQ ID NO: 192          moltype = AA  length = 315
FEATURE                 Location/Qualifiers
source                  1..315
                        mol_type = protein
                        organism = synthetic construct
SEQUENCE: 192
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGSGGG RQLYSALANK   300
CCYVGCTKQS LAQFC                                                    315

SEQ ID NO: 193          moltype = AA  length = 315
FEATURE                 Location/Qualifiers
source                  1..315
                        mol_type = protein
                        organism = synthetic construct
SEQUENCE: 193
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGSGGG RQLYSALANK   300
CCKVGCTKQS LAQFC                                                    315

SEQ ID NO: 194          moltype = DNA  length = 945
FEATURE                 Location/Qualifiers
source                  1..945
                        mol_type = other DNA
                        organism = synthetic construct
SEQUENCE: 194
atggagactg acacactcct cctttgggtt ttgctgttgt gggtgcctgg atctactggc    60
gacaagaccc atacatgtcc gccttgtcct gcgcctgagg cagcaggcgg accatcagtc   120
ttcttgtttc cccccaagcc gaaggacacc cttatgatct cacgcacccc cgaagtaact   180
tgtgtagtcg ttgatgtctc acacgaagac ccggaagtaa agtttaattg gtatgtcgat   240
ggtgttgagg tccacaacgc taaaacgaaa ccgcgggaag aacaatacaa ctccacatat   300
cgagtagtct ccgtcctgac tgttcttcac caggactggc tgaatggtaa agaatacaaa   360
tgtaaagtga gtaacaaggc ccttgcagca cccatcgaga gacgatatc caaagccaag   420
gggcaaccgc gcgagccaca agtttacacg ctcccaccct caagagacga actcaccaaa   480
aatcaagtgt ccctgacatg tctggtgaaa ggattctatc ccagcgacat agctgtagaa   540
tgggagagta atggccaacc cgaaaacaat tacaaaacta cccccccggt tttggatagt   600
gatggttcat tcttcctcta tagtaaactt accgtggata gtctcggtg cagcaggggg   660
aacgtgttta gctgttcagt cctccatgag gcactccata gtcactatac gcaaaagtca   720
ttgtcccttt ctccgggcaa gggcgggtca gactcctggc aggaagaggt aattaagctt   780
tgtgggcgag aactcgttag ggcacagata gcaatctgcg ggaaaagtac agcttccgat   840
gctgccgggg ctgacgccaa tgcgggagca cgccagctct actcagccct cgccaacaag   900
tgttgtcatg taggttgcac caaaagaagt ctggcacagt tttgc                   945

SEQ ID NO: 195          moltype = DNA  length = 945
FEATURE                 Location/Qualifiers
source                  1..945
                        mol_type = other DNA
                        organism = synthetic construct
SEQUENCE: 195
atggaaacag acactcttct tttgtgggtc ttgttgctct gggtccctgg ctcaacaggc    60
gacaagacgc atacttgtcc tccctgccca gctcccgaag cggctggggg gccctctgtc   120
tttctgtttc cgcctaagcc caaggacacg ctcatgataa gtcgcactcc ggaagtcacc   180
tgtgttgtcg tcgatgttag ccatgaagat ccagaggtga aatttaactg gtacgtcgac   240
ggagtggagg ttcacaatgc taaaaccaaa ccgcgagaag agcaataca ttccacgtat   300
agggtcgtct ccgtcctgac agtactccat caggattggc tgaatggaaa agaatacaag   360
tgcaaggttt ccaataaagc cttggccgca cctattgaga aaacgatatc aaaagctaag   420
ggacaacctc gggagccgca agtatataca ctcccccctt ctaggagaca actgacaaaa   480
aaccaagtta gtctgacttg tcttgtgaaa ggttttttacc cgagtgatat agccgtagaa   540
tgggagagca atgccagcc cgaaaacaat tacaaaacaa ctcccccagt attggacagt   600
gacgggtcat ttttttttgta ttctaaattg accgtagaca gtcacgctg caacaagggg   660
aatgtattta gctgttccgt ccttcatgag gcgctccata gccattacac tcagaagtct   720
ttgtcactgt caccgggcaa gggtggttct gattcatggc aagaggaagt gattaagctg   780
```

```
tgcggtcggg agttggtaag agctcaaatt gcgatttgtg gcaagagcac tgcgtccgat   840
gccgcaggtg ctaatgccga cgccggtgcg agacagcttt attctgcgct ggccaacaag   900
tgctgccacg tcggatgcac caaacggagc cttgctcagt tttgc                   945

SEQ ID NO: 196         moltype = DNA   length = 945
FEATURE                Location/Qualifiers
source                 1..945
                       mol_type = other DNA
                       organism = synthetic construct
SEQUENCE: 196
atggaaaccg acaccctgct tctctgggtg ctgctgctct gggtaccagg gtctacaggt    60
gacaaaactc atacttgtcc accatgccca gcccccgagg cggctggcgg ccccagcgta   120
ttcctttcc ccccaaaacc taaggacacg cttatgatat ctagaacccc ggaggtcaca   180
tgtgtcgtcg tagacgtaag tcacgaagat cctgaagtca agtttaactg gtacgtcgat   240
ggagtcgagg tccataatgc taaaacgaag cctcgcgaag aacagtataa ttctacctat   300
cgcgtagtct ctgtcctcac cgtcttgcat caagactggt tgaacggcaa ggagtacaag   360
tgtaaggttt caaacaaagc ccttgccgcg ccgatagaga aacaattag caaagcgaag   420
gggcagccga gagagccgca agtgtatacc cttcctccta gtagagcga gttgaccaaa   480
aaccaggtgt cacttacatg cctcgtgaaa ggcttctacc cgagtgatat tgcagtcgag   540
tgggaatcca acgccagcc cgagaataac tacaaaacga cgccgcccgt actgacagt   600
gatggaagtt tttttttgta ctcaaaactc acggttgaca aaagtcggtg gcagcaaggg   660
aacgttttta gctgctctgt cctccatgaa gcactccatt ctcattatac ccagaagtct   720
ctgtctctct cccctggtaa gggaggttc gacagttggc aggaagaggt aataaaactc   780
tgcggtcgag agcttgttcg agcacaaatt gctatatgtg gaaaatctac cgcttcagac   840
gccgccggga ctgatgcgga tgccggggct cgccagctct atagcgcctt ggccaacaaa   900
tgttgtcacg ttggctgcac gaagcgctcc ctggctcagt tttgc                   945

SEQ ID NO: 197         moltype = DNA   length = 945
FEATURE                Location/Qualifiers
source                 1..945
                       mol_type = other DNA
                       organism = synthetic construct
SEQUENCE: 197
atggaaacgg atacgctgtt gttgtgggtt ctgctcttgt gggtgccagg gagcacaggt    60
gataaaaccc acacttgccc accttgccct cgcgccggaag ccgccggagg acctagtgtt   120
ttcctctttc cccctaagcc caaagacacg ttgatgatct ctcggacacc ggaagtaact   180
tgtgtcgttg tggatgtgtc acatgaggat cccgaggtga aatttaattg gtacgttgac   240
ggcgtggagg tgcataacgc aaagactaaa ccacgcgagg agcagtataa ttctacatac   300
cgggttgtct cagttctcac agttcttcat caggattggt tgaatgaaa ggagtacaaa   360
tgcaaagtgt ccaacaaagc gcttgctgcg ccgattgaaa agacgatttc aaaggcaaaa   420
gggcagcccc gcgaaccca gtatatact tgcctccct cacgcgatga actgactaag   480
aaccaggtga gcctgacttg tttggttaag ggttttatc caagtgacat tgctgttgaa   540
tgggagtcca atggccagcc tgagaataac tacaaaacga caccctcctgt acttgacagc   600
gacggctcct tttttcttta ttcaaaactc acagtggaca aatccaggtg gcagcagggt   660
aacgtctttt cttgcagcgt gctccacgaa gctttgcatt cacattatac gcaaaaatcc   720
ttgtcattgt cccaggtaa gggcggaagc gactcatggc aagaagaagt cattaaactt   780
tgtggacggg agctggttag ggcacagatt gctatttgtg gtaagtac ggctagtgac   840
gcagcgggcg ccgaagcgga agctggtgca aggcagcttt actctgctct ggctaacaag   900
tgttgtcacg ttgggtgtac caagcggtcc cttgcgcaat tctgc                   945

SEQ ID NO: 198         moltype = DNA   length = 945
FEATURE                Location/Qualifiers
source                 1..945
                       mol_type = other DNA
                       organism = synthetic construct
SEQUENCE: 198
atggagactg atacacttct tctctgggtc ctcctcctct gggttccagg ctcaacaggt    60
gataaaactc atacttgccc cccctgcccc gcgcctgaag ctgcagggggg gccatcagtc   120
ttcttgtttc caccaaaacc taaggatact ctcatgatta gccggacccc tgaggtgaca   180
tgtgttgtgg tcgatgtatc tcatgaagat cccgaagtaa aatttaactg gtacgtagac   240
ggggttgaag ttcataacgc gaaaacgaaa cctcgggagg agcaatataa tagcacgtat   300
agagttgttt cagtccttac agttctccac caagactggc tgaatggcaa ggagtataag   360
tgtaaagtat ccaataaagc cttggctgcg ccaatcgaga gacgatcag caaagccaaa   420
ggtcagcctc gcgaaccgca ggtctataca ttgccccctt cacgcgacga actcacgaaa   480
aatcaagtct ctttgacttg ccttgtgaaa ggcttctacc cctccgatat tgccgtcgaa   540
tgggaaagca atggacagcc ggaaaataat tacaaaacga caccccccgt gttggattcc   600
gatgggtcct tcttcctcta ttccaagctg acggtcgata agtctcgatg gcagcaggga   660
aatgtcttct cttgctccgt ccttcatgag gcattgcaca gccattatac tcaaaagagt   720
ctctctctgt ctccaggcaa aggggttcc gactcttggc aagaagaggt cataaaactg   780
tgcggccggg agctcgtcag agcgcagatc gctatatgtg gaaaatccac cgcgagtgac   840
gcagcaggtg cacaagccga cgcaggagct aggcaactgt actcagccct tgccaataag   900
tgttgtcacg taggttgtac taaacgctcc ctggcacaat tttgt                   945

SEQ ID NO: 199         moltype = DNA   length = 945
FEATURE                Location/Qualifiers
source                 1..945
                       mol_type = other DNA
                       organism = synthetic construct
SEQUENCE: 199
```

```
atggaaaccg ataccttgct cctttgggtt ctgctccttt gggtccctgg aagtacaggg    60
gataagacac acacgtgccc accctgcccc gccccagagg cagccggagg tcctagtgtg   120
tttctgttcc ccccaaagcc caaggacacc cttatgatat ctaggacacc agaagttacg   180
tgcgtcgttg tggacgttag ccacgaagac ccagaagtga agtttaattg gtacgttgat   240
ggagtcgaag tgcacaatgc aaaaacaaaa ccacgaagca agcagtataa cagtacttat   300
agagtagtca gcgtccttac tgtattgcat caggattggc tgaatgggaa ggaatatataa  360
tgtaaggtta gcaataaagc ccttgcggct cctatcgaga aaactattag caaagcaaag   420
ggccaacccc gagagcccca agtttataca ctgccaccca gtcgagatga gctgactaaa   480
aatcaagtat ccctgacctg cttggttaag gggttttatc ctagtgacat cgcggttgag   540
tgggaatcca acggccaacc ggagaataat tacaaaacca cgccacctgt attggattcc   600
gatggtagct tctttctcta tagtaaactt acagtcgata agtcaagatg gcagcaggga   660
aacgtatttt catgctcagt tctgcatgag gccttgcact cccattacac tcaaaaatca   720
ctgagcctca gtcctggtaa gggtggctct gactcatggc aggaggaagt aatcaagctg   780
tgtgggaggg aattggtaag ggctcagatt gcaatttgtg gaaagagcac agcgtctgac   840
gctgcaggtg ccgacgcaca ggcgggcgcg aggcagctct acagtgctct tgcgaacaag   900
tgttgtcatg taggttgcac gaaacgaagt ttggcgcaat tctgt              945

SEQ ID NO: 200          moltype = DNA   length = 945
FEATURE                 Location/Qualifiers
source                  1..945
                        mol_type = other DNA
                        organism = synthetic construct
SEQUENCE: 200
atggagactg acactctcct tctttgggtg ctgttgctct gggttcccgg aagcacgggg    60
gataaaacac acacctgccc cccttgccca gcacctgaag cagcgggtgg tcccagcgtt   120
tttcttttcc ccctaagcc aaggacacg ctcatgataa gtcgcaccc ggaggtcacc     180
tgcgtcgttg ttgacgtatc acatgaagat cctgaggtga agtttaattg gtacgtagat   240
ggtgttgagg tccacaacgc aaagacgaaa ccgagggaag aacagtacaa cagtacttat   300
cgcgtagtct ccgttctgac tgtcctgcat caagattggc tgaacgggaa ggagtacaag   360
tgcaaagtta gtaacaaggc tctcgcggcc ccaattgaga agcagatatc caaagcgaaa   420
ggacagccga gagagcccca agtctacact ctgcccccctt ccagggatga gctcaccaaa  480
aatcaggtca gtctcacgtg cctggttaag ggattctacc caagtgatat agcagttgaa   540
tgggagagta acggccagcc cgagaacaac tataaaacta caccgccgt tcttgattcc    600
gatgggtctt tcttccttta tagtaagctc accgttgata agtcccgatg gcagcaaggt   660
aatgtcttct catgttcagt tctcatgaa gccctgcatt cccattatac acaaaagagc   720
ttgtccttgt caccgggcaa aggcggtagc gattcttggc aagaagaagt tataaagttg   780
tgcggtaggg aactggtacg cgctcaaata gctatatgcg gtaagtctac tgcttcagat   840
gcggctggcg cacaggcaca ggccggtgct agacaactct atagtgcgct ggccaacaag   900
tgctgccatg tggggtgtac aaaacggagt cttgcccagt tttgt              945

SEQ ID NO: 201          moltype = DNA   length = 945
FEATURE                 Location/Qualifiers
source                  1..945
                        mol_type = other DNA
                        organism = synthetic construct
SEQUENCE: 201
atggaaactg acacgctttt gctttgggtc ctccttcttt gggttcccgg ctctactgga    60
gacaaaactc atacatgccc cccatgccca gcacccgaag cggccggagg tccgtctgtc   120
tttctgtttc cgccgaaacc taaagatacg ttgatgatta gcagaacccc tgaggtaaca   180
tgtgtggtag tcgatgtctc ccatgaggac cccgaggtaa agttcaattg gtatgttgac   240
ggcgtcgaag tccataacgc aaaaacgaag ccccgagagg agcaatataa cctctacctat  300
cgcgttgttt ctgttttgac tgtgttgcac caggattggc tcaacggcaa ggaatacaaa   360
tgtaaagtgt ccaacaaggc ccttgctgca cctatcgaaa aaacgattag taaggcaaag   420
ggacaaccgc gcgaaccaca ggtatatact ttgccgccta gcagagatga actcaccaag   480
aatcaagttt cccttacctg tttggttaaa ggatttttac cgtctgacat agctgttgaa   540
tgggagagca atggtcagcc ggaaaataat tataaaacca cccgccagt attggattca    600
gatgggtcct ttttcttgta ttctaaactt accgtggata gtctaggtg caacagggaa    660
aacgtctttt catgtagtgt acttcatgaa gccctccata gtcactacac gcagaaatcc   720
ttgtctctta gtccggggtga aggtgggtct gattcctggc aggaagaggt gataaagctc   780
tgtggtcggg aactttgttag ggcgcagatc gctattgcg gcaaatctac agcatcgagt   840
gccgccggag ctgatgcgaa cgcaggagcg aggcagctgt actccgcact tgctaacaag   900
tgttgccatg tcggctgcac caagaggagt cttgctcaat tctgc              945

SEQ ID NO: 202          moltype = DNA   length = 945
FEATURE                 Location/Qualifiers
source                  1..945
                        mol_type = other DNA
                        organism = synthetic construct
SEQUENCE: 202
atggaaaccg acaccctcct tctttgggtc ttgctgcttt gggttcctgg ttctactgga    60
gataagaccc atacatgccc gccatgtccc gcacccgagg cagcgggtgg accctctgtc   120
tttctgttcc ctccaaagcc aaaagatacc ctgatgatta gccgaacccc ggaggtgact   180
tgtgtcgtag tagatgtcag tcacgaggat cccgaagtaa agtttaattg gtatgtggac   240
ggtgtggagg tacataacgc taagacgaaa ccccgagagg aacaatacaa ctctacgtac   300
agggtcgtct cagtgctcac ggtcctgcac caggactggc ttaatgggaa ggaatatataa  360
tgcaaagtct ctaataaggc gcttgctgca cctattgaaa aaacgatttc taaggcgaag   420
ggacaacccc gggagccaca agtctacacc cttcctccaa gcagagatga gcttacgaaa   480
aatcaagtgt ctcttacgtg cctcgtaaag ggcttttacc catccgacat tgcggtggag   540
tgggaatcaa acgggcagcc ggaaaataac tacaaaacag cgccgcctgt attggattcc   600
```

```
gacggctctt tcttcctta cagcaaactg acagtcgata aatccagatg gcaacaaggg   660
aacgttttt catgttccgt tctgcatgaa gcccttcaca gtcattacac ccaaaagtca   720
cttcactt caccgggcga ggggggggtca gactcctggc aagaggaagt tataaagttg   780
tgcggcaggg aactggttag agcgcagata gcgatttgcg gaaaatctac tgcgagtgat   840
gctgcgggag cgaatgcgga cgccgggcc cgacagctct attccgcact cgccaataag   900
tgctgccatg ttggttgtac gaagagaagt cttgcacaat tttgc                  945

SEQ ID NO: 203           moltype = DNA   length = 945
FEATURE                  Location/Qualifiers
source                   1..945
                         mol_type = other DNA
                         organism = synthetic construct
SEQUENCE: 203
atggaaacag acacgctgct tttgtgggta ctgttgcttt gggtcccagg atccacaggt    60
gataagacac atacatgccc cccctgcccg gctcccgaag ctgccggggg accgtcagtg   120
ttttgtttc cgcccaagcc gaaggatact tgatgatta gtcggacacc agaagtgaca   180
tgtgttgtcg ttgacgtgag tcacgaggat cccgaggtca agttcaactg gtacgttgat   240
ggggttgaag ttcacaacgc taaaacgaaa ccccgcgaag agcagtataa tccccacttac  300
cgggtcgtca gtgtcctgac ggtcttgcac caggactggc tgaatggaaa ggaatacaag   360
tgtaaagttt ccaataaagc actggccgcc ccgatcgaaa aaacaatttc caaagctaag   420
ggacagccca gggaaccgca agtttatact cttccaccct cccgggatga actgaccaaa   480
aaccagtgt ctttgacgtg cctcgtaaag ggcttctcac cgtcagacat agctgtcgaa   540
tgggagtcta atgacagcc ggaaaacaat tataagacta caccgccggt gcttgatagt   600
gatgaagtt tcttttgta ctccaaactt acggtcgata aaagccggtg gcagcaggga   660
aacgtattca gttgtagcgt tctgcatgaa gctcttcatt ctcactacac ccagaagtct   720
ctgtctctga gccccggaga gggtggatct gattcttggc aggaagaagt gataaagttg   780
tgcggccggg aattggtacg cgcccagata gccatttgcg ggaagtctac ggcgagtgac   840
gcagcaggtg ctgacgcgga cgctggtgct agacagctgt attctgccct ggctaataag   900
tgttgccacg ttggctgcac caagagatcc ctggcccaat tctgt                  945

SEQ ID NO: 204           moltype = DNA   length = 945
FEATURE                  Location/Qualifiers
source                   1..945
                         mol_type = other DNA
                         organism = synthetic construct
SEQUENCE: 204
atggaaactg acactttgct gttgtgggtc ctcctgttgt gggtcccgg aagtacagga    60
gacaagacac atacttgtcc cccctgccca gctccagaag ctgccggagg gccgtcagtg   120
ttccttttcc ctccaaaacc taaggatacg ctttatgattt ctcgaacgcc agaggttacg   180
tgtgtagtcg tggacgtttc ccacgaggat cctgaggtca agtttaactg gtatgtagac   240
ggggttgagg tccataatgc caagacaaag ccgcgcgagg aacaatacaa cagtacatat   300
agggtggtga gcgtcctcac agtcttgcat caagattggc tcaacggcaa agagtacaaa   360
tgtaaggtta gcaacaaagc cctcgctgct ccatcgaaa acgatttc taaggcgaaa   420
ggccaaccac gagaaccgca agtatatact cttccccctt cacgggacga gctgaccaaa   480
aaccaggtat ccttgacttg cctggtcaaa ggattttacc cctctgatat tgcggtcgag   540
tgggagagta atgggcaacc agaaaataat tataaaacga cccccccggt actcgacagt   600
gatgggtctt ttttcctgta ttctaagctt acggttgata gtcgtagtag gcagcaaggg   660
aatgtcttct catgtagtgt tctgcatgaa gcacttcatt ctcactatac tcagaaatct   720
cttccctta gtccgggaga aggtgggagc gatagttggc aagaggaggt gataaaactg   780
tgtggtcggg agctggtgag agcccaaata gctatctgcg gcaaatcaac agcaagtgat   840
gcggcaggag cggaagcgga ggcgggagcg cggcaattgt atagtgccct tgctaataaa   900
tgctgtcacg ttgggtgtac taaacgatct cttgctcaat tctgc                  945

SEQ ID NO: 205           moltype = DNA   length = 945
FEATURE                  Location/Qualifiers
source                   1..945
                         mol_type = other DNA
                         organism = synthetic construct
SEQUENCE: 205
atggagacgg atacgttgtt gctttgggtc ctcctgttgt gggtgcccgg ctctaccggt    60
gataaaaccc atacatgtcc tccgtgtccc gctccagaag ccgctggcgg gccatctgtg   120
ttttgttcc ccccaagcc taaggatacg ttgatgatca gcaggacccc ggaggttaca   180
tgcgtagtag ttgacgtttc tcatgaagac ccagaagtaa aatttaactg gtatgtcgat   240
ggcgtgaag tacataatgc taaaactaag cccagggagg agcaatacaa ttcaacgtac   300
cgagttgtga gtgtccttac ggtcctgcac caagactggt tgaacggcaa agagtacaaa   360
tgcaaagtgt ctaacaaggc attggccgcg cctatagaaa agaccattag caaagcaaaa   420
gggcagcctc gggaaccca ggtctacacg ctgccacctt cccgagatga attgacgaaa   480
aaccaggtct cctttgacctg cttggtaaaa ggcttctcac caagcgacat tgcagtggag   540
tgggagtcta acgggcaacc cgaaaacaac tataagacga ctccccctgt tcttgattct   600
gatgggagtt ttttctgta cagtaagttg acagtggata aatcaagatg gcagcaaggt   660
aatgtcttct cttgttcagt gcttcacgaa gcattgcatt ctcactacac acaaaagtct   720
ttgtccttgg ctccaggtga aggcggtagc gattcatggc aagaagaagt cattaagctg   780
tgtggaaggg aactggttag ggcccaaatt gcgtatatgt gaaagtctac ggcgagtgat   840
gcggccggtg ctcaagcgga tgcgggtgct agacagttgt actcagccct tgcgaacaaa   900
tgttgtcacg ttggctgtac gaaacgcagc cttgctcaat tctgc                  945

SEQ ID NO: 206           moltype = DNA   length = 945
FEATURE                  Location/Qualifiers
source                   1..945
```

|   |   |
|---|---|
|  | mol_type = other DNA |
|  | organism = synthetic construct |

SEQUENCE: 206
```
atggaaactg acacccttct gctctgggta ctcttgttgt gggtcccgg cagtacaggc   60
gataaaactc acacatgccc cccatgccca gcaccggaag ctgccggagg accgtctgta  120
ttcctctttc cgcccaaacc gaaagacacg ttgatgattt ctcggactcc cgaggtaact  180
tgtgtcgtgg tcgacgtctc acacgaggac ccggaggtca aatttaactg gtatgtcgat  240
ggggtggagt ccataatgc taagacgaag cccagagaag aacagtataa ctctacttat  300
agagttgtaa gcgtgctcac tgtattgcac caggactggc tcaacgggaa agaatataag  360
tgtaaggtct caaacaaagc tctcgcagcc ccgatagaga aaacaatatc taaggccaag  420
ggccaaccgc gcgagccgca ggtttataca cttccaccct cccgcgatga gctgaccaag  480
aaccaggtct ctctcacctg tctcgtaaag gcttttatc cctccgacat tgcagtggag  540
tgggaatcaa acgccagcc ggaaaataat tacaagacca ctcctcccgt cctcgactcc  600
gatgggtcat ttttcctgta cagtaagctc accgttgata agtcaaggtg gcagcagggc  660
aacgtgttta gctgtagtgt tctgcatgag gcgctccaca gtcactacac ccagaaaagt  720
ctgagcctt ccccaggtga gggtggtagc gatagctggc aggaggaagt aattaaactc  780
tgcggtagag aattggtaag ggcccaaatt gccatctgcg gaaagagcac cgcatcagat  840
gctgcgggcg cggatgcgca ggctggtgct aggcaactct actctgccct ggcgaataaa  900
tgttgccacg tcggttgcac gaaacgaagt ttggctcaat tttgc         945
```

SEQ ID NO: 207  moltype = DNA  length = 945
FEATURE    Location/Qualifiers
source     1..945
           mol_type = other DNA
           organism = synthetic construct SEQUENCE: 207
```
atggaaacgg acacacttct cttgtgggtt cttctgctct gggttcccgg cagtacaggc   60
gacaaaacac atacatgccc cccttgcccg gctcccgagg ccgccggtgg tcctagcgtc  120
tttcttttcc ctcccaaacc caaagacaca cttatgatta gcagaactcc cgaggtaaca  180
tgtgtggtcg tagacgtaag tcacgaagat cccgaagtta aattcaactg gtacgtagat  240
ggtgtggaag ttcataatgc aaaaaccaaa ccgcgagagg aacagtataa ctctacctac  300
cgcgtggtct cagtgctgac tgtcctgcat caggactggc tcaacgggaa ggaatataag  360
tgcaaagtga gtaataaggc ccttgcagct cccatagaaa agacgatatc aaaggctaaa  420
ggacagccga gggagccaca ggtgtacact ttgcctccga gtagagatga actcactaaa  480
aaccagtaa gtttgacatg cctggtcaaa ggttttttacc ccagtgatat agcggttgag  540
tgggagtcca atgggcaacc ggagaacaac tataagacta ctccaccgtg cctggatagc  600
gatgaagtt ttttttcttta ctcaaagctg acggtggata agatcgatg cagcagggc  660
aatgtgttta gctgttctgt gcttcacgaa gcacttcact ctcattatac ccagaagtca  720
ttgagccttt ccctggtga aggagggtca gattcctggc aggaggaggt tataagcctg  780
tgtggccggg aactcgtgcg agctcaaatt gcgatctgtg aaaatccac cgctagtgat  840
gcggcgggag cacaagctca agcgggcgct cgacaacttt atagcgcttt ggctaataag  900
tgctgccatg tgggttgtac aaagcgcagc ctcgctcaat tttgc         945
```

SEQ ID NO: 208  moltype = DNA  length = 945
FEATURE    Location/Qualifiers
source     1..945
           mol_type = other DNA
           organism = synthetic construct SEQUENCE: 208
```
atggaaacag acactctcct cctgtgggta cttctcttgt gggtaccagg atccaccggg   60
gataagacgc acacttgccc tccttgcccg gcacccgaag ccgctggtgg gcctagtcta  120
ttcctgttcc ccccgaagcc gaaggatact cttatgattt cacgcacgcc cgaggttaca  180
tgcgtagtag tggacgtatc tcacgaagat cccgaagtca agttcaattg gtatgtcgac  240
ggagtagaag ttcacaacgc aaagacaaaa ccgcgggaag agcaatacaa ctccacgtac  300
cgcgtcgttt ctgttcttac ggtcttgcac caggactggc tcaatggcaa ggagtataag  360
tgcaaggtat ccaacaaggc ccttgccgca cctattgaaa agactatcag caaggccaag  420
ggacagccaa gggagcctca agtctacacg ctcccgccta gtagagacga gttgacaaag  480
aatcaagtga gtttgacttg tctggttaaa ggttttttacc cgtcagatat tgcagtagaa  540
tgggaatcta acggacaacc cgaaaacaac tataaaacga cgcctcctgt gttggattca  600
gatgggtcat ttttttctcta ctcaaagctc acggtagata atcaagatg gcaacaaggc  660
aatgtatttt cctgctccgt gctccacgag gctctgcaca gccattatac gcaaaagagt  720
ctgtctttga gcccaggtga gggtggctcc gattcctggc aggaggaagt aattaagttg  780
tgcggcaggg aacttgttcg cgcacaaata gccatttgtg gtcagagcac agcatcagat  840
gccgccggag ccgacgccaa gcaggtgcc cgccaacttt attctgccct cgcaaacaaa  900
tgctgccacg tcggctgcac gaagaggagc ctcgcccaat tttgc         945
```

SEQ ID NO: 209  moltype = DNA  length = 945
FEATURE    Location/Qualifiers
source     1..945
           mol_type = other DNA
           organism = synthetic construct SEQUENCE: 209
```
atggaaacag acacgctgct cctctgggtg ttgcttctct gggtgcctgg cagtacaggt   60
gataagaccc atacgtgccc gccatgtcca gccccccgagg cagccggagg tccttccgtt  120
ttccttttcc cccctaagcc caaggacact ctgatgatct cccggacgcc tgaagtcact  180
tgcgtagtcg tagacgtttc acatgaggat ccagaagtta aatttaactg gtacgtcgat  240
ggcgtcgagg tccataacgc gaaaaccaag cccaggggag aacaatataa ctccacctat  300
agggtcgtga gtgtgctcac cgttttgcac caagactggc tcaacgggaa agagtacaaa  360
tgtaaagttt caaataaggc tttggccgcc ccaatagaga agactatatc caaggctaag  420
```

```
ggacagcctc gagaaccgca ggtatatacg cttcctccgt ctagggatga actcacaaaa    480
aaccaggttt ctttgacctg cttggtaaag ggattttatc cctccgacat tgcggtcgaa    540
tgggagagca acggacagcc ggaaaacaat tacaaaacga caccccccggt tttggactct    600
gatgaagct tcttcctcta tagtaagttg accgtagaca agtctcgctg gcagcaggga     660
aacgtcttca gttgctcagt tctccatgag gcgttgcata gtcactatac acagaagagt    720
cttagtttgt ctccaggaga aggaggttc gattcttggc aagaggaggt aatcaaattg     780
tgtggccgag aacttgttag agctcagata gccatctgcg gacagtctac ggcgtccgat    840
gcggccggag ctaatgctga cgcaggtgcg cgacagctgt actccgcact ggcgaataag    900
tgctgccacg tgggatgcac taagcggtct ctcgcgcaat tctgt                    945
```

```
SEQ ID NO: 210           moltype = DNA   length = 945
FEATURE                  Location/Qualifiers
source                   1..945
                         mol_type = other DNA
                         organism = synthetic construct
SEQUENCE: 210
atggagaccg acactctttt gctctgggtg ctgttgctgt gggttccagg ttcaacggga    60
gataaaaccc acacctgtcc accatgcccg gcgccggaag ccgccggggg acccagcgta    120
tttcttttcc cccccaagcc caaagacacg ctgatgattt cacgaacgcc ggaggtgact    180
tgcgtggtag tggacgtctc ccatgaggat cccgaagtta aatttaattg gtatgtagat    240
ggtgttgagg tccataatgc taaaacaaag ccgcgggaag agcaatataa ctccacctat    300
agagtggtct ctgtactcac tgtcctgcac caggattggc tgaatgggaa agagtacaag    360
tgtaaagtta gcaacaaagc gctcgccgcg cctatcgaaa aaacgatttc caaagcaaag    420
ggccaaccac gagaacccca ggtttacacc ctgccaccca gtcgagatga actcactaag    480
aatcaggtgt cccttacatg cctcgtcaag ggattctatc cgagcgatat agcggtggaa    540
tgggagagta acggtcaacc cgaaaataac tataaaacca ctccgccggt actcgattct    600
gacggttcct tctttctttta ttccaaactg actgtagaca aatcacggtg gcagcagggc    660
aacgtgttta gctgctctgt actccatgag gccttgcatt ctcattatac tcaaaagagt    720
ctgagtctga gtccaggtga agggggttcc gattcatggc aagaggaagt cattaaactc    780
tgccgaaggg aacttgtaag agcacaaatc gcgatttgtg ggcaatctac cgcatccgac    840
gcggctgggg cagatgcaga tgccggagcg aggcagctgt attcagcatt ggctaacaaa    900
tgttgccatg ttggatgtac gaagagatca cttgcacagt tctgt                   945
```

```
SEQ ID NO: 211           moltype = DNA   length = 945
FEATURE                  Location/Qualifiers
source                   1..945
                         mol_type = other DNA
                         organism = synthetic construct
SEQUENCE: 211
atggaaactg acaccctcct tctctgggta ctgctcttgt gggttccagg ctctactggc    60
gataagactc atacctgccc gcccgtgtccc gcacccgagg ctgccggagg gccatcagtg   120
ttcctttcc caccaaagcc gaaggataca cttatgatca gcaggacacc cgaagtgacc    180
tgtgtagtcg tagacgtgtc ccacgaagac cccgaagtaa aatttaattg gtatgtcgat    240
ggcgtagagt ccacaacgc gaaaacgaaa ccccgcgaag aacaatataa ttccacatac     300
cgagttgtca gcgtcctcac tgttctccat caggactggc tgaatgggaa ggaatataag    360
tgcaaggtct caaacaaggc gctggcggcc cccatagaga aaacgattc taaggccaaa    420
ggacagccac gggaaccgca ggtctatacg ctcccaccta gtaggggatga gttgaccaag    480
aatcaggtat ccctcacatg tctcgtcaag ggattctatc cagcgacat agccgtggag     540
tgggaatcta acggtcaacc tgagaataac tataaaacaa cccccccggt cctcgactcc    600
gatggtagct tctttctgta ttccaaactg acggtagata aaagccgatg caacagggt     660
aacgtcttta gttgttctgt attgcacgag gcgctccata gtcactacac acagaagtct    720
ttgagcctct cacctgggga gggggtagc gattcttggc aggaggaagt gatcaaactg    780
tgcggcaggg aactggtcag agcacagata gcaatatgcg gtcagagtac ggcctctgac   840
gccgccggtc cggaggctga ggcaggggcg agacagctct acagcgctct tgcaaataag   900
tgttgtcacg tgggggtgcac aaagagatcc ttggcgcaat tttgt                   945
```

```
SEQ ID NO: 212           moltype = DNA   length = 945
FEATURE                  Location/Qualifiers
source                   1..945
                         mol_type = other DNA
                         organism = synthetic construct
SEQUENCE: 212
atggaaaccg atacattgct tttgtgggtc ttgttgctgt gggtgcccgg ttctactggt    60
gataagaccc acacatgtcc gccatgtcca gccccagagg cagcagggg cccgtccgta    120
ttcttgttc ccccgaaacc caaagatacc cttatgatta gtcgaactcc agaagtcacg     180
tgtgtggtgg tggacgtatc ccacgaggac cccgaagtga aatttcaattg gtatgtggac   240
ggggtggaag tccataacgc taagacgaag cccagagagg agcagtacaa ttctacctat    300
cgggttgtat ctgtgcttac tgttctccat caagattggc tgaacgggaa ggaatacaaa    360
tgtaaagtta gtaacaaagc attggcagct cctatcgaaa gacgataag caaggctaaa    420
ggtcaacccc gagagcctca ggtctacact ttgccgccct ccaggatga gcttaccaag   480
aaccaagtga gcttgacgtg tctcgtgaag ggattctacc catcagatat agcggtagaa   540
tgggagtcta atgggcagcc cgagaacaac tataagacca cccctcccgt tcttgactcc   600
gacggttcct ttttcttgta ctccaaactc acggtcgaca gtctaggtg gcagcaaggc   660
aatgtcttcc gttgttcgt gctgcacgaa gctcttcatt ctcactatac acaaaaagt    720
ctgagtcttt cacctggaga gggggttcc gattcttggc aggaagaagt cattaagctg    780
tgcggcagag aacttgtgcg cgcacaaatt gctatttgtg gacagtcaac tgcatctgac   840
gccgctggag cccaagcgga cgcaggggca aggcagcttt attcagcgct tgcgaataag   900
tgttgccatg tgggttgcac gaaacgaagc ctggcgcaat tttgt                   945
```

| SEQ ID NO: 213 | moltype = DNA length = 945 |
|---|---|
| FEATURE | Location/Qualifiers |
| source | 1..945 |
| | mol_type = other DNA |
| | organism = synthetic construct |

SEQUENCE: 213

```
atggagactg atacattgtt gctttgggta ctcttgcttt gggtgcccgg aagtacaggg   60
gataagacac atacatgtcc tccctgtccc gctccggagg cagccggtgg gccttcagtt  120
ttcttgtttc cgccgaagcc taaggacacg ttgatgatat cccgaacacc agaggtcaca  180
tgcgtcgtcg tggacgtctc acacgaggac cctgaagtga aattcaactg gtatgtagac  240
ggggtcgaag ttcacaatgc gaaaactaaa cctcgcgagg agcaatataa ctcaacatac  300
cgcgtagtgt ccgtcttgac tgtccttcat caggattggc tgaatggtaa agaatataaa  360
tgtaaagttt ctaataaagc gcttgcggca cccattgaga gacaatttc caaagccaaa  420
ggccaacccc gagagcctca ggtatatacg ctgcctccgt ctcgagatga gttgacaaaa  480
aatcaagtca gcttgacttg tcttgtaaag gggttctatc cgtcagacat agcagtggag  540
tgggaatcca acgggcaacc agaaaataat tacaaaacca ctccgcccgt gcttgactca  600
gatgggagct tcttccttta tagcaaactt acggtagata aatccagatg gcagcaaggc  660
aacgtattca gctgtagtgt gctgcatgaa gcgcttcact cccattatac tcaaaaatct  720
ctttctctgt caccgggcga gggcggaagt gatagttggc aggaagaggt catcaagctc  780
tgtgggagag agcttgtacg cgctcagatt gctatatgcg gccagtcaac tgcaagcgat  840
gcagcgggtg ccgatgccca agcggggca cggcaactct actcagccct cgcgaataaa  900
tgttgtcatg tagggtgtac taagagaagc ctcgcgcaat tttgt                  945
```

| SEQ ID NO: 214 | moltype = DNA length = 945 |
|---|---|
| FEATURE | Location/Qualifiers |
| source | 1..945 |
| | mol_type = other DNA |
| | organism = synthetic construct |

SEQUENCE: 214

```
atggaaactg atactcttct tttgtgggta ctgttgttgt gggtcccagg aagtaccggc   60
gataaaacgc atacttgccc gccgtgccca gcacctgagg cagccggcgg ccctagtgtc  120
ttcttgttcc cgcccaagcc caaggataca ctcatgatct cccgaacgcc agaggtcaca  180
tgcgtagttg ttgacgtttc ccatgaggac cctgaagtga aatttaactg gtacgtcgac  240
ggcgttgagg ttcacaacgc taagactaag ccaagagagg aacagtacaa ttcaacttat  300
agagtggtgt ctgtattgac agttctccat caggattggc tgaacggaaa agaatatatag  360
tgcaaggtct caaataaggc gctcgctgca cccatagaaa aaaccatatc aaaagcgaag  420
gggcaaccaa gagaacccca ggtgtacacg ctccccccgt ccagagatga actcacgaag  480
aatcaagtgt cactcacatg tcttgtaaag gggttctacc cctctgatat tgccgtagaa  540
tgggaaagca acggacagcc cgagaataac tacaagacga caccgccagt tcttgattct  600
gacggaagct ttttcctcta ttcaaaattg accgttgaca agtcccgatg caacagggc   660
aacgttttct catgctccgt ccttcacgaa gccttgcatt cccactatac gcagaagagt  720
ctctctttga gccccggaga gggaggcagt gattcatggc aagaggaagt gatcaaactt  780
tgcggcagag aattggttag agcccagatt gccatttgtg gacaaagtac ggcctcagat  840
gctgcggggg cacaagctca ggcgggcgca cgcagttgt acagtgctct ggcgaataag  900
tgctgccacg ttggttgcac caagcgatcc ttggcgcaat tttgc                  945
```

| SEQ ID NO: 215 | moltype = DNA length = 945 |
|---|---|
| FEATURE | Location/Qualifiers |
| source | 1..945 |
| | mol_type = other DNA |
| | organism = synthetic construct |

SEQUENCE: 215

```
atggaaacag atacgctcct tttgtgggta ctgttgttgt gggtgcccgg ctctacgggc   60
gacaagactc atacttgtcc gccctgcccc gctcctgagg ctgccggagg cccttcagta  120
ttcttgtttc cgccgaaacc gaaggatacc ttgatgatta gtaggacacg ggaagtcacc  180
tgcgtagtgg tggacgtaag ccacgaagat cccgaagtaa agtttaattg gtatgttgat  240
ggcgtagagg tgcataatgc gaaaaccaaa cctagggagg aacagtacaa tagtacttac  300
cgcgtagtgt cagtgcttac cgtgctgcat caggactggc ttaatgggaa ggaatacaaa  360
tgtaaagtat ccaataaagc gctggcggct cccatcgaga aaacgatctc aaaagccaaa  420
ggacaaccac gggaaccgca ggtctatact ctgccaactt caagagacga acttaccaag  480
aaccaagtct cattgacgtg cttggtaaaa ggttttatc cgtctgacat cgctgttgaa  540
tgggagtcta acgccagcc ggagaacaat tacaaaacaa ctccaccagt cttggattca  600
gatgggtctt ttttttgta ttcaaagctt accgttgaca aaagccgctg caacaagga   660
aacgttttca gctgcagtgt gctgcacgaa gcgctccaca gtcattatac ccagaaattt  720
ttgagcctgt ctccagggga aggtgggagt gactcttggc aagaagaggt tatcaaactt  780
tgcgggcggg agctggtaag ggcccaaatt gcaatatgcg gcaaagtac tgcatctgat  840
gccgctgggg ccgatgctaa cgcggggca agacaacttt atagcgcgtt ggcgaacaaa  900
tgctgtcatg tgggatgcac caaacaaagt ttggcgcaat tttgt                  945
```

| SEQ ID NO: 216 | moltype = DNA length = 945 |
|---|---|
| FEATURE | Location/Qualifiers |
| source | 1..945 |
| | mol_type = other DNA |
| | organism = synthetic construct |

SEQUENCE: 216

```
atggaaaccg atacctgct gctttgggtg ctcttgctgt gggttccgg ttccacgggt    60
gataaaactc acacgtgtcc gccatgcccc gcacctgaag cggcgggtgg tccgagcgtg  120
tttttgtttc cgcctaagcc caaggatacc ctgatgatta gtcggacacc cgaagtaaca  180
tgtgtcgtcg tggatgtaag tcacgaggat cccgaagtga aattcaactg gtatgtggat  240
```

331

-continued

```
ggagttgaag tccataatgc gaaaacaaaa ccgagagagg aacagtacaa ctcaacatac  300
cgggtggtaa gtgtactgac ggtactccac caggactggc tgaatggtaa ggagtacaaa  360
tgcaaagttt caaataaggc gctcgctgcc cccatcgaga aaaccattag taaggctaaa  420
ggtcaaccta gggagccaca agtatataca ttgccgcctt ctagagatga gctgaccaaa  480
aaccaggtca gcctgacctg tttggtgaaa ggcttctatc caagcgacat tgctgtcgag  540
tgggagtcaa atgggcagcc ggaaaataac tataaaacga ctcctcctgt tctcgactcc  600
gatggttcat tcttcctcta ctcaaagctt accgtggata aatccaggtg gcaacaaggt  660
aacgtgttct catgttccgt tctgcacgaa gcactgcatt cccattatac acaaaaatcc  720
ctgagcctct cacctgggga gggcggaagc gatagttcga aagaggaagt aataaagctg  780
tgtggcaggg aactcgtaag ggctcagatt gcgatatgtg gaaaaagcac tgcttctgac  840
gccgcagggg ccaacgcaga tgctggcgcc cgacaactct attctgcgct tgcgaacaag  900
tgttgtcatg taggatgtac caagcaaagc cttgctcagt tctgt              945
```

```
SEQ ID NO: 217       moltype = DNA   length = 945
FEATURE              Location/Qualifiers
source               1..945
                     mol_type = other DNA
                     organism = synthetic construct
SEQUENCE: 217
atggagaccg atacactctt gctctgggtc cttcttcttt gggttccagg ctccacagga   60
gacaaaaccc acacttgtcc gccctgtccc gctccggagg ctgcaggcgg cccaagtgtg  120
tttcttttcc cccaaagcc gaaagacacc ttgatgataa cccgcacacc cgaagtgact  180
tgcgttgtcg tcgacgtgtc tcatgaggac ccagaagtca agtttaattg gtacgttgat  240
ggcgtggaag ttcacaatgc gaaaactaag cccagagagg agcaatataa ctcaacctac  300
cgggtggtaa gtgttctgac agttctccac caggactggt tgaacggaaa agaatacaaa  360
tgcaaagtga gtaacaaagc cctggctgcc cctatcgaaa agaccatatc caaagcgaag  420
ggccagccac gggaaccgca agtatataca cttccaccat ctagagatga gcttacaaag  480
aaccaggtgt cccttacctg ccttgtcaaa ggcttctatc cctctgacat cgcagtggag  540
tgggagtcca acggacaacc agagaacaac tataagacaa cgccgccagt actggattca  600
gatggttcat tcttcttgta ttctaaactg actgttgata atcccgatg gcagcagggc  660
aacgttttta gttgtagtgt tctgcacgaa gcccttcatt cccattatac acaaaaatcc  720
ctttccctca gcccaggcga gggaggaagt gacagttggc aagaggaggt gataaagctc  780
tgtgggaggg agctggtacg cgcacagatt gcaatctgcg gaaagagcac agcaagcgat  840
gctgctgggg ccgatgccga tgctggcgct cgacaattgt attcagctct tgctaacaaa  900
tgctgtcacg taggatgcac taaacagagc cttgctcaat tttgt              945
```

```
SEQ ID NO: 218       moltype = DNA   length = 945
FEATURE              Location/Qualifiers
source               1..945
                     mol_type = other DNA
                     organism = synthetic construct
SEQUENCE: 218
atggaaaccg acactcttct gctgtgggtt cttctcctgt gggtgcctgg atcaaccgga   60
gataagaccc acacatgtcc accatgccca gccccagaag cggcaggtgg tccttctgtg  120
tttctctttc ctcccaaacc gaaagatact ctgatgataa gccggacccc agaagttacg  180
tgcgttgtag tagacgtgtc tcacgaggac ccagaagtga agtttaactg gtatgtcgac  240
ggtgtagaag ttcataatgc gaaaacaaag cccagggagg aacaatataa ttcaacgtac  300
cgggtcgttt ccgtgctgac agttctgcac caagattggc tcaacgggaa agagtacaaa  360
tgcaaagtat caaataaggc cttggctgcg ccgattgaaa agacgatttc caaagcaaag  420
ggccagccaa gggaacccca ggtctatacc ctccctccta gcagagatga acttacaaaa  480
aaccaagtct ccctcacctg cctggtcaaa ggattctatc cctcagatat cgcagtagaa  540
tgggaaagta acgggcagcc cgaaaacaat tataagacca ctcctccagt actcgattca  600
gacggtagct tctttctgta ttccaagctg accgtagata aaagtaggtg gcagcaaggt  660
aatgtcttct catgtagtgt acttcatgag gcgttgcatt cccattacac gcaaaagtct  720
ttgagtctca gtccgggtga aggaggtagc gattcttcgc aggaagaagt aattaagctg  780
tgcggccggg agctcgtcag ggctcagata gctatatgcg gcaagagcac ggccagtgat  840
gctgctggtg cagaggctga agcaggtgcc aggcagttgt acagcgcact cgctaataag  900
tgttgccacg tggggtgtac aaagcaatct ttggcacaat tctgt              945
```

```
SEQ ID NO: 219       moltype = DNA   length = 945
FEATURE              Location/Qualifiers
source               1..945
                     mol_type = other DNA
                     organism = synthetic construct
SEQUENCE: 219
atggagactg atactttgct gctgtgggtt ctccttcttt gggtcccagg ttccacagga   60
gataagaccc atacttgtcc tccgtgcccg gcaccagagg ctgcgggtgg cccatccgtt  120
ttcctgtttc cgccaaagcc taaggatact ctgatgattt cacgcacacc cgaagtgacc  180
tgcgtggtgg tcgacgtatc tcacgaagac ccagaggtaa aattcaattg gtacgtggac  240
ggcgtcgagg ttcataacgc gaaaactaag ccgagagaag agcagtacaa ctctacgtat  300
cgcgtggtgt ccgtactgac agtattgcat caggactggt tgaatggcaa ggagtataag  360
tgcaaggtat ctaataaggc attggctgcc ccaatagaaa aacgatcag caaagcaaag  420
gggcagccgc gcgagccgca ggtatataca cttccaccat cacgggatga gttgacgaaa  480
aatcaagtct cttctcacatg tctggtaaaa ggtttctatc cttctgatat cgccgtggaa  540
tgggaaagca acggccaacc cgaaaacaac tataagacga cgccgccggt actcgacagc  600
gacggaagct tttctctgta ttccaagttg acagtggaca agtctcgatg gcagcaagga  660
aacgtgttct catgttctgt tcttcacgaa gcccttcata gccattatac tcagaaatcc  720
ctctcactct ccccaggtga aggggaagt gactcttggc aagaagaagt cattaagctt  780
tgcggtcgag aattggttcg ggctcaaata gctatttgtg gcaagtccac ggcaagtgat  840
```

```
gcagcggggg ctcaggcaga cgcgggcgca aggcagcttt attccgcact tgcaaataag    900
tgctgtcacg tcggatgtac taaacaatca cttgcacaat tctgc                    945

SEQ ID NO: 220         moltype = DNA   length = 945
FEATURE                Location/Qualifiers
source                 1..945
                       mol_type = other DNA
                       organism = synthetic construct
SEQUENCE: 220
atggagaccg acacacttct cctctgggtc ctgctccttt gggtgccagg cagtacaggt     60
gacaagacac atacatgtcc cccatgccct gcacccgaag ctgctggggg gcccagcgtg    120
ttcctgtttc cgccgaagcc caaggacaca ttgatgatta gtagaacccc agaggtaact    180
tgtgttgtgg tcgatgtgtc acatgaagac cccgaggtaa agtttaactg gtatgtggat    240
ggggtagagg tacataatgc aaaaaccaag ccgcgggagg agcagtataa ttcaacctat    300
cgagtcgtgt cagtcttgac cgtgctccac caggactggc ttaacggtaa ggagtataaa    360
tgcaaagtca gtaataaggc attggccgcc ccattgagaa gaccatcag taaagctaag     420
gggcaaccta gagagccaca ggtttacacc ctccctccct ccgggatga actcaccaaa    480
aaccaggtgt cccttacttg tttggtaaag ggcttttatc cttctgatat tgctgttgaa    540
tgggagtcta acgggcaacc tgaaaataac tacaaaacaa ctccccccgt tctggactct    600
gatgggtcat tcttcctta ttcaaaattg acagttgata agagtagatg gcaacaaggc    660
aacgtatttt catgttctgt gctccacgag gctctccatt cccactacac acagaaaagt    720
ctctcactgt ccccaggaga gggcgggagc gactcttggc aggaagaagt aatcaagttg    780
tgtggcaggg aactcgtacg cgctcagatt gcaatatgcg ggaaatccac ggcaagtgac    840
gctgccgggg ccgacgcgca agcaggggca cggcagcttt actccgccct cgcaaataaa    900
tgttgtcatg tgggatgcac taaacagtcc cttgcccagt tttgc                   945

SEQ ID NO: 221         moltype = DNA   length = 945
FEATURE                Location/Qualifiers
source                 1..945
                       mol_type = other DNA
                       organism = synthetic construct
SEQUENCE: 221
atggagacag atacactgct tctgtgggtg ctcttgcttt gggtcccgg ttccacaggc      60
gataaaaccc atacctgtcc accatgcccc gcgccagagg cagcgggtgg tccaagcgtt    120
ttccttttc caccgaaacc aaaagataca cttatgatat caaggacccc cgaggtaacg    180
tgcgtcgtag ttgacgtttc tcacgaagat cccgaggtga aattcaattg gtacgtagat    240
ggtgtagagg tacacaatgc gaagacaaaa ccgcgggaag agcagtataa tagcacatac    300
agagtcgtga gcgtcctcac cgtacttcac caagattggc tgaatggaaa ggagtacaaa    360
tgtaaggtaa gtaataaagc acttgcggcc cccatcgaga aaactatcag taaagcaaaa    420
gggcaaccac gagaacccca ggtctacact ttgccaccat cacggggatga actgacaaaa    480
aatcaggtgt cactcacttg ccttgttaaa ggttctatc ctagtgacat agcggtagaa     540
tgggagtcta acgggcagcc tgagaacaat tataaaacta cgcccctgt tcttgattcc     600
gatggatcat ttttctcta ctccaaactc accgtagaca atccgctg gcagcagggc      660
aacgtgttta gttgcagcgt tcttcacgaa gcacttcact cacattacac acaaaagtcc    720
ctgagcttga gtcctgggga gggtggatct gattcttggc aggaagaagt tataaaactt    780
tgtggcagag agttggtccg cgcacaaatc gccatatgtg gtaaaagcac agcgtctgac    840
gcggcggag cgcaagccca ggcggggct cggcaactct actcagccct ggctaacaag     900
tgctgtcacg tgggatgcac taaacaaagt ctggcgcagt tctgc                   945

SEQ ID NO: 222         moltype = DNA   length = 945
FEATURE                Location/Qualifiers
source                 1..945
                       mol_type = other DNA
                       organism = synthetic construct
SEQUENCE: 222
atggagaccg atacgttgct gttgtgggtt ttgttgctgt gggtacctgg atctacaggt     60
gacaaaaccc atacgtgtcc cccgtgtccg gctccagagg ctgcgggagg accgtctgtg    120
ttcttgttcc cgccgaagcc taaagatacg ctgatgatta gtcggacccc cgaggtgacc    180
tgcgtggtag tagacgtatc tcatgaagat ccggaagtaa agtttaactg gtacgtagac    240
ggcgtcgagg tacataatgc caagacgaaa cccagagaag agcaatataa tagcacttat    300
cgagttgtaa gcgtattgac ggtccttcac caggactggt tgaacggcaa agagtacaaa    360
tgtaaggtat ccaataaagc attggctgcg ccaattgaaa agacaatttc aaagcgaag     420
gggcaacctc gagagccgca agtctacacg ctgccaccga gtaggatga attgactaag    480
aatcaggtga gtctcacgtg tctcgtgaag gggttttacc cagtgatat tgcgtgaa      540
tgggagtcca acggtcagcc agaaaataat tataaaacaa cgccccctgt attggattcc    600
gacgggagct ttttcctgta ctcaaaactc accgtagata agagtcgctg gcaacagggc    660
aacgtattct catgtagcgt tctgcacgag gcgctgcact ctcactacac acagaagagt    720
ttgagtttgt cccctggcga aggaggttct gattcctggc aggaggaggt gattaagctg    780
tgtggccgcg aattggtgag ggctcaaatt gctatttgcg gacagagcac agcgtccgat    840
gccgccggcg cagatgctaa tgccggtgca aggcaactgt actccgctct cgcaaataag    900
tgttgtcatg tcggctgcac caagcaatcc ctggcccagt tttgc                   945

SEQ ID NO: 223         moltype = DNA   length = 945
FEATURE                Location/Qualifiers
source                 1..945
                       mol_type = other DNA
                       organism = synthetic construct
SEQUENCE: 223
atggagacag atacgctctt gctgtgggta ctcctcctct gggtcccagg ctcaacgggc     60
```

```
gacaagactc acacttgtcc cccatgtcca gcaccggaag ctgccggcgg tccctcagtt   120
ttccttttcc cccccaaacc caaggacacc cttatgattt caaggacacc agaggtaacg   180
tgcgtagtgg tggacgtcag tcatgaagac ccagaggtaa agtttaactg gtacgtggat   240
ggggtagagg ttcataatgc taaaacaaaa ccacgcgagg aacagtacaa tagtacgtat   300
agagtggtct ccgttcttac ggtgctgcat caggactggc tgaacggaaa agagtacaag   360
tgtaaggtta gcaataaggc gctggcggcc ccaatcgaaa agacgatttc taaggccaaa   420
ggccagccaa gggagccaca agtatatacc cttcccccct cccgagatga gctgactaag   480
aatcaagtca gtctcacctg ccttgtcaaa gggttctacc catccgatat tgctgttgaa   540
tgggagtcta atggccagcc ggagaacaat tacaagacaa ctccgcctgt attggattcc   600
gacgggtctt ttttcctcta ttcaaaactc acagtagaca aaagtcgatg gcagcaaggt   660
aacgtgtttt cttgctctgt gttgcatgaa gcacttcatt ctcattatac tcaaaaatca   720
ttgagcctca gtccaggcga aggggtagt  gactcatggc aggaggaggt aatcaagctt   780
tgcggacgag agttggtcag ggcccagata gctatttgtg tcagtccac  ggcgagtgac   840
gcagcagggg cgaatgccga tgcaggagca agacaactgt attctgctct ggccaacaag   900
tgttgtcatg tagggtgtac taaacaaagt ctcgcccagt tctgc                   945

SEQ ID NO: 224      moltype = DNA   length = 945
FEATURE             Location/Qualifiers
source              1..945
                    mol_type = other DNA
                    organism = synthetic construct
SEQUENCE: 224
atggaaacgg atacgctgtt gttgtgggtc ttgctcctgt gggtcccgg  atccacaggt   60
gataaaaccc acacctgtcc cccatgtccg gctcccgaag cagcgggggg cccttcagtt   120
tttctctttc cccccaaacc gaaagacacg ctgatgatta gcagaactcc agaggttacc   180
tgtgtagttg tggacgtttc acacgaggat cccgaggtta aattcaactg gtatgtggac   240
ggcgtcgaag tgcataatgc aaaaacaaag ccccggggaa aacaatataa tagtacctat   300
agggtcgttt ccgtactgac cgtacttcat caagattggc tcaatgggaa ggaatacaaa   360
tgtaaagtga gtaataaagc cctggcggca ccgatcgaaa aaaccatttc aaaggctaag   420
ggacaaccgc gcgaacctca ggtctatacc ttgcccccct cacgcgacga gcttacgaag   480
aatcaggtaa gccttacttg tcttgtcaag ggttttacc  ccagcgacat agctgtcgag   540
tgggaatcca atgccaacc  ggagaataat tacaaaacta cccctcctgt tcttgatagc   600
gacgaagct  tcttcttgta ttccaaactc acagtagata aaagtaggtg gcagcagggc   660
aatgtatttt cttgcagcgt cctgcatgaa gcactgcata gccattatac tcaaaagtcc   720
ctgtctttgt ctcctggaga gggcggaagc gattcttggc aagaggaagt tattaagctg   780
tgcgggcgcg aacttgtgag ggctcaaata gcgatatgtg tcagagcac  cgctagcgat   840
gcggctggtg cagacgccga tgccggtgct aggcaacttt acagtgcact tgcgaataag   900
tgctgtcacg tcggatgtac taaacaaagc ctcgcccagt tctgc                   945

SEQ ID NO: 225      moltype = DNA   length = 945
FEATURE             Location/Qualifiers
source              1..945
                    mol_type = other DNA
                    organism = synthetic construct
SEQUENCE: 225
atggaaacgg atactcttct tttgtgggtt cttcttctgt gggtaccagg aagtactggt   60
gataaaacac atacttgccc tccttgtccg gctcccgaag ccgcaggtgg accttccgtc   120
tttcttttcc cacccaaacc taagagacact ttgatgatta gccggaccc  cgaggtaacc   180
tgtgtcgtag ttgacgtttc ccatgaagac cccgaagtta agttcaactg gtatgtcgac   240
ggcgtcgagg tgcacaacgc gaagactaag ccaagagagg agcaatacaa ttcaacttac   300
agggtcgtgt ccgtccttgac agtgcttcat caagactggc ttaatggaaa ggaatacaaa   360
tgtaaagtct ccaacaaggc tctcgcagcg cccattgaga aaacgatatc caaagcgaag   420
ggtcaaccaa gagaaccca  ggtttacacc ctccccccta gtcgggacga gcttacgaag   480
aaccaggtca gtttgacatg cctggtgaaa ggcttctatc cgtcagacat cgccgtagag   540
tgggaaagca acgggcaacc cgagaacaac tataagacga ctccccccgt gttggatagc   600
gatggctctt tcttcctgta ctctaagctg accgtagata atccaggtg  gcaacagggg   660
aacgtgtttt catgctcagt gctccatgaa gccctccatt cacactatac acaaaagtct   720
ttgtcactgt cccccggtga aggcggcagt gatagctggc aagaagaagt cataaagctc   780
tgtggtcgcg agcttgttag ggcccaaatt gcgatctgtg tcagtcaac  ggcttctgac   840
gccgccgag  cggaagccga ggcgggtgct cggcaattgt attcagcact ggcgaacaaa   900
tgttgccatg ttggttgtac taaacaaagc ctggcccagt tttgc                   945

SEQ ID NO: 226      moltype = DNA   length = 945
FEATURE             Location/Qualifiers
source              1..945
                    mol_type = other DNA
                    organism = synthetic construct
SEQUENCE: 226
atggagaccg ataccttgtt gctgtgggtg cttcttctct gggttccggg atctacagga   60
gacaagactc acacttgtcc accctgtcca gcacctgaag ccgctggtgg accatctgtc   120
tttctgttcc cccctaaacc aaaggataca cttatgatca gcagaacacc tgaagtcaca   180
tgcgttgtgg tagacgtttc ccacgaggat cctgaagtga agtttaactg gtacgtggat   240
ggcgttgagg ttcataatgc caagacgaaa cctcggggag agcagtataa ttctactat   300
agggtggtaa gcgtactgac agtcctccat caagactggt gaacgggaa  ggaatacaag   360
tgtaaagttt ccaacaaagc tctggcggcc cctatagaaa agacaatatc aaaagcgaaa   420
gggcaaccca gagagcctca agtatataca ttgcccccta gcagagacga attgacgaaa   480
aatcaggtct ctctcacgtg cctcgtgaag ggcttctatc ctagtgatat agctgtggaa   540
tgggaatcca atggacagcc agaaaacaac tacaagacca cgcccccgt  cttggattcc   600
gacgggtcat tcttcctgta cagcaagctg actgtcgaca gagtcgatg  gcaacagggc   660
```

```
aacgtctttta gctgcagcgt cctgcacgaa gctctgcata gtcattacac ccaaaagtcc  720
ctttctctct cccctggtga aggcggttcc gattcatggc aagaagaagt aattaagctc  780
tgtggacgag agcttgtccg agcacaaatt gcgatctgcg ggcagagtac cgcatctgac  840
gctgctggcg cgcaggcaga tgcgggtgca cggcagcttt attcagctct cgccaacaag  900
tgttgtcatg tggggtgtac aaagcagagc cttgcccagt tttgt              945

SEQ ID NO: 227           moltype = DNA   length = 945
FEATURE                  Location/Qualifiers
source                   1..945
                         mol_type = other DNA
                         organism = synthetic construct
SEQUENCE: 227
atggaaacgg acacactgct gctttgggtt ctcttgctgt gggtcccagg ctctacaggg   60
gataagaccc atacgtgtcc cccttgccct gcacccgagg cggctggggg cccttccgta  120
ttcttgtttc ctcctaagcc caaagatacc ttgatgataa gtcgaacgcc agaagtgact  180
tgcgttgttg tggatgtctc ccacgaggat ccagaagtca aatttaactg gtatgtcgat  240
ggggtcgaag tgcataatgc taaaacgaaa cccagagagg aacaatacaa ttcaactac   300
cgcgtagtca gtgttcttac tgtgctccat caggattggc tcaatgggaa agaatacaag  360
tgtaaagtct caaataaagc attggcggcc cctatagaga agaccataag caaggctaaa  420
ggtcagccta gggagcctca agtatatacc ttgcctccta gcagagatga gttgaccaag  480
aaccaggtca gcctcacatg cctggtgaaa gggttttacc catctgatat tgccgtcgag  540
tgggaaagta atgggcagcc agagaacaac tacaagacga caccaccggt actggatagt  600
gacggaagtt ttttctctta cagtaagctc acagtcgaca aaagccggtg gcaacaagga  660
aatgtatttt catgtagcgt acttcatgaa gccctccact ctcattacac gcagaagtca  720
ctttcactta gtccggtga gggtggaagc gatagctggc aagaggaggt tatcaagctc  780
tgtggacgag aactcgtgag agcgcaaatt gcaatctgcg ggcagagcac ggcgagtgat  840
gcggccgggg cggacgcgca agcaggagca cgacaacttt atagtgcttt ggctaataaa  900
tgttgccacg ttggatgtac taaacagagc ttggcacagt tttgc              945

SEQ ID NO: 228           moltype = DNA   length = 945
FEATURE                  Location/Qualifiers
source                   1..945
                         mol_type = other DNA
                         organism = synthetic construct
SEQUENCE: 228
atggagactg atacactgct tctgtgggta ttgttgttgt gggtcccgg ttccacaggt    60
gataaaacgc acacttgtcc gccatgtccg cacctgagg cagcgggagg accgtccgtg   120
tttctgtttc cccctaaacc aaaggacacg ctgatgatca gccgaacacc tgaagtaaca  180
tgcgtggtcg ttgacgtgtc tcacgaggat ccagaagtaa agttcaattg gtatgttgac  240
ggagttgaag tacataatgc taagactaaa ccccgcgaag aacaatataa ttctacgtac  300
agagttgtat ccgtgctcac ggtacttcac caagattggc ttaacgggaa agaatataag  360
tgtaaggtct caaataaggc cctggctgct ccgatcgaaa aaacgatatc aaaggcaaag  420
ggtcaacctc gggagcctca agtatatacc ctccccccat ctaggaggatga gctgacaaag  480
aaccaagttt cactgacctg tctcgtaaag ggtttctatc cttctgacat cgcagttgaa  540
tgggagtcca acgccaacc agagaacaac tataagacga cacccccgt gttggacagt   600
gacggaagtt ttttcctgta ctccaagctg acggttgata aaagtagatg gcaacaagga  660
aatgttttca gttgttctgt gttgcacgag gccctccact cacactatac ccaaaaagt   720
ttgtctctga gtcccggtga aggcgggagc gattcatggc aggaggaagt aatcaaactt  780
tgtgggcgag aactggtcag ggcgcaaata gcgatatgtg ggcaaagcac agcttcagat  840
gcagccggtc tcaagctca ggctggagct cgacagcttt atagccctt ggctaataaa   900
tgttgtcacg ttggctgtac gaagcagagc ctggcacagt tctgc              945

SEQ ID NO: 229           moltype = DNA   length = 945
FEATURE                  Location/Qualifiers
source                   1..945
                         mol_type = other DNA
                         organism = synthetic construct
SEQUENCE: 229
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggtttgtct cagttctcac agttcttcat caggattggc tgaatgaaa ggagtacaaa  360
tgcaaagtgt ccaacaaagc gcttgctgcg ccgattgaaa agacgatttc aaaggcaaaa  420
gggcagcccc gcgaaccca gtatatact ttgcctccct cacgcgatga actgactaag   480
aaccaggtga gcctgacttg tttggttaag ggtttttatc caagtgacat tgctgttgaa  540
tgggagtcca atggccagcc tgagaataac tacaaaacga cacctcctgt acttgacagt  600
gacggctcct tttttctta ttcaaaactc acagtggaca atcaggtg gcagcagggt   660
aacgtctttt cttgcagcgt gctccacgaa gctttgcatt cacattatac gcaaaaatcc  720
ttgtcattgt ccccaggtaa gggcggaagc gactcatacc aagaagaagt cattaaactt  780
tgtggacggg agctggttag ggcacagatt gctatttgtg gtaagtctac ggctagtgac  840
gcagcgggcg ccgaagcgga agctggtgca aggcagcttt actctgctct ggctaacaag  900
tgttgtcacg ttgggtgtac caagcggtcc cttgcgcaat tctgc              945

SEQ ID NO: 230           moltype = DNA   length = 945
FEATURE                  Location/Qualifiers
source                   1..945
                         mol_type = other DNA
```

```
                              organism = synthetic construct
SEQUENCE: 230
atggaaacgg atacgctgtt gttgtgggtt ctgctcttgt gggtgccagg gagcacaggt    60
gataaaaccc acacttgccc accttgccct gcgccggaag ccgccggagg acctagtgtt   120
ttcctctttc cccctaagcc caaagacacg ttgatgatct ctcggacacc ggaagtaact   180
tgtgtcgttg tggatgtgtc acatgaggat cccgaggtga aatttaattg gtacgttgac   240
ggcgtggagg tgcataacgc aaagactaaa ccacgcgagg agcagtataa ttctacatac   300
cgggttgtct cagttctcac agttcttcat caggattggt tgaatggaaa ggagtacaaa   360
tgcaaagtgt ccaacaaagc gcttgctgcg ccgattgaaa agacgatttc aaaggcaaaa   420
gggcagcccc gcgaacccca agtatatact ttgcctccct cacgcgatga actgactaag   480
aaccaggtga gcctgacttg tttggttaag ggttttatc caagtgacat tgctgttgaa    540
tgggagtcca atggccagcc tgagaataac tacaaaacga cacctcctgt acttgacagc   600
gacggctcct tttttcttta ttcaaaactc acagtggaca aatccaggtg gcagcagggt   660
aacgtctttt cttgcagcgt gctccacgaa gctttgcatt cacattatac gcaaaaatcc   720
ttgtcattgt ccccaggtaa gggcggaagc gactcatttc aagaagaagt cattaaactt   780
tgtggacggg agctggttag ggacagatt gctatttgtg gtaagtctac ggctagtgac    840
gcagcgggcg ccgaagcgga agctggtgca aggcagcttt actctgctct ggctaacaag   900
tgttgtcacg ttgggtgtac caagcggtcc cttgcgcaat tctgc                   945

SEQ ID NO: 231          moltype = DNA   length = 945
FEATURE                 Location/Qualifiers
source                  1..945
                        mol_type = other DNA
                        organism = synthetic construct
SEQUENCE: 231
atggaaacgg atacgctgtt gttgtgggtt ctgctcttgt gggtgccagg gagcacaggt    60
gataaaaccc acacttgccc accttgccct gcgccggaag ccgccggagg acctagtgtt   120
ttcctctttc cccctaagcc caaagacacg ttgatgatct ctcggacacc ggaagtaact   180
tgtgtcgttg tggatgtgtc acatgaggat cccgaggtga aatttaattg gtacgttgac   240
ggcgtggagg tgcataacgc aaagactaaa ccacgcgagg agcagtataa ttctacatac   300
cgggttgtct cagttctcac agttcttcat caggattggt tgaatggaaa ggagtacaaa   360
tgcaaagtgt ccaacaaagc gcttgctgcg ccgattgaaa agacgatttc aaaggcaaaa   420
gggcagcccc gcgaacccca agtatatact ttgcctccct cacgcgatga actgactaag   480
aaccaggtga gcctgacttg tttggttaag ggttttatc caagtgacat tgctgttgaa    540
tgggagtcca atggccagcc tgagaataac tacaaaacga cacctcctgt acttgacagc   600
gacggctcct tttttcttta ttcaaaactc acagtggaca aatccaggtg gcagcagggt   660
aacgtctttt cttgcagcgt gctccacgaa gctttgcatt cacattatac gcaaaaatcc   720
ttgtcattgt ccccaggtaa gggcggaagc gactcacttc aagaagaagt cattaaactt   780
tgtggacggg agctggttag ggcacagatt gctatttgtg gtaagtctac ggctagtgac   840
gcagcgggcg ccgaagcgga agctggtgca aggcagcttt actctgctct ggctaacaag   900
tgttgtcacg ttgggtgtac caagcggtcc cttgcgcaat tctgc                   945

SEQ ID NO: 232          moltype = DNA   length = 945
FEATURE                 Location/Qualifiers
source                  1..945
                        mol_type = other DNA
                        organism = synthetic construct
SEQUENCE: 232
atggaaacgg atacgctgtt gttgtgggtt ctgctcttgt gggtgccagg gagcacaggt    60
gataaaaccc acacttgccc accttgccct gcgccggaag ccgccggagg acctagtgtt   120
ttcctctttc cccctaagcc caaagacacg ttgatgatct ctcggacacc ggaagtaact   180
tgtgtcgttg tggatgtgtc acatgaggat cccgaggtga aatttaattg gtacgttgac   240
ggcgtggagg tgcataacgc aaagactaaa ccacgcgagg agcagtataa ttctacatac   300
cgggttgtct cagttctcac agttcttcat caggattggt tgaatggaaa ggagtacaaa   360
tgcaaagtgt ccaacaaagc gcttgctgcg ccgattgaaa agacgatttc aaaggcaaaa   420
gggcagcccc gcgaacccca agtatatact ttgcctccct cacgcgatga actgactaag   480
aaccaggtga gcctgacttg tttggttaag ggttttatc caagtgacat tgctgttgaa    540
tgggagtcca atggccagcc tgagaataac tacaaaacga cacctcctgt acttgacagc   600
gacggctcct tttttcttta ttcaaaactc acagtggaca aatccaggtg gcagcagggt   660
aacgtctttt cttgcagcgt gctccacgaa gctttgcatt cacattatac gcaaaaatcc   720
ttgtcattgt ccccaggtaa gggcggaagc gactcaattc aagaagaagt cattaaactt   780
tgtggacggg agctggttag ggcacagatt gctatttgtg gtaagtctac ggctagtgac   840
gcagcgggcg ccgaagcgga agctggtgca aggcagcttt actctgctct ggctaacaag   900
tgttgtcacg ttgggtgtac caagcggtcc cttgcgcaat tctgc                   945

SEQ ID NO: 233          moltype = DNA   length = 945
FEATURE                 Location/Qualifiers
source                  1..945
                        mol_type = other DNA
                        organism = synthetic construct
SEQUENCE: 233
atggaaacgg atacgctgtt gttgtgggtt ctgctcttgt gggtgccagg gagcacaggt    60
gataaaaccc acacttgccc accttgccct gcgccggaag ccgccggagg acctagtgtt   120
ttcctctttc cccctaagcc caaagacacg ttgatgatct ctcggacacc ggaagtaact   180
tgtgtcgttg tggatgtgtc acatgaggat cccgaggtga aatttaattg gtacgttgac   240
ggcgtggagg tgcataacgc aaagactaaa ccacgcgagg agcagtataa ttctacatac   300
cgggttgtct cagttctcac agttcttcat caggattggt tgaatggaaa ggagtacaaa   360
tgcaaagtgt ccaacaaagc gcttgctgcg ccgattgaaa agacgatttc aaaggcaaaa   420
gggcagcccc gcgaacccca agtatatact ttgcctccct cacgcgatga actgactaag   480
```

```
aaccaggtga gcctgacttg tttggttaag ggttttatc caagtgacat tgctgttgaa   540
tgggagtcca atggccagcc tgagaataac tacaaaacga cacctcctgt acttgacagc   600
gacggctcct ttttttcttta ttcaaaactc acagtggaca aatccaggtg gcagcagggt   660
aacgtctttt cttgcagcgt gctccacgaa gctttgcatt cacattatac gcaaaaatcc   720
ttgtcattgt ccccaggtaa gggcggaagc gactcatggc aagaagaagt cattaaactt   780
tgtggacggg agctggttag ggcacagatt gctatttgtg gtaagtctac ggctagtgac   840
gcagcgggcg ccgaagcgga agctggtgca aggcagcttt actctgctct ggctaacaag   900
tgttgttacg ttgggtgtac caagcggtcc cttgcgcaat tctgc                   945

SEQ ID NO: 234           moltype = DNA  length = 945
FEATURE                  Location/Qualifiers
source                   1..945
                         mol_type = other DNA
                         organism = synthetic construct
SEQUENCE: 234
atggaaacgg atacgctgtt gttgtgggtt ctgctcttgt gggtgccagg gagcacaggt    60
gataaaaccc acacttgccc accttgccct gcgccggaag ccgccggagg acctagtgtt   120
ttcctctttc cccctaagcc caaagacacg ttgatgatct ctcggacacc ggaagtaact   180
tgtgtcgttg tggatgtgtc acatgaggat cccgaggtga aatttaattg gtacgttgac   240
ggcgtggagg tgcataacgc aaagactaaa ccacgcgagg agcagtataa ttctacatac   300
cgggttgtct cagttctcac agttcttcat caggattggt tgaatggaaa ggagtacaaa   360
tgcaaagtgt ccaacaaagc gcttgctgcg ccgattaaaa gacgattc aaaggcaaaa    420
gggcagcccc gcgaacccca agtatatact ttgcctccct cacgcgatga actgactaag   480
aaccaggtga gcctgacttg tttggttaag ggttttatc caagtgacat tgctgttgaa   540
tgggagtcca atggccagcc tgagaataac tacaaaacga cacctcctgt acttgacagc   600
gacggctcct ttttttcttta ttcaaaactc acagtggaca aatccaggtg gcagcagggt   660
aacgtctttt cttgcagcgt gctccacgaa gctttgcatt cacattatac gcaaaaatcc   720
ttgtcattgt ccccaggtaa gggcggaagc gactcatggc aagaagaagt cattaaactt   780
tgtggacggg agctggttag ggcacagatt gctatttgtg gtaagtctac ggctagtgac   840
gcagcgggcg ccgaagcgga agctggtgca aggcagcttt actctgctct ggctaacaag   900
tgttgtcttg ttgggtgtac caagcggtcc cttgcgcaat tctgc                   945

SEQ ID NO: 235           moltype = DNA  length = 945
FEATURE                  Location/Qualifiers
source                   1..945
                         mol_type = other DNA
                         organism = synthetic construct
SEQUENCE: 235
atggaaacgg atacgctgtt gttgtgggtt ctgctcttgt gggtgccagg gagcacaggt    60
gataaaaccc acacttgccc accttgccct gcgccggaag ccgccggagg acctagtgtt   120
ttcctctttc cccctaagcc caaagacacg ttgatgatct ctcggacacc ggaagtaact   180
tgtgtcgttg tggatgtgtc acatgaggat cccgaggtga aatttaattg gtacgttgac   240
ggcgtggagg tgcataacgc aaagactaaa ccacgcgagg agcagtataa ttctacatac   300
cgggttgtct cagttctcac agttcttcat caggattggt tgaatggaaa ggagtacaaa   360
tgcaaagtgt ccaacaaagc gcttgctgcg ccgattaaa agacgattc aaaggcaaaa    420
gggcagcccc gcgaacccca agtatatact ttgcctccct cacgcgatga actgactaag   480
aaccaggtga gcctgacttg tttggttaag ggttttatc caagtgacat tgctgttgaa   540
tgggagtcca atggccagcc tgagaataac tacaaaacga cacctcctgt acttgacagc   600
gacggctcct ttttttcttta ttcaaaactc acagtggaca aatccaggtg gcagcagggt   660
aacgtctttt cttgcagcgt gctccacgaa gctttgcatt cacattatac gcaaaaatcc   720
ttgtcattgt ccccaggtaa gggcggaagc gactcatggc aagaagaagt cattaaactt   780
tgtggacggg agctggttag ggcacagatt gctatttgtg gtaagtctac ggctagtgac   840
gcagcgggcg ccgaagcgga agctggtgca aggcagcttt actctgctct ggctaacaag   900
tgttgtcaag ttgggtgtac caagcggtcc cttgcgcaat tctgc                   945

SEQ ID NO: 236           moltype = DNA  length = 945
FEATURE                  Location/Qualifiers
source                   1..945
                         mol_type = other DNA
                         organism = synthetic construct
SEQUENCE: 236
atggaaacgg atacgctgtt gttgtgggtt ctgctcttgt gggtgccagg gagcacaggt    60
gataaaaccc acacttgccc accttgccct gcgccggaag ccgccggagg acctagtgtt   120
ttcctctttc cccctaagcc caaagacacg ttgatgatct ctcggacacc ggaagtaact   180
tgtgtcgttg tggatgtgtc acatgaggat cccgaggtga aatttaattg gtacgttgac   240
ggcgtggagg tgcataacgc aaagactaaa ccacgcgagg agcagtataa ttctacatac   300
cgggttgtct cagttctcac agttcttcat caggattggt tgaatggaaa ggagtacaaa   360
tgcaaagtgt ccaacaaagc gcttgctgcg ccgattaaa agacgattc aaaggcaaaa    420
gggcagcccc gcgaacccca agtatatact ttgcctccct cacgcgatga actgactaag   480
aaccaggtga gcctgacttg tttggttaag ggttttatc caagtgacat tgctgttgaa   540
tgggagtcca atggccagcc tgagaataac tacaaaacga cacctcctgt acttgacagc   600
gacggctcct ttttttcttta ttcaaaactc acagtggaca aatccaggtg gcagcagggt   660
aacgtctttt cttgcagcgt gctccacgaa gctttgcatt cacattatac gcaaaaatcc   720
ttgtcattgt ccccaggtaa gggcggaagc gactcatggc aagaagaagt cattaaactt   780
tgtggacggg agctggttag ggcacagatt gctatttgtg gtaagtctac ggctagtgac   840
gcagcgggcg ccgaagcgga agctggtgca aggcagcttt actctgctct ggctaacaag   900
tgttgtaaag ttgggtgtac caagcggtcc cttgcgcaat tctgc                   945

SEQ ID NO: 237           moltype = DNA  length = 945
```

| FEATURE | Location/Qualifiers |
|---|---|
| source | 1..945<br>mol_type = other DNA<br>organism = synthetic construct |

SEQUENCE: 237

```
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggttgtct cagttctcac agttcttcat caggattggt tgaatggaaa ggagtacaaa  360
tgcaaagtgt ccaacaaagc gcttgctgcg ccgattgaaa agacgatttc aaaggcaaaa  420
gggcagcccc gcgaacccca gtatatact  ttgcctccct cacgcgatga actgactaag  480
aaccaggtga gcctgacttg tttggttaag ggttttttatc caagtgacat tgctgttgaa  540
tgggagtcca atggccagcc tgagaataac tacaaaacga cacctcctgt acttgacagc  600
gacggctcct ttttttcttta ttcaaaactc acagtggaca aatccaggtg gcagcagggt  660
aacgtctttt cttgcagcgt gctccacgaa gctttgcatt cacattatac gcaaaaatcc  720
ttgtcattgt ccccaggtga aggcggaagc gactcatacc aagaagaagt cattaaactt  780
tgtggacggg agctggttag ggcacagatt gctatttgtg gtaagtctac ggctagtgac  840
gcagcgggcg ccgaagcgga agctggtgca aggcagcttt actctgctct ggctaacaag  900
tgttgttacg ttgggtgtac caagcggtcc cttgcgcaat tctgc                   945
```

| SEQ ID NO: 238 | moltype = DNA  length = 945 |
|---|---|
| FEATURE | Location/Qualifiers |
| source | 1..945<br>mol_type = other DNA<br>organism = synthetic construct |

SEQUENCE: 238

```
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggttgtct cagttcttcat caggattggt tgaatggaaa ggagtacaaa               360
tgcaaagtgt ccaacaaagc gcttgctgcg ccgattgaaa agacgatttc aaaggcaaaa  420
gggcagcccc gcgaacccca gtatatact  ttgcctccct cacgcgatga actgactaag  480
aaccaggtga gcctgacttg tttggttaag ggttttttatc caagtgacat tgctgttgaa  540
tgggagtcca atggccagcc tgagaataac tacaaaacga cacctcctgt acttgacagc  600
gacggctcct ttttttcttta ttcaaaactc acagtggaca aatccaggtg gcagcagggt  660
aacgtctttt cttgcagcgt gctccacgaa gctttgcatt cacattatac gcaaaaatcc  720
ttgtcattgt ccccaggtga aggcggaagc gactcatacc aagaagaagt cattaaactt  780
tgtggacggg agctggttag ggcacagatt gctatttgtg gtaagtctac ggctagtgac  840
gcagcgggcg ccgaagcgga agctggtgca aggcagcttt actctgctct ggctaacaag  900
tgttgtaaag ttgggtgtac caagcggtcc cttgcgcaat tctgc                   945
```

| SEQ ID NO: 239 | moltype = DNA  length = 945 |
|---|---|
| FEATURE | Location/Qualifiers |
| source | 1..945<br>mol_type = other DNA<br>organism = synthetic construct |

SEQUENCE: 239

```
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggttgtct cagttctcac agttcttcat caggattggt tgaatggaaa ggagtacaaa  360
tgcaaagtgt ccaacaaagc gcttgctgcg ccgattgaaa agacgatttc aaaggcaaaa  420
gggcagcccc gcgaacccca gtatatact  ttgcctccct cacgcgatga actgactaag  480
aaccaggtga gcctgacttg tttggttaag ggttttttatc caagtgacat tgctgttgaa  540
tgggagtcca atggccagcc tgagaataac tacaaaacga cacctcctgt acttgacagc  600
gacggctcct ttttttcttta ttcaaaactc acagtggaca aatccaggtg gcagcagggt  660
aacgtctttt cttgcagcgt gctccacgaa gctttgcatt cacattatac gcaaaaatcc  720
ttgtcattgt ccccaggtga aggcggaagc gactcatacc aagaagaagt cattaaactt  780
tgtggacggg agctggttag ggcacagatt gctatttgtg gtaagtctac gggaggagaa  840
ggctctggag gcgaaggaga aggggcgga  agacagcttt actctgctct ggctaacaag  900
tgttgttacg ttgggtgtac caagcggtcc cttgcgcaat tctgc                   945
```

| SEQ ID NO: 240 | moltype = DNA  length = 945 |
|---|---|
| FEATURE | Location/Qualifiers |
| source | 1..945<br>mol_type = other DNA<br>organism = synthetic construct |

SEQUENCE: 240

```
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
```

```
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca agtatatact ttgcctccct cacgcgatga actgactaag    480
aaccaggtga gcctgacttg tttggttaag ggtttttatc caagtgacat tgctgttgaa    540
tgggagtcca atggccagcc tgagaataac tacaaaacga cacctcctgt acttgacagc    600
gacggctcct ttttcttta ttcaaaactc acagtggaca aatccaggtg gcagcagggt    660
aacgtctttt cttgcagcgt gctccacgaa gctttgcatt cacattatac gcaaaaatcc    720
ttgtcattgt ccccaggtga aggcggaagc gactcatacc aagaagaagt cattaaactt    780
tgtggacggg agctggttag ggcacagatt gctatttgtg gtaagtctac gggaggagaa    840
ggctctggag gcgaaggaga aggggcgga agacagcttt actctgctct ggctaacaag    900
tgttgtaaag ttgggtgtac caagcggtcc cttgcgcaat tctgc                    945

SEQ ID NO: 241        moltype = DNA  length = 945
FEATURE               Location/Qualifiers
source                1..945
                      mol_type = other DNA
                      organism = synthetic construct
SEQUENCE: 241
atggaaacgg atacgctgtt gttgtgggtt ctgctcttgt gggtgccagg gagcacaggt     60
gataaaaccc acacttgccc accttgccct gcgccggaag ccgccggagg acctagtgtt    120
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca agtatatact ttgcctccct cacgcgatga actgactaag    480
aaccaggtga gcctgacttg tttggttaag ggtttttatc caagtgacat tgctgttgaa    540
tgggagtcca atgccagcc tgagaataac tacaaaacga cacctcctgt acttgacagc    600
gacggctcct ttttcttta ttcaaaactc acagtggaca aatccaggtg gcagcagggt    660
aacgtctttt cttgcagcgt gctccacgaa gctttgcatt cacattatac gcaaaaatcc    720
ttgtcattgt ccccaggtga aggcggaagc gactcatacc aagaagaagt cattaaactt    780
tgtggacggg agctggttag ggcacagatt gctatttgtg gtaagtctac gggaggagaa    840
ggctctggag gcgaaggatc tggggcgga agacagcttt actctgctct ggctaacaag    900
tgttgttacg ttgggtgtac caagcggtcc cttgcgcaat tctgc                    945

SEQ ID NO: 242        moltype = DNA  length = 945
FEATURE               Location/Qualifiers
source                1..945
                      mol_type = other DNA
                      organism = synthetic construct
SEQUENCE: 242
atggaaacgg atacgctgtt gttgtgggtt ctgctcttgt gggtgccagg gagcacaggt     60
gataaaaccc acacttgccc accttgccct gcgccggaag ccgccggagg acctagtgtt    120
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca agtatatact ttgcctccct cacgcgatga actgactaag    480
aaccaggtga gcctgacttg tttggttaag ggtttttatc caagtgacat tgctgttgaa    540
tgggagtcca atggccagcc tgagaataac tacaaaacga cacctcctgt acttgacagc    600
gacggctcct ttttcttta ttcaaaactc acagtggaca aatccaggtg gcagcagggt    660
aacgtctttt cttgcagcgt gctccacgaa gctttgcatt cacattatac gcaaaaatcc    720
ttgtcattgt ccccaggtga aggcggaagc gactcatacc aagaagaagt cattaaactt    780
tgtggacggg agctggttag ggcacagatt gctatttgtg gtaagtctac gggaggagaa    840
ggctctggag gcgaaggatc tggggcgga agacagcttt actctgctct ggctaacaag    900
tgttgtaaag ttgggtgtac caagcggtcc cttgcgcaat tctgc                    945

SEQ ID NO: 243        moltype = DNA  length = 945
FEATURE               Location/Qualifiers
source                1..945
                      mol_type = other DNA
                      organism = synthetic construct
SEQUENCE: 243
atggaaacgg atacgctgtt gttgtgggtt ctgctcttgt gggtgccagg gagcacaggt     60
gataaaaccc acacttgccc accttgccct gcgccggaag ccgccggagg acctagtgtt    120
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca agtatatact ttgcctccct cacgcgatga actgactaag    480
aaccaggtga gcctgacttg tttggttaag ggtttttatc caagtgacat tgctgttgaa    540
tgggagtcca atggccagcc tgagaataac tacaaaacga cacctcctgt acttgacagc    600
gacggctcct ttttcttta ttcaaaactc acagtggaca aatccaggtg gcagcagggt    660
aacgtctttt cttgcagcgt gctccacgaa gctttgcatt cacattatac gcaaaaatcc    720
ttgtcattgt ccccaggtaa aggcggaagc gactcatacc aagaagaagt cattaaactt    780
tgtggacggg agctggttag ggcacagatt gctatttgtg gtaagtctac ggctagtgac    840
gcagcgggcg ccgaagcgga agctggtgca aggcagcttt actctgctct ggctaacaag    900
```

```
tgttgttacg ttgggtgtac caagcaatcc cttgcgcaat tctgc             945

SEQ ID NO: 244         moltype = DNA   length = 945
FEATURE                Location/Qualifiers
source                 1..945
                       mol_type = other DNA
                       organism = synthetic construct
SEQUENCE: 244
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggttgtct cagttctcac agttcttcat caggattggt tgaatggaaa ggagtacaaa  360
tgcaaagtgt ccaacaaagc gcttgctgcg ccgattgaaa agacgatttc aaaggcaaaa  420
gggcagcccc gcgaacccca gtatatact tgcctccct cacgcgatga actgactaag  480
aaccaggtga gcctgacttg tttggttaag ggtttttatc caagtgacat tgctgttgaa  540
tgggagtcca atggccagcc tgagaataac tacaaaacga cacctcctgt acttgacagc  600
gacggctcct ttttcttta ttcaaaactc acagtggaca aatccaggtg gcagcagggt  660
aacgtctttt cttgcagcgt gctccacgaa gctttgcatt cacattatac gcaaaaatcc  720
ttgtcattgt ccccaggtaa gggcggaagc gactcatacc aagaagaagt cattaaactt  780
tgtggacggg agctggttag ggcacagatt gctatttgtg gtaagtctac ggctagtgac  840
gcagcgggcg ccgaagcgga agctggtgca aggcagcttt actctgctct ggctaacaag  900
tgttgtaaag ttgggtgtac caagcaatcc cttgcgcaat tctgc             945

SEQ ID NO: 245         moltype = DNA   length = 945
FEATURE                Location/Qualifiers
source                 1..945
                       mol_type = other DNA
                       organism = synthetic construct
SEQUENCE: 245
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggttgtct cagttctcac agttcttcat caggattggt tgaatggaaa ggagtacaaa  360
tgcaaagtgt ccaacaaagc gcttgctgcg ccgattgaaa agacgatttc aaaggcaaaa  420
gggcagcccc gcgaacccca gtatatact tgcctccct cacgcgatga actgactaag  480
aaccaggtga gcctgacttg tttggttaag ggtttttatc caagtgacat tgctgttgaa  540
tgggagtcca atggccagcc tgagaataac tacaaaacga cacctcctgt acttgacagc  600
gacggctcct ttttcttta ttcaaaactc acagtggaca aatccaggtg gcagcagggt  660
aacgtctttt cttgcagcgt gctccacgaa gctttgcatt cacattatac gcaaaaatcc  720
ttgtcattgt ccccaggtaa gggcggaagc gactcatacc aagaagaagt cattaaactt  780
tgtggacggg agctggttag ggcacagatt gctatttgtg gtaagtctac gggaggagaa  840
ggctctggag gcgaaggaga aggggcgga agacagcttt actctgctct ggctaacaag  900
tgttgttacg ttgggtgtac caagcaatcc cttgcgcaat tctgc             945

SEQ ID NO: 246         moltype = DNA   length = 945
FEATURE                Location/Qualifiers
source                 1..945
                       mol_type = other DNA
                       organism = synthetic construct
SEQUENCE: 246
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggttgtct cagttctcac agttcttcat caggattggt tgaatggaaa ggagtacaaa  360
tgcaaagtgt ccaacaaagc gcttgctgcg ccgattgaaa agacgatttc aaaggcaaaa  420
gggcagcccc gcgaacccca gtatatact tgcctccct cacgcgatga actgactaag  480
aaccaggtga gcctgacttg tttggttaag ggtttttatc caagtgacat tgctgttgaa  540
tgggagtcca atggccagcc tgagaataac tacaaaacga cacctcctgt acttgacagc  600
gacggctcct ttttcttta ttcaaaactc acagtggaca aatccaggtg gcagcagggt  660
aacgtctttt cttgcagcgt gctccacgaa gctttgcatt cacattatac gcaaaaatcc  720
ttgtcattgt ccccaggtaa gggcggaagc gactcatacc aagaagaagt cattaaactt  780
tgtggacggg agctggttag ggcacagatt gctatttgtg gtaagtctac gggaggagaa  840
ggctctggag gcgaaggaga aggggcgga agacagcttt actctgctct ggctaacaag  900
tgttgtaaag ttgggtgtac caagcaatcc cttgcgcaat tctgc             945

SEQ ID NO: 247         moltype = DNA   length = 945
FEATURE                Location/Qualifiers
source                 1..945
                       mol_type = other DNA
                       organism = synthetic construct
SEQUENCE: 247
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
```

```
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca agtatatact ttgcctccct cacgcgatga actgactaag    480
aaccaggtga gcctgacttg tttggttaag ggttttatc caagtgacat tgctgttgaa     540
tgggagtcca atggccagcc tgagaataac tacaaaacga cacctcctgt acttgacagc    600
gacggctcct tttttctta ttcaaaactc acagtggaca aatccaggtg gcagcagggt     660
aacgtctttt cttgcagcgt gctccacgaa gctttgcatt cacattatac gcaaaaatcc    720
ttgtcattgt ccccaggtaa gggcggaagc gactcatacc aagaagaagt cattaaactt    780
tgtggacggg agctggttag ggcacagatt gctatttgtg gtaagtctac gggaggagaa    840
ggctctggag gcgaaggatc tggggcggag agacagcttt actctgctct ggctaacaag    900
tgttgttacg ttgggtgtac caagcaatcc cttgcgcaat tctgc                    945

SEQ ID NO: 248          moltype = DNA   length = 945
FEATURE                 Location/Qualifiers
source                  1..945
                        mol_type = other DNA
                        organism = synthetic construct
SEQUENCE: 248
atggaaacgg atacgctgtt gttgtgggtt ctgctcttgt gggtgccagg gagcacaggt     60
gataaaaccc acacttgccc accttgccct gcgccggaag ccgccggagg acctagtgtt    120
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca agtatatact ttgcctccct cacgcgatga actgactaag    480
aaccaggtga gcctgacttg tttggttaag ggttttatc caagtgacat tgctgttgaa     540
tgggagtcca atggccagcc tgagaataac tacaaaacga cacctcctgt acttgacagc    600
gacggctcct tttttctta ttcaaaactc acagtggaca aatccaggtg gcagcagggt     660
aacgtctttt cttgcagcgt gctccacgaa gctttgcatt cacattatac gcaaaaatcc    720
ttgtcattgt ccccaggtaa gggcggaagc gactcatacc aagaagaagt cattaaactt    780
tgtggacggg agctggttag ggcacagatt gctatttgtg gtaagtctac gggaggagaa    840
ggctctggag gcgaaggatc tggggcggag agacagcttt actctgctct ggctaacaag    900
tgttgtaaag ttgggtgtac caagcaatcc cttgcgcaat tctgc                    945

SEQ ID NO: 249          moltype = AA   length = 29
FEATURE                 Location/Qualifiers
source                  1..29
                        mol_type = protein
                        organism = synthetic construct
SEQUENCE: 249
DSWMEEVIKL CGRELVRAQI AICGMSTWS                                       29

SEQ ID NO: 250          moltype = AA   length = 27
FEATURE                 Location/Qualifiers
source                  1..27
                        mol_type = protein
                        organism = synthetic construct
VARIANT                 4
                        note = X is absent or any amino acid
VARIANT                 25
                        note = X is absent or any amino acid
SEQUENCE: 250
DSWXEEVIKL CGRELVRAQI AICGXST                                         27

SEQ ID NO: 251          moltype = AA   length = 29
FEATURE                 Location/Qualifiers
source                  1..29
                        mol_type = protein
                        organism = synthetic construct
SEQUENCE: 251
DSWKEEVIKL CGRELVRAQI AICGKSTAS                                       29

SEQ ID NO: 252          moltype = AA   length = 29
FEATURE                 Location/Qualifiers
source                  1..29
                        mol_type = protein
                        organism = synthetic construct
SEQUENCE: 252
DSWKEEVIKL CGRELVRAQI AICGKSTWS                                       29

SEQ ID NO: 253          moltype = AA   length = 29
FEATURE                 Location/Qualifiers
source                  1..29
                        mol_type = protein
                        organism = synthetic construct
```

```
SEQUENCE: 253
DSWMEEVIKL CGRELVRAQI AICGKSTAS                                              29

SEQ ID NO: 254          moltype = AA  length = 29
FEATURE                 Location/Qualifiers
source                  1..29
                        mol_type = protein
                        organism = synthetic construct
SEQUENCE: 254
DSWMEEVIKL CGRELVRAQI AICGKSTWS                                              29

SEQ ID NO: 255          moltype = AA  length = 27
FEATURE                 Location/Qualifiers
source                  1..27
                        mol_type = protein
                        organism = synthetic construct
SEQUENCE: 255
DSWKEEVIKL CGRELVRAQI AICGKST                                                27

SEQ ID NO: 256          moltype = AA  length = 27
FEATURE                 Location/Qualifiers
source                  1..27
                        mol_type = protein
                        organism = synthetic construct
SEQUENCE: 256
DSWMEEVIKL CGRELVRAQI AICGKST                                                27

SEQ ID NO: 257          moltype = AA  length = 24
FEATURE                 Location/Qualifiers
source                  1..24
                        mol_type = protein
                        organism = synthetic construct
SEQUENCE: 257
QLYSALANKC CHVGCTKRSL ARFC                                                   24

SEQ ID NO: 258          moltype = AA  length = 25
FEATURE                 Location/Qualifiers
source                  1..25
                        mol_type = protein
                        organism = synthetic construct
VARIANT                 1
                        note = X is absent or any amino acid
VARIANT                 3
                        note = X is absent or any amino acid
VARIANT                 23
                        note = X is absent or any amino acid
SEQUENCE: 258
XQXYSALANK CCHVGCTKRS LAXFC                                                  25

SEQ ID NO: 259          moltype = AA  length = 25
FEATURE                 Location/Qualifiers
source                  1..25
                        mol_type = protein
                        organism = synthetic construct
SEQUENCE: 259
RQLYSALANK CCHVGCTKRS LARFC                                                  25

SEQ ID NO: 260          moltype = AA  length = 25
FEATURE                 Location/Qualifiers
source                  1..25
                        mol_type = protein
                        organism = synthetic construct
SEQUENCE: 260
RQLYSALANK CCHVGCTKRS LAQFC                                                  25

SEQ ID NO: 261          moltype = AA  length = 25
FEATURE                 Location/Qualifiers
source                  1..25
                        mol_type = protein
                        organism = synthetic construct
SEQUENCE: 261
RQLYSALANK CCHVGCTKRS LAEFC                                                  25

SEQ ID NO: 262          moltype =     length =
SEQUENCE: 262
000

SEQ ID NO: 263          moltype =     length =
SEQUENCE: 263
```

```
000

SEQ ID NO: 264           moltype =   length =
SEQUENCE: 264
000

SEQ ID NO: 265           moltype =   length =
SEQUENCE: 265
000

SEQ ID NO: 266           moltype =   length =
SEQUENCE: 266
000

SEQ ID NO: 267           moltype = AA   length = 4
FEATURE                  Location/Qualifiers
source                   1..4
                         mol_type = protein
                         organism = synthetic construct
SEQUENCE: 267
GGGE                                                                     4

SEQ ID NO: 268           moltype = AA   length = 4
FEATURE                  Location/Qualifiers
source                   1..4
                         mol_type = protein
                         organism = synthetic construct
SEQUENCE: 268
GEGE                                                                     4

SEQ ID NO: 269           moltype = AA   length = 4
FEATURE                  Location/Qualifiers
source                   1..4
                         mol_type = protein
                         organism = synthetic construct
SEQUENCE: 269
GGEG                                                                     4

SEQ ID NO: 270           moltype = AA   length = 4
FEATURE                  Location/Qualifiers
source                   1..4
                         mol_type = protein
                         organism = synthetic construct
SEQUENCE: 270
GEGG                                                                     4

SEQ ID NO: 271           moltype = AA   length = 4
FEATURE                  Location/Qualifiers
source                   1..4
                         mol_type = protein
                         organism = synthetic construct
SEQUENCE: 271
GGEE                                                                     4

SEQ ID NO: 272           moltype = AA   length = 13
FEATURE                  Location/Qualifiers
source                   1..13
                         mol_type = protein
                         organism = synthetic construct
SEQUENCE: 272
GGGEGGGEGG GEG                                                          13

SEQ ID NO: 273           moltype = AA   length = 15
FEATURE                  Location/Qualifiers
source                   1..15
                         mol_type = protein
                         organism = synthetic construct
SEQUENCE: 273
GGGEGGGEGG GEGGG                                                        15

SEQ ID NO: 274           moltype = AA   length = 13
FEATURE                  Location/Qualifiers
source                   1..13
                         mol_type = protein
                         organism = synthetic construct
SEQUENCE: 274
GEGGGEEGGG EGG                                                          13

SEQ ID NO: 275           moltype = AA   length = 13
```

```
FEATURE                 Location/Qualifiers
source                  1..13
                        mol_type = protein
                        organism = synthetic construct
SEQUENCE: 275
GGGEEGGGEE GGG                                                          13

SEQ ID NO: 276          moltype = AA   length = 13
FEATURE                 Location/Qualifiers
source                  1..13
                        mol_type = protein
                        organism = synthetic construct
SEQUENCE: 276
GGEGEGGEGE GGS                                                          13

SEQ ID NO: 277          moltype = AA   length = 12
FEATURE                 Location/Qualifiers
source                  1..12
                        mol_type = protein
                        organism = synthetic construct
SEQUENCE: 277
GGGEGGGEGG GE                                                           12

SEQ ID NO: 278          moltype = AA   length = 65
FEATURE                 Location/Qualifiers
source                  1..65
                        mol_type = protein
                        organism = synthetic construct
SEQUENCE: 278
DSWKEEVIKL CGRELVRAQI AICGKSTGGG EGGGEGGGEG RQLYSALANK CCHVGCTKRS        60
LARFC                                                                   65

SEQ ID NO: 279          moltype = AA   length = 66
FEATURE                 Location/Qualifiers
source                  1..66
                        mol_type = protein
                        organism = synthetic construct
SEQUENCE: 279
DSWKEEVIKL CGRELVRAQI AICGKSTGGG EGGGEGGGEG GGQLYSALAN KCCHVGCTKR        60
SLARFC                                                                  66

SEQ ID NO: 280          moltype = AA   length = 65
FEATURE                 Location/Qualifiers
source                  1..65
                        mol_type = protein
                        organism = synthetic construct
SEQUENCE: 280
DSWMEEVIKL CGRELVRAQI AICGKSTGGG EGGGEGGGEG RQLYSALANK CCHVGCTKRS        60
LARFC                                                                   65

SEQ ID NO: 281          moltype = AA   length = 65
FEATURE                 Location/Qualifiers
source                  1..65
                        mol_type = protein
                        organism = synthetic construct
SEQUENCE: 281
DSWQEEVIKL CGRELVRAQI AICGKSTGGG EGGGEGGGEG RQLYSALANK CCHVGCTKRS        60
LARFC                                                                   65

SEQ ID NO: 282          moltype = AA   length = 66
FEATURE                 Location/Qualifiers
source                  1..66
                        mol_type = protein
                        organism = synthetic construct
SEQUENCE: 282
DSWMEEVIKL CGRELVRAQI AICGKSTGGG EGGGEGGGEG GGQLYSALAN KCCHVGCTKR        60
SLARFC                                                                  66

SEQ ID NO: 283          moltype = AA   length = 66
FEATURE                 Location/Qualifiers
source                  1..66
                        mol_type = protein
                        organism = synthetic construct
SEQUENCE: 283
DSWQEEVIKL CGRELVRAQI AICGKSTGGG EGGGEGGGEG GGQLYSALAN KCCHVGCTKR        60
SLARFC                                                                  66

SEQ ID NO: 284          moltype = AA   length = 65
FEATURE                 Location/Qualifiers
```

```
                              -continued source                  1..65
                        mol_type = protein
                        organism = synthetic construct
SEQUENCE: 284
DSWMEEVIKL CGRELVRAQI AICGKSTGGE GGGEEGGGEG GQLYSALANK CCHVGCTKRS    60
LARFC                                                                65

SEQ ID NO: 285          moltype = AA  length = 65
FEATURE                 Location/Qualifiers
source                  1..65
                        mol_type = protein
                        organism = synthetic construct
SEQUENCE: 285
DSWQEEVIKL CGRELVRAQI AICGKSTGGE GGGEEGGGEG GQLYSALANK CCHVGCTKRS    60
LARFC                                                                65

SEQ ID NO: 286          moltype = AA  length = 65
FEATURE                 Location/Qualifiers
source                  1..65
                        mol_type = protein
                        organism = synthetic construct
SEQUENCE: 286
DSWMEEVIKL CGRELVRAQI AICGKSTGGE GGGEEGGGEG GQLYSALANK CCHVGCTKRS    60
LARFC                                                                65

SEQ ID NO: 287          moltype = AA  length = 65
FEATURE                 Location/Qualifiers
source                  1..65
                        mol_type = protein
                        organism = synthetic construct
SEQUENCE: 287
DSWQEEVIKL CGRELVRAQI AICGKSTGGE GGGEEGGGEG GQLYSALANK CCHVGCTKRS    60
LARFC                                                                65

SEQ ID NO: 288          moltype = AA  length = 65
FEATURE                 Location/Qualifiers
source                  1..65
                        mol_type = protein
                        organism = synthetic construct
SEQUENCE: 288
DSWQEEVIKL CGRELVRAQI AICGKSTGGG EGGGEGGGEG RQLYSALANK CCHVGCTKRS    60
LAQFC                                                                65

SEQ ID NO: 289          moltype = AA  length = 65
FEATURE                 Location/Qualifiers
source                  1..65
                        mol_type = protein
                        organism = synthetic construct
SEQUENCE: 289
DSWQEEVIKL CGRELVRAQI AICGKSTGGG EGGGEGGGEG RQLYSALANK CCHVGCTKRS    60
LARFC                                                                65

SEQ ID NO: 290          moltype = AA  length = 65
FEATURE                 Location/Qualifiers
source                  1..65
                        mol_type = protein
                        organism = synthetic construct
SEQUENCE: 290
DSWQEEVIKL CGRELVRAQI AICGKSTGGG EGGGEGGGEG RQLYSALANK CCHVGCTKRS    60
LAQFC                                                                65

SEQ ID NO: 291          moltype = AA  length = 65
FEATURE                 Location/Qualifiers
source                  1..65
                        mol_type = protein
                        organism = synthetic construct
SEQUENCE: 291
DSWQEEVIKL CGRELVRAQI AICGKSTGGG EEGGGEEGGG RQLYSALANK CCHVGCTKRS    60
LARFC                                                                65

SEQ ID NO: 292          moltype = AA  length = 65
FEATURE                 Location/Qualifiers
source                  1..65
                        mol_type = protein
                        organism = synthetic construct
SEQUENCE: 292
DSWQEEVIKL CGRELVRAQI AICGKSTGGG EEGGGEEGGG RQLYSALANK CCHVGCTKRS    60
LAQFC                                                                65
```

```
SEQ ID NO: 293          moltype = AA  length = 65
FEATURE                 Location/Qualifiers
source                  1..65
                        mol_type = protein
                        organism = synthetic construct
SEQUENCE: 293
DSWQEEVIKL CGRELVRAQI AICGKSTGGG EEGGGEEGGG RQLYSALANK CCHVGCTKRS   60
LARFC                                                              65

SEQ ID NO: 294          moltype = AA  length = 65
FEATURE                 Location/Qualifiers
source                  1..65
                        mol_type = protein
                        organism = synthetic construct
SEQUENCE: 294
DSWQEEVIKL CGRELVRAQI AICGKSTGGG EEGGGEEGGG RQLYSALANK CCHVGCTKRS   60
LAQFC                                                              65

SEQ ID NO: 295          moltype = AA  length = 65
FEATURE                 Location/Qualifiers
source                  1..65
                        mol_type = protein
                        organism = synthetic construct
SEQUENCE: 295
DSWQEEVIKL CGRELVRAQI AICGKSTGGE GEGGEGEGGS RQLYSALANK CCHVGCTKRS   60
LAQFC                                                              65

SEQ ID NO: 296          moltype = AA  length = 65
FEATURE                 Location/Qualifiers
source                  1..65
                        mol_type = protein
                        organism = synthetic construct
SEQUENCE: 296
DSWQEEVIKL CGRELVRAQI AICGKSTGGE GEGGEGEGGS RQLYSALANK CCHVGCTKRS   60
LARFC                                                              65

SEQ ID NO: 297          moltype = AA  length = 65
FEATURE                 Location/Qualifiers
source                  1..65
                        mol_type = protein
                        organism = synthetic construct
SEQUENCE: 297
DSWQEEVIKL CGRELVRAQI AICGKSTGGE GEGGEGEGGS RQLYSALANK CCHVGCTKRS   60
LAQFC                                                              65

SEQ ID NO: 298          moltype =     length =
SEQUENCE: 298
000

SEQ ID NO: 299          moltype = AA  length = 4
FEATURE                 Location/Qualifiers
source                  1..4
                        mol_type = protein
                        organism = synthetic construct
SEQUENCE: 299
EGGS                                                                4

SEQ ID NO: 300          moltype = AA  length = 295
FEATURE                 Location/Qualifiers
source                  1..295
                        mol_type = protein
                        organism = synthetic construct
SEQUENCE: 300
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWKEEVIKL  240
CGRELVRAQI AICGKSTGGG EGGGEGGGEG RQLYSALANK CCHVGCTKRS LARFC       295

SEQ ID NO: 301          moltype = AA  length = 296
FEATURE                 Location/Qualifiers
source                  1..296
                        mol_type = protein
                        organism = synthetic construct
SEQUENCE: 301
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWKEEVIKL  240
```

```
CGRELVRAQI AICGKSTGGG EGGGEGGGEG GGQLYSALAN KCCHVGCTKR SLARFC       296

SEQ ID NO: 302          moltype = AA   length = 295
FEATURE                 Location/Qualifiers
source                  1..295
                        mol_type = protein
                        organism = synthetic construct
SEQUENCE: 302
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWMEEVIKL   240
CGRELVRAQI AICGKSTGGG EGGGEGGGEG RQLYSALANK CCHVGCTKRS LARFC        295

SEQ ID NO: 303          moltype = AA   length = 295
FEATURE                 Location/Qualifiers
source                  1..295
                        mol_type = protein
                        organism = synthetic construct
SEQUENCE: 303
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWQEEVIKL   240
CGRELVRAQI AICGKSTGGG EGGGEGGGEG RQLYSALANK CCHVGCTKRS LARFC        295

SEQ ID NO: 304          moltype = AA   length = 295
FEATURE                 Location/Qualifiers
source                  1..295
                        mol_type = protein
                        organism = synthetic construct
SEQUENCE: 304
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTGGG EGGGEGGGEG RQLYSALANK CCHVGCTKRS LARFC        295

SEQ ID NO: 305          moltype = AA   length = 296
FEATURE                 Location/Qualifiers
source                  1..296
                        mol_type = protein
                        organism = synthetic construct
SEQUENCE: 305
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWMEEVIKL   240
CGRELVRAQI AICGKSTGGG EGGGEGGGEG GGQLYSALAN KCCHVGCTKR SLARFC       296

SEQ ID NO: 306          moltype = AA   length = 296
FEATURE                 Location/Qualifiers
source                  1..296
                        mol_type = protein
                        organism = synthetic construct
SEQUENCE: 306
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWQEEVIKL   240
CGRELVRAQI AICGKSTGGG EGGGEGGGEG GGQLYSALAN KCCHVGCTKR SLARFC       296

SEQ ID NO: 307          moltype = AA   length = 296
FEATURE                 Location/Qualifiers
source                  1..296
                        mol_type = protein
                        organism = synthetic construct
SEQUENCE: 307
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTGGG EGGGEGGGEG GGQLYSALAN KCCHVGCTKR SLARFC       296

SEQ ID NO: 308          moltype = AA   length = 295
FEATURE                 Location/Qualifiers
source                  1..295
                        mol_type = protein
                        organism = synthetic construct
```

```
SEQUENCE: 308
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWMEEVIKL   240
CGRELVRAQI AICGKSTGGE GGGEEGGGEG GQLYSALANK CCHVGCTKRS LARFC        295

SEQ ID NO: 309          moltype = AA  length = 295
FEATURE                 Location/Qualifiers
source                  1..295
                        mol_type = protein
                        organism = synthetic construct
SEQUENCE: 309
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWQEEVIKL   240
CGRELVRAQI AICGKSTGGE GGGEEGGGEG GQLYSALANK CCHVGCTKRS LARFC        295

SEQ ID NO: 310          moltype = AA  length = 294
FEATURE                 Location/Qualifiers
source                  1..294
                        mol_type = protein
                        organism = synthetic construct
SEQUENCE: 310
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGSD SWMEEVIKLC   240
GRELVRAQIA ICGKSTGGEG GGEEGGGEGG QLYSALANKC CHVGCTKRSL ARFC         294

SEQ ID NO: 311          moltype = AA  length = 294
FEATURE                 Location/Qualifiers
source                  1..294
                        mol_type = protein
                        organism = synthetic construct
SEQUENCE: 311
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGSD SWQEEVIKLC   240
GRELVRAQIA ICGKSTGGEG GGEEGGGEGG QLYSALANKC CHVGCTKRSL ARFC         294

SEQ ID NO: 312          moltype = AA  length = 295
FEATURE                 Location/Qualifiers
source                  1..295
                        mol_type = protein
                        organism = synthetic construct
SEQUENCE: 312
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWQEEVIKL   240
CGRELVRAQI AICGKSTGGG EGGGEGGGEG RQLYSALANK CCHVGCTKRS LAQFC        295

SEQ ID NO: 313          moltype = AA  length = 295
FEATURE                 Location/Qualifiers
source                  1..295
                        mol_type = protein
                        organism = synthetic construct
SEQUENCE: 313
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTGGG EGGGEGGGEG RQLYSALANK CCHVGCTKRS LAQFC        295

SEQ ID NO: 314          moltype = AA  length = 294
FEATURE                 Location/Qualifiers
source                  1..294
                        mol_type = protein
                        organism = synthetic construct
SEQUENCE: 314
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGSD SWQEEVIKLC   240
GRELVRAQIA ICGKSTGGGE GGGEGGGEGR QLYSALANKC CHVGCTKRSL ARFC         294
```

```
SEQ ID NO: 315          moltype = AA  length = 294
FEATURE                 Location/Qualifiers
source                  1..294
                        mol_type = protein
                        organism = synthetic construct
SEQUENCE: 315
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGGGSD SWQEEVIKLC   240
GRELVRAQIA ICGKSTGGGE GGGEGGGEGR QLYSALANKC CHVGCTKRSL ARFC         294

SEQ ID NO: 316          moltype = AA  length = 294
FEATURE                 Location/Qualifiers
source                  1..294
                        mol_type = protein
                        organism = synthetic construct
SEQUENCE: 316
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGGGSD SWQEEVIKLC   240
GRELVRAQIA ICGKSTGGGE GGGEGGGEGR QLYSALANKC CHVGCTKRSL AQFC         294

SEQ ID NO: 317          moltype = AA  length = 294
FEATURE                 Location/Qualifiers
source                  1..294
                        mol_type = protein
                        organism = synthetic construct
SEQUENCE: 317
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGGGSD SWQEEVIKLC   240
GRELVRAQIA ICGKSTGGGE GGGEGGGEGR QLYSALANKC CHVGCTKRSL AQFC         294

SEQ ID NO: 318          moltype = AA  length = 295
FEATURE                 Location/Qualifiers
source                  1..295
                        mol_type = protein
                        organism = synthetic construct
SEQUENCE: 318
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWQEEVIKL   240
CGRELVRAQI AICGKSTGGG EEGGGEEGGG RQLYSALANK CCHVGCTKRS LARFC        295

SEQ ID NO: 319          moltype = AA  length = 295
FEATURE                 Location/Qualifiers
source                  1..295
                        mol_type = protein
                        organism = synthetic construct
SEQUENCE: 319
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTGGG EEGGGEEGGG RQLYSALANK CCHVGCTKRS LARFC        295

SEQ ID NO: 320          moltype = AA  length = 295
FEATURE                 Location/Qualifiers
source                  1..295
                        mol_type = protein
                        organism = synthetic construct
SEQUENCE: 320
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWQEEVIKL   240
CGRELVRAQI AICGKSTGGG EEGGGEEGGG RQLYSALANK CCHVGCTKRS LAQFC        295

SEQ ID NO: 321          moltype = AA  length = 295
FEATURE                 Location/Qualifiers
source                  1..295
                        mol_type = protein
                        organism = synthetic construct
SEQUENCE: 321
DKTHTCPPCP APEAAGGPSV FLFPPKPKDT LMISRTPEVT CVVVDVSHED PEVKFNWYVD    60
```

```
GVEVHNAKTK PREEQYNSTY RVVSVLTVLH QDWLNGKEYK CKVSNKALAA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVLHE ALHSHYTQKS LSLSPGKGGS DSWQEEVIKL    240
CGRELVRAQI AICGKSTGGG EEGGGEEGGG RQLYSALANK CCHVGCTKRS LAQFC         295

SEQ ID NO: 322              moltype = AA  length = 294
FEATURE                     Location/Qualifiers
source                      1..294
                            mol_type = protein
                            organism = synthetic construct
SEQUENCE: 322
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALAA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGGGSD SWQEEVIKLC    240
GRELVRAQIA ICGKSTGGGE EGGGEEGGGR QLYSALANKC CHVGCTKRSL ARFC          294

SEQ ID NO: 323              moltype = AA  length = 294
FEATURE                     Location/Qualifiers
source                      1..294
                            mol_type = protein
                            organism = synthetic construct
SEQUENCE: 323
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALAA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVLHE ALHSHYTQKS LSLSPGGGSD SWQEEVIKLC    240
GRELVRAQIA ICGKSTGGGE EGGGEEGGGR QLYSALANKC CHVGCTKRSL ARFC          294

SEQ ID NO: 324              moltype = AA  length = 294
FEATURE                     Location/Qualifiers
source                      1..294
                            mol_type = protein
                            organism = synthetic construct
SEQUENCE: 324
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALAA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGGGSD SWQEEVIKLC    240
GRELVRAQIA ICGKSTGGGE EGGGEEGGGR QLYSALANKC CHVGCTKRSL AQFC          294

SEQ ID NO: 325              moltype = AA  length = 294
FEATURE                     Location/Qualifiers
source                      1..294
                            mol_type = protein
                            organism = synthetic construct
SEQUENCE: 325
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALAA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVLHE ALHSHYTQKS LSLSPGGGSD SWQEEVIKLC    240
GRELVRAQIA ICGKSTGGGE EGGGEEGGGR QLYSALANKC CHVGCTKRSL AQFC          294

SEQ ID NO: 326              moltype = AA  length = 295
FEATURE                     Location/Qualifiers
source                      1..295
                            mol_type = protein
                            organism = synthetic construct
SEQUENCE: 326
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALAA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVLHE ALHSHYTQKS LSLSPGKGGS DSWQEEVIKL    240
CGRELVRAQI AICGKSTGGE GEGGEGEGGS RQLYSALANK CCHVGCTKRS LAQFC         295

SEQ ID NO: 327              moltype = AA  length = 294
FEATURE                     Location/Qualifiers
source                      1..294
                            mol_type = protein
                            organism = synthetic construct
SEQUENCE: 327
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALAA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVLHE ALHSHYTQKS LSLSPGGGSD SWQEEVIKLC    240
GRELVRAQIA ICGKSTGGEG EGGEGEGGSR QLYSALANKC CHVGCTKRSL ARFC          294

SEQ ID NO: 328              moltype = AA  length = 294
FEATURE                     Location/Qualifiers
```

```
                        source                  1..294
                                                mol_type = protein
                                                organism = synthetic construct
SEQUENCE: 328
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGGGSD SWQEEVIKLC   240
GRELVRAQIA ICGKSTGGEG EGGEGEGGSR QLYSALANKC CHVGCTKRSL AQFC         294

SEQ ID NO: 329           moltype = AA  length = 20
FEATURE                  Location/Qualifiers
source                   1..20
                         mol_type = protein
                         organism = synthetic construct
SEQUENCE: 329
METDTLLLWV LLLWVPGSTG                                                20

SEQ ID NO: 330           moltype = AA  length = 315
FEATURE                  Location/Qualifiers
source                   1..315
                         mol_type = protein
                         organism = synthetic construct
SEQUENCE: 330
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALPA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVMHE ALHNHYTQKS   240
LSLSPGKGGS DSWKEEVIKL CGRELVRAQI AICGKSTGGG EGGGEGGGEG RQLYSALANK   300
CCHVGCTKRS LARFC                                                   315

SEQ ID NO: 331           moltype = AA  length = 316
FEATURE                  Location/Qualifiers
source                   1..316
                         mol_type = protein
                         organism = synthetic construct
SEQUENCE: 331
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALPA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVMHE ALHNHYTQKS   240
LSLSPGKGGS DSWKEEVIKL CGRELVRAQI AICGKSTGGG EGGGEGGGEG GGQLYSALAN   300
KCCHVGCTKR SLARFC                                                  316

SEQ ID NO: 332           moltype = AA  length = 315
FEATURE                  Location/Qualifiers
source                   1..315
                         mol_type = protein
                         organism = synthetic construct
SEQUENCE: 332
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALPA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVMHE ALHNHYTQKS   240
LSLSPGKGGS DSWMEEVIKL CGRELVRAQI AICGKSTGGG EGGGEGGGEG RQLYSALANK   300
CCHVGCTKRS LARFC                                                   315

SEQ ID NO: 333           moltype = AA  length = 315
FEATURE                  Location/Qualifiers
source                   1..315
                         mol_type = protein
                         organism = synthetic construct
SEQUENCE: 333
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALPA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVMHE ALHNHYTQKS   240
LSLSPGKGGS DSWQEEVIKL CGRELVRAQI AICGKSTGGG EGGGEGGGEG RQLYSALANK   300
CCHVGCTKRS LARFC                                                   315

SEQ ID NO: 334           moltype = AA  length = 315
FEATURE                  Location/Qualifiers
source                   1..315
                         mol_type = protein
                         organism = synthetic construct
SEQUENCE: 334
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
```

```
WESNGQPENN YKTTPPVLDS DGSFFLYSKL TVDKSRWQQG NVFSCSVLHE ALHSHYTQKS    240
LSLSPGKGGS DSWQEEVIKL CGRELVRAQI AICGKSTGGG EGGGEGGGEG RQLYSALANK    300
CCHVGCTKRS LARFC                                                    315

SEQ ID NO: 335          moltype = AA   length = 316
FEATURE                 Location/Qualifiers
source                  1..316
                        mol_type = protein
                        organism = synthetic construct
SEQUENCE: 335
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALPA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVMHE ALHNHYTQKS    240
LSLSPGKGGS DSWMEEVIKL CGRELVRAQI AICGKSTGGG EGGGEGGGEG GGQLYSALAN    300
KCCHVGCTKR SLARFC                                                   316

SEQ ID NO: 336          moltype = AA   length = 316
FEATURE                 Location/Qualifiers
source                  1..316
                        mol_type = protein
                        organism = synthetic construct
SEQUENCE: 336
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALPA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVMHE ALHNHYTQKS    240
LSLSPGKGGS DSWQEEVIKL CGRELVRAQI AICGKSTGGG EGGGEGGGEG GGQLYSALAN    300
KCCHVGCTKR SLARFC                                                   316

SEQ ID NO: 337          moltype = AA   length = 316
FEATURE                 Location/Qualifiers
source                  1..316
                        mol_type = protein
                        organism = synthetic construct
SEQUENCE: 337
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGKGGS DSWQEEVIKL CGRELVRAQI AICGKSTGGG EGGGEGGGEG GGQLYSALAN    300
KCCHVGCTKR SLARFC                                                   316

SEQ ID NO: 338          moltype = AA   length = 315
FEATURE                 Location/Qualifiers
source                  1..315
                        mol_type = protein
                        organism = synthetic construct
SEQUENCE: 338
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALPA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVMHE ALHNHYTQKS    240
LSLSPGKGGS DSWMEEVIKL CGRELVRAQI AICGKSTGGE GGGEEGGGEG GQLYSALANK    300
CCHVGCTKRS LARFC                                                    315

SEQ ID NO: 339          moltype = AA   length = 315
FEATURE                 Location/Qualifiers
source                  1..315
                        mol_type = protein
                        organism = synthetic construct
SEQUENCE: 339
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALPA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVMHE ALHNHYTQKS    240
LSLSPGKGGS DSWQEEVIKL CGRELVRAQI AICGKSTGGE GGGEEGGGEG GQLYSALANK    300
CCHVGCTKRS LARFC                                                    315

SEQ ID NO: 340          moltype = AA   length = 314
FEATURE                 Location/Qualifiers
source                  1..314
                        mol_type = protein
                        organism = synthetic construct
SEQUENCE: 340
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALPA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVMHE ALHNHYTQKS    240
```

```
LSLSPGGGSD SWMEEVIKLC GRELVRAQIA ICGKSTGGEG GGEEGGGEGG QLYSALANKC    300
CHVGCTKRSL ARFC                                                     314

SEQ ID NO: 341            moltype = AA  length = 314
FEATURE                   Location/Qualifiers
source                    1..314
                          mol_type = protein
                          organism = synthetic construct
SEQUENCE: 341
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALPA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVMHE ALHNHYTQKS    240
LSLSPGGGSD SWQEEVIKLC GRELVRAQIA ICGKSTGGEG GGEEGGGEGG QLYSALANKC    300
CHVGCTKRSL ARFC                                                     314

SEQ ID NO: 342            moltype = AA  length = 315
FEATURE                   Location/Qualifiers
source                    1..315
                          mol_type = protein
                          organism = synthetic construct
SEQUENCE: 342
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVMHE ALHNHYTQKS    240
LSLSPGKGGS DSWQEEVIKL CGRELVRAQI AICGKSTGGG EGGGEGGGEG RQLYSALANK    300
CCHVGCTKRS LAQFC                                                    315

SEQ ID NO: 343            moltype = AA  length = 315
FEATURE                   Location/Qualifiers
source                    1..315
                          mol_type = protein
                          organism = synthetic construct
SEQUENCE: 343
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGKGGS DSWQEEVIKL CGRELVRAQI AICGKSTGGG EGGGEGGGEG RQLYSALANK    300
CCHVGCTKRS LAQFC                                                    315

SEQ ID NO: 344            moltype = AA  length = 314
FEATURE                   Location/Qualifiers
source                    1..314
                          mol_type = protein
                          organism = synthetic construct
SEQUENCE: 344
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVMHE ALHNHYTQKS    240
LSLSPGGGSD SWQEEVIKLC GRELVRAQIA ICGKSTGGGE GGGEGGGEGR QLYSALANKC    300
CHVGCTKRSL ARFC                                                     314

SEQ ID NO: 345            moltype = AA  length = 314
FEATURE                   Location/Qualifiers
source                    1..314
                          mol_type = protein
                          organism = synthetic construct
SEQUENCE: 345
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVLHE ALHSHYTQKS    240
LSLSPGGGSD SWQEEVIKLC GRELVRAQIA ICGKSTGGGE GGGEGGGEGR QLYSALANKC    300
CHVGCTKRSL ARFC                                                     314

SEQ ID NO: 346            moltype = AA  length = 314
FEATURE                   Location/Qualifiers
source                    1..314
                          mol_type = protein
                          organism = synthetic construct
SEQUENCE: 346
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK    120
CKVSNKALAA PIEKTISKAK GQPREPQVYT LPPSRDELTK NQVSLTCLVK GFYPSDIAVE    180
WESNGQPENN YKTTPPVLDS DGSFFLYSKL TVDKSRWQQG NVFSCSVMHE ALHNHYTQKS    240
LSLSPGGGSD SWQEEVIKLC GRELVRAQIA ICGKSTGGGE GGGEGGGEGR QLYSALANKC    300
```

```
CHVGCTKRSL AQFC                                                         314

SEQ ID NO: 347          moltype = AA  length = 314
FEATURE                 Location/Qualifiers
source                  1..314
                        mol_type = protein
                        organism = synthetic construct
SEQUENCE: 347
METDTLLLWV LLLWVPGSTG DKTHTCPPCP APEAAGGPSV FLFPPKPKDT LMISRTPEVT        60
CVVVDVSHED PEVKFNWYVD GVEVHNAKTK PREEQYNSTY RVVSVLTVLH QDWLNGKEYK       120
CKVSNKALAA PIEKTISKAK GQPREPQVYT LPPSRDELTK NQVSLTCLVK GFYPSDIAVE       180
WESNGQPENN YKTTPPVLDS DGSFFLYSKL TVDKSRWQQG NVFSCSVLHE ALHSHYTQKS       240
LSLSPGGGSD SWQEEVIKLC GRELVRAQIA ICGKSTGGGE GGGEGGGEGR QLYSALANKC       300
CHVGCTKRSL AQFC                                                         314

SEQ ID NO: 348          moltype = AA  length = 315
FEATURE                 Location/Qualifiers
source                  1..315
                        mol_type = protein
                        organism = synthetic construct
SEQUENCE: 348
METDTLLLWV LLLWVPGSTG DKTHTCPPCP APEAAGGPSV FLFPPKPKDT LMISRTPEVT        60
CVVVDVSHED PEVKFNWYVD GVEVHNAKTK PREEQYNSTY RVVSVLTVLH QDWLNGKEYK       120
CKVSNKALAA PIEKTISKAK GQPREPQVYT LPPSRDELTK NQVSLTCLVK GFYPSDIAVE       180
WESNGQPENN YKTTPPVLDS DGSFFLYSKL TVDKSRWQQG NVFSCSVMHE ALHNHYTQKS       240
LSLSPGKGGS DSWQEEVIKL CGRELVRAQI AICGKSTGGG EEGGGEEGGG RQLYSALANK       300
CCHVGCTKRS LARFC                                                        315

SEQ ID NO: 349          moltype = AA  length = 315
FEATURE                 Location/Qualifiers
source                  1..315
                        mol_type = protein
                        organism = synthetic construct
SEQUENCE: 349
METDTLLLWV LLLWVPGSTG DKTHTCPPCP APEAAGGPSV FLFPPKPKDT LMISRTPEVT        60
CVVVDVSHED PEVKFNWYVD GVEVHNAKTK PREEQYNSTY RVVSVLTVLH QDWLNGKEYK       120
CKVSNKALAA PIEKTISKAK GQPREPQVYT LPPSRDELTK NQVSLTCLVK GFYPSDIAVE       180
WESNGQPENN YKTTPPVLDS DGSFFLYSKL TVDKSRWQQG NVFSCSVLHE ALHSHYTQKS       240
LSLSPGKGGS DSWQEEVIKL CGRELVRAQI AICGKSTGGG EEGGGEEGGG RQLYSALANK       300
CCHVGCTKRS LARFC                                                        315

SEQ ID NO: 350          moltype = AA  length = 315
FEATURE                 Location/Qualifiers
source                  1..315
                        mol_type = protein
                        organism = synthetic construct
SEQUENCE: 350
METDTLLLWV LLLWVPGSTG DKTHTCPPCP APEAAGGPSV FLFPPKPKDT LMISRTPEVT        60
CVVVDVSHED PEVKFNWYVD GVEVHNAKTK PREEQYNSTY RVVSVLTVLH QDWLNGKEYK       120
CKVSNKALAA PIEKTISKAK GQPREPQVYT LPPSRDELTK NQVSLTCLVK GFYPSDIAVE       180
WESNGQPENN YKTTPPVLDS DGSFFLYSKL TVDKSRWQQG NVFSCSVMHE ALHNHYTQKS       240
LSLSPGKGGS DSWQEEVIKL CGRELVRAQI AICGKSTGGG EEGGGEEGGG RQLYSALANK       300
CCHVGCTKRS LAQFC                                                        315

SEQ ID NO: 351          moltype = AA  length = 315
FEATURE                 Location/Qualifiers
source                  1..315
                        mol_type = protein
                        organism = synthetic construct
SEQUENCE: 351
METDTLLLWV LLLWVPGSTG DKTHTCPPCP APEAAGGPSV FLFPPKPKDT LMISRTPEVT        60
CVVVDVSHED PEVKFNWYVD GVEVHNAKTK PREEQYNSTY RVVSVLTVLH QDWLNGKEYK       120
CKVSNKALAA PIEKTISKAK GQPREPQVYT LPPSRDELTK NQVSLTCLVK GFYPSDIAVE       180
WESNGQPENN YKTTPPVLDS DGSFFLYSKL TVDKSRWQQG NVFSCSVLHE ALHSHYTQKS       240
LSLSPGKGGS DSWQEEVIKL CGRELVRAQI AICGKSTGGG EEGGGEEGGG RQLYSALANK       300
CCHVGCTKRS LAQFC                                                        315

SEQ ID NO: 352          moltype = AA  length = 314
FEATURE                 Location/Qualifiers
source                  1..314
                        mol_type = protein
                        organism = synthetic construct
SEQUENCE: 352
METDTLLLWV LLLWVPGSTG DKTHTCPPCP APEAAGGPSV FLFPPKPKDT LMISRTPEVT        60
CVVVDVSHED PEVKFNWYVD GVEVHNAKTK PREEQYNSTY RVVSVLTVLH QDWLNGKEYK       120
CKVSNKALAA PIEKTISKAK GQPREPQVYT LPPSRDELTK NQVSLTCLVK GFYPSDIAVE       180
WESNGQPENN YKTTPPVLDS DGSFFLYSKL TVDKSRWQQG NVFSCSVMHE ALHNHYTQKS       240
LSLSPGGGSD SWQEEVIKLC GRELVRAQIA ICGKSTGGGE EGGGEEGGGR QLYSALANKC       300
CHVGCTKRSL ARFC                                                         314
```

```
SEQ ID NO: 353          moltype = AA  length = 314
FEATURE                 Location/Qualifiers
source                  1..314
                        mol_type = protein
                        organism = synthetic construct
SEQUENCE: 353
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK 120
CKVSNKALAA PIEKTISKAK GQPREPQVYT LPPSRDELTK NQVSLTCLVK GFYPSDIAVE 180
WESNGQPENN YKTTPPVLDS DGSFFLYSKL TVDKSRWQQG NVFSCSVLHE ALHSHYTQKS 240
LSLSPGGGSD SWQEEVIKLC GRELVRAQIA ICGKSTGGGE EGGGEEGGGR QLYSALANKC 300
CHVGCTKRSL ARFC                                                  314

SEQ ID NO: 354          moltype = AA  length = 314
FEATURE                 Location/Qualifiers
source                  1..314
                        mol_type = protein
                        organism = synthetic construct
SEQUENCE: 354
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK 120
CKVSNKALAA PIEKTISKAK GQPREPQVYT LPPSRDELTK NQVSLTCLVK GFYPSDIAVE 180
WESNGQPENN YKTTPPVLDS DGSFFLYSKL TVDKSRWQQG NVFSCSVMHE ALHNHYTQKS 240
LSLSPGGGSD SWQEEVIKLC GRELVRAQIA ICGKSTGGGE EGGGEEGGGR QLYSALANKC 300
CHVGCTKRSL AQFC                                                  314

SEQ ID NO: 355          moltype = AA  length = 314
FEATURE                 Location/Qualifiers
source                  1..314
                        mol_type = protein
                        organism = synthetic construct
SEQUENCE: 355
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK 120
CKVSNKALAA PIEKTISKAK GQPREPQVYT LPPSRDELTK NQVSLTCLVK GFYPSDIAVE 180
WESNGQPENN YKTTPPVLDS DGSFFLYSKL TVDKSRWQQG NVFSCSVLHE ALHSHYTQKS 240
LSLSPGGGSD SWQEEVIKLC GRELVRAQIA ICGKSTGGGE EGGGEEGGGR QLYSALANKC 300
CHVGCTKRSL AQFC                                                  314

SEQ ID NO: 356          moltype = AA  length = 315
FEATURE                 Location/Qualifiers
source                  1..315
                        mol_type = protein
                        organism = synthetic construct
SEQUENCE: 356
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK 120
CKVSNKALAA PIEKTISKAK GQPREPQVYT LPPSRDELTK NQVSLTCLVK GFYPSDIAVE 180
WESNGQPENN YKTTPPVLDS DGSFFLYSKL TVDKSRWQQG NVFSCSVLHE ALHSHYTQKS 240
LSLSPGKGGS DSWQEEVIKL CGRELVRAQI AICGKSTGGE GEGGEGEGGS RQLYSALANK 300
CCHVGCTKRS LAQFC                                                 315

SEQ ID NO: 357          moltype = AA  length = 314
FEATURE                 Location/Qualifiers
source                  1..314
                        mol_type = protein
                        organism = synthetic construct
SEQUENCE: 357
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK 120
CKVSNKALAA PIEKTISKAK GQPREPQVYT LPPSRDELTK NQVSLTCLVK GFYPSDIAVE 180
WESNGQPENN YKTTPPVLDS DGSFFLYSKL TVDKSRWQQG NVFSCSVLHE ALHSHYTQKS 240
LSLSPGGGSD SWQEEVIKLC GRELVRAQIA ICGKSTGGEG EGGEGEGGSR QLYSALANKC 300
CHVGCTKRSL ARFC                                                  314

SEQ ID NO: 358          moltype = AA  length = 314
FEATURE                 Location/Qualifiers
source                  1..314
                        mol_type = protein
                        organism = synthetic construct
SEQUENCE: 358
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK 120
CKVSNKALAA PIEKTISKAK GQPREPQVYT LPPSRDELTK NQVSLTCLVK GFYPSDIAVE 180
WESNGQPENN YKTTPPVLDS DGSFFLYSKL TVDKSRWQQG NVFSCSVLHE ALHSHYTQKS 240
LSLSPGGGSD SWQEEVIKLC GRELVRAQIA ICGKSTGGEG EGGEGEGGSR QLYSALANKC 300
CHVGCTKRSL AQFC                                                  314
```

```
SEQ ID NO: 359           moltype = AA  length = 295
FEATURE                  Location/Qualifiers
source                   1..295
                         mol_type = protein
                         organism = synthetic construct
SEQUENCE: 359
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWKEEVIKL   240
CGRELVRAQI AICGKSTASD AAGANANAGA RQLYSALANK CCHVGCTKRS LAQFC        295

SEQ ID NO: 360           moltype = AA  length = 295
FEATURE                  Location/Qualifiers
source                   1..295
                         mol_type = protein
                         organism = synthetic construct
SEQUENCE: 360
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGS DSWKEEVIKL   240
CGRELVRAQI AICGKSTASD AAGANANAGA RQLYSALANK CCHVGCTKRS LAEFC        295

SEQ ID NO: 361           moltype = AA  length = 295
FEATURE                  Location/Qualifiers
source                   1..295
                         mol_type = protein
                         organism = synthetic construct
SEQUENCE: 361
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWKEEVIKL   240
CGRELVRAQI AICGKSTGGG EGGGEGGGEG RQLYSALANK CCHVGCTKRS LARFC        295

SEQ ID NO: 362           moltype = AA  length = 296
FEATURE                  Location/Qualifiers
source                   1..296
                         mol_type = protein
                         organism = synthetic construct
SEQUENCE: 362
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWKEEVIKL   240
CGRELVRAQI AICGKSTGGG EGGGEGGGEG GGQLYSALAN KCCHVGCTKR SLARFC       296

SEQ ID NO: 363           moltype = AA  length = 295
FEATURE                  Location/Qualifiers
source                   1..295
                         mol_type = protein
                         organism = synthetic construct
SEQUENCE: 363
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWMEEVIKL   240
CGRELVRAQI AICGKSTGGG EGGGEGGGEG RQLYSALANK CCHVGCTKRS LARFC        295

SEQ ID NO: 364           moltype = AA  length = 296
FEATURE                  Location/Qualifiers
source                   1..296
                         mol_type = protein
                         organism = synthetic construct
SEQUENCE: 364
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWMEEVIKL   240
CGRELVRAQI AICGKSTGGG EGGGEGGGEG GGQLYSALAN KCCHVGCTKR SLARFC       296

SEQ ID NO: 365           moltype = AA  length = 295
FEATURE                  Location/Qualifiers
source                   1..295
                         mol_type = protein
                         organism = synthetic construct
SEQUENCE: 365
DKTHTCPPCP APEAAGGPSV FLFPPKPKDT LMISRTPEVT CVVVDVSHED PEVKFNWYVD    60
```

```
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWMEEVIKL   240
CGRELVRAQI AICGKSTGGE GGGEEGGGEG GQLYSALANK CCHVGCTKRS LARFC        295

SEQ ID NO: 366           moltype = AA  length = 295
FEATURE                  Location/Qualifiers
source                   1..295
                         mol_type = protein
                         organism = synthetic construct
SEQUENCE: 366
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWQEEVIKL   240
CGRELVRAQI AICGKSTGGE GGGEEGGGEG GQLYSALANK CCHVGCTKRS LARFC        295

SEQ ID NO: 367           moltype = AA  length = 294
FEATURE                  Location/Qualifiers
source                   1..294
                         mol_type = protein
                         organism = synthetic construct
SEQUENCE: 367
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGGGSD SWMEEVIKLC   240
GRELVRAQIA ICGKSTGGEG GGEEGGGEGG QLYSALANKC CHVGCTKRSL ARFC         294

SEQ ID NO: 368           moltype = AA  length = 294
FEATURE                  Location/Qualifiers
source                   1..294
                         mol_type = protein
                         organism = synthetic construct
SEQUENCE: 368
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGGGSD SWQEEVIKLC   240
GRELVRAQIA ICGKSTGGEG GGEEGGGEGG QLYSALANKC CHVGCTKRSL ARFC         294

SEQ ID NO: 369           moltype = AA  length = 295
FEATURE                  Location/Qualifiers
source                   1..295
                         mol_type = protein
                         organism = synthetic construct
SEQUENCE: 369
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWKEEVIKL   240
CGRELVRAQI AICGKSTASD AAGANANAGA RQLYSALANK CCHVGCTKRS LAQFC        295

SEQ ID NO: 370           moltype = AA  length = 295
FEATURE                  Location/Qualifiers
source                   1..295
                         mol_type = protein
                         organism = synthetic construct
SEQUENCE: 370
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALAA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVLHE ALHSHYTQKS LSLSPGKGGS DSWKEEVIKL   240
CGRELVRAQI AICGKSTASD AAGANANAGA RQLYSALANK CCHVGCTKRS LAEFC        295

SEQ ID NO: 371           moltype = AA  length = 315
FEATURE                  Location/Qualifiers
source                   1..315
                         mol_type = protein
                         organism = synthetic construct
SEQUENCE: 371
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWKEEVIKL CGRELVRAQI AICGKSTGGG EGGGEGGGEG RQLYSALANK   300
CCHVGCTKRS LARFC                                                    315

SEQ ID NO: 372           moltype = AA  length = 316
```

```
FEATURE                 Location/Qualifiers
source                  1..316
                        mol_type = protein
                        organism = synthetic construct
SEQUENCE: 372
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWKEEVIKL CGRELVRAQI AICGKSTGGG EGGGEGGGEG GGQLYSALAN   300
KCCHVGCTKR SLARFC                                                   316

SEQ ID NO: 373          moltype = AA  length = 315
FEATURE                 Location/Qualifiers
source                  1..315
                        mol_type = protein
                        organism = synthetic construct
SEQUENCE: 373
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWMEEVIKL CGRELVRAQI AICGKSTGGG EGGGEGGGEG RQLYSALANK   300
CCHVGCTKRS LARFC                                                    315

SEQ ID NO: 374          moltype = AA  length = 316
FEATURE                 Location/Qualifiers
source                  1..316
                        mol_type = protein
                        organism = synthetic construct
SEQUENCE: 374
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWMEEVIKL CGRELVRAQI AICGKSTGGG EGGGEGGGEG GGQLYSALAN   300
KCCHVGCTKR SLARFC                                                   316

SEQ ID NO: 375          moltype = AA  length = 315
FEATURE                 Location/Qualifiers
source                  1..315
                        mol_type = protein
                        organism = synthetic construct
SEQUENCE: 375
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWMEEVIKL CGRELVRAQI AICGKSTGGE GGGEEGGGEG GQLYSALANK   300
CCHVGCTKRS LARFC                                                    315

SEQ ID NO: 376          moltype = AA  length = 315
FEATURE                 Location/Qualifiers
source                  1..315
                        mol_type = protein
                        organism = synthetic construct
SEQUENCE: 376
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWQEEVIKL CGRELVRAQI AICGKSTGGE GGGEEGGGEG GQLYSALANK   300
CCHVGCTKRS LARFC                                                    315

SEQ ID NO: 377          moltype = AA  length = 314
FEATURE                 Location/Qualifiers
source                  1..314
                        mol_type = protein
                        organism = synthetic construct
SEQUENCE: 377
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGGGSD SWMEEVIKLC GRELVRAQIA ICGKSTGGEG GGEEGGGEGG QLYSALANKC   300
CHVGCTKRSL ARFC                                                     314

SEQ ID NO: 378          moltype = AA  length = 314
FEATURE                 Location/Qualifiers
```

```
source                      1..314
                            mol_type = protein
                            organism = synthetic construct
SEQUENCE: 378
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGGGSD SWQEEVIKLC GRELVRAQIA ICGKSTGGEG GGEEGGGEGG QLYSALANKC   300
CHVGCTKRSL ARFC                                                    314

SEQ ID NO: 379              moltype = AA  length = 315
FEATURE                     Location/Qualifiers
source                      1..315
                            mol_type = protein
                            organism = synthetic construct
SEQUENCE: 379
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWKEEVIKL CGRELVRAQI AICGKSTASD AAGANANAGA RQLYSALANK   300
CCHVGCTKRS LAQFC                                                   315

SEQ ID NO: 380              moltype = AA  length = 315
FEATURE                     Location/Qualifiers
source                      1..315
                            mol_type = protein
                            organism = synthetic construct
SEQUENCE: 380
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSWKEEVIKL CGRELVRAQI AICGKSTASD AAGANANAGA RQLYSALANK   300
CCHVGCTKRS LAEFC                                                   315

SEQ ID NO: 381              moltype = DNA  length = 945
FEATURE                     Location/Qualifiers
source                      1..945
                            mol_type = other DNA
                            organism = synthetic construct
SEQUENCE: 381
atggagacgg acactttgct gctttgggta ctgctgcttt gggttcctgg atctactggc    60
gataaaacac acacgtgtcc ccctgcccg gctccagagg cggctgtgg tcccagcgta    120
ttcttgtttc ctcccaaacc taaggatacg ctcatgatat cccgcacccc agaagttacg   180
tgtgtagtcg tcgacgtcag tcacgaagat ccagaggtca aatttaactg gtatgtcgac   240
ggagtagagg tccacaatgc gaaaaccaag cccagagaag agcagtacaa ctccacgtat   300
cgcgtcgtct ccgtcctcac cgtactccat caagattggc tgaatgggaa agagtataaa   360
tgcaaagtat ctaacaaggc tctgccagct ccgataaaa agactatatc aaaggccaag   420
gggcagccaa gggagcctca agtctatact ttgcccccat ctcgggatga gcttacgaaa   480
aaccaggtca gccttacctg tcttgttaaa ggtttttatc cgagtgacat cgcagtggaa   540
tgggaatcta atggtcaacc tgaaacaat tacaaaacca caccgccagt attggacagc   600
gatggtagtt ttttttcttta ctcaaaactg actgtagata aaagcagatg gcagcagggc   660
aatgtctttt catgtagcgt tatgcatgag gctcttcaca accactatac ccaaaagtca   720
ttgtctctta gtcccggaaa gggcggaagt gattcttgga aggaggaggt aatcaagttg   780
tgcgggcgag agttggtacg ggcacagatc gcgatatgcg gaaaatccac aggtggggc    840
gaaggaggag gtgagggtgg aggtgaagga cgacagttgt attccgcctt ggcaaacaag   900
tgttgccatg tgggttgcac aaaacgcagt cttgcccgct tctgt                   945

SEQ ID NO: 382              moltype = DNA  length = 948
FEATURE                     Location/Qualifiers
source                      1..948
                            mol_type = other DNA
                            organism = synthetic construct
SEQUENCE: 382
atggagaccg atacgctgtt gctgtgggta ttgcttctct gggtgcccgg ctcaactggg    60
gataagacac atacatgccc tcctgtccg gctccagagg cagcgggggg tccatcagtc   120
ttcctttttc cgcctaaacc taaggataca ctgatgatct ctcgaacacc ggaggtcact   180
tgtgttgtcg ttgacgtatc acatgaggat cccgaagtaa agttcaactg gtatgtcgat   240
ggtgtggagg tcataatgc taaaactaaa ccacgggagg agcaatataa ttccacatat   300
agggtcgtga gcgtgttgac ggtgcttcat caagactggc ttaatgggaa ggaatataaa   360
tgcaaagtgt caaataaagc acttcctgcg ccaatcgaga aaacaattag taaggcaaag   420
gggcagccgc gagaacctca ggtgtacacc ttgccgcctt ctagaacga gctcacaaag   480
aaccaagttt ccctgacttg cctcgttaag gggttttatc cgtccgatat agccgtggag   540
tgggagtcaa acgccaaccc ggaaaataat tacaaaacga cacccccagt attggatagt   600
gacggctctt ttttcctta ttctaagctg actgtggaca aaagccgctg gcagcagggc   660
aatgtctttt catgcagcgt aatgcatgaa gcccttcaca accactacac gcaaaaatcc   720
ctttccttgt caccggcaa gggcggatct gactcctgga agaggaagt tataaaactc   780
```

```
tgtggccgag aacttgttcg agctcaaatc gcgatttgtg gtaagtcaac gggtgggggc   840
gaaggtggag gcgagggtgg gggagaagga ggaggccagt tgtactcagc tcttgcaaat   900
aagtgttgcc acgttggttg tacgaagcgg agccttgctc gcttctgc                948

SEQ ID NO: 383         moltype = DNA   length = 945
FEATURE                Location/Qualifiers
source                 1..945
                       mol_type = other DNA
                       organism = synthetic construct
SEQUENCE: 383
atggaaactg atactcttct gctgtgggtc ctgctgctgt gggttccagg atctactgga    60
gacaaaacac atacttgtcc gccttgcccg gcacccgaag cggccggcgg acccagtgtc   120
tttctcttcc cacccaaacc gaaagacact ctgatgattt ccaggacgcc tgaagtgacc   180
tgcgttgtag ttgatgtatc acacgaggat cccgaggtca agttcaattg gtatgtagat   240
ggggtggagg tccataatgc aaagacgaag ccacgggagg aacagtacaa ctctacgtac   300
agagttgtca gtgttttgac cgtccttcat caggattggc tgaacggtaa agaatataaa   360
tgcaaggtta gcaataaagc tttgcccgcc cctatagaga aaacgatcag taaggcgaag   420
gggcagccta gggaacccca ggtatatacc ttgccgccaa gtcgagatga gctgacgaag   480
aaccaagtga gtctgacatg cctcgtgaag ggcttctatc cgagcgatat cgctgtcgaa   540
tgggagagca atgggcagcc tgagaataac tataaaacaa cgccaccgt cctcgactcc   600
gatggctcat tcttcctgta cagtaaactt acagtagata gagtagatg gcagcagggt   660
aacgtcttta gttgctccgt gatgcacgag gcattgcaca atcattacac tcaaaaatct   720
ctgtccctga gtccgggcaa aggcggttca gatagctgga tggaggaggt cataaagctt   780
tgtggacgag aactcgttcg cgcccagata gctatttgtg ggaaatcaac cgggggtgga   840
gaaggtggcg gagaagggg aggcgaaggg cgccaactgt attctgcatt ggctaataag   900
tgctgtcacg taggatgtac aaaaaggtct ctggcgagat tctgc                   945

SEQ ID NO: 384         moltype = DNA   length = 945
FEATURE                Location/Qualifiers
source                 1..945
                       mol_type = other DNA
                       organism = synthetic construct
SEQUENCE: 384
atggagaccg acaccctctt gttgtgggtt ctcctcttgt gggtgcccgg cagtactgga    60
gacaagacgc acacttgtcc accttgccct cgccggaag tgctggagg ccccagtgtc   120
tttttgttcc cgcccaaacc gaaggacact ttgatgataa gtcgcacgcc cgaggttacc   180
tgtgtggttg tcgatgtctc acacgaagat ccggaggtga agtttaattg gtatgtagat   240
ggcgtggagg ttcataacgc caaaacgaaa cccagagaag aacaatataa cagtacatat   300
cgagtagtat ccgttctcac tgtcctgcat caagactggt tgaacgggaa ggaatataaa   360
tgcaaggtga gcaataaagc actcccggcc ccaatcgaaa agaccatcag caaagcgaag   420
gggcaacctc gagaacccca ggtatatacg ctccccccta gtcgggatga acttactaaa   480
aatcaggtta gcctcacttg ccttgttaaa gggttctatc ccagtgatat tgccgtcgaa   540
tgggaatcaa acgggcagcc ggaaaataac tacaagacaa cccctcctgt gctcgatagc   600
gatggctctt ttttcctcta cagcaaactt accgttgata gagccggtg gcaacaaggt   660
aatgttttct cctgctccgt tatgcatgaa gcactccata accattatac ccaaaaagc   720
ctgtcactta gtccgggtaa aggaggtagt gattcttggc aggaggaggt aatcaaactt   780
tgtgtggggg agctggtacg agctcagatt gctatatgtg gaaaaagcac gggcggagga   840
gaaggaggtg gcgaaggcgg gggtgaaggt cggcaactct actccgctct cgctaataag   900
tgctgccacg tcgggtgtac gaagcgctcc ctggcgcgat tctgc                   945

SEQ ID NO: 385         moltype = DNA   length = 945
FEATURE                Location/Qualifiers
source                 1..945
                       mol_type = other DNA
                       organism = synthetic construct
SEQUENCE: 385
atggaaacag ataccctcct cctctgggtc cttcttcttt gggtgcctgg ctcaactgga    60
gataaaacgc acacgtgtcc gccctgccca gcgcctgaag ccgcaggcgg gccgtccgtc   120
ttcctcttc ctccaaaacc caaagacaca ttttatgatca gtaggacccc agaggtaacc   180
tgcgtcgtgg tcgacgtttc ccatgaagac ccagaggtca agttcaactg gtacgtcgac   240
ggtgtcgaag tacataatgc taaaacgaag cctcgggaag agcagtacaa ctctacctac   300
cgcgtcgttt ccgtactcac cgtacttcac caggactggc ttaacggtaa agagtataaa   360
tgcaaagtat ctaataaggc tctcgccgcg ccgattgaga gacaatttc aaaggccaag   420
gggcagccgc gggagcccca agtgtatacc ttgccccgc cccgagatga gctgactaaa   480
aaccaagtaa gcttgacttg cttggtcaaa ggcttctacc cttccgatat agctgtcgaa   540
tgggagtcaa atgccaacc agagaacaat tataaaacta cacccccggt cttggattct   600
gatggctcat tttttctcta ttctaaactg accgtggata gtctcgctg gcagcaaggt   660
aacgtgttca gttgctctgt tcttcacgaa gcactgcaca gtcattacac tcagaagagt   720
cttagcctga gccctggtaa aggggttct gattcctggc aggaggaagt aataaaaact   780
tgtggccggg agttggtacg ggcgcagatt gcgatatgcg gtaagagcac cggcggaggc   840
gaaggcggtg gggaaggagg aggagaaggg agacaactct attccgcatt ggcaaataag   900
tgctgccacg tcgggtgtac caaacgatcc cttgcacggt tctgt                   945

SEQ ID NO: 386         moltype = DNA   length = 948
FEATURE                Location/Qualifiers
source                 1..948
                       mol_type = other DNA
                       organism = synthetic construct
SEQUENCE: 386
```

```
atggagacgg acaccctcct tctctgggtt ttgctccttt gggtccctgg ttccactgga   60
gataagaccc atacgtgccc cccttgcccc gcgcctgagg cagcgggtgg cccatcagtc  120
tttttgttcc cgcccaagcc aaaggacacc ctcatgatta gtagaacacc ggaggttacg  180
tgcgtcgtag tggatgtcag ccacgaggat cccgaggtta agtttaactg gtacgttgat  240
ggggttggag tccataatgc gaagactaag ccgagagga aacagtacaa ttccacgtat  300
agagttgtct ctgtactgac tgtgctgcat caagattggc ttaacggtaa ggagtacaag  360
tgcaaagtct ctaataaggc tcttcctgca cccattgaga aaactataag caaagcaaaa  420
ggtcaacctc gcgaacctca ggtgtacaca ctgccaccct ctagggacga gcttaccaaa  480
aatcaagtat ctcttacctg cctttgtgaaa gggttttatc cctcagatat tgccgttgag  540
tgggagtcta acggacaacc tgagaacaac tataagacta ctcccccggt gcttgattca  600
gacgggagtt tttttttgta tagcaaactt accgtcgaca aaagccgtgg gcaacagggc  660
aatgtattca gttgttctgt aatgcatgaa gctttgcata atcattacac ccaaaagagt  720
ctttccctgt ctcctggaaa aggggggtca gactcctgga tggaggaggt gatcaaactg  780
tgtgggagag agctcgtccg ggctcagata gctatatgcg gcaagtctac gggtggggga  840
gagggcggag gagagggcgg tggagaagga ggcggccaac tctacagcgc tctggccaat  900
aaatgttgtc atgtcgggtg tactaagcgc tcactggcac gcttttgc    948

SEQ ID NO: 387          moltype = DNA   length = 948
FEATURE                 Location/Qualifiers
source                  1..948
                        mol_type = other DNA
                        organism = synthetic construct
SEQUENCE: 387
atggaaaccg acacccttt gttgtgggta ttgctgttgt gggttccgg tagcacgggg   60
gacaagacgc atacatgccc gccatgcccg gcccccgaag ctgctggggg accatccgta  120
ttcctcttcc ctcccaaacc aaaagacacg ttgatgataa gtagaacacc agaggtaacg  180
tgcgtggttg tcgatgtttc ccacgaagat ccggaggtaa aattcaattg gtatgtagat  240
ggggtggaag tgcacaatgc caaaacaaag ccgcgagaga acaatacaa tagtacttac  300
cgggttgtga gcgtgctcac ggtgttgcac caagactggc tcaacggcaa ggaatacaag  360
tgcaaagtat ctaataaagc tctgcctgcg ccgatagaga agccatcag taaggccaaa  420
gggcagcccc gagagccgca gtttacactt cttcctccga gcagagatga attgaccaag  480
aaccaagtaa gttgacgtg cctggtgaag ggcttctacc cctcagacat tgcggtggag  540
tgggaaagta atggtcaacc ggaaaacaac tacaagacca cgccgccgt cctcgactcc  600
gatgggtctt tctttcttta ttcaaagttg acagtagata agtcaaggtg gcagcaaggt  660
aacgtcttta gttgtagtgt aatgcacgag gccctgcata atcattatac ccaaaagagt  720
ttgagcctct caccaggaaa aggcggatca gacagctggc aggaggaggt aattaaattg  780
tgtgggacgg agtggtcag gcgcaaata gccatctgcg gtaagagcac gggtggagga  840
gagggtggag gggaaggtgg gggagaaggc ggcgggcagc tctattctgc actcgccaac  900
aagtgttgtc acgtcggatg cacaaagaga tctcttgctc gattctgc     948

SEQ ID NO: 388          moltype = DNA   length = 948
FEATURE                 Location/Qualifiers
source                  1..948
                        mol_type = other DNA
                        organism = synthetic construct
SEQUENCE: 388
atggagactg atactccttt gttgtgggta ctgctcctgt gggttccagg ctccacagga   60
gacaaaacac acacctgtcc gccttgcccg gctcctgaag ccgcgggtgg ccctagtgtg  120
ttttgtttc cgccgaaacc taaggatacc ctcatgataa gccggacgcc cgaggttacc  180
tgtgtcgtgg tcgatgttag tcatgaggat ccagaagtca agtttaattg gtacgtcgac  240
ggcgttgaag tccacaatgc aaaaaactaaa ccgcgagaag aacagtacaa ctccacctac  300
agagttgtct cagtttttgac agttctccat caggattggc tcaatggaaa ggaatataag  360
tgcaaggtca gcaataaagc gcttgccgcc cctatagaga agaccattag caaggcgaaa  420
ggacagcccc gcgagcccca ggtctatacg ctgcctccta gcagagatga gctcacgaaa  480
aatcaggtca gcttgacatg cttggtgaag ggcttctacc ccagtgacat gcagttggaa  540
tgggagagca acggccaacc tgagaacaac tacaaaacaa cgcccccggt tcttgacagc  600
gatgggtcct tctttcttta ctctaagctt acagttgata aaagcaggtg gcagcagggg  660
aatgtgttct catgttccgt actgcatgag gctctgcatt tcactacac ccaaaaaagc  720
cttagcctga gccccggtaa gggaggtagt gactcatgge aagaggaagt gattaagctc  780
tgcggccggg agttggtgag agcccaaatc gccatttgcg gtaaaagtac cggagggggc  840
gagggaggag gcgaaggtgg aggtgaagga ggtggacagt tgtactcagc tcttgcaaat  900
aaatgttgtc atgttggttg cacgaaaaga tctcttgcga ggttctgt     948

SEQ ID NO: 389          moltype = DNA   length = 945
FEATURE                 Location/Qualifiers
source                  1..945
                        mol_type = other DNA
                        organism = synthetic construct
SEQUENCE: 389
atggagactg acactctttt gttgtgggtg cttcttctgt gggtacctgg atccactggg   60
gataagacgc atacttgtcc accgtgcccc gcaccggaag cggctggtgg tccatcagtt  120
tttctgttcc caccgaaacc taaggacacg ttgatgatat cacggacacc agaggttacg  180
tgcgtagtgg tggatgtgag ccacgaggat ccagaagtta aatttaattg gtacgtagat  240
ggagtgaagg ttcataatgc gaagacaaag cctcgcgagg aacagtataa ttccaccctat  300
cgcgtcgtat ctgtgcttac ggtacttcac caagactggt tgaacggtaa ggaatataaa  360
tgcaaggttt ccaataaagc acttcctgcg ccaattgaga agacaatatc caaagctaaa  420
ggtcaaccca gggaaccgca gtctacactt ctcccccgt ctcgcgatga attgacgaag  480
aaccaggtta gtctcacctg cctggtcaag gggtttttacc cctctgacat agctgtgaa  540
tgggagtcta atggacagcc agagaacaat tacaaaacga cccccccggt cctcgattct  600
```

```
gatgggagtt ttttttcttta ttcaaaattg actgtcgata agtcaagatg gcaacagggt  660
aacgtatttt cttgcagtgt tatgcatgaa gcattgcaca accactatac acaaaaatca  720
ttgagtttga gtcccggtaa aggggggaagc gactcatgga tggaagaagt aatcaagctg  780
tgcgggcgag agcttgtgcg agctcagata gcaatctgtg gtaagtctac aggtggagag  840
ggtggcggtg aagaaggcgg gggagaggga ggccagcttt attctgccct ggctaacaag  900
tgctgtcacg ttggatgcac gaagcgctcc ctggcccgat tctgc                   945

SEQ ID NO: 390            moltype = DNA   length = 945
FEATURE                   Location/Qualifiers
source                    1..945
                          mol_type = other DNA
                          organism = synthetic construct
SEQUENCE: 390
atggaaaccg atacattgct tttgtgggtc ctccttcttt gggttcctgg ctctacaggc  60
gataagacgc atacttgtcc cccatgtccc gctccggaag ccgctggcgg ccccctccgtt  120
tttctgttcc cgccgaaacc gaaagacacc ctgatgatat cacgcactcc cgaggtcact  180
tgcgtggtag tcgatgttag tcatgaagat cctgaggtca aattcaattg gtatgtagat  240
ggcgttgagg tacacaacgc gaagacaaaa ccccgagaag aacagtataa ctcaacctac  300
cgcgtagttt cagttcttac cgtactgcac caagactggt tgaacggtaa agagtacaaa  360
tgtaaagtca gcaataaagc tttgccagca cctatcgaaa aaaccatcag taaggccaag  420
ggtcaaccca gggagccgca agtgtacact cttcccccta gcagggatga attgaccaag  480
aatcaagtct ctttgacgtg cctcgttaag ggtttctctc agccgatat agccgtagaa  540
tgggagtcta acgtcagcc agaaaataac tataagacaa ccccgcctgt tttggattcc  600
gacggctctt ttttttctcta ctctaagttg accgttgata agagcagatg gcagcaggga  660
aacgtatttt cttgttccgt gatgcacgaa gccctgcaca atcactatac gcaaaagtct  720
ctgagcttga gtcccggtaa aggcggttct gactcctgaa aggaggaagt cataaaactc  780
tgcggaagag agctcgtaag ggcgcaaatc gctatttgtg gtaagagcac cggtggggaa  840
ggaggcggtg aagagggtgg cggcgagggt gggcaattgt attccgcgct tgccaataaa  900
tgttgtcacg taggctgcac aaagcgaagt ctcgctaggt tctgc                   945

SEQ ID NO: 391            moltype = DNA   length = 942
FEATURE                   Location/Qualifiers
source                    1..942
                          mol_type = other DNA
                          organism = synthetic construct
SEQUENCE: 391
atggaaaccg acaccttgct tttgtgggtg ctcttgctgt gggttccggg gagcactggc  60
gacaagaccc acacatgtcc cccgtgtccg gcaccagaag cagcgggggg accgtcagta  120
ttcttgtttc caccgaagcc caaagcacat ttgatgattt cacgaactcc tgaagttacc  180
tgtgtggttg tagatgtatc acacgaagac ccagaagtca aattcaattg gtatgtcgac  240
gggggttgaag ttcacaatgc gaagacgaag ccccggagg aacagtacaa cagcacgtac  300
agggttgtga gcgttcttac tgtattgcac caggattggc tcaacggcaa ggagtataaa  360
tgtaaagttt ctaataaggc tcttcctgcc ccaattgaaa aagcgatatc taaagcgaag  420
ggccaaccac gggaacctca ggtgtacaca cttccgccta gcagggatga gttgaccaag  480
aatcaagtct ctttgacgtg cctggtcaag ggtttttacc catcagatat cgccgtcgaa  540
tgggagtcaa acggacaacc cgaaaataac tataaaacta ctccaccagt tctggatagc  600
gacggctcat ttttttctgta ttcaaagctc actgtagaca agtctaggtg gcagcagggt  660
aatgtcttct cctgctcagt aatgcatgag gctcttcaca accactatac tcaaaagagc  720
cttttccctgt cacctggcgg tggaagcgac tcatggatgg aggaggtaat aaagctctgc  780
ggaagagaac tggtacgcgc acaaatcgca atttgtggta agagtactgg cggggaagga  840
ggtggggaag aaggggggcgg tgagggcgga cagctctatt ctgcacttgc aaacaaatgt  900
tgccacgtgg gatgtactaa gcgaagcctt gcaagattct gc                       942

SEQ ID NO: 392            moltype = DNA   length = 942
FEATURE                   Location/Qualifiers
source                    1..942
                          mol_type = other DNA
                          organism = synthetic construct
SEQUENCE: 392
atggagaccg acacactgtt gctgtgggta ctcctcctgt gggtgccagg aagcacgggc  60
gataaaaccc acacatgccc tccatgccct gctccagagg ccgccggtgg gccatcagtt  120
ttcttgtttc cgcctaaacc aaaggacacg cttatgatct ccaggacccc cgaagttacg  180
tgtgtggtgg ttgatgttag tcacgaggac ccggaagtca agttcaactg gtacgttgat  240
ggtgtagagg tgcacaatgc aaagacgaag ccacgcgaag aacaatacaa cagcacatat  300
cgagttgtga gcgtactcac ggtactgcat caggactggc tgaacggtaa agaatacaaa  360
tgtaaagtct ccaataaggc acttcctgcg ccgatagaaa aaacgatcag taaggccaag  420
ggccaacccc gagaaccaca ggtatatacg ctcccaccgt cacgagacga gttgacaaaa  480
aatcaggtct ccctgacttg cctcgtgaaa ggttttatc cctcagatat tgctgttgag  540
tgggaaagca atgggcagcc agagaataat tataagacga ctcctccgt tttggattcc  600
gacggtagtt ttttttcttgta tagtaagctt actgtagaca agtcaagatg gcaacaaggt  660
aatgtgttct cttgctcagt tatgcatgaa gctcttcata accattacac gcaaaagagt  720
ctcagtctga gccccggtgg cggtagcgac agttggcagg aagaggtgat taagttgtgc  780
ggtcgcgagc tcgttcgggc ccaaattgca atctgcggaa aatctacggg cggagagggc  840
ggggtgagg agggtggggg tgaagtgggg cagctctata cgcccttgc gaataaatgt  900
tgtcacgtcg gatgcacaaa gaggtccctc gccaggttct gc                       942

SEQ ID NO: 393            moltype = DNA   length = 945
FEATURE                   Location/Qualifiers
source                    1..945
```

```
                        mol_type = other DNA
                        organism = synthetic construct
SEQUENCE: 393
atggaaactg acacactgtt gctgtgggtg ctgctccttt gggtacccgg atcaaccggg    60
gataagaccc acacttgccc cccttgccct gcccccgaag cggccggagg tcctttcagta  120
tttttgtttc caccgaaacc caaagatact ttgatgatat caagaactcc tgaagtcacc   180
tgcgtggtag ttgacgtatc tcatgaggat cccgaggtga agttcaattg gtacgtcgat   240
ggcgtcgagg ttcataacgc taagactaag ccgaggaag agcaatataa ttccacttat    300
agggtggtgt ccgtcttgac tgttttgcac caggattggt gaacgggaa agagtacaaa    360
tgtaaggtga gtaataaagc tttggctgct cccatcgaaa agacaataag caaggccaag   420
gggcaacctc gggagccgca ggtgtacacc cttcctccca gtagagacga actgacaaaa   480
aaccaggtgt ccctgacctg ccttgtgaag gggttttacc cgagcgacat agcggttgaa   540
tgggagagca acgggcaacc cgagaacaac tacaaaacta caccgcctgt cctggactcc   600
gatggaagct tcttcctcta ctccaaactg accgtggaca aagcagatg gcaacaagga    660
aacgtattct catgctcagt aatgcacgaa gcattgcaca atcactacac ccaaaagtcc   720
ctctcactct cccctggtaa gggcggatca gactcatggc aagaggaggt aattaagttg   780
tgcgggaggg agctcgtccg cgcgcaaata gccatttgtg gcaagtccac tggaggaggc   840
gagggtggag gagagggtgg tggggagggc aggcaactct acagtgcgct cgccaataaa   900
tgctgccatg ttgggtgcac gaagcgcagt ctcgcacaat tctgc                   945

SEQ ID NO: 394          moltype = DNA   length = 945
FEATURE                 Location/Qualifiers
source                  1..945
                        mol_type = other DNA
                        organism = synthetic construct
SEQUENCE: 394
atggagaccg acactctgct gctctgggta ctcttgctgt gggtgcctgg gtctactggg    60
gataagaccc acacgtgtcc tccatgtccg gcaccggagg ctgctggcgg gccttctgta   120
ttcctcttcc cacccaagcc aaaagacaca ttgatgtat caaggacgcc ggaagtcacc    180
tgtgttgttg tggacgtttc ccatgaagac ccagaggtaa aattcaattg gtatgtggac   240
ggcgtagagg ttcacaacgc caaaaccaaa ccccgagagg aacagtataa tagcacatat   300
cgagtagtat ctgttctcac agtgctccat caagactggc ttaatggtaa agagtataaa   360
tgcaaagttt ccaataaagc cctcgctgca ccgatcgaga agacaatcag taaagcgaag   420
ggccagcctc gggaaccgca ggtgtatact cttccaccct caaggacga gctcactaaa    480
aaccaagttt cattgacatg cctcgtcaaa ggtttctacc catcagacat cgccggtcgaa 540
tgggaaagta atgggcagcc ggaaaacaac tataaaacga cgccgccgt cttggattct    600
gatggttcat tttttcttta ctctaaattg accgtcgata aaagtaggtg gcaacaagga   660
aatgtttttt cctgctccgt cctgcatgaa gcgttgcaca gtcactatac ccagaagagt   720
ctttctttgt caccgggaaa aggcggttca gattcatgc aggaagaagt aattaaactc    780
tgtggccgcg agcttgttag ggcgcagata gccatatgtg gtaaaagcac cggaggaggt   840
gaaggcggag gcgaaggagg tgggaagga agacaattgt attctgcact gcaaataaa    900
tgctgtcatg tggggtgcac gaaacgcagt cttgcacaat tttgt                   945

SEQ ID NO: 395          moltype = DNA   length = 942
FEATURE                 Location/Qualifiers
source                  1..942
                        mol_type = other DNA
                        organism = synthetic construct
SEQUENCE: 395
atggaaaccg atacgctgct tctttgggtt cttctcctct gggttccagg gtccaccggc    60
gacaaaaccc atacctgccc cccttgccct gcaccagaaa cggcgggagg acctagcgtt   120
tttcttttc ctccgaaacc gaaagatacc ctcatgatat caagaacacc tgaggttact    180
tgcgttgtcg tggacgtgag tcacgaagac cccgaggtga agttcaactg gtatgttgat   240
ggagtggagg tccataatgc aaaaacgaaa ccgagagaag aacaatacaa ctctacatat   300
cgagtcgtgt cagtactcac ggttttgcat caagattgc tgaacggtaa ggagtacaaa   360
tgtaaggtta gcaacaaggc tctcgcggcg ccgatagaaa agactataag taaagcaaaa   420
ggccagccca gagaacctca agtttacact ctgcctccca gcagagatga actgactaaa   480
aatcaggttt cattgacctg tctcgtcaag gttttttatc caagcgacat agcagttgaa   540
tgggaaagca acggtcaacc agaaaataat tacaaaacca ctccaccagt cttggactcc   600
gacggatcct tctttctcta ttcaaaattg acggtggata atctaggtg gcagcaaggc   660
aacgtcttct cttgtagcgt tatgcatgag gcgctgcaca accactacac acaaaagtct   720
cttagtttga gcccgggcgg cggaagcgac tcttggcaag aggaagtgat aaaactctgt   780
ggtcgagaat tggtacgcgc gcagatcgct atctgcggca agtccacagg ggagggaa     840
ggtggcgggg aaggtggtgg cgagggcagg cagttgtata tgcacttgc caacaagtgc    900
tgccatgtgg ggtgcaccaa gcgcagtttg gcacggttc gc                       942

SEQ ID NO: 396          moltype = DNA   length = 942
FEATURE                 Location/Qualifiers
source                  1..942
                        mol_type = other DNA
                        organism = synthetic construct
SEQUENCE: 396
atggaaacgg acaccttct gctctgggta ctgctgctct gggttcctgg ttctaccggt     60
gataaaactc acacttgtcc cccgtgtccg gcaccagaag ccgcaggagg gccatctgtc   120
tttcttttc cccaaaacc caaggataca ctgatgatct cccgcactcc cgaagttact    180
tgtgtcgtag tagacgtttc tcacgaggac ccagaggtga aattcaattg gtatgttgac   240
ggagtagagg tgcataatgc caagacaaag ccccgagagg aacaatacaa ttcaacctac   300
agagtagtgt ccgttcttac ggttctccat caggattggc tcaacggtaa ggaatataag   360
tgcaaggtaa gcaacaaagc gctggccgca cccattgaga aaccatttc aaaagctaaa   420
```

```
ggccaacccc gcgaaccaca agtttatact ctcccccccaa gtcgcgatga acttacaaaa    480
aatcaagtct cattgacgtg cttggtcaaa ggcttctacc cgagcgatat cgctgttgaa    540
tgggagtcta atggacaacc ggaaaataac tataaaacta cacccccagt cctcgattca    600
gacggcagct tcttcctgta ttcaaaactg acgttgaca aatcacgctg caacagggt     660
aacgttttttt cctgtagcgt tcttcatgaa gccttgcaca gtcactacac ccagaagtcc   720
cttagcttgt cacctggcgg gggttcagac tcttggcagg aggaggtaat caaactgtgc    780
ggaagagaac tggtgagggc tcagattgca atttgtggga agagcacggg tggcggtgaa    840
ggaggtggcg agggcggagg agaggggagg caactctaca gtgcgttggc taataaatgc    900
tgtcacgtcg gctgtactaa gagaagcctc gccagattt gc                        942

SEQ ID NO: 397          moltype = DNA  length = 942
FEATURE                 Location/Qualifiers
source                  1..942
                        mol_type = other DNA
                        organism = synthetic construct
SEQUENCE: 397
atggaaacag atactttgtt gctgtgggta ctcctcctct gggtacctgg gagcaccggg    60
gacaagacgc atacttgccc tccgtgccct gcaccagaag ccgctggtgg cccatctgtg   120
tttttgttcc cccctaagcc aaaagacaca ttgatgattt cacgaactcc agaagtgact   180
tgcgtagttg ttgacgtatc acacgaagac cccgaggtta aatttaattg gtatgtggac   240
gggtcgagg tgcataacgc caaaaccaaa ccccgggagg aacaatataa ctctacgtat    300
cgggtcgtat ctgtgttgac cgtccttcac caagattggt tgaacggcaa ggaatataag   360
tgtaaagtgt ctaataaagc attggctgcc ccgataaaa agacgatctc taaagccaag   420
ggccaaccca gagagcctca agtatatact ctcccaccga gtcgagatga gctcactaag    480
aaccaggtgt cactcacgtg tctggttaaa ggatttttacc ctagtgatat agccgtcgag   540
tgggaatcaa atgggcagcc ggagaataac tataagacaa cgcctccagt tctcgattcc    600
gatggtagct ttttccttta ctctaaactt acggtcgaca agtccaggtg gcaacagggc   660
aatgtatttt cttgctccgt catgcacgag gctttgcaca accattacac gcaaaagtca   720
ctgtccctgt ctcctggagg cggttctgac agttggcagg aggaggtaat caaattgtgt   780
gggcgggagt tggttagggc gcaaattgct atttggcgca aaagtactgg gggcggtgaa    840
ggcggaggcg agggaggagg agaaggtcga caactgtatt ctgccttggc gaacaaatgc   900
tgtcacgtcg gctgtacgaa acggtctttg gcccagtttt gt                       942

SEQ ID NO: 398          moltype = DNA  length = 942
FEATURE                 Location/Qualifiers
source                  1..942
                        mol_type = other DNA
                        organism = synthetic construct
SEQUENCE: 398
atggaaactg acactcttct gttgtgggtc cttctgctgt gggttcctgg ctctactgga   60
gataagacac acacttgtcc gccatgccct gcgccggaag cggcgggagg accgtccgtt   120
ttcctgttcc ctcccaaacc caagacacg ttgatgatta gtcgcacgcc agaagttacg    180
tgcgttgtcg tagatgtatc ccacgaagac cccgaggtga agttcaattg gtatgtagat   240
ggggtggagg tccataacgc taagaccaaa ccacgcgagg aacaatataa ttctacgtac   300
cgcgtagtga gcgttctcac agttcttcac caggattggc ttaacggcaa ggagtataag   360
tgtaaggtgt ctaataaggc cttggctgcc ccgatcgaaa aaacgataag taaagcaaag   420
ggtcaaccta gagaacccca agtgtacact ctcccgccat ggtcgggatga attgactaag   480
aaccaagtgt cactcacgtg tcttgtaaag ggcttctacc catccgatat agccgttgag   540
tgggaatcca atggtcagcc agagaacaac tataagacaa ctccgcccgt acttgatagt   600
gacggttcct ttttcctttta cagtaaaattg acggtagata agtctcgctg gcagcaagga   660
aacgtcttttt cttgttcagt gcttcatgag gcgcttcact cacactatac tcagaagagt    720
ttgagtttgt ctccaggtgg aggcagcgac tcatggcaag aggaagtaat caaactgtgt    780
ggtcgcgaat tggtacgagc acagatcgcg atctgcggga aatcaacagg tggcggcgaa   840
ggcggcgggg aaggcggcgg cgaaggtagg caactttact cagcccttgc gaacaaatgt   900
tgccacgtag gctgtactaa gagaagtctc gcccagtttt gc                       942

SEQ ID NO: 399          moltype = DNA  length = 945
FEATURE                 Location/Qualifiers
source                  1..945
                        mol_type = other DNA
                        organism = synthetic construct
SEQUENCE: 399
atggagacag ataccttct gttgtgggtc cttctgcttt gggtgccggg aagtacaggc     60
gacaagactc ataccctgccc cccttgtcca gcaccagaag cctggcgg gccaagcgg    120
ttcctgtttc cacctaagcc caaagatacg ttgatgatca gccgcacccc ggaagtaacc   180
tgtgtagtag tagatgtgtc ccacgaagac cccgaagtaa agtttaattg gtacgtcgat   240
ggtgtcgaag tacataacgc taaaacgaag ccccgagaag agcagtacaa cagtacttac   300
agagtagttt ctgttcttac agtgctgcat caggattggc tgaacgggaa ggagtataaa   360
tgtaaagtct caaacaaggc acttgcggca ccaatagaga agacaatctc taaggccaaa   420
gggcagccta gagagccaca agtatatacg ctgccccca gcagggacga gctgacaaaa   480
aaccaagtgt cactgacctg ccttgttaag ggcttctatc cgagtgatat tgctgttgaa   540
tgggaaagta acgacagcc ggagaacaac tataaaacta ctccaccggt gttggatagt    600
gacggtagct ttttctctgta ctccaagttg acggtagaca aaagtcggtg gcagcagggg   660
aacgtcttct cttgttctgt catgcacgaa gctcttcaca atcactatac gcagaagtcc   720
ctctctctct ctcctgggaa gggtggtccc gacagcggc aggaggaggt cattaaactg    780
tgtggtagag agctggtacg ggctcaaatt gcaatttgtg gtaagagtac tggcggtggc    840
gaggaagggt gtgggagga gggcggaggt aggcagctct actctgctct cgccaacaag   900
tgttgtcacg tcgggtgtac taaaagatca cttgcccgct tttgt                    945
```

```
SEQ ID NO: 400          moltype = DNA   length = 945
FEATURE                 Location/Qualifiers
source                  1..945
                        mol_type = other DNA
                        organism = synthetic construct
SEQUENCE: 400
atggaaaccg ataccctgct cttgtgggtc ctcctgcttt gggtcccagg ttccacaggc    60
gacaaaacac atacatgccc gccgtgtccg gcgcctgaag cagcaggagg ccccagtgta   120
ttccttttcc ctccaaagcc aaaagatacg ttgatgatat ctaggacacc tgaggttacc   180
tgcgtcgtag tggacgtatc ccacgaagac ccagaagtca agtttaactg gtatgtggac   240
ggagtggagg tacacaatgc aaagacaaag ccgcgagagg aacaatataa ttccacctat   300
agagtcgtgt cagtccttac ggtcttgcac caggactggc tcaatggtaa ggagtataag   360
tgcaaagtat caaacaaagc tctcgcagcg cccatcgaaa agaccatcag caaagctaag   420
ggccagccaa gagagcctca agtgtacacg ttgccgcctt caagggacga gctcactaaa   480
aatcaggtat cacttacgtg tcttgtcaaa gggttttatc cttccgacat cgcggttgaa   540
tgggagagca atggacagcc ggagaataat tataaaacga cgccgccggt ccttgacagc   600
gatggttcat ttttcctttta ctcaaagctg acggttgata agtctaggtg gcagcagggg   660
aacgtctttt cctgtagtgt acttcatgag gcgctccatt ctcattacac tcagaagtca   720
ctgagcctttt cacccggcaa aggtggatca gactcctggc aagaagaggt aatcaaactc   780
tgtgggaggg aactcgttcg agcccagatt gcaatctgtg ggaaaagcac aggcggaggg   840
gaagaagggg gtggcgaaga aggtggggc aggcagctct attcagctct tgccaacaaa   900
tgctgtcatg taggctgcac aaagcgatca ctggcgagat tctgt                  945

SEQ ID NO: 401          moltype = DNA   length = 945
FEATURE                 Location/Qualifiers
source                  1..945
                        mol_type = other DNA
                        organism = synthetic construct
SEQUENCE: 401
atggaaaccg acaccctgct gctctgggtt cttctcctct gggttccggg ctcaaccgga    60
gataaaactc atacttgccc accctgcccg gctcccgagg cagcaggtgg accctcagta   120
ttttgttcc ctccgaaacc taaagataca cttatgatta gccggacccc tgaggtaacg   180
tgtgtggtgg ttgacgtaag tcatgaagat ccagaagtaa agtttaactg gtacgtagac   240
ggtgtggagg tacataatgc gaagacaaaa ccacgagagg aacagtataa ctctacctac   300
cgcgtagtaa gcgtacttac tgtgctccaa caagactggc ttaacgggaa agagtataag   360
tgtaaagtca gtaataaagc actggccgcc ccgatcgaaa aaacaatcag caaggccaaa   420
ggacaaccaa gggagcctca ggtctatact cttcccccga gtagggatga gcttaccaag   480
aaccaggtgt ctctgacatg ccttgtcaag ggattttacc cgagtgacat agccgtagaa   540
tgggagtcaa acggccaacc tgaaaacaac tataagacca cgcctcccgt actcgactca   600
gatggaagct ttttcctcta tagcaagctg accgtcgaca aaagtaggtg gcaacaggga   660
aacgtcttta gttgttccgt catgcacgaa gctttgcata ccattacac ccagaagagt   720
cttttccctttt ccctgggcaa ggggggctcc gactcctggc aagaggaagt aatcaaactg   780
tgtgggcgg agctttgtccg cgcgcaaata gccatttgcg gaaaaagtac tggaggagga   840
gaggaaggcg gcggcgagga aggtggggc aggcagctgt acagtgcctt ggctaacaag   900
tgctgccatg tcggctgtac gaaaaggtct cttgctcaat tctgt                  945

SEQ ID NO: 402          moltype = DNA   length = 945
FEATURE                 Location/Qualifiers
source                  1..945
                        mol_type = other DNA
                        organism = synthetic construct
SEQUENCE: 402
atggaaactg atactcttct cctttgggtg ctcctcctct gggttccgg gtccacaggc    60
gataagacac ataccgtgcc accctgccca gcacctgaag ctgcaggcgg ccccagcgta   120
ttcctgtttc ctccgaagcc gaaagacaca cttatgattt cccggacact gaggtaact   180
tgcgtcgtag tagatgtgtc tcacgaagac cccgaggtga aattcaactg gtacgttgat   240
ggtgtggaag ttcataatgc gaaaactaaa ccacgagagg agcaataaa ctcaacttat   300
agagttgtga gcgtcttgac ggtactgcac caggactggc tgaatggcaa agagtacaaa   360
tgcaaagtct caaataaggc gttggcggct cccatagaga aaactatcga caaagccaaa   420
ggtcaacctc gggagccaca agtgtatact cttccggcta gtcgcgacga gctcacaaag   480
aatcaggtga gtcttacttg tttggttaag ggtttctacc ccagtgacat tgcggtcgag   540
tgggaaagta acggacagcc tgaaaacaac tataaacaa cgcctccagt actcgattca   600
gatggttcat tctttcttta ttccaaactc acagtcgaca gagtagatg caacaaggg   660
aacgtgttta gctgtagcgt actccatgag gcactccact ctcactatac ccaaaagtct   720
ctcagcttgt cacccggaaa aggcggtctc gacagttgca aagaggaagt gattaaattg   780
tgtgggcggg aacttgtgag ggctcaaatc gcgatttgcg gcaagtccac tggtggcggc   840
gaggaaggag gaggtgaaga aggaggaggt aggcaactgt attcagcgtt ggcgaataaa   900
tgctgccatg ttggatgtac taaacggagc cttgctcagt tctgc                  945

SEQ ID NO: 403          moltype = DNA   length = 942
FEATURE                 Location/Qualifiers
source                  1..942
                        mol_type = other DNA
                        organism = synthetic construct
SEQUENCE: 403
atggaaactg acaccttgtt gctttgggta ttgcttctgt gggttccggg tagcacgggt    60
gataaaacgc atacttgccc tccttgcccg gcacctgaag ctgccggagg tccttccgtg   120
ttcctgttcc cacctaagcc aaaagacaca cttatgattt ctcgcacacc agaagtaacg   180
tgcgtcgtag ttgacgtctc ccatgaagac ccggaggtaa aatttaattg gtacgtcgac   240
```

```
ggggtagaag ttcataacgc aaagactaaa ccacgagaag agcaatacaa ctctacatac   300
agagtagtaa gcgttctcac cgttcttcat caagattggc tcaacggaaa ggagtataag   360
tgtaaggtgt ccaataaagc gttggccgca ccaatcgaaa agaccataag caaagccaaa   420
ggccaacccc gcgaaccgca ggtgtacaca cttcccccgt ccagggatga attgacaaaa   480
aaccaagttt ccctcacgtg tctcgtcaag ggattctacc cgagtgatat cgcagttgaa   540
tgggaaagca atggtcagcc cgagaataac tacaagacta ctcccctgt gttggactca    600
gacggctcat tcttcctcta cagtaagttg actgtggaca aaagtcggtg gcagcaaggc   660
aatgtcttca gttgtagtgt aatgcatgaa gcactccaca atcattacac ccaaaaatcc   720
ctgagcctgt ccccgggcgg aggttcagat tcatggcagg aggaagttat aaaactgtgc   780
gggcgagt tggtgagggc gcagatcgca atctgtgaa agagtacgtg aggtggcgaa      840
gagggtggtg gagaagaggg aggaggtcga caactgtatt ccgcgctcgc gaacaagtgt   900
tgccacgttg gctgcaccaa acgaagcctg gctcgatttt gc                      942

SEQ ID NO: 404          moltype = DNA   length = 942
FEATURE                 Location/Qualifiers
source                  1..942
                        mol_type = other DNA
                        organism = synthetic construct
SEQUENCE: 404
atggagactg acacccttct cctctgggtc ctcttgcttt gggtcccgg ctctactggt     60
gacaagacac acacttgtcc accttgcccg gctcccgagg cggcaggagg accaagcgtt   120
tttctgttcc ctcccaaacc aaaggatacg ctttatgatct ctcgaacgtc ggaagttact  180
tgcgtagtag ttgatgtctc ccatgaagat cccgaagtga agttcaactg gtatgtagat   240
ggtgtggaag ttcataacgc gaaaaccaaa ccacgcgaag aacagtataa cagtacttat   300
cgggttgttt cagtactcac ggtgctccat caagactggc ttaatggaaa ggagtataaa   360
tgtaaggtaa gtaacaaggc attggcggct cccatcgaa acaatctc caaagcaaaa      420
gggcaaccac gggagcctca ggtgtatacg ttgccgccca gcagagatga acttactaag   480
aatcaggtga gtctcacttg tctcgtcaag ggcttctatc ccagcgatat agccgtagaa   540
tgggagagta acggtcagcc ggagaacaac tacaaaacaa ccccgcctgt tttggactcc   600
gatgggagtt ttttctctcta cagcaaactc acggtagaca aaagcaggtg gcagcagggc   660
aatgtttca gttgctctgt tctccacgaa gccctccact cccactatac tcagaagtgc   720
ctgagtctct caccagggg aggtagcgat agctggcagg aggaagtgat caagttgtgc    780
gggcgcgaac tcgtgcggc acaaattgct atatgcggta aaagtacggg aggtggagag    840
gagggtggag gtgaagaagg cggtggtaga caattgtata gtgcgctcgc caacaagtgt   900
tgtcatgtcg ggtgtacgaa acggtccttg gcgcggtttt gc                      942

SEQ ID NO: 405          moltype = DNA   length = 942
FEATURE                 Location/Qualifiers
source                  1..942
                        mol_type = other DNA
                        organism = synthetic construct
SEQUENCE: 405
atggaaactg acacacttct tctgtgggta ctcttgttgt gggttccggg ctcaacgggt    60
gacaagacac atacttgtcc accatgtccc gccccagaag ctgcgggagg accatcagtt   120
tttttgttcc ccccgaaacc gaaggatacc ctcatgataa gtcgaacgcc cgaagtcact   180
tgcgtggtgg ttgatgttag ccacgaggac ccagaagtga agttcaactg gtacgtggac   240
ggggtggaag ttcataatgc gaaaacaaag cctcgcggag aacagtacaa ctctacatac   300
agggttgtgt ctgttttgac agtcttgcac caagattggc tcaacgggaa ggaatataag   360
tgtaaggtaa gcaataaagc actggcggcc ccgatcgaaa aaacgatatc caaggccaag   420
ggccagcccc gagagcctca ggtatatact ctgccgccaa gccgggatga actgactaaa   480
aaccaagtct ctttgacttg tcttgtcaag ggattttcaa caagtgacat tgccggtagag  540
tgggaaagca acggtcaacc agaaaacaat tacaagacga caccgccggt actcgactca   600
gatggatcct ttttcctgta tagcaagctc acagtggaca agtcccggtg gcagcaaggg   660
aacgtatttt catgcagcgt gatgcatgag gctcttcaca accattacac acagaaaagt   720
ctgtcattga gccctggcgg cgggagcgat tcttggcagg aagaagttat aaaactttgc   780
ggtcgagagc tggttcgggc acaaattgct atctgcggaa aatctacagg aggaggcgag   840
gagggagggg gcgaagaagg cgggggagga cagttgtaca gtgcgctcgc taacaagtgt   900
tgccacgtcg gttgcacaaa gagatccctg gctcaattct gt                      942

SEQ ID NO: 406          moltype = DNA   length = 942
FEATURE                 Location/Qualifiers
source                  1..942
                        mol_type = other DNA
                        organism = synthetic construct
SEQUENCE: 406
atggagacag atactctctt gctgtgggtg ctgctcttgt gggttcctgg aagtaccggt    60
gataaaactc acacctgtcc cccgtgtccc gcaccagaag cggccggtgg tccctccgtt   120
tttctcttcc ctcctaaacc taaggacaca cttatgatta gcagaactcc agaagttacg   180
tgcgtagtcg ttgacgttag tcatgaagat cctgaggtta agttcaactg gtacgtagac   240
ggagtagagg tccacaacgc caagacgaaa ccccgagaag agcagtataa ttctacctat   300
cgagttgttt cagtattgac ggtgcttcac caagattggc tgaatggcaa agagtataag   360
tgcaaggtaa gcaacaaagc actgcggct cctatcgaga aaactatttc aaagctaag    420
ggccagcctc gcgaaccaca agtctatacc tgcaccacga gtcgggacga actcaccaag   480
aaccaagtgt ctcttacttg cctcgttaaa ggtttttatc ccagcgacat agccgtcgaa   540
tgggagtcca atggccaacc tgagaacaac tataaaacta cccctcctgt acttgatagc   600
gacggaagtt ttttcctcta ttcaaaactc acagttgata gtctcgatg caacagggc    660
aacgtcttct cttgcagtgt gttgcatgaa gctctgcact ctcattacac acagaagagt   720
ttgtctctca gtccaggtgg cggctcagat agctggcagg aagaagtaat caagttgtgc   780
ggcagggaac tggtaagggc acagatagcc atttgtggaa aatctacggg tggcggtgag   840
```

```
gaaggcggcg gagaagaagg gggaggtcgg cagctgtata gtgcactcgc aaacaagtgc    900
tgccatgtcg ggtgcaccaa gcgatccctt gcccagtttt gc                      942

SEQ ID NO: 407          moltype = DNA  length = 945
FEATURE                 Location/Qualifiers
source                  1..945
                        mol_type = other DNA
                        organism = synthetic construct
SEQUENCE: 407
atggagacgg acactcttct cctgtgggtt ctcctcttgt gggttccagg atctaccggc    60
gataagacgc acacatgccc accctgtcct gcgcctgaag ccgcgggggg acccagcgtt    120
tttctcttcc cgccgaaacc gaaagacaca cttatgatca gccggactcc cgaggttacc    180
tgcgtggtgg tagatgtatc tcacgaggat cccgaggtca aattcaactg gtacgttgat    240
ggggttgaag ttcataatgc caaaacgaag ccaagagaag agcagtataa ctccacatat    300
agagttgttt ccgtcttgac tgttcttcac caagattggc tgaatgggaa ggagtacaaa    360
tgtaaagtta gcaacaaggc actcgccgct cccattgaaa aaactataag caaagctaag    420
ggccaaccgc gcgaaccaca ggtctacacg ttgccgccct ctaggacgaa actcacgaag    480
aatcaggttt cccttacctg cctcgttaaa ggattctacc cctctgacat acgcgttgaa    540
tgggagagca acggtcagcc tgagaacaac tacaaaacga cgcctccggt gttggattcc    600
gacggtagtt ttttcctcta tagtaagctg acagtggata atctcggtgc agcaagggg    660
aatgtattct cctgttcagt cctgcatgaa gccctccact cccattatac acagaaatct    720
cttctctga gtcccggtaa aggtgggagt gactcttggc aggaagaggt aattaagttg    780
tgtgaaggg agctggtaag agcacagatt gccatctgtg gcaaatccac gggcggcgaa    840
ggtgagggg gtgaggggga agggggtcc agacaactgt attctgctct ggcgaataag    900
tgttgccatg tagggtgcac taaacggtcc ttggcgcagt tctgt                   945

SEQ ID NO: 408          moltype = DNA  length = 942
FEATURE                 Location/Qualifiers
source                  1..942
                        mol_type = other DNA
                        organism = synthetic construct
SEQUENCE: 408
atggagactg acacactgct cctctgggtc cttttgctct gggttccggg gtccaccggt    60
gataaaactc atacgtgccc accttgcccc gcaccggagg ctgcggagg accctctgtg    120
ttcctgttcc cgccgaagcc taaagacaca ttgatgatca gtcgaacacc ggaagtcacc    180
tgtgtagtgg ttgatgtgag ccatgaggac cctgaagtaa aatttaactg gtatgttgat    240
ggcgtagaag tacacaacgc gaagactaaa ccaaggggaag agcaatacaa ctctacctat    300
agggtcgtta gcgtactgac tgtgcttcac caagactggc ttaacgggaa ggagtacaag    360
tgcaaagtga gcaataaggc cctcccgcg cctatcgaga aaaccatttc caaagccaag    420
ggtcaaccaa gggagcctca ggtttacacc ctgcccccct caagggatga gttgacaaaa    480
aaccaggtaa gtctgacgtg tctcgttaag ggattctacc cgtcagatat cgcggtagag    540
tgggagagca acggtcagcc agaaaataat tacaaaacaa cacctccagt tttggactct    600
gatgggagtt tttttctta ttctaagttg acagtggata agcacgctg gcaacagggg    660
aacgtattta gctgctcagt acttcatgaa gcgttgcatt ctcactacac acagaagagc    720
ctctccttga gtcccggagg tggctctgat tcttggcagg aggaggtaat aaaactttgt    780
ggtagagaac tggttcgcgc tcagatagct atttgtgaa aatccactgg cggtgaaggt    840
gaaggtggag aaggagaggg cggaagccgg cagttgtact ctgccctggc taataagtgc    900
tgtcacgtgg gctgcactaa gcggagcttg caagattttt gc                      942

SEQ ID NO: 409          moltype = DNA  length = 942
FEATURE                 Location/Qualifiers
source                  1..942
                        mol_type = other DNA
                        organism = synthetic construct
SEQUENCE: 409
atggaaaccg acacgctgct gctgtgggtg ctgttgttgt gggttccagg ctcaactggc    60
gataaaactc ataccgtgcc accttgtcct gcgcctgagg cagctggagg gcctagcgtg    120
ttcctgttcc cccccaaacc caagacacg ctcatgatta gccgaacccc tgaagtgacc    180
tgcgttgttg tggacgttaa gccacgaagac cccgaagtta gtttaattg gtacgtcgac    240
ggtgttgagg ttcataacgc gaagactaag ccgagagagg agcaatataa cagcacctac    300
cgcgtagtct cagttcttac cgtgctccac caggactggc ttaacgggaa ggaatacaaa    360
tgcaaagttt ccaacaaagc cttggcagcc ccaatagaga gacaatatc taaggcgaaa    420
ggccaaccgc gggaaccgca agtttatacc ctcccaccga gcaggatga gctgacaaaa    480
aatcaggttt ccctcacttg tctggtcaag ggatttttac cttcagacat agcgttgaa    540
tgggagagta atgggcagcc ggagaataat tacaagacca ccccccggt gttggacagc    600
gacggttcct tctttctcta ttctaaactt accgtcgaca atacgcgtg caacaagga    660
aatgtattct catgcagtgt attgcacgaa gctctgcact tcattacac ccaaaaatcc    720
ctctctctca gccctggcgg tggatctgat tcttggcagg aagaggtgat taactgtgt    780
gggcgagagc ttgtccgagc tcagatcgct atttgtgaa agataccgg aggcgaggt    840
gagggaggcg aaggcgaggg cggaagccgg caactctata gcgcactcgc taataaatgt    900
tgtcatgtcg gctgcacgaa gcgctcactg gcgcagttct gc                      942

SEQ ID NO: 410          moltype = DNA  length = 885
FEATURE                 Location/Qualifiers
source                  1..885
                        mol_type = other DNA
                        organism = synthetic construct
SEQUENCE: 410
gacaagaccc atacatgtcc gccttgtcct gcgcctgagg cagcaggcgg accatcagtc    60
```

```
ttcttgtttc cccccaagcc gaaggacacc cttatgatct cacgcacccc cgaagtaact    120
tgtgtagtcg ttgatgtctc acacgaagac ccgaagtaa  agtttaattg gtatgtcgat    180
ggtgttgagg tccacaacgc taaaacgaaa ccgcgggaag aacaatacaa ctccacatat    240
cgagtagtct ccgtcctgac tgttcttcac caggactggc tgaatggtaa agaatacaaa    300
tgtaaagtga gtaacaaggc ccttgcagca cccatcgaga agacgatatc caaagccaaa    360
gggcaaccgc gcgagccaca agtttacacg ctcccaccct caagagacga actcaccaaa    420
aatcaagtgt ccctgacatg tctggtgaaa ggattctatc ccagcgacat agctgtagaa    480
tgggagagta atggccaacc cgaaaacaat tacaaaacta ccccccggt  tttggatagt    540
gatggttcat tcttcctcta tagtaaactt accgtggata agtctcggtg gcagcagggg    600
aacgtgttta gctgttcagt cctccatgag gcactccata gtcactatac gcaaaagtca    660
ttgtcccttt ctccgggcaa gggcgggtca gactcctggc aggaagaggt aattaagctt    720
tgtgggcgag aactcgttag ggcacagata gcaatctgcg ggaaaagtac agcttccgat    780
gctgccgggg ctgacgccaa tgcggagca  cgccagctct actcagccct cgccaacaag    840
tgttgtcatg taggttgcac caaaagaagt ctggcacagt tttgc                    885

SEQ ID NO: 411           moltype = DNA   length = 885
FEATURE                  Location/Qualifiers
source                   1..885
                         mol_type = other DNA
                         organism = synthetic construct
SEQUENCE: 411
gacaagacgc atacttgtcc tccctgccca gctcccgaag cggctggggg gccctctgtc    60
tttctgtttc cgcctaagcc caaggacacg ctcatgataa gtcgcactcc ggaagtcacc    120
tgtgttgtcg tcgatgttag ccatgaagat ccagaggtga aatttaactg gtacgtcgac    180
ggagtggagg ttcacaatgc taaaaccaaa ccgcgagaag agcaatacaa ttccacgtat    240
agggtcgtct ccgtcctgac agtactccat caggattggc tgaatggaaa agaatacaag    300
tgcaaggttt ccaataaagc cttgccgca  cctattgaga aaacgatatc aaaagctaag    360
ggacaacctc gggagccgca agtatatca  ctcccccctt ctaggacga  actgacaaaa    420
aaccaagtta gtctgacttg tcttgtgaaa ggttttacc  cgagtgatat agccgtagaa    480
tgggagagca atggccagcc cgaaaacaat tacaaaacaa ctcccccagt attggacagt    540
gacgggtcat tttttttgta ttctaaattg accgtagaca agtcacgctg caacaaggg    600
aatgtattta gctgttccgt ccttcatgag gcgctccata gccattacac tcagaagtct    660
ttgtcactgt caccgggcaa gggtggttct gattcatggc aagaggaagt gattaagctg    720
tgcggtcggg agttggtaag agctcaaatt gcgatttgtg gcaagagcac tgcgtccgat    780
gccgcaggtg ctaatgccga cgccggtgcg agacagcttt attctgcgct ggccaacaag    840
tgctctgcgc tcggatgcac caaacggagc cttgctcagt tttgc                    885

SEQ ID NO: 412           moltype = DNA   length = 885
FEATURE                  Location/Qualifiers
source                   1..885
                         mol_type = other DNA
                         organism = synthetic construct
SEQUENCE: 412
gacaaaactc atacttgtcc accatgccca gccccgagg  cggctggcgg ccccagcgta    60
ttcctttttcc ccccaaaacc taaggacacg cttatgatat ctagaacccc ggaggtcaca    120
tgtgtcgtcg tagacgtaag tcacgaagat cctgaagtca agtttaactg gtacgtcgat    180
ggagtcgaag tccataatgc taaaacgaag cctcgcgaag aacagtataa ttctacctat    240
cgcgtagtct ctgtcctcac cgtcttgcat caagactggt tgaacggcaa ggagtacaag    300
tgtaaggttt caaacaaagc ccttgccgcg ccgatagaga aaacaattag caaagcgaag    360
gggcagccga gagagccgca agtgtatacc cttcctccta gtagagacga gttgaccaaa    420
aaccaggtgt cacttacatg cctcgtgaaa ggcttcaacc cgagtgatat tgcagtcgag    480
tgggaatcca acggccagcc cgagaataac tacaaaacga cgccgcccgt actgacagt    540
gatgaagtt  ttttttgta  ctcaaaactc acggttgaca aaagtcggtg gcagcaaggg    600
aacgttttta gctgctctgt cctccatgaa gcactccatt ctcattatac ccagaagtct    660
ctgtctctct cccctggtaa gggaggttct gacagttggc aggaagaggt aataaaactc    720
tgcggtcgag agcttgttcg agcacaaatt gctatatgtg gaaaatctac cgcttcagac    780
gccgccggag ctgatgcgga tgccggggct cgccagctct atagcgcctt ggccaacaaa    840
tgttgtcacg ttggctgcac gaagcgctcc ctggctcagt tttgc                    885

SEQ ID NO: 413           moltype = DNA   length = 885
FEATURE                  Location/Qualifiers
source                   1..885
                         mol_type = other DNA
                         organism = synthetic construct
SEQUENCE: 413
gataaaaccc acacttgccc accttgcccc gcgccggaag ccgccggagg acctagtgtt    60
ttcctctttc cccctaagcc caaagacacg ttgatgatct ctcggacacc ggaagtaact    120
tgtgtcgttg tggatgtgtc acatgaggat cccgaggtga aatttaattg gtacgttgac    180
ggcgtggagg tgcataacgc aaaagactaa a ccacgcgagg agcagtataa ttctacatat    240
cgggttgtct cagttctcac agttcttcat caggattggt tgaatggaaa ggagtacaaa    300
tgcaaagtgt ccaacaaagc gcttgctgcg ccgattgaaa agacgatttc aaaggcaaaa    360
gggcagcccc gcgaacccca agtatatact ttgcctccct cacgcgatga actgactaag    420
aaccaggtga gcctgacttg tttggttaag gttttttatc caagtgacat tgctgttgaa    480
tgggagagca atggccagcc tgagaataac tacaaaacga cacctcctgt acttgacaag    540
gacggctccc ttttttcttt  attcaaaactc acagtggaca aatccaggtg gcagcagggt    600
aacgtctttt cttgcagcgt gctccacgaa gctttgcatt cacattatac gcaaaaatcc    660
ttgtcattgt ccccaggtaa gggcggaagc gactcatggc aagaagaagt cattaaactt    720
tgtggacggg agctggttag ggcacagatt gctatttgtg gtaagtctac ggctagtgac    780
gcagcggggcg ccgaagcgga agctggtgca aggcagcttt actctgctct ggctaacaag    840
```

```
tgttgtcacg ttgggtgtac caagcggtcc cttgcgcaat tctgc                   885

SEQ ID NO: 414           moltype = DNA   length = 885
FEATURE                  Location/Qualifiers
source                   1..885
                         mol_type = other DNA
                         organism = synthetic construct
SEQUENCE: 414
gataaaactc atacttgccc cccctgcccc gcgcctgaag ctgcaggggg gccatcagtc    60
ttcttgtttc caccaaaacc taaggatact ctcatgatta gccggacccc tgaggtgaca   120
tgtgttgtgg tcgatgtatc tcatgaagat cccgaagtaa aatttaactg gtacgtagac   180
ggggttgaag ttcataacgc gaaaacgaaa cctcgggagg agcaatataa tagcacgtat   240
agagttgttt cagtccttac agttctccac caagactggc tgaatggcaa ggagtataag   300
tgtaaagtat ccaataaagc cttggctgcg ccaatcgaga agacgatcag caaagccaaa   360
ggtcagcctc gcgaaccgca ggtctataca ttgcccccct cacgcgacga actcacgaaa   420
aatcaagtct ctttgacttg ccttgtgaaa ggcttctacc cctccgatat tgccgtcgaa   480
tgggaaagca atggacagcc ggaaaataat tacaaaacga cacccccgt gttggattcc    540
gatgggtcct tcttcctcta ttccaagctg acggtcgata agtctcgatg gcagcaggga   600
aatgtcttct cttgctccgt ccttcatgag gcattgcaca gccattatac tcaaaagagt   660
ctctctctgt ctccaggcaa aggggggttcc gactcttggc aagaagaggt cataaaactg   720
tgcggccggg agctcgtcag agcgcagatc gctatatgtg gaaaatccac cgcgagtgac   780
gcagcaggtg cacaagccga cgcaggagct aggcaactgt actcagccct tgccaataag   840
tgttgtcacg taggttgtac taaacgctcc ctggcacaat tttgt                  885

SEQ ID NO: 415           moltype = DNA   length = 885
FEATURE                  Location/Qualifiers
source                   1..885
                         mol_type = other DNA
                         organism = synthetic construct
SEQUENCE: 415
gataagacac acacgtgccc accctgccct gccccagagg cagccggagg tcctagtgtg    60
tttctgttcc cccaaagcc caaggacacc cttatgatat ctaggacacc agaagttacg   120
tgcgtcgttg tggacgttag ccacgaagac ccagaagtga agtttaattg gtacgttgat   180
ggagtcgaag tgcacaatgc aaaaacaaaa ccacgagaag agcagtataa cagtacttat   240
agagtagtca gcgtccttac tgtattgcat caggatggg tgaatggaa ggaatataaa     300
tgtaaggtta gcaataaagc ccttgcggct cctatcgaga aaactattag caaagcaaag   360
ggccaacccc gagagcccca gtttataca ctgccaccca gtcgagatga gctgactaaa    420
aatcaagtat ccctgacctg cttggttaag gggttttatc ctagtgacat cgcggttgag   480
tgggaatcca acggccaacc ggagaataat tacaaaacca cgccacctgt attggattcc   540
gatggtagct tctttctcta tagtaaactt acagtcgata agtcaagatg gcagcaggga   600
aacgtatttt catgctcagt tctgcatgag gccttgcact cccattacac tcaaaaatca   660
ctgagcctca gtcctggtaa gggtggctct gactcatggc aggaggaagt aatcaagctg   720
tgtgggaggg aattggtaag ggctcagatt gcaatttgtg gaaagagcac agcgtctgac   780
gctgcaggtg ccgacgcaca ggcgggcgcg aggcagctct acagtgctct tgcgaacaag   840
tgttgtcatg taggttgcac gaaacgaagt ttggcgcaat tctgt                  885

SEQ ID NO: 416           moltype = DNA   length = 885
FEATURE                  Location/Qualifiers
source                   1..885
                         mol_type = other DNA
                         organism = synthetic construct
SEQUENCE: 416
gataaaacac acacctgccc cccttgccca gcacctgaag cagcgggtgg tcccagcgtt    60
tttctttcc cccctaagcc aaaggacacg ctcatgataa gtcgcaccc ggaggtcacc     120
tgcgtcgttg ttgacgtatc acatgaagat cctgaggtga agtttaattg gtacgtagat   180
ggtgttgagg tccacaacgc aaagacgaaa ccgagggaag aacagtacaa cagtacttat   240
cgcgtagtct ccgttctgac tgtcctgcat caagattggt tgaacgggaa ggagtacaag   300
tgcaaagtta gtaacaaggc tctcgcggcc ccaattgaga gacgatatc caaagcgaaa    360
ggacagccga gagagcccca agtctacact ctgccccctt ccagggatga gctcaccaaa   420
aatcaggtca gtctcacgtg cctggttaag ggattctacc caagtgatat agcagttgaa   480
tgggagagta acgccagcc cgagaacaac tataaaacta caccgcccgt tcttgattcc   540
gatgggtctt tcttccttta tagtaagctc accgttgata gtcccgatg gcagcaaggt    600
aatgtcttct catgttcagt tcttcatgaa gccctgcatt cccattatac acaaaagagc   660
ttgtccttgt caccgggcaa aggcggtagc gattcttggc aggaagaagt tataaagttg   720
tgcggtaggg aactggtacg cgctcaaata gctatatgcg gtaagtctac tgcttcagat   780
gcggctggcg cacaggcaca ggccggtgct agacaactct atagtgcgct ggccaacaag   840
tgctgccatg tggggtgtac aaaacggagt cttgcccagt tttgt                  885

SEQ ID NO: 417           moltype = DNA   length = 885
FEATURE                  Location/Qualifiers
source                   1..885
                         mol_type = other DNA
                         organism = synthetic construct
SEQUENCE: 417
gacaaaactc atacatgccc cccatgccca gcacccgaag cggccggagg tccgtctgtc    60
tttctgtttc cgccgaaacc taaagatacg ttgatgatta gcagaacccc tgaggtaaca   120
tgtgtggtag tcgatgtctc ccatgaggac cccgaggtaa agttcaattg gtatgttgac   180
ggcgtcgaag tccataacgc aaaaacgaag ccccgagagg agcaatataa ctctacctat   240
cgcgttgttt ctgttttgac tgtgttgcac caggattggc tcaacggcaa ggaatacaaa   300
```

```
tgtaaagtgt ccaacaaggc ccttgctgca cctatcgaaa aaacgattag taaggcaaag    360
ggacaaccgc gcgaaccaca ggtatatact ttgccgccta gcagagatga actcaccaag    420
aatcaagttt cccttacctg tttggttaaa ggattttacc cgtctgacat agctgttgaa    480
tgggagagca atggtcagcc ggaaaataat tataaaacca ccccgccagt attggattca    540
gatgggtcct ttttcttgta ttctaaactt accgtggata agtctaggtg gcaacaggga    600
aacgtctttt catgtagtgt acttcatgaa gccctccata gtcactacac cagaaatcc     660
ttgtctctta gtccgggtga aggtgggtct gattcctggc aggaagaggt gataaagctc    720
tgtggtcggg aacttgttag ggcgcagatc gctatttgcg gcaaatctac agcatcagat    780
gccgccggga ctgatgcgaa gcaggagcg aggcagctgt actccgcact tgctaacaag     840
tgttgccatg tcggctgcac caagaggagt cttgctcaat tctgc                    885

SEQ ID NO: 418       moltype = DNA   length = 885
FEATURE              Location/Qualifiers
source               1..885
                     mol_type = other DNA
                     organism = synthetic construct
SEQUENCE: 418
gataagaccc atacatgccc gccatgtccc gcacccgagg cagcgggtgg accctctgtc    60
tttctgttcc ctccaaagcc aaaagatacc ctgatgatta gccgaacccc ggaggtgact   120
tgtgtcgtag tagatgtcag tcacgaggat cccgaagtaa agtttaattg gtatgtggac   180
ggtgtggagg tacataacgc taagacgaaa ccccgagagg aacaatacaa ctctacgtac   240
agggtcgtct cagtgctcac ggtcctgcac caggactggc ttaatgggaa ggaatataaa   300
tgcaaagtct ctaataaggc gcttgctgca cctattgaaa aaacgatttc taaggcgaag   360
ggacaacccc gggagccaca agtctacacc cttcctccaa gcagagatga gcttacgaaa   420
aatcaagtgt ctcttacgtg cctcgtaaag ggcttttacc catccgacat gcggtggag    480
tgggaatcaa acgggcagcc ggaaaataac tacaaaacaa ccgcgcctgt attggattcc   540
gacggctctt tcttcctta cagcaaactg acagtcgata aatccagatg gcaacaaggg    600
aacgttttt catgttccgt tctgcatgaa gcccttcaca gtcattacac ccaaaagtca    660
cttttcactt caccgggcga gggggggtca gactcctggc aagaggaagt tataaagttg   720
tgcggcaggg aactggttag agcgcagata gcgatttgcg gaaaatctac tgcgagtgat   780
gctgcgggag cgaatgcgga cgccggggcc cgacagctct attccgcact cgccaataag   840
tgctgccatg ttggttgtac gaagagaagt cttgcacaat tttgc                   885

SEQ ID NO: 419       moltype = DNA   length = 885
FEATURE              Location/Qualifiers
source               1..885
                     mol_type = other DNA
                     organism = synthetic construct
SEQUENCE: 419
gataagacac atacatgccc cccctgcccg gctcccgaag ctgccggggg accgtcagtg    60
tttttgtttc cgcccaagcc gaaggatact tgatgatta gtcggacacc agaagtgaca   120
tgtgttgtcg ttgacgtgag tcacgaggat cccgaggtca agttcaactg gtacgttgat   180
ggggttgaag ttcacaacgc taaaacgaaa ccccgcgaag agcagtataa ctccacttac   240
cgggtcgtca gtgtcctgac ggtcttgcac caggactggc tgaatggaaa ggaatacaag   300
tgtaaagttt ccaataaagc actggccgcc ccgatcgaaa aaacaatttc caaagctaag   360
ggacagccca gggaaccgca agtttatact cttccaccct cccgggatga actgaccaaa   420
aaccagtgt ctttgacgtg cctcgtaaag ggcttctcac cgtcagacat agctgtcgaa    480
tgggagtcta atggacagcc ggaaaacaat tataagacta caccgccggt gcttgatagt   540
gatgaagttt ctttttgta ctccaaactt acggtcgata aaagccggtg gcagcaggga   600
aacgtattca gttgtagcgt tctgcatgaa gctcttcatt ctcactacac ccagaagtct   660
ctgtctctga gccccggaga gggtggatct gattcttggc aggaagaagt gataaagttg   720
tgcggccggg aattggtacg cgcccagata gccatttgcg ggaagtctac ggcgagtgac   780
gcagcaggtg ctgacgcgga cgctggtgct agacagctgt attctgccct ggctaataag   840
tgttgccacg ttggctgcac caagagatcc ctggcccaat tctgt                   885

SEQ ID NO: 420       moltype = DNA   length = 885
FEATURE              Location/Qualifiers
source               1..885
                     mol_type = other DNA
                     organism = synthetic construct
SEQUENCE: 420
gacaagacac atacttgtcc cccctgccca gctccagaag ctgccggagg gccgtcagtc    60
ttcctttttcc ctccaaaacc taaggatacg cttatgattt ctcgaacgcc agaggttacg   120
tgtgtagtcg tggacgtttc ccacgaggat cctgaggtca agttaactg gtatgtagac    180
ggggttgagg tccataatgc caagacaaag ccgcgcgagg aacaatacaa cagtacatat   240
agggtggtga gcgtcctcac agtcttgcat caagattggc tcaacggcaa agagtacaaa   300
tgtaaggtta gcaacaaagc cctcgctgct cccatcgaaa agacgatttc taaggcgaag   360
ggccaaccac gagaaccgca agtatatact cttcccccctt cacgggacga gctgaccaaa   420
aaccaggtat ccttgacttg cctggtcaaa ggatttacc cctctgatat tgccgtcgag    480
tgggagagta atgggcaacc agaaaataat tataaaacga ccccccggt actcgacagt    540
gatgggtctt ttttcctgta ttctaagctt acggttgata agtctagatg gcagcaaggg   600
aatgtcttct catgtagtgt tctgcatgaa gcacttcatt ctcactatac tcagaaatct   660
ctttcccttt gtccggaga aggtggggagc gatagttggc aagaggaggt gataaactg    720
gtggtcgggg agctggttgag agccccaaata gctatctgcg gcaaatcaac agcaagtgat   780
gcggcaggag cggaagcgga ggcgggagcg cggcaattgt atagtgccct tgctaataaa   840
tgctgtcacg ttgggtgtac taaacgatct cttgctcaat tctgc                   885

SEQ ID NO: 421       moltype = DNA   length = 885
FEATURE              Location/Qualifiers
```

```
source                  1..885
                        mol_type = other DNA
                        organism = synthetic construct
SEQUENCE: 421
gataaaaccc atacatgtcc tccgtgtccc gctccagaag ccgctggcgg gccatctgtg   60
tttttgttcc cccccaagcc taaggatacg ttgatgatca gcaggacccc ggaggttaca  120
tgcgtagtag ttgacgtttc tcatgaagac ccagaagtaa aatttaactg gtatgtcgat  180
ggcgtcgaag tacataatgc taaaactaag cccagggaag agcaatacaa ttcaacgtac  240
cgagttgtga gtgtccttac ggtcctgcac caagactggt tgaacggcaa agagtacaaa  300
tgcaaagtgt ctaacaaggc attggccgcg cctatagaaa agaccattag caaagcaaaa  360
gggcagcctc gggaacccca ggtctacacg ctgccacctt cccgagatga attgacgaaa  420
aaccaggtct ctttgacctg cttggttaaa ggcttctacc caagcgacat tgcagtggag  480
tgggagtcta acgggcaacc cgaaaacaac tataagacga ctccccctgt tcttgattct  540
gatgggagtt ttttttctgta cagtaagttg acagtggata aatcaagatg gcagcaaggt  600
aatgtcttct cttgttcagt gcttcacgaa gcattgcatt ctcactacac acaaaagtct  660
ttgtccttgt ctccaggtga aggcggtagc gattcatggc aagaagaagt cattaagctg  720
tgtggaaggg aactggttag ggcccaaatt gcgatatgtg gaaagtctac ggcgagtgat  780
gcggccggtg ctcaagcgga tgcgggtgct agacagttgt actcagccct tgcgaacaaa  840
tgttgtcacg ttggctgtac gaaacgcagc cttgctcaat tctgc              885

SEQ ID NO: 422          moltype = DNA   length = 885
FEATURE                 Location/Qualifiers
source                  1..885
                        mol_type = other DNA
                        organism = synthetic construct
SEQUENCE: 422
gataaaactc acacatgccc cccatgccca gcaccggaag ctgccggagg accgtctgta   60
ttcctctttc cgcccaaacc gaaagacacg ttgatgattt ctcggactcc cgaggtaact  120
tgtgtcgtgg tcgacgtctc acacgaggac ccggaggtca aatttaactg gtatgtcgat  180
ggggtggagg tccataatgc taagacgaag cccagagaag aacagtataa ctctacttat  240
agagttgtaa gcgtgctcac tgtattgcac caggactggc tcaacgggaa agaatataag  300
tgtaaggtct caaacaaagc tctcgcagcc ccgatagaga aaacaatatc taaggccaag  360
ggccaaccgc gcgagccgca ggtttataca cttccaccct cccgcgatga gctgaccaag  420
aaccaggtct ctctcacctg tctcgtaaag ggcttttatc cctccgacat tgcagtggag  480
tgggaatcaa acggccagcc ggaaaataat tacaagacca ctcctcccgt cctcgactcc  540
gatgggtcat ttttcctgta cagtaagctc accgttgata agtcaaggtg gcagcagggc  600
aacgtgttta gctgtagtgt tctgcatgag gcgctccaca gtcactacac ccagaaaagt  660
ctgagccttt ccccaggtga gggtggtagc gatagctggc aggaggaagt aattaaactc  720
tgcggtagag aattggtaag ggcccaaatt gccatctgcg gaaagagcac cgcatcgagt  780
gctgcgggcg cggatgcgca ggctggtgct aggcaactct actctgccct ggcgaataaa  840
tgttgccacg tcggttgcac gaaacgaagt ttggctcaat tttgc              885

SEQ ID NO: 423          moltype = DNA   length = 885
FEATURE                 Location/Qualifiers
source                  1..885
                        mol_type = other DNA
                        organism = synthetic construct
SEQUENCE: 423
gacaaaacac atacatgccc cccttgcccg gctcccgagg ccgccggtgg tcctagcgtc   60
tttctttttcc ctcccaaacc caaagacaca cttatgatta gcagaactcc cgaggtaaca  120
tgtgtggtcg tagacgtaag tcacgaagat cccgaagtta aattcaactg gtacgtgcac  180
ggtgtggaag ttcataatgc aaaaaccaaa ccgcgagagg aacagtataa ctctacctac  240
cgcgtggtct cagtgctgac tgtcctgcat caggactggc tcaacgggaa ggaatataag  300
tgcaaagtga gtaataaggc ccttgcagct cccatagaaa agacgatatc aaaggctaaa  360
ggacagccga gggagccaca ggtgtacact ttgcctccga gtagagatga actcactaaa  420
aaccaagtaa gtttgacatg cctggtcaaa ggtttttacc ccagtgatat agcggttgag  480
tgggagtcca atgggcaacc ggagaacaac tataagacta ctccacctgt cctggatagc  540
gatgaagttt ttttctttta ctcaaagctg acggtggata gagtcgatg gcagcagggc  600
aatgtgttta gctgttctgt gcttcacgaa gcacttcact ctcattatac ctcagaagtca  660
ttgagccttt cccctggtga aggagggtca gattcctggc aggaggaggt tataaagctg  720
tgtggccggg aactcgtgcg agctcaaatt gcgatctgtg gaaatccac cgctagtgat  780
gcggcgggag cacaagctca agcgggcgct cgacaacttt atagcgcttt ggctaataag  840
tgctgccatg tgggttgtac aaagcgcagc ctcgctcaat tttgc              885

SEQ ID NO: 424          moltype = DNA   length = 885
FEATURE                 Location/Qualifiers
source                  1..885
                        mol_type = other DNA
                        organism = synthetic construct
SEQUENCE: 424
gataagacgc acacttgccc tccttgcccg gcacccgaag ccgctggtgg gcctagtgta   60
ttcctgttcc ccccgaagcc gaaggatact cttatgattt cacgcacgcc cgaggttaca  120
tgcgtagtag tggacgtatc tcacgaagat cccgaagtca agttcaattg gtatgtcgac  180
ggagtagaag ttcacaacgc aaagacaaaa ccgcgggaag agcaatacaa ctccacgtac  240
cgcgtcgttt ctgttcttac ggtcttgcac caggactggc tcaatggcaa ggagtataag  300
tgcaaggtat ccaacaaggc ccttgccgca cctattgaaa agactatcag caaggccaag  360
ggacagccaa gggagcctca agtctacacg ctcccgccta gtagagacga gttgacaaag  420
aatcaagtga gtttgacttg tctggttaaa ggttttacc cgtcagatat tgcagtagaa  480
tgggaatcta acggacaacc cgaaaacaac tataaaacga cgcctcctgt gttggattca  540
```

```
gatgggtcat tttttctcta ctcaaagctc acggtagata aatcaagatg gcaacaaggc    600
aatgtatttt cctgctccgt gctccacgag gctctgcaca gccattatac gcaaaagagt    660
ctgtctttga gcccaggtga gggtggctcc gattcctggc aggaggaagt aattaagttg    720
tgcggcaggn aacttgttcg cgcacaaata gccatttgtg gtcagagcac agcatcgat    780
gccgccggag ccgacgccaa cgcaggtgcc cgccaacttt attctgccct cgcaaacaaa    840
tgctgccacg tcggctgcac gaagaggagc ctcgcccaat tttgc                    885

SEQ ID NO: 425           moltype = DNA   length = 885
FEATURE                  Location/Qualifiers
source                   1..885
                         mol_type = other DNA
                         organism = synthetic construct
SEQUENCE: 425
gataagaccc atacgtgccc gccatgtcca gcccccgagg cagccggagg tccttccgtt    60
ttcctttttcc cccctaagcc caaggacact ctgatgatct cccggacgcc tgaagtcact   120
tgcgtagtcg tagacgtttc acatgaggat ccagaagtta aatttaactg gtacgtcgat   180
ggcgtcgagg tccataacgc gaaaaccaag cccaggagg aacaatataa ctccacctat    240
agggtcgtga gtgtgctcac cgtttgcac caagactggc tcaacgggaa agagtacaaa    300
tgtaaagttt caaataaggc tttgccgcc ccaatagaaa agactatatc caaggctaag    360
ggacagcctc gagaaccgca ggtatatacg cttcctccgt ctaggatga actcacaaaa    420
aaccaggttt ctttgacctg cttggtaaag ggattttatc cctccgacat tgcggtcgaa    480
tgggagagca acggacagcc ggaaaacaat tacaaaacga caccccccgg ttttgactct    540
gatgaagct tcttcctcta tagtaagttg accgtagaca agtctcgctg gcagcaggga    600
aacgtcttca gttgctcagt tctccatgag gcgttgcata gtcactatac acagaagagt    660
cttagttttgt ctccaggaga aggaggttct gattcttggc aagaggaagt aatcaaattg    720
tgtggccgag aacttgttag agctcagata gccatctacg gccatctacg ggcgtccgat    780
gcggccggag ctaatgctga cgcaggtgcg cgacagctgt actccgcact ggcgaataag    840
tgctgccacg tgggatgcac taagcggtct ccgcgcaat tctgt                    885

SEQ ID NO: 426           moltype = DNA   length = 885
FEATURE                  Location/Qualifiers
source                   1..885
                         mol_type = other DNA
                         organism = synthetic construct
SEQUENCE: 426
gataaaaccc acacctgtcc accatgcccg gcgccggaag ccgccggggg acccagcgta    60
tttctttttcc cccccaagcc caaagacacg ctgatgattt cacgaacgcc ggaggtgact   120
tgcgtggtag tggacgtctc ccatgaggat cccgaagtta aatttaattg gtatgtagat   180
ggtgttgagg tccataatgc taaaacaaag ccgcgggaag agcaatataa ctccacctat    240
agagtggtct ctgtactcac tgtcctgcac caggattggc tgaatgggaa agagtacaag    300
tgtaaagtta gcaacaaagc gctcgccgcg cctatcgaaa aaacgatttc caaagcaaag    360
ggccaaccac gagaacccca ggtttacacc ctgccaccca gtcgagatga actcactaag    420
aatcaggtgt ccccttacatg cctcgtcaag ggattctatc cagcgcgatat agccgtgaag    480
tgggagagta acggtcaacc cgaaaataac tataaaacca ctccgccggt actcgattct    540
gacggttcct tctttcttta ttccaaactg actgtagaca aatcacgtgt gcagcagggc    600
aacgtgttta gctgctctgt actccatgag gccttgcatt ctcattatac tcaaaagagt    660
ctgagtctga gtccaggtga aggggggttcc gattcatgtc aagaggaagt cattaaactc    720
tgcggaaggg aacttgtaag agcacaaatc gcgatttgtg ggcaatctac cgcatccgac    780
gcggctggag cagatgcaga tgccggagcg aggcagctgt attcagcatt ggctaacaaa    840
tgttgccatg ttggatgtac gaagagatca cttgcacagt tctgt                    885

SEQ ID NO: 427           moltype = DNA   length = 885
FEATURE                  Location/Qualifiers
source                   1..885
                         mol_type = other DNA
                         organism = synthetic construct
SEQUENCE: 427
gataagactc atacctgccc gccctgtccc gcacccgagg ctgccggagg gccatcagtg    60
ttcctttttcc caccaaagcc gaaggataca ctttatgatca gcaggacacc cgaagtgacc   120
tgtgtagtcg tagacgtgtc ccacgaagac cccgaagtaa aatttaattg gtatgtcgat   180
ggcgtagagg tccacaacgc gaaaacgaaa ccccgcgaag aacaatataa ttccacatac    240
cgagttgtca gcgtcctcac tgttctccat caggactggc tgaatgggaa ggaatataag    300
tgcaaggtct caaacaaggc gctggcggcc cccatagaga aaacgatttc taaggccaaa    360
ggacagccac gggaaccgca ggtctatacg ctcccaccta gtaggatga gttgaccaaa    420
aatcaggtat cccctcacatg tctcgtcaag ggattctatc ccagcgacat agccgtggag    480
tgggaatcta acggtcaacc tgagaataac tataaaacaa ccccccccggt cctcgactcc    540
gatggtagct tctttctgta ttccaaactg acggtagata aagccgatg gcaacagggt    600
aacgtcttta gttgttctgt attgcacgag gcgctccata gtcactacac acagaagtct    660
ttgagcctct cacctgggga gggggtagc gattcttggc aagaggaagt gatcaaactg    720
tgcggcaggg aactggtcag agcacagata gcaatgtcgc gtcagagtac ggcctctgac    780
gccgccggtc cggaggctga ggcaggggcg agacagctct cagcgctct tgcaaataag    840
tgtgtcacg tggggtgcac aaagagatcc ttggcgcaat tttgt                    885

SEQ ID NO: 428           moltype = DNA   length = 885
FEATURE                  Location/Qualifiers
source                   1..885
                         mol_type = other DNA
                         organism = synthetic construct
SEQUENCE: 428
```

```
gataagaccc acacatgtcc gccatgtcca gccccagagg cagcaggggg cccgtccgta   60
ttcttgtttc ccccgaaacc caaagatacc cttatgatta gtcgaactcc agaagtcacg  120
tgtgtggtgg tggacgtatc ccacgaggac cccgaagtga aattcaattg gtatgtggac  180
ggggtggaag tccataacgc taagacgaag cccagagagg agcagtacaa ttctacctat  240
cgggttgtat ctgtgcttac tgttctccat caagattggc tgaacggaga ggaatacaaa  300
tgtaaagtta gtaacaaagc attggcagct cctatcgaaa agacgataag caaggctaaa  360
ggtcaacccc gagagcctca ggtctacact ttgccgccct ccaggatgga gcttaccaag  420
aaccaagtga gcttgacgtg tctcgtgaag ggattctacc catcagatat agcggtagaa  480
tgggagtcta atgggcagcc cgagaacaac tataagacca cccctcccgt tcttgactct  540
gacggttcct ttttcttgta ctccaaactc acggtcgaca agtctaggtg gcagcaaggc  600
aatgttttca gttgttccgt gctgcacgaa gctcttcatt ctcactatac gcaaaaaagc  660
ctgagtcttt cacctggaga gggggttcc gattcttggc aggaagaagt cattaagctg  720
tgcggcagag aacttgtgcg cgcacaaatt gctatttgtg gacagtcaac tgcatctgac  780
gccgctggag cccaagcgga cgcaggggca aggcagcttt attcagcgct gcgaataag   840
tgttgccatg tgggttgcac gaaacgaagc ctggcgcaat tttgt                  885

SEQ ID NO: 429        moltype = DNA  length = 885
FEATURE               Location/Qualifiers
source                1..885
                      mol_type = other DNA
                      organism = synthetic construct
SEQUENCE: 429
gataagacac atacatgtcc tcccgtgccc gctccggagg cagccggtgg gccttcagtt   60
ttcttgtttc cgccgaagcc taaggacacg ttgatgatat cccgaacacc agaggtcaca  120
tgcgtcgtcg tggacgtctc acacgaggac cctgaagtga aattcaactg gtatgtagac  180
ggggtcgaag ttcacaatgc gaaaactaaa cctcgcgagg agcaatataa ctcaacatac  240
cgcgtagtgt ccgtcttgac tgtccttcat caggattggc tgaatggtaa agaatataaa  300
tgtaaagttt ctaataaagc gcttgcggca cccattgaga gacaatttc caaagccaaa   360
ggccaacccc gagagcctca ggtatatacg ctgcctccgt ctcgagatga gttgacaaaa  420
aatcaagtca gcttgacttg tcttgtaaag gggttctatc cgtcagacat agcagtggga  480
tgggaatcca acgggcaacc agaaaataat tacaaaacca ctccgcccgt gcttgactca  540
gatgggagct tcttcctta tagcaaactt acggtagata aatccagatg gcagcaaggc   600
aacgtattca gctgtagtgt gctgcatgaa gcgcttcact cccattatac tcaaaaatct  660
ctttctctgt caccgggcga gggcggaagt gatagttggc aggaagaggt catcaagctc  720
tgtgggagag agcttgtacg cgctcagatt gctatatgcg gccagtcaac tgcaagcgtc  780
gcagcgggtg ccgatgccca agcggggca cggcaactct actcagccct cgcgaataaa   840
tgttgtcatg tagggtgtac taagagaagc ctcgcgcaat tttgt                  885

SEQ ID NO: 430        moltype = DNA  length = 885
FEATURE               Location/Qualifiers
source                1..885
                      mol_type = other DNA
                      organism = synthetic construct
SEQUENCE: 430
gataaaacgc atacttgccc gccgtgccca gcacctgagg cagccggcgg ccctagtgtc   60
ttcttgttcc cgcccaagcc caaggataca ctcatgatct cccgaacgcc agaggtcaca  120
tgcgtagttg ttgacgtttc ccatgaggac cctgaagtga aatttaactg gtacgtcgac  180
ggcgttgagg ttcacaacgc taagactaag ccaagagagg aacagtacaa ttcaactat   240
agagtggtgt ctgtattgac agttctccat caggattggc tgaacggaaa agaatataag  300
tgcaaggtct caaataaggc gctcgctgca cccatagaaa aaaccatatc aaaagcgaag  360
gggcaaccaa gagaacccca ggtgtacacg ctccccccgt ccagagatga actcacgaag  420
aatcaagtgt cactcacatg tcttgtaaag gggttctacc cctctgatat tgccgtagaa  480
tgggaaagca acggacagcc cgagaataac tacaagacga caccgccagt tcttgattct  540
gacgaagct ttttcctcta ttcaaaattg accgttgaca gtcccgatg caacagggc    600
aacgttttct catgctccgt ccttcacgaa gccttgcatt cccactatac gcagaagagt  660
ctctctttga gccccggaga gggaggcagt gattcatggc aagaggaagt gatcaaactt  720
tgcggcagag aattggttag agccagatt gccatttgtg gacaaagtac ggcctcagat   780
gctgcgggg cacaagctca ggcgggcgca cgccagttgt acagtgctct ggcgaataag   840
tgctgccacg ttggttgcac caagcgatcc ttggcgcaat tttgc                  885

SEQ ID NO: 431        moltype = DNA  length = 885
FEATURE               Location/Qualifiers
source                1..885
                      mol_type = other DNA
                      organism = synthetic construct
SEQUENCE: 431
gacaagactc atacttgtcc gccctgcccc gctcctgagg ctgccggagg cccttcagta   60
ttcttgtttc cgccgaaacc gaaggatacc ttgatgatta gtaggacacg gaagtcacc   120
tgcgtagttg tggacgtaag ccacgaagat cccgaagtaa agtttaattg gtatgttgat  180
ggcgtagagg tgcataatgc gaaaaccaaa cctagggagg aacagtacaa tagtacttac  240
cgcgtagtgt cagtgcttac cgtgctgcat caggactggc ttaatgggaa ggaatacaaa  300
tgtaaagtat ccaataaagc gctggcggct cccatcgaga aaacgatctc aaaagccaaa  360
ggacaaccac gggaaccgca ggtctatact ctgccacctt caagagacga acttaccaag  420
aaccaagtct cattgacgtg cttggtaaaa gttttttatc cgtctgacat cgctgttgaa  480
tgggagtcta acggcagcc ggagaacaat tacaaaacaa ctccaccagt cttggattca   540
gatgggtctt ttttttgta ttcaaagctt accgttgaca aaagccgctg caacaagga    600
aacgttttca gctgcagtgt gctgcacgaa gcgctccaca gtcattatac ccagaaatct  660
ttgagcctgt ctccagggga aggtgggagt gactcttggc aagaagaggt tatcaaactt  720
tgcgggcggg agctggtaag ggcccaaatt gcaatatgcg gcaaaagtac tgcatctgat  780
```

```
gccgctgggg ccgatgctaa cgcgggcgca agacaacttt atagcgcgtt ggcgaacaaa    840
tgctgtcatg tgggatgcac caaacaaagt ttggcgcaat tttgt                    885

SEQ ID NO: 432          moltype = DNA   length = 885
FEATURE                 Location/Qualifiers
source                  1..885
                        mol_type = other DNA
                        organism = synthetic construct
SEQUENCE: 432
gataaaactc acacgtgtcc gccatgcccc gcacctgaag cggcgggtgg tccgagcgtg    60
tttttgtttc cgcctaagcc caaggatacc ctgatgatta gtcggacacc cgaagtaaca   120
tgtgtcgtcg tggatgtaag tcacgaggat cccgaagtga aattcaactg gtatgtggat   180
ggagttgaag tccataatgc gaaaacaaaa ccgagagagg aacagtacaa ctcaacatac   240
cgggtggtaa gtgtactgac ggtactccac caggactggc tgaatggtaa ggagtacaaa   300
tgcaaagttt caaataaggc gctcgctgcc cccatcgaga aaaccattag taaggctaaa   360
ggtcaaccta gggagccaca agtatataca ttgccgcctt ctagagatga gctgaccaaa   420
aaccaggtca gcctgacctg tttggtgaaa ggcttctatc caagcgacat tgctgtcgag   480
tgggagtcaa atgggcagcc ggaaaataac tataaaacga ctcctcctgt tctcgactcc   540
gatggttcat tcttcctcta ctcaaagctt accgtggata aatccaggtg caacaaggtg   600
aacgtgttct catgttccgt tctgcacgaa gcactgcatt cccattatac acaaaaatcc   660
ctgagcctct cacctgggga gggcggaagc gatagttggc aagaggaagt aataaagctg   720
tgtggcaggg aactcgtaag ggctcagatt gcgatatgtg gaaaaagcac tgcttctgac   780
gccgcagggg ccaacgcaga tgctggcgcc cgacaactct attctgcgct tgcgaacaag   840
tgttgtcatg taggatgtac caagcaaagc cttgctcagt tctgt                   885

SEQ ID NO: 433          moltype = DNA   length = 885
FEATURE                 Location/Qualifiers
source                  1..885
                        mol_type = other DNA
                        organism = synthetic construct
SEQUENCE: 433
gacaaaaccc acacttgtcc gccctgtccc gctccggagg ctgcaggcgg cccaagtgtg    60
tttcttttcc ccccaaagcc gaaagacacc ttgatgatat cccgcacacc cgaagtgact   120
tgcgttgtcg tcgacgtgtc tcatgaggac ccagaagtca agtttaattg gtacgttgat   180
ggcgtggaag ttcacaatgc gaaaactaag cccagagagg agcaatataa ctcaacctac   240
cgggtggtaa gtgttctgac agttctccac caggactggt tgaacggaaa agaatacaaa   300
tgcaaagtga gtaacaaagc cctggctgcc cctatcgaaa agaccatatc caaagcgaag   360
ggccagccac gggaaccgca agtatataca cttccaccat ctagagatga gcttacaaag   420
aaccaggtgt cccttacctg cctttgtcaaa ggcttctatc cctctgacat cgcagtggag   480
tgggagtcca acggacaacc agagaacaac tataagacaa cgccgccagt actggattca   540
gatggttcat tcttcttgta ttctaaactg actgttgata aatcccgatg gcagcagggc   600
aacgttttta gttgtagtgt tctgcacgaa gcccttcatt cccattatac acaaaaatct   660
ctttcctca gcccaggcga gggaggaagt gacagttgga agaggaggt gataaagctc   720
tgtgggaggg agctggtacg cgcacagatt gcaatctgcg gaaagagcac agcaagcgat   780
gctgctgggg ccgatgccga tgctggcgct cgacaattgt attcagctct tgctaacaaa   840
tgctgtcacg taggatgcac taaacagagc cttgctcaat tttgt                   885

SEQ ID NO: 434          moltype = DNA   length = 885
FEATURE                 Location/Qualifiers
source                  1..885
                        mol_type = other DNA
                        organism = synthetic construct
SEQUENCE: 434
gataagaccc acacatgtcc accatgccca gccccagaag cggcaggtgg tccttctgtg    60
tttctctttc ctcccaaacc gaaagatact ctgatgataa gccggacccc agaagttacg   120
tgcgttgtag tagacgtgtc tcacgaggac ccagaagtga agtttaactg gtatgtcgac   180
ggtgtagaag ttcataatgc gaaaacaaag cccagggaag aacaatataa ttcaacgtac   240
cgggtcgttt ccgtgctgac agttctgcac caagattggc tcaacgggaa agagtacaaa   300
tgcaaagtat caaataaggc cttggctgcg ccgattgaaa agacgatttc caaagcaaag   360
ggccagccaa gggaacccca ggtctatacc ctccctccta gcagagatga acttacaaaa   420
aaccaagtct ccctcacctg cctggtcaaa ggattctatc cctcagatat agcagtagaa   480
tgggaaagta acgggcagcc cgaaacaat tataagacca ctcctccagt actcgattca   540
gacggtagct tctttctgta ttccaagctg accgtagata aaagtaggtg gcagcaaggt   600
aatgtcttct catgtagtgt acttcatgag gcgttgcatt cccattacac acaaaagtct   660
ttgagtctca gtccgggtga aggaggtagc gattcttggc aggaagaagt aattaagctg   720
tgcggccggg agctcgtcag ggctcagata gctatatgcg gcaagagcac ggccagtgat   780
gctgctggtg cagaggctga agcaggtgcc aggcagttgt acagcgcact cgctaataag   840
tgttgccacg tgggtgtac aaagcaatct ttggcacaat tctgt                    885

SEQ ID NO: 435          moltype = DNA   length = 885
FEATURE                 Location/Qualifiers
source                  1..885
                        mol_type = other DNA
                        organism = synthetic construct
SEQUENCE: 435
gataagaccc atacttgtcc tccgtgcccg gcaccagagg ctgcgggtgg cccatccgtt    60
ttcctgtttc cgccaaagcc taaggatact ctgatgattt cacgcacacc cgaagtgacc   120
tgcgtggtgg tcgacgtatc tcacgaagac ccagaggtaa aattcaattg gtacgtggac   180
ggcgtcgagg ttcataacgc gaaaactaag ccgagagaag agcagtacaa ctctacgtat   240
```

```
cgcgtggtgt ccgtactgac agtattgcat caggactggt tgaatggcaa ggagtataag   300
tgcaaggtat ctaataaggc attggctgcc ccaatagaga aaacgatcag caaagcaaag   360
gggcagccgc gcgagccgca ggtatataca cttccaccat cacgggatga gttgacgaaa   420
aatcaagtct ctctcacatg tctggtaaaa ggtttctatc cttctgatat cgccgtggaa   480
tgggaaagca acggccaacc cgaaaacaac tataagacga cgccgccggt actcgacagc   540
gacggaagct tttcttgta ttccaagttg acagtggaca agtctcgatg gcagcaagga   600
aacgtgttct catgttctgt tcttcacgaa gcccttcata gccattatac tcagaaatct   660
ctctcactct ccccaggtga agggggaagt gactcttggc aagaagaagt cattaagctt   720
tgcggtcgag aattggttcg ggctcaaata gctatttgtg gcaagtccac ggcaagtgat   780
gcagcggggg ctcaggcaga cgcgggcgca aggcagcttt attccgcact tgcaaataag   840
tgctgtcacg tcggatgtac taaacaatca cttgcacaat tctgc                   885

SEQ ID NO: 436           moltype = DNA   length = 885
FEATURE                  Location/Qualifiers
source                   1..885
                         mol_type = other DNA
                         organism = synthetic construct
SEQUENCE: 436
gacaagacac atacatgtcc cccatgccct gcacccgaag ctgctggggg gcccagcgtg   60
ttcctgtttc cgccgaagcc caaggacaca ttgatgatta gtagaacccc agaggtaact   120
tgtgttgtgg tcgatgtgtc acatgaagac cccgaggtaa agtttaactg gtatgtggat   180
ggggtagagg tacataatgc aaaaaccaag ccgcgggagg agcagtataa ttcaacctat   240
cgagtcgtgt cagtcttgac cgtgctccac caggactggc ttaacggtaa ggagtataaa   300
tgcaaagtca gtaataaggc attggccgcc ccattgaga agaccatcag taaagcaag    360
gggcaaccta gagagccaca ggtttacacc ctccctccct cccgggatga actcaccaaa   420
aaccaaggtc cccttacttg tttggtaaag ggcttttatc cttctgatat tgctgttgaa   480
tgggagtcta acgggcaacc tgaaaataac tacaaaacaa ctccccccgt tctggactct   540
gatgggtcat tcttccttta ttcaaaattg acagttgata agagtagatg gcaacaaggc   600
aacgtatttt catgttctgt gctccacgag gctctccatt cccactacac acagaaaagt   660
ctctcactgt ccccaggaga gggcgggagc gactcttggc aggaagaagt aatcaagttg   720
tgtggcaggg aactcgtacg cgctcagatt gcaatatgcg ggaaatccac ggcaagtgac   780
gctgccgggg ccgacgcgca agcagggggca cggcagcttt actccgccct cgcaaataaa   840
tgttgtcatg tgggatgcac taaacagtcc cttgcccagt tttgc                   885

SEQ ID NO: 437           moltype = DNA   length = 885
FEATURE                  Location/Qualifiers
source                   1..885
                         mol_type = other DNA
                         organism = synthetic construct
SEQUENCE: 437
gataaaaccc atacctgtcc accatgcccc gcgccagagg cagcgggtgg tccaagcgtt   60
ttccttttc caccgaaacc aaaagataca cttatgatat caaggacccc cgaggtaacg   120
tgcgtcgtag ttgacgtttc tcacgaagat cccgaggtga aattcaattg gtacgtagat   180
ggtgtagagg tacacaatgc gaagacaaaa ccgcgggaag agcagtataa tagcacatac   240
agagtcgtga gcgtcctcac cgtacttcac caagattggc tgaatggaaa ggagtacaaa   300
tgtaaggtaa gtaataaagc acttgcggcc cccatcgaga aaactatcag taaagcaaaa   360
gggcaaccac gagaacccca ggtctacact ttgccaccat gcgatggatga actgaccaaa   420
aatcaggtgt cactcacttg ccttgttaaa gggttctatc ctagtgacat agcggtagaa   480
tgggagtcta acgggcagcc tgagaacaat tataaaacta cgccccctgt tcttgattcc   540
gatggatcat tttttctcta ctccaaactc accgtagaca aatcccgctg gcagcagggc   600
aacgtgttta gttgcagcgt tcttcacgaa gcacttcact cacattacac acaaaagtcc   660
ctgagcttga gtcctgggga gggtggatct gattcttggc aggaagaagt tataaaactt   720
tgtggcagag agttggtccg cgcacaaatc gccatatgtg gtaaaagcac agcgtctgac   780
gcggcggag cgcaagccca ggcggggggct cggcaactct actcagccct ggctaacaag   840
tgctgtcacg tgggatgcac taaacaaagt ctggcgcagt tctgc                   885

SEQ ID NO: 438           moltype = DNA   length = 885
FEATURE                  Location/Qualifiers
source                   1..885
                         mol_type = other DNA
                         organism = synthetic construct
SEQUENCE: 438
gacaaaaccc atacgtgtcc cccgtgtccg gctccagagg ctgcgggagg accgtctgtg   60
ttcttgttcc cgccgaagcc taaagatacg ctgatgatta ccggacccc cgaggtgacg   120
tgcgtggtag tagacgtatc tcatgaagat ccggaagtaa agtttaactg gtacgtagac   180
ggcgtcgagg tacataatgc caagacgaaa cccagagaag agcaatataa tagcacttat   240
cgagttgtaa gcgtattgac ggtccttcac caggactggt tgaacggcaa agagtacaaa   300
tgtaaggtat ccaataaagc attggctgcg ccaattgaaa agacaatttg caaagcgaag   360
gggcaacctc gagagccgca agtctacacg ctgccaccga gtaggatga attgactaag   420
aatcaggtga gtctcacgtg tctcgtgaag ggggttttacc ccagtgatat tgcggtagaa   480
tgggagtcca acggtcagcc agaaaataat tataaaacaa cgccccctgt attggattct   540
gacgggagct ttttcctgta ctcaaaactc accgtagata agagtcgctg gcaacagggc   600
aacgtatttt catgtagcgt tctgcacgag gcgctgcact ctcactacac acagaagagt   660
ttgagttttgt ccctggga aggaggttct gattcctggc aggaggaggt gattaagctg   720
tgtggccgcg aattggtgag ggctcaaatt gctatttgcg gacaggagcac agcgtccgat   780
gccgccggcg cagatgctaa tgccggtgca aggcaactgt actccgctct cgccaataag   840
tgttgtcatg tcggctgcac caagcaatcc ctggcccagt tttgc                   885

SEQ ID NO: 439           moltype = DNA   length = 885
```

```
FEATURE                 Location/Qualifiers
source                  1..885
                        mol_type = other DNA
                        organism = synthetic construct
SEQUENCE: 439
gacaagactc acacttgtcc cccatgtcca gcaccggaag ctgccggcgg tccctcagtt    60
ttccttttcc cccccaaacc caaggacacc cttatgattt caaggacacc agaggtaacg   120
tgcgtagtgg tggacgtcag tcatgaagac ccagaggtaa agtttaactg gtacgtggat   180
ggggtagagg ttcataatgc taaaacaaaa ccacgcgagg aacagtacaa tagtacgtat   240
agagtggtct ccgttcttac ggtgctgcat caggactggc tgaacgaaa agagtacaag   300
tgtaaggtta gcaataaggc gctggcggcc ccaatcgaaa agacgatttc taaggccaaa   360
ggccagccaa gggagccaca agtatatacc cttcccccctt cccgagatga gctgactaag   420
aatcaagtca gtctcacctg ccttgtcaaa gggttctacc catccgatat tgctgttgaa   480
tgggagtcta atggccagcc ggagaacaat tacaagacaa ctccgcctgt attggattcc   540
gacgggtctt ttttcctcta ttcaaaactc acagtagaca aaagtcgatg gcagcaaggt   600
aacgtgttt cttgctctgt gttgcatgaa gcacttcatt ctcattatac tcaaaaatca   660
ttgagcctca gtccaggcga aggggtagt gactcatggc aggaggaggt aatcaagctt   720
tgcggacgag agttggtcag ggcccagata gctatttgtg gcgagtgac                780
gcagcagggg cgaatgccga tgcaggagca agacaactgt attctgctct ggccaacaag   840
tgttgtcatg tagggtgtac taaacaaagt ctcgcccagt tctgc                    885

SEQ ID NO: 440          moltype = DNA  length = 885
FEATURE                 Location/Qualifiers
source                  1..885
                        mol_type = other DNA
                        organism = synthetic construct
SEQUENCE: 440
gataaaaccc acacctgtcc cccatgtccg gctcccgaag cagcgggggg cccttcagtt    60
tttctctttc cccccaaacc gaaagacacg ctgatgatta gcagaactcc agaggttacc   120
tgtgtagttg tggacgtttc acacgaggat cccgaggtta aattcaactg gtatgtggac   180
ggcgtcgaag tgcataatgc aaaaacaaag ccccggggaag aacaatataa tagtacctat   240
agggtcgttt ccgtactgac cgtacttcat caagattggc tcaatgggaa ggaatacaaa   300
tgtaaagtga gtaataaagc cctggcggca ccgatcgaaa aaccatttc aaaggctaag   360
ggacaaccgc gcgaacctca ggtctatacc ttgccccctt cccgcgacga gcttacgaag   420
aatcaggtaa gccttacttg tcttgtcaag ggttttttacc ccagcgacat agctgtcgag   480
tgggaatcca atggccaacc ggagaataat tacaaaacta cccctcctgt tcttgatagc   540
gacggaagct tcttcttgta ttccaaactc acagtagata aaagtaggtg gcagcagggc   600
aatgtattt cttgcagcgt cctgcatgaa gcactgcata gccattatac tcaaaagtcc   660
ctgtctttgt ctcctggaga gggcggaagc gattcttgc aagaggaagt tattaagctg   720
tgcgggcgcg aacttgtgag ggctcaaata gcgatatgtg gtcagagcac cgctagcgat   780
gcggctggtg cagacgccga tgccggtgct aggcaacttt acagtgcact tgcgaataag   840
tgctgtcacg tcggatgtac taaacaaagc ctcgcccagt tctgc                    885

SEQ ID NO: 441          moltype = DNA  length = 885
FEATURE                 Location/Qualifiers
source                  1..885
                        mol_type = other DNA
                        organism = synthetic construct
SEQUENCE: 441
gataaaacac atacttgccc tccttgtccg gctcccgaag ccgcaggtgg accttccgtc    60
tttcttttcc cacccaaacc taaagacact ttgatgatta gccggacccc cgaggtacg   120
tgtgtcgtag ttgacgtttc ccatgaagac cccgaagtta agttcaactg gtatgtcgac   180
ggcgtcgagg tgcacaacgc gaagactaag ccaagagagg agcaataacaa ttcaacttac   240
agggtcgtgt ccgtcttgac agtgcttcat caagactggc ttaatgggaa ggaatacaaa   300
tgtaaagtct ccaacaaggc tctcgcagcg cccattgaga aaacgatatc caaagcgaag   360
ggtcaaccaa gagaaccca ggtttacacc ctccccccta gtcgggacga gcttacgaag   420
aaccaggtca gtttgacatg cctggtgaaa ggcttctatc cgtcagacat cgccgtagag   480
tgggaaagca acgggcaacc cgagaacaac tataagacga ctccccccggt gttggatagc   540
gatggctctt tcttcctgta ctctaagctg accgtagata aatccaggtg gcaacagggg   600
aacgtgttt catgctcagt gctccatgaa gccctccatt cacactatac acaaaagtct   660
ttgtcactgt ccccccggtga aggcggcagt gatagcctggc aagaagaagt cataaagctc   720
tgtggtcgcg agcttgttag ggcccaaatt gcgatctgtg gtcagtcaac ggcttctgac   780
gccgccggag cggaagccga ggcgggtgct cggcaattgt attcagcact ggcgaacaaa   840
tgttgccatg ttggttgtac taaacaaagc ctggcccagt tttgc                    885

SEQ ID NO: 442          moltype = DNA  length = 885
FEATURE                 Location/Qualifiers
source                  1..885
                        mol_type = other DNA
                        organism = synthetic construct
SEQUENCE: 442
gacaagactc acacttgtcc accctgtcca gcacctgaag ccgctggtgg accatctgtc    60
tttctgttcc cccctaaacc aaaggataca cttatgatca gcagaacacc tgaagtcaca   120
tgtgttgtgg tagacgtttc ccacgaggat cctgaagtga agtttaactg gtacgtggat   180
ggcgttgagg ttcataatgc caagacgaaa cctcggagg agcagtataa ttctacttat   240
agggtggtaa gctactgac agtcctccat caagactggt tgaacgggaa ggaatacaag   300
tgtaaagttt ccaacaaagc tctggcggcg cctatagaaa agacaatatc aaaagcgaaa   360
gggcaaccca gagagcctca agtatataca ttgccccta gcagagacga attgacgaaa   420
aatcaggtct ctctcacgtg cctcgtgaag ggcttctatc ctagtgatat agctgtggaa   480
```

```
tgggaatcca atggacagcc agaaaacaac tacaagacca cgccccccgt cttggattcc    540
gacgggtcat tcttcctgta cagcaagctg actgtcgaca agagtcgatg caacagggc    600
aacgtcttta gctgcagcgt cctgcacgaa gctctgcata gtcattacac ccaaaagtcc    660
cttttctctct cccctggtga aggcggttcc gattcatggc aagaagaagt aattaagctc    720
tgtggacgag agcttgtccg agcacaaatt gcgatctgcg gcagagtac cgcatctgac    780
gctgctggcg cgcaggcaga tgcgggtgca cggcagcttt attcagctct cgccaacaag    840
tgttgtcatg tggggtgtac aaagcagagc cttgcccagt tttgt                    885

SEQ ID NO: 443        moltype = DNA  length = 885
FEATURE               Location/Qualifiers
source                1..885
                      mol_type = other DNA
                      organism = synthetic construct
SEQUENCE: 443
gataagaccc atacgtgtcc cccttgccct gcacccgagg cggctggggg cccttccgta    60
ttcttgtttc ctcctaagcc caaagatacc ttgatgataa gtcgaacgcc agaagtgact    120
tgcgttgttg tggatgtctc ccacgaggat ccagaagtca aatttaactg gtatgtcgat    180
ggggtcgaag tgcataatgc taaaacgaaa cccagagagg aacaatacaa ttcaacatac    240
cgcgtagtca gtgttcttac tgtgctccat caggattggc tcaatgggaa agaatacaag    300
tgtaaagtct caaataaagc attggcggcc cctatagaga agaccataag caaggctaaa    360
ggtcagccta gggagcctca agtatatacc ttgcctccta gcagagatga gttgaccaag    420
aaccaggtca gcctcacatg cctggtgaaa gggttttacc catctgatat tgccgtcgag    480
tgggaaagta atgggcagcc agagaacaac tacaagacga caccaccggt actggatagt    540
gacgaagtt ttttctttta cagtaagctc acagtcgaca aaagccggtg gcaacaagga    600
aatgtatttt catgtagcgt acttcatgaa gccctccact ctcattacac gcagaagtca    660
ctttcactta gtccgggtga gggtggaagc gatgctggc agaggaggt tatcaagctc    720
tgtggacgag aactcgtgag agcgcaaatt gcaatctgcg ggcagagcac ggcgagtgat    780
gcggccgggg cggacgcgca agcaggagca cgacaacttt atagtgcttt ggctaataaa    840
tgttgccacg ttggatgtac taaacagagc ttggcacagt tttgc                    885

SEQ ID NO: 444        moltype = DNA  length = 885
FEATURE               Location/Qualifiers
source                1..885
                      mol_type = other DNA
                      organism = synthetic construct
SEQUENCE: 444
gataaaacgc acacttgtcc gccatgtccg gcacctgagg cagcgggagg accgtccgtg    60
tttctgtttc ccctaaaacc aaaggacacg ctgatgatca gccgaacacc tgaagtaaca    120
tgcgtggtcg ttgacgtgtc tcacgaggat ccagaagtaa agttcaattg gtatgttgac    180
ggagttgaag tacataatgc taagactaaa ccccgcgaag aacaatataa ttctacgtac    240
agagttgtat ccgtgctcac ggtacttcac caagattggc ttaacgggaa agaatataag    300
tgtaaggtct caaataaggc cctggctgct ccgatcgaaa aaacgatatc aaaggcaaag    360
ggtcaacctc gggagcctca agtatatacc ctcccccat ctaggatga gctgacaaag    420
aaccaagttt cactgacctg tctcgtaaag ggttttctatc cttctgacat cgcagttgaa    480
tgggagtcca acgccaacc agagaacaac tataagacga caccccccgt gttggacagt    540
gacggaagtt ttttcctgta ctccaagctg acggttgata aaagtagatg gcaacaagga    600
aatgttttca gttgttctgt gttgcacgag gccctccact cacactatac ccaaaaaagt    660
ttgtctctga gtcccggtga aggcgggagc gattcatggc aggaggaagt aatcaaactt    720
tgtgggcgag aactggtcag ggcgcaaata gcgatatgtg ggcaaagcac agcttcagat    780
gcagccggtc tcaagctca ggctggagct cgacagcttt atagcgcctt ggctaataaa    840
tgttgtcacg ttggctgtac gaagcagagc ctggcacagt tctgc                    885

SEQ ID NO: 445        moltype = DNA  length = 885
FEATURE               Location/Qualifiers
source                1..885
                      mol_type = other DNA
                      organism = synthetic construct
SEQUENCE: 445
gataaaaccc acacttgccc accttgccct gcgccggaag ccgccggagg acctagtgtt    60
ttcctctttc cccctaagcc caaagacacg ttgatgatct ctcggacacc ggaagtaact    120
tgtgtcgttg tggatgtgtc acatgaggat cccgaggtga aatttaattg gtacgttgac    180
ggcgtggagg tgcataacgc aaagactaaa ccacgcgagg agcagtataa ttctacatac    240
cgggttgtct cagttctcac agttcttcat caggattggt tgaatggaaa ggagtacaaa    300
tgcaaagtgt ccaacaaagc gcttgctgcg ccgattgaaa agacgattc aaaggcaaaa    360
gggcagcccc gcgaaccca gtatatact ttgcctccct cacgcgatga actgactaag    420
aaccaggtga gcctgacttg tttggttaag ggttttatc caagtgacat tgctgttgaa    480
tgggagtcca atgccagcc tgagaataac tacaaaacga caccctcctgt acttgacagc    540
gacggctcct ttttcttta ttcaaaactc acagtggaca aatccaggtg gcagcagggt    600
aacgtctttt cttgcagcgt gctccacgaa gctttgcatt cacattatac gcaaaaatcc    660
ttgtcattgt ccccaggtaa gggcggaagc gactcatacc aagaagaagt cattaaactt    720
tgtgggacggg agctggttag ggcacagatt gctatttgtg gtaagtctac ggctagtgac    780
gcagcgggcg ccgaagcgga agctggtgca aggcagcttt actctgctct ggctaacaag    840
tgttgtcacg ttgggtgtac caagcggtcc cttgcgcaat tctgc                    885

SEQ ID NO: 446        moltype = DNA  length = 885
FEATURE               Location/Qualifiers
source                1..885
                      mol_type = other DNA
                      organism = synthetic construct
```

```
SEQUENCE: 446
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttatc caagtgacat tgctgttgaa    480
tgggagtcca atggccagcc tgagaataac tacaaaacga caccctcctgt acttgacagc   540
gacggctcct ttttctttta ttcaaaactc acagtggaca aatccaggtg gcagcaggt    600
aacgtctttt cttgcagcgt gctccacgaa gctttgcatt cacattatac gcaaaaatcc   660
ttgtcattgt ccccaggtaa gggcggaagc gactcatttc aagaagaagt cattaaactt   720
tgtggacggg agctggttag gcacagatt gctatttgtg gtaagtctac ggctagtgac    780
gcagcgggcg ccgaagcgga agctggtgca aggcagcttt actctgctct ggctaacaag   840
tgttgtcacg ttgggtgtac caagcggtcc cttgcgcaat tctgc                   885

SEQ ID NO: 447            moltype = DNA   length = 885
FEATURE                   Location/Qualifiers
source                    1..885
                          mol_type = other DNA
                          organism = synthetic construct
SEQUENCE: 447
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttatc caagtgacat tgctgttgaa    480
tgggagtcca atggccagcc tgagaataac tacaaaacga cacctcctgt acttgacagc   540
gacggctcct ttttctttta ttcaaaactc acagtggaca aatccaggtg gcagcaggt    600
aacgtctttt cttgcagcgt gctccacgaa gctttgcatt cacattatac gcaaaaatcc   660
ttgtcattgt ccccaggtaa gggcggaagc gactcacttc aagaagaagt cattaaactt   720
tgtggacggg agctggttag gcacagatt gctatttgtg gtaagtctac ggctagtgac    780
gcagcgggcg ccgaagcgga agctggtgca aggcagcttt actctgctct ggctaacaag   840
tgttgtcacg ttgggtgtac caagcggtcc cttgcgcaat tctgc                   885

SEQ ID NO: 448            moltype = DNA   length = 885
FEATURE                   Location/Qualifiers
source                    1..885
                          mol_type = other DNA
                          organism = synthetic construct
SEQUENCE: 448
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttatc caagtgacat tgctgttgaa    480
tgggagtcca atggccagcc tgagaataac tacaaaacga cacctcctgt acttgacagc   540
gacggctcct ttttctttta ttcaaaactc acagtggaca aatccaggtg gcagcaggt    600
aacgtctttt cttgcagcgt gctccacgaa gctttgcatt cacattatac gcaaaaatcc   660
ttgtcattgt ccccaggtaa gggcggaagc gactcaattc aagaagaagt cattaaactt   720
tgtggacggg agctggttag gcacagatt gctatttgtg gtaagtctac ggctagtgac    780
gcagcgggcg ccgaagcgga agctggtgca aggcagcttt actctgctct ggctaacaag   840
tgttgtcacg ttgggtgtac caagcggtcc cttgcgcaat tctgc                   885

SEQ ID NO: 449            moltype = DNA   length = 885
FEATURE                   Location/Qualifiers
source                    1..885
                          mol_type = other DNA
                          organism = synthetic construct
SEQUENCE: 449
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttatc caagtgacat tgctgttgaa    480
tgggagtcca atggccagcc tgagaataac tacaaaacga cacctcctgt acttgacagc   540
gacggctcct ttttctttta ttcaaaactc acagtggaca aatccaggtg gcagcaggt    600
aacgtctttt cttgcagcgt gctccacgaa gctttgcatt cacattatac gcaaaaatcc   660
ttgtcattgt ccccaggtaa gggcggaagc gactcatggc aagaagaagt cattaaactt   720
```

```
tgtggacggg agctggttag ggcacagatt gctatttgtg gtaagtctac ggctagtgac   780
gcagcgggcg ccgaagcgga agctggtgca aggcagcttt actctgctct ggctaacaag   840
tgttgttacg ttgggtgtac caagcggtcc cttgcgcaat tctgc                   885

SEQ ID NO: 450          moltype = DNA   length = 885
FEATURE                 Location/Qualifiers
source                  1..885
                        mol_type = other DNA
                        organism = synthetic construct
SEQUENCE: 450
gataaaccc  acacttgccc accttgccct gcgccggaag ccgccggagg acctagtgtt    60
ttcctctttc ccctaagcc  caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatggc aagaagaagt cattaaactt   720
tgtggacggg agctggttag ggcacagatt gctatttgtg gtaagtctac ggctagtgac   780
gcagcgggcg ccgaagcgga agctggtgca aggcagcttt actctgctct ggctaacaag   840
tgttgtcttg ttgggtgtac caagcggtcc cttgcgcaat tctgc                   885

SEQ ID NO: 451          moltype = DNA   length = 885
FEATURE                 Location/Qualifiers
source                  1..885
                        mol_type = other DNA
                        organism = synthetic construct
SEQUENCE: 451
gataaaccc  acacttgccc accttgccct gcgccggaag ccgccggagg acctagtgtt    60
ttcctctttc ccctaagcc  caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatggc aagaagaagt cattaaactt   720
tgtggacggg agctggttag ggcacagatt gctatttgtg gtaagtctac ggctagtgac   780
gcagcgggcg ccgaagcgga agctggtgca aggcagcttt actctgctct ggctaacaag   840
tgttgtcaag ttgggtgtac caagcggtcc cttgcgcaat tctgc                   885

SEQ ID NO: 452          moltype = DNA   length = 885
FEATURE                 Location/Qualifiers
source                  1..885
                        mol_type = other DNA
                        organism = synthetic construct
SEQUENCE: 452
gataaaccc  acacttgccc accttgccct gcgccggaag ccgccggagg acctagtgtt    60
ttcctctttc ccctaagcc  caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatggc aagaagaagt cattaaactt   720
tgtggacggg agctggttag ggcacagatt gctatttgtg gtaagtctac ggctagtgac   780
gcagcgggcg ccgaagcgga agctggtgca aggcagcttt actctgctct ggctaacaag   840
tgttgtaaag ttgggtgtac caagcggtcc cttgcgcaat tctgc                   885

SEQ ID NO: 453          moltype = DNA   length = 885
FEATURE                 Location/Qualifiers
source                  1..885
                        mol_type = other DNA
                        organism = synthetic construct
SEQUENCE: 453
gataaaccc  acacttgccc accttgccct gcgccggaag ccgccggagg acctagtgtt    60
ttcctctttc ccctaagcc  caaagacacg ttgatgatct ctcggacacc ggaagtaact   120
tgtgtcgttg tggatgtgtc acatgaggat cccgaggtga aatttaattg gtacgttgac   180
```

```
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtga aggcggaagc gactcatacc aagaagaagt cattaaactt   720
tgtggacggg agctggttag ggcacagatt gctatttgtg gtaagtctac ggctagtgac   780
gcagcgggcg ccgaagcgga agctggtgca aggcagcttt actctgctct ggctaacaag   840
tgttgttacg ttgggtgtac caagcggtcc cttgcgcaat tctgc              885

SEQ ID NO: 454         moltype = DNA   length = 885
FEATURE                Location/Qualifiers
source                 1..885
                       mol_type = other DNA
                       organism = synthetic construct
SEQUENCE: 454
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtga aggcggaagc gactcatacc aagaagaagt cattaaactt   720
tgtggacggg agctggttag ggcacagatt gctatttgtg gtaagtctac ggctagtgac   780
gcagcgggcg ccgaagcgga agctggtgca aggcagcttt actctgctct ggctaacaag   840
tgttgtaaag ttgggtgtac caagcggtcc cttgcgcaat tctgc              885

SEQ ID NO: 455         moltype = DNA   length = 885
FEATURE                Location/Qualifiers
source                 1..885
                       mol_type = other DNA
                       organism = synthetic construct
SEQUENCE: 455
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtga aggcggaagc gactcatacc aagaagaagt cattaaactt   720
tgtggacggg agctggttag ggcacagatt gctatttgtg gtaagtctac gggaggagaa   780
ggctctggag gcgaaggaga aggggcgga agacagcttt actctgctct ggctaacaag   840
tgttgttacg ttgggtgtac caagcggtcc cttgcgcaat tctgc              885

SEQ ID NO: 456         moltype = DNA   length = 885
FEATURE                Location/Qualifiers
source                 1..885
                       mol_type = other DNA
                       organism = synthetic construct
SEQUENCE: 456
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtga aggcggaagc gactcatacc aagaagaagt cattaaactt   720
tgtggacggg agctggttag ggcacagatt gctatttgtg gtaagtctac gggaggagaa   780
ggctctggag gcgaaggaga aggggcgga agacagcttt actctgctct ggctaacaag   840
tgttgtaaag ttgggtgtac caagcggtcc cttgcgcaat tctgc              885
```

```
SEQ ID NO: 457          moltype = DNA  length = 885
FEATURE                 Location/Qualifiers
source                  1..885
                        mol_type = other DNA
                        organism = synthetic construct
SEQUENCE: 457
gataaaaccc acacttgccc accttgccct gcgccggaag ccgccggagg acctagtgtt   60
ttcctctttc cccctaagcc caaagacacg ttgatgatct ctcggacacc ggaagtaact  120
tgtgtcgttg tggatgtgtc acatgaggat cccgaggtga aatttaattg gtacgttgac  180
ggcgtggagg tgcataacgc aaagactaaa ccacgcgagg agcagtataa ttctacatac  240
cgggttgtct cagttctcac agttcttcat caggattggt tgaatggaaa ggagtacaaa  300
tgcaaagtgt ccaacaaagc gcttgctgcg ccgattgaaa agacgatttc aaaggcaaaa  360
gggcagcccc gcgaacccca agtatatact ttgcctccct cacgcgatga actgactaag  420
aaccaggtga gcctgacttg tttggttaag ggtttttatc caagtgacat tgctgttgaa  480
tgggagtcca atggccagcc tgagaataac tacaaaacga cacctcctgt acttgacagc  540
gacggctcct tttttcttta ttcaaaactc acagtggaca aatccaggtg gcagcagggt  600
aacgtctttt cttgcagcgt gctccacgaa gctttgcatt cacattatac gcaaaaatcc  660
ttgtcattgt ccccaggtga aggcggaagc gactcatacc aagaagaagt cattaaactt  720
tgtggacggg agctggttag ggcacagatt gctatttgtg gtaagtctac gggaggagaa  780
ggctctggag gcgaaggatc tggggcgga agacagcttt actctgctct ggctaacaag  840
tgttgttacg ttgggtgtac caagcggtcc cttgcgcaat tctgc                 885

SEQ ID NO: 458          moltype = DNA  length = 885
FEATURE                 Location/Qualifiers
source                  1..885
                        mol_type = other DNA
                        organism = synthetic construct
SEQUENCE: 458
gataaaaccc acacttgccc accttgccct gcgccggaag ccgccggagg acctagtgtt   60
ttcctctttc cccctaagcc caaagacacg ttgatgatct ctcggacacc ggaagtaact  120
tgtgtcgttg tggatgtgtc acatgaggat cccgaggtga aatttaattg gtacgttgac  180
ggcgtggagg tgcataacgc aaagactaaa ccacgcgagg agcagtataa ttctacatac  240
cgggttgtct cagttctcac agttcttcat caggattggt tgaatggaaa ggagtacaaa  300
tgcaaagtgt ccaacaaagc gcttgctgcg ccgattgaaa agacgatttc aaaggcaaaa  360
gggcagcccc gcgaacccca agtatatact ttgcctccct cacgcgatga actgactaag  420
aaccaggtga gcctgacttg tttggttaag ggtttttatc caagtgacat tgctgttgaa  480
tgggagtcca atggccagcc tgagaataac tacaaaacga cacctcctgt acttgacagc  540
gacggctcct tttttcttta ttcaaaactc acagtggaca aatccaggtg gcagcagggt  600
aacgtctttt cttgcagcgt gctccacgaa gctttgcatt cacattatac gcaaaaatcc  660
ttgtcattgt ccccaggtga aggcggaagc gactcatacc aagaagaagt cattaaactt  720
tgtggacggg agctggttag ggcacagatt gctatttgtg gtaagtctac gggaggagaa  780
ggctctggag gcgaaggatc tggggcgga agacagcttt actctgctct ggctaacaag  840
tgttgtaaag ttgggtgtac caagcggtcc cttgcgcaat tctgc                 885

SEQ ID NO: 459          moltype = DNA  length = 885
FEATURE                 Location/Qualifiers
source                  1..885
                        mol_type = other DNA
                        organism = synthetic construct
SEQUENCE: 459
gataaaaccc acacttgccc accttgccct gcgccggaag ccgccggagg acctagtgtt   60
ttcctctttc cccctaagcc caaagacacg ttgatgatct ctcggacacc ggaagtaact  120
tgtgtcgttg tggatgtgtc acatgaggat cccgaggtga aatttaattg gtacgttgac  180
ggcgtggagg tgcataacgc aaagactaaa ccacgcgagg agcagtataa ttctacatac  240
cgggttgtct cagttctcac agttcttcat caggattggt tgaatggaaa ggagtacaaa  300
tgcaaagtgt ccaacaaagc gcttgctgcg ccgattgaaa agacgatttc aaaggcaaaa  360
gggcagcccc gcgaacccca agtatatact ttgcctccct cacgcgatga actgactaag  420
aaccaggtga gcctgacttg tttggttaag ggtttttatc caagtgacat tgctgttgaa  480
tgggagtcca atggccagcc tgagaataac tacaaaacga cacctcctgt acttgacagc  540
gacggctcct tttttcttta ttcaaaactc acagtggaca aatccaggtg gcagcagggt  600
aacgtctttt cttgcagcgt gctccacgaa gctttgcatt cacattatac gcaaaaatcc  660
ttgtcattgt ccccaggtaa gggcggaagc gactcatacc aagaagaagt cattaaactt  720
tgtggacggg agctggttag ggcacagatt gctatttgtg gtaagtctac ggctagtgac  780
gcagcgggcg ccgaagcgga agctggtgca aggcagcttt actctgctct ggctaacaag  840
tgttgttacg ttgggtgtac caagcaatcc cttgcgcaat tctgc                 885

SEQ ID NO: 460          moltype = DNA  length = 885
FEATURE                 Location/Qualifiers
source                  1..885
                        mol_type = other DNA
                        organism = synthetic construct
SEQUENCE: 460
gataaaaccc acacttgccc accttgccct gcgccggaag ccgccggagg acctagtgtt   60
ttcctctttc cccctaagcc caaagacacg ttgatgatct ctcggacacc ggaagtaact  120
tgtgtcgttg tggatgtgtc acatgaggat cccgaggtga aatttaattg gtacgttgac  180
ggcgtggagg tgcataacgc aaagactaaa ccacgcgagg agcagtataa ttctacatac  240
cgggttgtct cagttctcac agttcttcat caggattggt tgaatggaaa ggagtacaaa  300
tgcaaagtgt ccaacaaagc gcttgctgcg ccgattgaaa agacgatttc aaaggcaaaa  360
gggcagcccc gcgaacccca agtatatact ttgcctccct cacgcgatga actgactaag  420
```

```
aaccaggtga gcctgacttg tttggttaag ggtttttatc caagtgacat tgctgttgaa  480
tgggagtcca atggccagcc tgagaataac tacaaaacga cacctcctgt acttgacagc  540
gacggctcct ttttctttta ttcaaaactc acagtggaca aatccaggtg gcagcagggt  600
aacgtctttt cttgcagcgt gctccacgaa gctttgcatt cacattatac gcaaaaatcc  660
ttgtcattgt ccccaggtaa gggcggaagc gactcatacc aagaagaagt cattaaactt  720
tgtggacggg agctggttag ggcacagatt gctatttgtg gtaagtctac ggctagtgac  780
gcagcgggcg ccgaagcgga agctggtgca aggcagcttt actctgctct ggctaacaag  840
tgttgtaaaa ttgggtgtac caagcaatcc cttgcgcaat tctgc                  885

SEQ ID NO: 461          moltype = DNA   length = 885
FEATURE                 Location/Qualifiers
source                  1..885
                        mol_type = other DNA
                        organism = synthetic construct
SEQUENCE: 461
gataaaaccc acacttgccc accttgccct gcgccggaag ccgccggagg acctagtgtt  60
ttcctctttc cccctaagcc caaagacacg ttgatgatct ctcggacacc ggaagtaact  120
tgtgtcgttg tggatgtgtc acatgaggat cccgaggtga aatttaattg gtacgttgac  180
ggcgtggagg tgcataacgc aaagactaaa ccacgcgagg agcagtataa ttctacatac  240
cgggttgtct cagttctcac agttcttcat caggattggt tgaatggaaa ggagtacaaa  300
tgcaaagtgt ccaacaaagc gcttgctgcg ccgattgaaa agacgatttc aaaggcaaaa  360
gggcagcccc gcgaacccca agtatatact ttgcctccct cacgcgatga actgactaag  420
aaccaggtga gcctgacttg tttggttaag ggtttttatc caagtgacat tgctgttgaa  480
tgggagtcca atggccagcc tgagaataac tacaaaacga cacctcctgt acttgacagc  540
gacggctcct ttttctttta ttcaaaactc acagtggaca aatccaggtg gcagcagggt  600
aacgtctttt cttgcagcgt gctccacgaa gctttgcatt cacattatac gcaaaaatcc  660
ttgtcattgt ccccaggtaa gggcggaagc gactcatacc aagaagaagt cattaaactt  720
tgtggacggg agctggttag ggcacagatt gctatttgtg gtaagtctac gggaggagaa  780
ggctctggag gcgaaggaga aggggcggaa agacagcttt actctgctct ggctaacaag  840
tgttgttacg ttgggtgtac caagcaatcc cttgcgcaat tctgc                  885

SEQ ID NO: 462          moltype = DNA   length = 885
FEATURE                 Location/Qualifiers
source                  1..885
                        mol_type = other DNA
                        organism = synthetic construct
SEQUENCE: 462
gataaaaccc acacttgccc accttgccct gcgccggaag ccgccggagg acctagtgtt  60
ttcctctttc cccctaagcc caaagacacg ttgatgatct ctcggacacc ggaagtaact  120
tgtgtcgttg tggatgtgtc acatgaggat cccgaggtga aatttaattg gtacgttgac  180
ggcgtggagg tgcataacgc aaagactaaa ccacgcgagg agcagtataa ttctacatac  240
cgggttgtct cagttctcac agttcttcat caggattggt tgaatggaaa ggagtacaaa  300
tgcaaagtgt ccaacaaagc gcttgctgcg ccgattgaaa agacgatttc aaaggcaaaa  360
gggcagcccc gcgaacccca agtatatact ttgcctccct cacgcgatga actgactaag  420
aaccaggtga gcctgacttg tttggttaag ggtttttatc caagtgacat tgctgttgaa  480
tgggagtcca atggccagcc tgagaataac tacaaaacga cacctcctgt acttgacagc  540
gacggctcct ttttctttta ttcaaaactc acagtggaca aatccaggtg gcagcagggt  600
aacgtctttt cttgcagcgt gctccacgaa gctttgcatt cacattatac gcaaaaatcc  660
ttgtcattgt ccccaggtaa gggcggaagc gactcatacc aagaagaagt cattaaactt  720
tgtggacggg agctggttag ggcacagatt gctatttgtg gtaagtctac gggaggagaa  780
ggctctggag gcgaaggaga aggggcggaa agacagcttt actctgctct ggctaacaag  840
tgttgtaaaa ttgggtgtac caagcaatcc cttgcgcaat tctgc                  885

SEQ ID NO: 463          moltype = DNA   length = 885
FEATURE                 Location/Qualifiers
source                  1..885
                        mol_type = other DNA
                        organism = synthetic construct
SEQUENCE: 463
gataaaaccc acacttgccc accttgccct gcgccggaag ccgccggagg acctagtgtt  60
ttcctctttc cccctaagcc caaagacacg ttgatgatct ctcggacacc ggaagtaact  120
tgtgtcgttg tggatgtgtc acatgaggat cccgaggtga aatttaattg gtacgttgac  180
ggcgtggagg tgcataacgc aaagactaaa ccacgcgagg agcagtataa ttctacatac  240
cgggttgtct cagttctcac agttcttcat caggattggt tgaatggaaa ggagtacaaa  300
tgcaaagtgt ccaacaaagc gcttgctgcg ccgattgaaa agacgatttc aaaggcaaaa  360
gggcagcccc gcgaacccca agtatatact ttgcctccct cacgcgatga actgactaag  420
aaccaggtga gcctgacttg tttggttaag ggtttttatc caagtgacat tgctgttgaa  480
tgggagtcca atggccagcc tgagaataac tacaaaacga cacctcctgt acttgacagc  540
gacggctcct ttttctttta ttcaaaactc acagtggaca aatccaggtg gcagcagggt  600
aacgtctttt cttgcagcgt gctccacgaa gctttgcatt cacattatac gcaaaaatcc  660
ttgtcattgt ccccaggtaa gggcggaagc gactcatacc aagaagaagt cattaaactt  720
tgtggacggg agctggttag ggcacagatt gctatttgtg gtaagtctac gggaggagaa  780
ggctctggag gcgaaggatc tggggcgga agacagcttt actctgctct ggctaacaag  840
tgttgttacg ttgggtgtac caagcaatcc cttgcgcaat tctgc                  885

SEQ ID NO: 464          moltype = DNA   length = 885
FEATURE                 Location/Qualifiers
source                  1..885
                        mol_type = other DNA
```

```
                            organism = synthetic construct
SEQUENCE: 464
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaaccca gtatatact ttgcctccct cacgcgatga actgactaag    420
aaccaggtga gcctgacttg tttggttaag ggttttatc caagtgacat tgctgttgaa    480
tgggagtcca atggccagcc tgagaataac tacaaaacga cacctcctgt acttgacagc   540
gacggctcct tttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatacc aagaagaagt cattaaactt   720
tgtggacggg agctggttag ggcacagatt gctatttgtg gtaagtctac ggagggagaa   780
ggctctggag gcgaaggatc tggggcggga gacagctttt actctgctct ggctaacaag   840
tgttgtaaag ttgggtgtac caagcaatcc cttgcgcaat tctgc                   885

SEQ ID NO: 465          moltype = DNA   length = 885
FEATURE                 Location/Qualifiers
source                  1..885
                        mol_type = other DNA
                        organism = synthetic construct
SEQUENCE: 465
gataaaacac acacgtgtcc cccctgcccg gctccagagg cggctggtgg tcccagcgta    60
ttctttgttc ctcccaaacc taaggatacg ctcatgatat cccgcacccc agaagttacg   120
tgtgtagtcg tcgacgtcag tcacgaagat ccagaggtca aatttaactg gtatgtcgac   180
ggagtagagg tccacaatgc gaaaaccaag cccagagaag agcagtacaa ctccacgtat   240
cgcgtcgtct ccgtcctcac cgtactccat caagattggc tgaatgggaa agagtataaa   300
tgcaaagtat ctaacaaggc tctgccagct ccgatagaaa agacgatatc aaaggccaag   360
gggcagccaa gggagcctca agtctatact ttgcccccat ctcgggatga gcttacgaaa   420
aaccaggtca gccttacctg tcttgttaaa ggttttatc cgagtgacat cgcagtggaa    480
tgggaatcta atggtcaacc tgaaaacaat tacaaaacca cccgccagt attggacagc    540
gatggtagtt tttttctta ctcaaaactg actgtagata aaagcagatg gcagcagggc    600
aatgtctttt catgtagcgt tatgcatgag gctcttcaca accactatac ccaaaagtca   660
ttgtctctta gtcccggaaa gggcggaagt gattcttgga aggaggaggt aatcaagttg   720
tgcgggcgag agttggtacg ggcacagatc gcgatatgcg gaaatccac aggtgggggc    780
gaaggaggag gtgagggtgg aggtgaagga cgacagttgt attccgcctt ggcaaacaag   840
tgttgccatg tgggttgcac aaaacgcagt cttgcccgct tctgt                   885

SEQ ID NO: 466          moltype = DNA   length = 888
FEATURE                 Location/Qualifiers
source                  1..888
                        mol_type = other DNA
                        organism = synthetic construct
SEQUENCE: 466
gataagacac atacatgccc tccctgtccg gctccagagg cagccggggg tccatcagtc    60
ttccttttc cgcctaaacc taaggataca ctgatgatct ctcgaacacc ggaggtcact    120
tgtgttgtcg ttgacgtatc acatgaggat cccgaagtaa agttcaactg gtatgtcgat   180
ggtgtggagg ttcataatgc taaaactaaa ccacgggagg agcaatataa ttccacatat   240
agggtcgtga gcgtgttgac ggtgcttcat caagactggc ttaatgggaa ggaatataaa   300
tgcaaagtgt caaatgaagc acttcctgcg ccaatcgaga aaacaattag taaggcaaag   360
gggcagccgc gagaacctca ggtgtacacc ttgccgcctt ctagagacga gctcacaaag   420
aaccaagttt ccctgacttg cctcgttaag gggtttttatc cgtccgatat agccgtggag   480
tgggagtcaa acggccaacc ggaaaataat tacaaaacga cacccccagt attggatagt   540
gacggctctt ttttccttta ttctaagctg actgtggaca aaagccgctg gcagcagggc   600
aatgtctttt catgcagcgt aatgcatgaa gccctgcaca accactacac gcaaaaatcc   660
cttccttgt caccgggcaa gggcggctct gactcctgga agaggaagt tataaaactc    720
tgtggccgag aacttgttcg agctcaaatc gcgatttgtg gtaagtcaac gggtgggggc   780
gaaggtggag gcgagggtgg gggagaagga ggaggccagt tgtactcagc tcttgcaaat   840
aagtgttgcc acgttggttg tacgaagcgg agccttgctc gcttctgc                888

SEQ ID NO: 467          moltype = DNA   length = 885
FEATURE                 Location/Qualifiers
source                  1..885
                        mol_type = other DNA
                        organism = synthetic construct
SEQUENCE: 467
gacaaaacac atacttgtcc gccttgcccg gcacccgaag cggccggcgg acccagtgtc    60
tttctcttcc cacccaaacc gaaagacact ctgatgattt ccaggacgcc tgaagtgacc   120
tgcgttgtag ttgatgtatc acacgaggat cccgaggtca agttcaattg gtatgtagat   180
ggggtggagg tccataatgc aaagacgaag ccacgggagg aacagtacaa ctctacgtac   240
agagttgtca gtgttttgac cgtccttcat caggattggc tgaacggtaa agaatataaa   300
tgcaaggtta gcaataaagc tttgccccgcc cctatagaga aacgatcag taaggcgaag   360
gggcagccta gggaacccca ggtatatacc ttgccgccaa gtcgagatga gctgacgaag   420
aaccaagtga gtctgacatg cctcgtgaag gccttctatc cgagcgatat cgctgtcgaa   480
tgggagagca atgggcagcc tgagaataac tataaaacaa cgccaccgt cctcgactcc    540
gatggctcat tcttcctgta cagtaaactt acagtagata gagtagatg gcagcagggt    600
aacgtcttta gttgctccgt gatgcacgag gcattgcaca atcattacac tcaaaaatct   660
```

```
ctgtccctga gtccgggcaa aggcggttca gatagctgga tgaggaggt cataaagctt   720
tgtggacgag aactcgttcg cgcccagata gctatttgtg ggaaatcaac cgggggtgga   780
gaaggtggcg gagaaggggg aggcgaaggg cgccaactgt attctgcatt ggctaataag   840
tgctgtcacg taggatgtac aaaaaggtct ctggcgagat tctgc                  885

SEQ ID NO: 468          moltype = DNA   length = 885
FEATURE                 Location/Qualifiers
source                  1..885
                        mol_type = other DNA
                        organism = synthetic construct
SEQUENCE: 468
gacaagacgc acacttgtcc accttgccct gcgccggaag ctgctggagg ccccagtgtc   60
tttttgttcc cgcccaaacc gaaggacact ttgatgataa gtcgcacgcc cgaggttacc   120
tgtgtggttg tcgatgtctc acacgaagat ccggaggtga agtttaattg gtatgtagat   180
ggcgtggagg ttcataacgc caaaacgaaa cccagagaag aacaatataa cagtacatat   240
cgagtagtat ccgttctcac tgtcctgcat caagactggt tgaacgggaa ggaatataag   300
tgcaaggtga gcaataaagc actcccggcc ccaatcgaaa agaccatcag caaagcgaag   360
gggcaacctc gagaacccca ggtatatacg ctccccccta gtcgggatga acttactaaa   420
aatcaggtta gcctcacttg ccttgttaaa gggttctatc ccagtgatat tgccgtcgaa   480
tgggaatcaa acgggcagcc ggaaaataac tacaagacaa cccctcctgt gctcgatagc   540
gatggctctt ttttcctcta cagcaaactt accgttgata gagccggtg gcaacaaggt   600
aatgttttct cctgctccgt tatgcatgaa gcactccata accattatac ccaaaaaagc   660
ctgtcactta gtccgggtaa aggaggtagt gattcttggc aggaggaggt aatcaaactt   720
tgtgggaggg agctggtacg agctcagatt gctatatgtg aaaaagcac gggcggagga   780
gaaggaggtg gcgaaggcgg gggtgaaggt cggcaactct actccgctct cgctaataag   840
tgctgccacg tcgggtgtac gaagcgctcc ctggcgcgat tctgc                  885

SEQ ID NO: 469          moltype = DNA   length = 885
FEATURE                 Location/Qualifiers
source                  1..885
                        mol_type = other DNA
                        organism = synthetic construct
SEQUENCE: 469
gataaaacgc acacgtgtcc gccctgccca gcgcctgaag ccgcaggcgg gccgtccgtc   60
ttcctctttc ctcccaaaac caaagacaca cttatgatca gtaggacccc agaggtaacc   120
tgcgtcgtgg tcgacgtttc ccatgaagac ccagaggtca agttcaactg gtacgtcgac   180
ggtgtcgaag tacataatgc taaaacgaag cctcgggaag agcagtacaa ctctacctac   240
cgcgtcgttt ccgtactcac cgtacttcac caggactggc ttaacggtaa agagtataaa   300
tgcaaagtat ctaataaggc tctcgccgcg ccgattgaga gacaatttc aaaggccaag   360
gggcagccgc gggagcccca agtgtatacc ttgcccccgt cccgagatga gctgactaaa   420
aaccaagtaa gctgacttg cttggtcaaa ggcttctacc cttccgatat agctgtcgaa   480
tgggagtcaa atggccaacc agagaacaat tataaaacta cacccccggt cttggattct   540
gatggctcat ttttctcta ttctaaactg accgtggata gtctcgctg gcagcaaggt   600
aacgtgttca gttgctctgt tcttcacgaa gcactgcaca gtcattacac tcagaagagt   660
cttagcctga gccctggtaa aggggggttct gattcctggc aggaggaagt aataaaactc   720
tgtggccgga agttggtacg ggcgcagatt gcgatatgcg gtaagagcac cggcggaggc   780
gaaggcggtg gggaaggagg aggagaaggg agacaactct attccgcatt ggcaaataag   840
tgctgccacg tcgggtgtac caaacgatcc cttgcacggt tctgt                  885

SEQ ID NO: 470          moltype = DNA   length = 888
FEATURE                 Location/Qualifiers
source                  1..888
                        mol_type = other DNA
                        organism = synthetic construct
SEQUENCE: 470
gataagaccc atacgtgccc cccttgccct gcgcctgagg cagcgggtgg cccatcagtc   60
tttttgttcc cgcccaagcc aaaggacacc tcatgattaa gtagaacacc ggaggttacg   120
tgcgtcgtag tggatgtcag ccacgaggat cccgaggtta agtttaactg gtacgttgat   180
ggggttgagg tccataatgc gaagactaag ccgagagagg aacagtacaa ttccacgtat   240
agagttgtct ctgtactgac tgtgctgcat caagattgc ttaacggtaa ggagtacaag   300
tgcaaagtct ctaataaggc tcttcctgca cccattgaga aaactataag caaagcaaaa   360
ggtcaacctc gcgaacctca ggtgtacaca ctgccaccct ctagggacga gcttaccaaa   420
aatcaagtat ctcttacctg ccttgtgaaa gggttttatc cctcagatat tgcggttgag   480
tgggagtcta acggacaacc tgagaacaac tataagacta ctccccccgt gcttgattca   540
gacgggagtt ttttttgta tagcaaactt accgtcgaca aaagccggtg caacagggc   600
aatgtattca gttgttctgt aatgcatgaa gctttgcata atcattacac ccaaaagagt   660
ctttccctgt ctcctggaaa aggggggtca gactcctgga tggaggaggt gatcaaactg   720
tgtgggagag agctcgtccg ggctcagata gctatatgcg gcaagtctac gggtggggga   780
gagggcgag gagagggcgg tggagaagga ggcggccaac tctacagcgc tctggccaat   840
aaatgttgtc atgtcgggtg tactaagcgc tcactggcac gcttttgc               888

SEQ ID NO: 471          moltype = DNA   length = 888
FEATURE                 Location/Qualifiers
source                  1..888
                        mol_type = other DNA
                        organism = synthetic construct
SEQUENCE: 471
gacaagacgc atacatgccc gccatgcccg gcccccgaag ctgctggggg accatccgta   60
ttcctcttcc ctcccaaacc aaaagacacg ttgatgataa gtagaacacc agaggtaacg   120
```

```
tgcgtggttg tcgatgtttc ccacgaagat ccggaggtaa aattcaattg gtatgtagat    180
ggggtggaag tgcacaatgc caaaacaaag ccgcgagaag aacaatacaa tagtacttac    240
cgggttgtga gcgtgctcac ggtgttgcac caagactggc tcaacggcaa ggaatacaag    300
tgcaaagtat ctaataaagc tctgcctgcg ccgatagaga agaccatcag taaggccaaa    360
gggcagcccc gagagccgca agtttacact cttcctccga cagagatga attgaccaag    420
aaccaagtaa gtttgacgtg cctggtgaag ggcttctacc cctcagacat tgccgtggaa    480
tgggaaagta atggtcaacc ggaaaacaac tacaagacca cgccgcccgt cctcgactcc    540
gatgggtctt tctttcttta ttcaaagttg acagtagata agtcaaggtg gcagcaaggt    600
aacgtgttta gttgtagtgt aatgcacgag gccctgcata atcattatac ccaaaagagt    660
ttgagcctct caccaggaaa aggcggatca gacagctggc aggaggaggt aattaaattg    720
tgtgacgggg agttggtcag ggcgcaaata gccatctgcg gtaagagcac gggtggagga    780
gagggtggag gggaaggtgg gggagaaggc ggcgggcagc tctattctgc actcgccaac    840
aagtgttgtc acgtcggatg cacaaagaga tctcttgctc gattctgc                 888
```

SEQ ID NO: 472          moltype = DNA  length = 888
FEATURE               Location/Qualifiers
source                1..888
                       mol_type = other DNA
                       organism = synthetic construct

```
SEQUENCE: 472
gacaaaacac acacctgtcc gccttgcccg gctcctgaag ccgcgggtgg ccctagtgtg    60
tttttgtttc cgccgaaacc taaggatacc ctcatgataa gccgacgcc cgaggttacc    120
tgtgtcgtgg tcgatgttag tcatgaggat ccagaagtca agtttaattg gtacgtcgac    180
ggcgttgaag tccacaatgc aaaaactaaa ccgcgagaag aacagtacaa ctccacctac    240
agagttgtct cagttttgac agttctccat caggattggc tcaatggaaa ggaatataag    300
tgcaaggtca gcaataaagc gcttgccgcc cctatagaga agaccattag caaggcgaaa    360
ggacagcccc gcgagcccca ggtctatacg ctgcctccta gcagagatga gctcacgaaa    420
aatcaggtca gcttgacatg cttggtgaag ggcttctacc ccagtgacat cgcagttgaa    480
tgggagagca acggccaacc tgagaacaac tacaaaacaa cgcccccggt tcttgacagc    540
gatgggtcct tctttctta ctctaagctt acagttgata aaagcaggtg gcagcagggg    600
aatgtgttct catgttccgt actgcatgag gctctgcatt tcactacac ccaaaaaagc    660
cttagcctga gccccggtaa ggaggtagt gactcatggc aagaggaagt gattaagctc    720
tgcggccggg agttggtgag agcccaaatc gccatttgcg gtaaaagtac cggaggggc    780
gagggaggag gcgaaggtgg aggtgaagga ggtggacagt tgtactcagc tcttgcaaat    840
aaaatgttgtc atgttggttg cacgaaaaga tctcttgcga ggttctgt                888
```

SEQ ID NO: 473          moltype = DNA  length = 885
FEATURE               Location/Qualifiers
source                1..885
                       mol_type = other DNA
                       organism = synthetic construct

```
SEQUENCE: 473
gataagacgc atacttgtcc accgtgcccc gcaccggaag cggctggtgg tccatcagtt    60
tttctgttcc caccgaaacc taaggacacg ttgatgatat cacggacacc agaggttacg    120
tgcgtagtgg tggatgtgag ccacgaggat ccagaagtta aatttaattg gtacgtagat    180
ggagtggagg ttcataatgc gaagacaaag cctcgcgagg aacagtataa ttccaccttat   240
cgcgtcgtat ctgtgcttac ggtacttcac caagactggt tgaacggtaa ggaatataaa    300
tgcaaggttt ccaataaagc acttcctgcg ccaattgaga agacaatatc caaagctaaa    360
ggtcaaccca gggaaccgca agtctacact ctcccccgt ctcgcgatga attgacgaag    420
aaccaggtta gtctcacctg cctggtcaag gggttttacc cctctgacat agctgtgaaa    480
tgggagtcta atggacagcc agagaacaat tacaaaacga cccccccggt cctcgattct    540
gatgggagtt tttttcttta ttcaaaattg actgtcgata agtcaagatg gcaacagggt    600
aacgtatttt cttgcagtgt tatgcatgaa gcattgcaca accactatac acaaaaatca    660
ttgagtttga gtcccggtaa aggggaagc gactcatgga tggaagaagt aatcaagctg    720
tgcgggcgag agcttgtgcg agctcagata gcaatctgtg gtaagtctac aggtggagag    780
ggtgcggtga agaaggcgg gggagaggga ggccagcttt attctgccct ggctaacaag    840
tgctgtcacg ttggatgcac gaagcgctcc ctggcccgat tctgc                     885
```

SEQ ID NO: 474          moltype = DNA  length = 885
FEATURE               Location/Qualifiers
source                1..885
                       mol_type = other DNA
                       organism = synthetic construct

```
SEQUENCE: 474
gataagacgc atacttgtcc cccatgtccc gctccggaag ccgctggcgg cccctccgtt    60
tttctgttcc cgccgaaacc gaaagacacc ctgatgatat cacgcactcc cgaggtcact    120
tgcgtggtag tcgatgttag tcatgaagat cctgaggtca aattcaattg gtatgtagat    180
ggcgttgagg tacacaacgc gaagacaaaa ccccgagaag aacagtataa ctcaacctac    240
cgcgtagttt cagttcttac cgtactgcac caagactggt tgaacggtaa agatacaaa    300
tgtaaagtca gcaataaagc tttgccagca cctatcgaaa aaaccatcag taaggccaag    360
ggtcaaccca gggagccgca agtgtacact cttcccccta gcagggatga attgaccaag    420
aatcaggtct ctttgacgtg cctcgttaag ggttttctatc ccagcgatat agccgtgaaa    480
tgggagtcta acggtcagcc agaaaataac tataagacaa ccccgcctgt tttgattcc    540
gacggtctt tttttctcta ctctaagttg accgttgata agacagatg gcagcaggga    600
aacgtatttt cttgttccgt gatgcacgaa gccctgcaca atcactatac gcaaagtgtc    660
ctgagcttga gtccgggtaa aggcggtct gactcctggc aggaggaagt cataaaactc    720
tgcggaaaga agctcgtaag ggcgcaaatc gctatttgtg gtaagagcac cggtggggaa    780
ggaggcggtg aagagggtgg cggcgagggt ggcaattgg attccgcgct tgccaataaa    840
tgttgtcacg taggctgcac aaaagcgaagt ctcgctaggt tctgc                    885
```

SEQ ID NO: 475         moltype = DNA   length = 882
FEATURE                Location/Qualifiers
source                 1..882
                       mol_type = other DNA
                       organism = synthetic construct
SEQUENCE: 475
gacaagaccc acacatgtcc cccgtgtccg gcaccagaag cagcgggggg accgtcagta    60
ttcttgtttc caccgaagcc caaagacaca ttgatgattt cacgaactcc tgaagttacc   120
tgtgtggttg tagatgtatc acacgaagac ccagaagtca aattcaattg gtatgtcgac   180
ggggttgaag ttcacaatgc gaagacgaag ccccgggagg aacagtacaa cagcacgtac   240
agggttgtga gcgttcttac tgtattgcac caggattggc tcaacggcaa ggagtataaa   300
tgtaaagttt ctaataaggc tcttcctgcc caattgaaa agacgatatc taaagcgaag    360
ggccaaccac gggaacctca ggtgtacaca cttccgccta gcagggatga gttgaccaag   420
aatcaagtct ctttgacgtg cctggtcaag gggttttacc catcagatat cgccgtcgaa   480
tgggagtcaa acggacaacc cgaaaataac tataaaacta ctccaccagt tctggatagc   540
gacggctcat ttttctgta ttcaaagctc actgtagaca agtctaggtg gcagcagggt    600
aatgtcttct cctgctcagt aatgcatgag gctcttcaca accactatac tcaaaagagc   660
ctttccctgt cacctggcgg tggaagcgac tcatggatgg aggaggtaat aaagctctgc   720
ggaagagaac tggtacgcgc acaaatcgca atttgtggta agagtactgg cggggaagga   780
ggtggggaag aaggggggcgg tgagggcgga cagctctatt ctgcacttgc aaacaaatgt   840
tgccacgtgg gatgtactaa gcgaagcctt gcaagattct gc                      882

SEQ ID NO: 476         moltype = DNA   length = 882
FEATURE                Location/Qualifiers
source                 1..882
                       mol_type = other DNA
                       organism = synthetic construct
SEQUENCE: 476
gataaaaccc acacatgccc tccatgccct gctccagagg ccgccggtgg gccatcagtt    60
ttcttgtttc cgcctaaacc aaaggacacg cttatgatct ccaggacccc cgaagttacg   120
tgtgtggtgg ttgatgttag tcacgaggac ccggaagtca agttcaactg gtacgttgat   180
ggtgtagagg tgcacaatgc aaagacgaag ccacgcgaag aacaatacaa cagcacatat   240
cgagttgtga gcgtactcac ggtactgcat caggactggc tgaacggtaa agaatacaaa   300
tgtaaagtct ccaataaggc acttcctgcg ccgataagaa aaacgatcag taaggccaag   360
ggccaaccc gagaaccaca ggtatatacg ctcccaccgt cacgagacga gttgacaaaa    420
aatcaggtct ccctgacttg cctcgtgaaa ggtttttatc cctcagatat tgctgttgag   480
tgggaaagca atgggcagcc agagaataat tataagacga ctcctccggt tttggattcc   540
gacggtagtt ttttcttgta tagtaagctt actgtagaca agtcaagatg gcaacaagt    600
aatgtgttct cttgctcagt tatgcatgaa gctcttcata accattacac gcaaaagagt   660
ctcagtctga gcccggtgg cggtagcgac agttggcagg aagaggtgat taagttgtgc    720
ggtcgcgagc tcgttcgggc ccaaattgca atctgcggaa aatctacggg cggagagggc   780
ggggtgagg agggtggggg tgaaggtggg cagctctata gcgcccttgc gaataaatgt    840
tgtcacgtcg gatgcacaaa gaggtccctc gccaggttct gc                      882

SEQ ID NO: 477         moltype = DNA   length = 885
FEATURE                Location/Qualifiers
source                 1..885
                       mol_type = other DNA
                       organism = synthetic construct
SEQUENCE: 477
gataagaccc acacttgccc cccttgccct gccccgaag cggccggagg tccttcagta     60
tttttgtttc caccgaaacc caaagatact ttgatgatat caagaactcc tgaagtcacc   120
tgcgtggtag ttgacgtatc tcatgaggat cccgaggtga agttcaattg gtacgtcgat   180
ggcgtcgagg ttcataacgc taagactaag ccgagggaag agcaatataa ttccacttat   240
agggtggtgt ccgtcttgac tgtttttgcac caggattggt tgaacgggaa agagtacaaa   300
tgtaaggtga gtaataaagc tttggctgct cccatcgaaa agacaataag caaggccaag   360
gggcaacctc gggagccgca ggtgtacacc cttcctccca gtagagacga actgacaaaa   420
aaccaggtgt ccctgacctg ccttgtgaag gggttttcac cgagcgacat agccggttgaa    480
tgggagagca acgggcaacc cgagaacaac tacaaaacta caccgcctgt cctggactcc   540
gatggaagct tcttcctcta ctccaaactg accgtggaca aaagcagatg gcaacaagga   600
aacgtattct catgctcagt aatgcacgaa gcattgcaca tcactacac ccaaaagtcc    660
ctctcactct cccctggtaa gggcggatca gactcatggc aagaggaggt aattaagttg   720
tgcgggaggg agctcgtccg cgcgcaaata gccatttgtg gcaagtccac tggagaggcc   780
gagggtggag gagagggtgg tggggagggc aggcaactct acagtgcgct cgccaataaa   840
tgctgccatg ttgggtgcac gaagcgcagt ctcgcacaat tctgc                    885

SEQ ID NO: 478         moltype = DNA   length = 885
FEATURE                Location/Qualifiers
source                 1..885
                       mol_type = other DNA
                       organism = synthetic construct
SEQUENCE: 478
gataagaccc acacgtgtcc tccatgtccg gcaccggagg ctgctggcgg gccttctgta    60
ttcctcttcc cacccaagcc aaaagacaca ttgatgatat caaggacgcc ggaagtcacc   120
tgtgttgttg tggacgtttc ccatgaagac ccagaggtaa aattcaattg gtatgtggac   180
ggcgtagagg ttcacaacgc caaaaccaaa ccccgagagg aacagtataa tagcacatat   240
cgagtagtat ctgttctcac agtgctccat caagactggc ttaatggtaa agagtataaa   300
tgcaaagttt ccaataaagc cctcgctgca ccgatcgaga agacaatcag taaagcgaag   360

```
ggccagcctc gggaaccgca ggtgtatact cttccaccct caagagacga gctcactaaa 420
aaccaagttt cattgacatg cctcgtcaaa ggtttctacc catcagacat cgcggtcgaa 480
tgggaaagta atgggcagcc ggaaaacaac tataaaacga cgccgcccgt cttggattct 540
gatggttcat ttttctttta ctctaaattg accgtcgata aaagtaggtg gcaacaagga 600
aatgttttt cctgctccgt cctgcatgaa gcgttgcaca gtcactatac ccagaagagt 660
ctttctttgt cacccggaaa aggcggttca gattcatggc aggaagaagt aattaaactc 720
tgtggccgcg agcttgttag ggcgcagata gccatatgtg gtaaaagcac cggaggaggt 780
gaaggcggag gcgaaggagg tggggaagga agacaattgt attctgcact tgcaaataaa 840
tgctgtcatg tggggtgcac gaaacgcagt cttgcacaat tttgt 885
```

SEQ ID NO: 479        moltype = DNA  length = 882
FEATURE               Location/Qualifiers
source                1..882
                       mol_type = other DNA
                       organism = synthetic construct
SEQUENCE: 479

```
gacaaaaccc atacctgccc cccttgccct gcaccagaag cggcgggagg acctagcgtt 60
tttctttttc ctccgaaacc gaaagatacc ctcatgatat caagaacacc tgaggttact 120
tgcgttgtcg tggacgtgag tcacgaagac cccgaggtga agttcaactg gtatgtagat 180
ggagtggagg tccataatgc aaaaacgaaa ccgagagaa aacaatacaa ctctacatat 240
cgagtcgtgt cagtactcac ggttttgcat caagattggc tgaacggtaa ggagtacaag 300
tgtaaggtta gcaacaaggc tctcgcggcg ccgatagaaa agactataag taaagcaaaa 360
ggccagccca gagaacctca gtttacact ctgcctccca gcagagatga actgactaaa 420
aatcaggttt cattgacctg tctcgtcaag ggtttttatc caagcgacat agcagttgaa 480
tgggaaagca acgtcaacc agaaaataat tacaaaacca ctccaccagt cttggactct 540
gacggatcct tctttctcta ttcaaaattg acggtagata aatctaggtg gcagcaaggc 600
aacgtcttct cttgtagcgt tatgcatgag gcgctgcaca accactacac acaaaagtct 660
cttagtttga gcccgggcgg cggaagcgac tcttggcaag aggaagtgat aaaactctgt 720
ggtcgagaat tggtacgcgc gcagatcgct atctgcggca agtccacagg gggaggggaa 780
ggtggcgggg aaggtggtgg cgagggcagg cagttgtata gtgcacttgc caacaagtgc 840
tgccatgtgg ggtcaccaa gcgcagttg gcacggttct gc 882
```

SEQ ID NO: 480        moltype = DNA  length = 882
FEATURE               Location/Qualifiers
source                1..882
                       mol_type = other DNA
                       organism = synthetic construct
SEQUENCE: 480

```
gataaaactc acacttgtcc cccgtgtccg gcaccagaag ccgcaggagg gccatctgtc 60
tttcttttc ccccaaaacc caaggataca ctgatgatct cccgcactcc cgaagttact 120
tgtgtcgtag tagacgtttc tcacgaggac ccagaggtga aattcaattg gtatgttgac 180
ggagtagagg tgcataatgc caagacaaag ccccgagagg aacaatacaa ttcaacctac 240
agagtagtgt ccgttcttac ggttctccat caggattggc tcaacggtaa ggaatataag 300
tgcaaggtaa gcaacaaagc gctggccgca cccattgaga aaaccatttc aaaagctaaa 360
ggccaacccc gcgaaccaca agtttatact ctcccccccaa gtcgcgatga acttacaaaa 420
aatcaagtct cattgacgtg cttggtcaaa ggcttctacc cgagcgatat cgctgttgaa 480
tgggagtcta atggaacaac ggaaaataac tataaaacta caccccccagt cctcgattca 540
gacggcagct tcttcctgta ttcaaaactg acggttgaca aatcacgctg gcaacagggt 600
aacgtttttt cctgtagcgt tcttcatgaa gccttgcaca gtcactacac ccagaagtcc 660
cttagcttgt cacctggcgg gggttcagac tcttggcagg aggaggtaat caaactgtgc 720
ggaagagaac tggtgagggc tcagattgca atttgtggag cacgcggg tggcggtgaa 780
ggaggtggcg agggcggagg agagggggagg caactctaca gtgcgttggc taataaatgc 840
tgtcacgtcg gctgtactaa gagaagcctc gccagatttt gc 882
```

SEQ ID NO: 481        moltype = DNA  length = 882
FEATURE               Location/Qualifiers
source                1..882
                       mol_type = other DNA
                       organism = synthetic construct
SEQUENCE: 481

```
gacaagacgc atacttgccc tccgtgccct gcaccagaag ccgctggtgg cccatctgtg 60
tttttgttcc cccctaagcc aaaagacaca ttgatgattt cacgaactcc agaagtgact 120
tgcgtagttg ttgacgtatc acacgaagac cccgaggtta aatttaattg gtatgtgac 180
ggggtcgagg tgcataacgc caaaaccaaa ccccggagag aacaatataa ctctacgtta 240
cgggtcgtat ctgtgttgac cgtccttcac caagattggt tgaacggcaa ggaatataag 300
tgtaaagtgt ctaataaagc attggctgcc ccgatagaaa agacgatctc taagccaag 360
ggccaaccca gagagcctca gtatatact ctccccaccga gtcgagatga gctcactaag 420
aaccaggtgt cactcacgtg tctggttaaa ggatttttacc ctagtgatat agccgtcgag 480
tgggaatcaa atgggcagcc ggagaataac tataagacca cgcctccagt tctcgattcc 540
gatggtagct ttttccttta ctctaaactt acggtcgaca agtccaggtg gcaacagggc 600
aatgtatttt cttgctccgt catgcacgag gctttgcaca accattacac gcaaaagtca 660
ctgtccctgt ctcctggagg cggttctgac agttggcagg aggaggtaat caaattgtgt 720
gggcgggagt tggttagggc gcaaattgct atttgcggca aaagtactgg ggcggtgaa 780
ggcggaggcg agggaggagg agaaggtcga caactctatt ctgccttggc gaacaaatgc 840
tgtcacgtcg gctgtacgaa acggtctttg gcccagtttt gt 882
```

SEQ ID NO: 482        moltype = DNA  length = 882
FEATURE               Location/Qualifiers
source                1..882

```
                     mol_type = other DNA
                     organism = synthetic construct
SEQUENCE: 482
gataagacac acacttgtcc gccatgccct gcgccggaag cggcgggagg accgtccgtt    60
ttcctgttcc ctcccaaacc caaagacacg ttgatgatta gtcgcacgcc agaagttacg   120
tgcgttgtcg tagatgtatc ccacgaagac cccgaggtga agttcaattg gtatgtagat   180
ggggtggagg tccataacgc taagaccaaa ccacgcgagg aacaatataa ttctacgtac   240
cgcgtagtga gcgttctcac agttcttcac caggattggc ttaacggcaa ggagtataag   300
tgtaaggtgt ctaataaggc cttggctgcc ccgatcgaaa aaacgataag taaagcaaag   360
ggtcaaccta gagaacccca agtgtacact ctcccgccat cacgggatga attgactaag   420
aaccaagtgt cactcacgtg tcttgtaaag ggcttctacc catccgatat agccgttgag   480
tgggaatcca atggtcagcc agagaacaac tataagacaa ctccgcccgt acttgatagt   540
gacggttcct ttttccttta cagtaaattg acggtagata agtctcgctg gcagcaagga   600
aacgtctttt cttgttcagt gcttcatgag gcgcttcact cacactatac tcagaagagt   660
ttgagtttgt ctccaggtgg aggcagcgac tcatggcaag aggaagtaat caaactgtgt   720
ggtcgcgaat tggtacgagc acagatcgcg atctgcggga aatcaacagg tggcggcgaa   780
ggcggcgggg aaggcggcgg cgaaggtagg caactttact cagcccttgc gaacaaatgt   840
tgccacgtag gctgtactaa gagaagtctc gcccagtttt gc                      882

SEQ ID NO: 483       moltype = DNA  length = 885
FEATURE              Location/Qualifiers
source               1..885
                     mol_type = other DNA
                     organism = synthetic construct
SEQUENCE: 483
gacaagactc atacctgccc cccttgtcca gcaccagaag cagctggcgg gccaagcgtg    60
ttcctgtttc cacctaagcc caaagatacg ttgatgatca gccgcacccc ggaagtaacc   120
tgtgtagtag tagatgtgtc ccacgaagac cccgaagtaa agtttaattg gtacgtcgat   180
ggtgtcgaag tacataacgc taaaacgaag ccccgagaag agcagtacaa cagtacttac   240
agagtagttt ctgttcttac agtgctgcat caggattggc tgaacgggaa ggagtataaa   300
tgtaaagtct caaacaaggc acttgcggca ccaatagaaa agacaatatc taaggccaaa   360
gggcagccta gagagccaca agtatatacg ctgcccccca gcagggacga gctgacaaag   420
aaccaagtgt cactgacctg ccttgttaag ggcttctatc cgagtgatat tgctgttgaa   480
tgggaaagta acggacagcc ggagaacaac tataaaacta ctccaccegt gttggatagt   540
gacggtagct ttttctgta ctccaagttg acggtagaca aaagtcggtg gcagcagggg   600
aacgtatttt cttgttctgt catgcacgaa gctcttcaca atcactatac gcagaagtcc   660
ctctctctct ctcctgggaa gggtggttcc gacagctggc aggaggaggt cattaaactg   720
tgtggtagag agctggtacg ggctcaaatt gcaatttgtg gtaagagtac tggcggtggc   780
gaggaagggg gtgggagga gggcggaggt aggcagctct actctgctct cgccaacaag   840
tgttgtcacg tcgggtgtac taaaagatca cttgcccgct tttgt                   885

SEQ ID NO: 484       moltype = DNA  length = 885
FEATURE              Location/Qualifiers
source               1..885
                     mol_type = other DNA
                     organism = synthetic construct
SEQUENCE: 484
gacaaaacac atacatgccc gccgtgtccg gcgcctgaag cagcaggagg ccccagtgta    60
ttcctttttcc ctccaaagcc aaaagatacg ttgatgatat ctaggacacc tgaggttacc   120
tgcgtcgtag tggacgtatc ccacgaagac ccagaagtca agtttaactg gtatgtggac   180
ggagtgggag tacacaatgc aaagacaaag ccgcgagagg aacaatataa ttccacctat   240
agagtcgtgt cagtccttac ggtcttgcac caggactggc tcaatggtaa ggagtataag   300
tgcaaagtat caaacaaagc tctcgcagcg cccatcgaaa agaccatcag caaagctaag   360
ggccagccaa gagagcctca agtgtacacg ttgccgcctt caaggacgga gctcactaaa   420
aatcaggtat cacttacgtg tcttgtcaaa gggttttatc cttccgacat cgcggttgaa   480
tgggagagca atggacagcc ggagaataat tataaaacga cgccgccggt ccttgacagc   540
gatggttcat ttttcctta ctcaaagctg acggttgata agtctaggtg gcagcagggg   600
aacgtctttt cctgtagtgt acttcatgag gcgctccatt ctcattacac tcagaagtca   660
ctgagccttt cacccggcaa aggtggatca gactcctggc aagaagaggt aatcaaactc   720
tgtgtgaggg aactcgttcg agcccagatt gcaatctggc ggaaaagcac aggcggaggg   780
gaagaagggg gtggcgaaga aggtggggc aggcagctct attcagctct gccaacaaa    840
tgctgtcatg taggctgcac aaagcgatca ctggcgagat tctgt                   885

SEQ ID NO: 485       moltype = DNA  length = 885
FEATURE              Location/Qualifiers
source               1..885
                     mol_type = other DNA
                     organism = synthetic construct
SEQUENCE: 485
gataaaactc atacttgccc accctgcccg gctcccgagg cagcaggtgg accctcagta    60
tttttgttcc ctccgaaacc taaagataca cttatgatta gccggacccc tgaggtaacg   120
tgtgtggtgg ttgacgtaag tcatgaagat ccagaagtaa agtttaactg gtacgtagac   180
ggtgtggagg tacataatgc gaagacaaaa ccacgagagg aacagtataa ctctacctac   240
cgcgtagtaa gcgtacttac tgtgctccac caagactggc ttaacgggaa agagtataag   300
tgtaaagtca gtaataaagc actgccgcc ccgatcgaaa aaacaatcag caaggccaaa   360
ggacaaccaa gggagcctca ggtctatact cttcccccga gtaggatga gcttaccaag   420
aaccaggtgt ctctgacatg ccttgtcaag ggatttacc cgagtgacat agccgtgaaa   480
tgggagtcaa acggccaacc tgaaaacaac tataagacca cgcctccgt actcgactca   540
gatggaagct ttttcctcta tagcaagctg accgtcgaca aaagtaggtg gcaacaggga   600
```

```
aacgtcttta gttgttccgt catgcacgaa gctttgcata accattacac ccagaagagt   660
ctttcccttt ccctggcaa gggggctcc gactcctggc aagaggaagt aatcaaactg   720
tgtgggcgcg agcttgtccg cgcgcaaata gccatttgcg gaaaaagtac tggaggagga   780
gaggaaggcg gcggcgagga aggtgggggc aggcagctgt acagtgcctt ggctaacaag   840
tgctgccatg tcggctgtac gaaaaggtct cttgctcaat tctgt                  885

SEQ ID NO: 486         moltype = DNA  length = 885
FEATURE                Location/Qualifiers
source                 1..885
                       mol_type = other DNA
                       organism = synthetic construct
SEQUENCE: 486
gataagacac atacctgtcc accctgccca gcacctgaag ctgcaggcgg ccccagcgta   60
ttcctgtttc ctccgaagcc gaaagacaca cttatgattt cccggacgcc tgaggtaact   120
tgcgtcgtag tagatgtgtc tcacgaagac cccgaggtga aattcaactg gtacgttgat   180
ggtgtggaag ttcataatgc gaaaactaaa ccacgagagg agcaatataa ctcaacttat   240
agagttgtga gcgtcttgac ggtactgcac caggactggc tgaatggcaa agagtacaaa   300
tgcaaagtct caaataaggc gttggcggct cccatagaga aaactatcag caaagccaag   360
ggtcaacctc gggagccaca agtgtatact cttccgccta gtcgcgacga gctcacaaag   420
aatcaggtga gtcttacttg tttggttaag ggtttctacc ccagtgacat tgcggtcgag   480
tgggaaagta acgacagcc tgaaacaac tataaaacaa cgcctccagt actcgattca   540
gatggttcat tcttctttta ttccaaactc acagtcgaca agagtagatg gcaacaaggg   600
aacgtgtttta gctgtagcgt actccatgag gcactccact ctcactatac ccaaaagtct   660
ctcagcttgt cacccggaaa aggcggttct gacagttggc aagaggaagt gattaaattg   720
tgtgggcgga aacttgtgag ggctcaaatc gcgatttgcg gcaagtccac tggtggcggc   780
gaggaaggag gaggtgaaga aggaggaggt aggcaactgt attcagcgtt ggcgaataaa   840
tgctgccatg ttggatgtac taaacggagc cttgctcagt tctgc                  885

SEQ ID NO: 487         moltype = DNA  length = 882
FEATURE                Location/Qualifiers
source                 1..882
                       mol_type = other DNA
                       organism = synthetic construct
SEQUENCE: 487
gataaaacgc atacttgccc tccttgcccg gcacctgaag ctgccggagg tccttccgtg   60
ttcctgttcc caccttaagcc aaaagacaca cttatgattt ctcgcacacc agaagtaacg   120
tgcgtcgtag ttgacgtctc ccatgaagac ccggaggtaa aatttaattg gtacgtcgac   180
ggggtagaag ttcataacgc aaagactaaa ccacgagaag agcaataaca ctctacatac   240
agagtagtaa gcgttctcac cgttcttcat caagattggc tcaacggaaa ggagtataag   300
tgtaaggtgt ccaataaagc gttggccgca ccatcgaaa agaccataag caaagccaaa   360
ggccaacccc gcgaaccgca ggtgtacaca cttccccgt ccaggatga attgacaaaa   420
aaccaagttt ccctcacgtg tctcgtcaag ggattctacc cgagtgatat cgcagttgaa   480
tgggaaagca atggtcagcc cgagaataac tacaagacta ctccccctgt gttggactca   540
gacggctcat tcttcctcta cagtaagttg actgtggaca aaagtcggtg gcagcaaggc   600
aatgtcttca gttgtagtgt aatgcatgaa gcactccaca atcattacac ccaaaaatcc   660
ctgagcctgt ccccggcgg aggttcagat tcatggcagg aggaagttat aaaactgtgc   720
gggcgcgagt tggtgagggc gcagatcgca atctgtgaa agagtaccgg aggtggcgaa   780
gagggtggtg gagaagaggg aggaggtcga caactgtatt ccgcgctcgc gaacaagtgt   840
tgccacgttg gctgcaccaa acgaagcctg gctcgatttt gc                     882

SEQ ID NO: 488         moltype = DNA  length = 882
FEATURE                Location/Qualifiers
source                 1..882
                       mol_type = other DNA
                       organism = synthetic construct
SEQUENCE: 488
gacaagacac acacttgtcc accttgcccg gctcccgagg cggcaggagg accaagcgtt   60
tttctgttcc ctcccaaacc aaaggatacg cttatgatct ctcgaacgcc ggaagttact   120
tgcgtagtag ttgatgtctc ccatgaagat cccgaagtga agttcaactg gtatgtagat   180
ggtgtggaag ttcataacgc gaaaaccaaa ccacgcgaag aacagtataa cagtacttat   240
cgggttgttt cagtactcac ggtgctccat caagactggc ttaatggaaa ggagtataaa   300
tgtaaggtaa gtaacaaggc attggcggct cccatcgaga agacaatctc caaagcaaaa   360
gggcaaccac gggagcctca ggtgtatacg ttgccgccca gcagagatga acttactaag   420
aatcaggtga gtctcacttg tctcgtcaag agccttcagc ccagcgatat agccgtagaa   480
tgggagagta acgtcagcc ggagaacaac tacaaaacaa ccccgcctgt tttggactcc   540
gatgggagtt ttttctctca gcaaaactc acggtagaca aaagcaggtg gcagcagggc   600
aatgtttttca gttgctctgt tctccacgaa gccctccact cccactatac tcagaagtct   660
ctgagtctct caccaggggg aggtagcgat agctggcagg aggaagtgat caagttgtgc   720
gggcgcgaac tcgtgcgggc acaaattgct atatgcggta aaagtaccgg aggtggcgag   780
gagggtggag gtgaagaagg cggtggtaga caattgtata gtgcgctcgc caacaagtgt   840
tgtcatgtcg ggtgtacgaa acggtccttg gcgcggtttt gc                     882

SEQ ID NO: 489         moltype = DNA  length = 882
FEATURE                Location/Qualifiers
source                 1..882
                       mol_type = other DNA
                       organism = synthetic construct
SEQUENCE: 489
gacaagacac atacttgtcc accatgtccc gccccagaag ctgcgggagg accatcagtt   60
```

```
ttttgttcc ccccgaaacc gaaggatacc ctcatgataa gtcgaacgcc cgaagtcact    120
tgcgtggtgg ttgatgttag ccacgaggac ccagaagtga agttcaactg gtacgtggac    180
ggggtcgaag ttcataatgc gaaaacaaag cctcgcgagg aacagtacaa ctctacatac    240
agggttgtgt ctgttttgac agtcttgcac caagattggc tcaacgggaa ggaatataag    300
tgtaaggtaa gcaataaagc actggcggcc ccgatcgaaa aaacgatatc caaggccaaa    360
ggccagcccc gagagcctca ggtatatact ctgccgccaa gccgggatga actgactaaa    420
aaccaggtct ctttgacttg tcttgtcaag ggatttttacc caagtgacat tgcggtagag    480
tgggaaagca acggtcaacc agaaaacaat tacaagacga caccgccggt actcgactca    540
gatggatcct ttttcctgta tagcaagctg acagtgcaca agtccggtg gcagcaaggg    600
aacgtatttt catgcagcgt gatgcatgag gctcttcaca accattacac acagaaaagt    660
ctgtcattga gccctggcgg cgggagcgat tcttggcaag aagaagttat aaaactttgc    720
ggtcgagagc tggttcgggc acaaattgct atctgcggaa aatctacagg aggaggcgag    780
gagggagggg gcgaagaagg cggggggaga cagttgtaca gtgcgctcgc taacaagtgt    840
tgccacgtcg gttgcacaaa gagatccctg gctcaattct gt                      882

SEQ ID NO: 490           moltype = DNA  length = 882
FEATURE                  Location/Qualifiers
source                   1..882
                         mol_type = other DNA
                         organism = synthetic construct
SEQUENCE: 490
gataaaactc acacctgtcc cccgtgtccc gcaccagaag cggccggtgg tccctccgtt     60
tttctcttcc ctcctaaacc taaggacaca cttatgatta gcagaactcc agaagttacg    120
tgcgtagtcg ttgacgttag tcatgaagat cctgaggtta agttcaactg gtacgtagac    180
ggagtagagg tccacaacgc caagacgaaa ccccgagaag agcagtataa ttctacctat    240
cgagttgttt cagtattgac ggtgcttcac caagattggc tgaatggcaa aggatataag    300
tgcaaggtaa gcaacaaagc actcgcggct cctatcgaga aaactatttc caaagctaag    360
ggccagcctc gcgaaccaca agtctatacc ctgccaccga gtcgggacga actcaccaag    420
aaccaagtgt ctcttacttg cctcgttaaa ggttttatc ccagcgacat agccgtcgaa    480
tgggagtcca atggccaacc tgagaacaac tataaaacta ccctcctgt acttgatagc    540
gacggaagtt ttttcctcta ttcaaaactc acagttgata agtctcgatg gcaacagggc    600
aacgtcttct cttgcagtgt gttgcatgaa gctctgcact tcattacac acagaagagt    660
ttgtctctca gtcaggtgg cggctcagat agctggcagg aagaagtaat caagttgtgc    720
ggcagggaac tggtaagggc acagatagcc atttgtggaa aatctacggg tggcggtgag    780
gaaggcggcg gagaagaagg gggaggtcgg cagctgtata gtgcactcgc aaacaagtgc    840
tgccatgtcg ggtgcaccaa gcgatccctt gcccagttt gc                       882

SEQ ID NO: 491           moltype = DNA  length = 885
FEATURE                  Location/Qualifiers
source                   1..885
                         mol_type = other DNA
                         organism = synthetic construct
SEQUENCE: 491
gataagacgc acacatgccc accctgtcct gcgcctgaag ccgcgggggg acccagcgtt     60
tttctcttcc cgccgaaacc gaaagacaca cttatgatca gccggactcc cgaggttacc    120
tgcgtggtgg tagatgtatc tcacgaggat cccgaggtca aattcaactg gtacgttgat    180
ggggttgaag ttcataatgc caaaacgaag ccaagagaag agcagtataa ctccacatat    240
agagttgttt ccgtcttgac tgttcttcac caagattggc tgaatgggaa ggagtacaaa    300
tgtaaagtta gcaacaaggc actcgccgct cccattgaaa aaactataag caaagctaag    360
ggccaaccgc gcgaaccaca ggtctacacg ttgccgccct ctaggacgga actcacgaag    420
aatcgtttt cccttacctg cctcgttaaa ggattctacc cctctgacat agccggttga    480
tgggagagca acggtcagcc tgagaacaac tacaaaacga cgcctccggt gttggattcc    540
gacggtagtt ttttcctcta tagtaagctg acagtggata aatctcggtg gcagcaaggg    600
aatgtattct cctgttcagt cctgcatgaa gccctccact cccattatac acagaaatct    660
ctttctctga gtcccggtaa aggtgggagt gactcttggc aggaagaggt aattaagttg    720
tgtggaaggg agctggtaag agcacagatt gccatctgtg gcaaatccac gggcggcgaa    780
ggtgaggggg gtgaggggga agggggtcc agacaactgt attctgctct ggcgaataag    840
tgttgccatg tagggtgcac taaacggtcc ttggcgcagt tctgt                    885

SEQ ID NO: 492           moltype = DNA  length = 882
FEATURE                  Location/Qualifiers
source                   1..882
                         mol_type = other DNA
                         organism = synthetic construct
SEQUENCE: 492
gataaaactc atacgtgccc accttgcccc gcaccggagg ctgctggagg accctctgtc     60
ttcctgttcc cgccgaagcc taagacaca ttgatgatca gtcgaacacc ggaagtcacc    120
tgtgtagtgg ttgatgtgag ccatgaggac cctgaagtaa aatttaactg gtatgttgat    180
ggcgtagaag tacacaacgc gaagactaaa ccaagggaag agcaatacaa ctctacctat    240
agggtcgtta gcgtactgac tgtgcttcac caagactggc ttaacgggaa ggagtacaag    300
tgcaaagtga gcaataaggc cctcgccgcg cctatcgaga aaccatttc caaagccaag    360
ggtcaaccaa gggagcctca ggtttacacc ctgccccctt caaggatga gttgacaaaa    420
aaccaggtaa gtcgacgtg tctcgttaag ggattctacc cgtcagatat cgcggtagag    480
tgggagagca acggtcagcc agaaaataat tacaaaacga cacctccagt tttggactct    540
gatgggagtt ttttctctta ttctaagttg acagtggata agtcacgctg gcaacagggg    600
aacgtattta gctgctcagt acttcatgaa gcgttgcatt tcactacac acagaagagc    660
ctctccttga gtcccggagg tggctctgat tcttggcagg aggaggtaat aaaactttgt    720
ggtagagaac tggttcgcgc tcagatagct atttgtggaa aatccactgg cggtgaaggt    780
gaaggtggag aaggagaggg cggaagccgg cagttgtact ctgccctggc taataagtgc    840
```

```
tgtcacgtgg gctgcactaa gcggagcttg gcaagatttt gc                         882

SEQ ID NO: 493          moltype = DNA   length = 882
FEATURE                 Location/Qualifiers
source                  1..882
                        mol_type = other DNA
                        organism = synthetic construct
SEQUENCE: 493
gataaaactc atacctgtcc accttgtcct gcgcctgagg cagctggagg gcctagcgtg       60
ttcctgttcc cccccaaacc caaagacacg ctcatgatta gccgaacccc tgaagtgacc      120
tgcgttgttg tggacgtaag ccacgaagac cccgaagtta agtttaattg gtacgtcgac      180
ggtgttgagg ttcataacgc gaagactaag ccgagagagg agcaatataa cagcacctac      240
cgcgtagtct cagttcttac cgtgctccac caggactggc ttaacgggaa ggaatacaaa      300
tgcaaagttt ccaacaaagc cttggcagcc ccaatagaaa agacaatatc taaggcgaaa      360
ggccaaccgc gggaaccgca gtttataccc ctcccaccga gcagggatga gctgacaaaa      420
aatcaggttt ccctcacttg tctggtcaag ggatttttatc cttcagacat agccgttgaa     480
tgggagagta atgggcagcc ggagaataat tacaagacca cccccccggt gttggacagc      540
gacggttcct tctttctcta ttctaaactt accgtcgaca aatcacggtg gcaacaagga      600
aatgtattct catgcagtgt attgcacgaa gctctgcact tcattacac ccaaaaatcc       660
ctctctctca gccctggcgg tggatctgat tcttggcagg aagaggtgat taaactgtgt      720
gggcgagagc ttgtccgagc tcagatcgct atttgtggca agagtaccgg aggcgagggt      780
gagggaggcg aaggcgaggg cggaagccgg caactctata gcgcactcgc taataaatgt      840
tgtcatgtcg gctgcacgaa gcgctcactg gcgcagttct gc                        882

SEQ ID NO: 494          moltype = DNA   length = 36
FEATURE                 Location/Qualifiers
source                  1..36
                        mol_type = other DNA
                        organism = synthetic construct
SEQUENCE: 494
acgggaccga tccagcctcc ggactctaga gccacc                                 36

SEQ ID NO: 495          moltype = DNA   length = 36
FEATURE                 Location/Qualifiers
source                  1..36
                        mol_type = other DNA
                        organism = synthetic construct
SEQUENCE: 495
tgataaaccg gttagtaatg agtttgatat ctcgac                                 36

SEQ ID NO: 496          moltype = AA    length = 295
FEATURE                 Location/Qualifiers
source                  1..295
                        mol_type = protein
                        organism = synthetic construct
SEQUENCE: 496
DKTHTCPPCP APEAAGGPSV FLFPPKPKDT LMISRTPEVT CVVVDVSHED PEVKFNWYVD        60
GVEVHNAKTK PREEQYNSTY RVVSVLTVLH QDWLNGKEYK CKVSNKALAA PIEKTISKAK      120
GQPREPQVYT LPPSRDELTK NQVSLTCLVK GFYPSDIAVE WESNGQPENN YKTTPPVLDS      180
DGSFFLYSKL TVDKSRWQQG NVFSCSVLHE ALHSHYTQKS LSLSPGKGGS DSWKEEVIKL      240
CGRELVRAQI AICGKSTASD AAGANANAGA RQLYSALANK CCHVGCTKRS LARFC           295

SEQ ID NO: 497          moltype = AA    length = 309
FEATURE                 Location/Qualifiers
source                  1..309
                        mol_type = protein
                        organism = synthetic construct
SEQUENCE: 497
DKTHTCPPCP APELLGGPSV FLFPPKPKDT LMISRTPEVT CVVVDVSHED PEVKFNWYVD        60
GVEVHNAKTK PREEQYNSTY RVVSVLTVLH QDWLNGKEYK CKVSNKALPA PIEKTISKAK      120
GQPREPQVYT LPPSRDELTK NQVSLTCLVK GFYPSDIAVE WESNGQPENN YKTTPPVLDS      180
DGSFFLYSKL TVDKSRWQQG NVFSCSVMHE ALHNHYTQKS LSLSPGKGGG GSGGGGSGGG      240
GSQLYSALAN KCCHVGCTKR SLARFCGGGG SGGGGSGGGG SSWMEEVIKL CGRELVRAQI      300
AICGMSTWS                                                              309

SEQ ID NO: 498          moltype = AA    length = 329
FEATURE                 Location/Qualifiers
source                  1..329
                        mol_type = protein
                        organism = synthetic construct
SEQUENCE: 498
METDTLLLWV LLLWVPGSTG DKTHTCPPCP APELLGGPSV FLFPPKPKDT LMISRTPEVT        60
CVVVDVSHED PEVKFNWYVD GVEVHNAKTK PREEQYNSTY RVVSVLTVLH QDWLNGKEYK      120
CKVSNKALPA PIEKTISKAK GQPREPQVYT LPPSRDELTK NQVSLTCLVK GFYPSDIAVE      180
WESNGQPENN YKTTPPVLDS DGSFFLYSKL TVDKSRWQQG NVFSCSVMHE ALHNHYTQKS      240
LSLSPGKGGG GSGGGGSGGG GSQLYSALAN KCCHVGCTKR SLARFCGGGG SGGGGSGGGG      300
SSWMEEVIKL CGRELVRAQI AICGMSTWS                                        329

SEQ ID NO: 499          moltype = DNA   length = 927
```

```
FEATURE                  Location/Qualifiers
source                   1..927
                         mol_type = other DNA
                         organism = synthetic construct
SEQUENCE: 499
gataaaaccc atacgtgtcc tccatgccca gctcccgagc tgctcggtgg tccttcagtg    60
ttcctcttcc ccccaaagcc gaaggacacg ctcatgatta gtcgaacgcc agaggtgaca   120
tgtgtggtcg ttgatgtttc ccatgaggat ccggaagtta agttcaactg gtacgtagat   180
ggcgtggagg ttcacaatgc aaaaaccaag ccccgcgagg agcagtataa ctcaacctac   240
agagtagtat ctgtgctcac ggtcttgcat caggattggt tgaacgggaa ggaatacaag   300
tgtaaagtaa gtaataaggc actgccggcc cccatagaaa aaactatcag caaagctaaa   360
ggtcagccgc gggagccaca gtttacacac cttcctccta gtagagacga gctgacgaag   420
aatcaagttt ctttgacttg tctcgtgaag ggattctacc caagcgatat agctgtgagag   480
tgggaaagca acggacaacc agaaaataac tacaagacta caccccccgt tctcgattct   540
gatggctcat tcttcttgta ctcaaaattg acagttgaca aatctcgatg gcagcagggt   600
aacgtattta gttgctctgt tatgcacgaa gcgttgcata accactacac acagaagtca   660
ttgtcactga gcccaggaaa aggtggtggc gggtccggcg gtgaggtag cggtggcggg   720
ggctcccagc tttatagtgc ccttgcaaac aaatgttgcc acgtcggatg tacgaagcgc   780
agtttggcga gattctgtgg agggggcgga tccggaggcg ggggtccggg aggaggaggt   840
agctcatgga tggaagaggt aataaaactg tgcggacgcg agcttgtcag ggcccaaatc   900
gcaatttgtg gcatgagcac atggagt                                      927

SEQ ID NO: 500           moltype = DNA   length = 987
FEATURE                  Location/Qualifiers
source                   1..987
                         mol_type = other DNA
                         organism = synthetic construct
SEQUENCE: 500
atggaaactg atacctgtt gttgtgggtc cttttgcttt gggttccagg cagcaccgga    60
gataaaaccc atacgtgtcc tccatgccca gctcccgagc tgctcggtgg tccttcagtg   120
ttcctcttcc ccccaaagcc gaaggacacg ctcatgatta gtcgaacgcc agaggtgaca   180
tgtgtggtcg ttgatgtttc ccatgaggat ccggaagtta agttcaactg gtacgtagat   240
ggcgtggagg ttcacaatgc aaaaaccaag ccccgcgagg agcagtataa ctcaacctac   300
agagtagtat ctgtgctcac ggtcttgcat caggattggt tgaacgggaa ggaatacaag   360
tgtaaagtaa gtaataaggc actgccggcc cccatagaaa aaactatcag caaagctaaa   420
ggtcagccgc gggagccaca gtttacacac cttcctccta gtagagacga gctgacgaag   480
aatcaagttt ctttgacttg tctcgtgaag ggattctacc caagcgatat agctgtgagag   540
tgggaaagca acggacaacc agaaaataac tacaagacta caccccccgt tctcgattct   600
gatggctcat tcttcttgta ctcaaaattg acagttgaca aatctcgatg gcagcagggt   660
aacgtattta gttgctctgt tatgcacgaa gcgttgcata accactacac acagaagtca   720
ttgtcactga gcccaggaaa aggtggtggc gggtccggcg gtgaggtag cggtggcggg   780
ggctcccagc tttatagtgc ccttgcaaac aaatgttgcc acgtcggatg tacgaagcgc   840
agtttggcga gattctgtgg agggggcgga tccggaggcg ggggtccggg aggaggaggt   900
agctcatgga tggaagaggt aataaaactg tgcggacgcg agcttgtcag ggcccaaatc   960
gcaatttgtg gcatgagcac atggagt                                      987

SEQ ID NO: 501           moltype = AA   length = 185
FEATURE                  Location/Qualifiers
source                   1..185
                         mol_type = protein
                         organism = synthetic construct
SEQUENCE: 501
MPRLFFFHLL GVCLLLNQFS RAVADSWMEE VIKLCGRELV RAQIAICGMS TWSKRSLSQE    60
DAPQTPRPVA EIVPSFINKD TETINMMSEF VANLPQELKL TLSEMQPALP QLQQHVPVLK   120
DSSLLFEEFK KLIRNRQSEA ADSSPSELKY LGLDTHSRKK RQLYSALANK CCHVGCTKRS   180
LARFC                                                              185

SEQ ID NO: 502           moltype = AA   length = 15
FEATURE                  Location/Qualifiers
source                   1..15
                         mol_type = protein
                         organism = synthetic construct
SEQUENCE: 502
KLCGRELVRA QIAIC                                                    15

SEQ ID NO: 503           moltype = AA   length = 16
FEATURE                  Location/Qualifiers
source                   1..16
                         mol_type = protein
                         organism = synthetic construct
SEQUENCE: 503
KCCHVGCTKR SLARFC                                                   16

SEQ ID NO: 504           moltype = AA   length = 16
FEATURE                  Location/Qualifiers
source                   1..16
                         mol_type = protein
                         organism = synthetic construct
SEQUENCE: 504
```

```
KCCHVGCTKR SLAQFC                                                         16

SEQ ID NO: 505           moltype = AA   length = 15
FEATURE                  Location/Qualifiers
source                   1..15
                         mol_type = protein
                         organism = synthetic construct
VARIANT                  1
                         note = K, Q, D, E, L, I or Y
SEQUENCE: 505
XLCGRELVRA QIAIC                                                          15

SEQ ID NO: 506           moltype = AA   length = 16
FEATURE                  Location/Qualifiers
source                   1..16
                         mol_type = protein
                         organism = synthetic construct
VARIANT                  1
                         note = K, Q, D, E, L, I, or Y
VARIANT                  4
                         note = any amino acid except for M, W, and C
VARIANT                  9
                         note = K, Q, D, E, L, I, or Y
VARIANT                  10
                         note = Q, D, E, L, I, Y or R
VARIANT                  14
                         note = R, Q, E, D, N, S, or T
SEQUENCE: 506
XCCXVGCTXX SLAXFC                                                         16

SEQ ID NO: 507           moltype = AA   length = 24
FEATURE                  Location/Qualifiers
source                   1..24
                         mol_type = protein
                         organism = synthetic construct
SEQUENCE: 507
QLYSALANKC CQVGCTKQSL AQFC                                                24

SEQ ID NO: 508           moltype = AA   length = 65
FEATURE                  Location/Qualifiers
source                   1..65
                         mol_type = protein
                         organism = synthetic construct
SEQUENCE: 508
DSYQEEVIKL CGRELVRAQI AICGKSTGGE GSGGEGEGGG RQLYSALANK CCHVGCTKRS         60
LAQFC                                                                     65

SEQ ID NO: 509           moltype = AA   length = 65
FEATURE                  Location/Qualifiers
source                   1..65
                         mol_type = protein
                         organism = synthetic construct
SEQUENCE: 509
DSYQEEVIKL CGRELVRAQI AICGKSTGGE GSGGEGEGGG RQLYSALANK CCQVGCTKRS         60
LAQFC                                                                     65

SEQ ID NO: 510           moltype = AA   length = 65
FEATURE                  Location/Qualifiers
source                   1..65
                         mol_type = protein
                         organism = synthetic construct
SEQUENCE: 510
DSYQEEVIKL CGRELVRAQI AICGKSTGGE GSGGEGEGGG RQLYSALANK CCHVGCTKQS         60
LAQFC                                                                     65

SEQ ID NO: 511           moltype = AA   length = 65
FEATURE                  Location/Qualifiers
source                   1..65
                         mol_type = protein
                         organism = synthetic construct
SEQUENCE: 511
DSYQEEVIKL CGRELVRAQI AICGKSTGGE GSGGEGEGGG RQLYSALANK CCQVGCTKQS         60
LAQFC                                                                     65

SEQ ID NO: 512           moltype = AA   length = 65
FEATURE                  Location/Qualifiers
source                   1..65
                         mol_type = protein
                         organism = synthetic construct
```

```
SEQUENCE: 512
DSYQEEVIKL CGRELVRAQI AICGKSTGGE GSGGEGSGGG RQLYSALANK CCHVGCTKRS   60
LAQFC                                                              65

SEQ ID NO: 513          moltype = AA  length = 65
FEATURE                 Location/Qualifiers
source                  1..65
                        mol_type = protein
                        organism = synthetic construct
SEQUENCE: 513
DSYQEEVIKL CGRELVRAQI AICGKSTGGE GSGGEGSGGG RQLYSALANK CCQVGCTKRS   60
LAQFC                                                              65

SEQ ID NO: 514          moltype = AA  length = 65
FEATURE                 Location/Qualifiers
source                  1..65
                        mol_type = protein
                        organism = synthetic construct
SEQUENCE: 514
DSYQEEVIKL CGRELVRAQI AICGKSTGGE GSGGEGSGGG RQLYSALANK CCHVGCTKQS   60
LAQFC                                                              65

SEQ ID NO: 515          moltype = AA  length = 65
FEATURE                 Location/Qualifiers
source                  1..65
                        mol_type = protein
                        organism = synthetic construct
SEQUENCE: 515
DSYQEEVIKL CGRELVRAQI AICGKSTGGE GSGGEGSGGG RQLYSALANK CCQVGCTKQS   60
LAQFC                                                              65

SEQ ID NO: 516          moltype = AA  length = 295
FEATURE                 Location/Qualifiers
source                  1..295
                        mol_type = protein
                        organism = synthetic construct
SEQUENCE: 516
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGEGGG RQLYSALANK CCHVGCTKRS LAQFC       295

SEQ ID NO: 517          moltype = AA  length = 295
FEATURE                 Location/Qualifiers
source                  1..295
                        mol_type = protein
                        organism = synthetic construct
SEQUENCE: 517
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGEGGG RQLYSALANK CCQVGCTKRS LAQFC       295

SEQ ID NO: 518          moltype = AA  length = 295
FEATURE                 Location/Qualifiers
source                  1..295
                        mol_type = protein
                        organism = synthetic construct
SEQUENCE: 518
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGEGGG RQLYSALANK CCHVGCTKQS LAQFC       295

SEQ ID NO: 519          moltype = AA  length = 295
FEATURE                 Location/Qualifiers
source                  1..295
                        mol_type = protein
                        organism = synthetic construct
SEQUENCE: 519
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGEGGG RQLYSALANK CCQVGCTKQS LAQFC       295
```

```
SEQ ID NO: 520            moltype = AA  length = 295
FEATURE                   Location/Qualifiers
source                    1..295
                          mol_type = protein
                          organism = synthetic construct
SEQUENCE: 520
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGSGGG RQLYSALANK CCHVGCTKRS LAQFC       295

SEQ ID NO: 521            moltype = AA  length = 295
FEATURE                   Location/Qualifiers
source                    1..295
                          mol_type = protein
                          organism = synthetic construct
SEQUENCE: 521
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGSGGG RQLYSALANK CCQVGCTKRS LAQFC       295

SEQ ID NO: 522            moltype = AA  length = 295
FEATURE                   Location/Qualifiers
source                    1..295
                          mol_type = protein
                          organism = synthetic construct
SEQUENCE: 522
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGSGGG RQLYSALANK CCHVGCTKQS LAQFC       295

SEQ ID NO: 523            moltype = AA  length = 295
FEATURE                   Location/Qualifiers
source                    1..295
                          mol_type = protein
                          organism = synthetic construct
SEQUENCE: 523
DKTHTCPPCP APEAAGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSYQEEVIKL  240
CGRELVRAQI AICGKSTGGE GSGGEGSGGG RQLYSALANK CCQVGCTKQS LAQFC       295

SEQ ID NO: 524            moltype = AA  length = 315
FEATURE                   Location/Qualifiers
source                    1..315
                          mol_type = protein
                          organism = synthetic construct
SEQUENCE: 524
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSYQEEVIKL CGRELVRAQI AICGKSTGGE GSGGEGEGGG RQLYSALANK  300
CCHVGCTKRS LAQFC                                                   315

SEQ ID NO: 525            moltype = AA  length = 315
FEATURE                   Location/Qualifiers
source                    1..315
                          mol_type = protein
                          organism = synthetic construct
SEQUENCE: 525
METDTLLLWV LLLWVPGSTG DKTHTCPPCP APEAAGGPSV FLFPPKPKDT LMISRTPEVT   60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSYQEEVIKL CGRELVRAQI AICGKSTGGE GSGGEGEGGG RQLYSALANK  300
CCQVGCTKRS LAQFC                                                   315

SEQ ID NO: 526            moltype = AA  length = 315
FEATURE                   Location/Qualifiers
source                    1..315
                          mol_type = protein
                          organism = synthetic construct
```

```
SEQUENCE: 526
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGEGGG RQLYSALANK   300
CCHVGCTKQS LAQFC                                                   315

SEQ ID NO: 527          moltype = AA  length = 315
FEATURE                 Location/Qualifiers
source                  1..315
                        mol_type = protein
                        organism = synthetic construct
SEQUENCE: 527
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGEGGG RQLYSALANK   300
CCQVGCTKQS LAQFC                                                   315

SEQ ID NO: 528          moltype = AA  length = 315
FEATURE                 Location/Qualifiers
source                  1..315
                        mol_type = protein
                        organism = synthetic construct
SEQUENCE: 528
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGSGGG RQLYSALANK   300
CCHVGCTKRS LAQFC                                                   315

SEQ ID NO: 529          moltype = AA  length = 315
FEATURE                 Location/Qualifiers
source                  1..315
                        mol_type = protein
                        organism = synthetic construct
SEQUENCE: 529
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGSGGG RQLYSALANK   300
CCQVGCTKRS LAQFC                                                   315

SEQ ID NO: 530          moltype = AA  length = 315
FEATURE                 Location/Qualifiers
source                  1..315
                        mol_type = protein
                        organism = synthetic construct
SEQUENCE: 530
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGSGGG RQLYSALANK   300
CCHVGCTKQS LAQFC                                                   315

SEQ ID NO: 531          moltype = AA  length = 315
FEATURE                 Location/Qualifiers
source                  1..315
                        mol_type = protein
                        organism = synthetic construct
SEQUENCE: 531
METDTLLLWV LLLWVPGSTG DKTHTCPPCP APEAAGGPSV FLFPPKPKDT LMISRTPEVT    60
CVVVDVSHED PEVKFNWYVD GVEVHNAKTK PREEQYNSTY RVVSVLTVLH QDWLNGKEYK   120
CKVSNKALAA PIEKTISKAK GQPREPQVYT LPPSRDELTK NQVSLTCLVK GFYPSDIAVE   180
WESNGQPENN YKTTPPVLDS DGSFFLYSKL TVDKSRWQQG NVFSCSVLHE ALHSHYTQKS   240
LSLSPGKGGS DSYQEEVIKL CGRELVRAQI AICGKSTGGE GSGGEGSGGG RQLYSALANK   300
CCQVGCTKQS LAQFC                                                   315

SEQ ID NO: 532          moltype = DNA  length = 885
FEATURE                 Location/Qualifiers
source                  1..885
                        mol_type = other DNA
                        organism = synthetic construct
SEQUENCE: 532
```

```
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatacc aagaagaagt cattaaactt   720
tgtggacggg agctggttag gcacagatt gctatttgtg gtaagtctac gggaggagaa     780
ggctctggag gcgaaggaga aggggcgga aggcagcttt actctgctct ggctaacaag     840
tgttgtcacg ttgggtgtac caagcggtcc cttgcgcaat tctgc                    885

SEQ ID NO: 533          moltype = DNA  length = 885
FEATURE                 Location/Qualifiers
source                  1..885
                        mol_type = other DNA
                        organism = synthetic construct
SEQUENCE: 533
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatacc aagaagaagt cattaaactt   720
tgtggacggg agctggttag gcacagatt gctatttgtg gtaagtctac gggaggagaa     780
ggctctggag gcgaaggaga aggggcgga aggcagcttt actctgctct ggctaacaag     840
tgttgtcaag ttgggtgtac caagcggtcc cttgcgcaat tctgc                    885

SEQ ID NO: 534          moltype = DNA  length = 885
FEATURE                 Location/Qualifiers
source                  1..885
                        mol_type = other DNA
                        organism = synthetic construct
SEQUENCE: 534
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatacc aagaagaagt cattaaactt   720
tgtggacggg agctggttag gcacagatt gctatttgtg gtaagtctac gggaggagaa     780
ggctctggag gcgaaggaga aggggcgga aggcagcttt actctgctct ggctaacaag     840
tgttgtcacg ttgggtgtac caagcaatcc cttgcgcaat tctgc                    885

SEQ ID NO: 535          moltype = DNA  length = 885
FEATURE                 Location/Qualifiers
source                  1..885
                        mol_type = other DNA
                        organism = synthetic construct
SEQUENCE: 535
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga cacctcctgt acttgacagc   540
gacggctcct ttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatacc aagaagaagt cattaaactt   720
tgtggacggg agctggttag gcacagatt gctatttgtg gtaagtctac gggaggagaa     780
```

```
ggctctggag gcgaaggaga aggggggcgga aggcagcttt actctgctct ggctaacaag    840
tgttgtcaag ttgggtgtac caagcaatcc cttgcgcaat tctgc                     885

SEQ ID NO: 536          moltype = DNA   length = 885
FEATURE                 Location/Qualifiers
source                  1..885
                        mol_type = other DNA
                        organism = synthetic construct
SEQUENCE: 536
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga caccctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatacc aagaagaagt cattaaactt   720
tgtggacggg agctggttag ggcacagatt gctatttgtg gtaagtctac gggaggagaa   780
ggctctggag gcgaaggatc tggggggcgga aggcagcttt actctgctct ggctaacaag    840
tgttgtcacg ttgggtgtac caagcggtcc cttgcgcaat tctgc                     885

SEQ ID NO: 537          moltype = DNA   length = 885
FEATURE                 Location/Qualifiers
source                  1..885
                        mol_type = other DNA
                        organism = synthetic construct
SEQUENCE: 537
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga caccctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatacc aagaagaagt cattaaactt   720
tgtggacggg agctggttag ggcacagatt gctatttgtg gtaagtctac gggaggagaa   780
ggctctggag gcgaaggatc tggggggcgga aggcagcttt actctgctct ggctaacaag    840
tgttgtcaag ttgggtgtac caagcggtcc cttgcgcaat tctgc                     885

SEQ ID NO: 538          moltype = DNA   length = 885
FEATURE                 Location/Qualifiers
source                  1..885
                        mol_type = other DNA
                        organism = synthetic construct
SEQUENCE: 538
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
cgggttgtct cagttctcac agttcttcat caggattggt tgaatggaaa ggagtacaaa   300
tgcaaagtgt ccaacaaagc gcttgctgcg ccgattgaaa agacgatttc aaaggcaaaa   360
gggcagcccc gcgaacccca agtatatact ttgcctccct cacgcgatga actgactaag   420
aaccaggtga gcctgacttg tttggttaag ggttttttatc caagtgacat tgctgttgaa   480
tgggagtcca atggccagcc tgagaataac tacaaaacga caccctcctgt acttgacagc   540
gacggctcct ttttttcttta ttcaaaactc acagtggaca aatccaggtg gcagcagggt   600
aacgtctttt cttgcagcgt gctccacgaa gctttgcatt cacattatac gcaaaaatcc   660
ttgtcattgt ccccaggtaa gggcggaagc gactcatacc aagaagaagt cattaaactt   720
tgtggacggg agctggttag ggcacagatt gctatttgtg gtaagtctac gggaggagaa   780
ggctctggag gcgaaggatc tggggggcgga aggcagcttt actctgctct ggctaacaag    840
tgttgtcacg ttgggtgtac caagcaatcc cttgcgcaat tctgc                     885

SEQ ID NO: 539          moltype = DNA   length = 885
FEATURE                 Location/Qualifiers
source                  1..885
                        mol_type = other DNA
                        organism = synthetic construct
SEQUENCE: 539
gataaaaccc acacttgccc accttgccct gcgccggaag ccgccggagg acctagtgtt    60
ttcctctttc cccctaagcc caaagacacg ttgatgatct ctcggacacc ggaagtaact   120
tgtgtcgttg tggatgtgtc acatgaggat cccgaggtga aatttaattg gtacgttgac   180
ggcgtggagg tgcataacgc aaagactaaa ccacgcgagg agcagtataa ttctacatac   240
```

```
cgggttgtct cagttctcac agttcttcat caggattggt tgaatggaaa ggagtacaaa    300
tgcaaagtgt ccaacaaagc gcttgctgcg ccgattgaaa agacgatttc aaaggcaaaa    360
gggcagcccc gcgaacccca agtatatact ttgcctccct cacgcgatga actgactaag    420
aaccaggtga gcctgacttg tttggttaag ggttttatc caagtgacat tgctgttgaa     480
tgggagtcca atggccagcc tgagaataac tacaaaacga cacctcctgt acttgacagc    540
gacggctcct ttttcttta ttcaaaactc acagtggaca aatccaggtg gcagcagggt     600
aacgtctttt cttgcagcgt gctccacgaa gctttgcatt cacattatac gcaaaaatcc    660
ttgtcattgt ccccaggtaa gggcggaagc gactcatacc aagaagaagt cattaaactt    720
tgtgacggg agctggttag gcacagatt gctatttgtg gtaagtctac gggaggagaa      780
ggctctggag gcgaaggatc tggggcgga aggcagcttt actctgctct ggctaacaag     840
tgttgtcaag ttgggtgtac caagcaatcc cttgcgcaat tctgc                    885

SEQ ID NO: 540          moltype = DNA  length = 945
FEATURE                 Location/Qualifiers
source                  1..945
                        mol_type = other DNA
                        organism = synthetic construct
SEQUENCE: 540
atggaaacgg atacgctgtt gttgtgggtt ctgctcttgt gggtgccagg gagcacaggt    60
gataaaaccc acacttgccc accttgccct gcgccggaag ccgccggagg acctagtgtt    120
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca agtatatact ttgcctccct cacgcgatga actgactaag    480
aaccaggtga gcctgacttg tttggttaag ggttttatc caagtgacat tgctgttgaa     540
tgggagtcca atgccagcc tgagaataac tacaaaacga cacctcctgt acttgacagc     600
gacggctcct ttttcttta ttcaaaactc acagtggaca aatccaggtg gcagcagggt     660
aacgtctttt cttgcagcgt gctccacgaa gctttgcatt cacattatac gcaaaaatcc    720
ttgtcattgt ccccaggtaa gggcggaagc gactcatacc aagaagaagt cattaaactt    780
tgtgacggg agctggttag gcacagatt gctatttgtg gtaagtctac gggaggagaa      840
ggctctggag gcgaaggaga aggggcgga aggcagcttt actctgctct ggctaacaag     900
tgttgtcacg ttgggtgtac caagcggtcc cttgcgcaat tctgc                    945

SEQ ID NO: 541          moltype = DNA  length = 945
FEATURE                 Location/Qualifiers
source                  1..945
                        mol_type = other DNA
                        organism = synthetic construct
SEQUENCE: 541
atggaaacgg atacgctgtt gttgtgggtt ctgctcttgt gggtgccagg gagcacaggt    60
gataaaaccc acacttgccc accttgccct gcgccggaag ccgccggagg acctagtgtt    120
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca agtatatact ttgcctccct cacgcgatga actgactaag    480
aaccaggtga gcctgacttg tttggttaag ggttttatc caagtgacat tgctgttgaa     540
tgggagtcca atggccagcc tgagaataac tacaaaacga cacctcctgt acttgacagc    600
gacggctcct ttttcttta ttcaaaactc acagtggaca aatccaggtg gcagcagggt     660
aacgtctttt cttgcagcgt gctccacgaa gctttgcatt cacattatac gcaaaaatcc    720
ttgtcattgt ccccaggtaa gggcggaagc gactcatacc aagaagaagt cattaaactt    780
tgtgacggg agctggttag gcacagatt gctatttgtg gtaagtctac gggaggagaa      840
ggctctggag gcgaaggaga aggggcgga aggcagcttt actctgctct ggctaacaag     900
tgttgtcaag ttgggtgtac caagcggtcc cttgcgcaat tctgc                    945

SEQ ID NO: 542          moltype = DNA  length = 945
FEATURE                 Location/Qualifiers
source                  1..945
                        mol_type = other DNA
                        organism = synthetic construct
SEQUENCE: 542
atggaaacgg atacgctgtt gttgtgggtt ctgctcttgt gggtgccagg gagcacaggt    60
gataaaaccc acacttgccc accttgccct gcgccggaag ccgccggagg acctagtgtt    120
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca agtatatact ttgcctccct cacgcgatga actgactaag    480
aaccaggtga gcctgacttg tttggttaag ggttttatc caagtgacat tgctgttgaa     540
tgggagtcca atgccagcc tgagaataac tacaaaacga cacctcctgt acttgacagc     600
gacggctcct ttttcttta ttcaaaactc acagtggaca aatccaggtg gcagcagggt     660
aacgtctttt cttgcagcgt gctccacgaa gctttgcatt cacattatac gcaaaaatcc    720
ttgtcattgt ccccaggtaa gggcggaagc gactcatacc aagaagaagt cattaaactt    780
tgtgacggg agctggttag gcacagatt gctatttgtg gtaagtctac gggaggagaa      840
ggctctggag gcgaaggaga aggggcgga aggcagcttt actctgctct ggctaacaag     900
```

```
tgttgtcacg ttgggtgtac caagcaatcc cttgcgcaat tctgc              945

SEQ ID NO: 543         moltype = DNA   length = 945
FEATURE                Location/Qualifiers
source                 1..945
                       mol_type = other DNA
                       organism = synthetic construct
SEQUENCE: 543
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggttgtct cagttctcac agttcttcat caggattggt tgaatggaaa ggagtacaaa  360
tgcaaagtgt ccaacaaagc gcttgctgcg ccgattgaaa agacgatttc aaaggcaaaa  420
gggcagcccc gcgaacccca agtatatact ttgcctccct cacgcgatga actgactaag  480
aaccaggtga gcctgacttg tttggttaag ggttttttatc caagtgacat tgctgttgaa  540
tgggagtcca atggccagcc tgagaataac tacaaaacga cacctcctgt acttgacagc  600
gacggctcct tttttcttta ttcaaaactc acagtggaca aatccaggtg gcagcagggt  660
aacgtctttt cttgcagcgt gctccacgaa gctttgcatt cacattatac gcaaaaatcc  720
ttgtcattgt ccccaggtaa gggcggaagc gactcatacc aagaagaagt cattaaactt  780
tgtggacggg agctggttag ggcacagatt gctatttgtg gtaagtctac gggaggagaa  840
ggctctggag gcgaaggaga aggggggcgga aggcagcttt actctgctct ggctaacaag  900
tgttgtcaag ttgggtgtac caagcaatcc cttgcgcaat tctgc              945

SEQ ID NO: 544         moltype = DNA   length = 945
FEATURE                Location/Qualifiers
source                 1..945
                       mol_type = other DNA
                       organism = synthetic construct
SEQUENCE: 544
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggttgtct cagttctcac agttcttcat caggattggt tgaatggaaa ggagtacaaa  360
tgcaaagtgt ccaacaaagc gcttgctgcg ccgattgaaa agacgatttc aaaggcaaaa  420
gggcagcccc gcgaacccca agtatatact ttgcctccct cacgcgatga actgactaag  480
aaccaggtga gcctgacttg tttggttaag ggttttttatc caagtgacat tgctgttgaa  540
tgggagtcca atggccagcc tgagaataac tacaaaacga cacctcctgt acttgacagc  600
gacggctcct tttttcttta ttcaaaactc acagtggaca aatccaggtg gcagcagggt  660
aacgtctttt cttgcagcgt gctccacgaa gctttgcatt cacattatac gcaaaaatcc  720
ttgtcattgt ccccaggtaa gggcggaagc gactcatacc aagaagaagt cattaaactt  780
tgtggacggg agctggttag ggcacagatt gctatttgtg gtaagtctac gggaggagaa  840
ggctctggag gcgaaggatc tggggggcgga aggcagcttt actctgctct ggctaacaag  900
tgttgtcacg ttgggtgtac caagcggtcc cttgcgcaat tctgc              945

SEQ ID NO: 545         moltype = DNA   length = 945
FEATURE                Location/Qualifiers
source                 1..945
                       mol_type = other DNA
                       organism = synthetic construct
SEQUENCE: 545
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
ttcctctttc cccctaagcc caaagacacg ttgatgatct ctcggacacc ggaagtaact  180
tgtgtcgttg tggatgtgtc acatgaggat cccgaggtga aatttaattg gtacgttgac  240
ggcgtggagg tgcataacgc aaagactaaa ccacgcgagg agcagtataa ttctacatac  300
cgggttgtct cagttctcac agttcttcat caggattggt tgaatggaaa ggagtacaaa  360
tgcaaagtgt ccaacaaagc gcttgctgcg ccgattgaaa agacgatttc aaaggcaaaa  420
gggcagcccc gcgaacccca agtatatact ttgcctccct cacgcgatga actgactaag  480
aaccaggtga gcctgacttg tttggttaag ggttttttatc caagtgacat tgctgttgaa  540
tgggagtcca atggccagcc tgagaataac tacaaaacga cacctcctgt acttgacagc  600
gacggctcct tttttcttta ttcaaaactc acagtggaca aatccaggtg gcagcagggt  660
aacgtctttt cttgcagcgt gctccacgaa gctttgcatt cacattatac gcaaaaatcc  720
ttgtcattgt ccccaggtaa gggcggaagc gactcatacc aagaagaagt cattaaactt  780
tgtggacggg agctggttag ggcacagatt gctatttgtg gtaagtctac gggaggagaa  840
ggctctggag gcgaaggatc tggggggcgga aggcagcttt actctgctct ggctaacaag  900
tgttgtcaag ttgggtgtac caagcggtcc cttgcgcaat tctgc              945

SEQ ID NO: 546         moltype = DNA   length = 945
FEATURE                Location/Qualifiers
source                 1..945
                       mol_type = other DNA
                       organism = synthetic construct
SEQUENCE: 546
atggaaacgg atacgctgtt gttgtgggtt ctgctcttgt gggtgccagg gagcacaggt   60
gataaaaccc acacttgccc accttgccct gcgccggaag ccgccggagg acctagtgtt  120
```

```
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca gtatatact  ttgcctccct cacgcgatga actgactaag    480
aaccaggtga gcctgacttg tttggttaag ggttttatc caagtgacat tgctgttgaa    540
tgggagtcca atggccagcc tgagaataac tacaaaacga cacctcctgt acttgacagc    600
gacggctcct ttttctttta ttcaaaactc acagtggaca aatccaggtg gcagcagggt    660
aacgtctttt cttgcagcgt gctccacgaa gctttgcatt cacattatac gcaaaaatcc    720
ttgtcattgt ccccaggtaa gggcggaagc gactcatacc aagaagaagt cattaaactt    780
tgtggacggg agctggttag ggcacagatt gctatttgtg gtaagtctac gggaggagaa    840
ggctctggag gcgaaggatc tggggcgga aggcagcttt actctgctct ggctaacaag    900
tgttgtcacg ttgggtgtac caagcaatcc cttgcgcaat tctgc                   945

SEQ ID NO: 547         moltype = DNA  length = 945
FEATURE                Location/Qualifiers
source                 1..945
                       mol_type = other DNA
                       organism = synthetic construct
SEQUENCE: 547
atggaaacgg atacgctgtt gttgtgggtt ctgctcttgt gggtgccagg gagcacaggt    60
gataaaaccc acacttgccc ccttgccct gcgccggaag ccgccggagg acctagtgtt    120
ttcctctttc cccctaagcc caaagacacg ttgatgatct ctcggacacc ggaagtaact    180
tgtgtcgttg tggatgtgtc acatgaggat cccgaggtga aatttaattg gtacgttgac    240
ggcgtggagg tgcataacgc aaagactaaa ccacgcgagg agcagtataa ttctacatac    300
cgggttgtct cagttctcac agttcttcat caggattggt tgaatggaaa ggagtacaaa    360
tgcaaagtgt ccaacaaagc gcttgctgcg ccgattgaaa agacgatttc aaaggcaaaa    420
gggcagcccc gcgaacccca gtatatact  ttgcctccct cacgcgatga actgactaag    480
aaccaggtga gcctgacttg tttggttaag ggttttatc caagtgacat tgctgttgaa    540
tgggagtcca atggccagcc tgagaataac tacaaaacga cacctcctgt acttgacagc    600
gacggctcct ttttctttta ttcaaaactc acagtggaca aatccaggtg gcagcagggt    660
aacgtctttt cttgcagcgt gctccacgaa gctttgcatt cacattatac gcaaaaatcc    720
ttgtcattgt ccccaggtaa gggcggaagc gactcatacc aagaagaagt cattaaactt    780
tgtggacggg agctggttag ggcacagatt gctatttgtg gtaagtctac gggaggagaa    840
ggctctggag gcgaaggatc tggggcgga aggcagcttt actctgctct ggctaacaag    900
tgttgtcaag ttgggtgtac caagcaatcc cttgcgcaat tctgc                   945

SEQ ID NO: 548         moltype = AA  length = 19
FEATURE                Location/Qualifiers
source                 1..19
                       mol_type = protein
                       organism = synthetic construct
SEQUENCE: 548
MGWSCIILFL VATATGVHS                                                 19

SEQ ID NO: 549         moltype = AA  length = 314
FEATURE                Location/Qualifiers
source                 1..314
                       mol_type = protein
                       organism = synthetic construct
SEQUENCE: 549
MGWSCIILFL VATATGVHSD KTHTCPPCPA PEAAGGPSVF LFPPKPKDTL MISRTPEVTC    60
VVVDVSHEDP EVKFNWYVDG VEVHNAKTKP REEQYNSTYR VVSVLTVLHQ DWLNGKEYKC    120
KVSNKALAAP IEKTISKAKG QPREPQVYTL PPSRDELTKN QVSLTCLVKG FYPSDIAVEW    180
ESNGQPENNY KTTPPVLDSD GSFFLYSKLT VDKSRWQQGN VFSCSVLHEA LHSHYTQKSL    240
SLSPGKGGSD SWQEEVIKLC GRELVRAQIA ICGKSTASDA AGAEAEAGAR QLYSALANKC    300
CHVGCTKRSL AQFC                                                      314

SEQ ID NO: 550         moltype = AA  length = 24
FEATURE                Location/Qualifiers
source                 1..24
                       mol_type = protein
                       organism = synthetic construct
SEQUENCE: 550
QLYSALANKC CHVGCTKRSL AEFC                                           24

SEQ ID NO: 551         moltype = AA  length = 25
FEATURE                Location/Qualifiers
source                 1..25
                       mol_type = protein
                       organism = synthetic construct
SEQUENCE: 551
RQLYSALANK CCHVGCTKQS LAQFC                                          25

SEQ ID NO: 552         moltype = AA  length = 25
FEATURE                Location/Qualifiers
source                 1..25
                       mol_type = protein
```

```
                        organism = synthetic construct
SEQUENCE: 552
RQLYSALANK CCYVGCTKRS LAQFC                                         25

SEQ ID NO: 553          moltype = AA   length = 25
FEATURE                 Location/Qualifiers
source                  1..25
                        mol_type = protein
                        organism = synthetic construct
SEQUENCE: 553
RQLYSALANK CCLVGCTKRS LAQFC                                         25

SEQ ID NO: 554          moltype = AA   length = 25
FEATURE                 Location/Qualifiers
source                  1..25
                        mol_type = protein
                        organism = synthetic construct
SEQUENCE: 554
RQLYSALANK CCQVGCTKRS LAQFC                                         25

SEQ ID NO: 555          moltype = AA   length = 25
FEATURE                 Location/Qualifiers
source                  1..25
                        mol_type = protein
                        organism = synthetic construct
SEQUENCE: 555
RQLYSALANK CCKVGCTKRS LAQFC                                         25

SEQ ID NO: 556          moltype = AA   length = 25
FEATURE                 Location/Qualifiers
source                  1..25
                        mol_type = protein
                        organism = synthetic construct
SEQUENCE: 556
RQLYSALANK CCYVGCTKQS LAQFC                                         25

SEQ ID NO: 557          moltype = AA   length = 25
FEATURE                 Location/Qualifiers
source                  1..25
                        mol_type = protein
                        organism = synthetic construct
SEQUENCE: 557
RQLYSALANK CCKVGCTKQS LAQFC                                         25

SEQ ID NO: 558          moltype = AA   length = 25
FEATURE                 Location/Qualifiers
source                  1..25
                        mol_type = protein
                        organism = synthetic construct
SEQUENCE: 558
RQLYSALANK CCQVGCTKQS LAQFC                                         25
```